United States Patent
Adair et al.

(10) Patent No.: US 11,970,497 B2
(45) Date of Patent: Apr. 30, 2024

(54) TRICYCLIC AKR1C3 DEPENDENT KARS INHIBITORS

(71) Applicant: Novartis AG, Basel (CH)

(72) Inventors: Chris Adair, Brighton, MA (US); Tracy Chen, Litchfield, NH (US); Jian Ding, Bedford, MA (US); Christy Fryer, Cambridge, MA (US); Yuko Isome, Arlington, MA (US); Marie-Helene Larraufie, Barcelona (ES); Katsumasa Nakajima, Winchester, MA (US); Nik Savage, Somerville, MA (US); Ariel Sterling Twomey, Everett, MA (US)

(73) Assignee: Novartis AG, Basel (CH)

( * ) Notice: Subject to any disclaimer, the term of this patent is extended or adjusted under 35 U.S.C. 154(b) by 101 days.

(21) Appl. No.: 16/973,836

(22) PCT Filed: Jul. 31, 2020

(86) PCT No.: PCT/IB2020/057285
§ 371 (c)(1),
(2) Date: Dec. 10, 2020

(87) PCT Pub. No.: WO2021/005586
PCT Pub. Date: Jan. 14, 2021

(65) Prior Publication Data
US 2022/0315582 A1    Oct. 6, 2022

Related U.S. Application Data

(60) Provisional application No. 63/033,932, filed on Jun. 3, 2020, provisional application No. 63/009,513, filed on Apr. 14, 2020, provisional application No. 62/881,619, filed on Aug. 1, 2019.

(51) Int. Cl.
| | | |
|---|---|---|
| C07D 471/10 | (2006.01) | |
| A61P 35/00 | (2006.01) | |
| A61K 31/4747 | (2006.01) | |

(52) U.S. Cl.
CPC ............ *C07D 471/10* (2013.01); *A61P 35/00* (2018.01); *A61K 31/4747* (2013.01)

(58) Field of Classification Search
CPC .... C07D 471/10; A61K 31/4747; A61P 35/00
See application file for complete search history.

(56) References Cited

FOREIGN PATENT DOCUMENTS

| WO | 2010062571 A1 | 6/2010 |
|---|---|---|
| WO | 2021005586 A1 | 1/2021 |

OTHER PUBLICATIONS

Zhang et al. "The biological process of lysin-t-RNA charging is therapeutically targetable in liver cancer," Liver International, 2021, 41:206-219 (Year: 2021).*

(Continued)

*Primary Examiner* — Shengjun Wang
(74) *Attorney, Agent, or Firm* — Michelle Han

(57) ABSTRACT

The present invention relates to novel tricyclic compounds that are AKR1C3 dependent KARS inhibitor, processes for their preparation, pharmaceutical compositions, and medicaments containing them, and their use in diseases and disorders mediated by an AKR1C3 dependent KARS inhibitor.

22 Claims, 3 Drawing Sheets

Kinetic of conversion of Compound 40 to Compound 152 human AKR1C3 Kinetics

Km = 37.9 ± 5.7 µM;  kcat = 0.406 ± 0.026 min⁻¹

(56) References Cited

OTHER PUBLICATIONS

Acquaviva J. et al. "Targeting KRAS-Mutant Non-Small Cell Lung Cancer with the Hsp90 Inhibitor Ganetespib", Molecular Cancer Therapeutics, vol. 11, No. 12, pp. 2633-2643, 2012.

Kouznetsov Vladimir V et al. "3', 4'-Dihydrospiro[piperidine-4,2'-(1'H)quinoline] Derivatives as New Antioxidant Agents with Acetylcholinesterase Inhibitory Property", Letters in Drug Design and Discovery Bentham Science Publishers, vol. 7, No. 10, pp. 710-715, 2010.

Mendez Leonor Y Vargas et al. "Intramolecular N to N acyl Migration in conformationally mobile 1'-acyl-1-benzyl-3',4'-dihydro-1'spiropiperidine-4,2'-quinoline systems promoted by debenzylation conditions (HCOONH/Pd/C)", Central European Journal of Chemistry, vol. 9, No. 5, pp. 877-885, 2011.

Mendez Leonor Y Vargas et al. "An efficient synthesis of new 1-H-4'methyl1-3',4'-dihydrospiro[piperidine-4,2' (1H) quinoline] scaffolds", Tetrahedron Letters, Elseview Ltd, Amsterdam, NL, vol. 48, No. 14, pp. 2509-2512, 2007.

Belen'ky et al, Heterocyclic Compounds, Bol'shaya Russian Encycoplaedia, 2016, retrieved from https://bigenc.ru/chemistry/text/2356851 on Nov. 24, 2022.

Belikov, Relationship between the chemical structure, properties of compounds and their action on the body, Pharmaceutical Chemistry, 2007, 27-29, chapter 2.6.

Dyson, et al., Chemistry of synthetic drugs, 1964, 12-19.

Kummerer, Pharmaceuticals in the environment, Annual Review of Environment and Resources, Aug. 18, 2010, 57-75, 35.

Mashkovsky, Medicaments: A Guide for Doctors, Lekarstvennye Sredstva, 2005, 10-11, 15th edition.

\* cited by examiner

FIG 1: Kinetic of conversion of Compound 40 to Compound 152
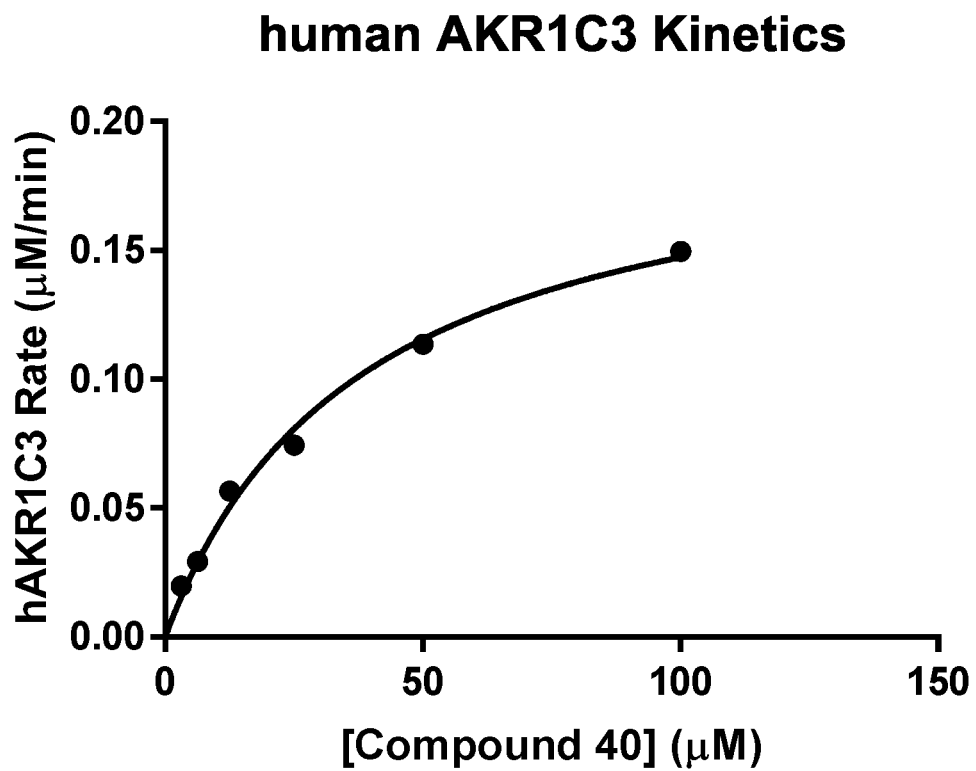
Km = 37.9 ± 5.7 µM;  kcat = 0.406 ± 0.026 min$^{-1}$ FIG. 2: Dose dependent *in vivo* efficacy of Compound 40 in high AKR1C3 expressing human lung cancer xenograft NCI-H1944
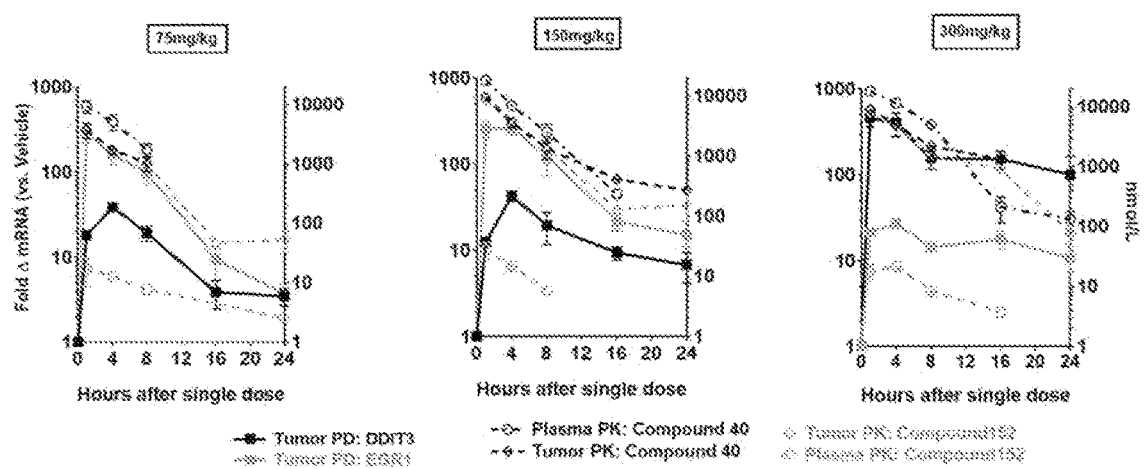

FIG. 3: Dose dependent *in vivo* efficacy of Compound 40 in the KEAP1 mutant and moderately AKR1C3 expressing human lung cancer xenografts NCI-H1944 and NCI-H460
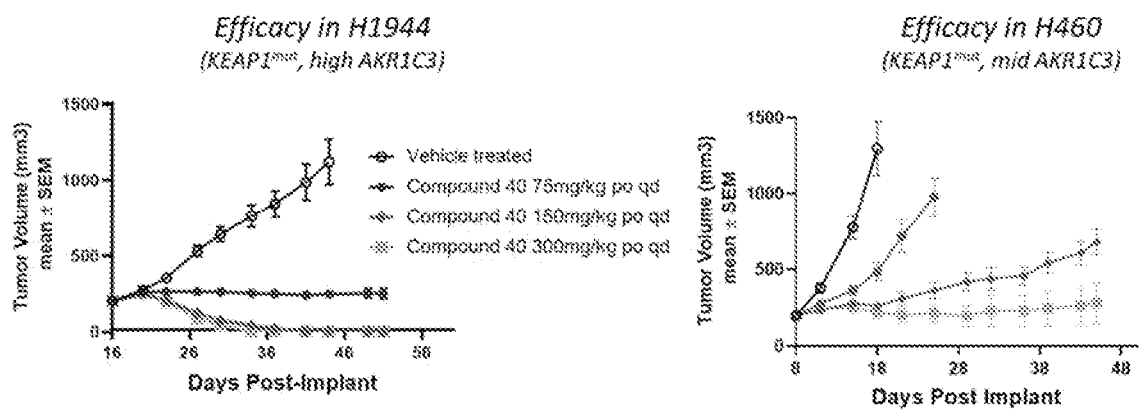

TRICYCLIC AKR1C3 DEPENDENT KARS INHIBITORS

FIELD OF THE INVENTION

The present invention relates to novel tricyclic compounds that are useful as AKR1C3 dependent KARS inhibitors. The present invention also relates to processes for the preparation of said compounds, pharmaceutical compositions comprising said compounds, methods of using said compounds in the treatment of various diseases and disorders, and medicaments containing them, and their use in diseases and disorders mediated by an AKR1C3 dependent KARS inhibitor.

BACKGROUND OF THE INVENTION

The NFE2 L2/NRF2-KEAP1 pathway has a strong genetic basis in cancer. The TCGA sequencing effort reported that this pathway was altered in 34% of lung squamous cell carcinomas (Hammerman P S et al. Comprehensive genomic characterization of squamous cell lung cancers. Nature 489, 519-525 (2012)). In addition, TCGA and other groups have reported significant mutation of this pathway in other solid tumor indications, including head and neck squamous cell carcinoma and hepatocellular carcinoma. Aberrant activation of the NRF2 pathway can occur by gain of function genetic alterations in NRF2 or loss of function genetic alterations in KEAP1 or CUL3 that lead to stabilization of NRF2 and elevated expression of its target genes. The uncontrolled transcription of those target genes confers advantages to cancer cells such as malignancy and protection against oxidative stress, chemotherapy and radiotherapy (Jaramillo M C, Zhang D D. The emerging role of the Nrf2-Keap1 signaling pathway in cancer Genes Dev. 27, 2179-2191 (2013)). Exacerbated NRF2 activity in tumors has been associated with poor prognosis (Shibata T, Ohta T, Tong K I, Kokubu A, Odogawa R, Tsuta K, Asamura H, Yamamoto M, Hirohashi S. Cancer related mutations in NRF2 impair its recognition by Keap1-Cul3 E3 ligase and promote malignancy. Proc Natl Acad Sci USA 105, 13568-13573 (2008)). To the best of our knowledge, there is currently no approved therapy to selectively target cancers with genetic alterations on the NRF2/KEAP1 pathway, which thus represents an unmet medical need.

Aldehyde keto reductase 1C3 (AKR1C3) is one of the numerous target genes of the transcription factor NRF2, whose expression is upregulated in NRF2/KEAP1 mutated cancers (MacLeod A K, Acosta-Jimenez L, Coates P J, McMahon M, Carey F A, Honda T, Henderson C J and Wolf C R. Aldo-keto reductases are biomarkers of NRF2 activity and are coordinately overexpressed in non-small cell lung cancer. Br J Cancer 115, 1530-1539 (2016)). AKR1C3 (also named type 2 3α(17β)-hydroxysteroid dehydrogenase) is an NADP(H)-dependent ketosteroid reductase, member of the aldo-keto reductase (AKR) superfamily, that plays a role in steroid hormone metabolism and signaling, as well as xenobiotic detoxification. Some known substrates for AKR1C3 are the endogenous substrates 5α-dihydrotestosterone, Δ4-androstene-3,17-dione and progesterone (Penning™, Burczynski M E, Jez J M, Hung C F, Lin H K, Ma H, Moore M, Palackal N, Ratnam K. Human 3α-hydroxysteroid dehydrogenase isoforms (AKR1C1-AKR1C4) of the aldo-keto reductase superfamily: functional plasticity and tissue distribution reveals roles in the inactivation and formation of male and female sex hormones. Biochem. J. 351, 67-77 (2000)), as well as the synthetic prodrugs coumberone (Halim M, Yee D J, Sames D. Imaging Induction of Cytoprotective Enzymes in Intact Human Cells: Coumberone, a Metabolic Reporter for Human AKR1C Enzymes Reveals Activation by Panaxytriol, an Active Component of Red Ginseng J. Am. Chem. Soc. 130, 14123-14128 (2008)), PR104 (Jamieson S M, Gu Y, Manesh D M, El-Hoss J, Jing D, Mackenzie K L, Guise C P, Foehrenbacher A, Pullen S M, Benito J, Smaill J B, Patterson A V, Mulaw M A, Konopleva M, Bohlander S K, Lock R B, Wilson W R. A novel fluorometric assay for aldo-keto reductase 1C3 predicts metabolic activation of the nitrogen mustard prodrug PR-104A in human leukaemia cells. Biochem Pharmacol. 88, 36-45 (2014)) and TH3424/OBI3424 (Threshold pharmaceuticals WO 2016/145092 A1). We report the identification of tricyclic ketone compounds that get converted to lysine t-RNA synthetase (KARS) inhibitors by AKR1C3 in the presence of NADPH. Lysine t-RNA synthetase is a ubiquitous enzyme essential for protein synthesis that is part of the multi-tRNA synthetase complex.

AKR1C3 dependent KARS inhibitors provide an attractive strategy to selectively treat tumors that overexpress AKR1C3 compared to normal tissues, such as NRF2/KEAP1 mutated cancers and other types of cancers reported to overexpress AKR1C3 (Guise C P, Abbattista M R, Singleton R S, Holford S D, Connolly J, Dachs G U, Fox S B, Pollock R, Harvey J, Guilford P, Doñate F, Wilson W R, Patterson A V. The bioreductive prodrug PR-104A is activated under aerobic conditions by human aldo-keto reductase 1C3. Cancer Res. 70, 1573-1584 (2010)) such as breast cancers (Lewis M J, Wiebe J P, Heathcote J G. Expression of progesterone metabolizing enzyme genes (AKR1C1, AKR1C2, AKR1C3, SRD5A1, SRD5A2) is altered in human breast carcinoma. BMC Cancer 4, 27 (2004)) and prostate cancers (Fung K M, Samara E N S, Wong C, Metwalli A, Krlin R, Bane B, Liu C Z, et al. Increased expression of type 2 3α-hydroxysteroid dehydrogenase/type 5 17β-hydroxysteroid dehydrogenase (AKR1C3) and its relationship with androgen receptor in prostate carcinoma. Endocr Relat Cancer 13, 169-180 (2006)).

There is currently no approved therapy that can target selectively NRF2/KEAP1 altered cancers or cancers with high AKR1C3 expression. Therefore, there is a need to provide new and/or alternative treatments for treating cancer patients, including selective AKR1C3 reductase dependent KARS inhibitor.

SUMMARY OF THE INVENTION

AKR1C3 dependent KARS inhibitors provides new treatments and therapies for patients suffering from cancers with genetic alterations on the NRF2/KEAP1 pathway. The invention provides compounds, pharmaceutically acceptable salts thereof, pharmaceutical compositions thereof and combinations thereof, which compounds are AKR1C3 dependent KARS inhibitors that get converted to lysine t-RNA synthetase (KARS) inhibitors by AKR1C3 in the presence of NADPH. Lysine t-RNA synthetase is a ubiquitous enzyme essential for protein synthesis that is part of the multi-tRNA synthetase complex. The invention further provides methods of treating, or preventing diseases and/or disorders related to high AKR1C3 expression or sensitivity to KARS inhibition, comprising administering to a subject in need thereof an effective amount of an AKR1C3 dependent KARS inhibitor.

Various embodiments of the invention are described herein.

Within certain aspects, provided herein is a compound of formula (I), or a pharmaceutically acceptable salt thereof:

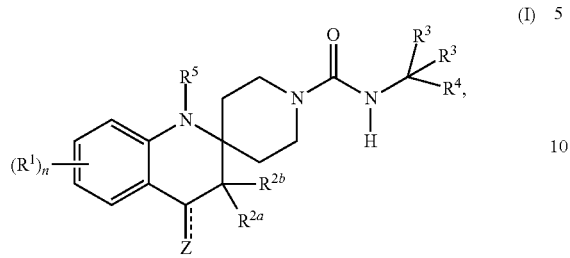

wherein:
= is a single bond or a double bond;
Z is either OH, when = is a single bond; or O, when = is a double bond;
each $R^1$ is independently selected from the group consisting of, $(C_1-C_6)$alkyl, $(C_1-C_6)$alkoxy, $(C_0-C_4)$alkylN$(R^8)_2$, and halo;
$R^{2a}$ and $R^{2b}$ are each independently selected from the group consisting of H, $(C_1-C_6)$ alkyl, and halo;
each $R^3$ is independently selected from the group consisting of H and halo:
$R^4$ is selected from the group consisting of aryl, a 5 to 6-membered heteroaryl comprising 1, 2, 3, or 4 heteroatoms independently selected from N, O, and S; and a 9 to 10-membered fused bicyclic heteroaryl comprising 1, 2, 3, or 4 heteroatoms independently selected from N, O, and S; wherein any of the foregoing is optionally substituted with one or more $R^6$;
$R^5$ is selected from the group consisting of H; $(C_1-C_6)$alkyl; $(C_2-C_6)$alkenyl; $(C_0-C_4)$alkylOR$^3$; $(C_1-C_4)$alkyl $(C_3-C_{10})$cycloalkyl; halo$(C_1-C_6)$alkyl; $(C_2-C_3)$alkynyl; $(C_1-C_4)$alkylN$(R^{10})_2$;
each $R^6$ is independently selected from the group consisting of halo; $(C_1-C_6)$alkyl; $(C_1-C_6)$alkoxy; halo$(C1-C_6)$alkyl; OH; aryl; 3 to 6-membered heterocycle; 5- to 6-membered heteroaryl; $(C_0-C_4)$alkylS(O)$_m(C_1-C_6)$alkyl; halo$(C_1-C_6)$alkoxy; $(C_0-C_4)$alkylS(O)$_m$N$(R^8)_2$; $(C_0-C_4)$alkyl N$(R^8)_2$; $(C_0-C_4)$alkyl(CO)OR$^7$; N$(R^8)$S(O)$_m(C_1-C_6)$alkyl; N$(R^8)$S(O)$_m(C_3-C_6)$cycloalkyl; OP(O)(OH)$_2$; $(C_0-C_3)$alkyl(CO)NHR$^{11}$; $(C_0-C_3)$alkylOR$^7$, and $(C_3-C_{10})$cycloalkyl; wherein each $R^6$, when not being halo, OH, or OP(O)(OH)$_2$, is optionally substituted with one to three $R^9$; or two neighboring $R^6$, together with the atoms to which they attach form a 5 to 7-membered heterocycle or $(C_5-C_8)$cycloalkyl;
each $R^7$ and $R^8$ is independently selected from the group consisting of H or $(C_1-C_6)$alkyl, that is optionally substituted with one to three $R^9$;
each $R^9$ is independently selected from the group consisting of halo; —OH; amino, $(C_1-C_4)$alkylamino, di$(C_1-C_4)$alkylamino, OP(O)(OH)$_2$; $(C_1-C_6)$alkyl; $(C_1-C_3)$ alkynyl; $(C_1-C_6)$alkoxy; halo$(C_1-C_6)$alkyl; $(C_0-C_4)$alkylS(O)$_m(C_1-C_6)$alkyl; halo$(C_1-C_6)$alkoxy; 3 to 6-membered heterocycle which is optionally substituted with oxo (=O); $(C_0-C_4)$alkylS(O)$_m$N$(R^{10})_2$; $(C_0-C_4)$alkyl(CO)R$^{10}$; $(C_0-C_4)$alkyl(CO)OR$^{11}$; $(C_0-C_4)$alkylNR$^1$S(O)$_m(C_1-C_6)$alkyl; $(C_0-C_4)$alkylOR$^{10}$; $(C_0-C_4)$alkylN$(R^{10})_2$; $(C_0-C_4)$alkylCN; $(C_0-C_4)$alkylN$(R^{10})_2$; and $(C_0-C_4)$alkyl(CO)N$(R^{10})_2$;
each $R^{10}$ is independently selected from the group consisting of H, $(C_1-C_6)$alkyl; or 3 to 6-membered heterocycle, wherein the 3 to 6-membered heterocycle is optionally substituted with one or more of $(C_1-C_6)$ alkyl; and oxo (=O);
each $R^{11}$ is selected from the group consisting of H; 4 to 6-membered heterocycle which is optionally substituted with one to four $R^{12}$; $(C_3-C_6)$cycloalkyl which is optionally substituted with one to four $R^{12}$ $(C_0-C_3)$alkyl $(C_3-C_6)$cycloalkyl $(C_1-C_3)$alkyl which is optionally substituted with halo; CH$_2$-aryl which is optionally substituted with one to three $R^{12}$; $(C_1-C_6)$alkyl; $(C_2-C_6)$alkenyl; or $(C_2-C_6)$alkynyl, wherein each of the $(C_1-C_6)$alkyl; $(C_2-C_6)$alkenyl; and $(C_2-C_6)$alkynyl is optionally substituted with one or more $R^{13}$;
each $R^{12}$ is independently selected from the group consisting of OH, $(C_1-C_3)$alkoxy, NH$_2$; or $(C_1-C_3)$alkyl optionally substituted with one or more OH;
each $R^{13}$ is independently selected from the group consisting of halo, OH, amino, $(C_1-C_4)$alkylamino, di$(C_1-C_4)$alkylamino, $(C_1-C_3)$alkoxy; and C(O)—$(C_3-C_8)$cycloalkyl;
m is 0, 1, or 2; and
n is 0, 1 or 2.

In another aspect, the invention provides a pharmaceutical composition comprising a compound of formula (I), or subformulae thereof, or a pharmaceutically acceptable salt thereof, and one or more pharmaceutically acceptable carriers.

In another aspect, the invention provides a combination, in particular a pharmaceutical combination comprising a compound of formula (I), or subformulae thereof, or a pharmaceutically acceptable salt thereof, and one or more therapeutic agents. In certain instances, compounds of the present invention are combined with other therapeutic agents, such as other anti-cancer agents, anti-nausea agents (or anti-emetics), a chemotherapy, pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In another aspect, the invention provides a method of modulating KARS activity in a subject in need thereof, the method comprises administering to the subject in need thereof a compound of formula (I), or subformulae thereof, or a pharmaceutically acceptable salt thereof.

In another aspect, the invention also provides a compound of formula (I), or subformulae thereof, or a pharmaceutically acceptable salt thereof, for use in the treatment, or prevention of cancer, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS).

In another aspect, the invention also provides a compound of formula (I), or subformulae thereof, or a pharmaceutically acceptable salt thereof, for use in the treatment, or prevention of cancer with genetic or epigenetic alteration in the genes NFE2 L2, KEAP1, CUL3, AKR1C3, or any other condition resulting in the activation of NRF2 transcriptional activity or AKR1C3 gene expression.

In another aspect, the invention also provides a compound of formula (I), or subformulae thereof, or a pharmaceutically acceptable salt thereof, for use in the treatment, or prevention of cancer with an AKR1C3 overexpression that is higher than a predetermined value.

BRIEF DESCRIPTION OF THE DRAWINGS

FIG. 1 illustrates the kinetic conversion of Compound 40 to Compound 152 in the presence of AKR1C3

FIG. 2 illustrates dose dependent in vivo efficacy of Compound 40 in high AKR1C3 expressing human lung cancer xenograft NCI-H1944

FIG. 3 illustrates dose dependent in vivo efficacy of Compound 40 in the KEAP1 mutant and 35 moderately AKR1C3 expressing human lung cancer xenograft NCI-H1944 and NCI-H460

DETAILED DESCRIPTION OF THE INVENTION

The invention therefore provides a compound of Formula (I): or a pharmaceutically acceptable salt thereof:

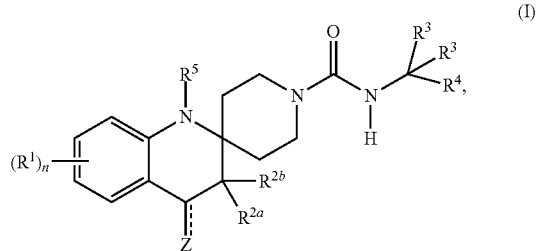

(I)

wherein:
= is a single bond or a double bond;
Z is either OH, when = is a single bond; or O, when = is a double bond;
each $R^1$ is independently selected from the group consisting of, $(C_1\text{-}C_6)$alkyl, $(C_1\text{-}C_6)$alkoxy, $(C_0\text{-}C_4)$alkylN$(R^3)_2$, and halo;
$R^{2a}$ and $R^{2b}$ are each independently selected from the group consisting of H, $(C_1\text{-}C_6)$ alkyl, and halo;
each $R^3$ is independently selected from the group consisting of H and halo;
$R^4$ is selected from the group consisting of aryl, a 5 to 6-membered heteroaryl comprising 1, 2, 3, or 4 heteroatoms independently selected from N, O, and S; and a 9 to 10-membered fused bicyclic heteroaryl comprising 1, 2, 3, or 4 heteroatoms independently selected from N, O, and S; wherein any of the foregoing is optionally substituted with one or more $R^6$;
$R^5$ is selected from the group consisting of H; $(C_1\text{-}C_6)$ alkyl; $(C_2\text{-}C_6)$alkenyl; $(C_0\text{-}C_4)$alkylOR; $(C_1\text{-}C_4)$alkyl $(C_3\text{-}C_{10})$cycloalkyl; halo$(C_1\text{-}C_6)$alkyl; $(C_2\text{-}C_3)$alkynyl; $(C_1\text{-}C_4)$alkylN$(R^{10})_2$;
each $R^6$ is independently selected from the group consisting of halo; $(C_1\text{-}C_6)$alkyl; $(C_1\text{-}C_6)$alkoxy; halo$(C_1\text{-}C_6)$alkyl; OH; aryl; 3 to 6-membered heterocycle; 5- to 6-membered heteroaryl; $(C_0\text{-}C_4)$ alkylS(O)$_m$$(C_1\text{-}C_6)$alkyl; halo$(C_1\text{-}C_6)$alkoxy; $(C_0\text{-}C_4)$alkylS(O)$_m$N$(R_6)_2$; $(C_0\text{-}C_4)$alkyl N$(R^8)_2$; $(C_0\text{-}C_4)$alkyl(CO)OR$^7$; N$(R^8)$S(O)$_m$$(C_1\text{-}C_6)$alkyl; N$(R^8)$S(O)$_m$$(C_3\text{-}C_6)$cycloalkyl; OP(O)(OH)$_2$, $(C_0\text{-}C_3)$alkyl(CO)NHR$^{11}$; $(C_0\text{-}C_3)$alkylOR$^7$, and $(C_3\text{-}C_{10})$cycloalkyl; wherein each $R^6$, when not being halo, OH, or OP(O)(OH)$_2$, is optionally substituted with one to three $R^9$; or two neighboring $R^6$, together with the atoms to which they attach form a 5 to 7-membered heterocycle or $(C_5\text{-}C_8)$cycloalkyl;
each $R^7$ and $R^8$ is independently selected from the group consisting of H or $(C_1\text{-}C_6)$alkyl, that is optionally substituted with one to three $R^9$;
each $R^9$ is independently selected from the group consisting of halo; —OH; amino, $(C_1\text{-}C_4)$alkylamino, di$(C_1\text{-}C_4)$alkylamino, OP(O)(OH)$_2$; $(C_1\text{-}C_6)$alkyl; $(C_1\text{-}C_3)$alkynyl; $(C_1\text{-}C_6)$alkoxy; halo$(C_1\text{-}C_6)$alkyl; $(C_0\text{-}C_4)$alkylS(O)$_m$$(C_1\text{-}C_6)$alkyl; halo$(C_1\text{-}C_6)$alkoxy; 3 to 6-membered heterocycle which is optionally substituted with oxo (=O); $(C_0\text{-}C_4)$alkylS(O)$_m$N$(R^{10})_2$; $(C_0\text{-}C_4)$alkyl(CO)R$^{11}$; $(C_0\text{-}C_4)$alkyl(CO)OR$^{11}$; $(C_0\text{-}C_4)$alkylNR$^{10}$S(O)$_m$$(C_1\text{-}C_6)$alkyl; $(C_0\text{-}C_4)$alkylOR$^{10}$; $(C_0\text{-}C_4)$alkylN$(R^{10})_2$; $(C_0\text{-}C_4)$alkylCN; $(C_0\text{-}C_4)$alkylN$(R^{10})_2$; and $(C_0\text{-}C_4)$alkyl(CO)N$(R^{10})_2$;
each $R^{10}$ is independently selected from the group consisting of H, $(C_1\text{-}C_6)$alkyl; or 3 to 6-membered heterocycle, wherein the 3 to 6-membered heterocycle is optionally substituted with one or more of $(C_1\text{-}C_6)$ alkyl; and oxo (=O);
each $R^{11}$ is selected from the group consisting of H; 4 to 6-membered heterocycle which is optionally substituted with one to four $R^{12}$; $(C_3\text{-}C_6)$cycloalkyl which is optionally substituted with one to four $R^{12}$; $(C_0\text{-}C_3)$ alkyl$(C_3\text{-}C_6)$cycloalkyl $(C_1\text{-}C_3)$alkyl which is optionally substituted with halo; CH$_2$-aryl which is optionally substituted with one to three $R^{12}$; $(C_1\text{-}C_6)$alkyl; $(C_2\text{-}C_6)$alkenyl; or $(C_2\text{-}C_6)$alkynyl, wherein each of the $(C_1\text{-}C_6)$alkyl; $(C_2\text{-}C_6)$alkenyl; and $(C_2\text{-}C_6)$alkynyl is optionally substituted with one or more $R^{13}$;
each $R^{12}$ is independently selected from the group consisting of OH, $(C_1\text{-}C_3)$alkoxy, NH$_2$; or $(C_1\text{-}C_3)$alkyl optionally substituted with one or more OH;
each $R^{13}$ is independently selected from the group consisting of halo, OH, amino, $(C_1\text{-}C_4)$alkylamino, di$(C_1\text{-}C_4)$alkylamino, $(C_1\text{-}C_3)$alkoxy; and C(O)—$(C_3\text{-}C_8)$cycloalkyl;
m is 0, 1, or 2; and
n is 0, 1 or 2.

Definitions

For the purpose of interpreting this specification, the following definitions will apply unless specified otherwise and when appropriate, terms used in the singular will also include the plural and vice versa. It must be noted that as used herein and in the appended claims, the singular forms "a", "an" and "the" include plural referents unless the context clearly dictates otherwise. Thus, for example, reference to "the compound" includes reference to one or more compounds; and so forth.

As used herein, the term "$(C_1-C_6)$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$(C_1-C_4)$alkyl" is to be construed accordingly. Examples of $(C_1-C_6)$alkyl include, but are not limited to, methyl, ethyl, n-propyl, 1-methylethyl (iso-propyl), n-butyl, n-pentyl and 1,1-dimethylethyl (t-butyl).

As used herein, the term "$(C_2-C_6)$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "$(C_2-C_4)$alkenyl" is to be construed accordingly. Examples of $(C_2-C_6)$alkenyl include, but are not limited to, ethenyl, prop-1-enyl, but-1-enyl, pent-1-enyl, pent-4-enyl and penta-1,4-dienyl.

As used herein, the term "$(C_2-C_6)$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$(C_2-C_4)$alkynyl" is to be construed accordingly. Examples of $(C_2-C_6)$alkynyl include, but are not limited to, ethynyl, prop-1-ynyl, but-1-ynyl, pent-1-ynyl, pent-4-ynyl and penta-1,4-diynyl.

As used herein, the term "$(C_1-C_6)$alkoxy" refers to a radical of the formula —OR, where $R_a$ is a $(C_1-C_6)$alkyl radical as generally defined above. Examples of $(C_1-C_6)$ alkoxy include, but are not limited to, methoxy, ethoxy, propoxy, isopropoxy, butoxy, isobutoxy, pentoxy, and hexoxy.

As used herein, the term "$(C_1-C_6)$alkoxy$(C_1-C_6)$alkyl" refers to a radical of the formula —$R_a$—O—$R_a$ where each $R_a$ is independently a $(C_1-C_6)$alkyl radical as defined above. The oxygen atom may be bonded to any carbon atom in either alkyl radical. Examples of $(C_1-C_6)$alkoxy$(C_1-C_6)$alkyl include, but are not limited to, methoxy-methyl, methoxy-ethyl, ethoxy-ethyl, 1-ethoxy-propyl and 2-methoxy-butyl.

As used herein, the term "$(C_1-C_4)$alkylcarbonyl" refers to a radical of the formula —C(=O)—$R_a$ where $R_a$ is a $(C_1-C_4)$alkyl radical as defined above.

As used herein, the term "$(C_1-C_6)$alkylcarbonyl$(C_1-C_6)$ alkyl" refers to a radical of the formula —$R_a$—C(=O)—$R_a$ where each $R_a$ is independently a $(C_1-C_6)$alkyl radical as defined above. The carbon atom of the carbonyl group may be bonded to any carbon atom in either alkyl radical.

As used herein, the term "$(C_1-C_6)$alkoxycarbonyl" refers to a radical of the formula —C(=O)—O—$R_a$ where $R_a$ is a $(C_1-C_6)$alkyl radical as defined above.

As used herein, the term "$(C_1-C_6)$alkoxycarbonyl$(C_1-C_6)$ alkyl" refers to a radical of the formula —$R_a$—C(=O)—O—$R_a$ where each $R_a$ is independently a $(C_1-C_6)$alkyl radical as defined above.

As used herein, the term "$(C_1-C_4)$alkoxycarbonylamino" refers to a radical of the formula —NH—C(=O)—O—$R_a$ where $R_a$ is a $(C_1-C_4)$alkyl radical as defined above.

As used herein, the term "hydroxy$(C_1-C_6)$alkyl" refers to a $(C_1-C_6)$alkyl radical as defined above, wherein one of the hydrogen atoms of the $C_{1-6}$alkyl radical is replaced by OH. Examples of hydroxy$(C_1-C_6)$alkyl include, but are not limited to, hydroxy-methyl, 2-hydroxy-ethyl, 2-hydroxy-propyl, 3-hydroxy-propyl and 5-hydroxy-pentyl.

As used herein, the term "amino$(C_1-C_6)$alkyl" refers to a $(C_1-C_6)$alkyl radical as defined above, wherein one of the hydrogen atoms of the $(C_1-C_6)$alkyl group is replaced by a primary amino group. Representative examples of amino $(C_1-C_6)$alkyl include, but are not limited to, amino-methyl, 2-amino-ethyl, 2-amino-propyl, 3-amino-propyl, 3-amino-pentyl and 5-amino-pentyl.

As used herein, the term "$(C_1-C_4)$alkylamino" refers to a radical of the formula —NH—$R_a$ where $R_a$ is a $(C_1-C_4)$alkyl radical as defined above.

As used herein, the term "$(C_1-C_4)$alkylamino$(C_1-C_6)$alkyl" refers to a radical of the formula —$R_{a1}$—NH—$R_{a2}$ where $R_{a1}$ is a $(C_1-C_6)$alkyl radical as defined above and $R_{a2}$ is a $(C_1-C_4)$alkyl radical as defined above. The nitrogen atom may be bonded to any carbon atom in either alkyl radical.

As used herein, the term "di$(C_1-C_4)$alkylamino" refers to a radical of the formula —N($R_a$)—$R_a$ where each $R_a$ is a $(C_1-C_4)$alkyl radical, which may be the same or different, as defined above.

As used herein, the term "di$(C_1-C_4)$alkylamino$(C_1-C_6)$ alkyl" refers to a radical of the formula —$R_{a1}$—N($R_{a2}$)—$R_{a2}$ where $R_{a1}$ is a $(C_1-C_6)$alkyl radical as defined above and each $R_{a2}$ is a $(C_1-C_4)$alkyl radical, which may be the same or different, as defined above. The nitrogen atom may be bonded to any carbon atom in any alkyl radical.

As used herein, the term "aminocarbonyl" refers to a radical of the formula —C(=O)—$NH_2$.

As used herein, the term "aminocarbonyl$C_{1-6}$-alkyl" refers to a radical of the formula —$R_a$—C(=O)—$NH_2$ where $R_a$ is a $(C_1-C_6)$alkyl radical as defined above.

As used herein, the term "$(C_1-C_4)$alkylaminocarbonyl" refers to a radical of the formula —C(=O)—NH—$R_a$ where $R_a$ is a $(C_1-C_4)$alkyl radical as defined above.

As used herein, the term "$(C_1-C_4)$alkylaminocarbonyl$C_{1-6}$alkyl" refers to a radical of the formula —$R_{a1}$—C(=O)—NH—$R_{a2}$ where $R_{a1}$ is a $(C_1-C_6)$alkyl radical as defined above and $R_{a2}$ is a $(C_1-C_4)$alkyl radical as defined above.

As used herein, the term "di$(C_1-C_4)$alkylaminocarbonyl" refers to a radical of the formula —C(=O)—N($R_a$)—$R_a$ where each $R_a$ is a $(C_1-C_4)$alkyl radical, which may be the same or different, as defined above.

As used herein, the term "di$(C_1-C_4)$alkylaminocarbonyl$C_{1-6}$alkyl" refers to a radical of the formula —$R_{a1}$—C(=O)—N($R_{a2}$)—$R_{a2}$ where $R_{a1}$ is a $C_{1-6}$-alkyl radical as defined above and each $R_{a2}$ is a $(C_1-C_4)$alkyl radical, which may be the same or different, as defined above.

As used herein, the term "$(C_3-C_8)$cycloalkyl$(C_0-C_6)$alkyl" refers to a stable monocyclic saturated hydrocarbon radical consisting solely of carbon and hydrogen atoms, having from three to eight carbon atoms, and which is attached to the rest of the molecule by a single bond or by a $(C_1-C_6)$alkyl radical as defined above. Examples of $(C_3-C_8)$cycloalkyl$(C_0-C_6)$alkyl include, but are not limited to, cyclopropyl, cyclopropyl-methyl, cyclobutyl, cyclobutyl-ethyl, cyclopentyl, cyclopentyl-propyl, cyclohexyl, cyclohepty and cyclooctyl.

The term "aryl" refers to 6- to 10-membered aromatic carbocyclic moieties having a single (e.g., phenyl) or a fused ring system (e.g., naphthalene). A typical aryl group is phenyl group.

As used herein, the term "phenyl$(C_0-C_6)$alkyl" refers to a phenyl ring attached to the rest of the molecule by a single bond or by a $(C_1-C_6)$alkyl radical as defined above. Examples of phenyl$(C_0-C_6)$alkyl include, but are not limited to, phenyl and benzyl.

As used herein, the term "phenyl$(C_0-C_6)$alkylamino$(C_1-C_6)$alkyl" refers to a radical of the formula $—R_a—NH—R_b$ where $R_a$ is a $(C_1-C_6)$alkyl radical as defined above and $R_b$ is a phenyl$(C_0-C_6)$alkyl radical as defined above.

As used herein, the term "phenyl$(C_0-C_6)$alkylamino$((C_1-C_4)$alkyl) $(C_1-C_6)$alkyl" refers to a radical of the formula $—R_{a1}—N(R_{a2})—R_b$ where $R_{a1}$ is a $(C_1-C_6)$alkyl radical as defined above, $R_{a2}$ is a $(C_1-C_4)$alkyl radical as defined above and $R_b$ is a phenyl$(C_0-C_6)$alkyl radical as defined above.

As used herein, halo refers to bromo, chloro, fluoro or iodo.

As used herein, the term "halo$(C_1-C_6)$alkyl" refers to $(C_1-C_6)$alkyl radical, as defined above, substituted by one or more halo radicals, as defined above. Examples of halogen $(C_1-C_6)$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

The term "heterocyclyl" refers to a saturated or partially saturated, but not aromatic, ring or ring systems, which include a monocyclic ring, fused rings, bridged rings and spirocyclic rings having the specified number of ring atoms. For example, heterocyclyl includes, but not limited to, 5- to 6-membered heterocyclyl, 4- to 10-membered heterocyclyl, 4- to 14-membered heterocyclyl and 5- to 14-membered heterocyclyl. Unless otherwise specified, the heterocyclyl contain 1 to 7, 1 to 5, 1 to 3, or 1 to 2 heteroatoms independently selected from the group consisting of nitrogen, oxygen and sulphur as ring members, where the N and S can also optionally be oxidized to various oxidation states. The heterocyclic group can be attached at a heteroatom or a carbon atom. Examples of such heterocyclyl include, but are not limited to, azetidine, oxetane, piperidine, piperazine, pyrroline, pyrrolidine, imidazolidine, imidazoline, morpholine, tetrahydrofuran, tetrahydrothiophene, tetrahydrothiopyran, tetrahydropyran, 1,4-dioxane, 1,4 oxathiane, hexahydropyrimidinyl, 3-azabicyclo[3.1.0]hexane, azepane, 3-azabicyclo[3.2.2]nonane, decahydroisoquinoline, 2-azaspiro[3.3]heptane, 2-oxa-6-azaspiro[3.3]heptane, 2,6-diazaspiro[3.3]heptane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, 1,4-dioxa-8-aza-spiro[4.5]decane, 3-oxa-1,8-diazaspiro[4.5]decane, octahydropyrrolo[3,2-b]pyrrol, and the like.

The term "fused heterocyclyl" refers to a heterocyclyl, as defined above, which is fused to an aryl (e.g., phenyl) or a heteroaryl ring as defined above. Examples of such fused heterocyclyl include, but are not limited to, 1,2,3,4-tetrahydroisoquinoline, indoline, isoindoline, 1,2,3,4-tetrahydro-2,7-naphthyridine, 5,6,7,8-tetrahydro-1,7-naphthyridine, 1,2,3,4-tetrahydro-2,6-naphthyridine, 5,6,7,8-tetrahydro-1,6-naphthyridine, 2,3,4,5-tetrahydro-1H-benzo[d]azepine, 1,2,3,4-tetrahydro-1,4-epiminonaphthalene, 2,3-dihydrobenzofurane, 5,6,7,8-tetrahydropyrido[3,4-b]pyrazine, and the like. As used herein, the term "heterocyclyl $(C_0-C_6)$alkyl" refers to a heterocyclic ring as defined above which is attached to the rest of the molecule by a single bond or by a $(C_1-C_6)$alkyl radical as defined above.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a hetereoaryl fused to an aryl (e.g., phenyl). As used herein, the term "heteroaryl$(C_0-C_6)$alkyl" refers to a heteroaryl ring as defined above which is attached to the rest of the molecule by a single bond or by a $(C_1-C_6)$alkyl radical as defined above.

Unless specified otherwise, the term "compounds of the present invention" refers to compounds of formula (I), and subformulae thereof, such as compounds of formula (II), (III), and (IV), as defined herein, and salts thereof, as well as all stereoisomers (including diastereoisomers and enantiomers), rotamers, tautomers and isotopically labeled compounds (including deuterium substitutions), as well as inherently formed moieties. The term "compounds of the (present) invention" or "a compound of the (present) invention" refers to a compound as defined in any one of the embodiments mentioned below.

Various embodiments of the invention are described herein, it will be recognized that features specified in each embodiment may be combined with other specified features to provide further embodiments of the present invention.

In embodiment 1, the invention provides a compound of formula (I), or a pharmaceutically acceptable salt thereof, as described above.

In embodiment 2, the invention provides a compound of embodiment 1, wherein $R^4$ is phenyl optionally substituted with one or more $R^6$.

In embodiment 3, the invention provides a compound of embodiment 1, wherein $R^4$ is 5 to 6-membered heteroaryl optionally substituted with one or more $R^6$.

In embodiment 4, the invention provides a compound of embodiment 3, wherein $R^4$ is pyridyl.

In embodiment 5, the invention provides a compound of embodiment 3, wherein $R^4$ is selected from the group consisting of furyl, oxazolyl, pyrazolyl, isoxazolyl, thiophenyl, imidazolyl, and oxadiazolyl.

In embodiment 6, the invention provides a compound of embodiment 2, being of formula (II),

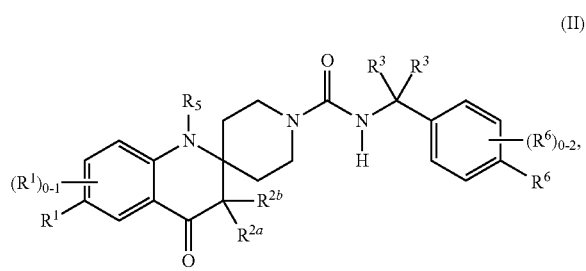

(II)

or a pharmaceutically acceptable salt thereof.

In embodiment 7, the invention provides a compound of embodiment 1, being of formula (III),

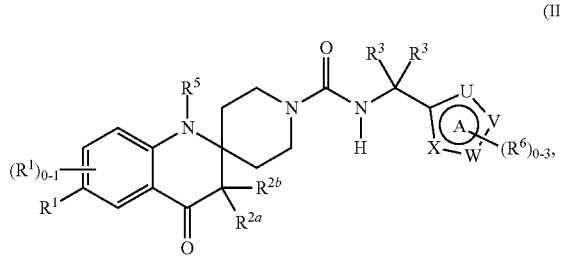

(III)

or a pharmaceutically acceptable salt thereof,
wherein ring A is a 5-membered heteroaryl and
u, v, w, and x are each independently selected from the group CH, O, S, N, and NH, provided that at least one of u, v, w, and x is O, S, N or NH.

In embodiment 8, the invention provides a compound of any one of embodiments 1, 3, 5, or 7, wherein n is 1 or 2; and
$R^4$ is

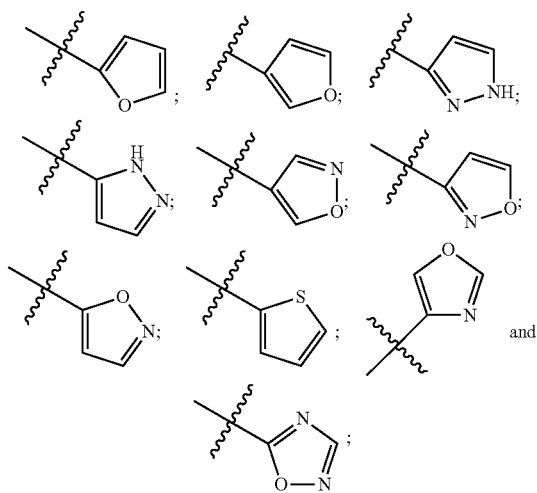

wherein $R^4$ is optionally substituted with one to three $R^6$.

In embodiment 9, the invention provides a compound of any one of embodiments 1-8, wherein n is 1 or 2, and at least one $R^1$ is halo.

In embodiment 10, the invention provides a compound of any one of embodiments 1-9, wherein n is 1 or 2, and at least one $R^1$ is F.

In embodiment 11, the invention provides a compound of any one of embodiments 1-10, wherein n is 1.

In embodiment 12, the invention provides a compound of any one of embodiments 1-11, wherein Z is O.

In embodiment 13, the invention provides a compound of any one of embodiments 1-12, wherein $R^{2a}$ and $R^{2b}$ are each H.

In embodiment 14, the invention provides a compound of any one of embodiments 1-13, wherein $R^5$ is H; $(C_1-C_6)$ alkyl; $(C_2-C_6)$alkenyl; or $(C_0-C_4)$alkylOR$^3$.

In embodiment 15, the invention provides a compound of any one of embodiments 1-14, wherein $R^5$ is H or $(C_1-C_2)$ alkyl.

In embodiment 16, the invention provides a compound of any one of embodiments 1-15, wherein $R^5$ is H.

In embodiment 17, the invention provides a compound of any one of embodiments 1-16, wherein each $R^3$ is H.

In embodiment 18, the invention provides a compound of any one of embodiments 1-17, wherein each $R^3$ is deuterium.

In embodiment 19, the invention provides a compound of any one of embodiments 1-18, wherein each $R^6$ is independently selected from halo and $(C_0-C_4)$alkylN(R$^8$)$_2$.

In embodiment 20, the invention provides a compound of any one of embodiments 1-19, wherein $R^6$ is halo.

In embodiment 21, the invention provides a compound of embodiment 1, wherein the compound is selected from:
6'-fluoro-N-((5-methylfuran-2-yl)methyl)-4'-oxo-3',4'-dihydro-1'H-spiro[piperidine-4,2'-quinoline]-1-carboxamide;
6'-fluoro-N-(4-fluoro-2-methoxybenzyl)-1'-methyl-4'-oxo-3',4'-dihydro-1'H-spiro[piperidine-4,2'-quinoline]-1-carboxamide;
6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide;
4-((6'-fluoro-4'-oxo-3',4'-dihydro-1'H-spiro[piperidine-4,2'-quinoline]-1-carboxamido)methyl)phenyl dihydrogen phosphate;
N-(2,4-difluorobenzyl)-6'-fluoro-1'-methyl-4'-oxo-3',4'-dihydro-1'H-spiro[piperidine-4,2'-quinoline]-1-carboxamide;
1'-ethyl-6'-fluoro-N-(4-fluorobenzyl)-4'-oxo-3',4'-dihydro-1'H-spiro[piperidine-4,2'-quinoline]-1-carboxamide;
6'-fluoro-1'-methyl-N-((5-methylfuran-2-yl)methyl)-4'-oxo-3',4'-dihydro-1'H-spiro[piperidine-4,2'-quinoline]-1-carboxamide;
6'-fluoro-N-(4-fluoro-3-methoxybenzyl)-1'-methyl-4'-oxo-3',4'-dihydro-1'H-spiro[piperidine-4,2'-quinoline]-1-carboxamide;
6'-fluoro-N-(4-fluorobenzyl)-1'-methyl-4'-oxo-3',4'-dihydro-1'H-spiro[piperidine-4,2'-quinoline]-1-carboxamide;
6',8'-difluoro-N-((2-methylfuran-3-yl)methyl)-4'-oxo-3',4'-dihydro-1'H-spiro[piperidine-4,2'-quinoline]-1-carboxamide;
N-(3-carbamoyl-4-fluorobe;nzyl)-6',8'-difluoro-4'-oxo-3',4'-dihydro-1'H-spiro[piperidine-4,2'-quinoline]-1-carboxamide
6'-fluoro-N-((4-fluorophenyl)methyl-d2)-4'-oxo-3',4'-dihydro-1'H-spiro[piperidine-4,2'-quinoline]-1-carboxamide;
N-(3-carbamoyl-4-fluorobenzyl)-1'-ethyl-6'-fluoro-4'-oxo-3',4'-dihydro-1H-spiro[piperidine-4,2'-quinoline]-1-carboxamide;
6'-fluoro-N-(4-fluorobenzyl)-1'-(2-methoxyethyl)-4'-oxo-3',4'-dihydro-1'H-spiro[piperidine-4,2'-quinoline]-1-carboxamide;
6'-fluoro-N-(4-fluoro-3-(oxazol-5-yl)benzyl)-4'-oxo-3',4'-dihydro-1'H-spiro[piperidine-4,2'-quinoline]-1-carboxamide;
N-(2,4-difluorobenzyl)-6'-fluoro-4'-oxo-3',4'-dihydro-1'H-spiro[piperidine-4,2'-quinoline]-1-carboxamide;
N-(2,4-difluoro-5-((2-hydroxyethyl)amino)benzyl)-6'-fluoro-1'-methyl-4'-oxo-3',4'-dihydro-1H-spiro[piperidine-4,2'-quinoline]-1-carboxamide;
N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide;
6'-fluoro-N-(4-fluorobenzyl)-1'-(2-hydroxyethyl)-4'-oxo-3',4'-dihydro-1'H-spiro[piperidine-4,2'-quinoline]-1-carboxamide;

6'-fluoro-N-(4-fluoro-2-((2-methoxyethyl)amino)benzyl)-1'-methyl-4'-oxo-3',4'-dihydro-1H-spiro[piperidine-4,2'-quinoline]-1-carboxamide;

6'-fluoro-N-(4-fluoro-3-((2-methoxyethyl)amino)benzyl)-1'-methyl-4'-oxo-3',4'-dihydro-1H-spiro[piperidine-4,2'-quinoline]-1-carboxamide;

N-((5-chlorofuran-2-yl)methyl)-6'-fluoro-4'-oxo-3',4'-dihydro-1'H-spiro[piperidine-4,2'-quinoline]-1-carboxamide;

6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide;

N-(3-carbamoyl-4-fluorobenzyl)-6'-fluoro-4'-oxo-3',4'-dihydro-1'H-spiro[piperidine-4,2'-quinoline]-1-carboxamide;

1'-ethyl-6'-fluoro-N-(4-fluoro-3-((2-hydroxyethyl)amino)benzyl)-4'-oxo-3',4'-dihydro-1H-spiro[piperidine-4,2'-quinoline]-1-carboxamide;

N-(3-amino-2,4-difluorobenzyl)-1'-ethyl-6'-fluoro-4'-oxo-3',4'-dihydro-1H-spiro[piperidine-4,2'-quinoline]-1-carboxamide;

N-(3-amino-4-fluorobenzyl)-6'-fluoro-1'-methyl-4'-oxo-3',4'-dihydro-1'H-spiro[piperidine-4,2'-quinoline]-1-carboxamide;

2-((2-fluoro-5-(((6'-fluoro-1'-methyl-4'-oxo-3',4'-dihydro-1'H-spiro[piperidine-4,2'-quinoline]-1-carboxamido)methyl)phenyl)amino)ethyl dihydrogen phosphate;

N-(3-amino-4-fluorobenzyl)-1'-ethyl-6'-fluoro-4'-oxo-3',4'-dihydro-1'H-spiro[piperidine-4,2'-quinoline]-1-carboxamide:

6'-fluoro-N-(4-fluoro-3-sulfamoylbenzyl)-4'-oxo-3',4'-dihydro-1'H-spiro[piperidine-4,2'-quinoline]-1-carboxamide;

N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide;

N-benzyl-6'-fluoro-4'-oxo-3',4'-dihydro-1'H-spiro[piperidine-4,2'-quinoline]-1-carboxamide N-((2,4-dimethylfuran-3-yl)methyl)-6'-fluoro-4'-oxo-3',4'-dihydro-1'H-spiro[piperidine-4,2'-quinoline]-1-carboxamide;

6',8'-difluoro-N-(3-(oxazol-5-yl)benzyl)-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-1'-methyl-4'-oxo-3',4'-dihydro-1H-spiro[piperidine-4,2'-quinoline]-1-carboxamide;

N-((1H-pyrazol-4-yl)methyl)-6'-fluoro-4'-oxo-3',4'-dihydro-1'H-spiro[piperidine-4,2'-quinoline]-1-carboxamide;

N-((4-carbamoylfuran-2-yl)methyl)-6',8'-difluoro-4'-oxo-3',4'-dihydro-1'H-spiro[piperidine-4,2'-quinoline]-1-carboxamide;

6'-fluoro-N-(4-hydroxybenzyl)-4'-oxo-3',4'-dihydro-1H-spiro[piperidine-4,2'-quinoline]-1-carboxamide;

6'-fluoro-N-(4-fluorobenzyl)-4'-oxo-3',4'-dihydro-1'H-spiro[piperidine-4,2'-quinoline]-1-carboxamide;

N-(3-carbamoyl-4-fluorobenzyl)-6'-fluoro-1'-methyl-4'-oxo-3',4'-dihydro-1H-spiro[piperidine-4,2'-quinoline]-1-carboxamide;

N-(3-amino-2,4-difluorobenzyl)-6'-fluoro-1'-methyl-4'-oxo-3',4'-dihydro-1H-spiro[piperidine-4,2'-quinoline]-1-carboxamide;

6'-fluoro-N-(4-fluoro-2-hydroxybenzyl)-4'-oxo-3',4'-dihydro-1'H-spiro[piperidine-4,2'-quinoline]-1-carboxamide;

N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

(S)—N-(3-((2,3-dihydroxypropyl)amino)-4-fluorobenzyl)-6'-fluoro-1'-methyl-4'-oxo-3',4'-dihydro-1H-spiro[piperidine-4,2'-quinoline]-1-carboxamide;

6',8'-difluoro-N-(furan-3-ylmethyl)-4'-oxo-3',4'-dihydro-1'H-spiro[piperidine-4,2'-quinoline]-1-carboxamide;

N-((1H-pyrazol-3-yl)methyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-4'-oxo-3',4'-dihydro-1'H-spiro[piperidine-4,2'-quinoline]-1-carboxamide;

N-(4-amino-2,5-difluorobenzyl)-6'-fluoro-4'-oxo-3',4'-dihydro-1'H-spiro[piperidine-4,2'-quinoline]-1-carboxamide;

N-(5-amino-2,4-difluorobenzyl)-1'-ethyl-6'-fluoro-4'-oxo-3',4'-dihydro-1'H-spiro[piperidine-4,2'-quinoline]-1-carboxamide;

6'-fluoro-N-(4-fluoro-2-(2,2,2-trifluoroethoxy)benzyl)-4'-oxo-3',4'-dihydro-1'H-spiro[piperidine-4,2'-quinoline]-1-carboxamide;

N-(2-(ethylamino)-4-fluorobenzyl)-6'-fluoro-1'-methyl-4'-oxo-3',4'-dihydro-1'H-spiro[piperidine-4,2'-quinoline]-1-carboxamide;

N-(benzo[d][1,3]dioxol-4-ylmethyl)-6',8'-difluoro-4'-oxo-3',4'-dihydro-1'H-spiro[piperidine-4,2'-quinoline]-1-carboxamide;

6',8'-difluoro-N-(4-hydroxybenzyl)-4'-oxo-3',4'-dihydro-1'H-spiro[piperidine-4,2'-quinoline]-1-carboxamide;

6'-fluoro-N-(4-fluoro-3-(methylsulfonamido)benzyl)-1'-methyl-4'-oxo-3',4'-dihydro-1'H-spiro[piperidine-4,2'-quinoline]-1-carboxamide;

N-(4-amino-3-fluorobenzyl)-6'-fluoro-4'-oxo-3',4'-dihydro-1'H-spiro[piperidine-4,2'-quinoline]-1-carboxamide;

N-(4-amino-2,3-difluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide;

6'-fluoro-N-((2-methylfuran-3-yl)methyl)-4'-oxo-3',4'-dihydro-1'H-spiro[piperidine-4,2'-quinoline]-1-carboxamide;

6'-fluoro-N-(4-fluoro-3-((3-hydroxycyclobutyl)carbamoyl)benzyl)-4'-oxo-3',4'-dihydro-1'H-spiro[piperidine-4,2'-quinoline]-1-carboxamide;

Methyl 2-fluoro-5-(((6'-fluoro-4'-oxo-3',4'-dihydro-1'H-spiro[piperidine-4,2'-quinoline]-1-carboxamido)methyl)benzoate;

N-(3-(2-amino-2-oxoethyl)-4-fluorobenzyl)-6'-fluoro-1'-methyl-4'-oxo-3',4'-dihydro-1'H-spiro[piperidine-4,2'-quinoline]-1-carboxamide;

6',8'-difluoro-N-((3-hydroxypyridin-2-yl)methyl)-4'-oxo-3',4'-dihydro-1'H-spiro[piperidine-4,2'-quinoline]-1-carboxamide;

6'-fluoro-N-(4-fluoro-3-(methylcarbamoyl)benzyl)-4'-oxo-3',4'-dihydro-1'H-spiro[piperidine-4,2'-quinoline]-1-carboxamide;

N-(4-amino-3,5-difluorobenzyl)-6'-fluoro-4'-oxo-3',4'-dihydro-1'H-spiro[piperidine-4,2'-quinoline]-1-carboxamide;

N-((6-(dimethylamino)pyridin-2-yl)methyl)-6',8'-difluoro-4'-oxo-3',4'-dihydro-1'H-spiro[piperidine-4,2'-quinoline]-1-carboxamide:

6'-fluoro-N-(4-fluoro-2-(trifluoromethyl)benzyl)-4'-oxo-3',4'-dihydro-1'H-spiro[piperidine-4,2'-quinoline]-1-carboxamide;

N-(2-chloro-4-fluorobenzyl)-6'-fluoro-4'-oxo-3',4'-dihydro-1'H-spiro[piperidine-4,2'-quinoline]-1-carboxamide;

N-(3-carbamoylbenzyl)-6'-fluoro-4'-oxo-3',4'-dihydro-1'H-spiro[piperidine-4,2'-quinoline]-1-carboxamide;

6'-fluoro-N-(4-fluoro-3-(2-hydroxyethoxy)benzyl)-4'-oxo-3',4'-dihydro-1'H-spiro[piperidine-4,2'-quinoline]-1-carboxamide;

N-(2,4-difluoro-5-(2-hydroxyethoxy)benzyl)-6'-fluoro-4'-oxo-3',4'-dihydro-1'H-spiro[piperidine-4,2'-quinoline]-1-carboxamide;

6'-fluoro-N-((5-methyl-1H-pyrazol-3-yl)methyl)-4'-oxo-3',4'-dihydro-1'H-spiro[piperidine-4,2'-quinoline]-1-carboxamide;

N-(3-amino-4-fluorobenzyl)-6',8'-difluoro-4'-oxo-3',4'-dihydro-1'H-spiro[piperidine-4,2'-quinoline]-1-carboxamide;

6'-fluoro-4'-oxo-N-(3-sulfamoylbenzyl)-3',4'-dihydro-1'H-spiro[piperidine-4,2'-quinoline]-1-carboxamide;

N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide;

N-(4-aminobenzyl)-6'-fluoro-1'-methyl-4'-oxo-3',4'-dihydro-1'H-spiro[piperidine-4,2'-quinoline]-1-carboxamide;

N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;

N-(3-carbamoyl-4-fluoro-2-methylbenzyl)-6'-fluoro-4'-oxo-3',4'-dihydro-1'H-spiro[piperidine-4,2'-quinoline]-1-carboxamide;

N-(4-amino-2,6-difluorobenzyl)-6'-fluoro-4'-oxo-3',4'-dihydro-1'H-spiro[piperidine-4,2'-quinoline]-1-carboxamide;

N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide;

6'-fluoro-N-(4-fluoro-3-(hydroxymethyl)benzyl)-4'-oxo-3',4'-dihydro-1'H-spiro[piperidine-4,2'-quinoline]-1-carboxamide;

N-(3-amino-2,4-difluorobenzyl)-6'-fluoro-4'-oxo-3',4'-dihydro-1'H-spiro[piperidine-4,2'-quinoline]-1-carboxamide;

(E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide;

6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide;

N-(4-amino-3-chlorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(4-aminobenzyl)-6'-fluoro-4'-oxo-3',4'-dihydro-1'H-spiro[piperidine-4,2'-quinoline]-1-carboxamide;

6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide;

N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-(1-hydroxyethyl)benzyl)-1'-methyl-4'-oxo-3',4'-dihydro-1'H-spiro[piperidine-4,2'-quinoline]-1-carboxamide;

N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide;

(R)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(3-amino-4-fluorobenzyl)-6'-fluoro-4'-oxo-3',4'-dihydro-1'H-spiro[piperidine-4,2'-quinoline]-1-carboxamide;

6'-fluoro-4'-oxo-N-((2-(trifluoromethyl)furan-3-yl)methyl)-3',4'-dihydro-1'H-spiro[piperidine-4,2'-quinoline]-1-carboxamide;

6'-fluoro-N-(4-fluoro-3-((2-hydroxy-2-methylpropyl)carbamoyl)benzyl)-1'-methyl-4'-oxo-3',4'-dihydro-1'H-spiro[piperidine-4,2'-quinoline]-1-carboxamide;

N-(4-amino-2-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)amino)benzyl)-4'-oxo-3',4'-dihydro-1'H-spiro[piperidine-4,2'-quinoline]-1-carboxamide;

N-(3-((2-cyclopropyl-2-oxoethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2,2,2-trifluoroethyl)carbamoyl)benzyl)-4'-oxo-3',4'-dihydro-1'H-spiro[piperidine-4,2'-quinoline]-1-carboxamide;

6'-fluoro-N-(4-fluoro-3-(3-methoxyazetidin-1-yl)benzyl)-4'-oxo-3',4'-dihydro-1'H-spiro[piperidine-4,2'-quinoline]-1-carboxamide:

N-(3-(2-amino-2-oxoethyl)-4-fluorobenzyl)-6'-fluoro-4'-oxo-3',4'-dihydro-1H-spiro[piperidine-4,2'-quinoline]-1-carboxamide;

N-(4-amino-2-(trifluoromethyl)benzyl)-6'-fluoro-4'-oxo-3',4'-dihydro-1'H-spiro[piperidine-4,2'-quinoline]-1-carboxamide;

6'-fluoro-N-(4-fluoro-3-(oxetan-3-ylcarbamoyl)benzyl)-4'-oxo-3',4'-dihydro-1H-spiro[piperidine-4,2'-quinoline]-1-carboxamide;

N-((3-ethyl-5-methylisoxazol-4-yl)methyl)-6'-fluoro-4'-oxo-3',4'-dihydro-1H-spiro[piperidine-4,2'-quinoline]-1-carboxamide;

6'-fluoro-N-(isoxazol-4-ylmethyl)-4'-oxo-3',4'-dihydro-1'H-spiro[piperidine-4,2'-quinoline]-1-carboxamide;

N-(4-(difluoromethoxy)-3-fluorobenzyl)-6',8'-difluoro-4'-oxo-3',4'-dihydro-1H-spiro[piperidine-4,2'-quinoline]-1-carboxamide;

N-(3-carbamoyl-2,4-difluorobenzyl)-6'-fluoro-4'-oxo-3',4'-dihydro-1'H-spiro[piperidine-4,2'-quinoline]-1-carboxamide;

N-((2,5-dimethylfuran-3-yl)methyl)-6'-fluoro-4'-oxo-3',4'-dihydro-1'H-spiro[piperidine-4,2'-quinoline]-1-carboxamide;

N-(4-amino-2-chlorobenzyl)-6'-fluoro-4'-oxo-3',4'-dihydro-1'H-spiro[piperidine-4,2'-quinoline]-1-carboxamide;

N-(4-amino-3-(trifluoromethyl)benzyl)-6'-fluoro-4'-oxo-3',4'-dihydro-1'H-spiro[piperidine-4,2'-quinoline]-1-carboxamide;

N-(3-((2,2-dimethyl-3-morpholino-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-2-methoxybenzyl)-4'-oxo-3',4'-dihydro-1'H-spiro[piperidine-4,2'-quinoline]-1-carboxamide;

6',8'-difluoro-N-((2-methoxypyridin-4-yl)methyl)-4'-oxo-3',4'-dihydro-1H-spiro[piperidine-4,2'-quinoline]-1-carboxamide;

N-(4-amino-2-methylbenzyl)-6'-fluoro-4'-oxo-3',4'-dihydro-1'H-spiro[piperidine-4,2'-quinoline]-1-carboxamide;

(S)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

6'-fluoro-N-(isoxazol-3-ylmethyl)-4'-oxo-3',4'-dihydro-1'H-spiro[piperidine-4,2'-quinoline]-1-carboxamide;

N-(4-amino-3-methylbenzyl)-6'-fluoro-4'-oxo-3',4'-dihydro-1'H-spiro[piperidine-4,2'-quinoline]-1-carboxamide;

N-((1H-indol-6-yl)methyl)-6'-fluoro-4'-oxo-3',4'-dihydro-1'H-spiro[piperidine-4,2'-quinoline]-1-carboxamide;

6'-fluoro-N-(4-fluoro-3-(((2-methyloxazol-5-yl)methyl)carbamoyl)benzyl)-4'-oxo-3',4'-dihydro-1'H-spiro[piperidine-4,2'-quinoline]-1-carboxamide;

(E)-6'-fluoro-N-(4-fluoro-3-((4-hydroxybut-2-en-1-yl)carbamoyl)benzyl)-4'-oxo-3',4'-dihydro-1'H-spiro[piperidine-4,2'-quinoline]-1-carboxamide;

6',8'-difluoro-N-((5-methylthiophen-2-yl)methyl)-4'-oxo-3',4'-dihydro-1'H-spiro[piperidine-4,2'-quinoline]-1-carboxamide;

6'-fluoro-N-(isoxazol-5-ylmethyl)-4'-oxo-3',4'-dihydro-1'H-spiro[piperidine-4,2'-quinoline]-1-carboxamide;

6',8'-difluoro-N-((6-fluoropyridin-3-yl)methyl)-4'-oxo-3',4'-dihydro-1'H-spiro[piperidine-4,2'-quinoline]-1-carboxamide;

N-(5-amino-2,4-difluorobenzyl)-6'-fluoro-4'-oxo-3',4'-dihydro-1'H-spiro[piperidine-4,2'-quinoline]-1-carboxamide;

6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide;

6'-fluoro-N-(4-fluoro-3-(prop-2-yn-1-ylcarbamoyl)benzyl)-4'-oxo-3',4'-dihydro-1'H-spiro[piperidine-4,2'-quinoline]-1-carboxamide;

6',8'-difluoro-N-(3-(hydroxymethyl)benzyl)-4'-oxo-3',4'-dihydro-1'H-spiro[piperidine-4,2'-quinoline]-1-carboxamide;

N-(3-(1H-imidazol-2-yl)benzyl)-6'-fluoro-4'-oxo-3',4'-dihydro-1'H-spiro[piperidine-4,2'-quinoline]-1-carboxamide;

6'-fluoro-N-(4-fluoro-3-(methylsulfonamido)benzyl)-4'-oxo-3',4'-dihydro-1'H-spiro[piperidine-4,2'-quinoline]-1-carboxamide;

6',8'-difluoro-N-(4-fluoro-3-(hydroxymethyl)benzyl)-4'-oxo-3',4'-dihydro-1'H-spiro[piperidine-4,2'-quinoline]-1-carboxamide;

N-(3-(cyclopropanesulfonamido)-4-fluorobenzyl)-6'-fluoro-4'-oxo-3',4'-dihydro-1'H-spiro[piperidine-4,2'-quinoline]-1-carboxamide;

6'-fluoro-N-((3-methyl-1,2,4-oxadiazol-5-yl)methyl)-4'-oxo-3',4'-dihydro-1'H-spiro[piperidine-4,2'-quinoline]-1-carboxamide;

6'-fluoro-N-(4-fluoro-3-(1-hydroxyethyl)benzyl)-4'-oxo-3',4'-dihydro-1'H-spiro[piperidine-4,2'-quinoline]-1-carboxamide;

N-((6-aminopyridin-3-yl)methyl)-6'-fluoro-4'-oxo-3',4'-dihydro-1'H-spiro[piperidine-4,2'-quinoline]-1-carboxamide;

N-(2-amino-4-fluorobenzyl)-6'-fluoro-4'-oxo-3',4'-dihydro-1'H-spiro[piperidine-4,2'-quinoline]-1-carboxamide;

6'-fluoro-N-(oxazol-4-ylmethyl)-4'-oxo-3',4'-dihydro-1'H-spiro[piperidine-4,2'-quinoline]-1-carboxamide;

6'-fluoro-N-(4-fluoro-3-(2-hydroxypropan-2-yl)benzyl)-1'-methyl-4'-oxo-3',4'-dihydro-1'H-spiro[piperidine-4,2'-quinoline]-1-carboxamide;

3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoic acid;

N-(benzo[c][1,2,5]oxadiazol-4-ylmethyl)-6'-fluoro-4'-oxo-3',4'-dihydro-1'H-spiro[piperidine-4,2'-quinoline]-1-carboxamide;

N-(3-carbamoyl-4-fluorobenzyl)-6'-fluoro-8'-methyl-4'-oxo-3',4'-dihydro-1'H-spiro[piperidine-4,2'-quinoline]-1-carboxamide;

6'-fluoro-N-(4-fluoro-3-(propylcarbamoyl)benzyl)-4'-oxo-3',4'-dihydro-1'H-spiro[piperidine-4,2'-quinoline]-1-carboxamide;

N-(3-(1H-1,2,4-triazol-1-yl)benzyl)-6',8'-difluoro-4'-oxo-3',4'-dihydro-1'H-spiro[piperidine-4,2'-quinoline]-1-carboxamide;

6'-fluoro-N-((1-methyl-1H-pyrazol-4-yl)methyl)-4'-oxo-3',4'-dihydro-1'H-spiro[piperidine-4,2'-quinoline]-1-carboxamide;

6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide;

6'-fluoro-N-(4-fluoro-3-(sulfamoylmethyl)benzyl)-4'-oxo-3',4'-dihydro-1'H-spiro[piperidine-4,2'-quinoline]-1-carboxamide;

3-((2-fluoro-5-((6'-fluoro-1'-methyl-4'-oxo-3',4'-dihydro-1'H-spiro[piperidine-4,2'-quinoline]-1-carboxamido)methyl)phenyl)amino)propanoic acid;

(R)—N-(3-(1-amino-2,2,2-trifluoroethyl)-4-fluorobenzyl)-6'-fluoro-1'-methyl-4'-oxo-3',4'-dihydro-1'H-spiro[piperidine-4,2'-quinoline]-1-carboxamide;

N-(4-(difluoromethoxy)benzyl)-6',8'-difluoro-4'-oxo-3',4'-dihydro-1'H-spiro[piperidine-4,2'-quinoline]-1-carboxamide;

(R)-6'-fluoro-N-(4-fluorobenzyl)-4'-hydroxy-1'-methyl-3',4'-dihydro-1'H-spiro[piperidine-4,2'-quinoline]-1-carboxamide;

(S)-6'-fluoro-N-(4-fluorobenzyl)-4'-hydroxy-1'-methyl-3',4'-dihydro-1'H-spiro[piperidine-4,2'-quinoline]-1-carboxamide;

(R)-6'-fluoro-N-(4-fluorobenzyl)-4'-hydroxy-3',4'-dihydro-1'H-spiro[piperidine-4,2'-quinoline]-1-carboxamide;

(S)-6'-fluoro-N-(4-fluorobenzyl)-4'-hydroxy-3',4'-dihydro-1'H-spiro[piperidine-4,2'-quinoline]-1-carboxamide;

(R)-6'-fluoro-N-(4-fluoro-2-hydroxybenzyl)-4'-hydroxy-3',4'-dihydro-1'H-spiro[piperidine-4,2'-quinoline]-1-carboxamide;

(S)-6'-fluoro-N-(4-fluoro-2-hydroxybenzyl)-4'-hydroxy-3',4'-dihydro-1'H-spiro[piperidine-4,2'-quinoline]-1-carboxamide N-(3-carbamoyl-4-fluorobenzyl)-6'-fluoro-4'-hydroxy-1'-methyl-3',4'-dihydro-1'H-spiro[piperidine-4,2'-quinoline]-1-carboxamide;

N-(2,4-difluoro-5-((2-hydroxyethyl)amino)benzyl)-6'-fluoro-4'-hydroxy-1'-methyl-3',4'-dihydro-1'H-spiro[piperidine-4,2'-quinoline]-1-carboxamide;

N-(3-carbamoyl-4-fluorobenzyl)-6',8'-difluoro-4'-hydroxy-3',4'-dihydro-1'H-spiro[piperidine-4,2'-quinoline]-1-carboxamide;
N-(3-amino-4-fluorobenzyl)-6'-fluoro-4'-hydroxy-3',4'-dihydro-1'H-spiro[piperidine-4,2'-quinoline]-1-carboxamide;
6'-fluoro-N-(4-fluoro-3-(hydroxymethyl)benzyl)-4'-hydroxy-3',4'-dihydro-1'H-spiro[piperidine-4,2'-quinoline]-1-carboxamide;
N-(3-carbamoyl-4-fluorobenzyl)-6'-fluoro-4'-hydroxy-3',4'-dihydro-1'H-spiro[piperidine-4,2'-quinoline]-1-carboxamide;
N-(3-(2-amino-2-oxoethyl)-4-fluorobenzyl)-6'-fluoro-4'-hydroxy-1'-methyl-3',4'-dihydro-1'H-spiro[piperidine-4,2'-quinoline]-1-carboxamide;
6'-fluoro-N-(4-fluoro-3-((3-hydroxycyclobutyl)carbamoyl)benzyl)-4'-hydroxy-3',4'-dihydro-1'H-spiro[piperidine-4,2'-quinoline]-1-carboxamide;
6'-fluoro-N-(4-fluoro-3-(2-hydroxyethoxy)benzyl)-4'-hydroxy-1'-methyl-3',4'-dihydro-1'H-spiro[piperidine-4,2'-quinoline]-1-carboxamide;
6'-fluoro-N-(4-fluoro-3-(methylsulfonamido)benzyl)-4'-hydroxy-3',4'-dihydro-1'H-spiro[piperidine-4,2'-quinoline]-1-carboxamide;
6'-fluoro-N-(4-fluoro-3-((2-hydroxyethyl)amino)benzyl)-4'-hydroxy-1'-methyl-3',4'-dihydro-1'H-spiro[piperidine-4,2'-quinoline]-1-carboxamide;
6'-fluoro-N-(4-fluoro-2-((2-methoxyethyl)amino)benzyl)-4'-hydroxy-1'-methyl-3',4'-dihydro-1'H-spiro[piperidine-4,2'-quinoline]-1-carboxamide;
N-(3-((R)-1-amino-2,2,2-trifluoroethyl)-4-fluorobenzyl)-6'-fluoro-4'-hydroxy-1'-methyl-3',4'-dihydro-1'H-spiro[piperidine-4,2'-quinoline]-1-carboxamide;
6'-fluoro-N-(4-fluoro-2-methoxybenzyl)-4'-hydroxy-3',4'-dihydro-1'H-spiro[piperidine-4,2'-quinoline]-1-carboxamide;
(R)-6'-fluoro-4'-hydroxy-N-((2-methylfuran-3-yl)methyl)-3',4'-dihydro-1'H-spiro[piperidine-4,2'-quinoline]-1-carboxamide;
(R)—N-(4-amino-3-fluorobenzyl)-6'-fluoro-4'-hydroxy-3',4'-dihydro-1'H-spiro[piperidine-4,2'-quinoline]-1-carboxamide; and
(S)—N-(4-amino-3-fluorobenzyl)-6'-fluoro-4'-hydroxy-3',4'-dihydro-1'H-spiro[piperidine-4,2'-quinoline]-1-carboxamide;
or a pharmaceutically acceptable salt thereof.

In embodiment 22, the invention provides a compound of embodiment 2, wherein the compound is selected from:
6'-fluoro-N-(4-fluoro-2-methoxybenzyl)-1'-methyl-4'-oxo-3',4'-dihydro-1'H-spiro[piperidine-4,2'-quinoline]-1-carboxamide;
6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide;
4-((6'-fluoro-4'-oxo-3',4'-dihydro-1'H-spiro[piperidine-4,2'-quinoline]-1-carboxamido)methyl)phenyl dihydrogen phosphate;
N-(2,4-difluorobenzyl)-6'-fluoro-1'-methyl-4'-oxo-3',4'-dihydro-1'H-spiro[piperidine-4,2'-quinoline]-1-carboxamide;
1'-ethyl-6'-fluoro-N-(4-fluorobenzyl)-4'-oxo-3',4'-dihydro-1'H-spiro[piperidine-4,2'-quinoline]-1-carboxamide;
6'-fluoro-N-(4-fluoro-3-methoxybenzyl)-1'-methyl-4'-oxo-3',4'-dihydro-1'H-spiro[piperidine-4,2'-quinoline]-1-carboxamide;
6'-fluoro-N-(4-fluorobenzyl)-1'-methyl-4'-oxo-3',4'-dihydro-1'H-spiro[piperidine-4,2'-quinoline]-1-carboxamide;
N-(3-carbamoyl-4-fluorobenzyl)-6',8'-difluoro-4'-oxo-3',4'-dihydro-1'H-spiro[piperidine-4,2'-quinoline]-1-carboxamide;
6'-fluoro-N-((4-fluorophenyl)methyl-d2)-4'-oxo-3',4'-dihydro-1'H-spiro[piperidine-4,2'-quinoline]-1-carboxamide;
N-(3-carbamoyl-4-fluorobenzyl)-1'-ethyl-6'-fluoro-4'-oxo-3',4'-dihydro-1'H-spiro[piperidine-4,2'-quinoline]-1-carboxamide;
6'-fluoro-N-(4-fluorobenzyl)-1'-(2-methoxyethyl)-4'-oxo-3',4'-dihydro-1'H-spiro[piperidine-4,2'-quinoline]-1-carboxamide;
6'-fluoro-N-(4-fluoro-3-(oxazol-5-yl)benzyl)-4'-oxo-3',4'-dihydro-1'H-spiro[piperidine-4,2'-quinoline]-1-carboxamide;
N-(2,4-difluorobenzyl)-6'-fluoro-4'-oxo-3',4'-dihydro-1'H-spiro[piperidine-4,2'-quinoline]-1-carboxamide;
N-(2,4-difluoro-5-((2-hydroxyethyl)amino)benzyl)-6'-fluoro-1'-methyl-4'-oxo-3',4'-dihydro-1'H-spiro[piperidine-4,2'-quinoline]-1-carboxamide;
N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide;
6'-fluoro-N-(4-fluorobenzyl)-1'-(2-hydroxyethyl)-4'-oxo-3',4'-dihydro-1'H-spiro[piperidine-4,2'-quinoline]-1-carboxamide:
6'-fluoro-N-(4-fluoro-2-((2-methoxyethyl)amino)benzyl)-1'-methyl-4'-oxo-3',4'-dihydro-1'H-spiro[piperidine-4,2'-quinoline]-1-carboxamide;
6'-fluoro-N-(4-fluoro-3-((2-methoxyethyl)amino)benzyl)-1'-methyl-4'-oxo-3',4'-dihydro-1'H-spiro[piperidine-4,2'-quinoline]-1-carboxamide;
6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide;
N-(3-carbamoyl-4-fluorobenzyl)-6'-fluoro-4'-oxo-3',4'-dihydro-1'H-spiro[piperidine-4,2'-quinoline]-1-carboxamide;
1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;
N-(3-amino-2,4-difluorobenzyl)-1'-ethyl-6'-fluoro-4'-oxo-3',4'-dihydro-1'H-spiro[piperidine-4,2'-quinoline]-1-carboxamide;
N-(3-amino-4-fluorobenzyl)-6'-fluoro-1'-methyl-4'-oxo-3',4'-dihydro-1'H-spiro[piperidine-4,2'-quinoline]-1-carboxamide;
2-((2-fluoro-5-((6'-fluoro-1'-methyl-4'-oxo-3',4'-dihydro-1'H-spiro[piperidine-4,2'-quinoline]-1-carboxamido)methyl)phenyl)amino)ethyl dihydrogen phosphate;
N-(3-amino-4-fluorobenzyl)-1'-ethyl-6'-fluoro-4'-oxo-3',4'-dihydro-1'H-spiro[piperidine-4,2'-quinoline]-1-carboxamide;
6'-fluoro-N-(4-fluoro-3-sulfamoylbenzyl)-4'-oxo-3',4'-dihydro-1'H-spiro[piperidine-4,2'-quinoline]-1-carboxamide;
N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide;
6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide;
N-benzyl-6'-fluoro-4'-oxo-3',4'-dihydro-1'H-spiro[piperidine-4,2'-quinoline]-1-carboxamide;

6',8'-difluoro-N-(3-(oxazol-5-yl)benzyl)-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide;

6'-fluoro-N-(4-hydroxybenzyl)-4'-oxo-3',4'-dihydro-1'H-spiro[piperidine-4,2'-quinoline]-1-carboxamide;

6'-fluoro-N-(4-fluorobenzyl)-4'-oxo-3',4'-dihydro-1'H-spiro[piperidine-4,2'-quinoline]-1-carboxamide;

N-(3-carbamoyl-4-fluorobenzyl)-6'-fluoro-1'-methyl-4'-oxo-3',4'-dihydro-1'H-spiro[piperidine-4,2'-quinoline]-1-carboxamide;

N-(3-amino-2,4-difluorobenzyl)-6'-fluoro-1'-methyl-4'-oxo-3',4'-dihydro-1'H-spiro[piperidine-4,2'-quinoline]-1-carboxamide:

6'-fluoro-N-(4-fluoro-2-hydroxybenzyl)-4'-oxo-3',4'-dihydro-1'H-spiro[piperidine-4,2'-quinoline]-1-carboxamide;

N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

(S)—N-(3-((2,3-dihydroxypropyl)amino)-4-fluorobenzyl)-6'-fluoro-1'-methyl-4'-oxo-3',4'-dihydro-1H-spiro[piperidine-4,2'-quinoline]-1-carboxamide;

6'-fluoro-N-(4-fluoro-3-((2-hydroxyethyl)carbamoyl)benzyl)-4'-oxo-3',4'-dihydro-1H-spiro[piperidine-4,2'-quinoline]-1-carboxamide;

N-(4-amino-2,5-difluorobenzyl)-6'-fluoro-4'-oxo-3',4'-dihydro-1'H-spiro[piperidine-4,2'-quinoline]-1-carboxamide;

N-(5-amino-2,4-difluorobenzyl)-1'-ethyl-6'-fluoro-4'-oxo-3',4'-dihydro-1H-spiro[piperidine-4,2'-quinoline]-1-carboxamide;

6'-fluoro-N-(4-fluoro-2-(2,2,2-trifluoroethoxy)benzyl)-4'-oxo-3',4'-dihydro-1H-spiro[piperidine-4,2'-quinoline]-1-carboxamide;

N-(2-(ethylamino)-4-fluorobenzyl)-6'-fluoro-1'-methyl-4'-oxo-3',4'-dihydro-1H-spiro[piperidine-4,2'-quinoline]-1-carboxamide;

N-(benzo[d][1,3]dioxol-4-ylmethyl)-6',8'-difluoro-4'-oxo-3',4'-dihydro-1H-spiro[piperidine-4,2'-quinoline]-1-carboxamide;

6',8'-difluoro-N-(4-hydroxybenzyl)-4'-oxo-3',4'-dihydro-1'H-spiro[piperidine-4,2'-quinoline]-1-carboxamide;

6'-fluoro-N-(4-fluoro-3-(methylsulfonamido)benzyl)-1'-methyl-4'-oxo-3',4'-dihydro-1H-spiro[piperidine-4,2'-quinoline]-1-carboxamide;

N-(4-amino-3-fluorobenzyl)-6'-fluoro-4'-oxo-3',4'-dihydro-1'H-spiro[piperidine-4,2'-quinoline]-1-carboxamide;

N-(4-amino-2,3-difluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)carbamoyl)benzyl)-1'-methyl-4'-oxo-3',4'-dihydro-1H-spiro[piperidine-4,2'-quinoline]-1-carboxamide;

6'-fluoro-N-(4-fluoro-3-((3-hydroxycyclobutyl)carbamoyl)benzyl)-4'-oxo-3',4'-dihydro-1H-spiro[piperidine-4,2'-quinoline]-1-carboxamide;

methyl 2-fluoro-5-(((6'-fluoro-4'-oxo-3',4'-dihydro-1'H-spiro[piperidine-4,2'-quinoline]-1-carboxamido)methyl)benzoate;

N-(3-(2-amino-2-oxoethyl)-4-fluorobenzyl)-6'-fluoro-1'-methyl-4'-oxo-3',4'-dihydro-1H-spiro[piperidine-4,2'-quinoline]-1-carboxamide;

6'-fluoro-N-(4-fluoro-3-(methylcarbamoyl)benzyl)-4'-oxo-3',4'-dihydro-1H-spiro[piperidine-4,2'-quinoline]-1-carboxamide:

N-(4-amino-3,5-difluorobenzyl)-6'-fluoro-4'-oxo-3',4'-dihydro-1'H-spiro[piperidine-4,2'-quinoline]-1-carboxamide;

6'-fluoro-N-(4-fluoro-2-(trifluoromethyl)benzyl)-4'-oxo-3',4'-dihydro-1'H-spiro[piperidine-4,2'-quinoline]-1-carboxamide;

N-(2-chloro-4-fluorobenzyl)-6'-fluoro-4'-oxo-3',4'-dihydro-1'H-spiro[piperidine-4,2'-quinoline]-1-carboxamide;

N-(3-carbamoylbenzyl)-6'-fluoro-4'-oxo-3',4'-dihydro-1'H-spiro[piperidine-4,2'-quinoline]-1-carboxamide;

6'-fluoro-N-(4-fluoro-3-(2-hydroxyethoxy)benzyl)-4'-oxo-3',4'-dihydro-1'H-spiro[piperidine-4,2'-quinoline]-1-carboxamide;

N-(2,4-difluoro-5-(2-hydroxyethoxy)benzyl)-6'-fluoro-4'-oxo-3',4'-dihydro-1'H-spiro[piperidine-4,2'-quinoline]-1-carboxamide;

N-(3-amino-4-fluorobenzyl)-6',8'-difluoro-4'-oxo-3',4'-dihydro-1'H-spiro[piperidine-4,2'-quinoline]-1-carboxamide;

6'-fluoro-4'-oxo-N-(3-sulfamoylbenzyl)-3',4'-dihydro-1'H-spiro[piperidine-4,2'-quinoline]-1-carboxamide;

N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide;

N-(4-aminobenzyl)-6'-fluoro-1'-methyl-4'-oxo-3',4'-dihydro-1'H-spiro[piperidine-4,2'-quinoline]-1-carboxamide;

N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;

N-(3-carbamoyl-4-fluoro-2-methylbenzyl)-6'-fluoro-4'-oxo-3',4'-dihydro-1'H-spiro[piperidine-4,2'-quinoline]-1-carboxamide;

N-(4-amino-2,6-difluorobenzyl)-6'-fluoro-4'-oxo-3',4'-dihydro-1'H-spiro[piperidine-4,2'-quinoline]-1-carboxamide;

N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide;

6'-fluoro-N-(4-fluoro-3-(hydroxymethyl)benzyl)-4'-oxo-3',4'-dihydro-1'H-spiro[piperidine-4,2'-quinoline]-1-carboxamide;

N-(3-amino-2,4-difluorobenzyl)-6'-fluoro-4'-oxo-3',4'-dihydro-1'H-spiro[piperidine-4,2'-quinoline]-1-carboxamide:

(E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide;

6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide;

N-(4-amino-3-chlorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(4-aminobenzyl)-6'-fluoro-4'-oxo-3',4'-dihydro-1'H-spiro[piperidine-4,2'-quinoline]-1-carboxamide;

6'-fluoro-N-(4-fluoro-3-((2-(2-oxopyrrolidin-1-yl)ethyl)
amino)benzyl)-1'-methyl-4'-oxo-3',4'-dihydro-1'H-spiro
[piperidine-4,2'-quinoline]-1-carboxamide;

N-(2,4-difluoro-3-((2-hydroxyethyl)amino)benzyl)-6'-
fluoro-1'-methyl-4'-oxo-3',4'-dihydro-1'H-spiro[piperi-
dine-4,2'-quinoline]-1-carboxamide;

6'-fluoro-N-(4-fluoro-3-(1-hydroxyethyl)benzyl)-1'-methyl-
4'-oxo-3',4'-dihydro-1'H-spiro[piperidine-4,2'-quinoline]-
1-carboxamide;

(R)-6'-fluoro-N-(4-fluoro-3-((2-hydroxypropyl)carbamoyl)
benzyl)-1'-methyl-4'-oxo-3',4'-dihydro-1'H-spiro[piperi-
dine-4,2'-quinoline]-1-carboxamide;

N-(3-amino-4-fluorobenzyl)-6'-fluoro-4'-oxo-3',4'-dihydro-
1'H-spiro[piperidine-4,2'-quinoline]-1-carboxamide;

6'-fluoro-N-(4-fluoro-3-((2-hydroxy-2-methylpropyl)car-
bamoyl)benzyl)-1'-methyl-4'-oxo-3',4'-dihydro-1'H-spiro
[piperidine-4,2'-quinoline]-1-carboxamide;

N-(4-amino-2-fluorobenzyl)-6'-fluoro-4'-oxo-3',4'-dihydro-
1'H-spiro[piperidine-4,2'-quinoline]-1-carboxamide;

6'-fluoro-N-(4-fluoro-3-((2-methoxyethyl)amino)benzyl)-
4'-oxo-3',4'-dihydro-1'H-spiro[piperidine-4,2'-quinoline]-
1-carboxamide;

N-(3-((2-cyclopropyl-2-oxoethyl)carbamoyl)-4-fluoroben-
zyl)-6'-fluoro-4'-oxo-3',4'-dihydro-1'H-spiro[piperidine-
4,2'-quinoline]-1-carboxamide;

6'-fluoro-N-(4-fluoro-3-((2,2,2-trifluoroethyl)carbamoyl)
benzyl)-4'-oxo-3',4'-dihydro-1'H-spiro[piperidine-4,2'-
quinoline]-1-carboxamide;

6'-fluoro-N-(4-fluoro-3-(3-methoxyazetidin-1-yl)benzyl)-
4'-oxo-3',4'-dihydro-1'H-spiro[piperidine-4,2'-quinoline]-
1-carboxamide;

N-(3-(2-amino-2-oxoethyl)-4-fluorobenzyl)-6'-fluoro-4'-
oxo-3',4'-dihydro-1'H-spiro[piperidine-4,2'-quinoline]-1-
carboxamide;

N-(4-amino-2-(trifluoromethyl)benzyl)-6'-fluoro-4'-oxo-3',
4'-dihydro-1'H-spiro[piperidine-4,2'-quinoline]-1-carbox-
amide:

6'-fluoro-N-(4-fluoro-3-(oxetan-3-ylcarbamoyl)benzyl)-4'-
oxo-3',4'-dihydro-1H-spiro[piperidine-4,2'-quinoline]-1-
carboxamide;

N-(4-(difluoromethoxy)-3-fluorobenzyl)-6',8'-difluoro-4'-
oxo-3',4'-dihydro-1H-spiro[piperidine-4,2'-quinoline]-1-
carboxamide;

N-(3-carbamoyl-2,4-difluorobenzyl)-6'-fluoro-4'-oxo-3',4'-
dihydro-1'H-spiro[piperidine-4,2'-quinoline]-1-carbox-
amide;

N-(4-amino-2-chlorobenzyl)-6'-fluoro-4'-oxo-3',4'-dihydro-
1'H-spiro[piperidine-4,2'-quinoline]-1-carboxamide;

N-(4-amino-3-(trifluoromethyl)benzyl)-6'-fluoro-4'-oxo-3',
4'-dihydro-1'H-spiro[piperidine-4,2'-quinoline]-1-carbox-
amide;

N-(3-((2,2-dimethyl-3-morpholino-3-oxopropyl)amino)-4-
fluorobenzyl)-6'-fluoro-1'-methyl-4'-oxo-3',4'-dihydro-
1'H-spiro[piperidine-4,2'-quinoline]-1-carboxamide;

6'-fluoro-N-(4-fluoro-2-methoxybenzyl)-4'-oxo-3',4'-di-
hydro-1'H-spiro[piperidine-4,2'-quinoline]-1-carboxam-
ide;

N-(4-amino-2-methylbenzyl)-6'-fluoro-4'-oxo-3',4'-di-
hydro-1'H-spiro[piperidine-4,2'-quinoline]-1-carboxam-
ide;

(S)-6'-fluoro-N-(4-fluoro-3-((2-hydroxypropyl)carbamoyl)
benzyl)-1'-methyl-4'-oxo-3',4'-dihydro-1'H-spiro[piperi-
dine-4,2'-quinoline]-1-carboxamide;

N-(4-amino-3-methylbenzyl)-6'-fluoro-4'-oxo-3',4'-di-
hydro-1'H-spiro[piperidine-4,2'-quinoline]-1-carboxam-
ide;

6'-fluoro-N-(4-fluoro-3-(((2-methyloxazol-5-yl)methyl)car-
bamoyl)benzyl)-4'-oxo-3',4'-dihydro-1'H-spiro[piperi-
dine-4,2'-quinoline]-1-carboxamide;

(E)-6'-fluoro-N-(4-fluoro-3-((4-hydroxybut-2-en-1-yl)car-
bamoyl)benzyl)-4'-oxo-3',4'-dihydro-1'H-spiro[piperi-
dine-4,2'-quinoline]-1-carboxamide;

N-(5-amino-2,4-difluorobenzyl)-6'-fluoro-4'-oxo-3',4'-di-
hydro-1'H-spiro[piperidine-4,2'-quinoline]-1-carboxam-
ide;

6'-fluoro-N-(4-fluoro-3-(prop-2-yn-1-ylcarbamoyl)benzyl)-
4'-oxo-3',4'-dihydro-1H-spiro[piperidine-4,2'-quinoline]-
1-carboxamide;

6',8'-difluoro-N-(3-(hydroxymethyl)benzyl)-4'-oxo-3',4'-di-
hydro-1'H-spiro[piperidine-4,2'-quinoline]-1-carboxam-
ide;

N-(3-(1H-imidazol-2-yl)benzyl)-6'-fluoro-4'-oxo-3',4'-di-
hydro-1'H-spiro[piperidine-4,2'-quinoline]-1-carboxam-
ide;

6'-fluoro-N-(4-fluoro-3-(methylsulfonamido)benzyl)-4'-
oxo-3',4'-dihydro-1'H-spiro[piperidine-4,2'-quinoline]-1-
carboxamide;

6',8'-difluoro-N-(4-fluoro-3-(hydroxymethyl)benzyl)-4'-
oxo-3',4'-dihydro-1'H-spiro[piperidine-4,2'-quinoline]-1-
carboxamide:

N-(3-(cyclopropanesulfonamido)-4-fluorobenzyl)-6'-fluoro-
4'-oxo-3',4'-dihydro-1'H-spiro[piperidine-4,2'-quinoline]-
1-carboxamide;

6'-fluoro-N-(4-fluoro-3-(1-hydroxyethyl)benzyl)-4'-oxo-3',
4'-dihydro-1'H-spiro[piperidine-4,2'-quinoline]-1-carbox-
amide;

N-(2-amino-4-fluorobenzyl)-6'-fluoro-4'-oxo-3',4'-dihydro-
1'H-spiro[piperidine-4,2'-quinoline]-1-carboxamide;

6'-fluoro-N-(4-fluoro-3-(2-hydroxypropan-2-yl)benzyl)-1'-
methyl-4'-oxo-3',4'-dihydro-1'H-spiro[piperidine-4,2'-
quinoline]-1-carboxamide;

3-((2-fluoro-5-((6'-fluoro-1'-methyl-4'-oxo-3',4'-dihydro-
1'H-spiro[piperidine-4,2'-quinoline]-1-carboxamido)
methyl)phenyl)amino)-2,2-dimethylpropanoic acid;

N-(3-carbamoyl-4-fluorobenzyl)-6'-fluoro-8'-methyl-4'-
oxo-3',4'-dihydro-1'H-spiro[piperidine-4,2'-quinoline]-1-
carboxamide;

6'-fluoro-N-(4-fluoro-3-(propylcarbamoyl)benzyl)-4'-oxo-
3',4'-dihydro-1'H-spiro[piperidine-4,2'-quinoline]-1-car-
boxamide;

N-(3-(1H-1,2,4-triazol-1-yl)benzyl)-6',8'-difluoro-4'-oxo-3',
4'-dihydro-1'H-spiro[piperidine-4,2'-quinoline]-1-carbox-
amide;

6'-fluoro-N-(4-fluoro-3-(((2-hydroxyethyl)amino)methyl)
benzyl)-4'-oxo-3',4'-dihydro-1'H-spiro[piperidine-4,2'-
quinoline]-1-carboxamide;

6'-fluoro-N-(4-fluoro-3-(sulfamoylmethyl)benzyl)-4'-oxo-
3',4'-dihydro-1'H-spiro[piperidine-4,2'-quinoline]-1-car-
boxamide;

R)—N-(3-(1-amino-2,2,2-trifluoroethyl)-4-fluorobenzyl)-
6'-fluoro-1'-methyl-4'-oxo-3',4'-dihydro-1'H-spiro[piperi-
dine-4,2'-quinoline]-1-carboxamide; and N-(4-(difluoromethoxy)benzyl)-6',8'-difluoro-4'-oxo-3',4'-
dihydro-1'H-spiro[piperidine-4,2'-quinoline]-1-carbox-
amide;

or a pharmaceutically acceptable salt thereof.

In embodiment 23, the invention provides a compound of embodiment 5, wherein the compound is selected from:

6'-fluoro-N-((5-methylfuran-2-yl)methyl)-4'-oxo-3',4'-di-
hydro-1'H-spiro[piperidine-4,2'-quinoline]-1-carboxam-
ide;

6'-fluoro-1'-methyl-N-((5-methylfuran-2-yl)methyl)-4'-oxo-3',4'-dihydro-1'H-spiro[piperidine-4,2'-quinoline]-1-carboxamide;

6',8'-difluoro-N-((2-methylfuran-3-yl)methyl)-4'-oxo-3',4'-dihydro-1'H-spiro[piperidine-4,2'-quinoline]-1-carboxamide:

N-((5-chlorofuran-2-yl)methyl)-6'-fluoro-4'-oxo-3',4'-dihydro-1'H-spiro[piperidine-4,2'-quinoline]-1-carboxamide;

N-((2,4-dimethylfuran-3-yl)methyl)-6'-fluoro-4'-oxo-3',4'-dihydro-1'H-spiro[piperidine-4,2'-quinoline]-1-carboxamide;

N-((1H-pyrazol-4-yl)methyl)-6'-fluoro-4'-oxo-3',4'-dihydro-1'H-spiro[piperidine-4,2'-quinoline]-1-carboxamide;

N-((4-carbamoylfuran-2-yl)methyl)-6',8'-difluoro-4'-oxo-3',4'-dihydro-1H-spiro[piperidine-4,2'-quinoline]-1-carboxamide;

6',8'-difluoro-N-(furan-3-ylmethyl)-4'-oxo-3',4'-dihydro-1'H-spiro[piperidine-4,2'-quinoline]-1-carboxamide;

N-((1H-pyrazol-3-yl)methyl)-6'-fluoro-4'-oxo-3',4'-dihydro-1'H-spiro[piperidine-4,2'-quinoline]-1-carboxamide;

6'-fluoro-N-((2-methylfuran-3-yl)methyl)-4'-oxo-3',4'-dihydro-1'H-spiro[piperidine-4,2'-quinoline]-1-carboxamide;

6',8'-difluoro-N-((3-hydroxypyridin-2-yl)methyl)-4'-oxo-3',4'-dihydro-1H-spiro[piperidine-4,2'-quinoline]-1-carboxamide;

N-((6-(dimethylamino)pyridin-2-yl)methyl)-6',8'-difluoro-4'-oxo-3',4'-dihydro-1H-spiro[piperidine-4,2'-quinoline]-1-carboxamide;

6'-fluoro-N-((5-methyl-1H-pyrazol-3-yl)methyl)-4'-oxo-3',4'-dihydro-1'H-spiro[piperidine-4,2'-quinoline]-1-carboxamide;

N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide;

6'-fluoro-4'-oxo-N-((2-(trifluoromethyl)furan-3-yl)methyl)-3',4'-dihydro-1'H-spiro[piperidine-4,2'-quinoline]-1-carboxamide;

N-((3-ethyl-5-methylisoxazol-4-yl)methyl)-6'-fluoro-4'-oxo-3',4'-dihydro-1'H-spiro[piperidine-4,2'-quinoline]-1-carboxamide;

6'-fluoro-N-(isoxazol-4-ylmethyl)-4'-oxo-3',4'-dihydro-1'H-spiro[piperidine-4,2'-quinoline]-1-carboxamide;

N-((2,5-dimethylfuran-3-yl)methyl)-6'-fluoro-4'-oxo-3',4'-dihydro-1'H-spiro[piperidine-4,2'-quinoline]-1-carboxamide;

6',8'-difluoro-N-((2-methoxypyridin-4-yl)methyl)-4'-oxo-3',4'-dihydro-1'H-spiro[piperidine-4,2'-quinoline]-1-carboxamide;

6'-fluoro-N-(isoxazol-3-ylmethyl)-4'-oxo-3',4'-dihydro-1'H-spiro[piperidine-4,2'-quinoline]-1-carboxamide;

N-((1H-indol-6-yl)methyl)-6'-fluoro-4'-oxo-3',4'-dihydro-1'H-spiro[piperidine-4,2'-quinoline]-1-carboxamide;

6',8'-difluoro-N-((5-methylthiophen-2-yl)methyl)-4'-oxo-3',4'-dihydro-1'H-spiro[piperidine-4,2'-quinoline]-1-carboxamide;

6'-fluoro-N-(isoxazol-5-ylmethyl)-4'-oxo-3',4'-dihydro-1'H-spiro[piperidine-4,2'-quinoline]-1-carboxamide;

6',8'-difluoro-N-((6-fluoropyridin-3-yl)methyl)-4'-oxo-3',4'-dihydro-1'H-spiro[piperidine-4,2'-quinoline]-1-carboxamide;

6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide;

6'-fluoro-N-((3-methyl-1,2,4-oxadiazol-5-yl)methyl)-4'-oxo-3',4'-dihydro-1'H-spiro[piperidine-4,2'-quinoline]-1-carboxamide;

N-((6-aminopyridin-3-yl)methyl)-6'-fluoro-4'-oxo-3',4'-dihydro-1'H-spiro[piperidine-4,2'-quinoline]-1-carboxamide;

6'-fluoro-N-(oxazol-4-ylmethyl)-4'-oxo-3',4'-dihydro-1'H-spiro[piperidine-4,2'-quinoline]-1-carboxamide;

N-(benzo[c][1,2,5]oxadiazol-4-ylmethyl)-6'-fluoro-4'-oxo-3',4'-dihydro-1'H-spiro[piperidine-4,2'-quinoline]-1-carboxamide; and 6'-fluoro-N-((1-methyl-1H-pyrazol-4-yl)methyl)-4'-oxo-3',4'-dihydro-1'H-spiro[piperidine-4,2'-quinoline]-1-carboxamide;

or a pharmaceutically acceptable salt thereof.

In embodiment 24, the invention provides a pharmaceutical composition comprising a compound according to any one of embodiments 1 to 23, and one or more pharmaceutically acceptable carriers.

In embodiment 25, the invention provides a pharmaceutical combination comprising a compound of any one of embodiments 1 to 23, or a pharmaceutically acceptable salt thereof, and one or more therapeutic agents.

In embodiment 26, the invention provides a compound according to any one of embodiments 1 to 23, for use as a medicament, in particular for treating, or preventing an KARS mediated disease or condition.

In embodiment 27, the invention provides a compound according to any one of embodiments 1 to 23, for use in the treatment, or prevention of cancer, wherein the method comprises administering to the subject the compound of formulae (I) to (III), or a pharmaceutically acceptable salt thereof, according to any one of embodiments 1 to 7.

In embodiment 28, the invention provides a compound according to embodiment 23, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS), wherein the method comprises administering to the subject the compound of formulae (I) to (III), or a pharmaceutically acceptable salt thereof, according to any one of embodiments 1 to 7.

In embodiment 29, the invention provides a compound according to embodiment 28, wherein the non-small cell lung cancer (NSCLC) is selected from adenocarcinoma, squamous cell carcinoma, large cell carcinoma, large cell neuroendocrine carcinoma, adenosquamous carcinoma, and sarcomatoid carcinoma.

In embodiment 30, the invention provides a compound according to any one of embodiments 1 to 23, for use in the treatment, or prevention of cancer with genetic or epigenetic alteration in the genes NFE2 L2, KEAP1, CUL3, AKR1C3, or any other condition resulting in the activation of NRF2 transcriptional activity or AKR1C3 gene expression.

In embodiment 31, the invention provides a compound according to any embodiments 1 to 23, for use in the treatment, or prevention of cancer with an AKR1C3 overexpression that is higher than a predetermined value.

Depending on the choice of the starting materials and procedures, the compounds can be present in the form of one of the possible stereoisomers, or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be (E) or (Z) configuration. If the compound contains a disubstituted cycloalkyl, the cycloalkyl substituent may have a cis- or trans-configuration. All tautomeric forms are also intended to be included.

As used herein, the terms "salt" or "salts" refer to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of any one of formulae (I) to (IV), according to any one of embodiments 1 to 5, in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of any one of formulae (I) to (IV), in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I, respectively. Accordingly, it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by KARS, or (ii) disease sensitive to KARS inhibition, or (iii) characterized by activity (normal or abnormal) of KARS; or (2) reduce or inhibit disease sensitive to KARS inhibition. The invention further provides methods of treating, or preventing diseases and/or disorders related to high AKR1C3 expression or sensitivity to KARS inhibition, comprising administering to a subject in need thereof an effective amount of an AKR1C3 dependent KARS inhibitor.

As used herein, the term "subject" refers to primates (e.g., humans, male or female), monkeys, dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically, or in quality of life from such treatment.

As used herein, the term "a", "an", "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates, or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic compound may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) using a chiral adsorbent.

Method of Synthesizing the Compounds of the Invention

The compounds of the present invention may be prepared in accordance to the definition of compound of formula (I), by the routes described in the following Schemes or the Examples. All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed.

In the following general methods, $R_1$, $R_2$, $R_3$, $R_4$, $R_5$, $R_6$, are defined as above, or limited to designations in the Schemes. Unless otherwise stated, starting materials are either commercially available or are prepared by known methods.

General Synthetic Schemes

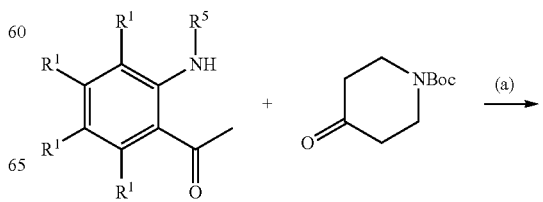

Scheme 1

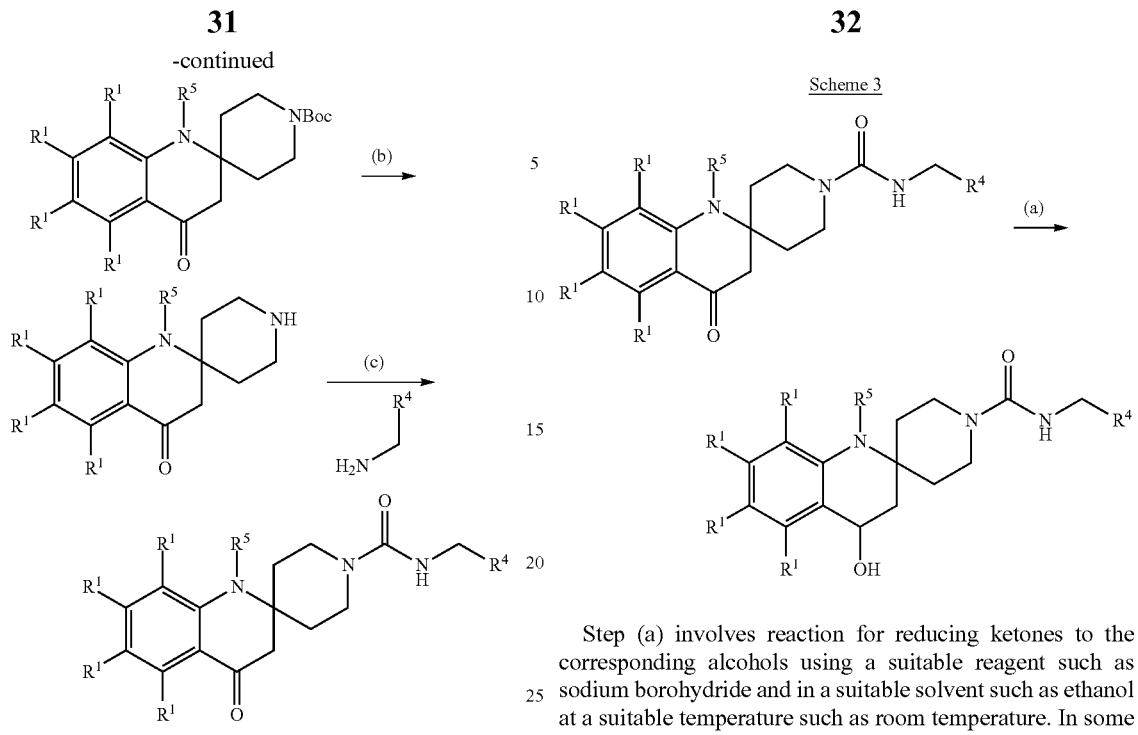

Step (a) involves condensation reaction of substituted aniline and N-Boc-4-oxopiperidine in the presence of pyrrolidine in a suitable solvent such as DMSO at a suitable temperature such as 140° C. Step (b) involves removal of N-protecting groups such as Boc and PMB group using reagents such as TFA in a suitable solvent such as DCM at room temperature. Step (c) involves formation of urea with primary amines using reagents such as CDI or triphosgene in a suitable solvent such as DMF and MeCN and base such as Hunig base at room temperature. Optionally, after step (c), the substituents of $R^4$ groups can be further transformed into new substituents by methods such as reductive amination, alkylation, sulfonylation, phosphorylation, O-deprotection, ester hydrolysis, and amidation.

Scheme 2

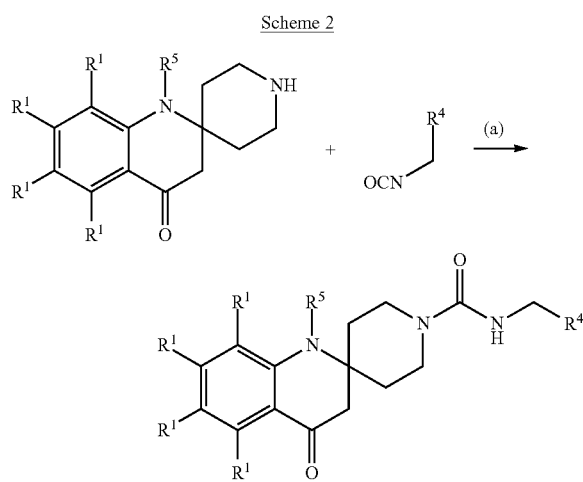

Step (a) involves reaction of spiro-piperidine compound and substituted isocyanate in a suitable solvent such as THF at a suitable temperature such as room temperature.

Step (a) involves reaction for reducing ketones to the corresponding alcohols using a suitable reagent such as sodium borohydride and in a suitable solvent such as ethanol at a suitable temperature such as room temperature. In some cases, enantiomers of the alcohols were separated by chromatography using chiral column.

Compounds of this embodiment are useful in the preparation of compounds of the invention, e.g., compounds of formulae (I) to (IV), or a pharmaceutically acceptable salt thereof.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Method of Use of the Invention

The compounds of any one of formulae (I) to (III) in free form or in pharmaceutically acceptable salt form, exhibit valuable pharmacological properties, e.g. IL-17 modulating properties, e.g. as indicated in in vitro tests as provided in the next sections, and are therefore indicated for therapy or for use as research chemicals, e.g. as tool compounds.

Compounds of the invention may be useful in the treatment, or prevention of cancer, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach, castration-resistant prostate cancer (CRPC), T-cell acute lymphoblastic leukemia (T-ALL), acute myeloid leukemia (AML), and myelodysplastic syndrome (MDS).

Thus, as a further aspect, the present invention provides the use of a compound of formula (I), (II), or (III), or a compound according to any of the preceding embodiments (i.e. according to embodiment 1 to 9e), or a pharmaceutically acceptable salt thereof, in therapy. In a further embodiment, the therapy is selected from a disease, which may be treated by an AKR1C3 dependent KARS inhibitor. In another embodiment, the disease is selected from the afore-mentioned list, suitably from cancer, in particular wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS).

Thus, as a further aspect, the present invention provides a compound of any one of formulae (I) to (III), or a compound according to any one of the preceding embodiments (i.e. according to any one of embodiments 1 to 9e), or a pharmaceutically acceptable salt thereof, for use in therapy. In a further embodiment, the therapy is selected from a disease which may be treated by an AKR1C3 dependent KARS inhibitor. In another embodiment, the disease is selected from the afore-mentioned list, suitably from cancer, in particular wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS).

In another aspect, the invention provides a method of treating, or preventing a disease which is treated by an AKR1C3 dependent KARS inhibitor comprising administration of a compound of any one of formulae (I) to (IV), or a compound according to any one of the preceding embodiments (i.e. according to any one of embodiments 1 to 5, or a pharmaceutically acceptable salt thereof. In a further embodiment, the disease is selected from the afore-mentioned list, suitably from cancer, in particular, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS).

Thus, as a further aspect, the present invention provides the use of a compound of any one of formulae (I) to (IV), or a compound according to any one of the preceding embodiments (i.e. according to any one of embodiments 1 to 5, or a pharmaceutically acceptable salt thereof, for the manufacture of a medicament. In a further embodiment, the medicament is for treatment, or prevention of a disease, which may be treated by an AKR1C3 dependent KARS inhibitor. In another embodiment, the disease is selected from the afore-mentioned list, suitably from cancer in particular, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS).

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable using in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^4$ molar and 10-9 molar concentrations. A therapeutically effective amount in vivo may range depending on the route of administration, between about 0.1-500 mg/kg, or between about 1-100 mg/kg.

Combination Product and Combination Therapy of the Invention

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g. powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before, or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I), (II), (III) or (IV), or a compound according to any one of the preceding embodiments (i.e. according to any one of embodiments 1 to 5, or a pharmaceutically acceptable salt thereof, and at least one other therapeutic agent as a combined preparation for simultaneous, separate or sequential use in therapy.

In one embodiment, the therapy is the treatment, or prevention of a disease or condition mediated by an AKR1C3 dependent KARS inhibitor. Products provided as a combined preparation include a composition comprising the compound of any one of formulae (I) to (IV), or a pharmaceutically acceptable salt thereof, and the other therapeutic agent(s) together in the same pharmaceutical composition, or the compound of any one of formulae (I) to (IV), or a pharmaceutically acceptable salt thereof, and the other therapeutic agent(s) in separate form, e.g. in the form of a kit.

In one embodiment, the invention provides a pharmaceutical combination comprising a compound of any one of formulae (I) to (IV), or a compound according to any one of the preceding embodiments (i.e. according to any one of embodiments 1 to 5, or a pharmaceutically acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any one of formulae (I) to (IV), or a compound according to any one of the preceding embodiments (i.e. according to any one of embodiments 1 to 5, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formulae (I) to (IV), or a compound according to any one of the preceding embodiments (i.e. according to any one of embodiments 1 to 5, or a pharmaceutically acceptable salt thereof, for treating, or preventing a disease or condition mediated by an AKR1C3 dependent KARS inhibitor, wherein the medicament is prepared for administration with another therapeutic agent. The invention also provides the use of another therapeutic agent for treating, or preventing a disease or condition mediated by an AKR1C3 dependent KARS inhibitor wherein the medicament is administered with a compound of any one of formulae (I) to (IV), or a pharmaceutically acceptable salt thereof.

The invention also provides a compound of any one of formulae (I) to (IV), or a compound according to any one of the preceding embodiments (i.e. according to any one of embodiments 1 to 5, or a pharmaceutically acceptable salt thereof, for use in a method of treating, or preventing a disease or condition mediated by an AKR1C3 dependent KARS inhibitor, wherein the compound of formula (I), (II), (III), or (IV), or a compound according to any one of the preceding embodiments (i.e. according to any one of embodiments 1 to 5, or a pharmaceutically acceptable salt thereof, is prepared for administration with another therapeutic agent. The invention also provides another therapeutic agent for use in a method of treating, or preventing a disease or condition mediated by AKR1C3 dependent KARS inhibitor, wherein the other therapeutic agent is prepared for administration with a compound of formula (I), (II), (III), or (IV), or a compound according to any one of the preceding embodiments (i.e. according to any one of embodiments 1 to 5, or a pharmaceutically acceptable salt thereof. The invention also provides a compound of formula (I), (II), (III), or (IV), or a compound according to any one of the preceding embodiments (i.e. according to any one of embodiments 1 to 5, or a pharmaceutically acceptable salt thereof, for use in a method of treating, or preventing a disease or condition mediated by an AKR1C3 dependent KARS inhibitor, wherein the compound of formula (I), (II), (III), or (IV), or a compound according to any one of the preceding embodiments (i.e. according to any one of embodiments 1 to 5, or a pharmaceutically acceptable salt thereof, is administered with another therapeutic agent. The invention also provides another therapeutic agent for use in a method of treating, or preventing a disease or condition mediated by AKR1C3 dependent KARS inhibitor, wherein the other therapeutic agent is administered with a compound of formula (I), (II), (III), or (IV), or a compound according to any one of the preceding embodiments (i.e. according to any one of embodiments 1 to 5, or a pharmaceutically acceptable salt thereof.

The invention also provides the use of a compound of any one of formulae (I) to (IV), or a compound according to any one of the preceding embodiments (i.e. according to any one of embodiments 1 to 5, or a pharmaceutically acceptable salt thereof, for treating, or preventing a disease or condition mediated by AKR1C3, wherein the patient has previously (e.g. within 24 hours) been treated with another therapeutic agent. The invention also provides the use of another therapeutic agent for treating a disease or condition mediated by an AKR1C3 dependent KARS inhibitor, wherein the patient has previously (e.g. within 24 hours) been treated with a compound of formula (I), (II), (III) or (IV), or a compound according to any one of the preceding embodiments (i.e. according to any one of embodiments 1 to 5, or a pharmaceutically acceptable salt thereof.

EXAMPLES

Exemplification of the Invention

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) Protective Groups in Organic Synthesis, 5th edition, John Wiley & Sons). These groups are removed at a convenient stage of the compound synthesis using methods that are readily apparent to those skilled in the art. Unless otherwise noted, reagents and solvents were used as received from commercial suppliers.

The chemical names were generated using ChemBioDraw Ultra from CambridgeSoft.

Temperatures are given in degrees Celsius. As used herein, unless specified otherwise, the term "room temperature" or "ambient temperature" means a temperature of from 15° C. to 30° C., such as of from 20° C. to 30° C., such as of from 20° C. to 25° C. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

Ac acetyl
ACN acetonitrile
AIBN azobisisobutyronitrile
app apparent
ATP adenosine 5-triphosphate
BINAP racemic 2,2'-bis(diphenylphosphino)-1,1'-binaphthyl
BOC tertiary butyl carboxy
br broad
BSA bovine serum albumin
Bu butyl
Cbz carbobenzyloxy
CDI carbonyldiimidazole
d doublet
DAST diethylaminosulfur trifluoride
dd doublet of doublets
ddd doublet of doublet of dublets
DCE dichloroethane
DCM dichloromethane
DDQ 2,3-Dichloro-5,6-dicyano-1,4-benzoquinone
DIPEA diisopropylethylamine
DMA dimethylacetamide
DMAP 4-dimethylaminopyridine
DME 1,4-dimethoxyethane
DMF N,N-dimethylformamide
DMSO dimethylsulfoxide
dppf 1,1-Bis(diphenylphosphino)ferrocene
dt doublet of triplets
EDTA ethylenediamine tetraacetic acid
ESI electrospray ionization
Et ethyl
EtOAc ethyl acetate
h hour(s)
HATU 1-[bis(dimethylamino)methylene]-1H-1,2,3-triazolo[4,5-b]pyridinium 3-oxid hexafluorophosphate
HBTU 1-[bis(dimethylamino)methylene]-1H-benzotriazoliumhexafluorophosphate(1-) 3-oxide
HOBt 1-hydroxy-7-azabenzotriazole
HPLC high pressure liquid chromatography
HRMS high resolution mass spectrometry
LAH lithium aluminum hydride
LCMS liquid chromatography and mass spectrometry
LHMDS lithium hexamethyldisilazide
MeCN acetonitrile MeOH methanol
MHz mega hertz
MTBE methyl t-butyl ether
MS mass spectrometry
m multiplet
mg milligram
min minutes
ml milliliter
mmol millimol
m/z mass to charge ratio
NBS N-bromosuccinimide
NCS N-chlorosuccinimide
NMR nuclear magnetic resonance
P para
PdCl$_2$(dppf)-CH$_2$Cl$_2$ 1,1'-Bis(diphenylphosphino)ferrocene-palladium(II)dichloride dichloromethane complex
Pd(OAc)$_2$ Palladium(II) acetate
Pd/C palladium on carbon
Ph phenyl
PMB para-methoxybenzyl
ppm parts per million
PyBOP benzotriazol-1-yloxytripyrrolidinophosphonium hexafluorophosphate
q quartet
rac racemic
RBF round bottom flask
Rt retention time
RT room temperature
s singlet
sat. saturated
SCX Strong cation exchange sorbent column
SEM [2-(trimethylsilyl)ethoxy]methyl
SFC supercritical fluid chromatography
t triplet
TBAF tetrabutylammonium fluoride
TBDMS t-butyldimethylsilyl
TBDPS t-butyldiphenylsilyl
TBME methyl tert-butyl ether
tBu tertiary butyl
td triplet of doublets
tdt triplet of doublet of triplets
TEA triethylamine
tert tertiary
TFA trifluoroacetic acid
THF tetrahydrofuran
TLC thin layer chromatography
TMS trimethylsilyl
Tris.HCl aminotris(hydroxymethyl)methane hydrochloride
Analytical Details
Instrumentation
LCMS Methods Employed in Characterization of Examples
LCMS data were recorded using Agilent 1100 HPLC systems with Waters Micromass ZQ, or Waters ACQUITY UPLC with Waters SQ detector or with Waters ACQUITY Qda detector. The methods used to acquire all LCMS data are described below.
LCMS Method 1
Column Sunfire C18 3.0×30 mm, 3.5 μm
Column Temperature 40° C.
Eluents A: H$_2$O containing 0.05% TFA, B: MeCN
Flow Rate 2.0 mL/min
Gradient 5% to 95% B in 1.7 min, 0.3 min 95% B
LCMS Method 2
Column XBridge C18 3.0×30 mm, 3.5 μm
Column Temperature 40° C.
Eluents A: H$_2$O+5 mM ammonium hydroxide, B: MeCN
Flow Rate 2.0 mL/min
Gradient 5% to 95% B in 1.7 min, 0.3 min 95% B
LCMS Method 3
Column AcQuity UPLC BEH C18 2.1×30 mm, 1.7 μm
Column Temperature 50° C.
Eluents A: 0.1% formic acid in water, B: 0.1% formic acid in MeCN
Flow Rate 1.0 mL/min
Gradient 2% to 98% B in 1.5 min, 0.3 min 98% B
LCMS Method 4
Column AcQuity UPLC BEH C18 2.1×50 mm, 1.7 μm
Column Temperature 50° C.
Eluents A: 5 mM NH$_4$OH in water, B: 5 mM NH$_4$OH in MeCN
Flow Rate 1.0 mL/min
Gradient 2% to 98% B in 1.5 min, 0.3 min 98% B
LCMS Method 5
Column AcQuity UPLC BEH C18 2.1×30 mm, 1.7 μm
Column Temperature 50° C.
Eluents A: 0.1% formic acid in water, B: 0.1% formic acid in MeCN
Flow Rate 1.0 mL/min
Gradient 40% to 98% B in 1.4 min, 0.65 min 98% B
LCMS Method 6
Column AcQuity UPLC BEH C18 2.1×30 mm, 1.7 μm
Column Temperature 50° C.
Eluents A: 5 mM NH$_4$OH in water, B: 5 mM NH$_4$OH in MeCN
Flow Rate 1.0 mL/min
Gradient 1% to 30% B in 1.2 min, 30% to 98% B in 0.95 min
LCMS Method 7
Column Sunfire C18 3.0×30 mm, 3.5 μm
Column Temperature 40° C.
Eluents A: H$_2$O containing 0.05% TFA, B: MeCN
Flow Rate 2.0 mL/min
Gradient 40% to 85% B in 1.7 min, 0.3 min 95% B
LCMS Method 8
Column XBridge C18 3.0×30 mm, 3.5 μm
Column Temperature 40° C.
Eluents A: H$_2$O+5 mM ammonium hydroxide, B: MeCN
Flow Rate 2.0 mL/min
Gradient 1% to 30% B in 1.2 min, 30% to 95% B in 0.65 min, 0.15 min 95% B
LCMS Method 9
Column Acquity HSS T3 1.8 μm 2.1×50 mm
Column Temperature 60° C.
Eluents A: H$_2$O+0.05% ammonium formic acid+3.75 mM ammonium acetate, B: MeCN+0.04% formic acid
Flow Rate 1.0 mL/min
Gradient 5% to 98% B in 1.4 min
NMR Employed in Characterization of Examples
$^1$H NMR spectra were obtained with Bruker Fourier transform spectrometers operating at frequencies as follows: $^1$H NMR: 400 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.50 ppm for CD$_3$SOCD$_3$, 3.31 ppm for CD$_3$OD, 1.94 for CD$_3$CN, 4.79 for D$_2$O, 5.32 for CD$_2$Cl$_2$, and 7.26 ppm for CDCl$_3$.
Methods Employed in the Purification of the Examples
Purification of intermediates and final products was carried out via either normal, reverse phase chromatography or supercritical fluid chromatography (SFC). Normal phase chromatography was carried out using prepacked SiO$_2$ cartridges (e.g., RediSep® Rf columns from Teledyne Isco, Inc.) eluting with gradients of appropriate solvent systems (e.g., heptane and ethyl acetate; DCM and MeOH; or unless otherwise indicated). Reverse phase preparative HPLC was carried out using the methods described below or unless otherwise indicated in the experimental section:
  (1) Basic method: XBridge 5 µm column, 5 mM NH$_4$OH in acetonitrile and Water.
  (2) TFA method: Sunfire 5 µm column, 0.1% TFA in acetonitrile and Water.
  (3) Formic acid method: XBridge 5 µm column; 0.1% formic acid in acetonitrile and Water.

All of the above three HPLC methods run a focused gradient from the starting % acetonitrile to the final % acetonitrile. The Initial and Final conditions for each gradient are as follows: Method 0: 2-12% acetonitrile; Method 1: 7.5-20% acetonitrile; Method 2: 10-30% acetonitrile; Method 3: 15-40% acetonitrile; Method 4: 25-50% acetonitrile; Method 5: 35-60% acetonitrile; Method 6: 45-70% acetonitrile; Method 7: 55-80% acetonitrile; Method 8: 65-95% acetonitrile; Method 9: 5-95% acetonitrile; and Method 10: 10-90% acetonitrile.

Supercritical fluid chromatography (SFC) was carried out using varying columns and gradients/mobile phases (specified in the experimental sections with 'column name and mobile phase') all with the same flow rate (80 g per minute), mass triggered collection, oven temperature 40° C., back pressure 120 bar parameters.

Chiral preparative SFC was used for separation of alcohol enantiomers, using conditions below.
  Column AD-H 21×250 mm
  Column Temperature 40° C.
  Eluent Ethanol with 10 mM NH$_4$OH
  Flow Rate 80 mL/min
  Backpressure 125 bar Synthesis of the Intermediates Intermediate 1: (5-methylfuran-2-yl)methanamine

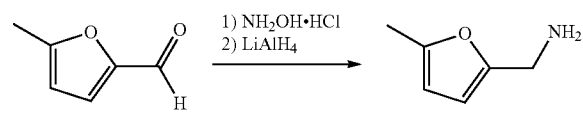

A solution of 5-methyl-2-furaldehyde (1.5 g, 14 mmol), hydroxyamine. HCl salt (1.89 g, 27.2 mmol), and sodium acetate (2.24 g, 27.2 mmol) in MeOH (20 mL) was stirred at RT for 18 h. The starting material was consumed, and two new peaks were observed in 1:1 ratio (LCMS: m/z for the product was not observed). The mixture was poured into sat. aqueous NaHCO$_3$ and extracted with EtOAc (3×100 mL). The combined organic extract was combined, dried with Na$_2$SO$_4$, filtered, and volatiles were removed in vacuo. The crude residue was purified by silica gel chromatography (EtOAc/Heptane) to give the oxime intermediate (1.49 g) as a white solid in ~1:1 Z/E isomers. $^1$H NMR (400 MHz, DMSO-d$_6$) δ $^1$H NMR (400 MHz, DMSO-d$_6$) (two sets of signals) δ 11.66 (s, 1H), 11.07 (s, 1H), 7.92 (s, 1H), 7.44 (s, 1H), 7.08 (d, J=3.3 Hz, 1H), 6.57 (d, J=3.2 Hz, 1H), 6.26 (dt, J=3.2, 0.9 Hz, 1H), 6.18 (dt, J=3.2, 1.1 Hz, 1H), 2.30 (d, J=0.9 Hz, 3H), 2.29 (d, J=1.0 Hz, 3H). This was taken up in THF (10 mL) and added dropwise to a solution of LiAlH$_4$ (2M in THF, 23.8 mL, 47.6 mmol) in THF (20 mL) in an ice bath. The mixture was allowed to warm to RT over 18 h. Starting material was consumed, and a new peak was observed in 1:1 ratio (LCMS: m/z for the product was not observed). The mixture was diluted with 200 mL of DCM, quenched by slowly adding 2 g of sodium sulfate decahydrate, and stirred for 10 min. Excess anhydrous Na$_2$SO$_4$ was added to remove trace water. The mixture was filtered over Celite and volatiles were removed in vacuo. The crude product was used directly in the next step without purification, and the identity of this molecule was confirmed as its derivative in the next step (Example 1).

Intermediate 2: 6'-fluoro-1'H-spiro[piperidine-4,2'-quinolin]-4'(3'H)-one

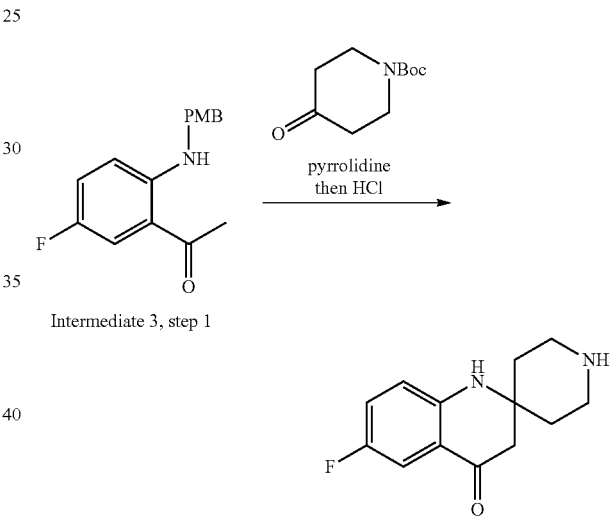

To a stirred solution of 1-(5-fluoro-2-((4-methoxybenzyl)amino)phenyl)ethan-1-one (obtained from Intermediate 3, step 1) (320 mg, 1.17 mmol) in MeOH (10 mL) was added tert-butyl 4-oxopiperidine-1-carboxylate (467 mg, 2.34 mmol) and pyrrolidine (0.194 mL, 2.34 mmol). The reaction was heated to reflux for 15 h. After partitioning the mixture between EtOAc and water, the combined organic phases were dried over Na$_2$SO$_4$ and concentrated. Silica gel chromatography (heptane/EtOAc, 100/0 to 70/30) afforded the spirocycle product (tert-butyl 6'-fluoro-1'-(4-methoxybenzyl)-4'-oxo-3',4'-dihydro-1'H-spiro[piperidine-4,2'-quinoline]-1-carboxylate) (350 mg), which was then dissolved in HCl (4M in dioxane, 1.171 mL, 4.68 mmol) and stirred at RT for 15 h. A yellow solid precipitated and was filtered to afford the title compound (265 mg, 74% yield) as a white powder. $^1$H NMR (400 MHz, DMSO-d$_6$) δ 7.24 (ddd, J=18.5, 9.2, 3.1 Hz, 2H), 7.07 (dd, J=9.0, 4.5 Hz, 1H), 3.56 (s, 2H), 3.31 (d, J=11.1 Hz, 2H), 3.09 (d, J=9.5 Hz, 2H), 1.83 (ddt, J=20.3, 14.1, 7.5 Hz, 4H).

Removal of PMB and Boc groups could also be done by TFA instead of HCl using a similar method to Intermediate 3, step 3.

Intermediate 3: 6'-fluoro-1'-methyl-1H-spiro[piperidine-4,2'-quinolin]-4'(3'H)-one

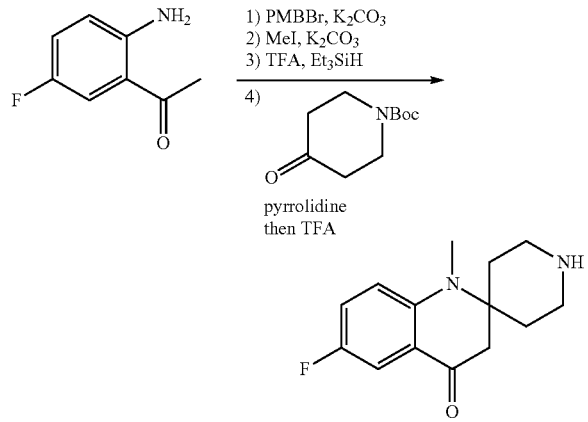

Step 1: Preparation of 1-(5-fluoro-2-((4-methoxybenzyl)amino)phenyl)ethan-1-one 1-(2-amino-5-fluorophenyl)ethanone (1.5 g, 9.79 mmol) was added to a solution of potassium carbonate (2.71 g, 19.59 mmol) in DMF (6 mL). The reaction was stirred at ambient temperature for 30 min. Then 1-(bromomethyl)-4-methoxybenzene (2.166 g, 10.77 mmol) was added dropwise to this solution and the reaction was heated at 80° C. for 18 h. The reaction was quenched with water and the aqueous layer was extracted with Et$_2$O (3×100 mL). The combined organic layers were dried over Na$_2$SO$_4$ and purified by silica gel chromatography (heptane/EtOAc=100/0 to 50/50) to yield the title compound (501 mg, 18.72% yield) as a yellow oil. $^1$H NMR (400 MHz, Chloroform-d) δ 9.07 (t, J=5.6 Hz, 1H), 7.45 (dd, J=9.8, 3.0 Hz, 1H), 7.27 (d, J=8.6 Hz, 2H), 7.09 (ddd, J=9.3, 7.7, 3.0 Hz, 1H), 6.89 (d, J=8.6 Hz, 2H), 6.62 (dd, J=9.3, 4.5 Hz, 1H), 4.39 (d, J=5.4 Hz, 2H), 3.82 (s, 3H), 2.59 (s, 3H).

Step 2: Preparation of 1-(5-fluoro-2-((4-methoxybenzyl)(methyl)amino)phenyl)ethan-1-one To a stirring solution of the product in step 1 (125 g, 457 mmol) and K$_2$CO$_3$ (190 g, 137 mmol) in DMF (1 L) was added MeI (286 mL, 457 mmol). The reaction was stirred at 75° C. for 24 h in a 4 L heat-jacketed reactor equipped with a cold condenser set at 5° C. The reactor was cooled to RT and additional K$_2$CO$_3$ (190 g, 137 mmol) and MeI (200 g, 141 mmol) were added. The reaction was heated to 75° C. for 24 h. The mixture was poured into water (7 L) and was extracted with MTBE (3×2 L). The organic extracts were combined, washed with 5% aqueous LiCl, dried with Na$_2$SO$_4$, filtered, and volatiles were removed in vacuo. The crude residue was passed through a silica gel plug, eluting with EtOAc. The filtrate was collected and volatiles were removed in vacuo to give the title compound (129 g, 83% yield) in ~85% purity. LCMS: m/z 288.2 (M+H).

Step 3: Preparation of 1-(5-fluoro-2-(methylamino)phenyl)ethan-1-one

To a mixture of the product in step 2 (129 g, 382 mmol) and triethylsilane (61.0 ml, 382 mmol) in a 2 L round-bottom flask was slowly added TFA (118 mL, 1526 mmol). The reaction vessel was equipped with a cold condenser set to 5° C. and the reaction was stirred at 70° C. for 18 h. Volatiles were removed in vacuo. The remaining TFA was quenched using 10% aqueous Na$_2$CO$_3$ to pH 10. The reaction was further diluted with water (2 L) and was transferred to a 6 L separatory funnel. The mixture was extracted with EtOAc (3×1 L). The organics were combined, washed with 5% aqueous LiCl (1 L), dried with Na$_2$SO$_4$, filtered, and volatiles were removed in vacuo. The crude oil was loaded onto a hand-packed silica gel dry-loading column and was purified by silica gel chromatography (DCM/heptane, 20% to 70%) using a 750 g column to give the title compound (57.3 g, 81% yield) in ~90% purity as a light-orange oil. LCMS: m/z 168.1 (M+H).

Step 4: Synthesis of 6'-fluoro-1'-methyl-1'H-spiro[piperidine-4,2'-quinolin]-4'(3'H)-one To a solution of the product in step 3 (57.3 g, 343 mmol) and tert-butyl 4-oxopiperidine-1-carboxylate (137 g, 685 mmol) in DMSO (300 mL) was added pyrrolidine (85 mL, 10 mmol). The reaction was heated at 140° C. for 24 h with a cold condenser set at 5° C. The mixture was poured into 2 L of water and extracted with EtOAc (3×750 mL). The organics were combined, washed with brine, dried with Na$_2$SO$_4$, filtered, and volatiles were removed in vacuo. The crude residue was then purified by silica gel chromatography (EtOAc/Heptane, 4:6) to give tert-butyl 6'-fluoro-1'-methyl-4'-oxo-3',4'-dihydro-1'H-spiro[piperidine-4,2'-quinoline]-1-carboxylate. LCMS: m/z 293.1 (M-tBu). This was dissolved in DCM (300 mL) and TFA (132 mL, 1714 mmol) was added. The reaction was stirred at RT for 18 h. Volatiles were removed in vacuo. The residue was then diluted in DCM and the remaining TFA was quenched by slow addition of 10% aqueous K$_2$CO$_3$ to pH ~10. The product was extracted with DCM (2×750 mL). The organics were combined, dried with Na$_2$SO$_4$, filtered, and volatiles were removed in vacuo. The crude residue was purified using a silica gel plug, eluting with MeOH/DCM (2:8) to give the title compound (45 g, 50.2% yield) as a brown solid in ~95% purity. LCMS: m/z 249.2 (M+H); $^1$H NMR (400 MHz, DMSO-d$_6$) δ 7.39-7.27 (m, 2H), 6.98-6.89 (m, 1H), 2.88 (s, 3H), 2.87-2.76 (m, 4H), 2.67-2.55 (m, 2H), 1.76 (td, J=12.5, 4.7 Hz, 2H), 1.56-1.44 (m, 2H).

Intermediate 4: 4-(aminomethyl)-2-fluoroaniline

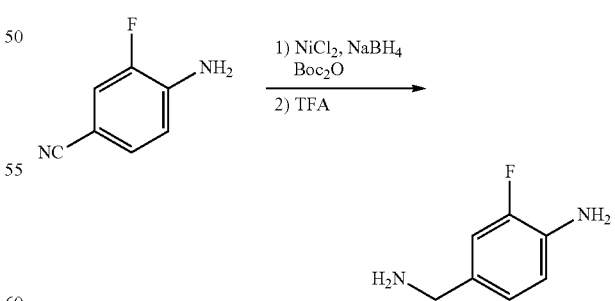

Step 1: Preparation of N-Boc 4-(aminomethyl)-2-fluoroaniline

To a solution of 4-amino-3-fluorobenzonitrile (1.00 g, 7.35 mmol) and Nickel(II) chloride (0.952 g, 7.35 mmol) in MeOH (10 mL) and THF (10 mL) in an ice bath was added a solution of Boc-anhydride (3.21 g, 14.7 mmol) in MeOH (2 mL). Sodium borohydride (0.834 g, 22.0 mmol) was added portion wise and the reaction was stirred at 0° C. for 72 h. The reaction mixture was filtered over a pad of Celite eluting with DCM. The filtrate was transferred to a separatory funnel and was diluted with sat. aqueous NaHCO$_3$. The mixture was extracted with DCM (3×75 mL). The organics were combined, dried with Na$_2$SO$_4$, filtered, and volatiles were removed in vacuo. The crude residue was then purified by silica gel chromatography (EtOAc/Heptane) to give the title compound. LCMS: m/z 185.1 (M+H-tBu); $^1$H NMR (400 MHz, DMSO-d$_6$) δ 7.21 (t, J=6.2 Hz, 1H), 6.83 (dd, J=12.5, 1.8 Hz, 1H), 6.78-6.62 (m, 2H), 4.97 (s, 2H), 3.95 (d, J=6.1 Hz, 2H), 1.37 (s, 9H).

Step 2: Preparation of 4-(aminomethyl)-2-fluoroaniline

The product in Step 1 was dissolved in DCM (10 mL), and trifluoroacetic acid (5.63 mL, 73.5 mmol) was added. The mixture was stirred at RT for 2 h. Volatiles were removed in vacuo. The residue was dissolved in 4 mL of DCM and was azeotroped with 10 mL of toluene to remove excess TFA. The resulting oil was dissolved in dioxane and 4 mL of 4M HCl in dioxane was added dropwise with stirring. The product precipitated from solution to form an off-white solid. The solid was then filtered and washed with dioxane (3×20 mL). The solid was dissolved in MeOH, volatiles were removed in vacuo and the sample was placed under high vacuum for 2 h. The crude product was used in the next step without purification. $^1$H NMR (400 MHz, DMSO-d$_6$) δ 8.23 (s, 3H), 7.22 (dd, J=12.3, 2.0 Hz, 1H), 7.03 (dd, J=8.2, 1.9 Hz, 1H), 6.87 (dd, J=9.2, 8.1 Hz, 1H), 5.23 (s, 2H), 3.86 (q, J=5.8 Hz, 2H).

Intermediate 5: 1'-ethyl-6'-fluoro-1'H-spiro[piperidine-4,2'-quinolin]-4'(3'H)-one

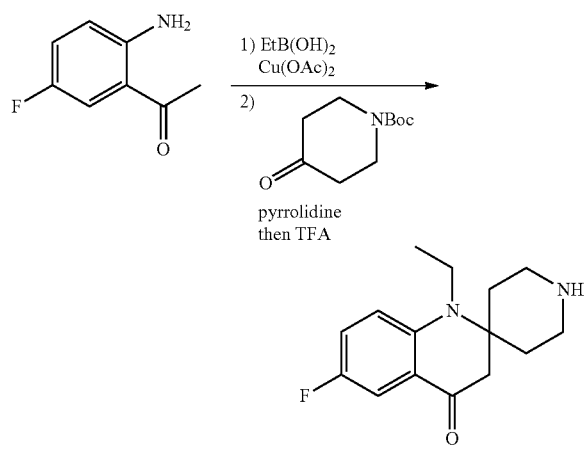

Step 1: Preparation of 1-(2-(ethylamino)-5-fluorophenyl)ethanone

To a solution of 1-(2-amino-5-fluorophenyl)ethanone (1500 mg, 9.8 mmol) and pyridine (2.75 mL, 34.0 mmol) in dioxane (200 mL) was added Cu(OAc)$_2$ (4269 mg, 23.5 mmol). The mixture was stirred for 15 min, then ethylboronic acid (1809 mg, 24.5 mmol) was added, and the reaction was refluxed for 8 h. The reaction mixture was allowed to cool down to RT, filtered through Celite and the volatiles were removed in vacuo. The crude oil was loaded onto a hand-packed silica gel dry-loading column and was purified by silica gel chromatography (EtOAc/heptane 0% to 50%) to afford the title compound (301 mg, 17% yield) in >95% purity as a yellow oil. LCMS: m/z 182.1 (M+H); $^1$H NMR (400 MHz, Chloroform-d) δ 8.59 (s, 1H), 7.43 (dd, J=9.9, 3.0 Hz, 1H), 7.16 (ddd, J=9.3, 7.8, 3.0 Hz, 1H), 6.67 (dd, J=9.3, 4.5 Hz, 1H), 3.24 (dt, J=10.6, 5.2 Hz, 2H), 2.57 (s, 3H), 1.33 (t, J=7.2 Hz, 3H).

Step 2: Preparation of 1'-ethyl-6'-fluoro-1'H-spiro[piperidine-4,2'-quinolin]-4'(3'H)-one The title compound was prepared by a method similar to the preparation of Intermediate 3, step 4. LCMS: m/z 263.2 (M+H); $^1$H NMR (400 MHz, Methanol-d$_4$) δ 7.39 (ddt, J=8.4, 5.4, 2.7 Hz, 1H), 7.29-7.16 (m, 1H), 6.91 (td, J=10.0, 4.0 Hz, 1H), 3.54-3.47 (m, 2H), 3.20-3.10 (m, 2H), 2.99-2.90 (m, 2H), 2.42 (t, J=6.3 Hz, 2H), 2.02 (td, J=13.5, 4.4 Hz, 1H), 1.90-1.75 (m, 1H), 1.27 (q, J=7.0 Hz, 3H).

Intermediate 6: 5-(aminomethyl)-2-fluorobenzamide

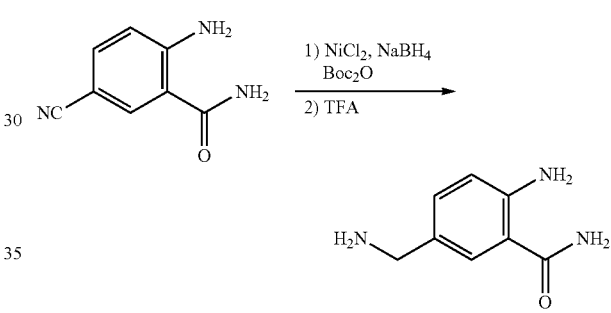

Step 1: Preparation of tert-butyl 3-carbamoyl-4-fluorobenzylcarbamate

The title compound was prepared by a method similar to Intermediate 4, step 1, using 5-cyano-2-fluorobenzamide instead of 4-amino-3-fluorobenzonitrile. The crude residue was purified by silica gel chromatography (EtOAc/Heptane) to give the title compound (1.1 g, 95% yield). LCMS: m/z 213.1 (M+H-tBu).

Step 2: Preparation of 5-(aminomethyl)-2-fluorobenzamide

The title compound was prepared by a method similar to Intermediate 4, step 2. The crude residue was passed through SiliaPrep SPE Cartridges Carbonate column (product number: SPE-R66030B)(5×5 g) to remove TFA to give the title compound (655 mg, 68% yield). LCMS: m/z 169.1 (M+H).

Intermediate 7: (4-fluorophenyl)methan-d$_2$-amine

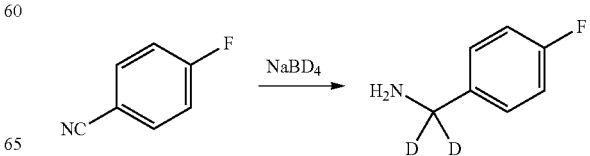

To a suspension of NaBD$_4$ (311 mg, 7.43 mmol) in dry THF (10 mL), a solution of TFA (0.573 mL, 7.43 mmol) in dry THF (3 mL) was added over 10 min at room temperature. Then, a solution of 4-fluorobenzonitrile (750 mg, 6.19 mmol) in dry THF (10 mL) was added and the reaction mixture was stirred overnight. The reaction was quenched by the addition of D$_2$O (3 mL), then water was added (20 mL), and the THF was removed under reduced pressure. The aqueous suspension was neutralized with sodium bicarbonate aqueous solution and extracted with DCM. The organic layers were combined, washed with water and then washed with 3 N HCl solution to perform a reverse extraction. The organic layer was discarded and the acid aqueous layer was neutralized with NaOH 1 N solution and extracted with DCM. This final organic layer was dried and concentrated under reduced pressure to give the title compound (290 mg, 35% yield) as a pale yellow oil. $^1$H NMR (400 MHz, Chloroform-d) δ 7.30 (ddd, J=8.6, 5.8, 3.2 Hz, 2H), 7.08-6.99 (m, 2H).

Intermediate 8: 6'-fluoro-1'-(2-methoxyethyl)-1'H-spiro[piperidine-4,2'-quinolin]-4'(3'H)-one

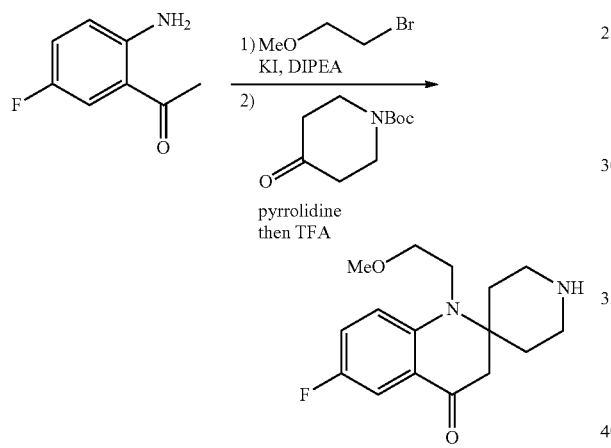

Step 1: Preparation of 1-(5-fluoro-2-((2-methoxyethyl)amino)phenyl)ethanone

To a microwave vial were added 1-(2-amino-5-fluorophenyl)ethan-1-one (200 mg, 1.3 mmol), DMF (3 mL), 1-bromo-2-methoxyethane (0.617 mL, 6.53 mmol), KI (1084 mg, 6.53 mmol) and DIPEA (1.140 mL, 6.53 mmol). The mixture was heated in the microwave for 3.5 h at 120° C. The reaction mixture was then diluted with EtOAc, washed with aqueous saturated sodium bicarbonate, dried over Na$_2$SO$_4$ and concentrated under reduced pressure. The residue was purified by silica gel chromatography (heptane/EtOAc=100/0 to 50/50) to yield the title compound (110 mg, 40% yield) as a yellow solid. LCMS: m/z 212.0 (M+H); $^1$H NMR (400 MHz, Chloroform-d) δ 8.72 (s, 1H), 7.33 (dd, J=9.8, 3.0 Hz, 1H), 7.04 (ddd, J=9.3, 7.8, 3.0 Hz, 1H), 6.59 (dd, J=9.3, 4.5 Hz, 1H), 3.55 (t, J=5.6 Hz, 2H), 3.34 (s, 3H), 3.30 (d, J=4.9 Hz, 2H), 2.47 (s, 3H).

Step 2: Preparation of 6'-fluoro-1'-(2-methoxyethyl)-1'H-spiro[piperidine-4,2'-quinolin]-4'(3'H)-one To a solution of the product in step 12) (110 mg, 0.521 mmol) in EtOH (5 mL) was added tert-butyl 4-oxopiperidine-1-carboxylate (135 mg, 0.677 mmol) and pyrrolidine (0.086 mL, 1.042 mmol). The reaction was heated in the microwave for 6 h at 110° C. The reaction mixture was then diluted with EtOAc, washed with aqueous saturated sodium bicarbonate, dried over Na$_2$SO$_4$ and concentrated under reduced pressure. The residue was purified by silica gel chromatography (EtOAc/heptane=0/100 to 30/70) to yield Boc-protected 6'-fluoro-1'-(2-methoxyethyl)-1'H-spiro[piperidine-4,2'-quinolin]-4'(3'H)-one. This Boc intermediate was then dissolved in DCM (1 mL), and TFA (0.120 mL, 1.562 mmol) was added. The reaction mixture was stirred at RT for 2 h and concentrated under reduced pressure. The reaction mixture was then diluted with EtOAc, washed with aqueous saturated sodium bicarbonate, dried over Na$_2$SO$_4$ and concentrated under reduced pressure to obtain the title compound as a free base (55 mg, 28.2% yield). LCMS: m/z 293.1 (M+H); $^1$H NMR (400 MHz, DMSO-d$_6$) δ 7.40-7.31 (m, 2H), 6.99 (dd, J=9.2, 4.1 Hz, 1H), 3.69-3.48 (m, 5H), 3.32 (s, 3H), 3.25-3.20 (m, 2H), 3.11-2.95 (m, 4H), 2.24 (t, J=13.2 Hz, 2H), 1.78 (d, J=14.0 Hz, 2H).

Intermediate 9: (4-fluoro-3-(oxazol-5-yl)phenyl)methanamine

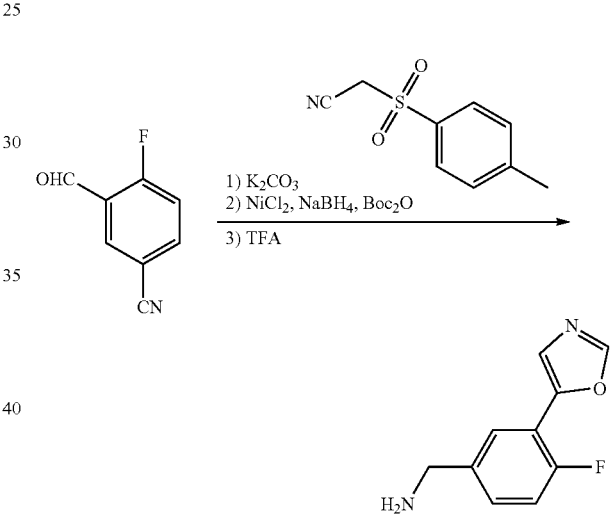

Step 1: Preparation of 4-fluoro-3-(oxazol-5-yl)benzonitrile

To a stirred solution of (p-tolylsulfonyl)methyl isocyanide (0.72 g, 3.688 mmol) in MeOH (15 mL) were added K$_2$CO$_3$ (0.60 g, 4.359 mmol) and 2-fluoro-5-bromobenzaldehye (0.5 g, 3.335 mmol). The reaction mixture was stirred at RT for 16 h, then concentrated under reduced pressure. The residue was diluted with DCM, washed with aqueous saturated sodium bicarbonate, dried over Na$_2$SO$_4$ and concentrated under reduced pressure. The residue was purified by silica gel chromatography (hexane/EtOAc=100/0 to 40/60) to yield the title compound as a white solid (0.43 g, 68% yield). LCMS: m/z 188.8 (M+H).

Step 2: Preparation of tert-butyl (4-fluoro-3-(oxazol-5-yl)benzyl)carbamate

The title compound was prepared by a method similar to Intermediate 4, step 1, using 4-fluoro-3-(oxazol-5-yl)benzonitrile instead of 4-amino-3-fluorobenzonitrile. The product was purified by silica gel chromatography (hexane/EtOAc=100/0 to 50/50), to yield the title compound as a yellow liquid (0.075 g, 48% yield). LCMS: m/z 293.3 (M+H).

Step 3: Preparation of (4-fluoro-3-(oxazol-5-yl)phenyl)methanamine

The title compound was prepared by a method similar to Intermediate 4, step 2, using tert-butyl (4-fluoro-3-(oxazol-5-yl)benzyl)carbamate instead of N-Boc 4-(aminomethyl)-2-fluoroaniline. The product (off-white solid) was obtained as a TFA salt by filtration (0.065 g, 83% yield). LCMS: m/z 193.15 (M+H).

Intermediate 10: 5-(aminomethyl)-2,4-difluoro-N-(2-methoxyethyl)aniline

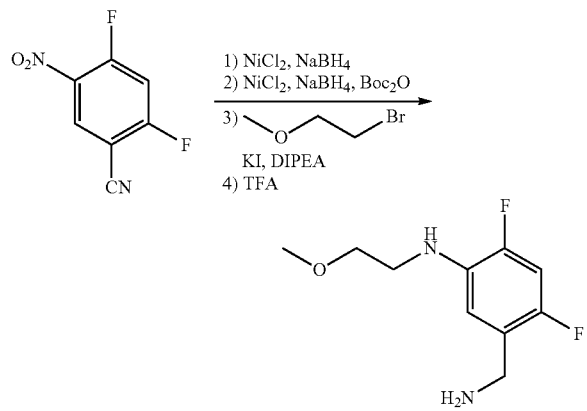

Step 1: Preparation of 5-amino-2,4-difluorobenzonitrile

To an ice-water cooled solution of 2,4-difluoro-5-nitrobenzonitrile (3 g, 16.30 mmol) in MeOH (10 mL) and THF (10 mL) was add NiCl$_2$.6H$_2$O (0.601 g, 4.07 mmol) followed by portion-wise addition of NaBH$_4$ (3.08 g, 81 mmol). After 30 min, the mixture was quench with diethylenetriamine (1.760 mL, 16.30 mmol) and stirred for 16 h. Volatiles were removed in vacuo. The crude residue was dissolved in EtOAc (30 mL) and washed with water (2×20 mL). The organic extracts were combined, washed with water, followed by brine (20 mL), dried with Na$_2$SO$_4$, filtered, and volatiles were removed in vacuo. The crude residue was purified by preparative HPLC (Basic, Method 2) to give the title compound (596 mg, 24% yield). LCMS: m/z 153.1 (M−H).

Step 2: Preparation of tert-butyl 5-amino-2,4-difluorobenzylcarbamate

The title compound was prepared by a method similar to Intermediate 4, Step 1. The crude residue was purified by silica gel chromatography (EtOAc/Heptane) to give the title compound (1.05 g, 25% yield). LCMS: m/z 259.1 (M−H).

Step 3: Preparation of tert-butyl (2,4-difluoro-5-((2-methoxyethyl)amino)benzyl)carbamate A microwave equipped with a stir bar was added the product in step 2 (330 mg, 2 mmol), DMF (2 mL), DIPEA (1.87 mL, 11 mmol), 1-bromo-2-methoxyethane (1.01 mL, 11 mmol) and potassium iodide (3.37 g, 20.33 mmol). The microwave vial was capped, and irradiated at 110° C. for 10 h. After cooling, the mixture was poured into EtOAc (20 mL) and was washed with saturated ammonia chloride (2×20 mL), followed by saturated sodium chloride (20 mL), dried with Na$_2$SO$_4$, filtered, and volatiles were removed in vacuo. The crude residue was purified by silica gel chromatography (MeOH/DCM) to give the title compound (520 mg, 40% yield). LCMS: m/z 261.0 (M+H-tBu).

Step 4: Preparation of 5-(aminomethyl)-2,4-difluoro-N-(2-methoxyethyl)aniline The title compound was prepared by a method similar to Intermediate 4, Step 2. The crude product was carried forward to next step (Example 17) without purification. LCMS: m/z 217.4 (M+H).

Intermediate 11: 2-(aminomethyl)-5-fluoro-N-(2-methoxyethyl)aniline

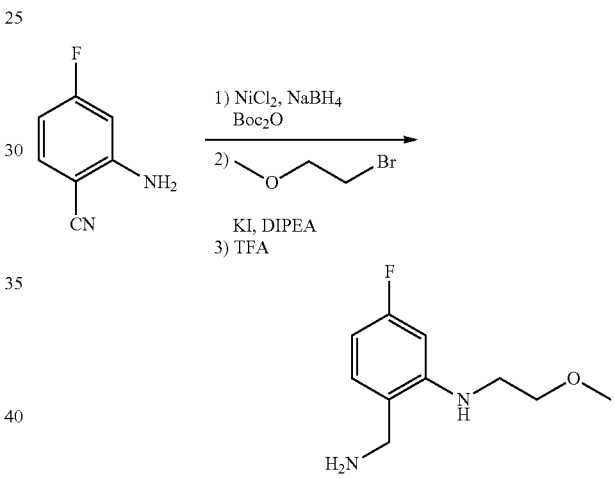

Step 1: Preparation of tert-butyl 2-amino-4-fluorobenzylcarbamate

The title compound was prepared by a method similar to Intermediate 4, step 1, using 2-amino-4-fluorobenzonitrile instead of 4-amino-3-fluorobenzonitrile. The crude residue was purified by reversed-phase HPLC (Basic, Method 4) to give the title compound (240 mg, 49.9% yield). LCMS: m/z 184.9 (M+H-tBu).

Step 2: Preparation of tert-butyl 4-fluoro-2-((2-methoxyethyl)amino)benzylcarbamate The title compound was prepared by a method similar to Intermediate 10, step 3. The crude residue was purified by silica gel chromatography (heptane/EtOAc) to give the title compound (150 mg, 63.8% yield). LCMS: m/z 299.2 (M+H); $^1$H NMR (400 MHz, Chloroform-d) δ 7.03-6.91 (m, 1H), 6.42-6.25 (m, 2H), 4.20 (d, J=6.2 Hz, 2H), 3.62 (t, J=5.6 Hz, 2H), 3.40 (s, 3H), 3.36-3.26 (m, 2H), 1.45 (s, 10H).

Step 3: Preparation of tert-butyl 2-amino-4-fluorobenzylcarbamate

The title compound was prepared by a method similar to Intermediate 4, step 2. The crude product was carried forward to next step (Example 20) without purification. LCMS: m/z 197.2 (M–H).

Intermediate 12: 5-(aminomethyl)-2-fluoro-N-(2-methoxyethyl)aniline

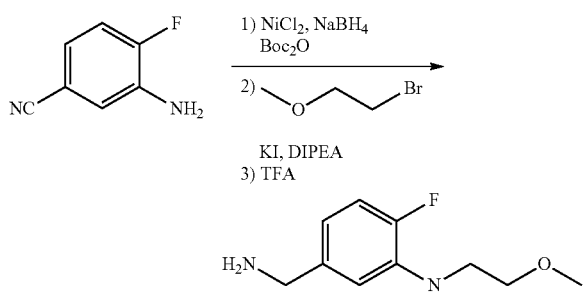

Step 1: Preparation of tert-butyl (3-amino-4-fluorobenzyl)carbamate

The title compound was prepared by a method similar to Intermediate 4, step 1, using 3-amino-4-fluorobenzonitrile instead of 4-amino-3-fluorobenzonitrile. The crude residue was purified by silica gel chromatography (hexane/EtOAc=100/0 to 35/65) to give the title compound (1810 mg, 51% yield). LCMS: m/z 240.0 (M+H); $^1$H NMR (400 MHz, Chloroform-d) δ 6.91 (dd, J=10.9, 8.3 Hz, 1H), 6.71 (d, J=8.5 Hz, 1H), 6.64-6.49 (m, 1H), 4.78 (br s, 1H), 4.18 (d, J=5.8 Hz, 2H), 3.79-3.68 (m, 1H), 3.65 (s, J=2.8 Hz, 1H), 1.45 (s, 9H).

Step 2: Preparation of tert-butyl 4-fluoro-3-((2-methoxyethyl)amino)benzylcarbamate The title compound was prepared by a method similar to Intermediate 10, step 3. The crude residue was purified by silica gel chromatography (heptane/EtOAc) to give the title compound (505 mg, 61% yield). $^1$H NMR (400 MHz, Chloroform-d) δ 6.91 (dd, J=11.4, 8.2 Hz, 1H), 6.65 (d, J=8.1 Hz, 1H), 6.55 (s, 1H), 4.22 (d, J=5.7 Hz, 2H), 3.68-3.58 (m, 2H), 3.40 (s, 3H), 3.31 (t, J=5.2 Hz, 2H), 1.46 (s, 9H).

Step 3: Preparation of 5-(aminomethyl)-2-fluoro-N-(2-methoxyethyl)aniline

The title compound was prepared by a method similar to Intermediate 4, step 2. The crude product was carried forward to next step (Example 21) without purification. $^1$H NMR (400 MHz, Chloroform-d) δ 6.91 (dd, J=11.4, 8.2 Hz, 1H), 6.69 (ddd, J=18.1, 8.4, 1.9 Hz, 1H), 6.60-6.51 (m, 1H), 3.79 (s, 2H), 3.72 (s, OH), 3.65-3.60 (m, 2H), 3.40 (d, J=2.0 Hz, 3H), 3.33 (dd, J=6.7, 4.1 Hz, 2H).

Intermediate 13: 3-(aminomethyl)-2,6-difluoroaniline

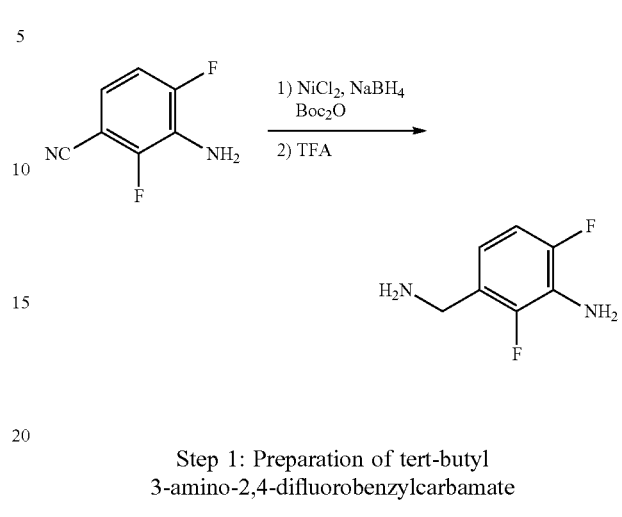

Step 1: Preparation of tert-butyl 3-amino-2,4-difluorobenzylcarbamate

To a stirred solution of 2,4-difluoro-3-nitrobenzonitrile (2 g, 10.86 mmol) in dry MeOH (120 mL), at 0° C., were added Boc$_2$O (3.78 mL, 16.30 mmol), NiCl$_2$.6H$_2$O (0.321 g, 2.173 mmol) and then NaBH$_4$ (2.88 g, 76 mmol) in small portion over 30 min. The resulting reatction mixture was allowed to warm to RT and left to stir for further 15 h, at which point diethylenetriamine (1.174 mL, 10.86 mmol) was added. The mixture was allowed to stir for 2 h before filtration on celite and solvent evaporation. The residue was dissolved in EtOAc, washed with aqueous saturated sodium bicarbonate, dried over Na$_2$SO$_4$ and concentrated under reduced pressure to yield the title compound (1.4 g, 50% yield). LCMS: m/z 259.0 (M+H).

Step 2: Preparation of 3-(aminomethyl)-2,6-difluoroaniline

The title compound was prepared by a method similar to Intermediate 4, step 2, The product was obtained as off-white solid (TFA salt) (0.580 g, 100% yield). The structural identity of this compound was confirmed as its derivative (Example 26).

Intermediate 14: 1,4-Dioxane-2-carbaldehyde

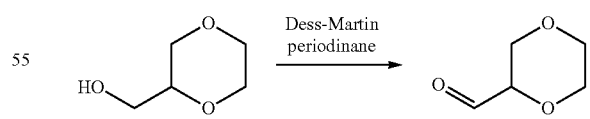

A mixture of (1,4-dioxan-2-yl)methanol (70 mg, 0.59 mmol) and Dess-Martin periodinane (261 mg, 0.615 mmol) in DCM (2 mL) was stirred at RT for 20 h, passed through a pad of silica (elution with DCM, followed by 10% EtOAc in DCM). The filtrate was concentrated in vacuo (70 mmHg) without heating. The crude product was used directly in the next step. The structural identity of the product was confirmed as its derivative in the next step (Example 31).

Intermediate 15: 5-(aminomethyl)-N-(2-((tert-butyldimethylsilyl)oxy)ethyl)-2-fluoroaniline

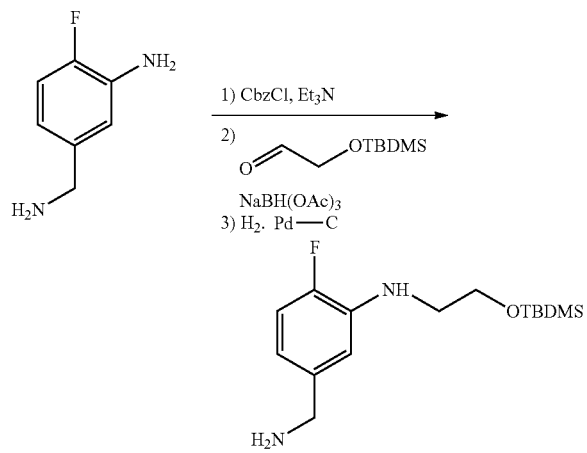

Step 1: Synthesis of benzyl (3-amino-4-fluorobenzyl)carbamate

Benzyl chlorformate (2.2 ml, 15 mmol) was added slowly to a solution of 5-(aminomethyl)-2-fluoroaniline (2.01 g, 14.34 mmol) and triethylamine (4.00 ml, 28.7 mmol) in THF (20 mL) at 0° C. The mixture was stirred at RT for 30 min and partitioned between EtOAc and brine. The combined organic extract was dried over MgSO₄ and concentrated. The crude product was purified by silica gel column chromatography (EtOAc/heptane) to give the title compound as a white solid (2.40 g). LCMS: m/z 275.3 (M+H).

Step 2: Synthesis of benzyl (3-((2-((tert-butyldimethylsilyl)oxy)ethyl)amino)-4-fluorobenzyl)carbamate A mixture of the product in Step 1 (2.00 g, 7.29 mmol), 2-(tert-butyldimethylsilyloxy)acetaldehyde (1.35 g, 7.74 mmol) and sodium triacetoxyborohydride (1.52 g, 7.17 mmol) in DCM (40 mL) was stirred at RT for 62 h. The mixture was concentrated and partitioned between EtOAc and aq. NH₄Cl. The combined organic extract was dried over MgSO₄, concentrated and purified by silica gel chromatography (EtOAc/heptane) to give the title compound as a colorless oil (2.33 g). LCMS: m/z 433.4 (M+H).

Step 3: Synthesis of 5-(aminomethyl)-N-(2-((tert-butyldimethylsilyl)oxy)ethyl)-2-fluoroaniline A mixture of the product in Step 2 (2.33 g, 5.39 mmol) and 10% Pd/C (0.12 g) in EtOH (30 mL) was hydrogenated under balloon pressure and at RT for 15 min, and filtered through Celite, and the filtrate was concentrated to give the crude product. Purification by silica gel chromatography (DCM/MeOH) gave the title compound as a light yellow oil (1.46 g). LCMS: m/z 299.4 (M+H).

Intermediate 16: (S)-5-(aminomethyl)-N-((2,2-dimethyl-1,3-dioxolan-4-yl)methyl)-2-fluoroaniline

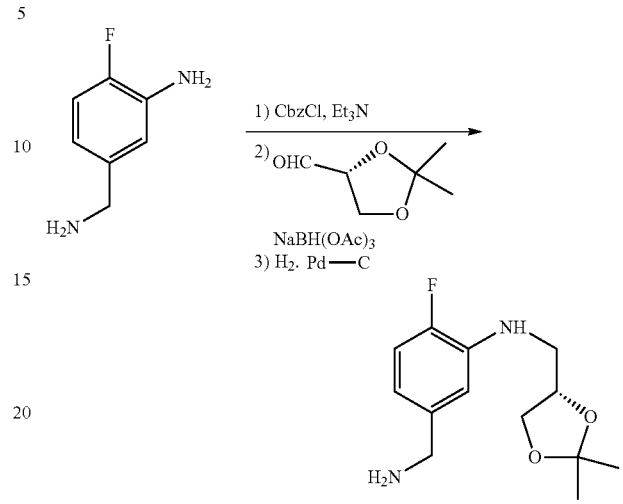

The title compound was prepared by a method similar to the preparation of Intermediate 15, using (R)-2,2-dimethyl-1,3-dioxolane-4-carbaldehyde instead of 2-(tert-butyldimethylsilyloxy)acetaldehyde in step 2. LCMS: m/z 255.3 (M+H).

Intermediate 17: 4-(aminomethyl)-2,5-difluoroaniline

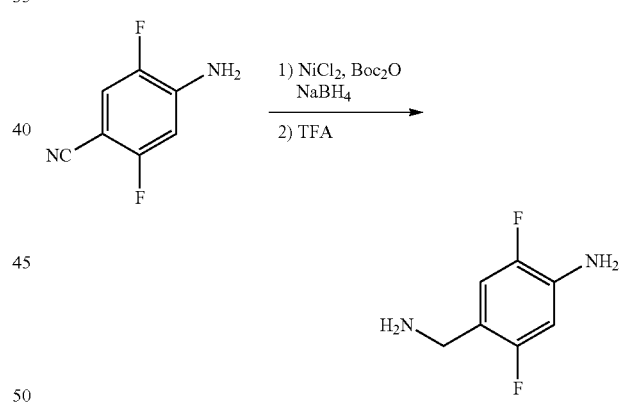

Step 1: Preparation of tert-butyl (4-amino-2,5-difluorobenzyl)carbamate

The title compound was prepared by a method similar to Intermediate 4, step 1, using 4-amino-2,5-difluorobenzonitrile instead of 4-amino-3-fluorobenzonitrile. LCMS: m/z 203.1 (M+H-tBu).

Step 2: Preparation of 4-(aminomethyl)-2,5-difluoroaniline

The title compound was prepared by a method similar to Intermediate 4, step 2. No m/z for the product (LCMS) was observed. The identity of the structure was confirmed as its derivative in the next step (Example 49).

Intermediate 18: 2-(aminomethyl)-N-ethyl-5-fluoroaniline

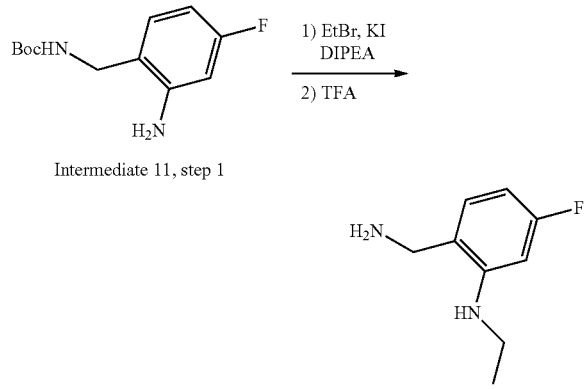

Step 1: Preparation of tert-butyl 2-(ethylamino)-4-fluorobenzylcarbamate

To a microwave vial were added the product from Intermediate 11, step 1 (135 mg, 0.562 mmol), DMF (8 mL), bromoethane (306 mg, 2.81 mmol), KI (466 mg, 2.81 mmol) and DIPEA (0.491 mL, 2.81 mmol). The mixture was heated in the microwave for 10 h at 110° C. The mixture was then diluted with EtOAc, washed with aqueous saturated sodium bicarbonate, dried over Na$_2$SO$_4$ and concentrated under reduced pressure. The residue was purified by silica gel chromatography (heptane/EtOAc) to yield the title compound as a yellow oil (0.030 g, 20% yield). LCMS: m/z 267.2 (M−H).

Step 2: Preparation of 2-(aminomethyl)-N-ethyl-5-fluoroaniline

The title compound was prepared by a method similar to Intermediate 4, step 2. The title compound was isolated as a free base (0.062 g, 61% yield). LCMS: m/z 167.1 (M−H).

Intermediate 19: (4-fluoro-3-(2-methoxyethoxy)phenyl)methanamine

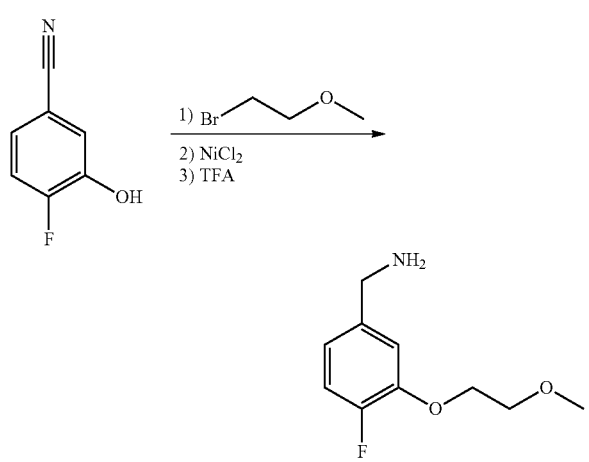

Step 1: Synthesis of 4-fluoro-3-(2-methoxyethoxy)benzonitrile

To a microwave vial was added 4-fluoro-3-hydroxy benzonitrile (1 g, 7.29 mmol), DMF, 1-bromo-2-methoxyethane (3.42 ml, 36.5 mmol), KI (6.05 g, 36.5 mmol) and DIPEA (6.37 ml, 36.5 mmol). The mixture was heated in the microwave for 10 h at 110° C. The mixture was diluted with EtOAc, washed with aqueous saturated sodium bicarbonate, dried over Na$_2$SO$_4$, and concentrated under reduced pressure onto a bed of Celite. The residue was purified by silica gel chromatography (EtOAc/heptane) to afford the title compound as a clear oil (1.2 g, 84% yield). LCMS: m/z 198.9 (M+H); $^1$H NMR (400 MHz, Chloroform-d) δ 7.31-7.26 (m, 3H), 7.18 (dd, J=10.7, 8.7 Hz, 1H), 4.26-4.20 (m, 2H), 3.84-3.78 (m, 2H), 3.48 (s, 3H).

Step 2: Synthesis of tert-butyl 4-fluoro-3-(2-methoxyethoxy)benzylcarbamate

The title compound was prepared by a method similar to Intermediate 4, step 1. The product was purified by silica gel chromatography (EtOAc/heptanes) to give the title compound as a clear oil (1.356 g, 73.7% yield). LCMS: m/z 243.3 (M+H (-tert-butyl)); $^1$H NMR (400 MHz, Chloroform-d) δ 7.03 (dd, J=11.1, 8.3 Hz, 1H), 6.95 (dd, J=8.1, 2.1 Hz, 1H), 6.83 (ddd, J=8.3, 4.3, 2.2 Hz, 1H), 4.26 (d, J=5.5 Hz, 2H), 4.23-4.18 (m, 2H), 3.81-3.75 (m, 2H), 3.48 (s, 3H), 1.48 (s, 9H).

Step 3: Synthesis of (4-fluoro-3-(2-methoxyethoxy)phenyl)methanamine

The title compound was prepared by a method similar to Intermediate 4, step 2. The mixture was concentrated and the residue was passed through SCX column to remove TFA with 7N NH$_3$ in MeOH. After removal of solvent, the title compound was obtained as a brown oil (166 mg, 99% yield). LCMS: m/z 200.2 (M+H).

Intermediate 20: 4-(aminomethyl)-2,3-difluoroaniline

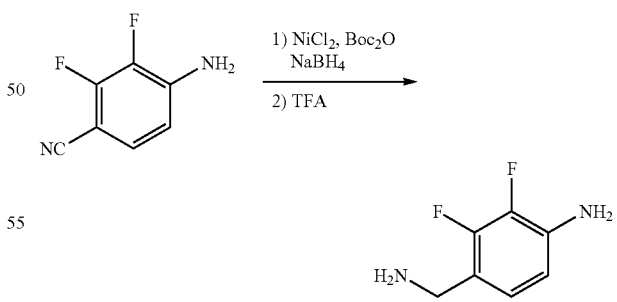

Step 1: Preparation of tert-butyl (4-amino-2,3-difluorobenzyl)carbamate

The title compound was prepared by a method similar to Intermediate 4, step 1, using 4-amino-2,5-difluorobenzonitrile instead of 4-amino-3-fluorobenzonitrile. LCMS: m/z 203.1 (M+H-tBu).

Step 2: Preparation of 4-(aminomethyl)-2,3-difluoroaniline

The title compound was prepared by a method similar to Intermediate 4, step 2. No m/z for the product (LCMS) was observed. The identity of the structure was confirmed as its derivative in the next step (Example 57).

Intermediate 21: methyl 5-(aminomethyl)-2-fluorobenzoate

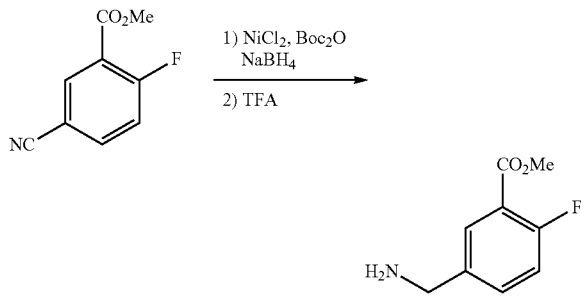

Step 1: Preparation of methyl 5-(((tert-butoxycarbonyl)amino)methyl)-2-fluorobenzoate The title compound was prepared by a method similar to Intermediate 4, step 1. The product was purified by silica gel chromatography (EtOAc/heptane) to give the title compound as a clear, viscous oil (1.26 g, 4.45 mmol, 39.8% yield). LCMS: m/z 228.1 (M+H-tBu).

Step 2: Preparation of methyl 5-(aminomethyl)-2-fluorobenzoate

The title compound was prepared by a method similar to Intermediate 4, step 2. LCMS: m/z 184.2 (M+H).

Intermediate 22: 2-(5-(aminomethyl)-2-fluorophenyl)acetamide

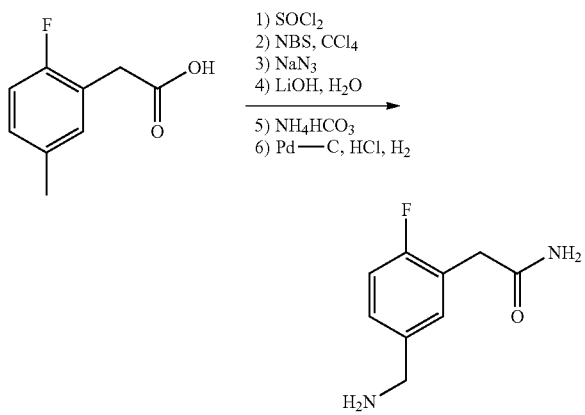

Step 1: Preparation of methyl 2-(2-fluoro-5-methylphenyl)acetate

To a stirred solution of 2-(2-fluoro-5-methylphenyl)acetic acid (0.5 g, 2.97 mmol) in MeOH (10 mL) was added thionyl chloride (0.3 mL, 5.94 mmol) at 0° C. The mixture was stirred at RT for 2 h. Completion of the reaction was monitored by TLC. The mixture was concentrated in vacuo. The crude residue was diluted with water and extracted with EtOAc. The organic extracts were combined, washed with saturated NaCl, dried over $Na_2SO_4$, filtered, and concentrated in vacuo to give the title compound (0.5 g, 92% yield) as yellow liquid. The crude product was carried forward to next step without purification.

Step 2: Preparation of methyl 2-(5-(bromomethyl)-2-fluorophenyl)acetate

To a stirred solution of the product in step 1 (0.5 g, 2.74 mmol) in $CCl_4$ (10 mL) was added NBS (0.51 g, 2.88 mmol), and AIBN (0.067 g, 0.41 mmol) at 0° C. The mixture was stirred at reflux for 3 h. The mixture was concentrated in vacuo. The crude residue was diluted with water and extracted with DCM. The organic extracts were combined, washed with water and saturated NaCl, dried over $Na_2SO_4$, filtered, and concentrated in vacuo. The crude residue was purified by silica gel chromatography (EtOAc/Heptane=1/9) to give the title compound (261 mg, 70% yield) as a colorless liquid.

Step 3: Preparation of methyl 2-(5-(azidomethyl)-2-fluorophenyl)acetate

To a stirred solution of the product in step 2 (0.5 g, 1.915 mmol) in DMF (5 mL) was added sodium azide (0.136 g, 2.106 mmol). The mixture was stirred at RT for 2 h. The mixture was concentrated in vacuo. The mixture was diluted with water and extracted with ether. The organic extracts were combined, washed with water and saturated NaCl, dried over $Na_2SO_4$, filtered, and concentrated in vacuo. The crude product was carried forward to next step without purification. (0.3 g, 71% yield). LCMS: m/z 196.1 (M+H-$N_2$).

Step 4: Preparation of 2-(5-(azidomethyl)-2-fluorophenyl)acetic acid

To a stirred solution of the product in step 3 (0.5 g, 2.24 mmol) in THF (2 mL), MeOH (2 mL) and water (2 mL) was added LiOH·$H_2O$ (0.18 g, 4.48 mmol). The mixture was stirred at RT for 2 h. The mixture was concentrated in vacuo. The crude mixture was acidified with 3N HCl aqueous solution. The product precipitated from solution to form an off-white solid. The solid was then filtered under vacuo. The crude product was carried forward to next step without purification. (0.41 g, 89% yield).

Step 5: Preparation of 2-(5-(azidomethyl)-2-fluorophenyl)acetamide

To a stirred solution of the product in step 4 (0.41 g, 1.96 mmol) in DMF (10 mL), was added pyridine (0.31 g, 3.92 mmol) followed by di-tert-butyl dicarbonate (1.32 g, 6.07 mmol), and $NH_4HCO_3$ (0.48 g, 6.07 mmol). The mixture was stirred at RT for 16 h. The mixture was diluted with saturated $NH_4Cl$ and extracted with EtOAc. The organic extracts were combined, washed with water and saturated NaCl, dried over $Na_2SO_4$, filtered, and concentrated in vacuo. The crude residue was purified by silica gel chromatography (EtOAc/DCM=45/55) to give the title compound (350 mg, 87% yield) as a white solid. LCMS: m/z 209.9 (M+H)

Step 6: 2-(5-(aminomethyl)-2-fluorophenyl)acetamide

To a stirred solution of the product in step 5 (0.2 g, 0.96 mmol) in ethanol (10 mL) under $N_2$ gas was added Pd/C 10% wet (0.05 g) and 1N aqueous solution HCl (2 drops). The mixture was hydrogenated at RT for 2 h. The reaction mixture was filtered over a pad of Celite and eluting with ethanol. The filtrate was concentrated in vacuo to give the title compound (160 mg, 76% yield) as an off-white solid. The crude product was carried forward to next step (Example 62) without purification.

Intermediate 23: 5-(aminomethyl)-2-fluoro-N-methylbenzamide

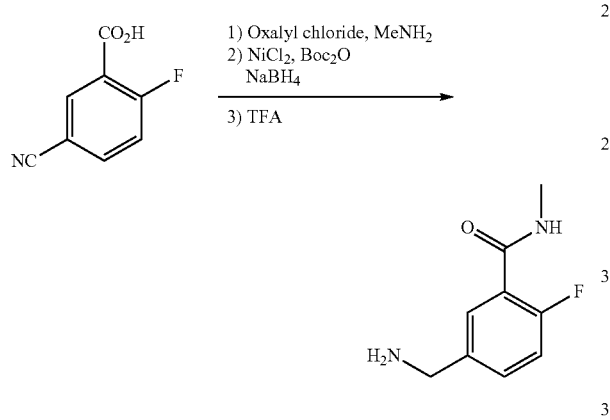

Step 1: Preparation of 5-cyano-2-fluoro-N-methylbenzamide

To a solution of 5-cyano-2-fluorobenzoic acid (1000 mg, 6.06 mmol) in DCM (5 mL) was added oxalyl chloride (1.060 mL, 12.11 mmol) followed by 1 drop of DMF. The mixture was stirred at RT for 1.5 h. The mixture was concentrated in vacuo, and the resulting residue was dissolved in DCM (3 mL) and cooled to 0° C. Methylamine (16.65 mL, 33.3 mmol) in THF (2 mL) was added and the reaction was allowed to stir at 0° C. for 0.5 h. The reaction mixture was quenched with water and the crude residue was concentrated in vacuo. The crude residue was diluted with water and the resulting solids were filtered, rinsed with water, and dried under vacuum. The crude product was carried forward to next step without purification. LCMS: m/z 179.1 (M+H); $^1$H NMR (400 MHz, Methanol-$d_4$) δ 8.08 (dd, 1H), 7.91 (ddd, J=8.7, 4.6, 2.2 Hz, 1H), 7.41 (dd, J=10.2, 8.7 Hz, 1H), 2.93 (s, 3H).

Step2 and Step 3: Preparation of tert-butyl 4-fluoro-3-(methylcarbamoyl)benzylcarbamate The title compound was prepared by a method similar to Intermediate 4. LCMS: m/z 183.2 (M+H); $^1$H NMR (400 MHz, Methanol-$d_4$) δ 8.09 (dd, J=6.5, 2.2 Hz, 1H), 7.91 (ddd, J=8.6, 4.6, 2.2 Hz, 1H), 7.42 (dd, J=10.2, 8.7 Hz, 1H), 2.93 (s, 3H).

Intermediate 24: 4-(aminomethyl)-2,6-difluoroaniline

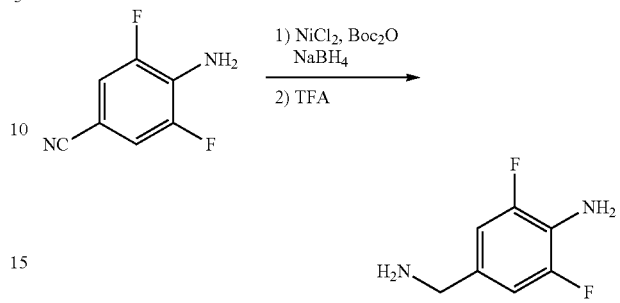

Step 1: Preparation of tert-butyl (4-amino-2,6-difluorobenzyl)carbamate

The title compound was prepared by a method similar to Intermediate 4, step 1, using 4-amino-2,6-difluorobenzonitrile instead of 4-amino-3-fluorobenzonitrile. LCMS: m/z 203.2 (M+H-tBu).

Step 2: Preparation of 4-(aminomethyl)-2,6-difluoroaniline

The title compound was prepared by a method similar to Intermediate 4, step 2. No m/z for the product (LCMS) was observed. The identity of the structure was confirmed as its derivative in the next step (Example 65).

Intermediate 25: (2,4-difluoro-5-(2-methoxyethoxy)phenyl)methanamine

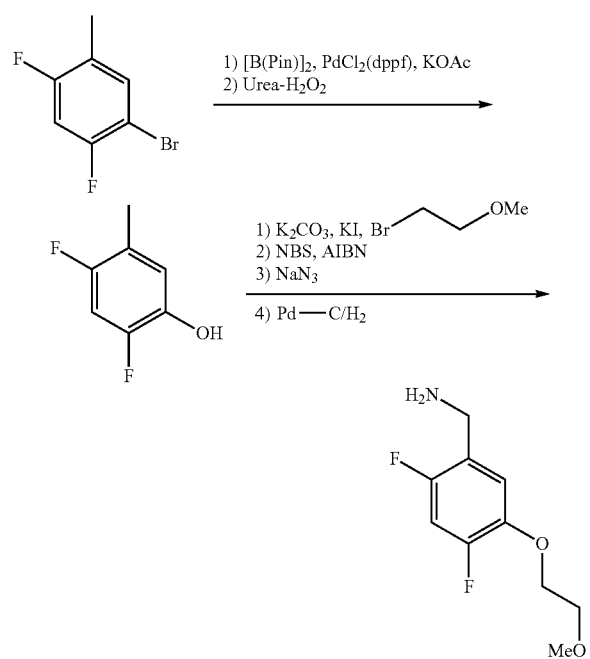

Step 1: Preparation of 2-(2,4-difluoro-5-methylphenyl)-4,4,5,5-tetramethyl-1,3,2-dioxaborolane To a degassed solution of bispinacolate diboron (1.2 g, 4.83 mmol) and 1-bromo-2,4-difluoro-5-methylbenzene (1.0 g, 4.83 mmol) in dioxane (10 mL) was added KOAc (1.0 g, 9.66 mmol) and PdCl$_2$(dppf) (0.39 g, 0.483 mmol). The reaction mixture was stirred in a sealed tube at 100° C. for 16 h, then filtered through Celite bed. The filtrate was concentrated, then diluted with DCM and washed with water. The organic phase was dried over Na$_2$SO$_4$ and concentrated under reduced pressure. The residue was purified by silica gel chromatography (heptane/EtOAc=100/0 to 90/10) to yield the title compound (0.7 g, 2.75 mmol, 57% yield).

Step 2: Preparation of 2,4-difluoro-5-methylphenol

To a solution of the product in step 1 (600 mg, 2.36 mmol) in MeOH (5 mL) was added urea-hydrogen peroxide adduct (266 mg, 2.83 mmol) at 0° C. The reaction mixture was stirred for 12 h at RT then concentrated and diluted with DCM and washed with water. The organic phase was dried over Na$_2$SO$_4$ and concentrated under reduced pressure to yield the title intermediate (700 mg) that was directly engaged as a crude in the next reaction.

Step 3: Preparation of 1,5-difluoro-2-(2-methoxyethoxy)-4-methylbenzene

The title compound was prepared by a method similar to Intermediate 19, using the product in step 2 instead of 4-fluoro-3-hydroxy benzonitrile, to yield the title compound (380 mg, 38% yield).

Step 4: Preparation of 1-(bromomethyl)-2,4-difluoro-5-(2-methoxyethoxy)benzene To a solution of the product in step 3 in CCl$_4$ (5 mL) was added NBS (245 mg, 1.39 mmol) and AIBN (22 mg, 0.138 mmol) at RT. The reaction mixture was stirred for 1 h at RT and then warmed to 50° C. for 2 h and to 80° C. for 12 h. The mixture was then concentrated, diluted with DCM and washed with water. The organic phase was dried over Na$_2$SO$_4$ and concentrated under reduced pressure. The residue was purified by silica gel chromatography (hexane/EtOAc=100/0 to 80/20) to yield the title compound as a colorless oil (150 mg, 38% yield).

Step 5: Preparation of 1-(azidomethyl)-2,4-difluoro-5-(2-methoxyethoxy)benzene To a solution of the product in step 4 (150 mg, 0.533 mmol) in DMF (5 mL) was added sodium azide (69 mg). The reaction mixture was stirred at RT for 16 h, then diluted with EtOAc and water. The organic layer was dried over Na$_2$SO$_4$ and concentrated under reduced pressure. The crude product was engaged directly in next reaction step.

Step 6: Preparation of (2,4-difluoro-5-(2-methoxyethoxy)phenyl)methanamine

To an degassed solution of the product in step 5 (60 mg, 0.246 mmol) in EtOH (20 mL) was added Pd/C (10 mg), and the reaction mixture was stirred under a H$_2$ balloon for 8 h. The reaction was then filtered through Celite pad, and the filtrate was concentrated under reduced pressure to yield the title compound (28 mg, 52% yield). LCMS: m/z 218 (M+H).

Intermediate 26: 6',8'-difluoro-1'H-spiro[piperidine-4,2'-quinolin]-4'(3'H)-one

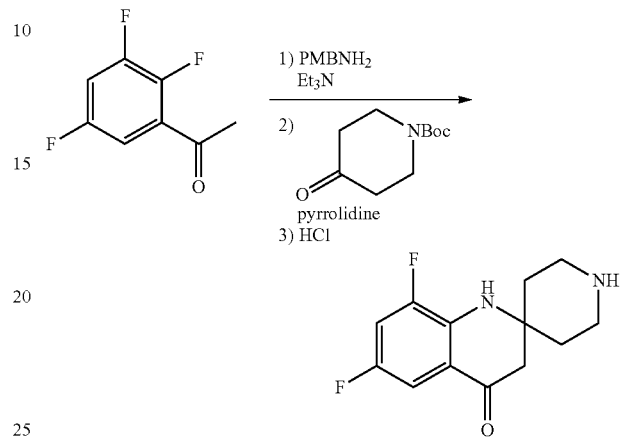

Step 1: Preparation of 1-(3,5-difluoro-2-((4-methoxybenzyl)amino)phenyl)ethan-1-one To a stirred solution of 1-(2,3,5-trifluorophenyl)ethan-1-one (12.0 g, 69.0 mmol) in DMSO (12 mL) were added p-methoxy benzyl amine (11.6 mL, 88.9 mmol) and TEA (12 mL, 82.7 mmol). The reaction mixture was stirred for 10 min at RT, then heated to 150° C. for 4 h. The reaction mixture was then quenched with water, extracted with EtOAc and washed with water and brine solution and dried over Na$_2$SO$_4$ and concentrated. The crude oil was purified by silica gel chromatography (EtOAc/hexane 0% to 10%) and recrystallized in n-pentane to afford the title compound (1.3 g, 6% yield) as a yellow oil.

Step 2: Preparation of 6',8'-difluoro-1'H-spiro[piperidine-4,2'-quinolin]-4'(3'H)-one The title compound was prepared by a method similar to the preparation of Intermediate 2 and isolated as a yellow solid (0.69 g, 59% yield). LCMS: m/z 253 (M+H); $^1$H NMR (300 MHz, DMSO-d$_6$): δ 7.46-7.38 (1H, m), 7.13-7.10 (1H, d), 6.37 (1H, s), 2.82-2.77 (2H, m), 2.72 (2H, s), 2.63-2.49 (2H, m), 1.64-1.60 (4H, m).

Intermediate 27: 3-(aminomethyl)benzenesulfonamide

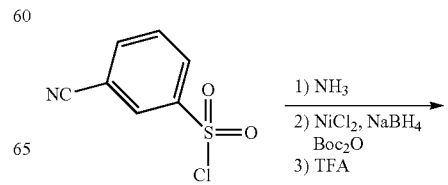

-continued

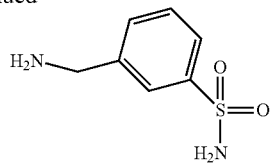

Step 1: Preparation of 3-cyanobenzenesulfonamide

To a stirred solution of 3-cyanobenzenesulfonyl chloride (0.5 g, 2.47 mmol) in THF (5 mL) was added NH$_3$ aqueous 25% solution (4.95 mmol) at 0° C., and the reaction mixture was stirred at RT for 16 h. The reaction was then concentrated, and diluted with EtOAc and water. The organic layer was dried over Na$_2$SO$_4$ and concentrated under reduced pressure to afford the title compound as a white solid (0.4 g, 88% yield).

Step 2: Preparation of tert-butyl (3-sulfamoylbenzyl)carbamate

The title compound was prepared by a method similar to Intermediate 4, step 1, using 3-cyanobenzenesulfonamide instead of 4-amino-3-fluorobenzonitrile. The product was purified by silica gel chromatography (hexane/EtOAc=70/30 to 55/45), to yield the title compound as a white solid (0.15 g, 65% yield). LCMS: m/z 248.9 (M–H).

Step 3: Preparation of 3-(aminomethyl)benzenesulfonamide

The title compound was prepared by a method similar to Intermediate 4, step 2, using tert-butyl (3-sulfamoylbenzyl)carbamate instead of N-Boc 4-(aminomethyl)-2-fluoroaniline. The product was obtained by filtration as an off-white solid (0.11 g, 90% yield). LCMS: m/z 187.3 (M+H).

Intermediate 28: 3-(aminomethyl)-2,6-difluoro-N-(2-methoxyethyl)aniline

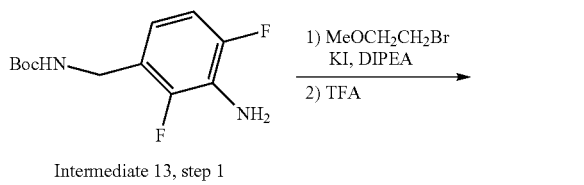

Intermediate 13, step 1

Step 1: Preparation of tert-butyl 2,4-difluoro-3-((2-methoxyethyl)amino)benzylcarbamate The title compound was prepared by a method similar to Intermediate 18, step 1, using tert-butyl 3-amino-2,4-difluorobenzylcarbamate (Intermediate 13, step 1) instead of tert-butyl (2-amino-4-fluorobenzyl)carbamate, and 1-bromo-2-methoxyethane instead of bromoethane. The product was purified by silica gel chromatography (heptane/EtOAc=100/0 to 50/50) to yield the title compound (0.345 g, 63% yield). LCMS: m/z 317.1 (M+H).

Step 2: Preparation of 3-(aminomethyl)-2,6-difluoro-N-(2-methoxyethyl)aniline The title compound was prepared by a method similar to Intermediate 4, step 2, using tert-butyl 2,4-difluoro-3-((2-methoxyethyl)amino)benzylcarbamate instead of N-Boc 4-(aminomethyl)-2-fluoroaniline. The titled compound was isolated as a TFA salt (0.650 g, 100% yield). LCMS: m/z 217.2 (M+H).

Intermediate 29: 3-(aminomethyl)-6-fluoro-2-methylbenzamide

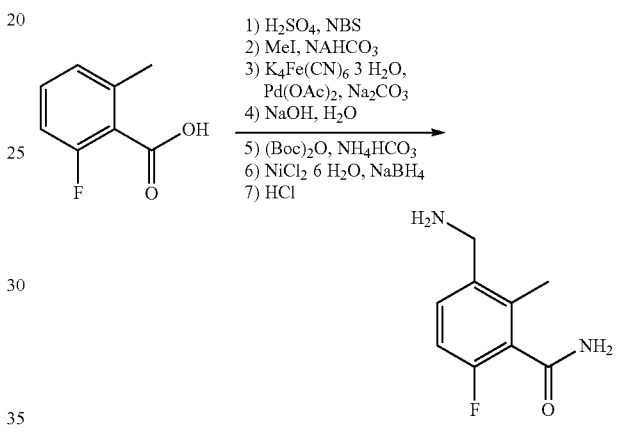

Step 1: Preparation of methyl 2-(2-fluoro-5-methylphenyl)acetate

To a stirred solution of 2-fluoro-6-methylbenzoic acid (2 g, 12.97 mmol) in concentrated H$_2$SO$_4$ (60 mL) at 0° C. was added NBS (2.41 g, 13.62 mmol). The mixture was stirred at RT for 3 h at 0° C. The mixture was brouth to RT and stirred for 16 h. The mixture was poured into ice water and was extracted with ether. The organic extracts were combined, washed with water and brine, dried over Na$_2$SO$_4$, filtered, and concentrated in vacuo to give the title compound (2.3 g, 76% yield) as an off-white solid. The crude product was carried forward to next step without purification. LCMS: m/z 231 (M–2H).

Step 2: Preparation of methyl 3-bromo-6-fluoro-2-methylbenzoate

To a stirred solution of the product in step 1 (1 g, 4.29 mmol) in DMF (10 mL) was added NaHCO$_3$ (1.08 g, 12.87 mmol). The mixture was stirred at RT for 15 min followed by addition of MeI (1.21 g, 8.58 mmol). The mixture was stirred at RT for 16 h. The mixture was poured into ice water and was extracted with EtOAc. The organic extracts were combined, washed with water and brine, dried over Na$_2$SO$_4$, filtered, and concentrated in vacuo to afford the title compound (0.85 g, 85% yield) as yellow liquid. The crude product was carried forward to next step without purification.

Step 3: Preparation of methyl 3-cyano-6-fluoro-2-methylbenzoate

To a stirred solution of the product in step 2 (1 g, 4.04 mmol) in DMA (10 mL) were potassium hexacyanoferrate (II) trihydrate (0.43 g, 1.01 mmol), Pd(OAc)$_2$ (45 mg, 0.2 mmol), and Na$_2$CO$_3$. The mixture was purged with argon and stirred at 140° C. for 16 h. The mixture was diluted with EtOAc (20 mL), and filtered on a pad of Celite. To the filtrate was added water and EtOAc. The organic layer was separated and washed with brine, dried over Na$_2$SO$_4$, filtered, and concentrated in vacuo. The crude residue was purified by ICO silica gel chromatography (EtOAc/Hexane=3:7) purified to give the title compound (0.35 g, 44% yield) as an off-white solid.

Step 4: Preparation of 3-cyano-6-fluoro-2-methylbenzoic acid

The title compound was prepared by a method similar to Intermediate 22, step 4, using the product in step 3 (0.35 g, 1.911 mmol) and sodium hydroxide (0.144 g, 3.623 mmol) instead of the product obtained for Intermediate 22, step 3 and lithium hydroxide, respectively. The mixture was concentrated concentrated in vacuo and extracted in EtOAc. Organic layer was discarded and aqueous layer was acidified with 3N HCl solution and extracted in DCM. Organic layer was dried over Na$_2$SO$_4$, filtered, concentrated in vacuo to give the title compound (0.3 g, 90% yield) as an off-white solid. The crude product was carried forward to next step without purification. LCMS: m/z 177.9 (M–H).

Step 5: Preparation of 3-cyano-6-fluoro-2-methylbenzamide

The title compound was prepared by a method similar to Intermediate 22, step 5. using the product in step 4. The crude residue was purified by silica gel chromatography (EtOAc/DCM=45/55) to give the title compound (80 mg, 75% yield) as an off-white solid.

Step 6: Preparation of tert-butyl 2-(3-carbamoyl-4-fluoro-2-methylphenyl)acetate The title compound was prepared by a method similar to Intermediate 4, step 1, using 3-cyano-6-fluoro-2-methylbenzamide instead of 4-amino-3-fluorobenzonitrile. The crude residue was then purified by silica gel chromatography (MeOH/DCM=1/9) to give the title compound (75 mg, 0.265 mmol, 59%) as an off-white solid.

Step 7: Preparation of 3-(aminomethyl)-6-fluoro-2-methylbenzamide

The title compound was prepared by a method similar to Intermediate 4, step 2, using tert-butyl 2-(3-carbamoyl-4-fluoro-2-methylphenyl)acetate instead of N-Boc 4-(aminomethyl)-2-fluoroaniline. The mixture was concentrated in vacuo. The solid obtained was filtered and dried under vacuum to give the title compound (55 mg, 95% yield) as an off-white solid. The crude product was carried forward to next step without purification. LCMS: m/z 183 (M+H).

Intermediate 30: 4-(aminomethyl)-3,5-difluoroaniline

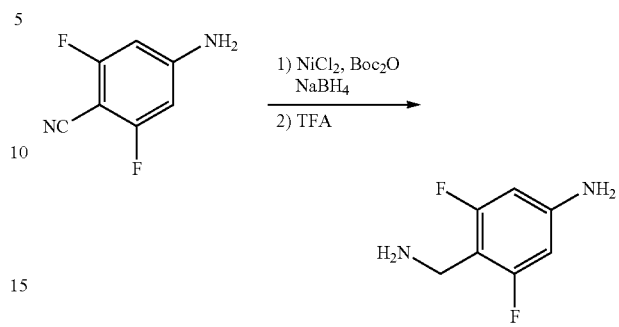

Step 1: Preparation of tert-butyl (4-amino-2,6-difluorobenzyl)carbamate

The title compound was prepared by a method similar to Intermediate 4, step 1, using 4-amino-2,6-difluorobenzonitrile instead of 4-amino-3-fluorobenzonitrile. LCMS: m/z 203.2 (M+H-tBu).

Step 2: Preparation of 4-(aminomethyl)-3,5-difluoroaniline

The title compound was prepared by a method similar to Intermediate 4, step 2. No m/z for the product (LCMS) was observed. The identity of the structure was confirmed as its derivative in the next step (Example 80).

Intermediate 31: (E)-1'-(but-2-en-1-yl)-6'-fluoro-1'H-spiro[piperidine-4,2'-quinolin]-4'(3'H)-one

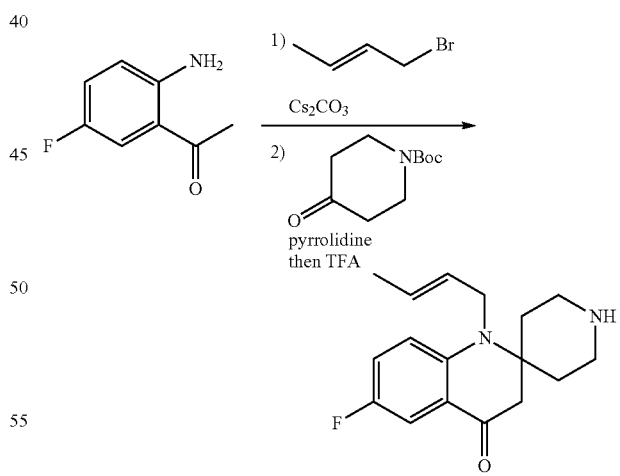

Step 1: Preparation of (E)-1-(2-(but-2-en-1-ylamino)-5-fluorophenyl)ethanone 1-(2-amino-5-fluorophenyl)ethanone (250 mg, 1.632 mmol) was added to a solution of Cs$_2$CO$_3$ (532 mg, 1.632 mmol) in DMF (15 mL). The reaction mixture was stirred at RT for 30 min. Then (E)-1-bromobut-2-ene (0.237 mL, 2.285 mmol) was added dropwise to this solution and the reaction was heated at 80° C. for 48 h. The reaction was quenched with water and the aqueous layer was extracted with Et₂O (3×20 mL). The combined organic layers were dried over Na₂SO₄ and purified by silica gel chromatography (heptane/EtOAc=100/0 to 70/30) to yield the title compound (280 mg, 79% yield) as a yellow solid. $^1$H NMR (400 MHz, DMSO-d₆) δ 7.65 (dt, J=10.3, 3.3 Hz, 1H), 7.35-7.25 (m, 1H), 6.75 (dd, J=9.4, 4.7 Hz, 1H), 5.72-5.62 (m, 1H), 5.59-5.47 (m, 1H), 3.85-3.75 (m, 2H), 2.53 (s, 3H), 1.71-1.64 (m, 3H).

Step 2: Preparation of (E)-1'-(but-2-en-1-yl)-6'-fluoro-1'H-spiro[piperidine-4,2'-quinolin]-4'(3'H)-one To a stirred solution of the product in step 1 (280 mg, 1.284 mmol) in MeOH (10 mL) was added tert-butyl 4-oxopiperidine-1-carboxylate (558 mg, 2.80 mmol) and pyrrolidine (0.231 mL, 2.80 mmol). The reaction was heated to reflux over 72 h. The reaction mixture was then diluted with EtOAc, washed with aqueous saturated sodium bicarbonate, dried over Na₂SO₄ and concentrated under reduced pressure. The residue was purified by silica gel chromatography (heptane/EtOAc=100/0 to 70/30) to afford Boc-protected (E)-1'-(but-2-en-1-yl)-6'-fluoro-1'H-spiro[piperidine-4,2'-quinolin]-4'(3'H)-one (370 mg). This Boc intermediate was then dissolved in HCl 4N in dioxane (1.399 mL, 5.60 mmol) and stirred at RT for 15 h. The HCl salt of the desired compound precipitated and was isolated by filtration (240 mg, 42% yield) as a yellow powder. The structural identity of this product was confirmed as it derivative (Example 85).

Intermediate 32: 4-(aminomethyl)-2-chloroaniline

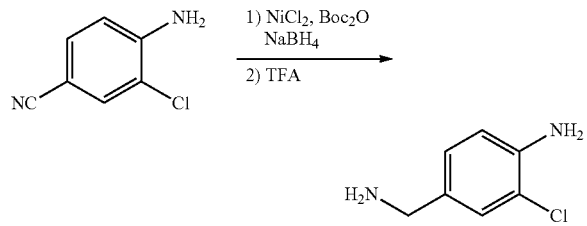

Step 1: Preparation of tert-butyl (4-amino-3-chlorobenzyl)carbamate

The title compound was prepared by a method similar to Intermediate 4, step 1, using 4-amino-3-chlorobenzonitrile instead of 4-amino-3-fluorobenzonitrile. LCMS: m/z 201.1 (M+H-tBu).

Step 2: Preparation of 4-(aminomethyl)-2-chloroaniline

The title compound was prepared by a method similar to Intermediate 4, step 2. No m/z for the product (LCMS) was observed. The identity of the structure was confirmed as its derivative in the next step (Example 87).

Intermediate 33: 2-(2-oxopyrrolidin-1-yl)acetaldehyde

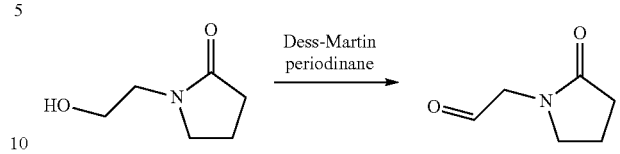

A mixture of 1-(2-hydroxyethyl)pyrrolidin-2-one (67 mg, 0.52 mmol) and Dess-Martin periodinane (280 mg, 0.660 mmol) in DCM (2 mL) was stirred at RT for 3 h, passed through a pad of silica (elution with DCM then 10% EtOAc in DCM). The filtrate was concentrated by rotatory evaporator (70 mmHg) without heating. The crude product was used directly in the next step (Example 90).

Intermediate 34: 4-(aminomethyl)-3-(trifluoromethyl)aniline

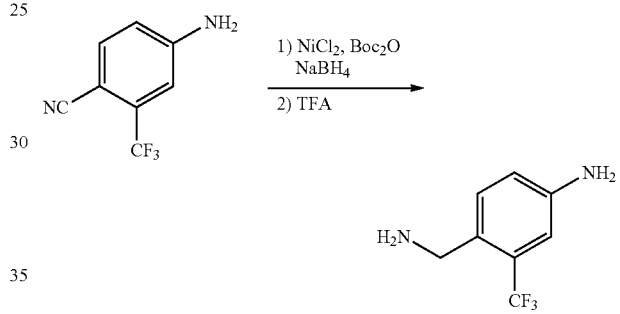

Step 1: Preparation of tert-butyl (4-amino-2-trifluoromethylbenzyl)carbamate

The title compound was prepared by a method similar to Intermediate 4, step 1, using 4-amino-2-(trifluoromethyl)benzonitrile instead of 4-amino-3-fluorobenzonitrile. LCMS: m/z 235.2 (M+H-tBu).

Step 2: Preparation of 4-(aminomethyl)-3-(trifluoromethyl)aniline

The title compound was prepared by a method similar to Intermediate 4, step 2. No m/z for the product (LCMS) was observed. The identity of the structure was confirmed as its derivative in the next step (Example 104).

Intermediate 35: 4-(aminomethyl)-3-chloroaniline

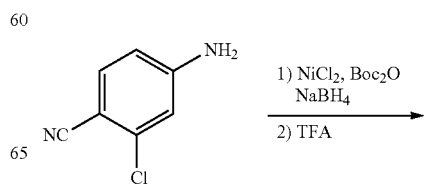

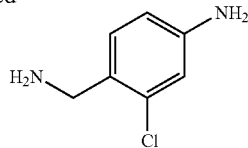

Step 1: Preparation of tert-butyl (4-amino-2-chlorobenzyl)carbamate

The title compound was prepared by a method similar to Intermediate 4, step 1, using 4-amino-2-chlorobenzonitrile instead of 4-amino-3-fluorobenzonitrile. LCMS: m/z 201.2 (M+H-tBu).

Step 2: Preparation of 4-(aminomethyl)-3-chloroaniline

The title compound was prepared by a method similar to Intermediate 4, step 2. No m/z for the product (LCMS) was observed. The identity of the structure was confirmed as its derivative in the next step (Example 111).

Intermediate 36: 4-(aminomethyl)-2-(trifluoromethyl)aniline

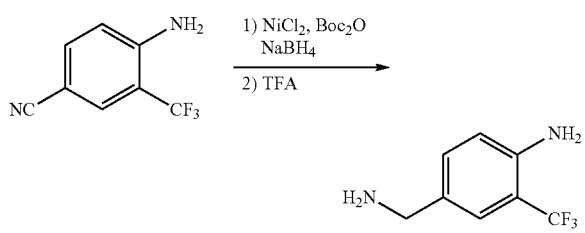

Step 1: Preparation of tert-butyl (4-amino-3-trifluoromethylbenzyl)carbamate The title compound was prepared by a method similar to Intermediate 4, step 1, using 4-amino-3-(trifluoromethyl)benzonitrile instead of 4-amino-3-fluorobenzonitrile. LCMS: m/z 190.1 (M-Boc).

Step 2: Preparation of 4-(aminomethyl)-2-(trifluoromethyl)aniline

The title compound was prepared by a method similar to Intermediate 4, step 2. LCMS: m/z 190.1 (M).

Intermediate 37: 4-(aminomethyl)-3-methylaniline

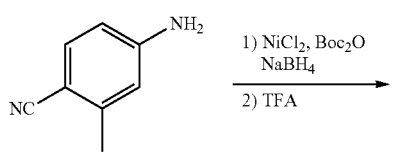

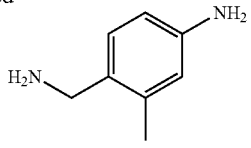

Step 1: Preparation of tert-butyl (4-amino-3-trifluoromethylbenzyl)carbamate The title compound was prepared by a method similar to Intermediate 4, step 1, using 4-amino-2-methylbenzonitrile instead of 4-amino-3-fluorobenzonitrile. LCMS: m/z not observed.

Step 2: Preparation of 4-(aminomethyl)-2-(trifluoromethyl)aniline

The title compound was prepared by a method similar to Intermediate 4, step 2. No m/z for the product (LCMS) was observed. The identity of the structure was confirmed as its derivative in the next step (Example 116).

Intermediate 38: 4-(aminomethyl)-2-methylaniline

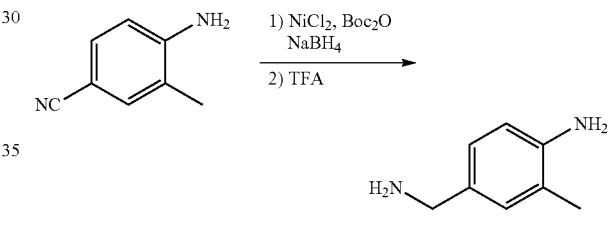

Step 1: Preparation of tert-butyl (4-amino-3-trifluoromethylbenzyl)carbamate The title compound was prepared by a method similar to Intermediate 4, step 1, using 4-amino-3-methylbenzonitrile instead of 4-amino-3-fluorobenzonitrile. LCMS: m/z 181.2 (M+H-tBu).

Step 2: Preparation of 4-(aminomethyl)-2-(trifluoromethyl)aniline

The title compound was prepared by a method similar to Intermediate 4, step 2. No m/z for the product (LCMS) was observed. The identity of the structure was confirmed as its derivative in the next step (Example 119).

Intermediate 39: N-(5-(aminomethyl)-2-fluorophenyl)methanesulfonamide

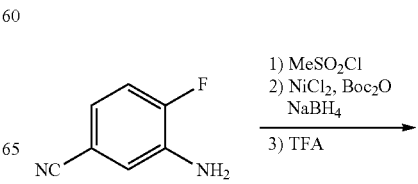

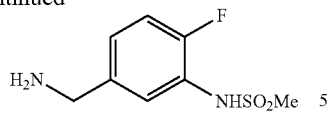
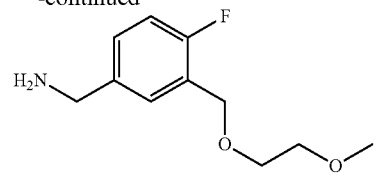

Step 1: Preparation of N-(5-cyano-2-fluorophenyl)methanesulfonamide

To an ice cold solution of 3-amino-4-fluorobenzonitrile (500 mg, 3.67 mmol) in pyridine (8162 µl) was added methylsulfonyl chloride (256 µl, 3.31 mmol) dropwise. The reaction was stirred at RT overnight. The reaction was concentrated and the residue was partitioned between 1N aqueous HCl and EtOAc. The organic layer was washed with brine, dried over MgSO$_4$ and filtered. The filtrate was concentrated to give the title compound as a pale pink solid (708 mg, 90% yield). HRMS: m/z 215.0292 (M+H).

Step 2: Preparation of tert-butyl 4-fluoro-3-(methylsulfonamido)benzylcarbamate The title compound was prepared by a method similar to Intermediate 4, step 1. LCMS: m/z 317.0 (M−H).

Step 3: Preparation of N-(5-(aminomethyl)-2-fluorophenyl)methanesulfonamide

The title compound was prepared by a method similar to Intermediate 4, step 2. The mixture was filtered through SCX column using 7N NH$_3$ in Methanol. The eluent was concentrated to afford the title compound as a white solid (50 mg, 72.9% yield). LCMS: m/z 218.1 (M+H).

Intermediate 40: Methyl 2,2-dimethyl-3-oxopropanoate

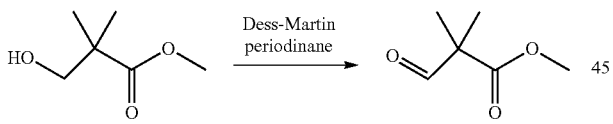

The title compound was prepared by a method similar to Intermediate 33, using methyl 3-hydroxy-2,2-dimethylpropanoate instead of 1-(2-hydroxyethyl)pyrrolidin-2-one. The crude product was used directly in the next step (Example 140).

Intermediate 41: (4fluoro-3-((2-methoxyethoxy)methyl)phenyl)methanamine

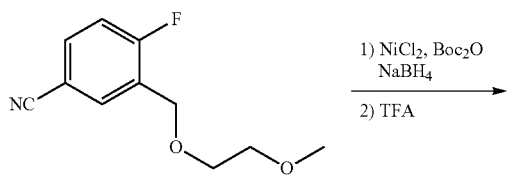

Step 1: Preparation of tert-butyl 4-fluoro-3-((2-methoxyethoxy)methyl)benzylcarbamate The title compound was prepared by a method similar to Intermediate 4, step 1, using 4-fluoro-3-((2-methoxyethoxy)methyl)benzonitrile instead of 4-amino-3-fluorobenzonitrile. LCMS: m/z 214.0 (M+H-Boc).

Step 2: Preparation of (4-fluoro-3-((2-methoxyethoxy)methyl)phenyl)methanamine The title compound was prepared by a method similar to Intermediate 4, step 2. The mixture was filtered through SCX column using 7N NH$_3$ in Methanol. The eluent was concentrated to afford the title compound as a yellow oil (95 mg, 78% yield). LCMS: m/z 214.0 (M+H).

Intermediate 42: 3-(aminomethyl)-2,6-difluorobenzamide

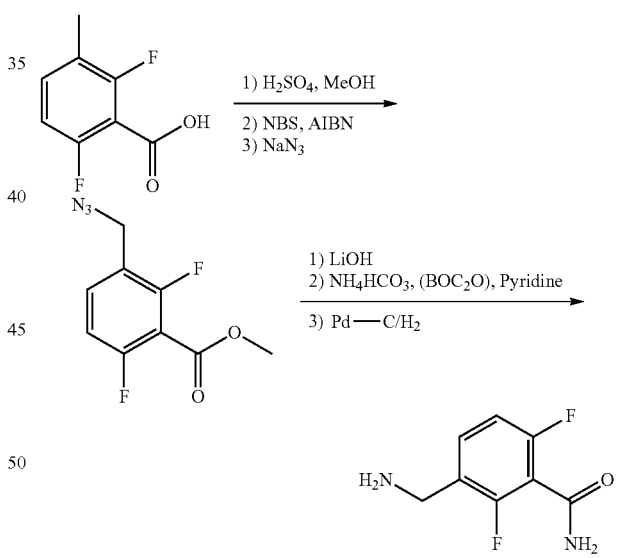

Step 1: Preparation of methyl 2,6-difluoro-3-methylbenzoate

To a solution of 2,6-difluoro-3-methylbenzoic acid (1.0 g, 5.81 mmol) in MeOH (10 mL) was added H$_2$SO$_4$ (2 mL) slowly at 0° C. The reaction mixture allowed to stirred for 16 h at 70° C., then concentrated under reduced pressure. The residue was then diluted with cold water, basified with saturated NaHCO$_3$ solution and extracted with DCM. The organic layer was washed with brine solution and dried over Na$_2$SO$_4$ and then concentrated under reduced pressure to afford the crude product as a colorless oil (600 mg, 55% yield), that was directly engaged in next reaction step.

Step 2: Preparation of methyl 3-(bromomethyl)-2,6-difluorobenzoate

The title compound was obtained by a method similar to Intermediate 25, step 4, using methyl 2,6-difluoro-3-methylbenzoate instead of 1,5-difluoro-2-(2-methoxyethoxy)-4-methylbenzene. The product was purified by silica gel chromatography (hexane/EtOAc=100/0 to 90/10) to yield the title compound (310 mg, 36% yield) as a white solid.

Step 3: Preparation of methyl 3-(azidomethyl)-2,6-difluorobenzoate

The title compound was obtained by a method similar to Intermediate 25, step 5, using methyl 3-(bromomethyl)-2,6-difluorobenzoate instead of 1-(bromomethyl)-2,4-difluoro-5-(2-methoxyethoxy)benzene. The crude product (250 mg, 95% yield) was engaged directly in the next reaction step.

Step 4: Preparation of 3-(azidomethyl)-2,6-difluorobenzoic acid

To a solution of methyl 3-(azidomethyl)-2,6-difluorobenzoate (250 mg, 1.10 mmol) in THF (8 mL) and MeOH (2 mL) was added LiOH.H$_2$O (230 mg, 5.50 mmol) and water (1.5 mL). The reaction mixture was allowed to stirred for 16 h at RT, then concentrated under reduced pressure. The residue was acidified with 2 N HCl solution and was extracted with EtOAc. The separated organic layer was washed with brine solution, dried over Na$_2$SO$_4$ and then concentrated under reduced pressure to provide the crude product (200 mg, 0.93 mmol) that was directly engaged in next reaction step. LCMS: m/z 211.8 (M–H).

Step 5: Preparation of 3-(azidomethyl)-2,6-difluorobenzamide

To a stirred solution of 3-(azidomethyl)-2,6-difluorobenzoic acid (200 mg, 0.93 mmol) in DMF (10 mL) was added pyridine (0.159 mL, 1.87 mmol) followed by (Boc)$_2$O (0.63 g, 2.90 mmol) and NH$_4$HCO$_3$ (230 mg, 2.90 mmol). The reaction mass was stirred at RT for 16 h. The Reaction mixture was then quenched with sat. NH$_4$Cl solution and extracted with EtOAc. The separated organic layer was washed with brine solution, dried over Na$_2$SO$_4$ and then concentrated under reduced pressure. The residue was purified by silica gel chromatography (hexane/EtOAc=100/0 to 50/50) to give the title product (120 mg, 63% yield as white solid). LCMS: m/z 212.9 (M+H).

Step 6: Preparation of 3-(aminomethyl)-2,6-difluorobenzamide

The title compound was obtained by a method similar to Intermediate 25, step 6, using 3-(azidomethyl)-2,6-difluorobenzamide instead of 11-(azidomethyl)-2,4-difluoro-5-(2-methoxyethoxy)benzene. The crude product (120 mg, 69% yield) was isolated as a yellow solid. LCMS: m/z 187.0 (M+H).

Intermediate 43: 2-(5-(aminomethyl)-2-fluorophenyl)propan-2-ol

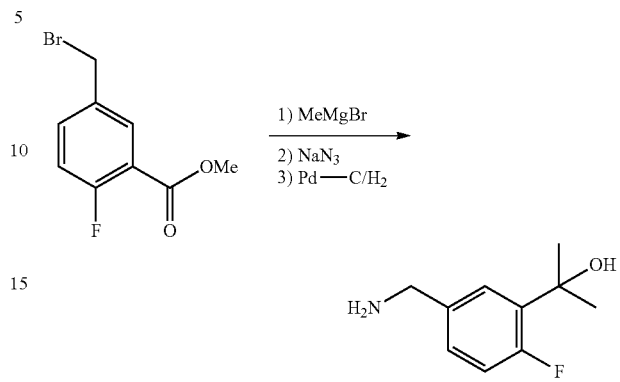

Step 1: Preparation of 2-(5-(bromomethyl)-2-fluorophenyl)propan-2-ol

To a solution of methyl 5-(bromomethyl)-2-fluorobenzoate (2.5 g, 10.12 mmol) in Et$_2$O (100 mL) was added MeMgBr 3.0 M solution in Et$_2$O (10.7 mL, 32.3 mmol) at 0° C. The reaction mixture was stirred at RT for 3 h then cooled to 0° C. and treated with NH$_4$Cl solution and EtOAc. After 15 min stirring, the organic layer was separated, washed with brine, dried over Na$_2$SO$_4$, and concentrated under reduced pressure. Crude compound was purified by silica gel chromatography (hexane/EtOAc=70/30) to afford the desired product (1.5 g, 60% yield) as yellow liquid.

Step 2: Preparation of 2-(5-(azidomethyl)-2-fluorophenyl)propan-2-ol

The title compound was obtained by a method similar to Intermediate 25, step 5 using 2-(5-(bromomethyl)-2-fluorophenyl)propan-2-ol. The crude product (1.1 g, 59% yield) was engaged in the next reaction.

Step 3: Preparation of 2-(5-(aminomethyl)-2-fluorophenyl)propan-2-ol

The title compound was obtained by a method similar to Intermediate 25, step 6 using 2-(5-(azidomethyl)-2-fluorophenyl)propan-2-ol. The crude product was purified by silica gel chromatography (DCM/MeOH=97/3) to afford the title compound (0.27 g, 28% yield).

Intermediate 44: 6'-fluoro-8'-methyl-1'H-spiro[piperidine-4,2'-quinolin]-4'(3'H)-one

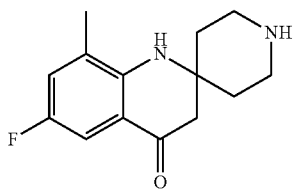

Step 1: Preparation of 1-(2-amino-5-fluoro-3-methylphenyl)ethan-1-one

To a solution of 2-bromo-4-fluoro-6-methylaniline (1.0 g, 4.90 mmol) in DMF (20 mL) were added ethoxy vinyl tributyl tin (2.6 g, 7.35 mmol) and Pd(PPh₃)₄ (57 mg, 0.05 mmol) at RT under argon. The reaction mixture was stirred in a sealed tube for 15 h at 110° C. The reaction mixture was then stirred with 20% HCl solution for 2 h, diluted water and extracted with EtOAc (2×50 mL). The combined organic layer were dried over Na₂SO₄ and concentrated under reduced pressure. The residue was purified by silica gel chromatography (hexane/EtOAc=100/0 to 30/70) to yield the title compound (600 mg, 73% yield).

Step 2: Preparation of 6'-fluoro-8'-methyl-1'H-spiro[piperidine-4,2'-quinolin]-4'(3'H)-one To a solution of 1-(2-amino-5-fluoro-3-methylphenyl)ethan-1-one (600 mg, 3.59 mmol) in EtOH (50 mL) was added tert-butyl 4-oxopiperidine-1-carboxylate (1.07 g, 5.38 mmol) and pyrrolidine (0.44 mL, 7.18 mmol). The reaction mixture was stirred at 120° C. for 48 h in sealed tube, then concentrated and diluted with water and extracted with EtOAc. The organic layer was dried over Na₂SO₄ and concentrated under reduced pressure. The residue was purified by silica gel chromatography (hexane/EtOAc=100/0 to 30/70) to yield Boc-protected 6'-fluoro-8'-methyl-1'H-spiro[piperidine-4,2'-quinolin]-4'(3'H)-one (380 mg). The Boc intermediate was diluted in dioxane (4 mL) and 2 mL of HCl 4N in dioxane was added. The reaction mixture was stirred at RT for 16 h, concentrated under reduced pressure, and the solid obtained was washed with ether and dried under vacuum to afford the title compound as an HCl salt (300 mg, 34% yield, yellow solid). LCMS: m/z 249.1 (M+H).

Intermediate 45: 1-(5-(aminomethyl)-2-fluorophenyl)ethanol

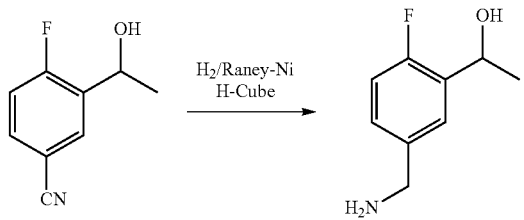

4-fluoro-3-(1-hydroxyethyl)benzonitrile (320 mg, 1.973 mmol) in methanol (10 mL) solution was run a H-cube PRO™ through a Raney Ni CatCarts® at 20° C. with H₂ pressure at 50 bar (1 mL/min) for 1 h. Volatiles were removed in vacuo. The crude residue was purified by a preparative HPLC (Basic, Method 2) to give the title compound (120 mg, 37% yield). LCMS: m/z 170.1 (M+H); ¹H NMR (400 MHz, Methanol-d₄) δ 7.52-7.45 (m, 1H), 7.28-7.19 (m, 1H), 6.99 (dd, J=10.4, 8.4 Hz, 1H), 5.11 (q, J=6.4 Hz, 1H), 3.79 (s, 2H), 1.43 (d, J=6.5 Hz, 3H).

Intermediate 46: (R)-1-(5-(aminomethyl)-2-fluorophenyl)-2,2,2-trifluoroethanamine

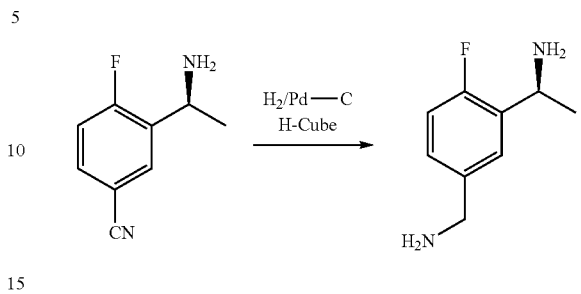

A solution of (R)-3-(1-amino-2,2,2-trifluoroethyl)-4-fluorobenzonitrile (218 mg, 1 mmol) in methanol (20 mL) was run a H-cube PRO™ through a Pd/C CatCarts® at 20° C. with H₂ pressure at 1 bar for 1 h at flow rate of 1 mL/min. The crude mixture was poured into 2×5 g SCX columns. The columns were flushed with MeOH (4×10 mL). The product was eluted from the column using a 7N methanoic ammonia solution (2×20 mL). The volatiles were removed in vacuo to give the title compound (178 mg, 80% yield). LCMS: m/z 223.3 (M+H). The crude product was carried forward to next step without purification.

Intermediate 47: (2-(trifluoromethyl)furan-3-yl)methanamine

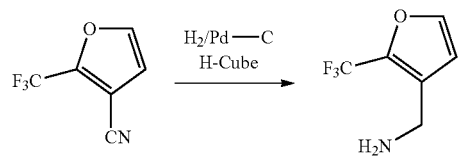

A solution of 2-(trifluoromethyl)furan-3-carbonitrile (150 mg, 0.931 mmol) in methanol (10 mL) was run a H-cube PRO™ through a Pd/C CatCarts® at 25° C. with H₂ pressure at 1 bar for 1 h at flow rate of 1 mL/min at 20° C. with H₂ pressure at 50 bar. Volatiles were removed in vacuo to give the title compound (60 mg, 39% yield). LCMS: m/z 166.1 (M+H). The crude product was carried forward to next step without further purification.

Intermediate 48: (4-fluoro-3-(3-methoxyazetidin-1-yl)phenyl)methanamine

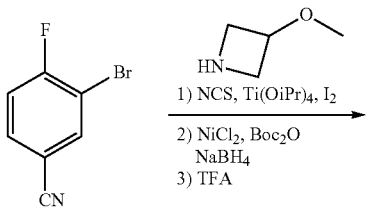

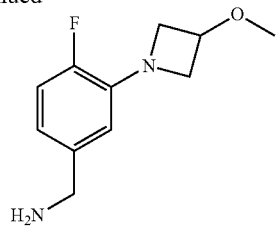

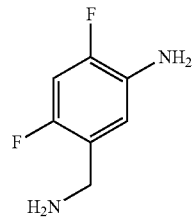

Step 1: Preparation of 4-fluoro-3-(3-methoxyazetidin-1-yl)benzonitrile

The title compound was prepared by referencing Angew. Chem. Int. Ed. 2011, 50, 8325-8328. An oven dried flask cooled −40° C. was added 1.3 M THF solution of isopropylmagnesium chloride lithium chloride (3846 µl, 5.00 mmol), and 3-bromo-4-fluorobenzonitrile (1 g, 5.00 mmol). The mixture was stirred for 3 h at −40° C., and then was then titrated with iodine. To an oven dried 10 mL vial under $N_2$, 3-methoxyazetidine (0.247 g, 2 mmol), and N-Chlorosuccinimide (0.668 g, 5.00 mmol) were stirred in toluene (5 mL). After 20 min, to a separate oven dried 10 mL vial at −40° C. under N2 was added toluene (5 mL) and 0.7 M solution of (5-cyano-2-fluorophenyl)magnesium bromide in THF, and titanium isopropoxide (1.421 g, 5.00 mmol) while stirring. After additional 5 min, the N-chloroaniline was cooled to −40° C., and the −40° C. solution was added by a syringe. The bath temperature was slowly brought to R.T over 1 h. After 3 h, the mixture was quenched with saturated aqueous solution of K2CO3 (10 mL). The cured mixture was diluted with of EtOAc (50 mL) and filtered. The aqueous layer was further extracted EtOAc (2×50 mL). The organic extracts were combined, dried with Na2SO4, filtered, and concentrated in vacuo. Purification was performed using silica gel chromatography with a gradient from neat hexanes to (85:15) hexanes/EtOAc. The crude residue was then purified by silica gel chromatography (EtOAc/Heptane, 85/15) to give titled compound (0.728 g, 85% yield). LCMS: MS m/z 207.3 (M+H).

Step 2 and Step 3: Preparation of (4-fluoro-3-(3-methoxyazetidin-1-yl)phenyl)methanamine The title compound was prepared by a method similar to Intermediate 4, using 4-fluoro-3-(3-methoxyazetidin-1-yl) benzonitrile instead of 4-amino-3-fluorobenzonitrile instead of 4-amino-3-fluorobenzonitrile gives title compound (33 mg, 28% yield over 2 steps) as a colorless oil. LCMS: m/z 211.2 (M+H).

Intermediate 49: 5-(aminomethyl)-2,4-difluoroaniline

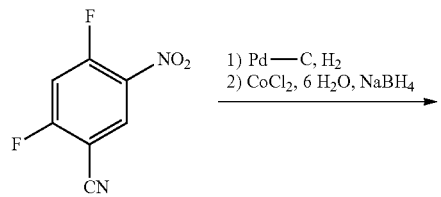

Step 1: Preparation of 5-amino-2,4-difluorobenzonitrile

To a stirred solution of 2,4-difluoro-5-nitrobenzonitrile (1.94 g, 10.56 mmol) in MeOH (40 mL) under $N_2$ gas was added Pd/C 10% wet (0.112 g, 1.056 mmol). The mixture was hydrogenated at RT for 16 h. The reaction mixture was filtered over a pad of Celite and eluted with MeOH. The filtrate was concentrated in vacuo, then purified by silica gel chromatography (heptane/EtOAc=100/0 to 50/50) to give the title compound (1.21 g, 74% yield) after concentration in vacuo. LCMS: m/z 153.1 (M−H); $^1$H NMR (400 MHz, DMFS-$d_6$) δ 7.44 (dd, J=11.3, 9.5 Hz, 1H), 7.08 (dd, J=9.3, 6.6 Hz, 1H), 5.56 (s, 2H).

Step 2: Preparation of 5-(aminomethyl)-2,4-difluoroaniline

To a solution of the product in step 1 (1.2 g, 7.84 mmol) in methanol (50 mL) was added cobalt(II) chloride hexahydrate ($CoCl_2.6H_2O$) (1.87 g, 7.84 mmol) followed by portion-wise addition of $NaBH_4$ (0.89 g, 23.53 mmol) at 0° C. The mixture was brought to RT and stirred for additional 12 h. The mixture was quenched by adjusting the pH to 13 with ammonium hydroxide and extracted with EtOAc (3×50 mL). The combined organic layer was washed with brine, dried over $Na_2SO_4$, and concentrated in vacuo. The crude was purified by a preparative reversed-phase HPLC (TFA, Method 0) to give the title compound (564 mg, 46% yield). LCMS: m/z 159.01 (M−H); $^1$H NMR (400 MHz, DMF-$d_7$) δ 7.07-6.91 (m, 1H), 6.82 (dd, J=10.0, 7.8 Hz, 1H), 3.72 (s, 2H).

Intermediate 50: benzo[c][1,2,5]oxadiazol-4-ylmethanamine

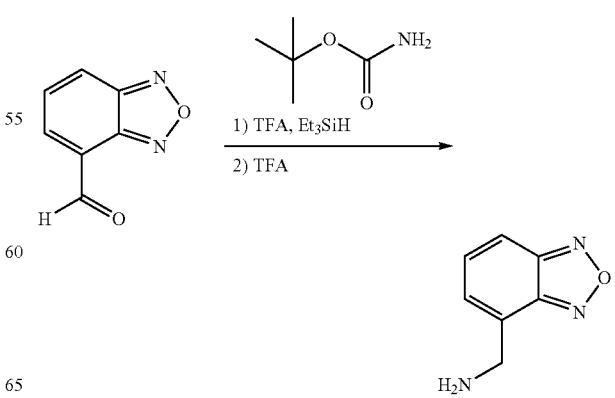

Step 1: Preparation of tert-butyl (benzo[c][1,2,5] oxadiazol-4-ylmethyl)carbamate To a stirred solution of benzo[c][1,2,5]oxadiazole-4-carbaldehyde (0.5 g, 3.37 mmol) in acetonitrile (20 mL) was added tert-butyl carbamate (1.18 g 10.13 mmol), triethylsilane (1.61 mL, 10.13 mmol), and TFA (0.5 mL) at RT. The mixture was stirred at RT for 16 h. The mixture was poured in to saturated aqueous NaHCO$_3$, and extracted with EtOAc. The organic layer was washed with saturated sodium chloride, and dried over Na$_2$SO$_4$, filtered, and concentrated in vacuo to give crude title product (450 mg, 53% yield) which was carried forward to next step without purification. LCMS: m/z 250.1 (M+H).

Step 2: Preparation of benzo[c][1,2,5]oxadiazol-4-ylmethanamine

A solution of the crude residue in step 1 in TFA (3 mL) was stirred at RT for 1 h. After the volatiles were removed in vacuo, and the crude residue was triturated with pentane (10 mL) and diethyl ether (10 mL), dried in vacuo to give crude title product (322 mg). The crude product was carried forward to next step without purification. LCMS: m/z 150.1 (M+H).

Intermediate 51: (5-(aminomethyl)-2-fluorophenyl)methanesulfonamide

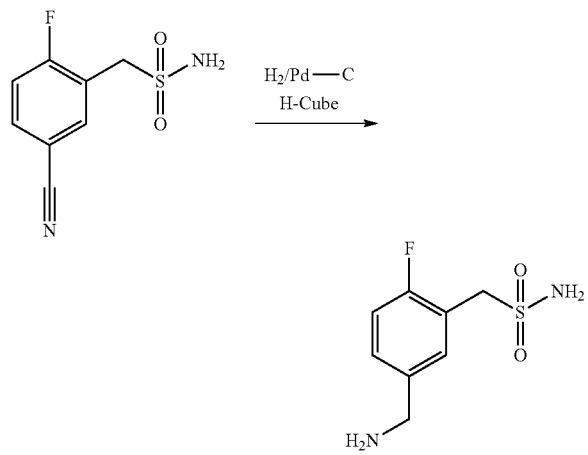

(5-Cyano-2-fluorophenyl)methanesulfonamide (480 mg, 2.241 mmol) in methanol (15 mL) solution was run a H-cube PRO™ through a Pd/C CatCarts® at 40° C. with H$_2$ pressure at 30 bar for 1 h at flow rate of 1 mL/min. The crude mixture was poured into 2×5 g SCX columns. The columns were flushed with MeOH (4×10 mL). The product was eluted from the column using a 7N methanoic ammonia solution (2×20 mL). The volatiles were removed in vacuo to give the title compound (484 mg, 99% yield). LCMS: m/z 219.0 (M+H). $^1$H NMR (400 MHz, Methanol-d$_4$) δ 7.46 (dd, J=7.0, 2.1 Hz, 1H), 7.37 (ddd, J=7.4, 4.9, 2.3 Hz, 1H), 7.17-7.07 (m, 1H), 4.40 (d, J=3.1 Hz, 2H), 3.82 (s, 2H).

SYNTHESIS OF THE EXAMPLES

Example 1: 6'-fluoro-N-((5-methylfuran-2-yl)methyl)-4'-oxo-3',4'-dihydro-1'H-spiro[piperidine-4,2'-quinoline]-1-carboxamide

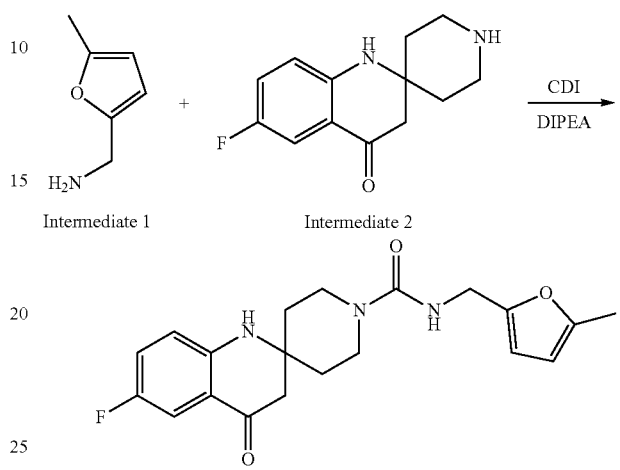

To a solution of (5-methylfuran-2-yl)methanamine (Intermediate 1) (50 mg, 0.23 mmol) in a mixture of DMF (1 mL) and acetonitrile (2 mL) in an ice bath was added CDI (40 mg, 0.25 mmol). Hunig's base (0.079 mL, 0.45 mmol) was then added, and the mixture was stirred for 30 min at this temperature. In a separate flask, a solution of Intermediate 2 as HCl salt (69 mg, 0.20 mmol) and Hunig's base (0.079 mL, 0.45 mmol) in DMF (1 mL) and acetonitrile (1 mL) was stirred at RT for 5 min. The mixture was then added to the cold reaction mixture of Intermediate 1 and CDI above. The mixture was heated at 40° C. for 18 h. The mixture was poured into saturated aqueous NaHCO$_3$ solution, and the product was extracted with EtOAc. The combined organic extract was dried over Na$_2$SO$_4$, filtered, and concentrated in vacuo. The crude residue was purified by silica gel chromatography (MeOH/DCM), followed by reverse-phase HPLC (Basic, Method 4) to give the title compound (18 mg, 21% yield) as a yellow solid after lyophilization. LCMS: m/z 372.4 (M+H); $^1$H NMR (400 MHz, DMSO-d$_6$) δ 7.28-7.16 (m, 2H), 6.96 (t, J=5.5 Hz, 1H), 6.93-6.86 (m, 1H), 6.80 (s, 1H), 6.01 (d, J=3.0 Hz, 1H), 5.99-5.91 (m, 1H), 4.14 (d, J=5.5 Hz, 2H), 3.50-3.26 (m, 4H), 2.60 (s, 2H), 2.21 (s, 3H), 1.66-1.46 (m, 4H).

Example 2: 6'-fluoro-N-(4-fluoro-2-methoxybenzyl)-1'-methyl-4'-oxo-3',4'-dihydro-1'H-spiro[piperidine-4,2'-quinoline]-1-carboxamide

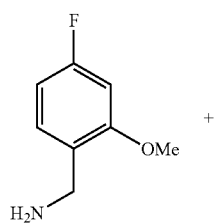

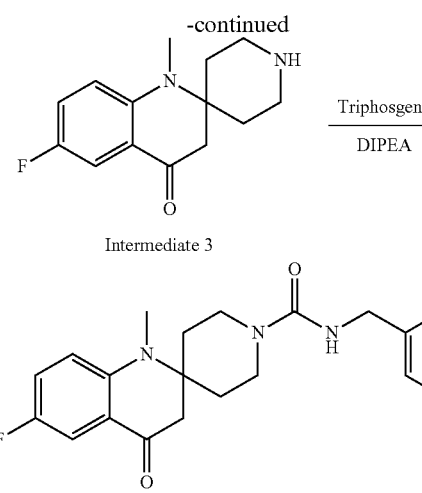

Intermediate 3

To a solution of (4-fluoro-2-methoxyphenyl)methanamine (60 mg, 0.39 mmol) in THF (7.5 mL) was added triphosgene (34.4 mg, 0.116 mmol) and DIPEA (0.135 mL, 0.773 mmol) at −20° C., and the reaction mixture was stirred for 1 h at −20° C. To this was then added a solution of intermediate 3 (110 mg, 0.387 mmol) and DIPEA (0.081 mL, 0.464 mmol) in 5 mL of THF at −20° C., and the mixture was allowed to warm to RT and stirred overnight. The reaction mixture was quenched with sat. NaHCO$_3$ aqueous solution, and the product was extracted with EtOAc. The EtOAc layer was concentrated, and purified by reverse-phase HPLC (Basic, Method 4) to give the title compound (82.6 mg, 50% yield). LCMS: m/z 429.9 (M); $^1$H NMR (400 MHz, DCM-d$_2$) δ 1.61 (d, J=12.4 Hz, 2H), 1.79 (td, J=12.9, 4.6 Hz, 2H), 2.77 (d, J=17.1 Hz, 5H), 2.84-2.96 (m, 2H), 3.73 (d, J=6.6 Hz, 5H), 4.21 (d, J=5.5 Hz, 2H), 4.95 (s, 1H), 6.42-6.62 (m, 2H), 6.70 (dd, J=9.3, 4.0 Hz, 1H), 7.01-7.21 (m, 2H), 7.39 (dd, J=8.6, 3.2 Hz, 1H).

Example 3: 6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide

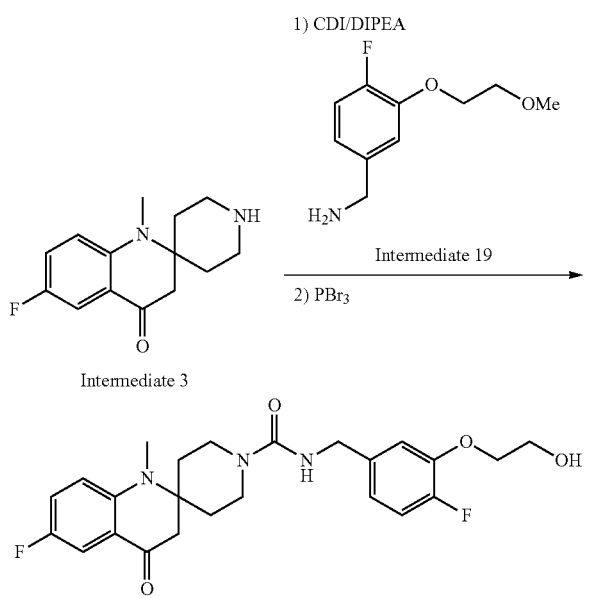

Step 1: Synthesis of 6'-fluoro-N-(4-fluoro-3-(2-methoxyethoxy)benzyl)-1'-methyl-4'-oxo-3',4'-dihydro-1'H-spiro[piperidine-4,2'-quinoline]-1-carboxamide The title compound was prepared by a method similar to Example 1, using Intermediate 19 and Intermediate 3 instead of Intermediates 1 and 2, respectively. The product was purified by silica gel chromatography (MeOH/DCM) to give the title compound (200 mg, 70% yield) as a yellow solid after lyophilization. LCMS: m/z 474.2 (M+H).

Step 2: Synthesis of 6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide To a cooled solution of the product in Step 1 (200 mg, 0.422 mmol) in DCM (4 mL) at 0° C. was slowly added BBr$_3$ (1M in THF, 1267 μL, 1.267 mmol). The reaction mixture was stirred at 0° C. for 1 h and then quenched by sat. aqueous NH$_4$Cl (15 mL) and extracted with DCM (2×5 mL). The organic layers were dried over sodium sulfate and concentrated under reduced pressure. The residue was purified by HPLC (Basic, Method 4) to afford the title compound as a yellow solid (100 mg, 51% yield). LCMS: m/z 460.1 (M+H); $^1$H NMR (400 MHz, Methanol-d$_4$) δ 7.43 (dd, J=8.7, 3.2 Hz, 1H), 7.24 (ddd, J=9.3, 7.9, 3.3 Hz, 1H), 7.09-6.97 (m, 2H), 6.94 (dd, J=9.3, 4.0 Hz, 1H), 6.85 (ddd, J=8.3, 4.3, 2.0 Hz, 1H), 4.29 (s, 2H), 4.10 (dd, J=5.3, 4.3 Hz, 2H), 3.95 (d, J=13.9 Hz, 2H), 3.88 (dd, J=5.4, 4.3 Hz, 2H), 3.12-3.01 (m, 2H), 2.94 (s, 3H), 2.93 (s, 2H), 1.93 (td, J=12.8, 4.7 Hz, 2H), 1.72 (d, J=13.2 Hz, 2H).

Example 4: 4-((6'-fluoro-4'-oxo-3',4'-dihydro-1'H-spiro[piperidine-4,2'-quinoline]-1-carboxamido)methyl)phenyl dihydrogen phosphate

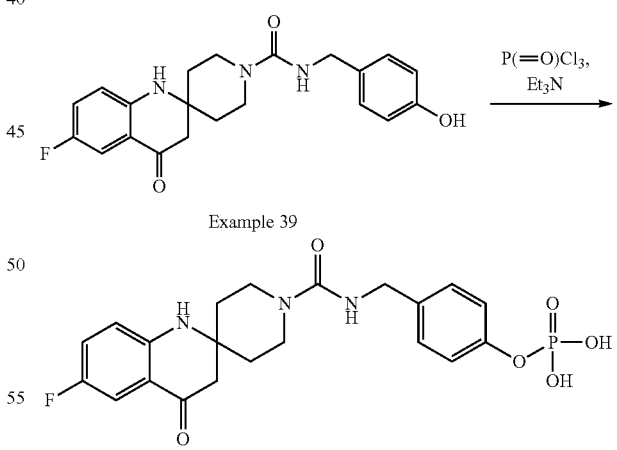

The title compound was prepared by a method similar to Example 28, using compound Example 39 instead of compound Example 36. The product was purified by reversed-phase HPLC (Basic, Method 0) to give the title compound (4 mg, 15% yield) as a yellow solid. LCMS: m/z 464.2 (M+H); $^1$H NMR (400 MHz, Methanol-d4) δ 7.29 (dd, J=9.0, 3.1 Hz, 1H), 7.26-7.07 (m, 5H), 6.86 (dd, J=9.0, 4.3 Hz, 1H), 4.29 (s, 2H), 3.57-3.42 (m, 4H), 2.66 (s, 2H), 1.82-1.62 (m, 4H).

Example 5: N-(2,4-difluorobenzyl)-6'-fluoro-1'-methyl-4'-oxo-3',4'-dihydro-1'H-spiro[piperidine-4,2'-quinoline]-1-carboxamide

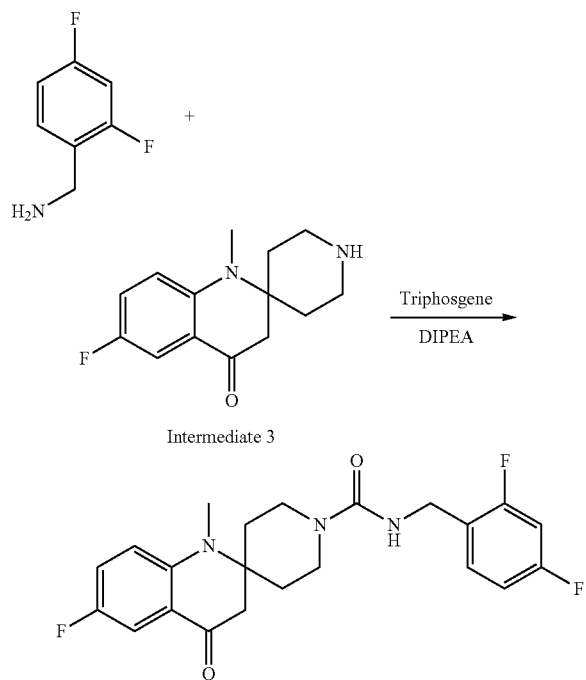

The title compound was prepared by a method similar to Example 2, using (2,4-difluorophenyl)methanamine instead of (4-fluoro-2-methoxyphenyl)methanamine. The crude residue was purified by preparative HPLC (Basic, Method 5) to give the title compound (120 mg, 22% yield) as a fluffy yellow solid after lyophilization. LCMS: m/z 418.1 (M+H); $^1$H NMR (400 MHz, Methanol-$d_4$) δ 7.47-7.31 (m, 2H), 7.30-7.20 (m, 1H), 6.99-6.85 (m, 3H), 4.36 (s, 2H), 3.99-3.90 (m, 2H), 3.11-3.00 (m, 2H), 2.97-2.90 (m, 5H), 1.93 (td, J=13.0, 4.6 Hz, 2H), 1.76-1.67 (m, 2H).

Example 6: 1'-ethyl-6'-fluoro-N-(4-fluorobenzyl)-4'-oxo-3',4'-dihydro-1'H-spiro[piperidine-4,2'-quinoline]-1-carboxamide

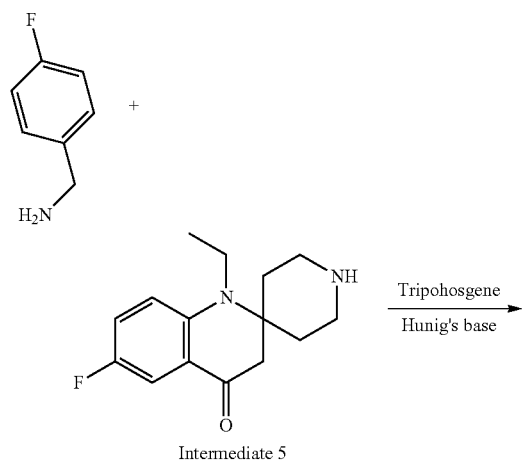

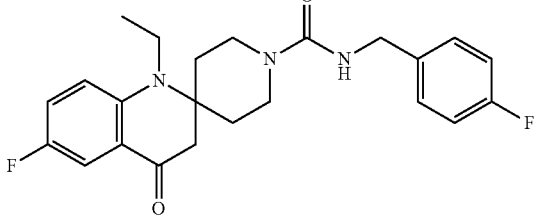

The title compound was prepared by a method similar to Example 2, using (4-fluorophenyl)methanamine and Intermediate 5 instead of (4-fluoro-2-methoxyphenyl)methanamine and Intermediate 3, respectively. The product was purified by SFC (column: Phenomenex Kinetex Biphenyl 21.2×150 mm 5 μm; mobile phase: MeOH) to give the title compound (65 mg, 51% yield) as a fluffy yellow solid after lyophilization. LCMS: m/z 414.3 (M+H); $^1$H NMR (400 MHz, Methanol-$d_4$) δ 7.40 (dd, J=8.7, 3.3 Hz, 1H), 7.36-7.28 (m, 2H), 7.28-7.21 (m, 1H), 7.07-6.99 (m, 2H), 6.90 (dd, J=9.4, 4.0 Hz, 1H), 4.32 (s, 2H), 4.00 (dd, J=11.8, 2.4 Hz, 2H), 3.44 (q, J=7.1 Hz, 2H), 3.08-2.97 (m, 2H), 2.91 (s, 2H), 1.90 (td, J=13.0, 4.8 Hz, 2H), 1.78 (d, J=13.5 Hz, 2H), 1.24 (t, J=7.1 Hz, 3H).

Example 7: 6'-fluoro-1'-methyl-N-((5-methylfuran-2-yl)methyl)-4'-oxo-3',4'-dihydro-1'H-spiro[piperidine-4,2'-quinoline]-1-carboxamide

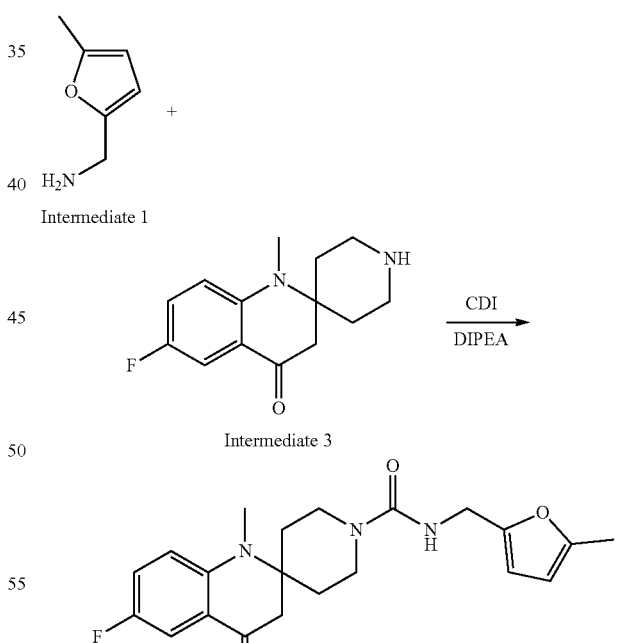

The title compound was prepared by a method similar to Example 1, using Intermediate 3 instead of Intermediate 2. The product was purified by silica gel chromatography (MeOH/DCM) followed by reversed-phase HPLC (Basic, Method 4) to give the title compound (12 mg, 11% yield) as a yellow solid after lyophilization. LCMS: m/z 386.4 (M+H); $^1$H NMR (400 MHz, DMSO-$d_6$) δ 7.46-7.25 (m, 2H), 7.06-6.86 (m, 2H), 6.02 (d, J=3.0 Hz, 1H), 5.99-5.91 (m, 1H), 4.14 (d, J=5.3 Hz, 2H), 3.99-3.77 (m, 2H), 3.00-2.76 (m, 7H), 2.21 (s, 3H), 1.78-1.72 (m, 2H), 1.62-1.48 (m, 2H).

Example 8: 6'-fluoro-N-(4-fluoro-3-methoxybenzyl)-1'-methyl-4'-oxo-3',4'-dihydro-1'H-spiro[piperidine-4,2'-quinoline]-1-carboxamide

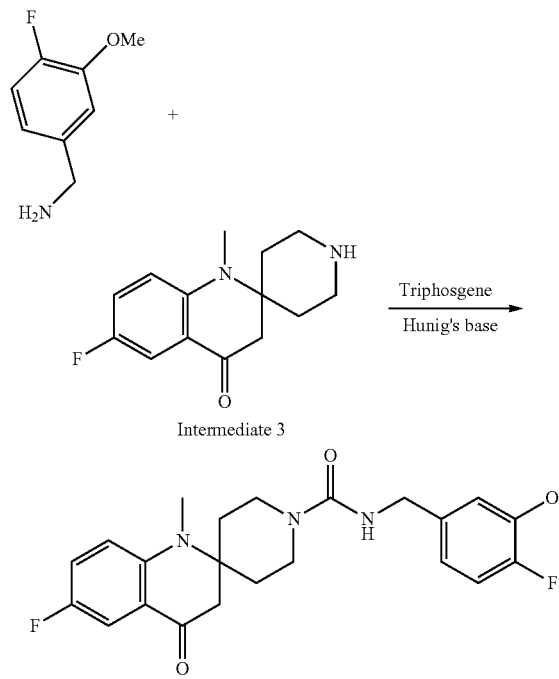

The title compound was prepared by a method similar to Example 2, using (4-fluoro-3-methoxyphenyl)methanamine instead of Intermediate 1. The product was purified by silica gel chromatography (DCM/MeOH=100/0 to 95/5), followed by SFC (column: Princeton DIOL 20×150 mm 5 μm; mobile phase: MeOH) to give the title compound (40 mg, 29% yield) as a fluffy yellow solid after lyophilization. LCMS: m/z 430.4 (M+H); $^1$H NMR (400 MHz, Methanol-$d_4$) δ 7.43 (dd, J=8.6, 3.2 Hz, 1H), 7.25 (ddd, J=9.3, 7.9, 3.3 Hz, 1H), 7.06-6.90 (m, 3H), 6.83 (ddd, J=8.2, 4.3, 2.0 Hz, 1H), 4.30 (s, 2H), 4.01-3.91 (m, 2H), 3.85 (s, 3H), 3.06 (td, J=14.3, 13.2, 2.7 Hz, 2H), 2.93 (d, J=3.0 Hz, 5H), 1.93 (td, J=13.0, 4.7 Hz, 2H), 1.72 (d, J=12.7 Hz, 2H).

Example 9: 6'-fluoro-N-(4-fluorobenzyl)-1'-methyl-4'-oxo-3',4'-dihydro-1'H-spiro[piperidine-4,2'-quinoline]-1-carboxamide

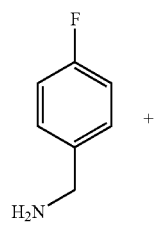

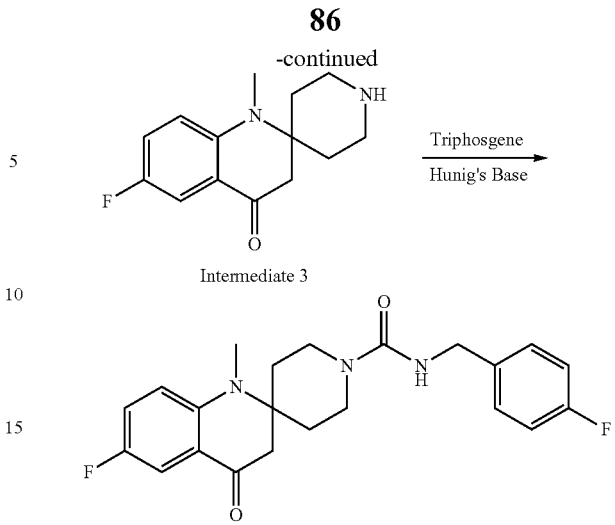

The title compound was prepared by a method similar to Example 2, using (4-fluorophenyl)methanamine instead of (4-fluoro-2-methoxyphenyl)methanamine. The crude residue was purified by preparative HPLC (Basic, Method 6) to give the title compound (42 mg, 12% yield) as a fluffy yellow solid after lyophilization. LCMS: m/z 400.2 (M+H); $^1$H NMR (400 MHz, DMSO-$d_6$) δ 7.40-7.31 (m, 2H), 7.31-7.23 (m, 2H), 7.17-7.06 (m, 3H), 7.00-6.92 (m, 1H), 4.20 (d, J=5.7 Hz, 2H), 3.93-3.85 (m, 2H), 2.95-2.82 (m, 7H), 1.75 (dt, J=12.7, 6.5 Hz, 2H), 1.60-1.52 (m, 2H).

Example 10: 6',8'-difluoro-N-((2-methylfuran-3-yl)methyl)-4'-oxo-3',4'-dihydro-1'H-spiro[piperidine-4,2'-quinoline]-1-carboxamide

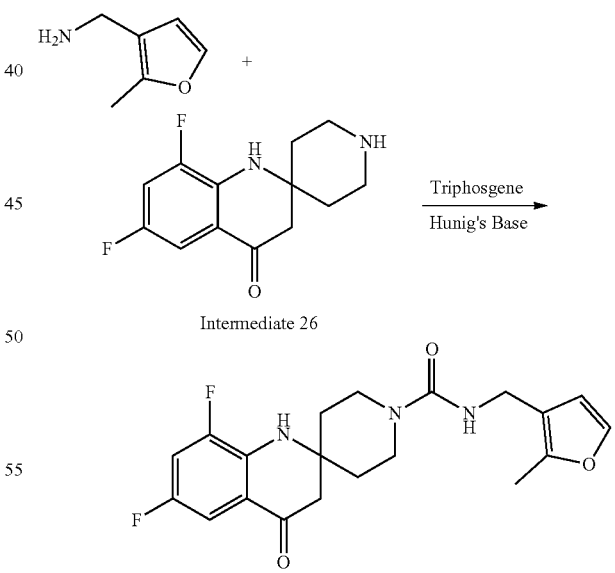

The title compound was prepared using a method similar to Example 2, using (2-methylfuran-3-yl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 390.1 (M+H); $^1$H NMR (400 MHz, Methanol-$d_4$) δ 7.26-7.12 (m, 3H), 6.32 (s, 1H), 4.12 (s, 2H), 3.69-3.63 (m, 2H), 3.36-3.29 (m, 2H), 2.81 (s, 2H), 2.27 (s, 3H), 1.82-1.73 (m, 4H).

Example 11: N-(3-carbamoyl-4-fluorobenzyl)-6',8'-difluoro-4'-oxo-3',4'-dihydro-1'H-spiro[piperidine-4,2'-quinoline]-1-carboxamide

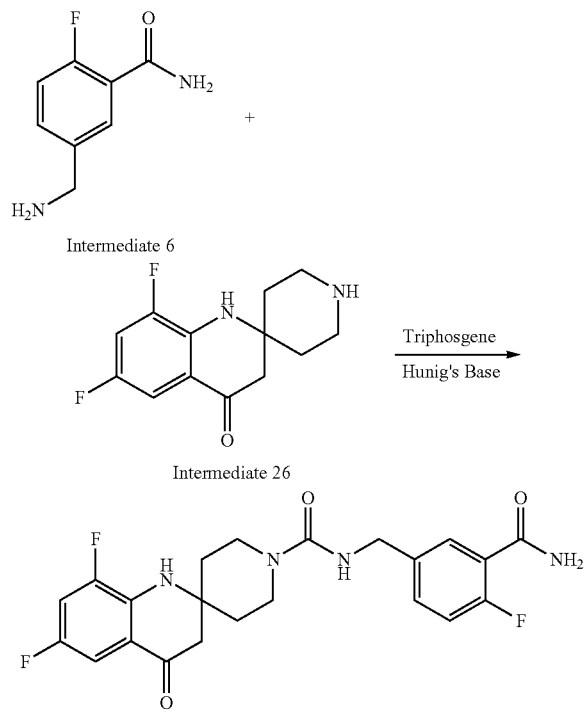

The title compound was prepared by a method similar to Example 2, using Intermediates 6 and 26 (free base) instead of (4-fluoro-2-methoxyphenyl)methanamine and Intermediate 3, respectively. The crude residue was purified by preparative HPLC (Basic, Method 4) to give the title compound (57 mg, 32% yield) as a fluffy yellow solid after lyophilization. LCMS: m/z 477.2 (M+H); $^1$H NMR (400 MHz, Methanol-$d_4$) δ 7.75 (dd, J=7.1, 2.3 Hz, 1H), 7.47 (ddd, J=7.4, 4.8, 2.4 Hz, 1H), 7.25-7.10 (m, 3H), 4.36 (s, 2H), 3.70 (dt, J=14.2, 5.1 Hz, 2H), 3.41-3.33 (m, 2H), 2.81 (s, 2H), 1.87-1.73 (m, 4H).

Example 12: 6'-fluoro-N-((4-fluorophenyl)methyl-d2)-4'-oxo-3',4'-dihydro-1'H-spiro[piperidine-4,2'-quinoline]-1-carboxamide

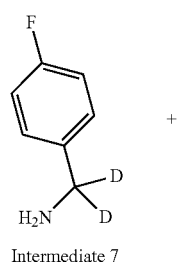

Intermediate 7

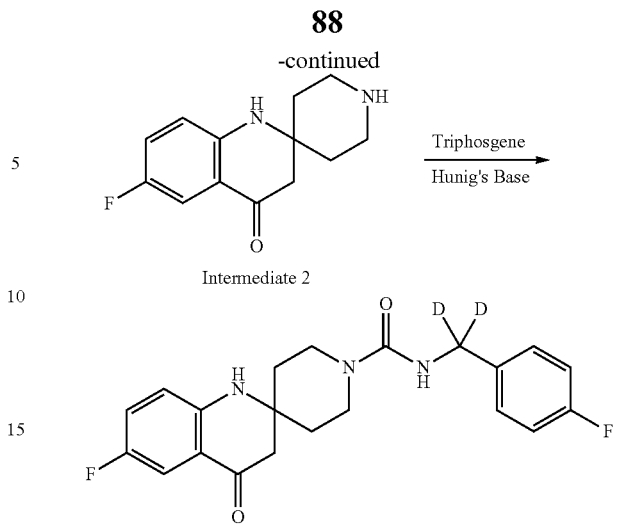

The title compound was prepared by a method similar to Example 2, using Intermediates 7 and 2 (HCl salt) instead of (4-fluoro-2-methoxyphenyl)methanamine and Intermediate 3, respectively. The product was purified by by preparative HPLC (Basic, Method 5), followed by SFC (column: Princeton DIOL 20×150 mm 5 μm; mobile phase: MeOH) to give the title compound (29 mg, 31% yield) as a fluffy yellow solid after lyophilization. LCMS: m/z 388.3 (M+H); $^1$H NMR (400 MHz, Methanol-$d_4$) δ 7.33-7.26 (m, 3H), 7.12 (ddd, J=9.0, 8.2, 3.1 Hz, 1H), 7.05-6.98 (m, 2H), 6.85 (dd, J=9.1, 4.3 Hz, 1H), 3.57-3.45 (m, 4H), 3.33 (d, J=1.7 Hz, 1H), 2.66 (s, 2H), 1.72 (tdt, J=13.3, 7.7, 4.6 Hz, 4H).

Example 13: N-(3-carbamoyl-4-fluorobenzyl)-1'-ethyl-6'-fluoro-4'-oxo-3',4'-dihydro-1'H-spiro[piperidine-4,2'-quinoline]-1-carboxamide

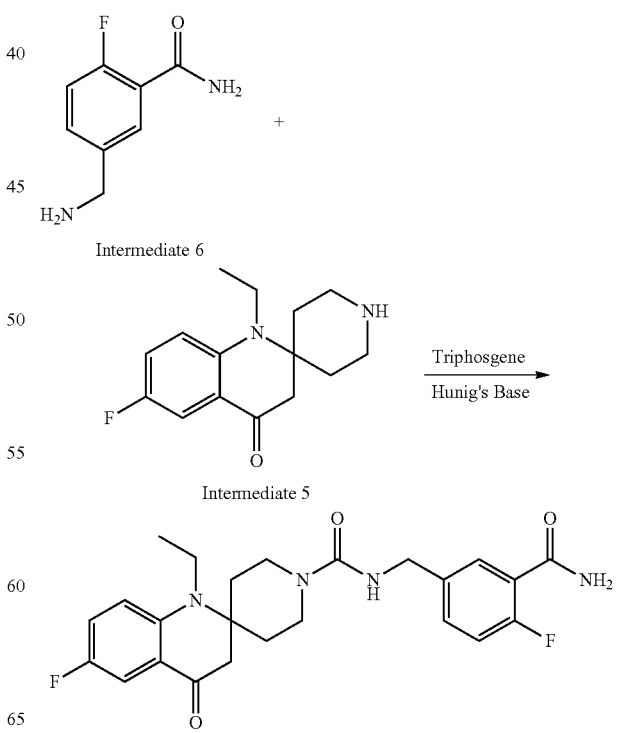

The title compound was prepared by a method similar to Example 2, using Intermediates 6 and 5 instead of (4-fluoro-2-methoxyphenyl)methanamine and Intermediate 3, respectively. The crude residue was purified by preparative HPLC (Basic, Method 4) to give the title compound (55 mg, 26% yield) as a fluffy yellow solid after lyophilization. LCMS: m/z 477.2 (M+H); $^1$H NMR (400 MHz, Methanol-$d_4$) δ 7.76 (dd, J=7.1, 2.3 Hz, 1H), 7.48 (dd, J=6.0, 2.4 Hz, 1H), 7.41 (dd, J=8.7, 3.2 Hz, 1H), 7.24 (ddd, J=9.4, 7.9, 3.3 Hz, 1H), 7.17 (dd, J=10.9, 8.5 Hz, 1H), 6.91 (dd, J=9.3, 4.0 Hz, 1H), 4.36 (s, 2H), 4.01 (d, J=13.8 Hz, 2H), 3.45 (q, J=7.1 Hz, 2H), 3.03 (t, J=11.9 Hz, 2H), 2.92 (s, 2H), 1.99-1.72 (m, 4H), 1.25 (t, J=7.1 Hz, 3H).

Example 14: 6'-fluoro-N-(4-fluorobenzyl)-1'-(2-methoxyethyl)-4'-oxo-3',4'-dihydro-1'H-spiro[piperidine-4,2'-quinoline]-1-carboxamide

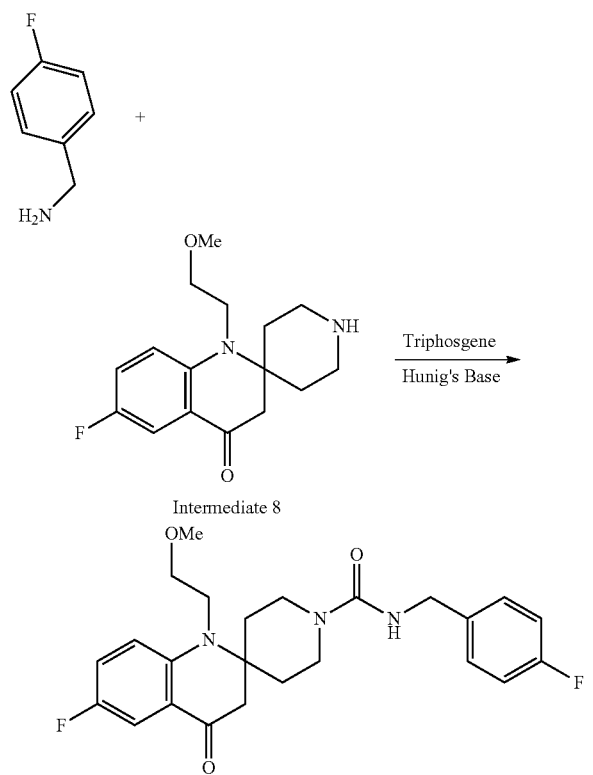

The title compound was prepared by a method similar to Example 2, using (4-fluorophenyl)methanamine and Intermediate 8 instead of (4-fluoro-2-methoxyphenyl)methanamine and Intermediate 3, respectively. The product was purified by preparative HPLC (Basic, Method 5) to give the title compound (14 mg, 21% yield) as a fluffy yellow solid after lyophilization. LCMS: m/z 444.3 (M+H); $^1$H NMR (400 MHz, Methanol-$d_4$) δ 7.41 (dd, J=8.6, 3.3 Hz, 1H), 7.35-7.27 (m, 2H), 7.23 (ddd, J=9.4, 7.9, 3.3 Hz, 1H), 7.05-7.00 (m, 2H), 6.96 (dd, J=9.4, 4.0 Hz, 1H), 4.32 (s, 2H), 3.97 (d, J=14.0 Hz, 2H), 3.61-3.50 (m, 4H), 3.33 (s, 3H), 3.08-2.98 (m, 2H), 2.92 (s, 2H), 1.93 (td, J=13.0, 4.7 Hz, 2H), 1.76 (d, J=13.6 Hz, 2H).

Example 15: 6'-fluoro-N-(4-fluoro-3-(oxazol-5-yl)benzyl)-4'-oxo-3',4'-dihydro-1'H-spiro[piperidine-4,2'-quinoline]-1-carboxamide

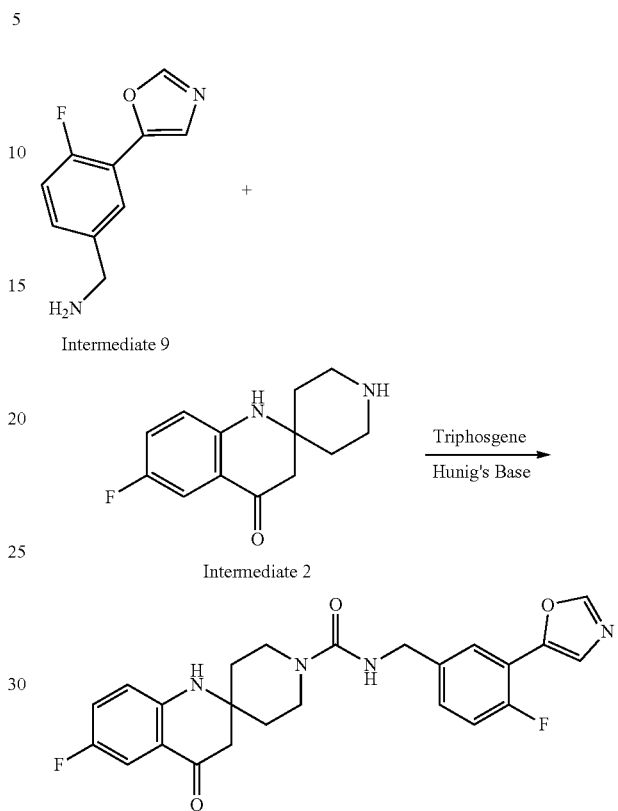

The title compound was prepared by a method similar to Example 2, using Intermediate 9 (TFA salt) and 2 (HCl salt) instead of (4-fluorophenyl)methanamine and Intermediate 3, respectively. The product was purified on preparative TLC plate using 5% MeOH in DCM as mobile phase, to give the title compound (49 mg, 44% yield) as a yellow solid. LCMS: m/z 452.9 (M+H); $^1$H NMR (400 MHz, DMSO-$d_6$) δ 8.56 (1H, s), 7.69-7.67 (1H, d), 7.54-7.53 (1H, d), 7.33-7.31 (2H, m), 7.24-7.20 (2H, m), 6.92-6.90 (1H, m), 6.82 (1H, s), 4.26-4.25 (2H, d), 3.46-3.38 (4H, m), 2.61 (2H, s), 1.59-1.55 (4H, m).

Example 16: N-(2,4-difluorobenzyl)-6'-fluoro-4'-oxo-3',4'-dihydro-1'H-spiro[piperidine-4,2'-quinoline]-1-carboxamide

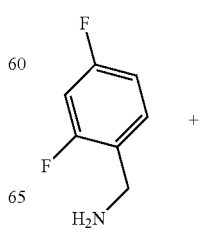

-continued

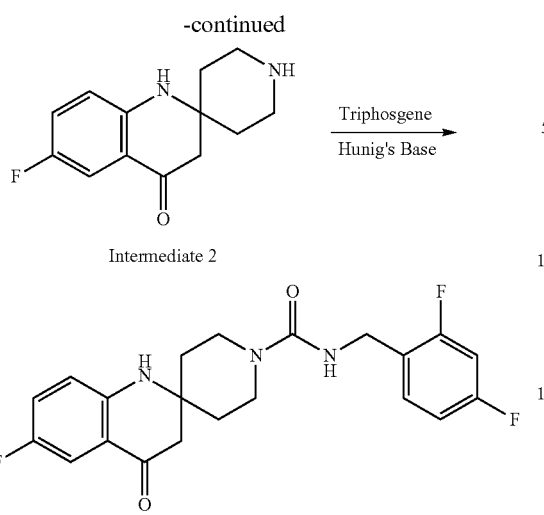

Intermediate 2

The title compound was prepared by a method similar to Example 2, using (2,4-difluorophenyl)methanamine and Intermediate 2 (HCl salt) instead of (4-fluorophenyl)methanamine and Intermediate 3, respectively. The product was purified by preparative SFC (column: Princeton DIOL 20×150 mm 5 μm; mobile phase: MeOH), to give the title compound (35 mg, 36% yield) as a yellow solid. LCMS: m/z 404.3 (M+H); $^1$H NMR (400 MHz, MeOH-$d_4$) δ 7.40-7.26 (m, 2H), 7.12 (ddd, J=9.0, 8.2, 3.1 Hz, 1H), 6.96-6.81 (m, 3H), 4.36 (s, 2H), 3.57-3.46 (m, 4H), 2.66 (s, 2H), 1.72 (tdt, J=13.3, 7.8, 4.6 Hz, 4H).

Example 17: N-(2,4-difluoro-5-((2-hydroxyethyl) amino)benzyl)-6'-fluoro-1'-methyl-4'-oxo-3',4'-dihydro-1'H-spiro[piperidine-4,2'-quinoline]-1-carboxamide Step 1: Synthesis of N-(2,4-difluoro-5-((2-methoxyethyl)amino)benzyl)-6'-fluoro-1'-methyl-4'-oxo-3',4'-dihydro-1'H-spiro[piperidine-4,2'-quinoline]-1-carboxamide The title compound was prepared by a method similar to Example 2, using Intermediate 10 instead of (4-fluoro-2-methoxyphenyl)methanamine. The crude residue was purified by preparative HPLC (Basic, Method 4) to give the title compound (48 mg, 16.2% yield) as a fluffy yellow solid after lyophilization. LCMS: m/z 491.2 (M+H).

Step 2: Synthesis of N-(2,4-difluoro-5-((2-hydroxyethyl)amino)benzyl)-6'-fluoro-1'-methyl-4'-oxo-3',4'-dihydro-1'H-spiro[piperidine-4,2'-quinoline]-1-carboxamide The title compound was prepared by a method similar to Example 3, Step 2. The product was purified by prep HPLC (Basic, Method 4) to afford the title compound (22 mg, 44.8% yield) as a yellow solid. HRMS: m/z 477.2110 (M+H); $^1$H NMR (400 MHz, Methanol-$d_4$) δ 7.43 (dd, J=8.6, 3.2 Hz, 1H), 7.30-7.19 (m, 1H), 6.98-6.90 (m, 1H), 6.81 (dd, J=11.4, 9.7 Hz, 1H), 6.75 (dd, J=9.6, 7.4 Hz, 1H), 4.32 (s, 2H), 3.99-3.90 (m, 2H), 3.73 (t, J=5.7 Hz, 2H), 3.23 (t, J=5.7 Hz, 3H), 3.11-3.00 (m, 2H), 2.93 (s, 3H), 2.93 (s, 2H), 1.92 (td, J=13.0, 4.6 Hz, 2H), 1.75-1.65 (m, 2H).

Example 18: N-(2,4-difluoro-5-((2-hydroxyethyl) amino)benzyl)-1'-ethyl-6'-fluoro-4'-oxo-3',4'-dihydro-1'H-spiro[piperidine-4,2'-quinoline]-1-carboxamide

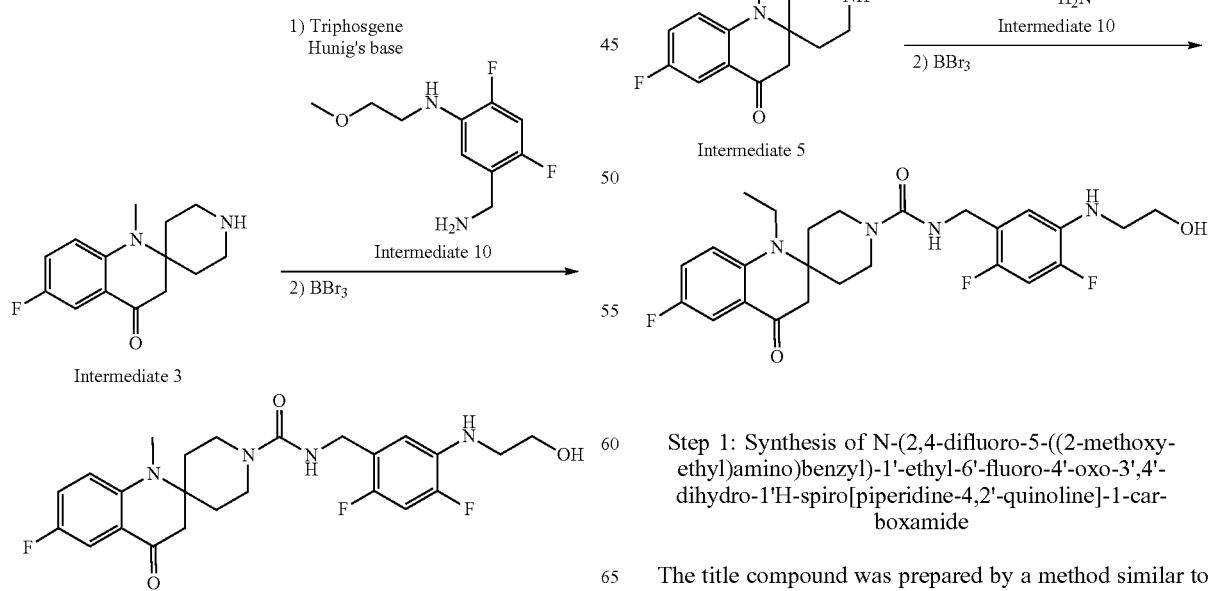

Step 1: Synthesis of N-(2,4-difluoro-5-((2-methoxyethyl)amino)benzyl)-1'-ethyl-6'-fluoro-4'-oxo-3',4'-dihydro-1'H-spiro[piperidine-4,2'-quinoline]-1-carboxamide The title compound was prepared by a method similar to Example 2, using Intermediates 10 and 5 instead of (4-fluoro-2-methoxyphenyl)methanamine and Intermediate 3, respectively. The crude residue was purified by preparative SFC (column: Princeton DEAP 20×150 mm 5 μm; mobile phase: MeOH) to give the title compound. HRMS: m/z 505.2423 (M+H).

Step 2: Synthesis of N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide The title compound was prepared by a method similar to to Example 3, Step 2. The product was then purified by preparative SFC (column: Princeton DEAP 20×150 mm 5 μm; mobile phase: MeOH) to afford the title compound (5 mg, 27.1% yield) as a yellow solid. HRMS: m/z 491.2265 (M+H); ¹H NMR (400 MHz, Methanol-d₄) δ 7.38 (dd, J=8.7, 3.3 Hz, 1H), 7.22 (m, J=9.4, 7.9, 3.3 Hz, 1H), 6.88 (dd, J=9.4, 4.0 Hz, 1H), 6.85-6.61 (m, 2H), 4.31 (s, 2H), 4.04-3.92 (m, 2H), 3.71 (t, J=5.7 Hz, 2H), 3.42 (q, J=7.0 Hz, 2H), 3.22 (t, J=5.7 Hz, 2H), 3.04-2.94 (m, 2H), 2.90 (s, 2H), 1.89 (td, J=13.0, 4.8 Hz, 2H), 1.76 (d, J=13.5 Hz, 2H), 1.22 (t, J=7.1 Hz, 3H).

Example 19: 6'-fluoro-N-(4-fluorobenzyl)-1'-(2-hydroxyethyl)-4'-oxo-3',4'-dihydro-1'H-spiro[piperidine-4,2'-quinoline]-1-carboxamide

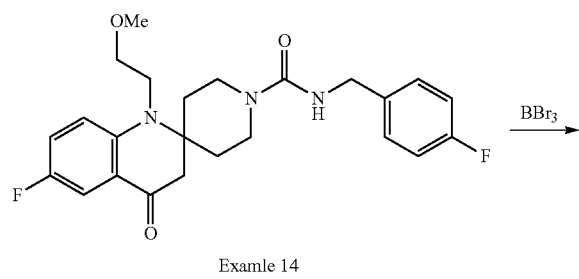

Examle 14

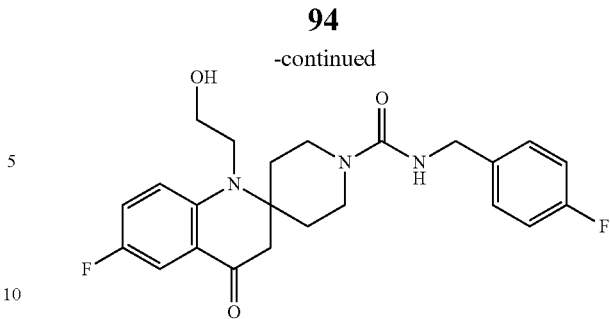

To a solution of Example 14 (65 mg, 0.147 mmol) in dry DCM (2 mL) at 0° C. was slowly added tribromoborane 1M in DCM (0.293 mL, 0.293 mmol). The reaction mixture was stirred at 0° C. for 30 min then quenched by saturated NH₄Cl aqueous solution and extracted with DCM and EtOAc. The combined organic layers were dried over Na₂SO₄ and concentrated under reduced pressure. The residue was purified by purified by preparative SFC (column: Princeton DEAP 20×150 mm 5 μm; mobile phase: MeOH) to yield the title compound (35 mg, 53% yield) as a yellow solid. LCMS: m/z 430.3 (M+H); ¹H NMR (400 MHz, Chloroform-d) δ 7.56 (dd, J=8.3, 3.2 Hz, 1H), 7.31-7.27 (m, 2H), 7.20 (td, J=8.4, 7.6, 3.2 Hz, 1H), 7.02 (t, J=8.7 Hz, 3H), 4.39 (s, 2H), 3.96-3.79 (m, 4H), 3.53 (t, J=6.1 Hz, 2H), 3.04 (t, J=11.9 Hz, 2H), 2.91 (s, 2H), 2.15-2.05 (m, 2H), 1.83 (d, J=13.3 Hz, 2H).

Example 20: 6'-fluoro-N-(4-fluoro-2-((2-methoxyethyl)amino)benzyl)-1'-methyl-4'-oxo-3',4'-dihydro-1'H-spiro[piperidine-4,2'-quinoline]-1-carboxamide

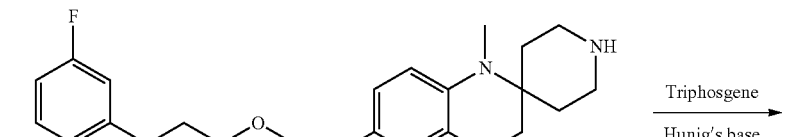

Intermediate 11        Intermediate 3

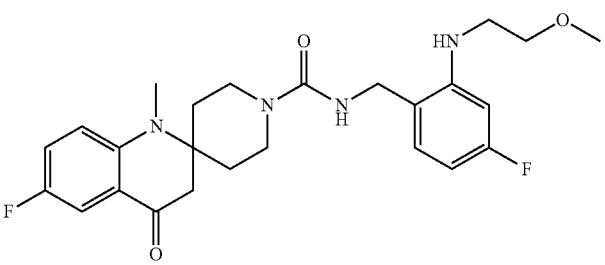

The title compound was prepared by a method similar to Example 2, using Intermediate 11 instead of (4-fluoro-2-methoxyphenyl)methanamine. The crude residue was purified by HPLC (Basic, Method 5) to give the title compound (40 mg, 93% yield) as a fluffy yellow solid after lyophilization. LCMS: m/z 473.0 (M+H); $^1$H NMR (400 MHz, Methanol-$d_4$) δ 7.42 (dd, J=8.6, 3.2 Hz, 1H), 7.25 (ddd, J=9.3, 7.9, 3.3 Hz, 1H), 7.03 (dd, J=8.2, 6.8 Hz, 1H), 6.94 (dd, J=9.4, 4.1 Hz, 1H), 6.33 (dd, J=12.1, 2.5 Hz, 1H), 6.26 (td, J=8.4, 2.5 Hz, 1H), 4.24 (s, 2H), 3.94 (d, J=13.9 Hz, 2H), 3.61 (t, J=5.5 Hz, 2H), 3.38 (s, 3H), 3.26 (t, J=5.5 Hz, 2H), 3.11-2.98 (m, 2H), 2.92 (d, J=4.5 Hz, 5H), 1.92 (td, J=12.7, 4.7 Hz, 2H), 1.70 (d, J=13.3 Hz, 2H).

Example 21: 6'-fluoro-N-(4-fluoro-3-(2-methoxyethoxy)benzyl)-1'-methyl-4'-oxo-3',4'-dihydro-1'H-spiro[piperidine-4,2'-quinoline]-1-carboxamide

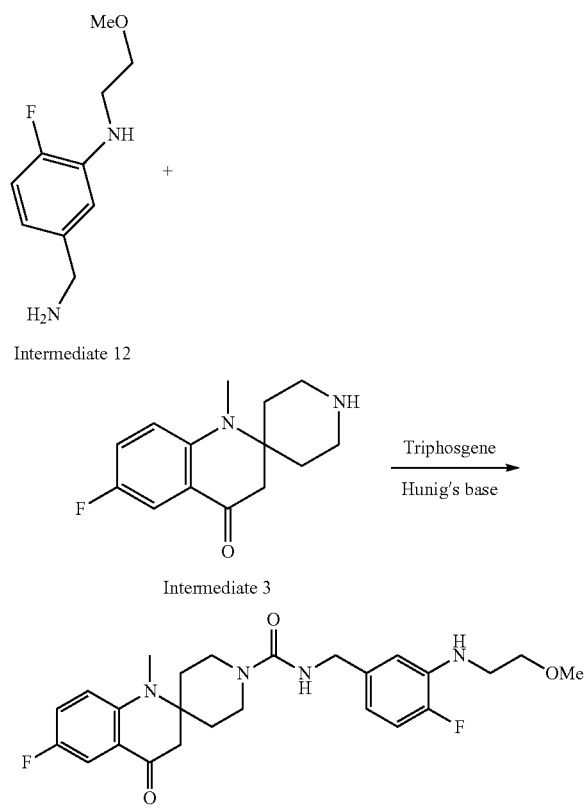

The title compound was prepared by a method similar to Example 2, using Intermediate 12 instead of (4-fluoro-2-methoxyphenyl)methanamine. The product was purified by silica gel chromatography (DCM/MeOH=100/0 to 90/10), followed by preparative HPLC (Basic, Method 5) to give the title compound (156 mg, 40% yield) as a fluffy yellow solid after lyophilization. LCMS: m/z 473.3 (M+H); $^1$H NMR (400 MHz, DMSO-$d_6$) δ 7.36 (ddd, J=10.5, 4.9, 2.6 Hz, 2H), 7.10-6.81 (m, 3H), 6.64 (dd, J=8.7, 1.9 Hz, 1H), 6.51-6.32 (m, 1H), 5.23 (s, 1H), 4.13 (d, J=5.5 Hz, 2H), 3.91 (d, J=13.8 Hz, 2H), 3.49 (d, J=6.0 Hz, 2H), 3.26 (s, 3H), 3.22 (d, J=4.9 Hz, 2H), 2.90 (d, J=10.2 Hz, 3H), 2.84 (s, 3H), 1.75 (td, J=12.9, 4.5 Hz, 2H), 1.56 (d, J=12.9 Hz, 2H).

Example 22: N-((5-chlorofuran-2-yl)methyl)-6'-fluoro-4'-oxo-3',4'-dihydro-1'H-spiro[piperidine-4,2'-quinoline]-1-carboxamide

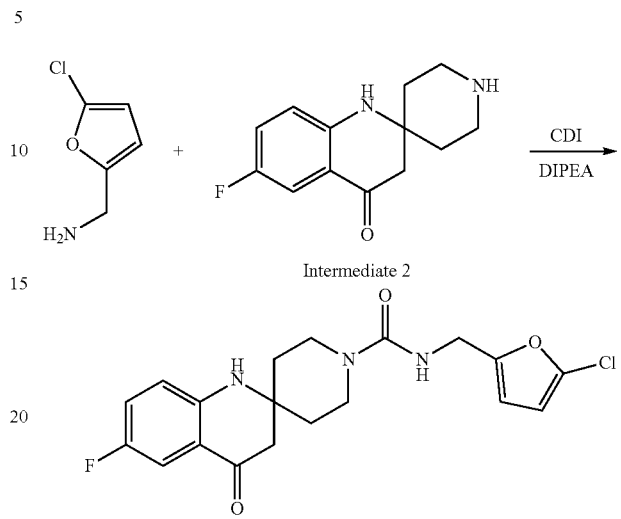

The title compound was prepared by a method similar to Example 1, using (5-chlorofuran-2-yl)methanamine (prepared according to J. Med. Chem. 2016, 59, 3471) instead of Intermediate 1. Intermediate 2 was HCl salt. The product was purified by silica gel chromatography (MeOH/DCM) followed by reversed-phase HPLC (Basic, Method 4) to give the title compound (27 mg, 25% yield) as a yellow solid after lyophilization. LCMS: m/z 392.3 (M+H); $^1$H NMR (400 MHz, DMSO-$d_6$) δ 7.27-7.17 (m, 2H), 7.06 (t, J=5.6 Hz, 1H), 6.97-6.85 (m, 1H), 6.80 (s, 1H), 6.36 (d, J=3.3 Hz, 1H), 6.26 (d, J=3.2 Hz, 1H), 4.16 (d, J=5.4 Hz, 2H), 3.52-3.28 (m, 4H), 2.60 (s, 2H), 1.69-1.45 (m, 4H).

Example 23: 6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide

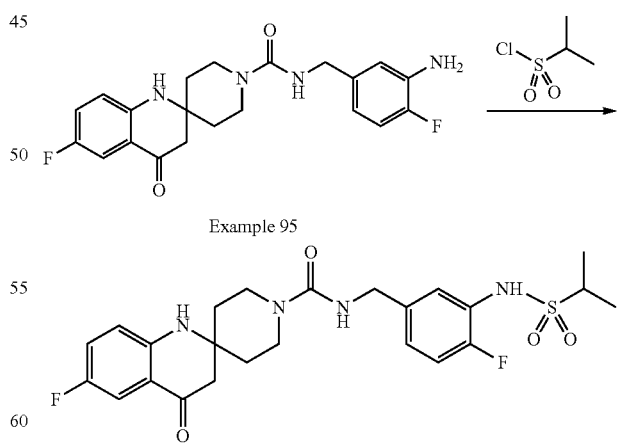

To a stirred solution of Example 95 (35 mg, 0.087 mmol) in DCM (437 μL) and pyridine (437 μL) was added 2-propanesulfonyl chloride (9.81 μL, 0.087 mmol). The reaction was allowed to stir at 50° C. The crude material was purified by HPLC (Basic, Method 3) to afford the title compound as a yellow solid (7.3 mg, 16% yield). LCMS: m/z 507.1 (M+H); $^1$H NMR (400 MHz, Methanol-$d_4$) δ 7.52 (d, J=7.0 Hz, 1H), 7.32 (dd, J=9.0, 3.0 Hz, 1H), 7.18-7.07 (m, 3H), 6.88 (dd, J=9.1, 4.3 Hz, 1H), 4.34 (s, 2H), 3.54 (t, J=5.5 Hz, 4H), 3.30-3.24 (m, 1H), 2.71 (s, 2H), 1.78 (h, J=7.6, 7.0 Hz, 4H), 1.38 (s, 3H), 1.36 (s, 3H).

Example 24: N-(3-carbamoyl-4-fluorobenzyl)-6'-fluoro-4'-oxo-3',4'-dihydro-1'H-spiro[piperidine-4,2'-quinoline]-1-carboxamide

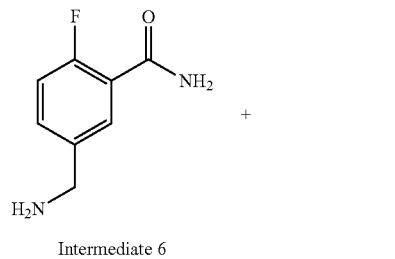

Intermediate 6

+

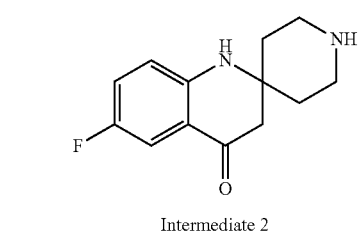

Intermediate 2

→ Triphosgene
Hunig's base

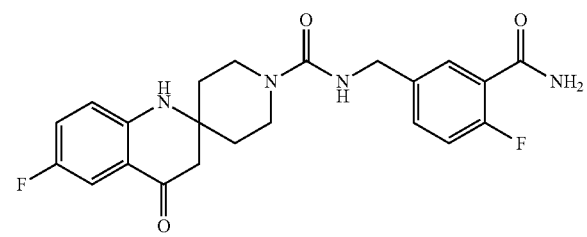

The title compound was prepared by a method similar to Example 2, using Intermediates 6 and 2 (free base) instead of (4-fluoro-2-methoxyphenyl)methanamine and Intermediate 3, respectively. The crude product was purified by preparative HPLC (Basic, Method 4) to give the title compound (110 mg, 39% yield) as a fluffy yellow solid after lyophilization. LCMS: m/z 429.1 (M+H); $^1$H NMR (400 MHz, Methanol-$d_4$) δ 7.75 (dd, J=7.1, 2.4 Hz, 1H), 7.47 (m, J=7.3, 4.8, 2.4 Hz, 1H), 7.30 (dd, J=9.0, 3.0 Hz, 1H), 7.22-7.08 (m, 2H), 6.88 (dd, J=9.1, 4.3 Hz, 1H), 4.36 (s, 2H), 3.52 (t, J=5.7 Hz, 4H), 2.68 (s, 2H), 1.82-1.68 (m, 4H).

Example 25: 1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide

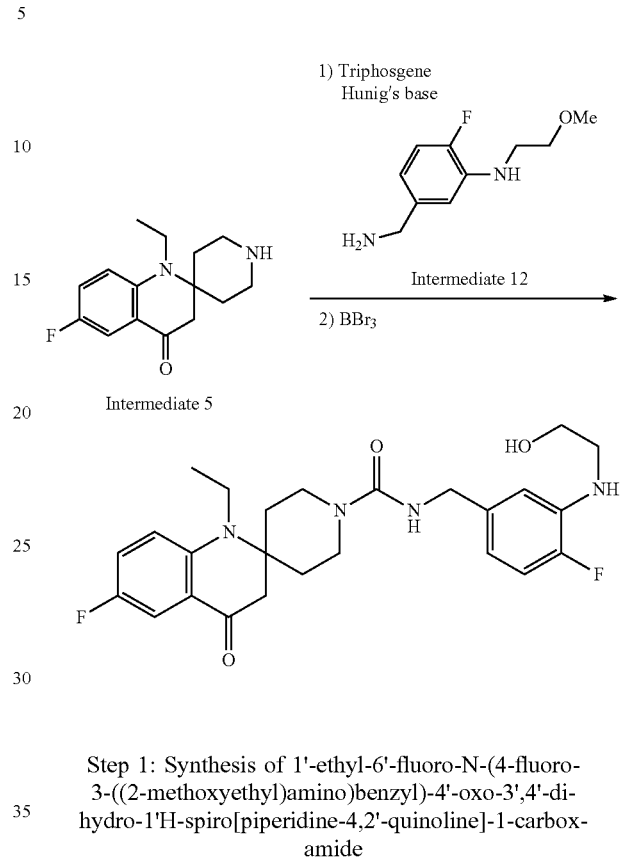

Step 1: Synthesis of 1'-ethyl-6'-fluoro-N-(4-fluoro-3-((2-methoxyethyl)amino)benzyl)-4'-oxo-3',4'-dihydro-1'H-spiro[piperidine-4,2'-quinoline]-1-carboxamide The title compound was prepared by a method similar to Example 2, using Intermediates 12 and 5 instead of (4-fluoro-2-methoxyphenyl)methanamine and Intermediate 3, respectively. The product was purified by preparative HPLC (Basic, Method 5) to give the title compound (15 mg, 13% yield) as a fluffy yellow solid after lyophilization. LCMS: m/z 487.3 (M+H).

Step 2: Synthesis of 1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide The title compound was prepared by a method similar to Example 19, using the product in step 1 instead of Example 14. The product was purified by preparative HPLC (Basic, Method 4) to give the title compound (3 mg, 31% yield) as a fluffy yellow solid after lyophilization. LCMS: m/z 473.3 (M+H); $^1$H NMR (400 MHz, DMSO-$d_6$) δ 7.38-7.27 (m, 2H), 7.06 (t, J=5.8 Hz, 1H), 6.95-6.85 (m, 2H), 6.64 (dd, J=8.7, 1.8 Hz, 1H), 6.43 (ddd, J=8.0, 4.5, 2.0 Hz, 1H), 5.16 (q, J=3.6 Hz, 1H), 4.77 (s, 1H), 4.13 (d, J=5.7 Hz, 2H), 3.94 (d, J=13.8 Hz, 2H), 3.57 (t, J=5.8 Hz, 2H), 3.39 (s, 2H), 3.11 (q, J=6.0 Hz, 2H), 2.87 (d, J=11.5 Hz, 4H), 1.81-1.56 (m, 4H), 1.14 (t, J=7.0 Hz, 3H).

Example 26: N-(3-amino-2,4-difluorobenzyl)-1'-ethyl-6'-fluoro-4'-oxo-3',4'-dihydro-1'H-spiro[piperidine-4,2'-quinoline]-1-carboxamide

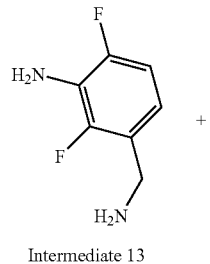

Intermediate 13

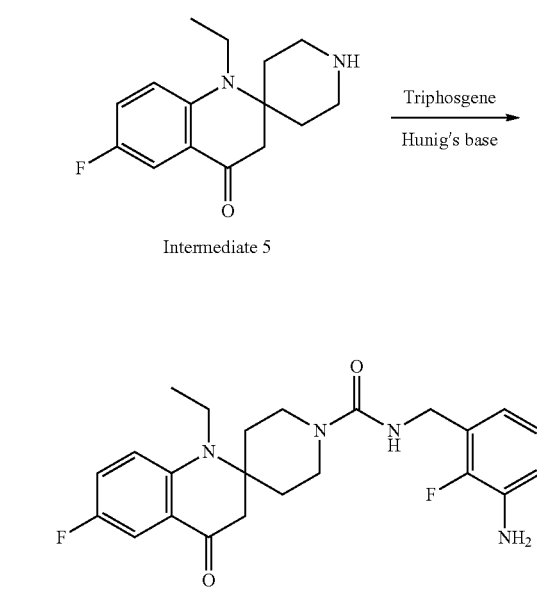

The title compound was prepared by a method similar to Example 2, using Intermediates 13 and 5 instead of (4-fluoro-2-methoxyphenyl)methanamine and Intermediate 3, respectively. The product was purified by preparative HPLC (Basic, Method 4) to give the title compound (5 mg, 5% yield) as a fluffy yellow solid after lyophilization. LCMS: m/z 447.3 (M+H); $^1$H NMR (400 MHz, Chloroform-d) δ 7.51 (dd, J=8.5, 3.3 Hz, 1H), 7.16 (ddd, J=9.3, 7.7, 3.2 Hz, 1H), 6.81-6.73 (m, 2H), 6.71-6.63 (m, 1H), 4.83 (s, 1H), 4.40 (d, J=4.4 Hz, 2H), 3.90 (d, J=13.6 Hz, 2H), 3.49 (s, 1H), 3.37 (q, J=7.1 Hz, 2H), 3.05-2.93 (m, 2H), 2.84 (s, 2H), 1.90 (dt, J=12.6, 6.7 Hz, 2H), 1.79 (d, J=13.2 Hz, 3H), 1.25 (d, J=7.1 Hz, 3H).

Example 27: N-(3-amino-4-fluorobenzyl)-6'-fluoro-1'-methyl-4'-oxo-3',4'-dihydro-1'H-spiro[piperidine-4,2'-quinoline]-1-carboxamide

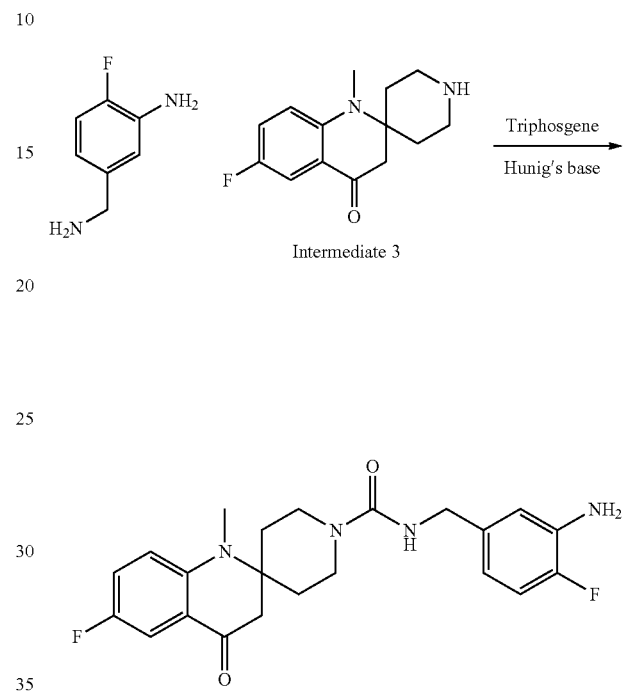

The title compound was prepared by a method similar to Example 2, using 5-(aminomethyl)-2-fluoroaniline instead of (4-fluoro-2-methoxyphenyl)methanamine. The crude residue was purified by preparative HPLC (Basic, Method 4) to give the title compound (110 mg, 37% yield) as a fluffy yellow solid after lyophilization. LCMS: m/z 415.3 (M+H); $^1$H NMR (400 MHz, Methanol-$d_4$) δ 7.43 (dd, J=8.7, 3.2 Hz, 1H), 7.25 (ddd, J=9.3, 8.0, 3.3 Hz, 1H), 6.94 (dd, J=9.4, 4.1 Hz, 1H), 6.86 (dd, J=11.2, 8.3 Hz, 1H), 6.77 (dd, J=8.6, 2.1 Hz, 1H), 6.60-6.51 (m, 1H), 4.22 (d, J=4.2 Hz, 2H), 3.95 (d, J=13.9 Hz, 2H), 3.10-3.00 (m, 2H), 2.94 (s, 3H), 2.93 (s, 2H), 1.99-1.86 (m, 2H), 1.71 (d, J=12.8 Hz, 2H).

Example 28: 6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide

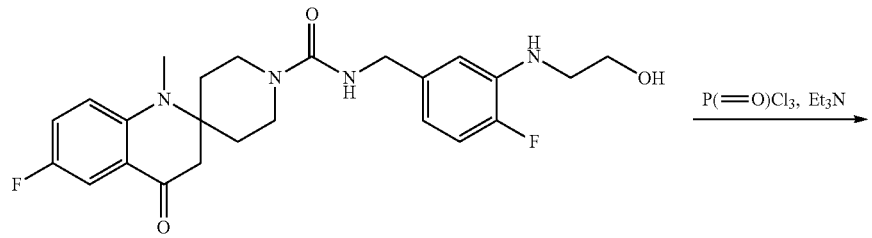

Example 36

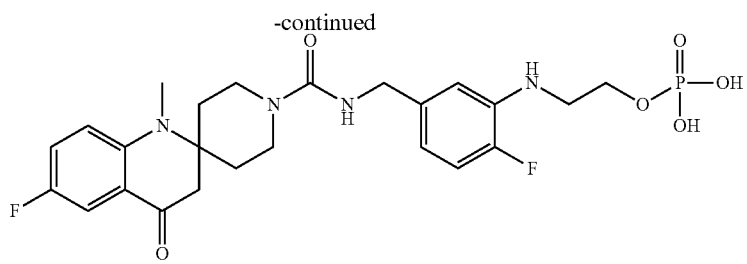

To a solution of Example 36 (300 mg, 0.654 mmol) and triethylamine (0.547 mL, 3.93 mmol) in THF (5 mL) in an ice bath was added phosphorous oxychloride (0.122 mL, 1.309 mmol) dropwise. The reaction mixture was removed from the ice bath after 5 min and was allowed to warm to RT over 30 min. The mixture was quenched slowly with $H_2O$ and was transferred to a separatory funnel. The aqueous layer was extracted with EtOAc/THF (1:1) (3×100 mL). The organic extracts were combined and concentrated in vacuo. The crude residue was purified by reversed-phased HPLC (Basic, Method 1) to give the title compound (222 mg, 60.5% yield) as a yellow solid after lyophilization. LCMS: m/z 539.2 (M+H); $^1$H NMR (400 MHz, Methanol-$d_4$) δ 7.42 (dd, J=8.7, 3.2 Hz, 1H), 7.24 (ddd, J=9.3, 7.9, 3.3 Hz, 1H), 6.95 (dd, J=9.4, 4.0 Hz, 1H), 6.85 (dd, J=11.7, 8.2 Hz, 1H), 6.75 (dd, J=8.4, 2.1 Hz, 1H), 6.52 (ddd, J=8.2, 4.5, 2.1 Hz, 1H), 4.26 (s, 2H), 4.10-4.01 (m, 2H), 4.01-3.92 (m, 2H), 3.38 (t, J=5.7 Hz, 2H), 3.11-3.00 (m, 2H), 2.98-2.87 (m, 5H), 1.93 (td, J=12.8, 4.7 Hz, 2H), 1.79-1.64 (m, 2H).

Example 29: N-(3-amino-4-fluorobenzyl)-1'-ethyl-6'-fluoro-4'-oxo-3',4'-dihydro-1'H-spiro[piperidine-4,2'-quinoline]-1-carboxamide

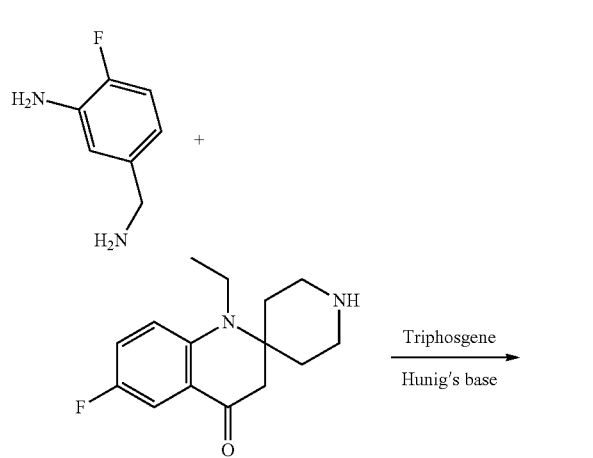

The title compound was prepared by a method similar to Example 2, using 5-(aminomethyl)-2-fluoroaniline and Intermediate 5 instead of (4-fluoro-2-methoxyphenyl)methanamine and Intermediate 3, respectively. The product was purified by silica gel chromatography (DCM/MeOH=100/0 to 90/10), then preparative HPLC (Basic, Method 4) to give the title compound (19 mg, 19% yield) as a fluffy yellow solid after lyophilization. LCMS: m/z 429.3 (M+H); $^1$H NMR (400 MHz, MeOH-$d_4$) δ 7.40 (dd, J=8.7, 3.3 Hz, 1H), 7.23 (ddd, J=9.4, 7.9, 3.3 Hz, 1H), 6.96-6.83 (m, 2H), 6.78 (dd, J=8.7, 2.1 Hz, 1H), 6.56 (ddd, J=8.2, 4.4, 2.2 Hz, 1H), 4.22 (s, 2H), 4.06-3.92 (m, 2H), 3.44 (q, J=7.0 Hz, 2H), 3.08-2.95 (m, 2H), 2.91 (s, 2H), 1.91 (td, J=13.0, 4.8 Hz, 2H), 1.78 (d, J=13.6 Hz, 2H), 1.24 (t, J=7.1 Hz, 3H).

Example 30: 6'-fluoro-N-(4-fluoro-3-sulfamoylbenzyl)-4'-oxo-3',4'-dihydro-1'H-spiro[piperidine-4,2'-quinoline]-1-carboxamide

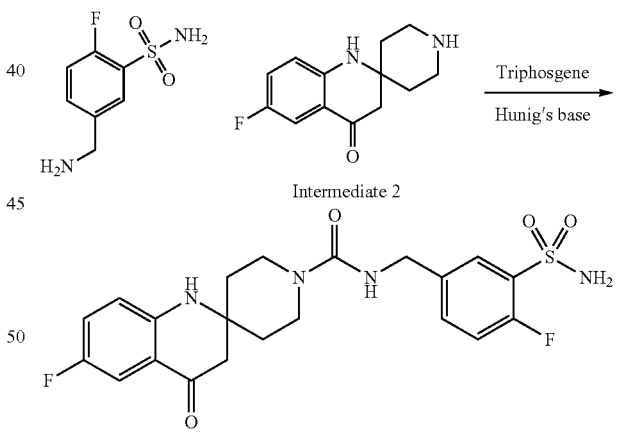

The title compound was prepared by a method similar to Example 2, using 5-(aminomethyl)-2-fluorobenzenesulfonamide and Intermediate 2 (free base) instead of (4-fluoro-2-methoxyphenyl)methanamine and Intermediate 3, respectively. The crude residue was purified by preparative HPLC (Basic, Method 4) to give the title compound (110 mg, 37% yield) as a fluffy yellow solid after lyophilization. LCMS: MS m/z 465.2 (M+H); $^1$H NMR (400 MHz, Methanol-$d_4$) δ 7.70 (dd, J=7.0, 2.4 Hz, 1H), 7.49-7.41 (m, 1H), 7.31 (dd, J=8.9, 3.0 Hz, 1H), 7.20-7.08 (m, 2H), 6.91-6.83 (m, 1H), 4.35 (s, 2H), 3.76-3.68 (m, 2H), 3.54-3.51 (m, 4H), 2.68 (s, 2H), 1.82-1.67 (m, 4H).

Example 31: N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide

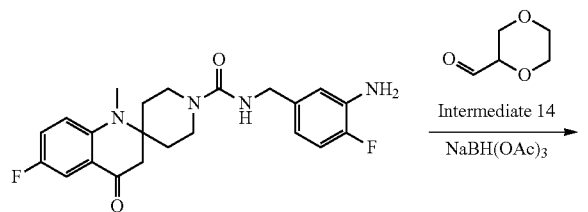

Example 27

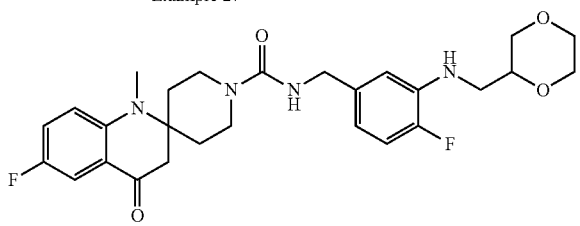

A mixture of Example 27 (50 mg, 0.121 mmol), Intermediate 14 (crude material) and NaBH(OAc)$_3$ (52 mg, 0.25 mmol) in DCM (5 mL) was stirred at RT for 16 h, partitioned between DCM and aqueous NH$_4$Cl solution. The combined organic extract was dried over MgSO$_4$, concentrated, and purified by reverse-phase HPLC (Basic, Method 4) to give the title compound as a yellow solid (9 mg, 14% yield). LCMS: m/z 515.4 (M+H); $^1$H NMR (400 MHz, Methanol-d$_4$) δ 7.43 (dd, J=8.7, 3.2 Hz, 1H), 7.27-7.22 (m, 1H), 6.94 (dd, J=9.4, 4.1 Hz, 1H), 6.86 (dd, J=11.7, 8.2 Hz, 1H), 6.70 (dd, J=8.5, 1.9 Hz, 1H), 6.56-6.50 (m, 1H), 4.25 (s, 2H), 3.99-3.91 (m, 2H), 3.84-3.75 (m, 3H), 3.73-3.65 (m, 2H), 3.62-3.53 (m, 1H), 3.42-3.35 (m, 1H), 3.21 (dd, J=13.4, 4.9 Hz, 1H), 3.13 (dd, J=13.4, 6.6 Hz, 1H), 3.10-3.01 (m, 2H), 2.94 (s, 3H), 2.92 (s, 2H), 1.93 (td, J=13.1, 4.7 Hz, 2H), 1.76-1.67 (m, 2H).

Example 32: 6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide

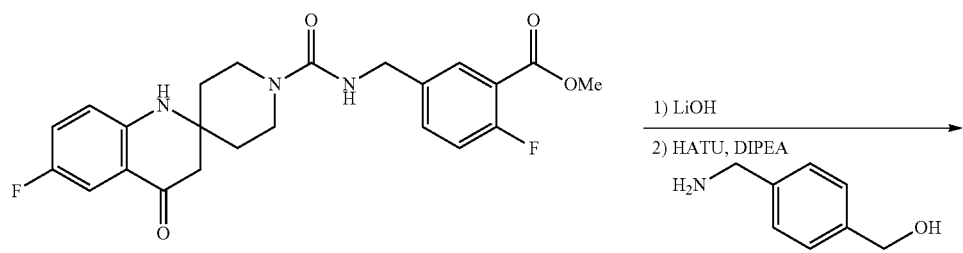

Example 61

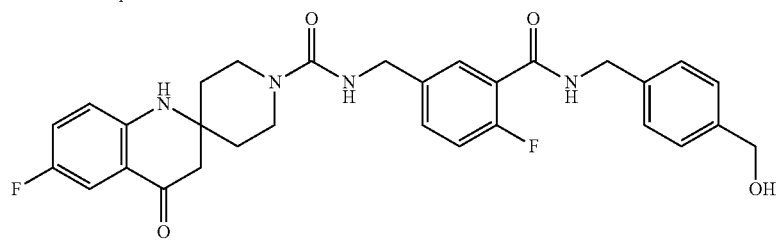

Step 1: Synthesis of 2-fluoro-5-((6'-fluoro-4'-oxo-3',4'-dihydro-1'H-spiro[piperidine-4,2'-quinolin]-1-ylcarboxamido)methyl)benzoic acid Example 61 (5.93 g, 13.37 mmol) in THF (10 mL) and Water (10 mL) was added LiOH (0.641 g, 26.7 mmol). The reaction mixture was stirred at RT for 16 h. Volatiles were concentrated in vacuo. The crude residue was triturated with MeOH/DCM, filtered, and dried in a vacuum oven for 16 h to obtain the title compound. LCMS: m/z 430.2 (M+H); $^1$H NMR (400 MHz, Methanol-d$_4$) δ 1H NMR (400 MHz, Methanol-d4) δ 7.63 (dd, J=6.9, 2.4 Hz, 1H), 7.36-7.26 (m, 2H), 7.17-7.08 (m, 1H), 7.07-6.98 (m, 1H), 6.91-6.83 (m, 1H), 4.33 (s, 2H), 3.51 (t, J=5.8 Hz, 4H), 2.68 (s, 2H), 1.82-1.66 (m, 4H).

Step 2: Synthesis of 6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide To anhydrous solution of the product in Step 1 (0.080 g, 0.180 mmol) in DMF (1 mL) was added DIPEA (0.047 mL, 0.271 mmol) followed by HATU (0.103 g, 0.271 mmol). The mixture was stirred at RT for 15 min, and (4-(aminomethyl)phenyl)methanol (0.025 g, 0.18 mmol) was added. The reaction mixture was stirred at RT for 18 h. The mixture was diluted with EtOAc (5 mL) and washed with saturated ammonia chloride (2×5 mL), and saturated NaCl (1×5 mL). The organic layer was dried with Na$_2$SO$_4$, filtered, and volatiles were concentrated in vacuo. The crude residue was dissolved in MeOH and purified by preparative reversed-phase HPLC (Basic, Method 4) to give the title compound (63 mg, 58% yield) as a fluffy yellow solid after lyophilization. HRMS: m/z 549.2341 (M+H); $^1$H NMR (400 MHz, Methanol-d$_4$) δ 7.65 (dd, J=6.9, 2.4 Hz, 1H), 7.49-7.40 (m, 1H), 7.40-7.26 (m, 5H), 7.21-7.07 (m, 2H), 6.90-6.79 (m, 1H), 4.62-4.56 (m, 4H), 4.35 (s, 2H), 3.51 (t, J=5.8 Hz, 4H), 2.67 (s, 2H), 1.82-1.66 (m, 4H).

Example 33: N-benzyl-6'-fluoro-4'-oxo-3',4'-dihydro-1'H-spiro[piperidine-4,2'-quinoline]-1-carboxamide

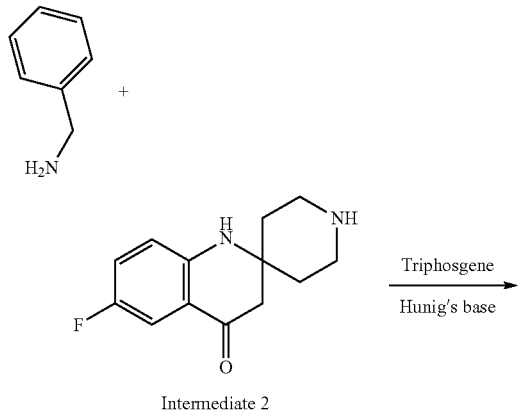

The title compound was prepared by a method similar to Example 2, using benzyl amine and Intermediate 2 (HCl salt) instead of (4-fluoro-2-methoxyphenyl)methanamine and Intermediate 3, respectively. The product was purified by silica gel chromatography (DCM/EtOAc=60/40 to 20/80), to give the title compound (74 mg, 35% yield) as a yellow solid. LCMS: m/z 368.05 (M+H); $^1$H NMR (400 MHz, DMSO-$d_6$) δ 7.31-7.27 (2H, m), 7.24-7.20 (5H, m), 7.12-7.08 (1H, m), 6.92-6.90 (1H, m), 6.80 (1H, s), 4.23-4.22 (2H, m), 3.46-3.40 (4H, m), 2.61 (2H, s), 1.60-1.55 (4H, m).

Example 34: N-((2,4-dimethylfuran-3-yl)methyl)-6'-fluoro-4'-oxo-3',4'-dihydro-1'H-spiro[piperidine-4,2'-quinoline]-1-carboxamide

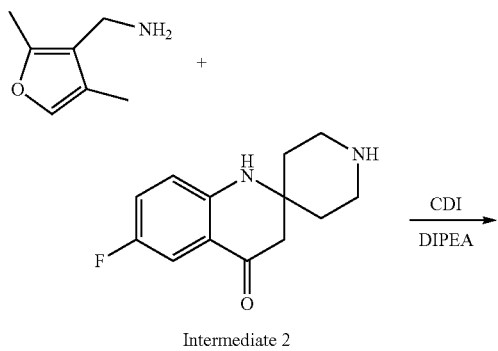

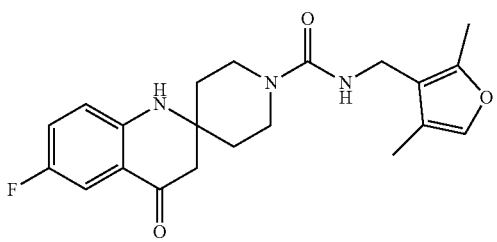

The title compound was prepared by a method similar to Example 1, using (2,4-dimethylfuran-3-yl)methanamine instead of Intermediate 1. Intermediate 2 was HCl salt. The product was purified by HPLC (Formic acid, Method 3) to give the title compound (29 mg, 27% yield) as a yellow solid. LCMS: m/z 386.3 (M+H); $^1$H NMR (400 MHz, DMSO-$d_6$) δ 7.29-7.10 (m, 3H), 6.94-6.85 (m, 1H), 6.79 (s, 1H), 6.64 (t, J=5.3 Hz, 1H), 3.95 (d, J=5.1 Hz, 2H), 3.56-3.21 (m, 4H), 2.59 (s, 2H), 2.20 (s, 3H), 1.89 (s, 3H), 1.64-1.44 (m, 4H).

Example 35: 6',8'-difluoro-N-(3-(oxazol-5-yl)benzyl)-4'-oxo-3',4'-dihydro-1'H-spiro[piperidine-4,2'-quinoline]-1-carboxamide

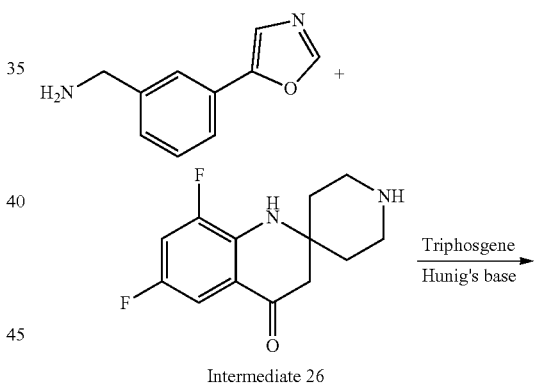

The title compound was prepared using a method similar to Example 2, using (3-(oxazol-5-yl)phenyl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 453.2 (M+H).

Example 36: 6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide

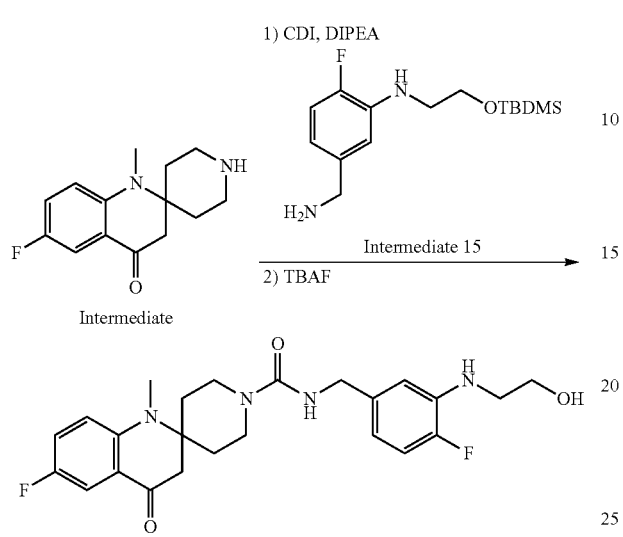

Step 1: Synthesis of N-(3-((2-((tert-butyldimethylsilyl)oxy)ethyl)amino)-4-fluorobenzyl)-6'-fluoro-1'-methyl-4'-oxo-3',4'-dihydro-1'H-spiro[piperidine-4,2'-quinoline]-1-carboxamide The title compound was prepared by a method similar to Example 1, using Intermediate 15 and Intermediate 3 instead of Intermediate 1 and Intermediate 2, respectively. LCMS: m/z 573.6 (M+H).

Step 2: Synthesis of 6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide The product in step 1 was taken up in THF (20 mL). To this was added TBAF (1M THF solution, 6.70 mL, 6.70 mmol). The mixture was stirred at RT for 2 h and partitioned between aqueous $NH_4Cl$ and EtOAc. The combined organic extract was dried over $Na_2SO_4$ and concentrated. The crude product was purified by silica gel chromatography (MeOH/DCM) to give the title compound (1.33 g, 86% yield) as a yellow solid. LCMS: m/z 459.5 (M+H); $^1$H NMR (400 MHz, DMSO-$d_6$) δ 7.44-7.28 (m, 2H), 7.03 (t, J=5.9 Hz, 1H), 7.00-6.87 (m, 2H), 6.63 (dd, J=8.7, 2.0 Hz, 1H), 6.42 (ddd, J=8.1, 4.5, 2.0 Hz, 1H), 5.24-5.07 (m, 1H), 4.77 (t, J=5.5 Hz, 1H), 4.13 (d, J=5.6 Hz, 2H), 4.01-3.81 (m, 2H), 3.57 (q, J=5.9 Hz, 2H), 3.12 (q, J=5.9 Hz, 2H), 2.98-2.79 (m, 7H), 1.76 (td, J=12.8, 4.6 Hz, 2H), 1.64-1.49 (m, 2H).

Example 37: N-((1H-pyrazol-4-yl)methyl)-6'-fluoro-4'-oxo-3',4'-dihydro-1'H-spiro[piperidine-4,2'-quinoline]-1-carboxamide

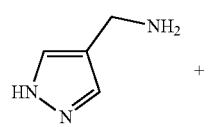

+

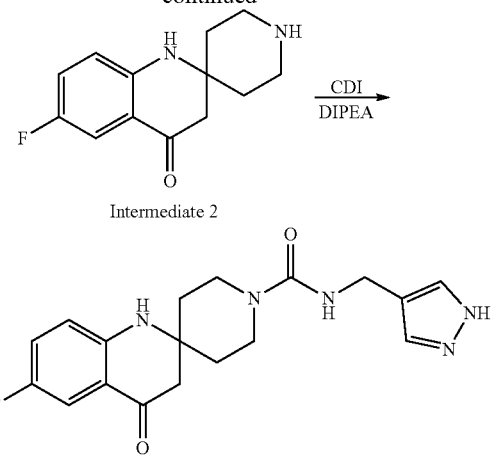

The title compound was prepared by a method similar to Example 1, using (1H-pyrazol-4-yl)methanamine instead of Intermediate 1. Intermediate 2 was HCl salt. The product was purified by silica gel chromatography (DCM/MeOH), followed by HPLC (Basic, Method 3) to give the title compound (29 mg, 36% yield) as a yellow solid. LCMS: m/z 358.3 (M+H); $^1$H NMR (400 MHz, DMSO-$d_6$) δ 12.57 (s, 1H), 7.45 (s, 2H), 7.30-7.12 (m, 2H), 6.95-6.85 (m, 1H), 6.86-6.73 (m, 2H), 4.07 (d, J=5.4 Hz, 2H), 3.53-3.19 (m, 4H), 2.60 (s, 2H), 1.65-1.42 (m, 4H).

Example 38: N-((4-carbamoylfuran-2-yl)methyl)-6',8'-difluoro-4'-oxo-3',4'-dihydro-1'H-spiro[piperidine-4,2'-quinoline]-1-carboxamide The title compound was prepared using a method similar to Example 2, using 5-(aminomethyl)furan-3-carboxamide and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 418.9 (M+H).

Example 39: 6'-fluoro-N-(4-hydroxybenzyl)-4'-oxo-3',4'-dihydro-1'H-spiro[piperidine-4,2'-quinoline]-1-carboxamide

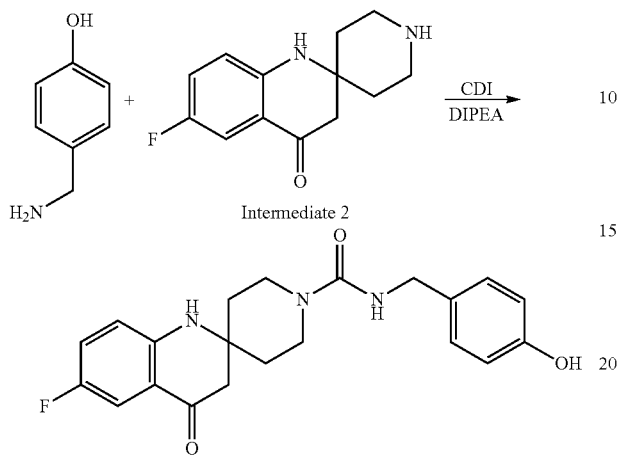

Intermediate 2

The title compound was prepared by a method similar to Example 1, using 4-hydroxybenzylamine instead of Intermediate 1. Intermediate 2 was HCl salt. The product was purified by silica gel chromatography (MeOH/DCM) followed by reversed-phase HPLC (Basic, Method 3) to give the title compound (17 mg, 8% yield) as a yellow solid. LCMS: m/z 384.3 (M+H). $^1$H NMR (400 MHz, DMSO-$d_6$) δ 9.22 (s, 1H), 7.28-7.16 (m, 2H), 7.09-7.00 (m, 2H), 6.97 (t, J=5.8 Hz, 1H), 6.94-6.86 (m, 1H), 6.80 (s, 1H), 6.71-6.63 (m, 2H), 4.10 (d, J=5.8 Hz, 2H), 3.49-3.28 (m, 4H), 2.60 (s, 2H), 1.66-1.46 (m, 4H).

Example 40: 6'-fluoro-N-(isoxazol-5-ylmethyl)-4'-oxo-3',4'-dihydro-1'H-spiro[piperidine-4,2'-quinoline]-1-carboxamide

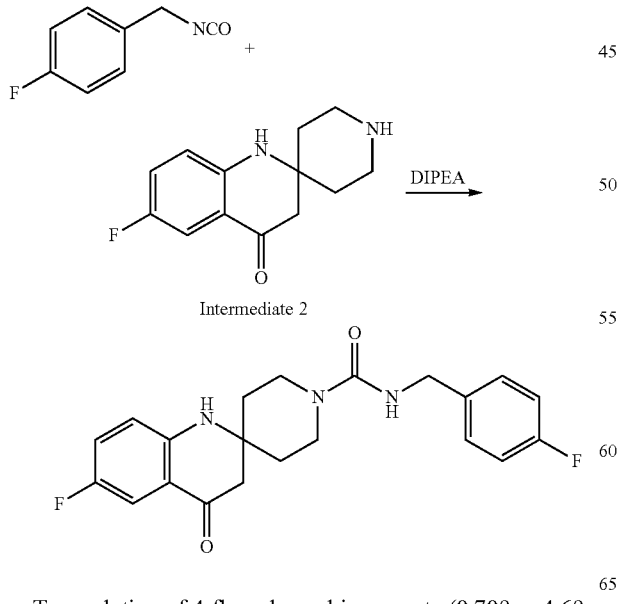

Intermediate 2

To a solution of 4-fluorobenzyl isocyanate (0.709 g, 4.69 mmol) in THF (1 mL) was added a solution of Intermediate 2 as TFA salt (1.42 g, 4.08 mmol) and Hunig's base (2.136 mL, 12.23 mmol) in THF (1 mL). The mixture was stirred at RT for 18 h. The reaction was poured into saturated aqueous NaHCO$_3$ and was extracted with EtOAc. The organics were combined, dried with Na$_2$SO$_4$, filtered, and volatiles were concentrated in vacuo. The crude residue was passed through a silica gel plug eluting with MeOH/DCM (5/95). The solvent was concentrated in vacuo and the solid was triturated with diethyl ether to give the title compound (1.1 g, 69% yield). LCMS: m/z 386.2 (M+H); $^1$H NMR (400 MHz, Methanol-$d_4$) δ 7.32-7.25 (m, 3H), 7.12 (ddd, J=9.2, 8.0, 3.0 Hz, 1H), 7.05-6.98 (m, 2H), 6.85 (dd, J=9.1, 4.3 Hz, 1H), 4.31 (s, 2H), 3.57-3.43 (m, 4H), 2.66 (s, 2H), 1.80-1.63 (m, 4H).

Example 41: N-(3-carbamoyl-4-fluorobenzyl)-6'-fluoro-1'-methyl-4'-oxo-3',4'-dihydro-1'H-spiro[piperidine-4,2'-quinoline]-1-carboxamide

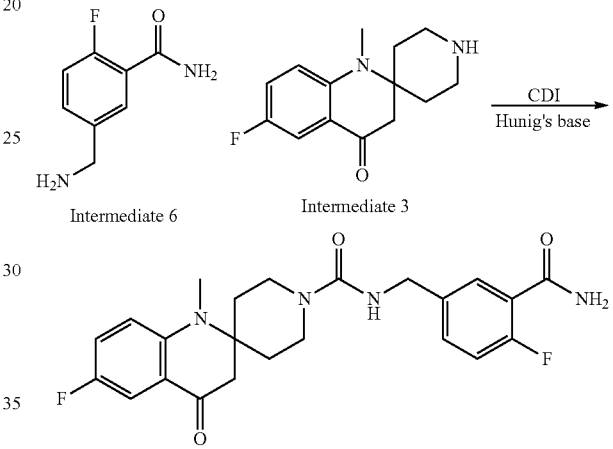

Intermediate 6    Intermediate 3

The title compound was prepared by a method similar to Example 1, using Intermediates 6 and 3 instead of Intermediates 1 and 2, respectively. The crude residue was purified by silica gel chromatography (MeOH/DCM=1:9) followed by a preparative reversed-phase HPLC (Basic, Method 4) to give the title compound (656 mg, 48% yield) as a fluffy yellow solid after lyophilization. HRMS: m/z 443.1886 (M+H); $^1$H NMR (400 MHz, Methanol-$d_4$) δ 7.80-7.73 (m, 1H), 7.53-7.41 (m, 2H), 7.32-7.22 (m, 1H), 7.22-7.13 (m, 1H), 7.01-6.92 (m, 1H), 4.37 (s, 2H), 4.03-3.93 (m, 2H), 3.14-3.04 (m, 2H), 2.97 (s, 3H), 2.95 (s, 2H), 2.03-1.91 (m, 2H), 1.78-1.70 (m, 2H).

Example 42: N-(3-amino-2,4-difluorobenzyl)-6'-fluoro-1'-methyl-4'-oxo-3',4'-dihydro-1'H-spiro[piperidine-4,2'-quinoline]-1-carboxamide

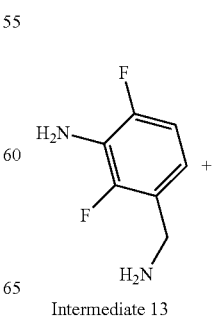

Intermediate 13

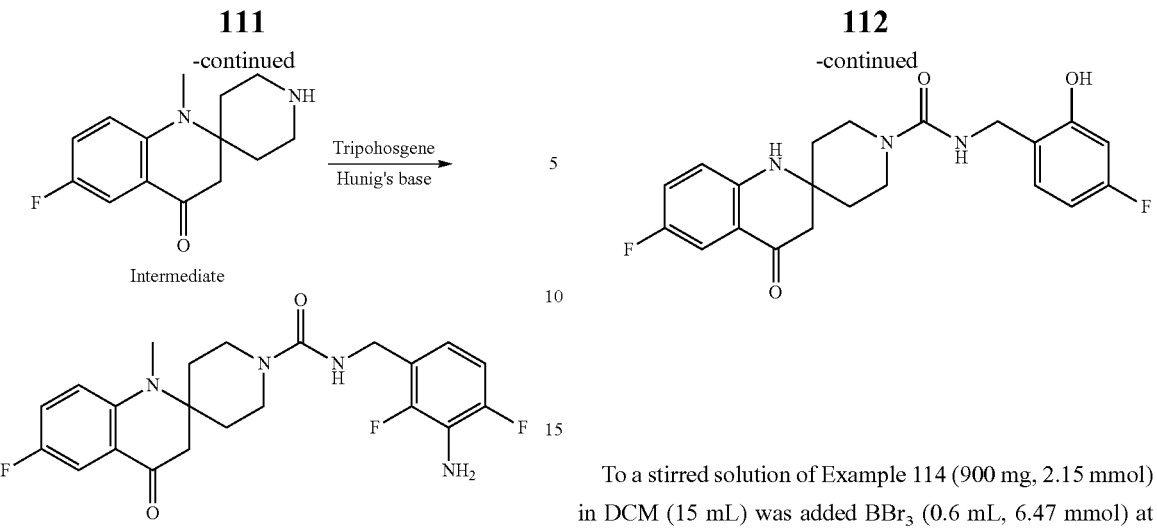

The title compound was prepared by a method similar to Example 2, using Intermediate 13 instead of (4-fluoro-2-methoxyphenyl)methanamine. The product was purified by preparative HPLC (Basic, Method 4) to give the title compound (15 mg, 22% yield) as a fluffy yellow solid after lyophilization. LCMS: m/z 433.3 (M+H).

Example 43: 6'-fluoro-N-(4-fluoro-2-hydroxybenzyl)-4'-oxo-3',4'-dihydro-1'H-spiro[piperidine-4,2'-quinoline]-1-carboxamide

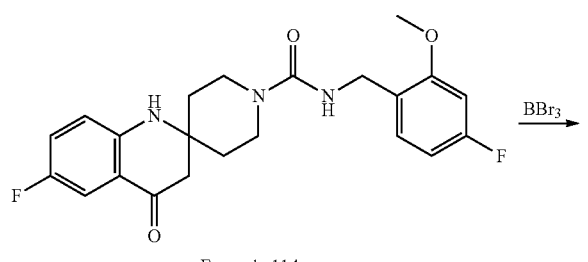

To a stirred solution of Example 114 (900 mg, 2.15 mmol) in DCM (15 mL) was added $BBr_3$ (0.6 mL, 6.47 mmol) at RT under nitrogen atmosphere and the reaction was stirred at RT for 4 h. The reaction was cooled to 0° C. and quenched with MeOH, then diluted with EtOAc and washed with water, dried over $Na_2SO_4$ and concentrated under reduced pressure. The product was purified by silica gel chromatography (DCM/MeOH=100/0 to 90/10), to give the title compound (500 mg, 58% yield) as a yellow solid. LCMS: m/z 402.3 (M+H); $^1$H NMR (400 MHz, DMSO-$d_6$) δ: 10.5 (1H, s), 7.24-7.19 (3H, m), 7.09-7.05 (1H, t), 6.90-6.87 (1H, m), 6.79 (1H, s), 6.59-6.52 (2H, m), 4.11-4.10 (2H, d), 3.45-3.32 (4H, m), 2.60 (2H, m), 1.58-1.55 (4H, m).

Example 44: N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide

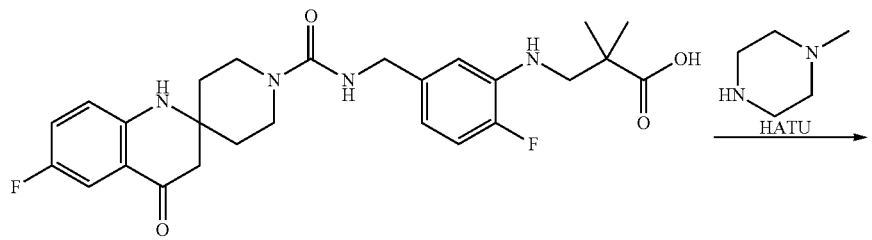

Example 140

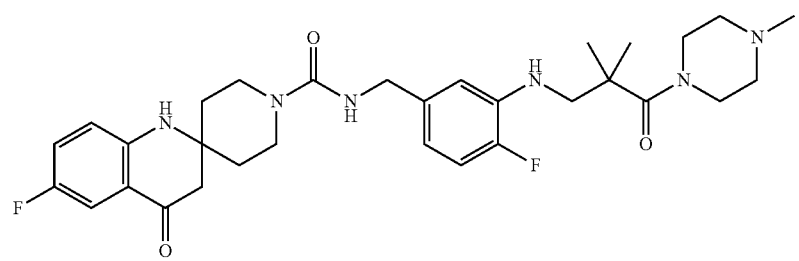

Compound Example 140 was prepared by hydrolysis of the corresponding methyl ester (43 mg, 0.081 mmol) as described in Example 140, Step 1. The curde carboxylic acid product (Example 140) was taken up in DMF (6 mL) and separated into two vials with equal volume. To one of the vials were added HATU (145 mg, 0.381 mmol) and N-Me piperazine (150 μL, 1.35 mmol). The mixture was stirred at RT for 2 h, partitioned between EtOAc and aqueous NH$_4$Cl solution. The combined organic extract was dried over MgSO$_4$, concentrated and purified by reverse-phase HPLC (Basic, Method 5) to give the title compound as a yellow solid (11 mg, 44% yield). LCMS: m/z 597.4 (M+H); $^1$H NMR (400 MHz, Methanol-d$_4$) δ 7.42 (dd, J=8.6, 3.2 Hz, 1H), 7.27-7.21 (m, 1H), 6.93 (dd, J=9.4, 4.0 Hz, 1H), 6.85 (dd, J=11.7, 8.2 Hz, 1H), 6.76 (dd, J=8.5, 1.9 Hz, 1H), 6.54-6.45 (m, 1H), 4.24 (s, 2H), 4.00-3.90 (m, 2H), 3.75-3.64 (m, 4H), 3.27 (s, 2H), 3.11-2.99 (m, 2H), 2.93 (s, 3H), 2.92 (s, 2H), 2.49-2.39 (m, 4H), 2.29 (s, 3H), 1.92 (td, J=13.0, 4.6 Hz, 2H), 1.75-1.66 (m, 2H), 1.35 (s, 6H).

Example 45: (S)—N-(3-((2,3-dihydroxypropyl)amino)-4-fluorobenzyl)-6'-fluoro-1'-methyl-4'-oxo-3',4'-dihydro-1'H-spiro[piperidine-4,2'-quinoline]-1-carboxamide

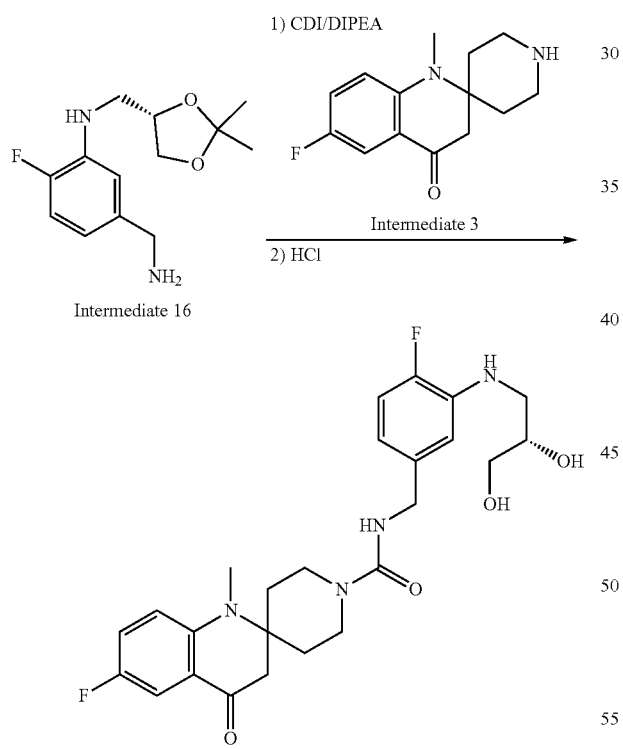

Step 1: Synthesis of (S)—N-(3-(((2,2-dimethyl-1,3-dioxolan-4-yl)methyl)amino)-4-fluorobenzyl)-6'-fluoro-1'-methyl-4'-oxo-3',4'-dihydro-1'H-spiro[piperidine-4,2'-quinoline]-1-carboxamide The title compound was prepared by a method similar to Example 1, using Intermediate 16 and Intermediate 3 instead of Intermediate 1 and Intermediate 2, respectively. The product was purified by silica gel chromatography (EtOAc) to give the title compound as a yellow oil (320 mg). LCMS: m/z 529.4 (M+H).

Step 2: Synthesis of (S)—N-(3-((2,3-dihydroxypropyl)amino)-4-fluorobenzyl)-6'-fluoro-1'-methyl-4'-oxo-3',4'-dihydro-1'H-spiro[piperidine-4,2'-quinoline]-1-carboxamide Aqueous HCl solution (3 M, 5 mL, 15 mmol) was added to a solution of the product in Step 1 (318 mg, 0.602 mmol) in THF (5 mL). The mixture was stirred at RT for 20 min, concentrated, and partitioned between EtOAc and aqueous K$_2$CO$_3$. The combined organic extract was dried over MgSO$_4$, concentrated, and purified by silica gel chromatography (DCM/MeOH) to give the title compound as a yellow solid (101 mg, 34% yield over 2 steps). LCMS: m/z 489.3 (M+H); $^1$H NMR (400 MHz, Methanol-d$_4$) δ 7.42 (dd, J=8.7, 3.2 Hz, 1H), 7.27-7.22 (m, 1H), 6.94 (dd, J=9.4, 4.1 Hz, 1H), 6.86 (dd, J=11.7, 8.2 Hz, 1H), 6.74 (dd, J=8.5, 2.1 Hz, 1H), 6.52 (ddd, J=8.2, 4.5, 2.2 Hz, 1H), 4.25 (s, 2H), 3.99-3.92 (m, 2H), 3.87-3.79 (m, 1H), 3.61-3.53 (m, 2H), 3.37-3.33 (m, 1H), 3.17-3.00 (m, 3H), 2.94 (s, 3H), 2.92 (s, 2H), 1.96-1.87 (m, 2H), 1.77-1.61 (m, 2H).

Example 46: 6',8'-difluoro-N-(furan-3-ylmethyl)-4'-oxo-3',4'-dihydro-1'H-spiro[piperidine-4,2'-quinoline]-1-carboxamide

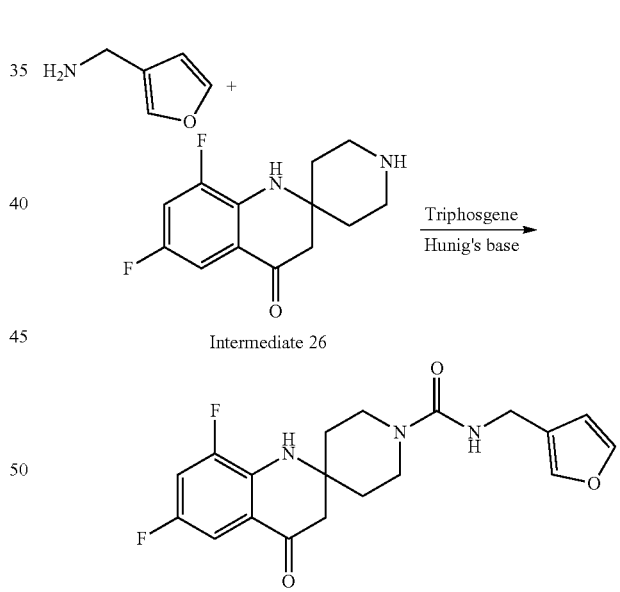

The title compound was prepared using a method similar to Example 2, using furan-3-ylmethanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 376.1 (M+H); $^1$H NMR (400 MHz, Methanol-d$_4$) δ 7.32 (s, 1H), 7.11-7.03 (m, 2H), 6.29 (s, 2H), 4.07 (d, J=8 Hz, 3H), 3.59-3.53 (m, 2H), 3.23 (s, 1H), 2.68 (s, 2H), 1.72-1.63 (m, 4H).

Example 47: N-((1H-pyrazol-3-yl)methyl)-6'-fluoro-4'-oxo-3',4'-dihydro-1'H-spiro[piperidine-4,2'-quinoline]-1-carboxamide

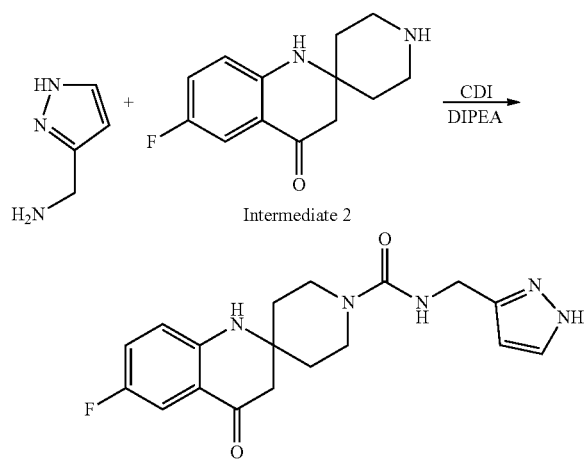

The title compound was prepared by a method similar to Example 1, using (1H-Pyrazol-3-yl)methylamine instead of Intermediate 1. Intermediate 2 was HCl salt. The product was purified by silica gel chromatography (MeOH/DCM) followed by reversed-phase HPLC (Basic, Method 2) to give the title compound (39 mg, 42% yield) as a white solid after lyophilization. LCMS: m/z 358.4 (M+H). $^1$H NMR (400 MHz, DMSO-$d_6$) δ 12.49 (s, 1H), 7.58 (s, 1H), 7.30-7.14 (m, 2H), 7.03-6.85 (m, 2H), 6.81 (s, 1H), 6.08 (s, 1H), 4.21 (d, J=5.5 Hz, 2H), 3.54-3.25 (m, 4H), 2.60 (s, 2H), 1.71-1.43 (m, 4H).

Example 48: 6'-fluoro-N-(4-fluoro-3-((2-hydroxyethyl)carbamoyl)benzyl)-4'-oxo-3',4'-dihydro-1'H-spiro[piperidine-4,2'-quinoline]-1-carboxamide

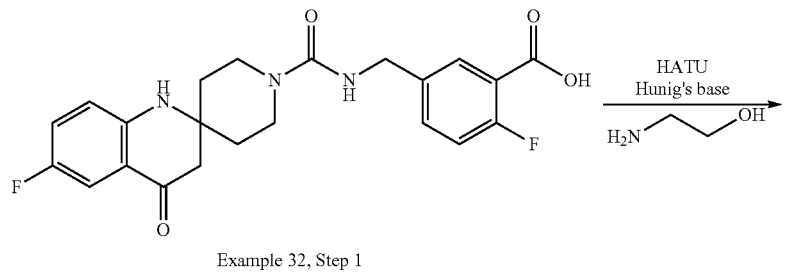

Example 32, Step 1

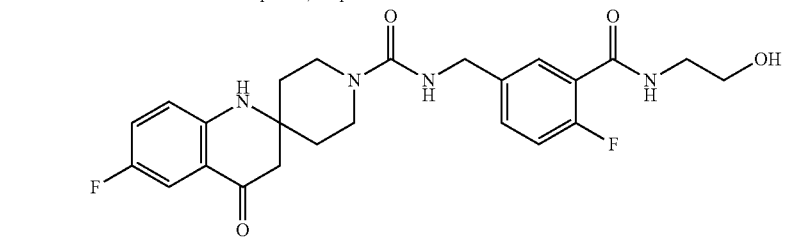

The title compound was prepared by a method similar to Example 32, Step 2. The crude residue was purified by silica gel chromatography (MeOH/DCM=1:9) followed by a preparative reversed-phase HPLC (Basic, Method 4) to give the title compound (656 mg, 48% yield) as a fluffy yellow solid after lyophilization. HRMS: m/z 473.2002 (M+H); $^1$H NMR (400 MHz, Methanol-$d_4$) δ 7.59 (dd, J=7.0, 2.3 Hz, 1H), 7.45-7.25 (m, 1H), 7.20 (dd, J=8.9, 3.0 Hz, 1H), 7.13-6.94 (m, 2H), 6.83-6.68 (m, 1H), 4.25 (s, 2H), 3.61 (t, J=5.8 Hz, 2H), 3.52-3.34 (m, 6H), 2.57 (s, 2H), 1.79-1.56 (m, 4H).

Example 49: N-(4-amino-2,5-difluorobenzyl)-6'-fluoro-4'-oxo-3',4'-dihydro-1'H-spiro[piperidine-4,2'-quinoline]-1-carboxamide

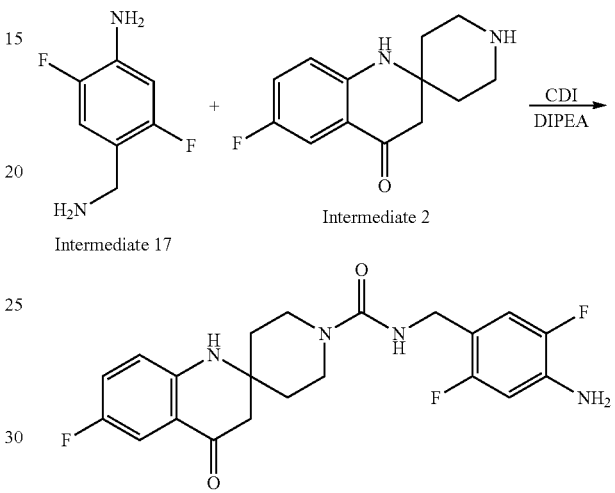

The title compound was prepared by a method similar to Example 1, using Intermediate 17 instead of Intermediate 1. Intermediate 2 was HCl salt. The product was purified by silica gel chromatography (MeOH/DCM) followed by reversed-phase HPLC (Basic, Method 4) to give the title compound (35 mg, 50% yield) as a yellow solid after lyophilization. LCMS: m/z=441.3 (M+Na). $^1$H NMR (400 MHz, DMSO-$d_6$) δ 7.30-7.15 (m, 2H), 6.96-6.84 (m, 3H), 6.78 (s, 1H), 6.47 (dd, J=11.6, 7.5 Hz, 1H), 5.28 (s, 2H), 4.08 (d, J=5.4 Hz, 2H), 3.49-3.32 (m, 4H), 2.60 (s, 2H), 1.67-1.47 (m, 4H).

Example 50: N-(5-amino-2,4-difluorobenzyl)-1'-ethyl-6'-fluoro-4'-oxo-3',4'-dihydro-1'H-spiro[piperidine-4,2'-quinoline]-1-carboxamide

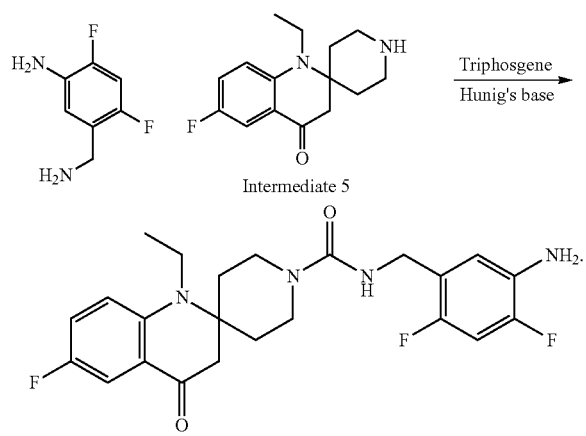

The title compound was prepared by a method similar to Example 2, using (2,4-difluorophenyl)methanamine and Intermediate 5 instead of (4-fluoro-2-methoxyphenyl)methanamine and Intermediate 3, respectively. The crude residue was purified by preparative HPLC (Basic, Method 4) to give the title compound (6 mg, 4% yield) as a fluffy yellow solid after lyophilization. HRMS: m/z 447.2004 (M+H); $^1$H NMR (400 MHz, Chloroform-d) δ 7.50 (d, 1H), 7.20-7.10 (m, 1H), 6.89-6.80 (m, 1H), 6.80-6.73 (m, 1H), 6.73-6.67 (m, 1H), 4.34 (d, J=5.6 Hz, 2H), 3.94-3.85 (m, 2H), 3.36 (q, J=7.1 Hz, 2H), 3.04-2.92 (m, 2H), 2.83 (s, 2H), 1.93-1.74 (m, 4H), 1.25-1.19 (m, 3H).

Example 51: 6'-fluoro-N-(4-fluoro-2-(2,2,2-trifluoroethoxy)benzyl)-4'-oxo-3',4'-dihydro-1'H-spiro[piperidine-4,2'-quinoline]-1-carboxamide

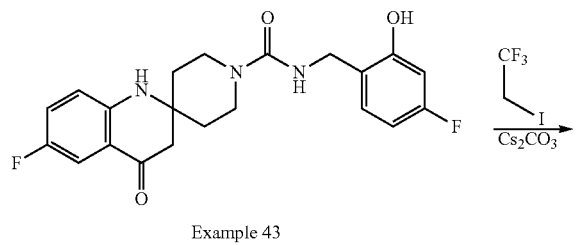

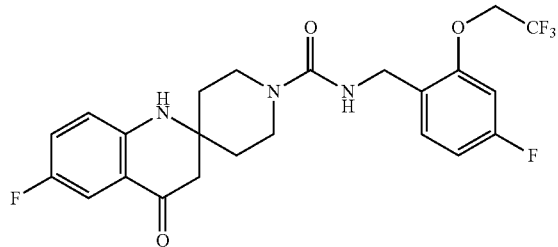

To a solution of Example 43 (50 mg, 0.124 mmol) in DMF (1.2 mL) was added 1,1,1-trifluoro-2-iodoethane (34 mg, 0.16 mmol) and cesium carbonate (60.8 mg, 0.186 mmol). The reaction mixture was heated to 70° C. overnight. The reaction mixture was diluted with water, and extracted with EtOAc. The EtOAc layer was concentrated, and purified with HPLC (Basic, Method 5), followed by silica gel column chromatography (Heptane/EtOAc) to give the title compound (8 mg, 6% yield). LCMS: m/z 484.1 (M+H); $^1$H NMR (400 MHz, DCM-d$_2$) δ 1.83 (m, 4H), 2.71 (s, 2H), 3.30-3.52 (m, 4H), 4.40 (s, 2H), 4.46 (q, J=8.1 Hz, 2H), 6.64 (dd, J=10.2, 2.4 Hz, 1H), 6.70-6.82 (m, 2H), 7.09-7.17 (m, 1H), 7.36 (dd, J=8.3, 6.7 Hz, 1H), 7.44 (dd, J=8.9, 3.0 Hz, 1H). No NH proton was observed.

Example 52: N-(2-(ethylamino)-4-fluorobenzyl)-6'-fluoro-1'-methyl-4'-oxo-3',4'-dihydro-1'H-spiro[piperidine-4,2'-quinoline]-1-carboxamide

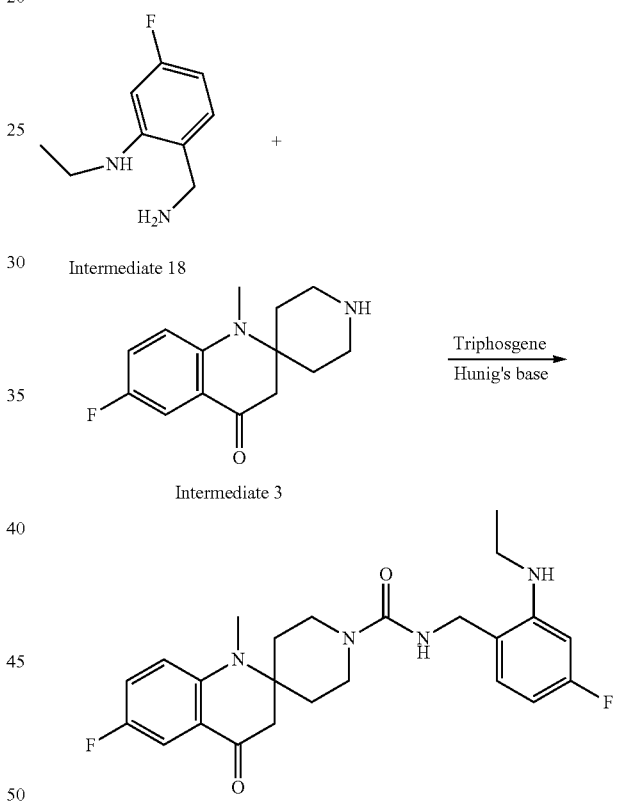

The title compound was prepared by a method similar to Example 2, using Intermediate 18 instead of (4-fluoro-2-methoxyphenyl)methanamine. The product was purified by SFC (column: Phenomenex Kinetex Biphenyl 21.2×150 mm 5 μm; mobile phase: MeOH), followed by preparative HPLC (Basic, Method 6) to give the title compound (10 mg, 17% yield) as a fluffy yellow solid after lyophilization. LCMS: m/z 443.3 (M+H). $^1$H NMR (400 MHz, DMSO-d$_6$) δ 7.34 (ddd, J=8.9, 6.7, 3.2 Hz, 2H), 7.10-6.86 (m, 3H), 6.29-6.21 (m, 2H), 6.10 (s, 1H), 4.09 (d, J=5.6 Hz, 2H), 3.88 (d, J=13.6 Hz, 2H), 3.01 (dt, J=12.1, 6.1 Hz, 2H), 2.87 (d, J=27.5 Hz, 7H), 1.75 (td, J=12.6, 4.0 Hz, 2H), 1.56 (d, J=12.8 Hz, 2H), 1.17 (t, J=7.1 Hz, 3H).

Example 53: N-(benzo[d][1,3]dioxol-4-ylmethyl)-6',8'-difluoro-4'-oxo-3',4'-dihydro-1'H-spiro[piperidine-4,2'-quinoline]-1-carboxamide

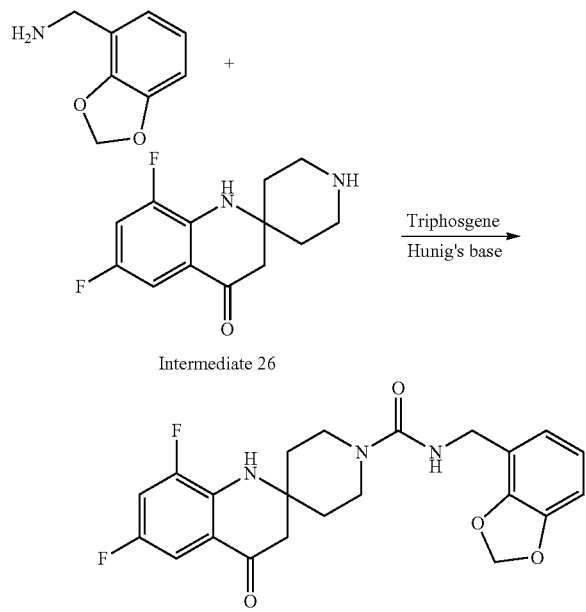

The title compound was prepared using a method similar to Example 2, using benzo[d][1,3]dioxol-4-ylmethanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 429.9 (M+H).

Example 54: 6',8'-difluoro-N-(4-hydroxybenzyl)-4'-oxo-3',4'-dihydro-1'H-spiro[piperidine-4,2'-quinoline]-1-carboxamide

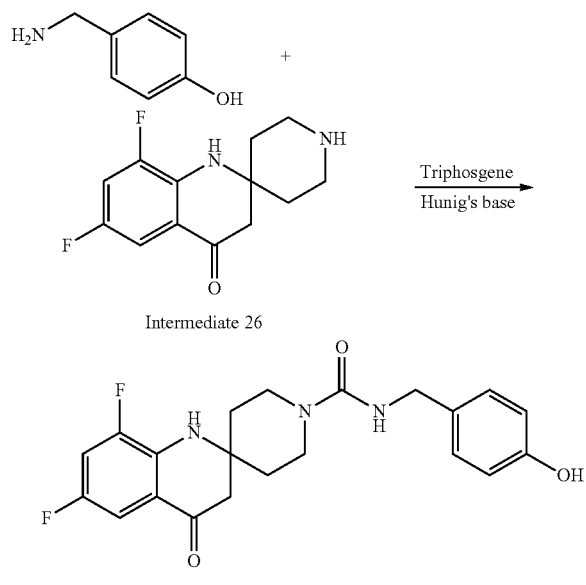

The title compound was prepared using a method similar to Example 2, using 4-(aminomethyl)phenol and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 402.1 (M+H).

Example 55: 6'-fluoro-N-(4-fluoro-3-(methylsulfonamido)benzyl)-1'-methyl-4'-oxo-3',4'-dihydro-1'H-spiro[piperidine-4,2'-quinoline]-1-carboxamide

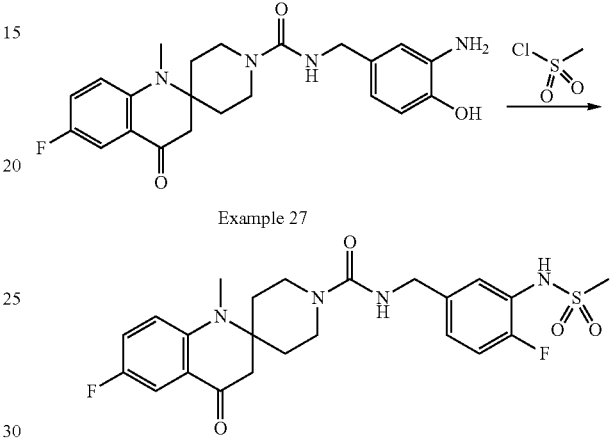

To a stirred solution of Example 27 (17 mg, 0.041 mmol) in DCM (300 μL) was added pyridine (3.32 μl, 0.041 mmol) and mesyl chloride (3.24 μl, 0.041 mmol). The reaction was heated at 50° C. for 2 h. The material was purified by reverse-phase HPLC (Basic, Method 2) to afford the title compound as a yellow solid (8 mg, 39.2% yield). LCMS: m/z 493.1 (M+H). $^1$H NMR (400 MHz, Methanol-d$_4$) δ 7.33 (dd, J=8.6, 3.2 Hz, 2H), 7.15 (ddd, J=9.3, 8.0, 3.2 Hz, 1H), 6.99 (dd, J=7.9, 1.5 Hz, 2H), 6.85 (dd, J=9.3, 4.0 Hz, 1H), 4.22 (s, 2H), 3.87 (d, J=14.0 Hz, 2H), 3.02-2.93 (m, 3H), 2.87 (s, 3H), 2.86 (s, 3H), 2.84 (s, 1H), 1.87 (td, J=13.1, 4.8 Hz, 2H), 1.62 (d, J=12.2 Hz, 2H).

Example 56: N-(4-amino-3-fluorobenzyl)-6'-fluoro-4'-oxo-3',4'-dihydro-1'H-spiro[piperidine-4,2'-quinoline]-1-carboxamide

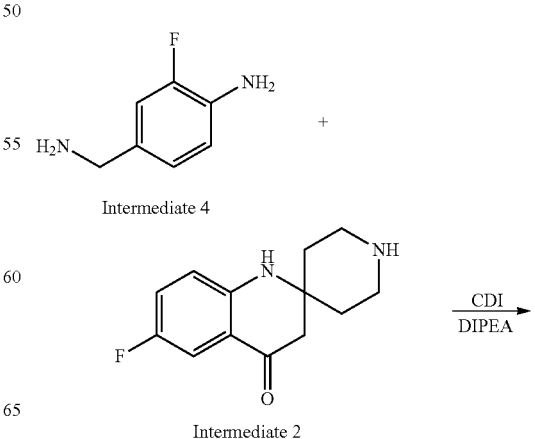

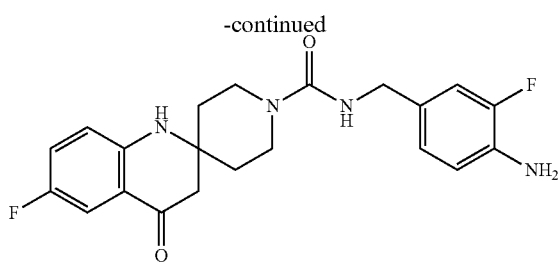

6.85-6.72 (m, 2H), 6.49 (td, J=8.4, 1.7 Hz, 1H), 5.34 (s, 2H), 4.12 (d, J=5.3 Hz, 2H), 3.49-3.27 (m, 4H), 2.60 (s, 2H), 1.65-1.45 (m, 4H).

Example 58: 6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide

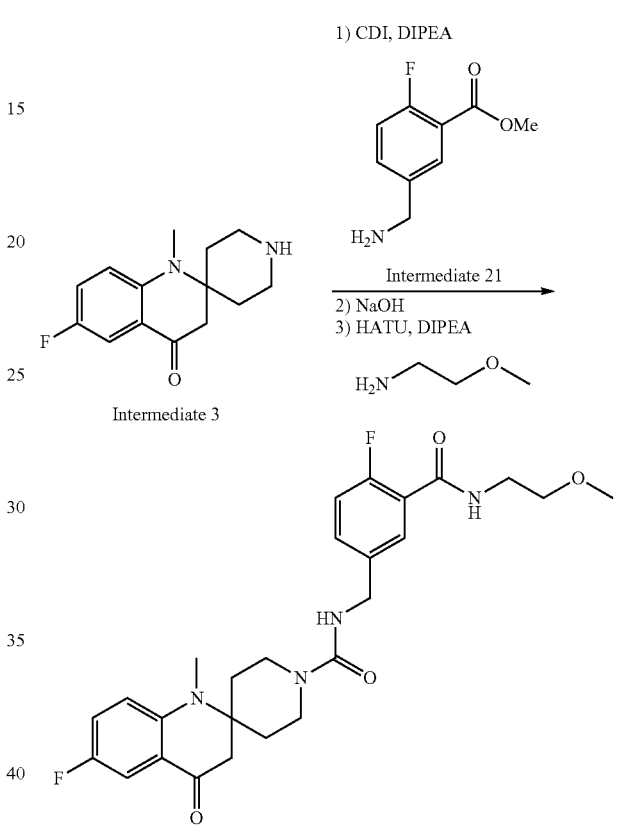

The title compound was prepared by a method similar to Example 1, using intermediate 4 instead of Intermediate 1. Intermediate 2 was TFA salt. The product was purified by silica gel chromatography (MeOH/DCM) followed by recrystallization in water/acetonitrile (95/5 v/v) to give the title compound (331 mg, 35% yield) as a crystalline yellow solid. LCMS: m/z 401.2 (M+H). $^1$H NMR (400 MHz, DMSO-$d_6$) δ 7.27-7.17 (m, 2H), 6.96 (t, J=5.8 Hz, 1H), 6.94-6.82 (m, 2H), 6.80 (s, 1H), 6.76 (dd, J=8.1, 1.9 Hz, 1H), 6.67 (dd, J=9.3, 8.1 Hz, 1H), 4.97 (s, 2H), 4.06 (d, J=5.5 Hz, 2H), 3.51-3.26 (m, 4H), 2.60 (s, 2H), 1.66-1.47 (m, 4H).

Example 57: N-(4-amino-2,3-difluorobenzyl)-6'-fluoro-4'-oxo-3',4'-dihydro-1'H-spiro[piperidine-4,2'-quinoline]-1-carboxamide

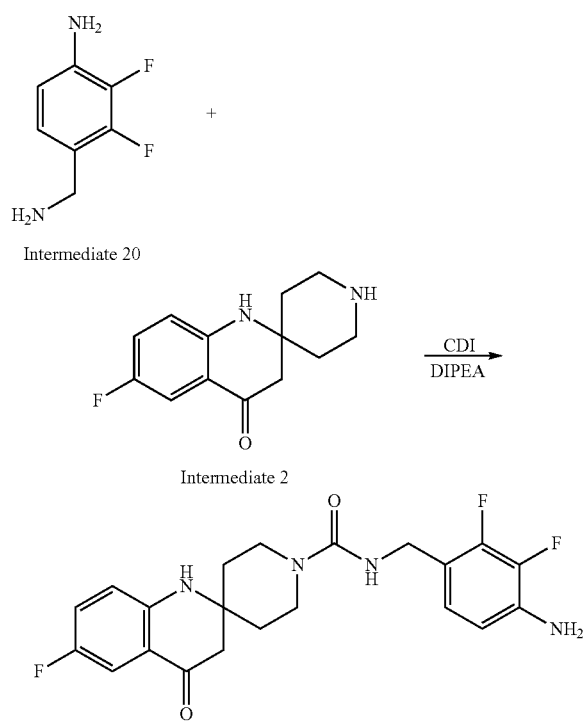

The title compound was prepared by a method similar to Example 1, using Intermediate 20 instead of Intermediate 1. Intermediate 2 was TFA salt. The product was purified by silica gel chromatography (MeOH/DCM) followed by reversed-phase HPLC (Basic, Method 4) to give the title compound (25 mg, 37% yield) as a yellow solid after lyophilization. LCMS: m/z 419.3 (M+H); $^1$H NMR (400 MHz, DMSO-$d_6$) δ 7.30-7.15 (m, 2H), 6.99-6.86 (m, 2H), Step 1: Synthesis of methyl 2-fluoro-5-(((6'-fluoro-1'-methyl-4'-oxo-3',4'-dihydro-1'H-spiro[piperidine-4,2'-quinoline]-1-carboxamido)methyl)benzoate The title compound was prepared by a method similar to Example 1, using Intermediates 21 and 3 instead of Intermediates 1 and 2, respectively. The crude residue was purified by silica gel chromatography (EtOAc/Heptane=3/7) to give the title compound (1.2 g, 30% yield) as a fluffy yellow solid after lyophilization. LCMS: m/z 458.5 (M+H).

Step 2: Synthesis of 2-fluoro-5-(((6'-fluoro-1'-methyl-4'-oxo-3',4'-dihydro-1'H-spiro[piperidine-4,2'-quinoline]-1-carboxamido) methyl)benzoic acid To the product in Step 1 (1.2 g, 2.62 mmol) in THF (10 mL) and water (5 mL) was added 6N solution of NaOH (2 mL, 12 mmol). The reaction mixture was stirred at RT for 3 h. Volatiles were concentrated in vacuo. The crude residue was added 3N aqueous solution of HCl dropwise with stirring. The product precipitated from solution, filtered, and dried in a vacuum oven for 16 h to obtain the title compound. (0.3 g, 27% yield). LCMS m/z 444.3 (M+H); $^1$H NMR (300

MHz, DMSO-d$_6$) δ 7.76-7.73 (1H, m), 7.49 (1H, m), 7.37-7.20 (4H, m), 6.97-6.92 (1H, m), 4.23-4.21 (2H, d), 3.91-3.87 (2H, d), 2.91 (3H, s), 2.84 (3H, s), 1.80-1.73 (2H, m), 1.58-1.54 (2H, d).

Step 3: Synthesis of 6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide The title compound was prepared by a method similar to Example 32, Step 2. The crude residue was purified by silica gel chromatography (MeOH/DCM=1:9) followed by a preparative reversed-phase HPLC (Basic, Method 4) to give the title compound (45 mg, 66% yield) as a fluffy yellow solid after lyophilization. HRMS: m/z 501.2364 (M+H); $^1$H NMR (400 MHz, Methanol-d$_4$) δ 7.69 (dd, J=7.0, 2.3 Hz, 1H), 7.51-7.41 (m, 2H), 7.32-7.22 (m, 1H), 7.22-7.12 (m, 1H), 6.97 (dd, J=9.4, 4.0 Hz, 1H), 4.37 (s, 2H), 4.02-3.93 (m, 2H), 3.58 (s, 4H), 3.40 (s, 3H), 3.14-3.04 (m, 2H), 2.99-2.93 (m, 5H), 2.03-1.90 (m, 2H), 1.78-1.70 (m, 2H).

Example 59: 6'-fluoro-N-((2-methylfuran-3-yl)methyl)-4'-oxo-3',4'-dihydro-1'H-spiro[piperidine-4,2'-quinoline]-1-carboxamide

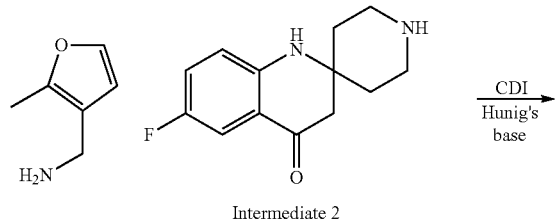

The title compound was prepared by a method similar to Example 1, using (2-methylfuran-3-yl)methanamine of Intermediate 1. Intermediate 2 was free base. The crude residue was purified by a preparative reversed-phase HPLC (Basic, Method 4) to give the title compound (656 mg, 48% yield) as a fluffy yellow solid after lyophilization. HRMS: m/z 372.1728 (M+H); $^1$H NMR (400 MHz, Methanol-d$_4$) δ 7.25-7.10 (m, 2H), 7.06-6.96 (m, 1H), 6.74 (dd, J=9.1, 4.2 Hz, 1H), 6.19 (d, J=1.9 Hz, 1H), 4.00 (s, 2H), 3.44-3.29 (m, 4H), 2.54 (s, 2H), 2.14 (s, 3H), 1.70-1.52 (m, 4H).

Example 60: 6'-fluoro-N-(4-fluoro-3-((3-hydroxycyclobutyl)carbamoyl)benzyl)-4'-oxo-3',4'-dihydro-1'H-spiro[piperidine-4,2'-quinoline]-1-carboxamide

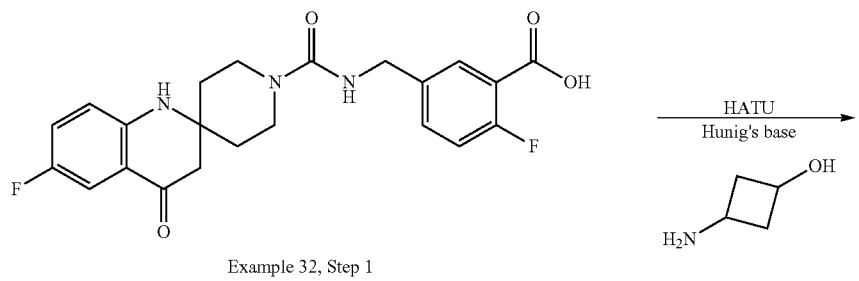

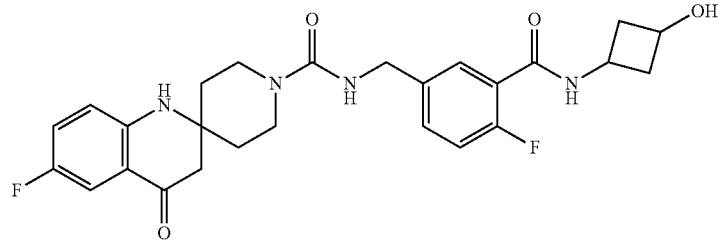

The title compound was prepared by a method similar to Example 32, Step 2, using 3-aminocyclobutanol instead of (4-(aminomethyl)phenyl)methanol. The crude residue was purified a preparative reversed-phase HPLC (Basic, Method 4) to give the title compound (88 mg, 98% yield) as a fluffy yellow solid after lyophilization. HRMS: m/z 499.2166 (M+H); $^1$H NMR (400 MHz, Methanol-d$_4$) δ 7.50-7.42 (m, 1H), 7.36-7.28 (m, 1H), 7.20 (dd, J=9.1, 3.1 Hz, 1H), 7.08-6.98 (m, 2H), 6.80-6.72 (m, 1H), 4.24 (s, 2H), 3.98-3.85 (m, 2H), 3.47-3.37 (m, 4H), 2.72-2.59 (m, 2H), 2.57 (s, 2H), 1.90-1.78 (m, 2H), 1.72-1.55 (m, 4H).

Example 61: methyl 2-fluoro-5-(((6'-fluoro-4'-oxo-3',4'-dihydro-1'H-spiro[piperidine-4,2'-quinoline]-1-carboxamido)methyl)benzoate

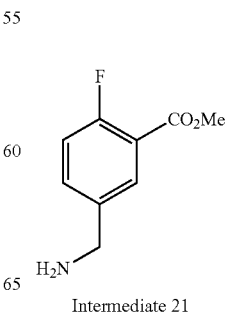

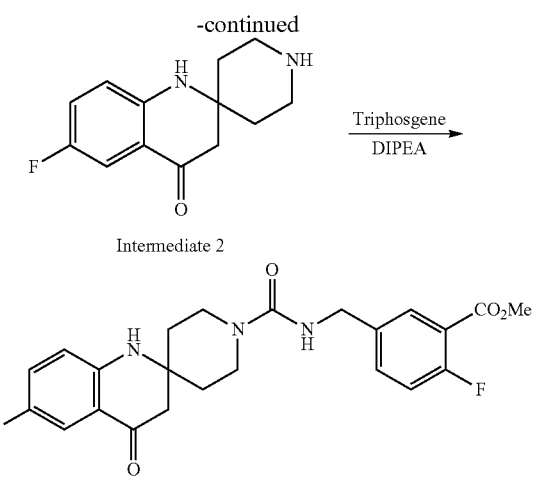

Intermediate 2

The title compound was prepared by a method similar to Example 2, using Intermediates 21 and 2 (HCl salt) instead of (4-fluoro-2-methoxyphenyl)methanamine and Intermediate 3, respectively. The product was purified by reverse-phase HPLC (Basic, Method 4) to afford the title compound (158 mg, 17.22% yield). LCMS: m/z 444.1 (M+H). $^1$H NMR (400 MHz, Methanol-$d_4$) δ 7.86 (dd, J=6.9, 2.4 Hz, 1H), 7.57-7.50 (m, 1H), 7.32 (dd, J=9.0, 3.1 Hz, 1H), 7.21-7.11 (m, 2H), 6.87 (dd, J=9.1, 4.3 Hz, 1H), 4.36 (s, 2H), 3.92 (s, 3H), 3.59-3.50 (m, 4H), 2.68 (s, 2H), 1.81-1.68 (m, 4H).

Example 62: N-(3-(2-amino-2-oxoethyl)-4-fluorobenzyl)-6'-fluoro-1'-methyl-4'-oxo-3',4'-dihydro-1'H-spiro[piperidine-4,2'-quinoline]-1-carboxamide

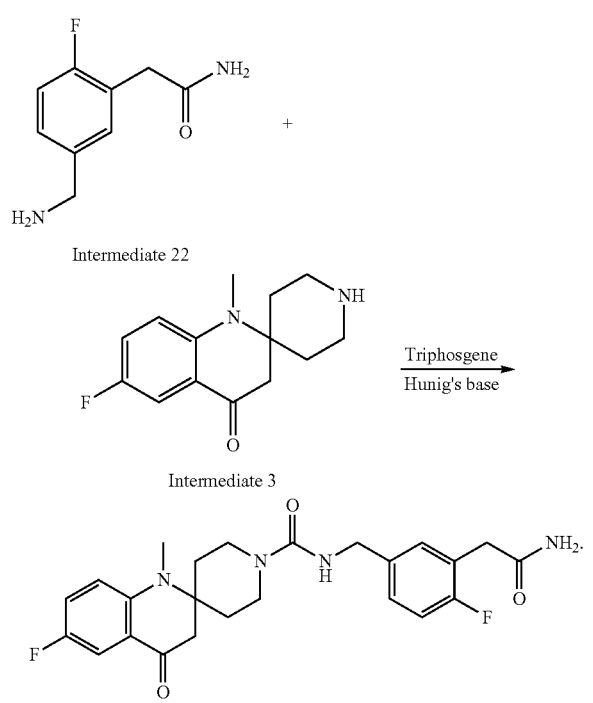

The title compound was prepared by a method similar to Example 2, using Intermediate 22 instead of (4-fluoro-2-methoxyphenyl)methanamine. The crude residue was purified by preparative HPLC to give the title compound (180 mg, 75% yield) as a fluffy yellow solid after lyophilization. LCMS: m/z 457.3 (M+H); $^1$H NMR (300 MHz, DMSO-$d_6$) δ 7.48 (1H, s), 7.37-7.32 (2H, m), 7.18-7.05 (4H, m), 7.03-6.94 (2H, m), 4.18-4.17 (2H, d), 3.92-3.88 (2H, m), 3.40 (3H, s), 2.91 (3H, s), 2.85 (3H, s), 1.77-1.74 (2H, m), 1.58-1.54 (2H, m).

Example 63: 6',8'-difluoro-N-((3-hydroxypyridin-2-yl)methyl)-4'-oxo-3',4'-dihydro-1'H-spiro[piperidine-4,2'-quinoline]-1-carboxamide

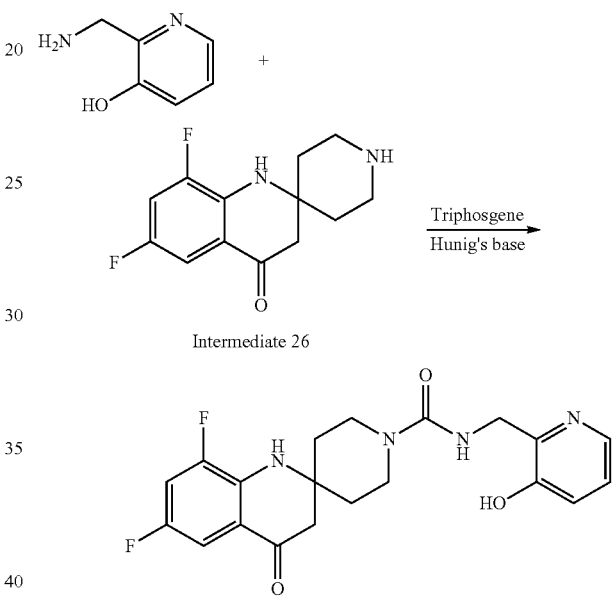

The title compound was prepared using a method similar to Example 2, using 2-(aminomethyl)pyridin-3-ol and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 403.1 (M+H).

Example 64: 6'-fluoro-N-(4-fluoro-3-(methylcarbamoyl)benzyl)-4'-oxo-3',4'-dihydro-1'H-spiro[piperidine-4,2'-quinoline]-1-carboxamide

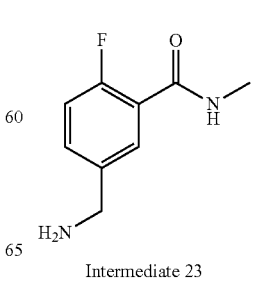

Intermediate 23

-continued

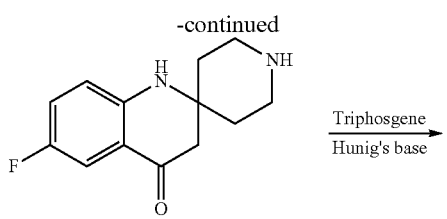

Intermediate 2

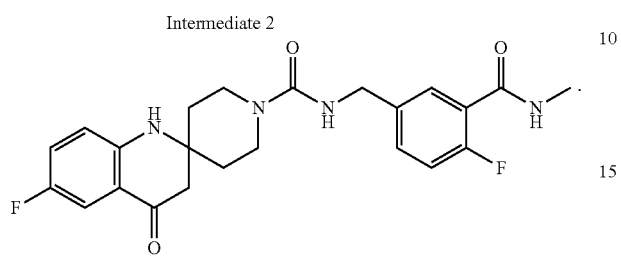

The title compound was prepared by a method similar to Example 2, using Intermediate 23 instead of (4-fluoro-2-methoxyphenyl)methanamine. Intermediate 2 was free base. The crude residue was purified by preparative HPLC (Basic, Method 4) to give the title compound (35 mg, 15% yield) as a fluffy yellow solid after lyophilization. LCMS: m/z 443.1 (M+H); $^1$H NMR (400 MHz, Methanol-$d_4$) δ 7.67 (dd, J=7.1, 2.4 Hz, 1H), 7.48-7.39 (m, 1H), 7.31 (dd, J=9.0, 3.0 Hz, 1H), 7.21-7.06 (m, 2H), 6.92-6.81 (m, 1H), 4.35 (s, 2H), 3.52 (t, J=5.7 Hz, 4H), 2.94 (s, 3H), 2.68 (s, 2H), 1.84-1.65 (m, 4H).

Example 65: N-(4-amino-3,5-difluorobenzyl)-6'-fluoro-4'-oxo-3',4'-dihydro-1'H-spiro[piperidine-4,2'-quinoline]-1-carboxamide

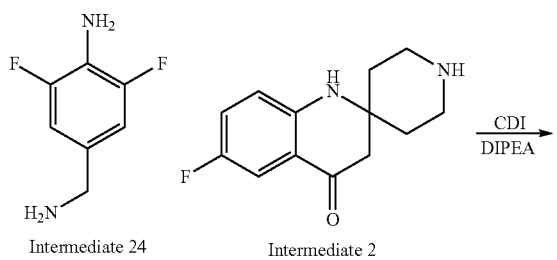

Intermediate 24    Intermediate 2

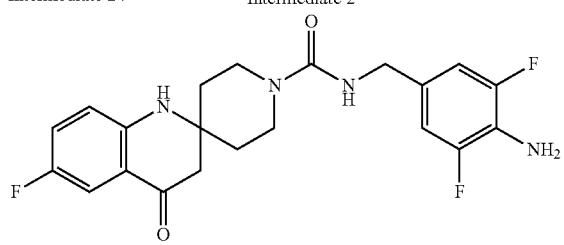

The title compound was prepared by a method similar to Example 1, using Intermediate 24 instead of Intermediate 1. Intermediate 2 was TFA salt. The product was purified by silica gel chromatography (MeOH/DCM) followed by reversed-phase HPLC (Basic, Method 4) to give the title compound (18 mg, 27% yield) as a yellow solid after lyophilization. LCMS: m/z 419.3 (M+H); 1H NMR (400 MHz, DMSO-$d_6$) δ 7.27-7.16 (m, 2H), 7.03 (t, J=5.7 Hz, 1H), 6.90 (ddd, J=8.3, 4.5, 1.3 Hz, 1H), 6.85-6.71 (m, 3H), 5.03 (s, 2H), 4.07 (d, J=5.7 Hz, 2H), 3.50-3.25 (m, 4H), 2.61 (s, 2H), 1.66-1.48 (m, 4H).

Example 66: N-((6-(dimethylamino)pyridin-2-yl)methyl)-6',8'-difluoro-4'-oxo-3',4'-dihydro-1'H-spiro[piperidine-4,2'-quinoline]-1-carboxamide

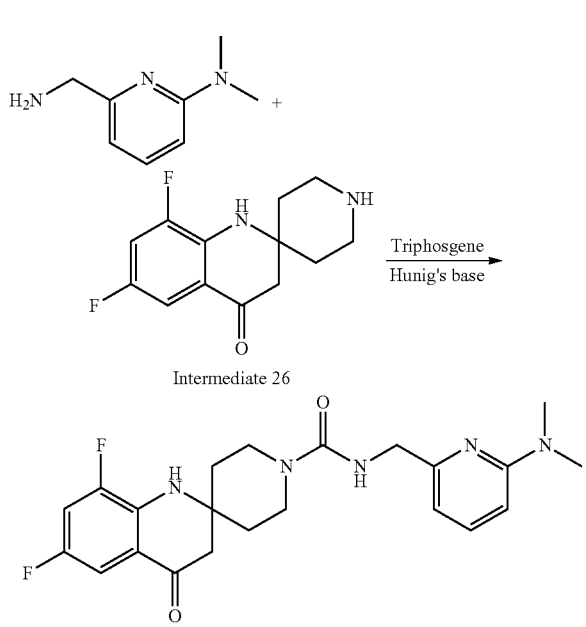

The title compound was prepared using a method similar to Example 2, using 6-(aminomethyl)-N,N-dimethylpyridin-2-amine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 430.3 (M+H).

Example 67: 6'-fluoro-N-(4-fluoro-2-(trifluoromethyl)benzyl)-4'-oxo-3',4'-dihydro-1'H-spiro[piperidine-4,2'-quinoline]-1-carboxamide

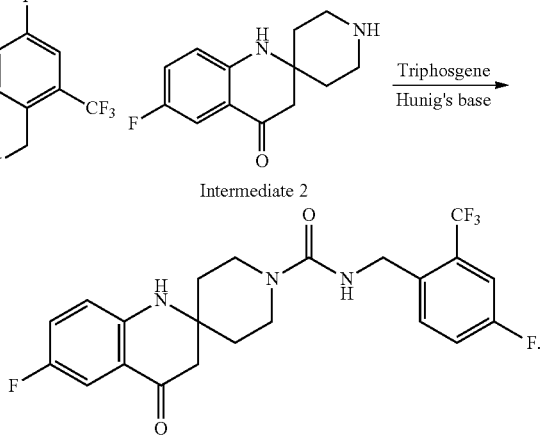

The title compound was prepared by a method similar to Example 2, using (4-fluoro-3-(trifluoromethyl)phenyl)methanamine and Intermediate 2 (HCl salt) instead of (4-fluoro-2-methoxyphenyl)methanamine and Intermediate 3, respectively. The crude residue was purified by preparative HPLC (Basic, Method 4) to give the title compound (5 mg, 4% yield) as a fluffy yellow solid after lyophilization. HRMS: m/z 454.1537 (M+H); $^1$H NMR (400 MHz, Methanol-$d_4$) δ 7.57-7.49 (m, 1H), 7.47-7.39 (m, 1H), 7.39-7.32 (m, 1H), 7.30 (dd, J=9.0, 3.1 Hz, 1H), 7.12 (ddd, J=9.2, 8.1, 3.1 Hz, 1H), 6.90-6.82 (m, 1H), 4.52 (s, 2H), 3.61-3.46 (m, 4H), 2.67 (s, 2H), 1.83-1.67 (m, 4H).

Example 68: N-(2-chloro-4-fluorobenzyl)-6'-fluoro-4'-oxo-3',4'-dihydro-1'H-spiro[piperidine-4,2'-quinoline]-1-carboxamide

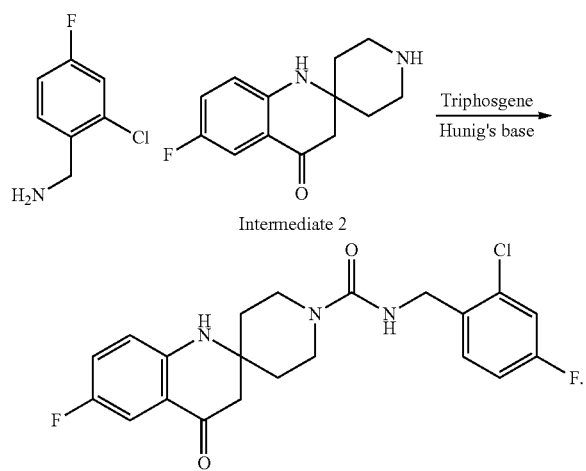

The title compound was prepared by a method similar to Example 2, using (2-chloro-4-fluorophenyl)methanamine and Intermediate 2 (HCl salt) instead of (4-fluoro-2-methoxyphenyl)methanamine and Intermediate 3, respectively. The crude residue was purified by preparative HPLC (Basic, Method 4) to give the title compound (5 mg, 4% yield) as a fluffy yellow solid after lyophilization. HRMS: m/z 420.1313 (M+H); $^1$H NMR (400 MHz, Methanol-$d_4$) δ 7.40-7.27 (m, 2H), 7.21 (dd, J=8.6, 2.6 Hz, 1H), 7.14 (ddd, J=9.2, 8.1, 3.1 Hz, 1H), 7.06 (td, J=8.4, 2.6 Hz, 1H), 6.87 (dd, J=9.1, 4.3 Hz, 1H), 4.41 (s, 2H), 3.62-3.45 (m, 4H), 2.68 (s, 2H), 1.84-1.67 (m, 4H).

Example 69: N-(3-carbamoylbenzyl)-6'-fluoro-4'-oxo-3',4'-dihydro-1'H-spiro[piperidine-4,2'-quinoline]-1-carboxamide

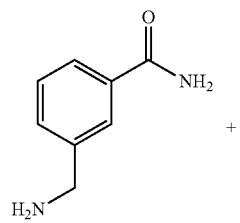

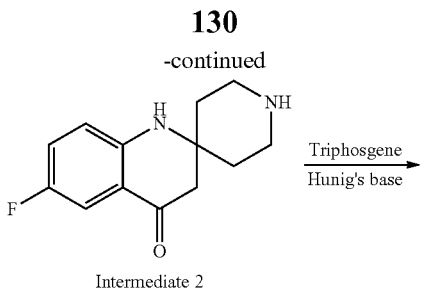

The title compound was prepared by a method similar to Example 2, using 3-(aminomethyl)benzamide and Intermediate 2 (HCl salt) instead of (4-fluoro-2-methoxyphenyl)methanamine and Intermediate 3, respectively. The crude residue was purified by preparative HPLC (Basic, Method 4) to give the title compound (58 mg, 25% yield) as a fluffy yellow solid after lyophilization. HRMS: m/z 411.1833 (M+H); $^1$H NMR (400 MHz, Methanol-$d_4$) δ 7.81-7.76 (m, 1H), 7.76-7.68 (m, 1H), 7.50-7.44 (m, 1H), 7.44-7.35 (m, 1H), 7.29 (dd, J=9.0, 3.1 Hz, 1H), 7.12 (ddd, J=9.0, 8.2, 3.1 Hz, 1H), 6.90-6.81 (m, 1H), 4.39 (s, 2H), 3.52 (t, J=5.8 Hz, 4H), 2.66 (s, 2H), 1.82-1.65 (m, 4H).

Example 70: 6'-fluoro-N-(4-fluoro-3-(2-hydroxyethoxy)benzyl)-4'-oxo-3',4'-dihydro-1'H-spiro[piperidine-4,2'-quinoline]-1-carboxamide

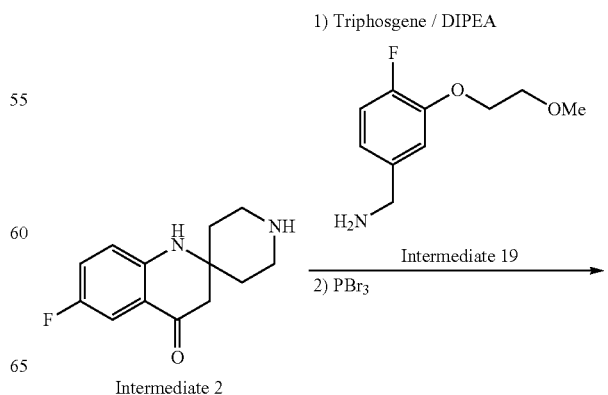

131
-continued

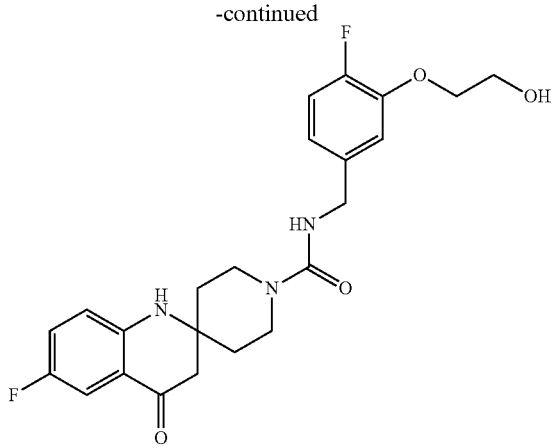

Step 1: Synthesis of 6'-fluoro-N-(4-fluoro-3-(2-methoxyethoxy)benzyl)-4'-oxo-3',4'-dihydro-1'H-spiro[piperidine-4,2'-quinoline]-1-carboxamide The title compound was prepared by a method similar to Example 2, using Intermediate 19 and Intermediate 2 (HCl salt) instead of (4-fluoro-2-methoxyphenyl)methanamine and Intermediate 3, respectively. The product was purified by reversed-phase HPLC (Basic, Method 2) to give the title compound (13 mg, 13% yield) as a yellow solid. LCMS: m/z 460.1 (M+H).

Step 2: Synthesis of 6'-fluoro-N-(4-fluoro-3-(2-hydroxyethoxy)benzyl)-4'-oxo-3',4'-dihydro-1'H-spiro[piperidine-4,2'-quinoline]-1-carboxamide The title compound was prepared by a method similar to Example 3, step 2. The product was purified by reverse-phase HPLC (Basic, Method 3) to afford the title compound as a yellow solid (3.1 mg, 23% yield). LCMS: m/z 446.1 (M+H); $^1$H NMR (400 MHz, MeOH-$d_4$): δ 7.30 (dd, J=8 Hz, 1H), 7.12 (td, J=8 Hz, 1H), 7.05-6.98 (m, 2H), 6.86-6.82 (m, 2H), 4.29 (s, 2H), 4.10 (t, J=4 Hz, 2H), 3.88 (t, J=4 Hz, 2H), 3.53-3.48 (m, 4H), 2.65 (s, 2H) 1.79-1.66 (m, 4H).

Example 71: N-(2,4-difluoro-5-(2-hydroxyethoxy)benzyl)-6'-fluoro-4'-oxo-3',4'-dihydro-1'H-spiro[piperidine-4,2'-quinoline]-1-carboxamide

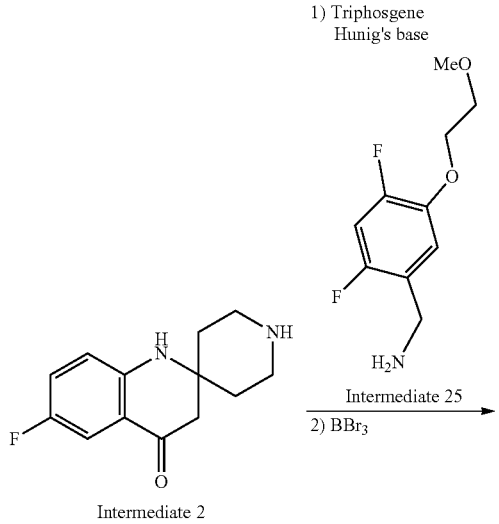

132
-continued

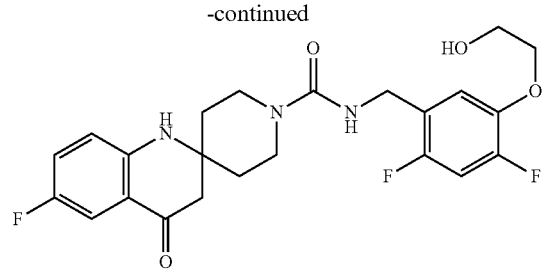

Step 1: Synthesis of N-(2,4-difluoro-5-(2-methoxyethoxy)benzyl)-6'-fluoro-4'-oxo-3',4'-dihydro-1'H-spiro[piperidine-4,2'-quinoline]-1-carboxamide The title compound was prepared by a method similar to Example 2, using intermediate 25 and Intermediate 2 (HCl salt) instead of (4-fluoro-2-methoxyphenyl)methanamine and Intermediate 3, respectively. The product directly engaged in the next step without purification. LCMS: m/z 478.0 (M+H).

Step 2: Synthesis of 1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide The title compound was prepared by a method similar to Example 19. The product was purified by preparative HPLC (column: Gemini NX 5μ C18 21.2 mm×150 mm; mobile phase: 0.05% ammonium hydroxide in water/ACN) to give the title compound (18 mg, 22% yield) as a yellow solid. LCMS: m/z 464 (M+H). $^1$H NMR (400 MHz, Chloroform-d) δ 7.47-7.44 (1H, m) 7.25-7.05 (2H, m), 6.86-6.81 (1H, t), 6.64-6.61 (1H, m), 4.89-4.86 (2H, br s), 4.38-4.37 (2H, d), 4.31 (1H, s), 3.96-3.93 (2H, br), 3.40-3.39 (3H, m), 2.68 (1H, s), 2.13 (1H, t), 1.83-1.74 (4H, m).

Example 72: 6'-fluoro-N-((5-methyl-1H-pyrazol-3-yl)methyl)-4'-oxo-3',4'-dihydro-1'H-spiro[piperidine-4,2'-quinoline]-1-carboxamide

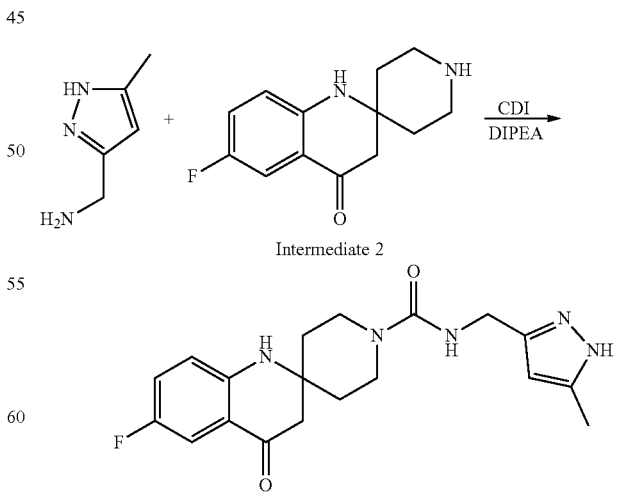

The title compound was prepared by a method similar to Example 1, using (5-methyl-1H-pyrazol-3-yl)methanamine instead of Intermediate 1. Intermediate 2 was HCl salt. The product was purified by silica gel chromatography (MeOH/DCM) followed by reversed-phase HPLC (Basic, Method 4) to give the title compound (21 mg, 31% yield) as a yellow solid after lyophilization. LCMS: m/z 372.3 (M+H). $^1$H NMR (400 MHz, DMSO-d$_6$) δ 12.10 (s, 1H), 7.30-7.13 (m, 2H), 6.95-6.83 (m, 2H), 6.80 (s, 1H), 5.83 (s, 1H), 4.12 (d, J=5.5 Hz, 2H), 3.51-3.21 (m, 4H), 2.60 (s, 2H), 2.15 (s, 3H), 1.65-1.45 (m, 4H).

Example 73: N-(3-amino-4-fluorobenzyl)-6',8'-difluoro-4'-oxo-3',4'-dihydro-1'H-spiro[piperidine-4,2'-quinoline]-1-carboxamide

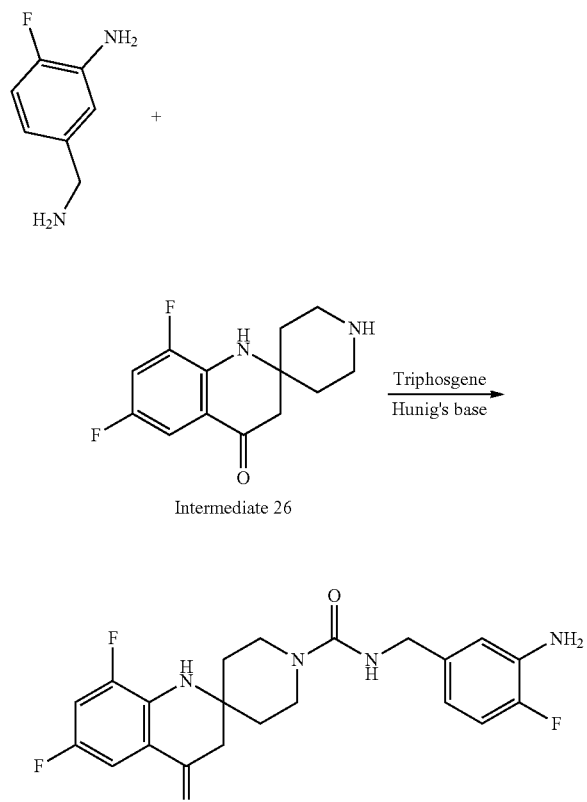

The title compound was prepared by a method similar to Example 2, using 5-(aminomethyl)-2-fluoroaniline and Intermediate 26 (HCl salt) instead of (4-fluoro-2-methoxyphenyl)methanamine and Intermediate 3, respectively. The product was purified by silica gel chromatography (DCM/MeOH=100/0 to 90/10), followed by preparative HPLC (Basic, Method 4) to give the title compound (44 mg, 34% yield) as a yellow solid. LCMS: m/z 419.2 (M+H); $^1$H NMR (400 MHz, DMSO-d$_6$) δ 7.44 (ddd, J=11.4, 8.5, 2.9 Hz, 1H), 7.22-7.05 (m, 1H), 7.00 (t, J=5.8 Hz, 1H), 6.87 (dd, J=11.5, 8.2 Hz, 1H), 6.64 (dd, J=8.9, 2.0 Hz, 1H), 6.48 (s, 1H), 6.38 (ddd, J=8.0, 4.4, 2.1 Hz, 1H), 5.06 (s, 2H), 4.07 (d, J=5.6 Hz, 2H), 3.78-3.50 (m, 2H), 3.08 (dt, J=13.4, 6.3 Hz, 2H), 2.79 (s, 2H), 1.79-1.54 (m, 4H).

Example 74: 6'-fluoro-4'-oxo-N-(3-sulfamoylbenzyl)-3',4'-dihydro-1'H-spiro[piperidine-4,2'-quinoline]-1-carboxamide

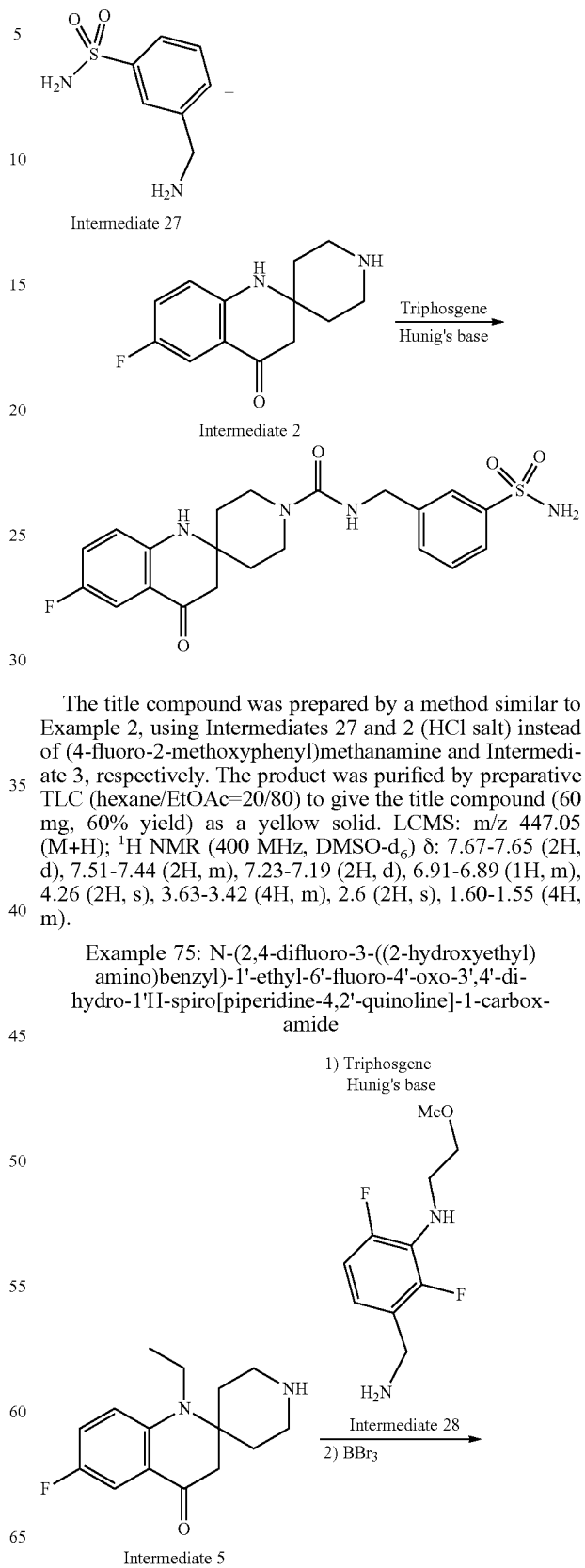

The title compound was prepared by a method similar to Example 2, using Intermediates 27 and 2 (HCl salt) instead of (4-fluoro-2-methoxyphenyl)methanamine and Intermediate 3, respectively. The product was purified by preparative TLC (hexane/EtOAc=20/80) to give the title compound (60 mg, 60% yield) as a yellow solid. LCMS: m/z 447.05 (M+H); $^1$H NMR (400 MHz, DMSO-d$_6$) δ: 7.67-7.65 (2H, d), 7.51-7.44 (2H, m), 7.23-7.19 (2H, d), 6.91-6.89 (1H, m), 4.26 (2H, s), 3.63-3.42 (4H, m), 2.6 (2H, s), 1.60-1.55 (4H, m).

Example 75: N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide -continued

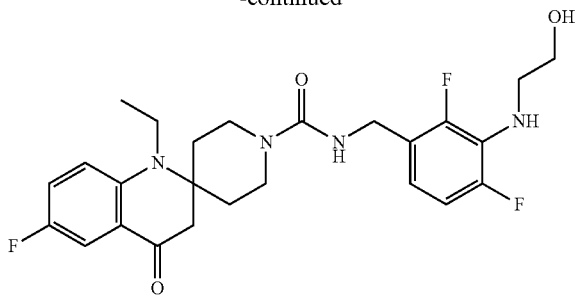

Step 1: Synthesis of N-(2,4-difluoro-3-((2-methoxyethyl)amino)benzyl)-1'-ethyl-6'-fluoro-4'-oxo-3',4'-dihydro-1'H-spiro[piperidine-4,2'-quinoline]-1-carboxamide The title compound was prepared by a method similar to Example 2, using Intermediates 28 and 5 instead of (4-fluoro-2-methoxyphenyl)methanamine and Intermediate 3, respectively. The product was purified by preparative HPLC (Basic, Method 4) to give the title compound (11 mg, 11% yield) as a fluffy yellow solid after lyophilization. LCMS: m/z 505.3 (M+H).

Step 2: N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide The title compound was prepared by a method similar to Example 19. The product was purified by preparative HPLC (Basic, Method 4) to give the title compound (4 mg, 41% yield) as a fluffy yellow solid after lyophilization. LCMS: m/z 491.3 (M+H). $^1$H NMR (400 MHz, DMSO-$d_6$) δ 7.40 (dd, J=8.7, 3.3 Hz, 1H), 7.23 (ddd, J=9.4, 7.9, 3.3 Hz, 1H), 6.90 (dd, J=9.4, 4.0 Hz, 1H), 6.86-6.76 (m, 1H), 6.69 (td, J=8.2, 5.9 Hz, 1H), 4.34 (s, 2H), 4.00 (d, J=14.1 Hz, 2H), 3.67 (t, J=5.6 Hz, 2H), 3.49-3.37 (m, 4H), 3.08-2.96 (m, 2H), 2.91 (s, 2H), 1.98-1.70 (m, 4H), 1.25 (t, J=7.1 Hz, 3H).

Example 76: N-(4-aminobenzyl)-6'-fluoro-1'-methyl-4'-oxo-3',4'-dihydro-1'H-spiro[piperidine-4,2'-quinoline]-1-carboxamide

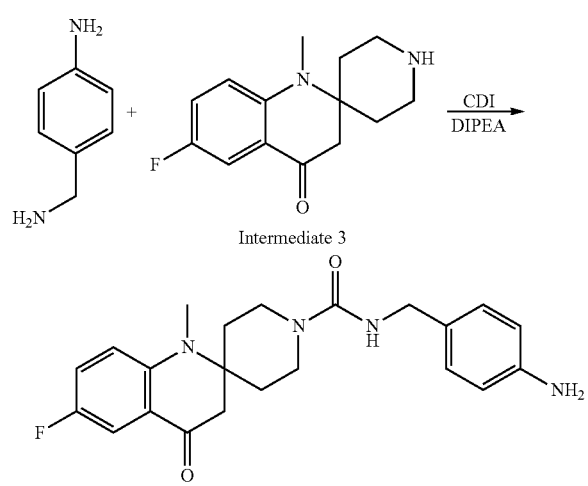

The title compound was prepared by a method similar to Example 1, using 4-(aminomethyl)aniline and Intermediate 3 instead of Intermediate 1 and Intermediate 2, respectively. The product was purified by silica gel chromatography (MeOH/DCM) followed by reversed-phase HPLC (Basic, Method 4) to give the title compound (42 mg, 32% yield) as a yellow solid after lyophilization. LCMS: m/z 419.2 (M+Na); $^1$H NMR (400 MHz, DMSO-$d_6$) δ 7.41-7.29 (m, 2H), 7.01-6.84 (m, 4H), 6.53-6.42 (m, 2H), 4.90 (s, 2H), 4.05 (d, J=5.6 Hz, 2H), 3.96-3.83 (m, 2H), 2.95-2.80 (m, 7H), 1.75 (td, J=12.8, 4.6 Hz, 2H), 1.62-1.48 (m, 2H).

Example 77: N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide

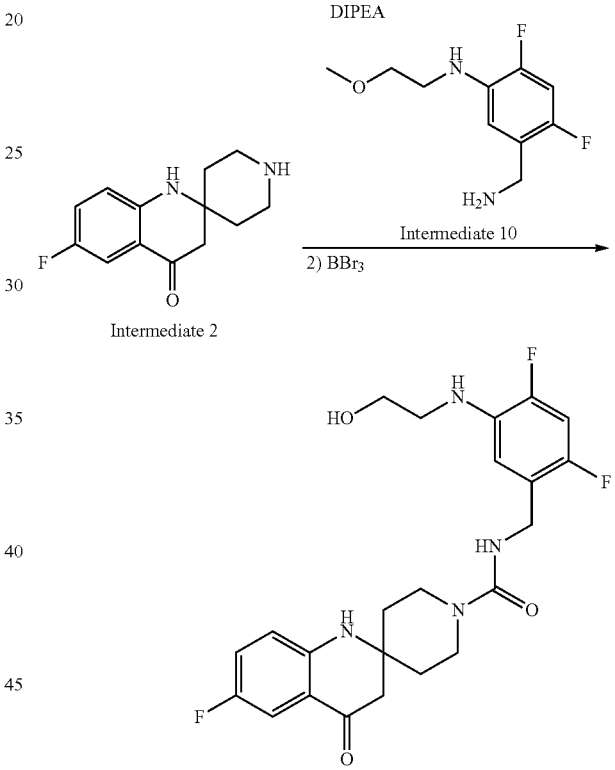

Step 1: Synthesis of N-(2,4-difluoro-5-((2-methoxyethyl)amino)benzyl)-6'-fluoro-4'-oxo-3',4'-dihydro-1'H-spiro[piperidine-4,2'-quinoline]-1-carboxamide The title compound was prepared by a method similar to Example 2, using Intermediates 10 and 2 (free base) instead of (4-fluoro-2-methoxyphenyl)methanamine and Intermediate 3, respectively. The crude residue was purified by preparative HPLC (Formic acid, Method 3) to give the title compound. HRMS: m/z 477.2118 (M+H).

Step 2: Synthesis of N-(2,4-difluoro-5-((2-hydroxyethylamino)benzyl)-6'-fluoro-4'-oxo-3',4'-dihydro-1'H-spiro[piperidine-4,2'-quinoline]-1-carboxamide The title compound was prepared by a method similar to Example 3, Step 2. The product was purified by preparative SFC (column: Princeton AMINO 20×150 mm 5 μm; mobile phase: MeOH) to afford the title compound (22 mg, 41% yield) as a yellow solid after lyopholization. HRMS: m/z 462.1879 (M+H); $^1$H NMR (400 MHz, Methanol-d$_4$) δ 7.29 (dd, J=9.0, 3.0 Hz, 1H), 7.15-7.08 (m, 1H), 6.88-6.69 (m, 3H), 4.31 (s, 2H), 3.73 (t, J=5.7 Hz, 2H), 3.50 (h, J=9.5 Hz, 4H), 3.23 (t, J=5.7 Hz, 2H), 2.65 (s, 2H), 1.71 (tdt, J=13.3, 7.4, 4.6 Hz, 4H).

Example 78: 6'-fluoro-N-(4-fluoro-3-((2-hydroxyethyl)amino)benzyl)-4'-oxo-3',4'-dihydro-1'H-spiro[piperidine-4,2'-quinoline]-1-carboxamide

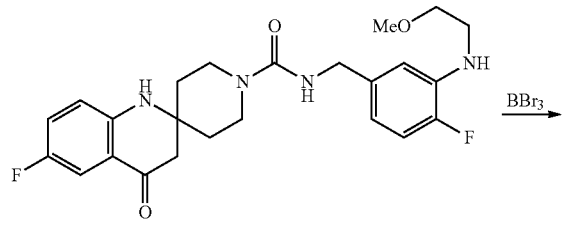

Example 99

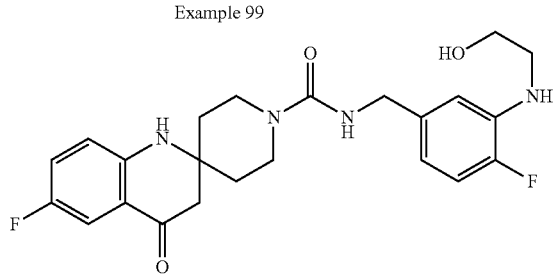

Example 99

The title compound was prepared by a method similar to Example 19. The product was purified by preparative HPLC (Basic, Method 4) to give the title compound (8 mg, 13% yield) as a fluffy yellow solid after lyophilization. LCMS: m/z 445.3 (M+H). $^1$H NMR (400 MHz, MeOH-d$_4$) δ 7.29 (dd, J=9.0, 3.0 Hz, 1H), 7.12 (ddd, J=9.0, 8.2, 3.1 Hz, 1H), 6.94-6.78 (m, 2H), 6.71 (dd, J=8.5, 2.0 Hz, 1H), 6.52 (ddd, J=8.1, 4.5, 2.1 Hz, 1H), 4.25 (s, 2H), 3.73 (t, J=5.7 Hz, 2H), 3.59-3.44 (m, 5H), 3.25 (d, J=5.7 Hz, 2H), 2.65 (s, 2H), 1.72 (tdt, J=13.3, 7.8, 4.6 Hz, 4H).

Example 79: N-(3-carbamoyl-4-fluoro-2-methylbenzyl)-6'-fluoro-4'-oxo-3',4'-dihydro-1'H-spiro[piperidine-4,2'-quinoline]-1-carboxamide

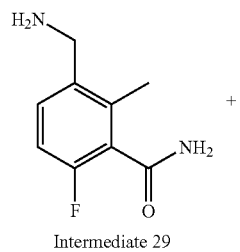

Intermediate 29

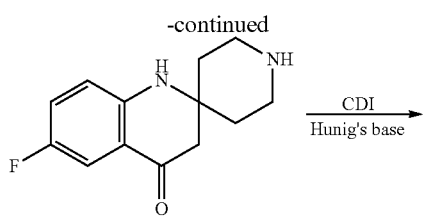

Intermediate 2

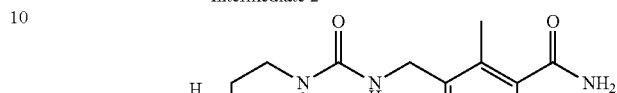

The title compound was prepared by a method similar to Example 1, using Intermediate 29 instead of Intermediate 1. Intermediate 2 was HCl salt. The crude material was purified on a preparatory TLC plate using mobile phase 7% of methanol in DCM as an eluent to afford afford the title compound (65 gm, 059% yield). LCMS: m/z 443.9 (M+H). $^1$H NMR (400 MHz, DMSO-d$_6$) δ 7.93 (1H, s), 7.65 (1H, d), 7.24-7.18 (3H, m), 7.03-6.98 (2H, m), 6.92-6.89 (1H, m), 6.80 (1H, m), 4.18 (2H, d), 3.44-3.38 (4H, m), 2.61 (2H, s), 2.22 (3H, s), 1.59-1.55 (4H, m)

Example 80: N-(4-amino-2,6-difluorobenzyl)-6'-fluoro-4'-oxo-3',4'-dihydro-1'H-spiro[piperidine-4,2'-quinoline]-1-carboxamide

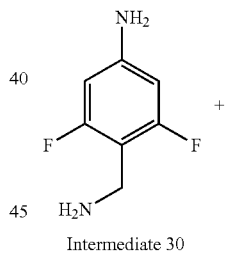

Intermediate 30

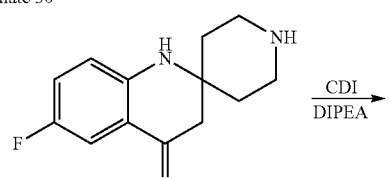

Intermediate 2

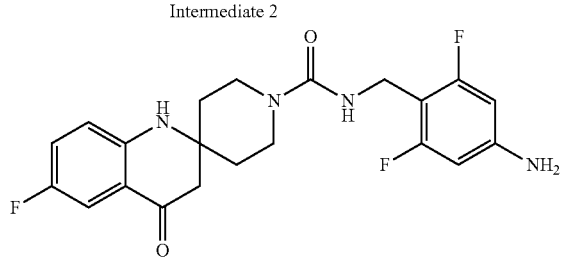

The title compound was prepared by a method similar to Example 1, using Intermediate 30 instead of Intermediate 1.

Intermediate 2 was HCl salt. The product was purified by silica gel chromatography (MeOH/DCM) followed by reversed-phase HPLC (Basic, Method 4) to give the title compound (14 mg, 21% yield) as a yellow solid after lyophilization. LCMS: m/z 419.3 (M+H). $^1$H NMR (400 MHz, DMSO-$d_6$) δ 7.28-7.14 (m, 2H), 6.97-6.84 (m, 1H), 6.76 (s, 1H), 6.55 (t, J=4.9 Hz, 1H), 6.21-6.07 (m, 2H), 5.60 (s, 2H), 4.08 (d, J=4.9 Hz, 2H), 3.44-3.23 (m, 4H), 2.58 (s, 2H), 1.65-1.41 (m, 4H).

Example 81: N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide

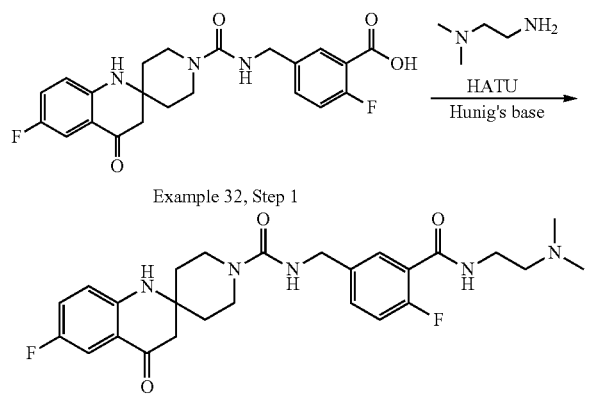

The title compound was prepared by a method similar to Example 32, Step 2, using $N^1,N^1$-dimethylethane-1,2-diamine instead of (4-(aminomethyl)phenyl)methanol. The product was purified by a preparative HPLC (Basic, Method 4) to give the title compound (135 mg, 97% yield). HRMS: m/z 500.2529 (M+H); $^1$H NMR (400 MHz, Methanol-$d_4$) δ 7.68 (dd, J=7.0, 2.4 Hz, 1H), 7.43 (ddd, J=8.4, 4.9, 2.4 Hz, 1H), 7.29 (dd, J=8.9, 3.1 Hz, 1H), 7.18-7.06 (m, 2H), 6.90-6.81 (m, 1H), 4.34 (s, 2H), 3.57-3.44 (m, 6H), 2.66 (s, 2H), 2.57 (t, J=6.9 Hz, 2H), 2.31 (s, 6H), 1.82-1.65 (m, 4H).

Example 82: 6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide

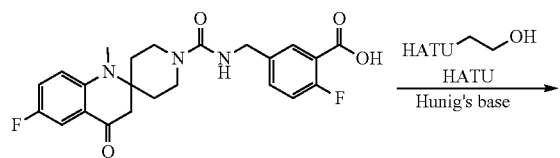

The title compound was prepared by a method similar to Example 32, Step 2, using 2-aminoethanol HCl salt instead of (4-(aminomethyl)phenyl)methanol. The crude residue was purified by a preparative HPLC (Basic, Method 4) to give the title compound (45 mg, 81% yield). HRMS: m/z 487.2182; $^1$H NMR (400 MHz, Methanol-$d_4$) δ 7.69 (dd, J=7.1, 2.3 Hz, 1H), 7.49-7.39 (m, 2H), 7.30-7.21 (m, 1H), 7.15 (dd, J=10.9, 8.4 Hz, 1H), 6.97-6.90 (m, 1H), 4.34 (s, 2H), 3.99-3.91 (m, 2H), 3.70 (t, J=5.8 Hz, 2H), 3.51 (t, J=5.8 Hz, 2H), 3.13-3.01 (m, 2H), 2.94 (s, 3H), 2.93 (s, 2H), 2.00-1.88 (m, 2H), 1.76-1.68 (m, 2H).

Example 83: 6'-fluoro-N-(4-fluoro-3-(hydroxymethyl)benzyl)-4'-oxo-3',4'-dihydro-1'H-spiro[piperidine-4,2'-quinoline]-1-carboxamide

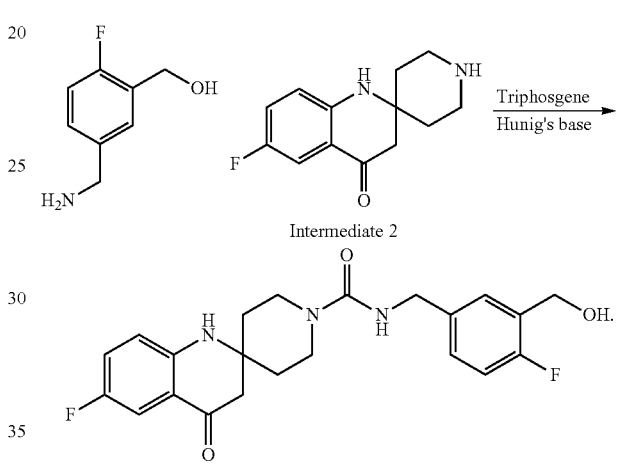

The title compound was prepared by a method similar to Example 2, using (5-(aminomethyl)-2-fluorophenyl)methanol and Intermediate 2 (HCl salt) instead of (4-fluoro-2-methoxyphenyl)methanamine and Intermediate 3, respectively. The crude residue was purified by preparative HPLC (Basic, Method 4) to give the title compound (60 mg, 35.7% yield) as a fluffy yellow solid after lyophilization. HRMS: m/z 416.1780 (M+H); $^1$H NMR (400 MHz, Methanol-$d_4$) δ 7.44-7.36 (m, 1H), 7.30 (dd, J=9.0, 3.0 Hz, 1H), 7.26-7.18 (m, 1H), 7.18-7.08 (m, 1H), 7.05-6.96 (m, 1H), 6.91-6.82 (m, 1H), 4.65 (s, 2H), 4.33 (s, 2H), 3.60-3.43 (m, 4H), 2.67 (s, 2H), 1.82-1.65 (m, 4H).

Example 84: N-(3-amino-2,4-difluorobenzyl)-6'-fluoro-4'-oxo-3',4'-dihydro-1'H-spiro[piperidine-4,2'-quinoline]-1-carboxamide

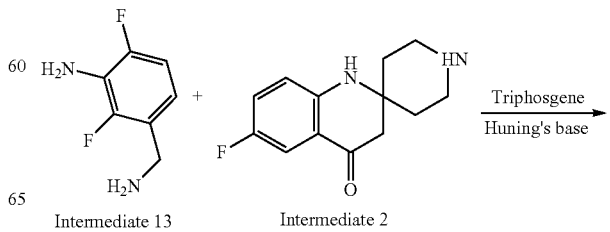

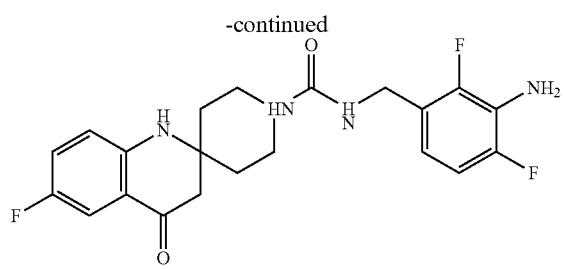

The title compound was prepared by a method similar to Example 2, using Intermediates 13 and 2 (HCl salt) instead of (4-fluoro-2-methoxyphenyl)methanamine and Intermediate 3, respectively. The product was purified by preparative HPLC (Basic, Method 4) to give the title compound (10 mg, 12% yield) as a yellow solid. LCMS: m/z 419.2 (M+H); $^1$H NMR (400 MHz, DMSO-$d_6$) δ 7.29-7.16 (m, 2H), 6.99 (t, J=5.7 Hz, 1H), 6.95-6.88 (m, 1H), 6.86-6.74 (m, 2H), 6.53-6.36 (m, 1H), 5.12 (s, 2H), 4.18 (d, J=5.4 Hz, 2H), 3.46-3.35 (m, 4H), 2.61 (s, 2H), 1.56 (qq, J=7.8, 3.8 Hz, 4H).

Example 85: (E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide

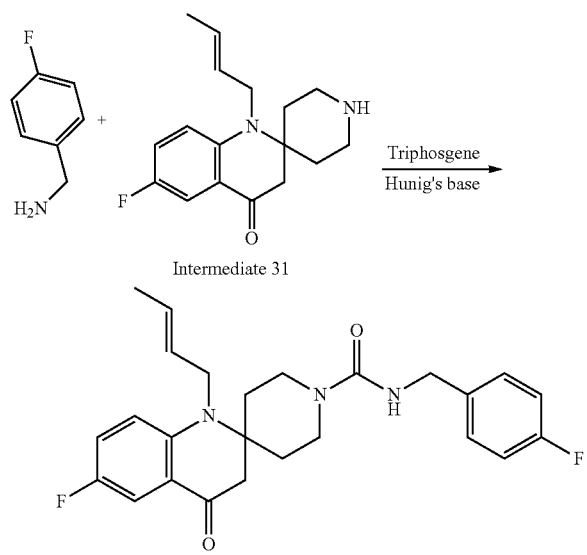

The title compound was prepared by a method similar to Example 2, using (4-fluorophenyl)methanamine and Intermediate 31 instead of (4-fluoro-2-methoxyphenyl)methanamine and Intermediate 3, respectively. The product was purified by preparative HPLC (Basic, Method 5) to give the title compound (21 mg, 21% yield) as a yellow solid. LCMS: m/z 440.2 (M+H); $^1$H NMR (400 MHz, MeOH-$d_4$) δ: 7.39 (dd, J=8.7, 3.2 Hz, 1H), 7.31 (dd, J=8.7, 5.4 Hz, 2H), 7.20 (ddd, J=9.4, 7.9, 3.3 Hz, 1H), 7.07-6.97 (m, 2H), 6.82 (dd, J=9.4, 4.0 Hz, 1H), 5.84-5.71 (m, 1H), 5.56 (dtd, J=15.3, 4.5, 1.6 Hz, 1H), 4.32 (s, 2H), 4.05-3.90 (m, 4H), 3.06-2.96 (m, 2H), 2.95 (s, 2H), 1.89 (td, J=13.1, 4.8 Hz, 2H), 1.78-1.67 (m, 5H).

Example 86: 6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide

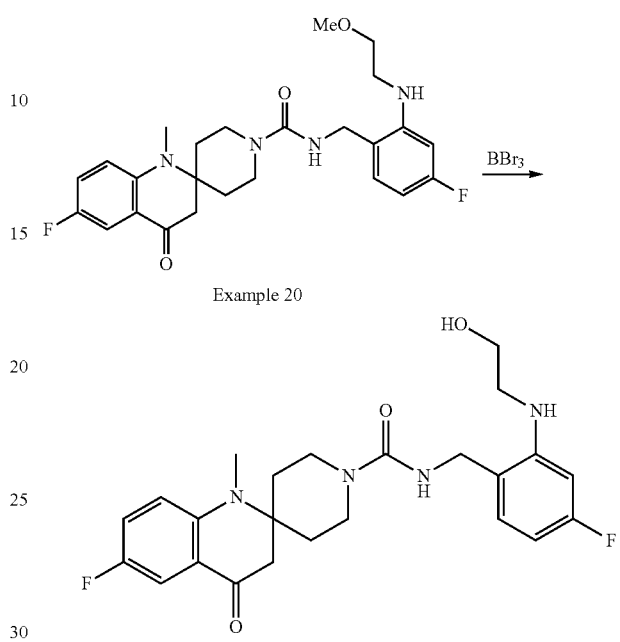

The title compound was prepared by a method similar to Example 19. The product was purified by preparative SFC (column: Princeton AMINO 20×150 mm 5 μm; mobile phase: MeOH) to give the title compound (10 mg, 39% yield) as a fluffy yellow solid after lyophilization. LCMS: m/z 459.2 (M+H); $^1$H NMR (400 MHz, Chloroform-d) δ 7.53 (dd, J=8.5, 3.2 Hz, 1H), 7.17 (ddd, J=9.2, 7.7, 3.2 Hz, 1H), 7.02 (t, J=7.2 Hz, 1H), 6.76 (dd, J=9.3, 4.0 Hz, 1H), 6.42 (d, J=18.3 Hz, 2H), 5.01 (s, 1H), 4.35 (d, J=4.2 Hz, 2H), 3.94 (d, J=4.4 Hz, 2H), 3.81 (d, J=13.2 Hz, 2H), 3.30-3.18 (m, 2H), 3.04 (t, J=11.5 Hz, 2H), 2.88 (s, 3H), 2.83 (s, 2H), 1.89 (td, J=13.1, 4.4 Hz, 2H), 1.73 (d, J=13.2 Hz, 2H).

Example 87: N-(4-amino-3-chlorobenzyl)-6'-fluoro-4'-oxo-3',4'-dihydro-1'H-spiro[piperidine-4,2'-quinoline]-1-carboxamide

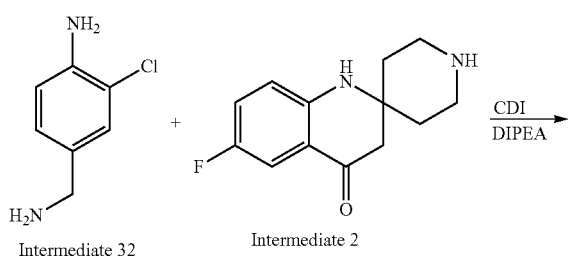

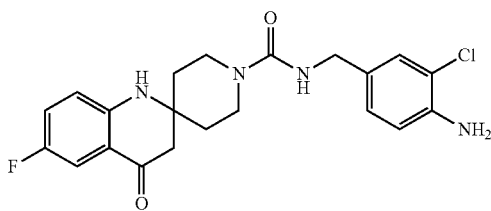

The title compound was prepared by a method similar to Example 1, using Intermediate 32 instead of Intermediate 1. Intermediate 2 was HCl salt. The product was purified by silica gel chromatography (MeOH/DCM) followed by reversed-phase HPLC (Basic, Method 4) to give the title compound (13 mg, 19% yield) as a yellow solid after lyophilization. LCMS: m/z 439.2 (M+Na); $^1$H NMR (400 MHz, DMSO-$d_6$) δ 7.26-7.17 (m, 2H), 7.07 (d, J=1.9 Hz, 1H), 6.98-6.87 (m, 3H), 6.78 (s, 1H), 6.71 (d, J=8.2 Hz, 1H), 5.16 (s, 2H), 4.05 (d, J=5.6 Hz, 2H), 3.49-3.32 (m, 4H), 2.60 (s, 2H), 1.66-1.47 (m, 4H).

Example 88: 6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide

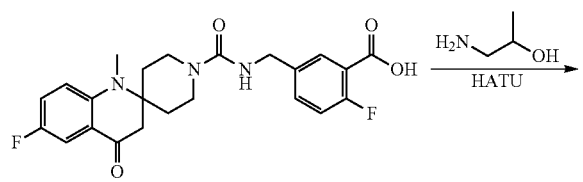

Example 58, Step 2

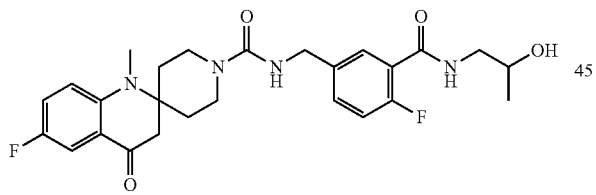

The title compound was prepared by a method similar to Example 32, Step 2, using 3-aminopropan-2-ol instead of (4-(aminomethyl)phenyl)methanol. The product was purified by reverse phase HPLC (Basic, Method 4) to give the title racemate compound (20 mg, 44% yield) as a fluffy yellow solid after lyophilization. LCMS: m/z 501.3 (M+H); $^1$H NMR (400 MHz, DMSO-$d_6$) δ 8.10 (td, J=5.9, 3.4 Hz, 1H), 7.53 (dd, J=7.4, 2.2 Hz, 1H), 7.36 (qd, J=7.9, 4.9 Hz, 3H), 7.25-7.13 (m, 2H), 7.01-6.91 (m, 1H), 4.75 (d, J=4.8 Hz, 1H), 4.22 (d, J=5.7 Hz, 2H), 3.90 (dt, J=13.4, 3.4 Hz, 2H), 3.76 (p, J=5.8 Hz, 1H), 3.20 (t, J=5.9 Hz, 2H), 2.88 (d, J=23.4 Hz, 7H), 1.77 (dt, J=12.7, 6.4 Hz, 2H), 1.57 (d, J=12.8 Hz, 2H), 1.07 (d, J=6.2 Hz, 3H).

Example 89: N-(4-aminobenzyl)-6'-fluoro-4'-oxo-3',4'-dihydro-1'H-spiro[piperidine-4,2'-quinoline]-1-carboxamide

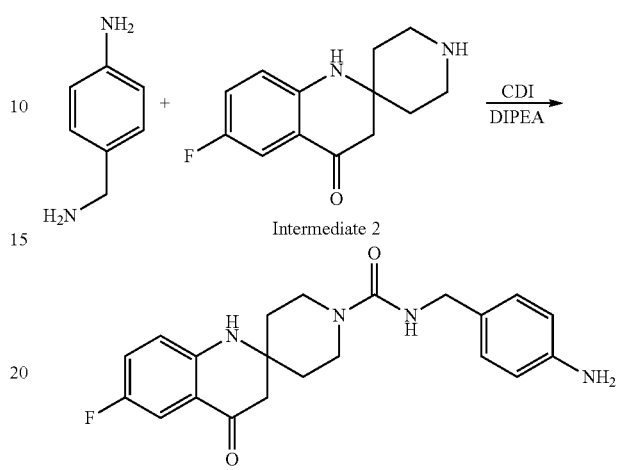

The title compound was prepared by a method similar to Example 1, using 4-aminobenzylamine instead of Intermediate 1. Intermediate 2 was HCl salt. The product was purified by silica gel chromatography (MeOH/DCM) followed by reversed-phase HPLC (Basic, Method 4) to give the title compound (23 mg, 32% yield) as a yellow solid after lyophilization. LCMS: m/z 383.4 (M+H); $^1$H NMR (400 MHz, DMSO-$d_6$) δ 7.29-7.14 (m, 2H), 6.97-6.83 (m, 4H), 6.80 (s, 1H), 6.53-6.42 (m, 2H), 4.90 (s, 2H), 4.05 (d, J=5.6 Hz, 2H), 3.48-3.27 (m, 4H), 2.60 (s, 2H), 1.65-1.46 (m, 4H).

Example 90: 6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide

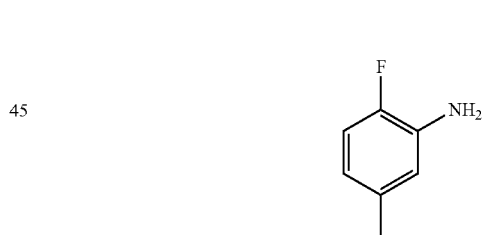

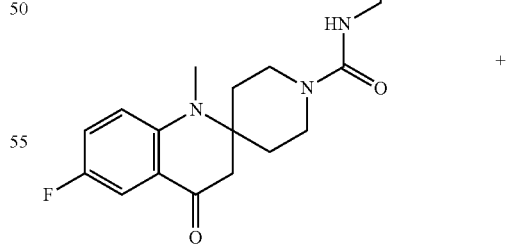

Example 27

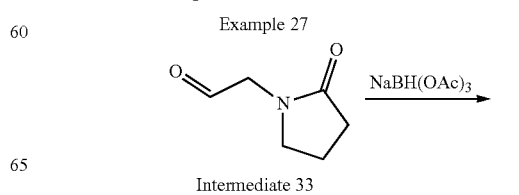

Intermediate 33

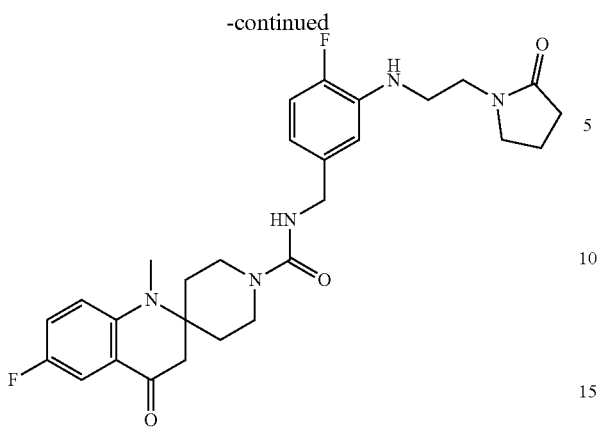

The title compound was prepared by a method similar to Example 31, using Intermediate 33 instead Intermediate 14. The product was purified by silica gel chromatography (DCM/MeOH), followed by reverse-phase HPLC (Basic, Method 4) to give the title compound (7 mg, 5% yield). LCMS: m/z 526.3 (M+H). $^1$H NMR (400 MHz, Methanol-$d_4$) δ 7.43 (dd, J=8.6, 3.2 Hz, 1H), 7.28-7.21 (m, 1H), 6.94 (dd, J=9.4, 4.0 Hz, 1H), 6.86 (dd, J=11.7, 8.2 Hz, 1H), 6.74 (dd, J=8.5, 1.9 Hz, 1H), 6.56-6.47 (m, 1H), 4.25 (s, 2H), 4.00-3.89 (m, 2H), 3.54-3.47 (m, 4H), 3.39-3.33 (m, 2H), 3.11-3.01 (m, 2H), 2.93 (s, 3H), 2.92 (s, 2H), 2.34 (t, J=8.1 Hz, 2H), 2.04-1.87 (m, 4H), 1.75-1.67 (m, 2H).

Example 91: N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide

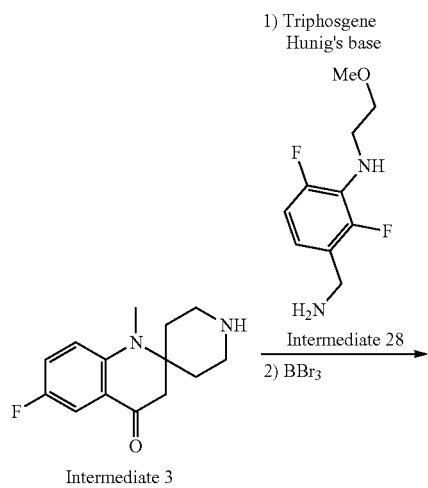

Step 1: Synthesis of N-(2,4-difluoro-3-((2-methoxyethyl)amino)benzyl)-6'-fluoro-1'-methyl-4'-oxo-3',4'-dihydro-1'H-spiro[piperidine-4,2'-quinoline]-1-carboxamide The title compound was prepared by a method similar to Example 2, using Intermediate 28 instead of (4-fluoro-2-methoxyphenyl)methanamine. The product was purified by preparative HPLC (Basic, Method 4) to give the title compound (30 mg, 43% yield) as a fluffy yellow solid after lyophilization. LCMS: m/z 491.3 (M+H).

Step 2: Synthesis of N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide The title compound was prepared by a method similar to Example 19. The product was purified by preparative HPLC (Basic, Method 4) to give the title compound (12 mg, 52% yield) as a fluffy yellow solid after lyophilization. LCMS: m/z 477.2 (M+H); $^1$H NMR (400 MHz, DMSO-$d_6$) δ 7.40-7.28 (m, 2H), 7.08-6.93 (m, 2H), 6.88 (ddd, J=11.7, 8.6, 1.5 Hz, 1H), 6.57 (td, J=8.2, 6.1 Hz, 1H), 4.82 (dt, J=6.3, 3.3 Hz, 1H), 4.73 (t, J=5.3 Hz, 1H), 4.19 (d, J=5.4 Hz, 2H), 3.90 (d, J=13.7 Hz, 2H), 3.50 (q, J=5.7 Hz, 2H), 3.27 (q, J=6.0 Hz, 2H), 2.88 (d, J=23.3 Hz, 7H), 1.77 (td, J=12.8, 4.5 Hz, 2H), 1.57 (d, J=12.9 Hz, 2H).

Example 92: 6'-fluoro-N-(4-fluoro-3-(1-hydroxyethyl)benzyl)-1'-methyl-4'-oxo-3',4'-dihydro-1'H-spiro[piperidine-4,2'-quinoline]-1-carboxamide

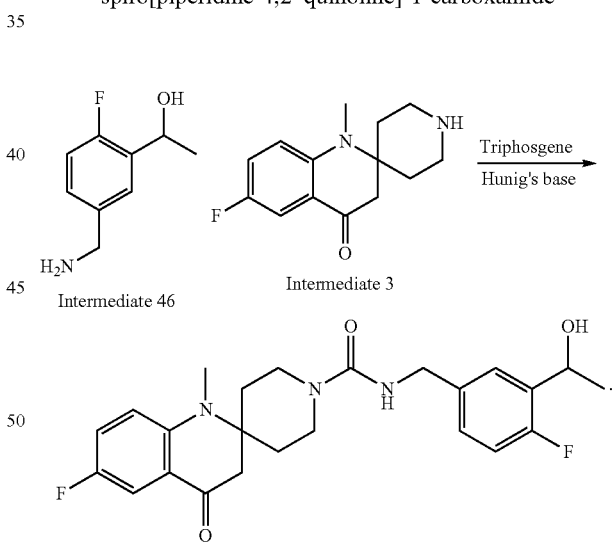

The title compound was prepared by a method similar to Example 2, using Intermediate 46 instead of (4-fluoro-2-methoxyphenyl)methanamine. The crude residue was purified by a preparative HPLC (Basic, Method 5) to give the title compound (52 mg, 41% yield) as a fluffy yellow solid after lyophilization. LCMS: MS m/z 444.1 (M+H); $^1$H NMR (400 MHz, Methanol-$d_4$) δ 7.50-7.40 (m, 2H), 7.31-7.22 (m, 1H), 7.22-7.15 (m, 1H), 7.02-6.91 (m, 2H), 5.11 (q, J=6.5 Hz, 1H), 4.34 (s, 2H), 4.01-3.93 (m, 2H), 3.13-3.03 (m, 2H), 2.96 (s, 3H), 2.94 (s, 2H), 2.01-1.89 (m, 2H), 1.77-1.69 (m, 2H), 1.43 (d, J=6.5 Hz, 3H).

Example 93: N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide

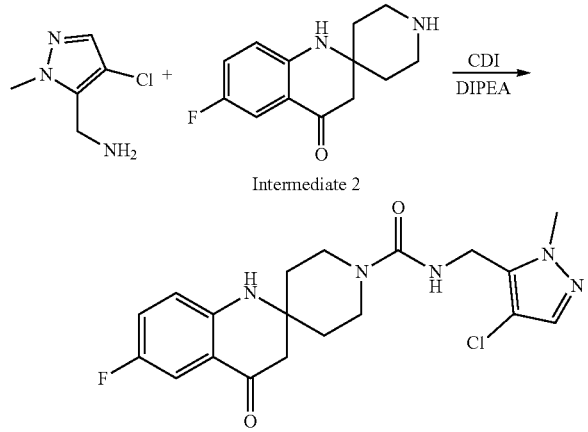

The title compound was prepared by a method similar to Example 1, using (4-chloro-1-methyl-1H-pyrazol-5-yl)methanamine instead of Intermediate 1. Intermediate 2 was HCl salt. The product was purified by silica gel chromatography (MeOH/DCM) followed by reversed-phase HPLC (Basic, Method 3) to give the title compound (26 mg, 39% yield) as a white solid after lyophilization. LCMS: m/z 406.4 (M+H); $^1$H NMR (400 MHz, DMSO-$d_6$) δ 7.44 (s, 1H), 7.26-7.17 (m, 2H), 7.01 (t, J=5.1 Hz, 1H), 6.90 (ddd, J=8.5, 4.5, 1.1 Hz, 1H), 6.79 (s, 1H), 4.25 (d, J=5.1 Hz, 2H), 3.80 (s, 3H), 3.50-3.26 (m, 4H), 2.60 (s, 2H), 1.65-1.45 (m, 4H).

Example 94: (R)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide

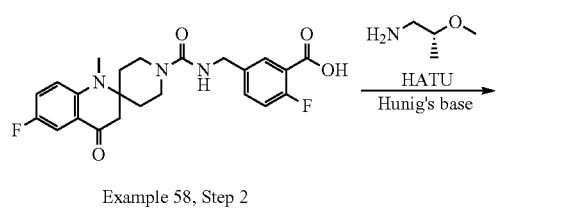

The title compound was prepared by a method similar to Example 32, Step 2, using (R)-1-aminopropan-2-ol instead of (4-(aminomethyl)phenyl)methanol. The crude residue was purified by a preparative reversed-phase HPLC (Basic, Method 4) to give the title compound (43 mg, 71% yield) as a fluffy yellow solid after lyophilization. LCMS: m/z 501.4 (M+H); $^1$H NMR (400 MHz, Methanol-$d_4$) δ 7.69 (dd, J=7.0, 2.3 Hz, 1H), 7.51-7.41 (m, 2H), 7.32-7.22 (m, 1H), 7.22-7.12 (m, 1H), 6.97 (dd, J=9.4, 4.0 Hz, 1H), 4.37 (s, 2H), 4.02-3.93 (m, 2H), 3.58 (s, 4H), 3.40 (s, 3H), 3.14-3.04 (m, 2H), 2.99-2.93 (m, 5H), 2.03-1.90 (m, 2H), 1.78-1.70 (m, 2H).

Example 95: N-(3-amino-4-fluorobenzyl)-6'-fluoro-4'-oxo-3',4'-dihydro-1'H-spiro[piperidine-4,2'-quinoline]-1-carboxamide

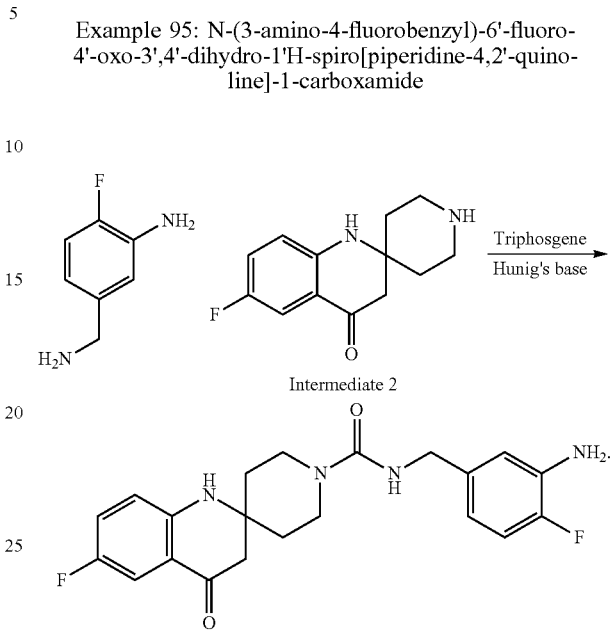

The title compound was prepared by a method similar to Example 2, using 5-(aminomethyl)-2-fluoroaniline and Intermediate 2 (free base) instead of (4-fluoro-2-methoxyphenyl)methanamine, and Intermediate 3, respectively. The crude residue was purified by a preparative HPLC (Basic, Method 4) to give the title compound (140 mg, 37% yield) as a fluffy yellow solid after lyophilization. HRMS: m/z 401.1785 (M+H); $^1$H NMR (400 MHz, Methanol-$d_4$) δ 7.30 (dd, J=9.0, 3.0 Hz, 1H), 7.18-7.08 (m, 1H), 6.92-6.82 (m, 2H), 6.77 (dd, J=8.6, 2.1 Hz, 1H), 6.61-6.53 (m, 1H), 4.23 (s, 2H), 3.50 (dq, J=14.4, 5.1, 4.1 Hz, 4H), 2.67 (s, 2H), 1.82-1.65 (m, 4H).

Example 96: 6'-fluoro-4'-oxo-N-((2-(trifluoromethyl)furan-3-yl)methyl)-3',4'-dihydro-1'H-spiro[piperidine-4,2'-quinoline]-1-carboxamide

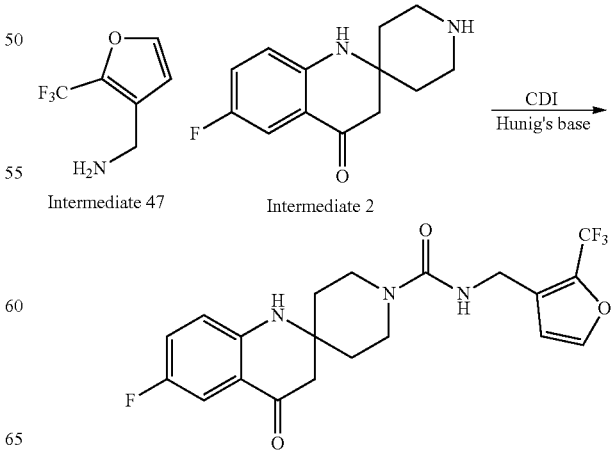

The title compound was prepared by a method similar to Example 1, using Intermediate 47 instead of Intermediate 1. Intermediate 2 was a free base. The crude residue was purified by a preparative reversed-phase HPLC (Basic, Method 2) to give the title compound (20.8 mg, 10% yield) as a fluffy yellow solid after lyophilization. HRMS: m/z 426.1465 (M+H); $^1$H NMR (400 MHz, Methanol-d$_4$) δ 7.63 (d, J=1.9 Hz, 1H), 7.32 (dd, J=9.1, 3.1 Hz, 1H), 7.19-7.09 (m, 1H), 6.87 (dd, J=9.0, 4.3 Hz, 1H), 6.58 (s, 1H), 4.35 (d, J=1.7 Hz, 2H), 3.60-3.44 (m, 4H), 2.68 (s, 2H), 1.83-1.66 (m, 4H).

Example 97: 6'-fluoro-N-(4-fluoro-3-((2-hydroxy-2-methylpropyl)carbamoyl)benzyl)-1'-methyl-4'-oxo-3',4'-dihydro-1'H-spiro[piperidine-4,2'-quinoline]-1-carboxamide

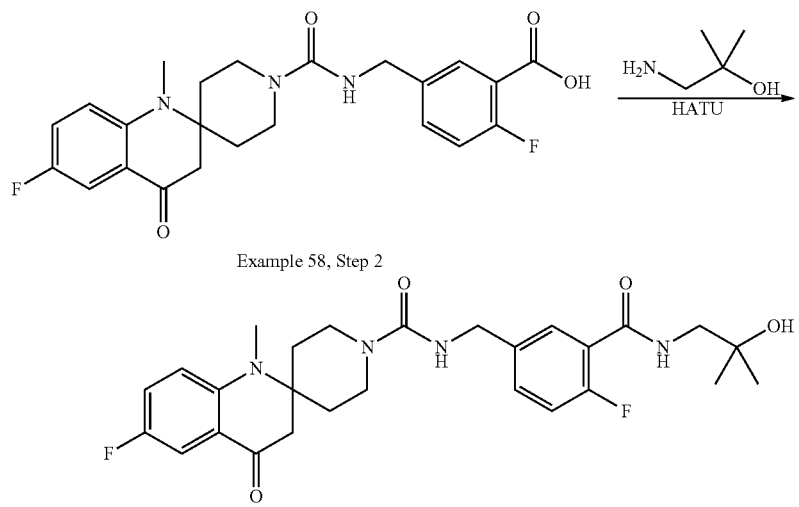

Example 58, Step 2

The title compound was prepared by a method similar to Example 32, Step 2, using 1-amino-2-methylpropan-2-ol instead of (4-(aminomethyl)phenyl)methanol. The product was purified by reverse phase HPLC (Basic, Method 4) to give the title compound (15 mg, 35% yield) as a fluffy yellow solid after lyophilization. LCMS: m/z 515.3 (M+H); $^1$H NMR (400 MHz, DMSO-d$_6$) δ 7.97 (d, J=4.5 Hz, 1H), 7.54 (dd, J=7.1, 2.4 Hz, 1H), 7.43-7.27 (m, 3H), 7.27-7.12 (m, 2H), 7.04-6.87 (m, 1H), 4.55 (s, 1H), 4.22 (d, J=5.6 Hz, 2H), 3.90 (d, J=13.4 Hz, 2H), 3.24 (d, J=5.9 Hz, 2H), 2.88 (d, J=23.5 Hz, 7H), 1.77 (td, J=12.7, 4.5 Hz, 2H), 1.57 (d, J=12.9 Hz, 2H), 1.11 (s, 6H).

Example 98: N-(4-amino-2-fluorobenzyl)-6'-fluoro-4'-oxo-3',4'-dihydro-1'H-spiro[piperidine-4,2'-quinoline]-1-carboxamide

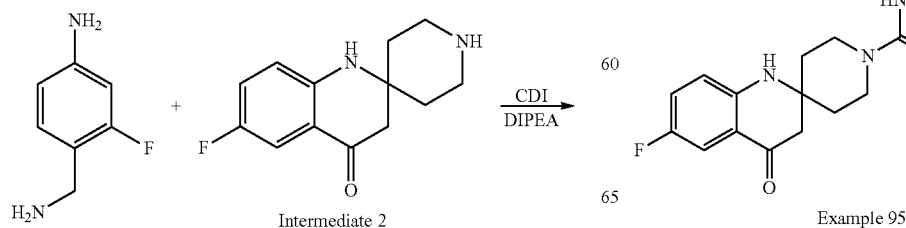

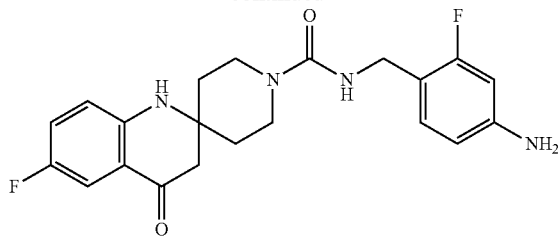

The title compound was prepared by a method similar to Example 1, using 4-(aminomethyl)-3-fluoroaniline instead of Intermediate 1. Intermediate 2 was HCl salt. The product was purified by silica gel chromatography (MeOH/DCM) followed by reversed-phase HPLC (Formic acid, Method 3) to give the title compound (17 mg, 23% yield) as a yellow solid after lyophilization. LCMS: m/z 401.4 (M+H); $^1$H NMR (400 MHz, DMSO-d$_6$) δ 7.31-7.14 (m, 2H), 7.02-6.85 (m, 2H), 6.85-6.72 (m, 2H), 6.32 (dd, J=8.2, 2.2 Hz, 1H), 6.26 (dd, J=12.7, 2.2 Hz, 1H), 5.22 (s, 2H), 4.09 (d, J=5.4 Hz, 2H), 3.52-3.24 (m, 4H), 2.60 (s, 2H), 1.67-1.46 (m, 4H).

Example 99: 6'-fluoro-N-(4-fluoro-3-((2-methoxyethyl)amino)benzyl)-4'-oxo-3',4'-dihydro-1'H-spiro[piperidine-4,2'-quinoline]-1-carboxamide

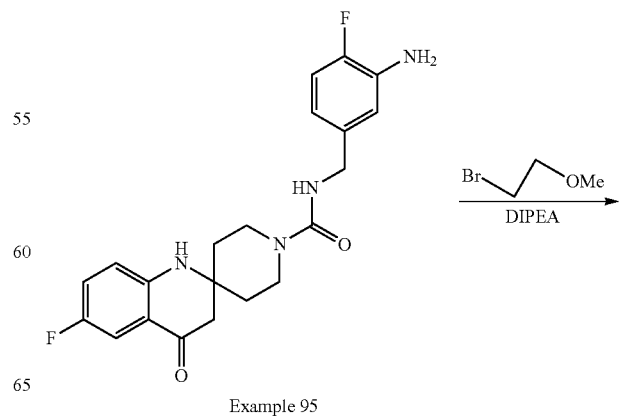

-continued

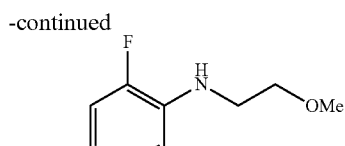

To a microwave vial was added Example 95 (25 mg, 0.062 mmol), DMF (5 mL), 1-bromo-2-methoxyethane (0.029 mL, 0.31 mmol), KI (51.8 mg, 0.312 mmol) and DIPEA (0.055 mL, 0.31 mmol). The mixture was heated in the microwave for 10 h at 110° C. The mixture was then diluted with EtOAc, washed with aqueous saturated sodium bicarbonate, dried over $Na_2SO_4$, filtered, and concentrated under reduced pressure. The residue was purified by HPLC (Basic, Method 4) to give the title the target compound (8.9 mg, 30.8% yield). LCMS: m/z 459.2 (M+H); $^1$H NMR (400 MHz, Methanol-$d_4$) δ 7.29 (dd, J=9.0, 3.0 Hz, 1H), 7.16-7.07 (m, 1H), 6.91-6.82 (m, 2H), 6.71 (dd, J=8.5, 1.9 Hz, 1H), 6.56-6.49 (m, 1H), 4.25 (s, 2H), 3.59 (t, J=5.6 Hz, 2H), 3.55-3.46 (m, 4H), 3.38 (s, 3H), 2.65 (s, 2H), 1.72 (dtt, J=13.5, 8.6, 3.8 Hz, 4H), 1.33 (dd, J=6.7, 4.8 Hz, 1H), 1.11 (d, J=6.6 Hz, 2H)

Example 100: N-(3-((2-cyclopropyl-2-oxoethyl)carbamoyl)-4-fluorobenzyl)-6'-fluoro-4'-oxo-3',4'-dihydro-1'H-spiro[piperidine-4,2'-quinoline]-1-carboxamide

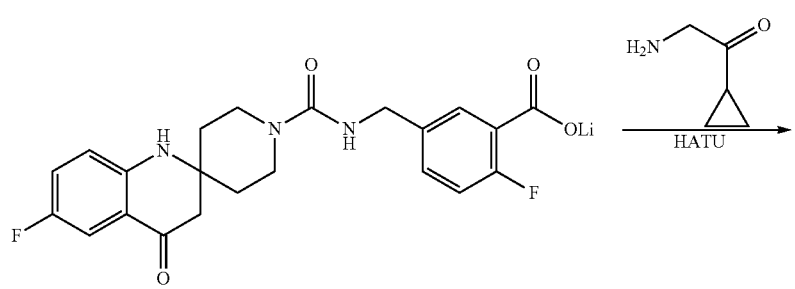

Example 32, step 1

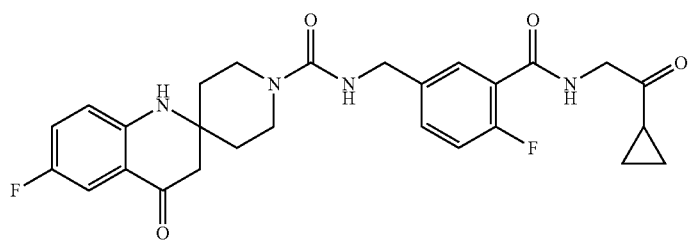

The title compound was prepared in a method similar to Example 32, step 2. The product was purified by reverse phase HPLC (Basic, Method 10) to give the title compound (7.3 mg, 28% yield) as a solid after lyophilization. LCMS: m/z 511.2 (M+H).

Example 101: 6'-fluoro-N-(4-fluoro-3-(((2,2,2-trifluoroethyl)carbamoyl)benzyl)-4'-oxo-3',4'-dihydro-1'H-spiro[piperidine-4,2'-quinoline]-1-carboxamide

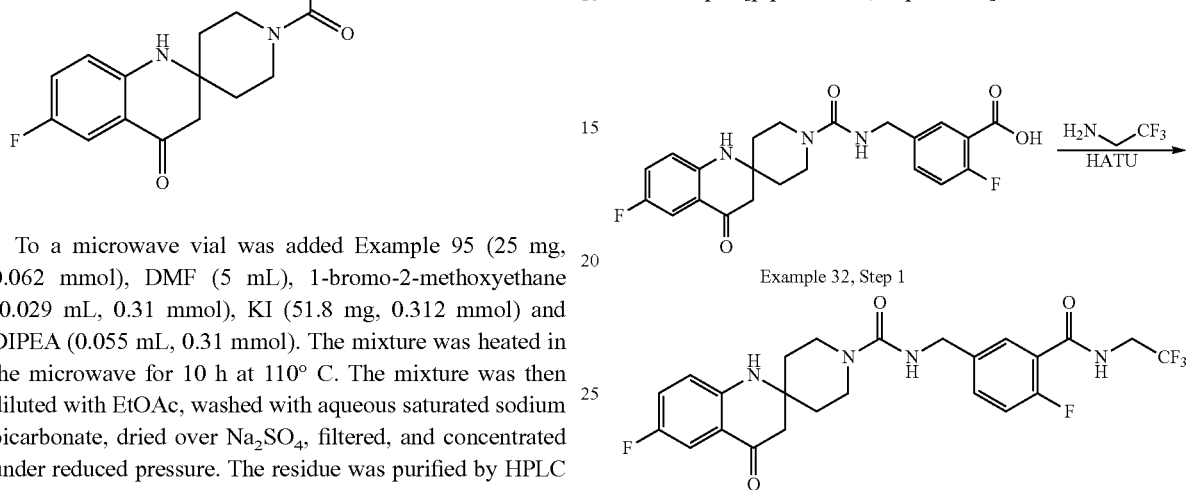

Example 32, Step 1

The title compound was prepared by a method similar to Example 32, Step 2, using 2,2,2-trifluoroethanamine instead of (4-(aminomethyl)phenyl)methanol. The product was purified by reverse phase HPLC (Basic, Method 4) to give the title compound (31 mg, 36% yield) as a yellow solid. LCMS: m/z 571.4 (M+H); $^1$H NMR (400 MHz, DMSO-$d_6$) δ 8.94 (td, J=6.3, 2.0 Hz, 1H), 7.50 (dd, J=6.9, 2.4 Hz, 1H), 7.42 (ddd, J=7.7, 5.0, 2.3 Hz, 1H), 7.31-7.11 (m, 4H), 6.98-6.86 (m, 1H), 6.79 (s, 1H), 4.23 (d, J=5.8 Hz, 2H), 4.08 (dddd, J=16.0, 9.7, 6.1, 3.2 Hz, 2H), 3.49-3.32 (m, 4H), 2.61 (s, 2H), 1.58 (qdd, J=13.2, 9.3, 4.4 Hz, 4H).

Example 102: 6'-fluoro-N-(4-fluoro-3-(3-methoxyazetidin-1-yl)benzyl)-4'-oxo-3',4'-dihydro-1'H-spiro[piperidine-4,2'-quinoline]-1-carboxamide

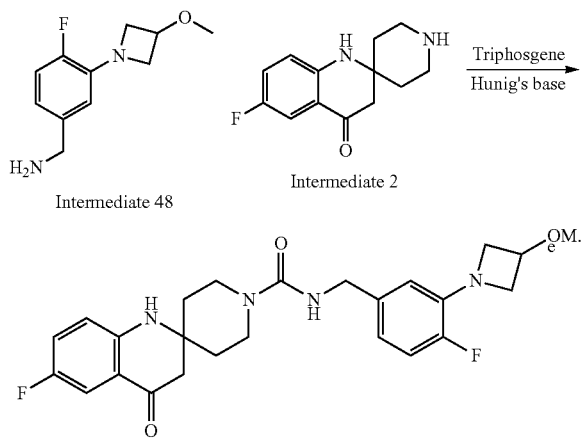

The title compound was prepared by a method similar to Example 2, using Intermediates 48 (44 mg, 0.209 mmol) and 2 (free base) instead of (4-fluoro-2-methoxyphenyl)methanamine and Intermediate 3, respectively. The crude residue was purified by a preparative HPLC (Basic, Method 5) followed by a SFC (column: Princeton DIOL 20×150 mm 5 µm; mobile phase: MeOH) to give the title compound (20 mg, 20% yield) as a fluffy yellow solid after lyophilization. LCMS: m/z 470.1 (M+H); $^1$H NMR (400 MHz, Methanol-$d_4$) δ 7.29 (dd, J=8.9, 3.0 Hz, 1H), 7.12 (ddd, J=9.2, 8.2, 3.1 Hz, 1H), 6.93-6.81 (m, 2H), 6.69-6.61 (m, 1H), 6.50 (dd, J=8.8, 2.3 Hz, 1H), 4.35-4.26 (m, 1H), 4.24 (s, 2H), 4.20-4.11 (m, 2H), 3.73-3.65 (m, 2H), 3.58-3.41 (m, 4H), 3.32 (s, 3H), 2.65 (s, 2H), 1.81-1.63 (m, 4H).

Example 103: N-(3-(2-amino-2-oxoethyl)-4-fluorobenzyl)-6'-fluoro-4'-oxo-3',4'-dihydro-1'Hspiro[piperidine-4,2'-quinoline]-1-carboxamide

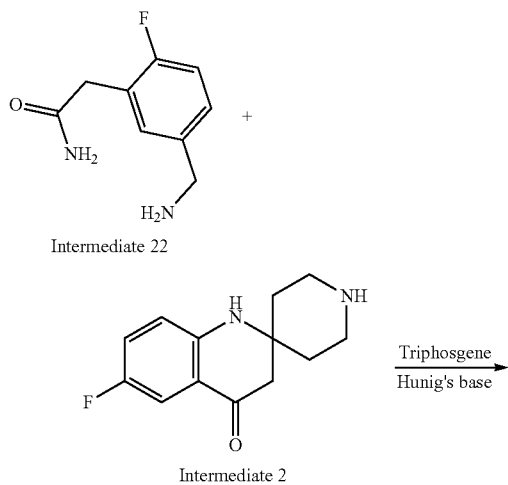

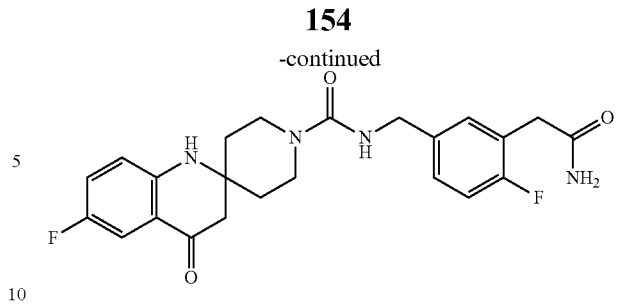

The title compound was prepared by a method similar to Example 2, using Intermediates 22 and 2 (HCl salt) instead of (4-fluoro-2-methoxyphenyl)methanamine and Intermediate 3, respectively. The product was purified by silica gel chromatography (DCM/MeOH=100/0 to 85/15) to give the title compound (27 mg, 12% yield) as a yellow solid. LCMS: m/z 442.9 (M+H); $^1$H NMR (400 MHz, DMSO-$d_6$) δ: 7.49 (1H, s), 7.24-7.04 (6H, m), 6.96 (1H, s), 6.92-6.88 (1H, m), 6.79 (1H, s), 4.18-4.12 (2H, d), 3.44-3.38 (5H, m), 2.66 (2H, s), 1.61-1.53 (4H, m).

Example 104: N-(4-amino-2-(trifluoromethyl)benzyl)-6'-fluoro-4'-oxo-3',4'-dihydro-1'H-spiro[piperidine-4,2'-quinoline]-1-carboxamide

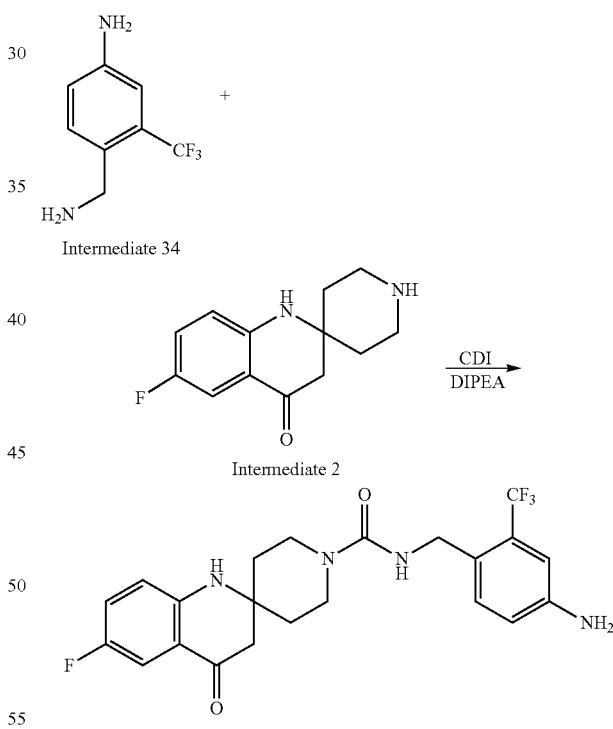

The title compound was prepared by a method similar to Example 1, using Intermediate 34 instead of Intermediate 1. Intermediate 2 was HCl salt. The product was purified by silica gel chromatography (MeOH/DCM) followed by reversed-phase HPLC (Formic acid, Method 4) to give the title compound (17 mg, 23% yield) as a yellow solid after lyophilization. LCMS: m/z=451.4 (M+H). $^1$H NMR (400 MHz, DMSO-$d_6$) δ 7.27-7.17 (m, 2H), 7.11 (d, J=8.5 Hz, 1H), 6.96-6.87 (m, 1H), 6.87-6.83 (m, 1H), 6.80 (s, 1H), 6.75 (dd, J=8.5, 2.3 Hz, 1H), 5.38 (s, 2H), 4.24 (d, J=5.3 Hz, 2H), 3.50-3.37 (m, 4H), 2.62 (s, 2H), 1.68-1.50 (m, 4H).

Example 105: 6'-fluoro-N-(4-fluoro-3-(oxetan-3-ylcarbamoyl)benzyl)-4'-oxo-3',4'-dihydro-1'H-spiro[piperidine-4,2'-quinoline]-1-carboxamide

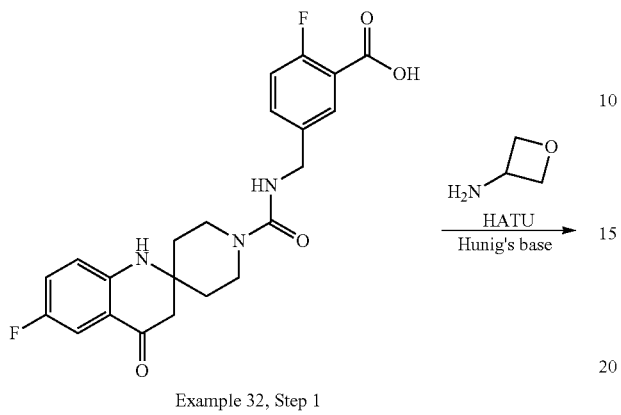

Example 32, Step 1

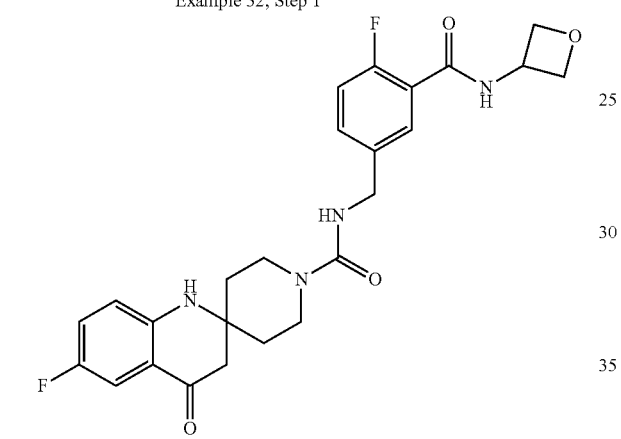

The title compound was prepared by a method similar to Example 32, Step 2, using oxetan-3-amine instead of (4-(aminomethyl)phenyl)methanol). The crude residue was purified by silica gel chromatography (EtOAc/Hexane=0/100 to 50/50) followed by a preparative reversed-phase HPLC (Basic, Method 3) to give the title compound (90 mg, 97% yield) as a fluffy yellow solid after lyophilization. LCMS: m/z 485.0 (M+H); $^1$H NMR (400 MHz, Methanol-$d_4$) δ 7.64-7.57 (m, 1H), 7.49-7.40 (m, 1H), 7.29 (dd, J=8.9, 3.1 Hz, 1H), 7.20-7.07 (m, 2H), 6.85 (dd, J=9.1, 4.3 Hz, 1H), 5.12 (ddt, J=8.2, 7.4, 6.1 Hz, 1H), 4.97-4.90 (m, 2H), 4.68 (t, J=6.5 Hz, 2H), 4.34 (s, 2H), 3.58-3.45 (m, 4H), 2.66 (s, 2H), 1.81-1.69 (m, 4H).

Example 106: N-((3-ethyl-5-methylisoxazol-4-yl)methyl)-6'-fluoro-4'-oxo-3',4'-dihydro-1'H-spiro[piperidine-4,2'-quinoline]-1-carboxamide

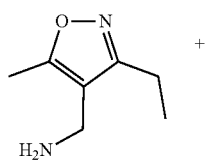 +

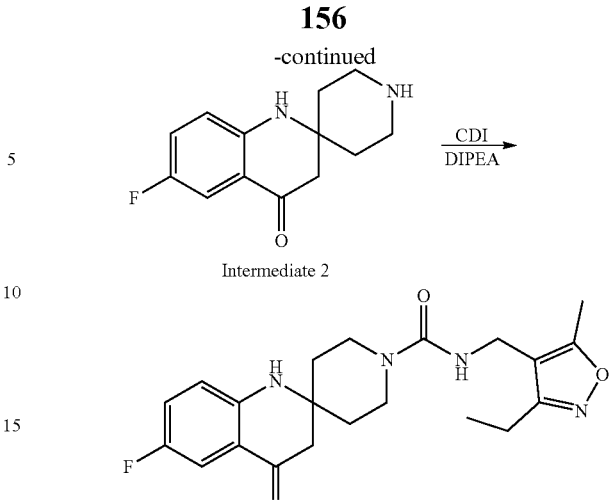

The title compound was prepared in a method similar to Example 1, using (3-ethyl-5-methylisoxazol-4-yl)methanamine instead of Intermediate 1. Intermediate 2 was HCl salt. The product was purified by reverse phase HPLC (Basic, Method 10) to give the title compound. LCMS: m/z 401.4 (M+H).

Example 107: 6'-fluoro-N-(isoxazol-4-ylmethyl)-4'-oxo-3',4'-dihydro-1'H-spiro[piperidine-4,2'-quinoline]-1-carboxamide The title compound was prepared by a method similar to Example 1, using 4-aminomethylisoxazole. HCl salt instead of Intermediate 1. Intermediate 2 was HCl salt. The product was purified by reversed-phase HPLC (Formic acid, Method 3) to give the title compound (22 mg, 28% yield) as a yellow solid. LCMS: m/z 359.4 (M+H); $^1$H NMR (400 MHz, Methanol-d4) δ 8.54 (s, 1H), 8.36 (s, 1H), 7.30 (dd, J=12, 4 Hz, 1H), 7.15-7.08 (m, 1H), 6.84 (dd, J=12, 4 Hz, 1H), 4.20 (s, 2H), 3.57-3.39 (m, 4H), 2.65 (s, 2H), 1.79-1.60 (m, 4H).

Example 108: N-(4-(difluoromethoxy)-3-fluorobenzyl)-6',8'-difluoro-4'-oxo-3',4'-dihydro-1'H-spiro[piperidine-4,2'-quinoline]-1-carboxamide

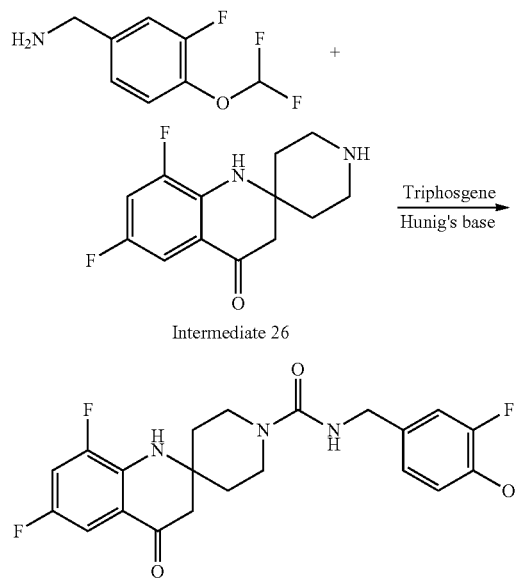

The title compound was prepared using a method similar to Example 2, using (4-(difluoromethoxy)-3-fluorophenyl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 470.1 (M+H); $^1$H NMR (400 MHz, Methanol-$d_4$) δ 7.23-7.20 (m, 5H), 6.61 (s, 1H), 4.34 (s, 2H), 3.74-3.68 (m, 2H), 3.40-3.33 (m, 2H), 2.81 (s, 2H), 1.83-1.80 (m, 4H).

Example 109: N-(3-carbamoyl-2,4-difluorobenzyl)-6'-fluoro-4'-oxo-3',4'-dihydro-1'H-spiro[piperidine-4,2'-quinoline]-1-carboxamide

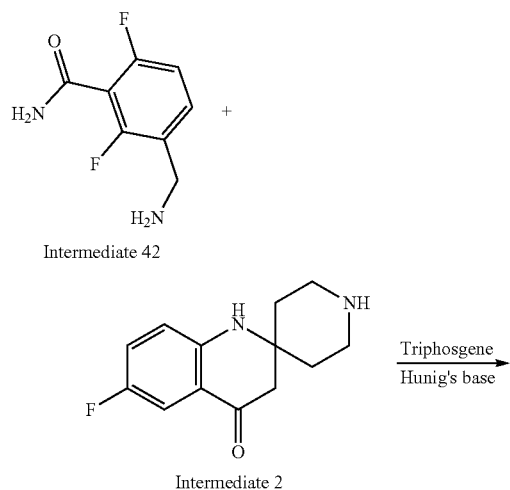

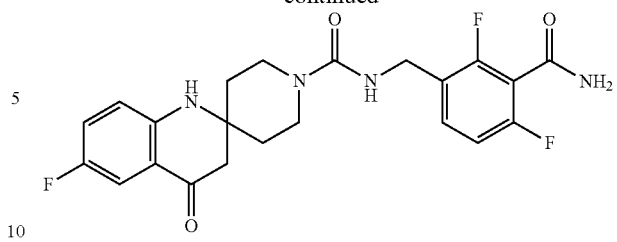

The title compound was prepared by a method similar to Example 2, using Intermediates 42 and 2 (HCl salt) instead of (4-fluoro-2-methoxyphenyl)methanamine and Intermediate 3, respectively. The product was purified by silica gel chromatography (DCM/MeOH=100/0 to 90/10) followed by preparative reverse-phase HPLC (column: Zorbax xdb C18 5µ 21.2 mm×150 mm; mobile phase: Water/MeCN) to give the title compound (29 mg, 20% yield) as a yellow solid. LCMS: m/z 446.95 (M+H); $^1$H NMR (400 MHz, Chloroform-d) δ 7.48-7.43 (2H, m), 7.08-7.07 (1H, d), 6.91 (1H, m), 6.67-6.63 (1H, m), 5.94 (1H, br, s), 5.11 (1H, br, s), 4.42-4.37 (3H, m), 3.49-3.48 (1H, d), 3.41-3.38 (4H, m), 2.67 (2H, s) 1.79-1.59 (4H, m).

Example 110: N-((2,5-dimethylfuran-3-yl)methyl)-6'-fluoro-4'-oxo-3',4'-dihydro-1'H-spiro[piperidine-4,2'-quinoline]-1-carboxamide

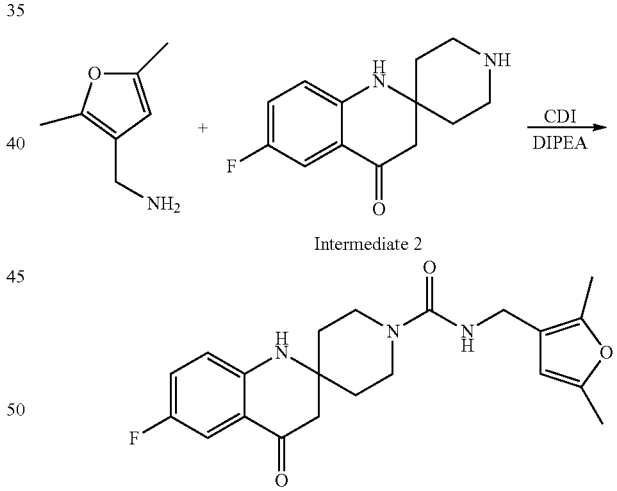

The title compound was prepared by a method similar to Example 1, using (2,5-dimethylfuran-3-yl)methanamine instead of Intermediate 1. The product was purified by reversed-phase HPLC (Basic, Method 5), followed by SFC (column: Princeton DIOL 20×150 mm 5 µM; mobile phase: MeOH) to give the title compound (15.6 mg, 10% yield) as a yellow solid. LCMS: m/z 384.2 (M+H); $^1$H NMR (400 MHz, Methanol-$d_4$) δ 7.29 (dd, J=8.9, 3.1 Hz, 1H), 7.11 (ddd, J=9.1, 8.2, 3.1 Hz, 1H), 6.84 (dd, J=9.1, 4.3 Hz, 1H), 5.86 (d, J=1.2 Hz, 1H), 4.03 (d, J=4.6 Hz, 2H), 3.50-3.43 (m, 4H), 2.64 (s, 2H), 2.17 (d, J=10.8 Hz, 6H), 1.70 (qdd, J=13.3, 9.1, 4.8 Hz, 4H).

Example 111: N-(4-amino-2-chlorobenzyl)-6'-fluoro-4'-oxo-3',4'-dihydro-1'H-spiro[piperidine-4,2'-quinoline]-1-carboxamide

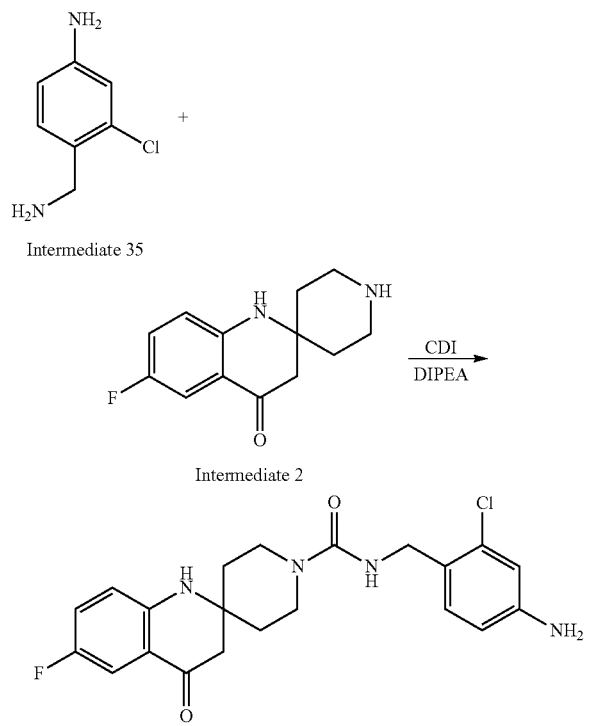

Intermediate 35

Intermediate 2

The title compound was prepared by a method similar to Example 1, using Intermediate 35 instead of Intermediate 1. Intermediate 2 was HCl salt. The product was purified by silica gel chromatography (MeOH/DCM) followed by reversed-phase HPLC (Basic, Method 4) to give the title compound (28 mg, 41% yield) as a yellow solid after lyophilization. LCMS: m/z 439.3 (M+Na); $^1$H NMR (400 MHz, DMSO-$d_6$) δ 7.26-7.17 (m, 2H), 7.00-6.88 (m, 2H), 6.84 (t, J=5.5 Hz, 1H), 6.79 (s, 1H), 6.58 (d, J=2.2 Hz, 1H), 6.47 (dd, J=8.3, 2.2 Hz, 1H), 5.21 (s, 2H), 4.14 (d, J=5.5 Hz, 2H), 3.51-3.34 (m, 4H), 2.61 (s, 2H), 1.69-1.48 (m, 4H).

Example 112: N-(4-amino-3-(trifluoromethyl)benzyl)-6'-fluoro-4'-oxo-3',4'-dihydro-1'H-spiro[piperidine-4,2'-quinoline]-1-carboxamide

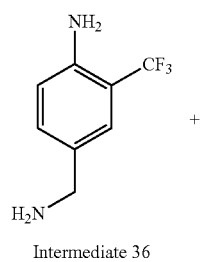

Intermediate 36

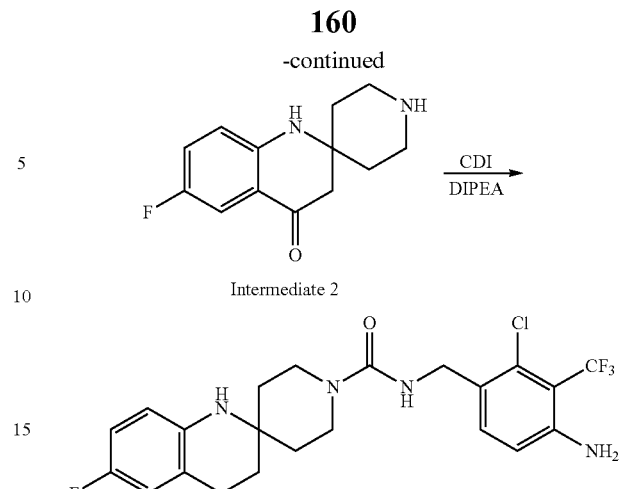

Intermediate 2

The title compound was prepared by a method similar to Example 1, using Intermediate 36 instead of Intermediate 1. Intermediate 2 was HCl salt. The product was purified by silica gel chromatography (MeOH/DCM) followed by reversed-phase HPLC (Basic, Method 4) to give the title compound (8 mg, 13% yield) as a yellow solid after lyophilization. LCMS: m/z 489.3 (M+39); $^1$H NMR (400 MHz, DMSO-$d_6$) δ 7.27-7.16 (m, 2H), 7.04-6.86 (m, 4H), 6.79 (s, 1H), 6.74 (d, J=8.2 Hz, 1H), 5.19 (s, 2H), 4.07 (d, J=5.6 Hz, 2H), 3.50-3.32 (m, 4H), 2.59 (s, 2H), 1.67-1.46 (m, 4H).

Example 113: 6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide

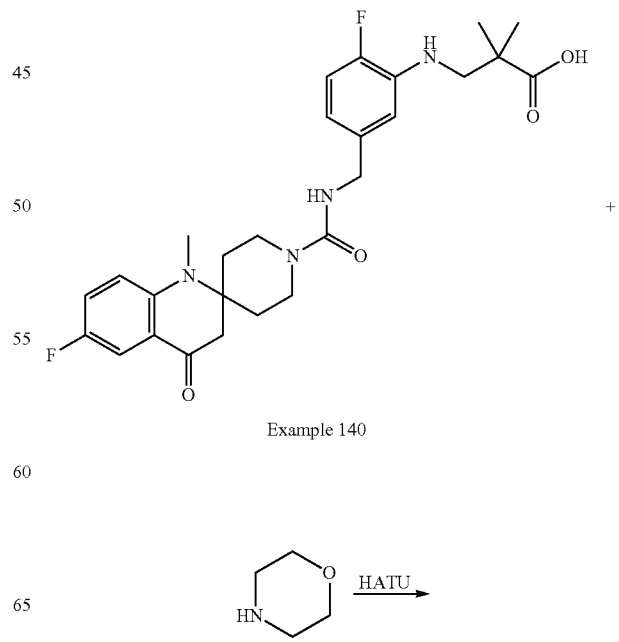

Example 140

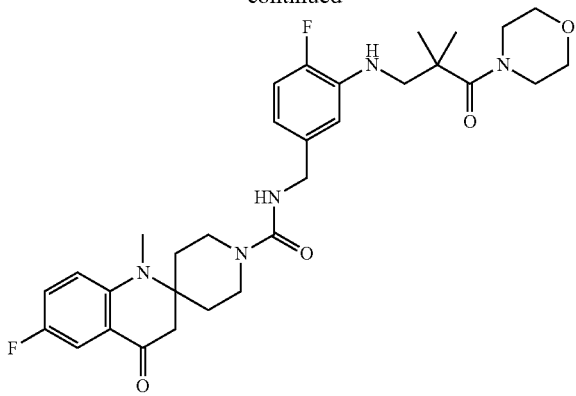

The title compound was prepared by a method similar to Example 44, using morpholine instead N-Me piperazine. The product was purified by by reverse-phase HPLC (Basic, Method 5) to give the title compound as a yellow solid (9 mg). LCMS: m/z 584.4 (M+H); $^1$H NMR (400 MHz, Methanol-$d_4$) δ 7.42 (dd, J=8.6, 3.2 Hz, 1H), 7.27-7.21 (m, 1H), 6.93 (dd, J=9.4, 4.0 Hz, 1H), 6.85 (dd, J=11.7, 8.2 Hz, 1H), 6.76 (dd, J=8.4, 1.8 Hz, 1H), 6.54-6.46 (m, 1H), 4.24 (s, 2H), 3.99-3.90 (m, 2H), 3.71-3.59 (m, 8H), 3.27 (s, 2H), 3.10-3.01 (m, 2H), 2.93 (s, 3H), 2.92 (s, 2H), 1.92 (td, J=12.9, 4.7 Hz, 2H), 1.74-1.66 (m, 2H), 1.35 (s, 6H).

Example 114: 6'-fluoro-N-(4-fluoro-2-methoxybenzyl)-4'-oxo-3',4'-dihydro-1'H-spiro[piperidine-4,2'-quinoline]-1-carboxamide

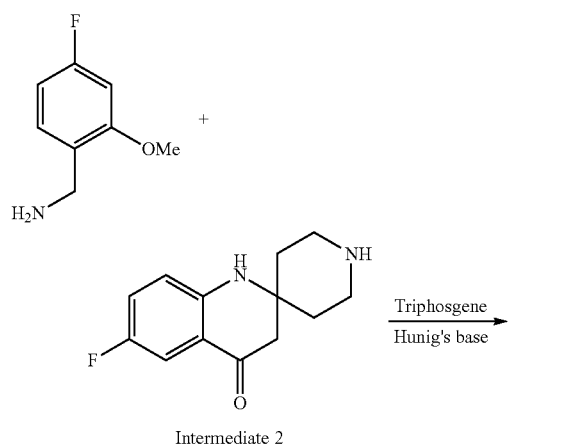

The title compound was prepared by a method similar to Example 2, using (4-fluoro-2-methoxyphenyl)methanamine and Intermediate 2 (HCl salt) instead of (4-fluoro-2-methoxyphenyl)methanamine and Intermediate 3, respectively. The crude residue was purified by a preparative HPLC (Basic, Method 5) followed by a SFC (column: Princeton DIOL 20×150 mm 5 μm; mobile phase: MeOH) to give the title compound (15 mg, 15% yield) as a yellow solid after lyophilization. LCMS: MS m/z 416.2 (M+H); $^1$H NMR (400 MHz, Methanol-$d_4$) δ 7.30 (dd, J=9.0, 3.0 Hz, 1H), 7.21-7.08 (m, 2H), 6.86 (dd, J=9.1, 4.3 Hz, 1H), 6.73 (dd, J=11.1, 2.4 Hz, 1H), 6.61 (td, J=8.4, 2.4 Hz, 1H), 4.30 (s, 2H), 3.84 (s, 3H), 3.56-3.46 (m, 4H), 2.66 (s, 2H), 1.72 (tdt, J=13.2, 7.7, 4.6 Hz, 4H).

Example 115: 6',8'-difluoro-N-((2-methoxypyridin-4-yl)methyl)-4'-oxo-3',4'-dihydro-1'H-spiro[piperidine-4,2'-quinoline]-1-carboxamide

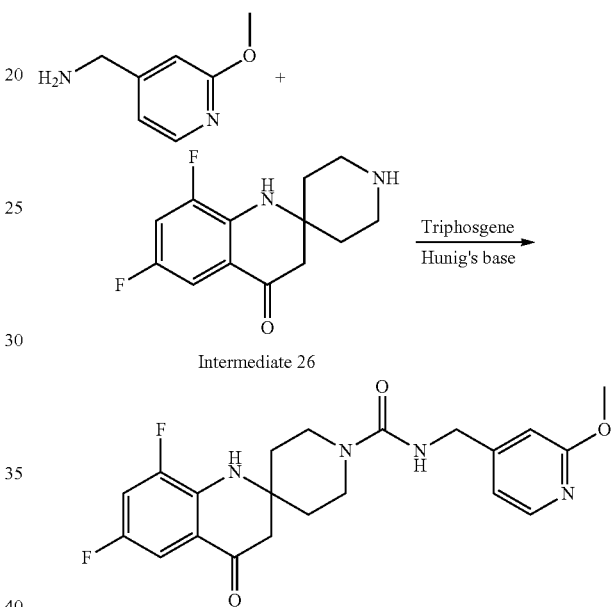

The title compound was prepared using a method similar to Example 2, using (2-methoxypyridin-4-yl)methanamine and intermediate 26 instead of (4-fluoro-2-methoxyphenyl)methanamine) and intermediate 3, respectively. The crude residue was purified by preparative HPLC (Formic acid, method 10) to give the title compound. LCMS: m/z 417.1 (M+H).

Example 116: N-(4-amino-2-methylbenzyl)-6'-fluoro-4'-oxo-3',4'-dihydro-1'H-spiro[piperidine-4,2'-quinoline]-1-carboxamide

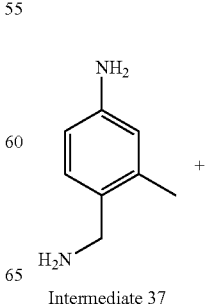

Intermediate 37

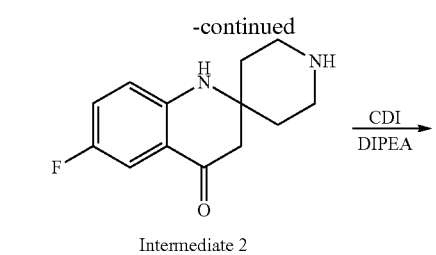

Intermediate 2

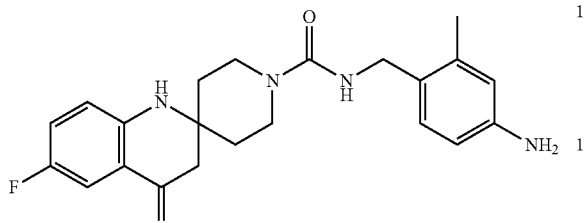

The title compound was prepared by a method similar to Example 1, using Intermediate 37 instead of Intermediate 1. Intermediate 2 was HCl salt. The product was purified by silica gel chromatography (MeOH/DCM) followed by reversed-phase HPLC (Basic, Method 4) to give the title compound (28 mg, 38% yield) as a yellow solid after lyophilization. LCMS: m/z 397.4 (M+H); $^1$H NMR (400 MHz, DMSO-$d_6$) δ 7.29-7.14 (m, 2H), 6.95-6.87 (m, 1H), 6.85 (d, J=7.9 Hz, 1H), 6.78 (s, 1H), 6.64 (t, J=5.3 Hz, 1H), 6.39-6.28 (m, 2H), 4.81 (s, 2H), 4.05 (d, J=5.3 Hz, 2H), 3.50-3.25 (m, 4H), 2.60 (s, 2H), 2.13 (s, 3H), 1.68-1.44 (m, 4H).

Example 117: (S)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide

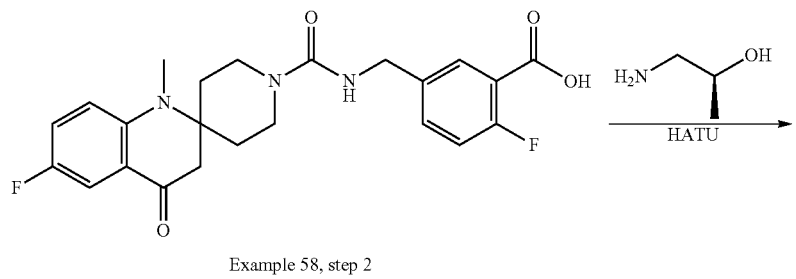

Example 58, step 2

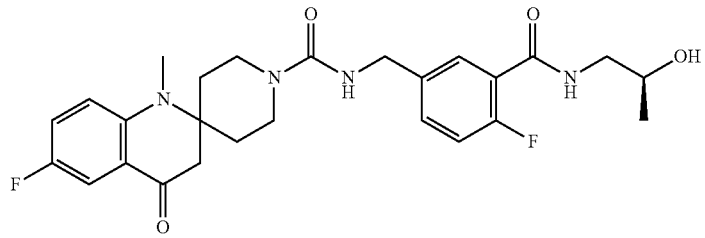

The title compound was prepared by a method similar to Example 32, Step 2, using the product from Example 58, step 2, and (S)-1-aminopropan-2-ol. The product was purified by reverse phase HPLC (Basic, Method 3) to give the title compound (20 mg, 34% yield) as a fluffy yellow solid after lyophilization. LCMS: m/z 501.4 (M+H); $^1$H NMR (400 MHz, DMSO-$d_6$) δ 8.10 (td, J=5.6, 3.3 Hz, 1H), 7.53 (dd, J=7.2, 2.4 Hz, 1H), 7.46-7.29 (m, 3H), 7.28-7.12 (m, 2H), 7.04-6.88 (m, 1H), 4.74 (d, J=4.8 Hz, 1H), 4.22 (d, J=5.6 Hz, 2H), 3.90 (dt, J=13.5, 3.8 Hz, 2H), 3.76 (qd, J=6.2, 4.9 Hz, 1H), 3.20 (t, J=5.9 Hz, 2H), 2.88 (d, J=23.3 Hz, 7H), 1.77 (td, J=12.8, 4.5 Hz, 2H), 1.57 (d, J=12.7 Hz, 2H), 1.07 (d, J=6.3 Hz, 3H).

Example 118: 6'-fluoro-N-(isoxazol-3-ylmethyl)-4'-oxo-3',4'-dihydro-1'H-spiro[piperidine-4,2'-quinoline]-1-carboxamide

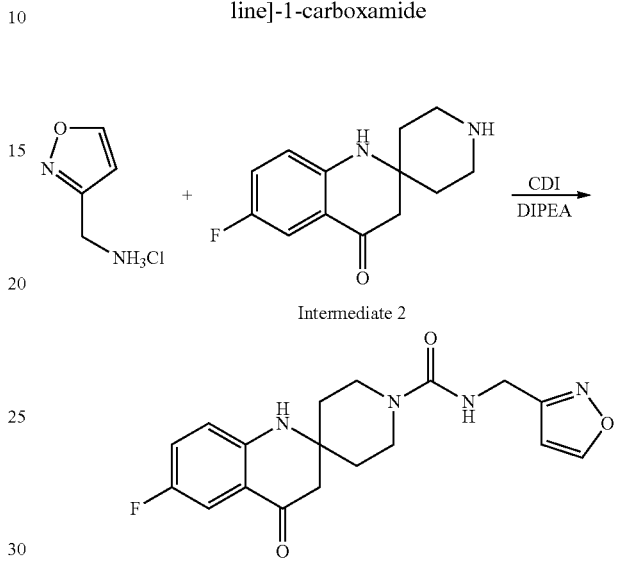

Intermediate 2

The title compound was prepared by a method similar to Example 1, using 3-aminomethylisoxazole. HCl salt instead of Intermediate 1. Intermediate 2 was HCl salt. The product was purified by silica gel chromatography (EtOAc) followed by reversed-phase HPLC (TFA, Method 3). After concentration, the product was taken up in MeOH and passed through a cartridge to remove TFA to give the title compound (45 mg, 56% yield) as a yellow solid. LCMS: m/z 359.4 (M+H); $^1$H NMR (400 MHz, Methanol-d4) δ 8.56 (d, J=1.6 Hz, 1H), 7.29 (dd, J=12, 4 Hz, 1H), 7.17-7.07 (m, 1H), 6.85 (dd, J=12, 4 Hz, 1H), 6.42 (d, J=1.6 Hz, 1H), 4.42 (s, 2H), 3.58-3.43 (m, 4H), 2.65 (s, 2H), 1.80-1.65 (m, 4H).

Example 119: N-(4-amino-3-methylbenzyl)-6'-fluoro-4'-oxo-3',4'-dihydro-1'H-spiro[piperidine-4,2'-quinoline]-1-carboxamide

Example 120: N-((1H-indol-6-yl)methyl)-6'-fluoro-4'-oxo-3',4'-dihydro-1'H-spiro[piperidine-4,2'-quinoline]-1-carboxamide

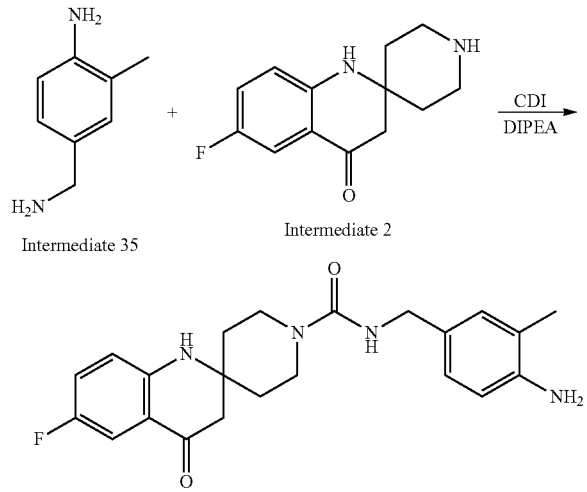

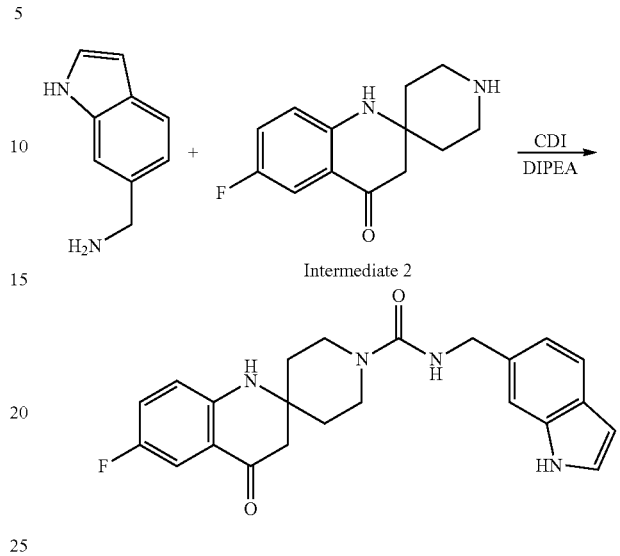

The title compound was prepared by a method similar to Example 1, using Intermediate 38 instead of Intermediate 1. Intermediate 2 was HCl salt. The product was purified by silica gel chromatography (MeOH/DCM) followed by reversed-phase HPLC (Basic, Method 3) to give the title compound (5 mg, 7% yield) as a yellow solid after lyophilization. LCMS: m/z 419.3 (M+Na); $^1$H NMR (400 MHz, DMSO-$d_6$) δ 7.27-7.16 (m, 2H), 6.95-6.86 (m, 1H), 6.86-6.72 (m, 4H), 6.51 (d, J=7.9 Hz, 1H), 4.65 (s, 2H), 4.03 (d, J=5.6 Hz, 2H), 3.48-3.33 (m, 4H), 2.59 (s, 2H), 2.02 (s, 3H), 1.66-1.46 (m, 4H).

The title compound was prepared by a method similar to Example 1, using 6-(aminomethyl)indole instead of Intermediate 1. Intermediate 2 was HCl salt. The product was purified by silica gel chromatography (MeOH/DCM) followed by reversed-phase HPLC (Basic, Method 4) to give the title compound (32 mg, 33% yield) as a yellow solid after lyophilization. LCMS: m/z 407.4 (M+H); $^1$H NMR (400 MHz, DMSO-$d_6$) δ 11.00 (s, 1H), 7.43 (d, J=8.1 Hz, 1H), 7.31-7.17 (m, 4H), 7.08 (t, J=5.7 Hz, 1H), 6.96-6.87 (m, 2H), 6.81 (s, 1H), 6.39-6.31 (m, 1H), 4.31 (d, J=5.7 Hz, 2H), 3.56-3.26 (m, 4H), 2.61 (s, 2H), 1.67-1.46 (m, 4H).

Example 121: 6'-fluoro-N-(4-fluoro-3-(((2-methyloxazol-5-yl)methyl)carbamoyl)benzyl)-4'-oxo-3',4'-dihydro-1'H-spiro[piperidine-4,2'-quinoline]-1-carboxamide

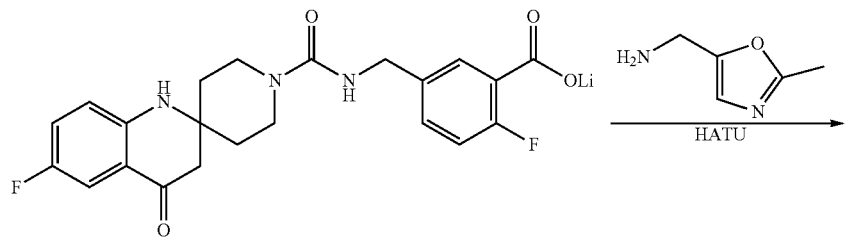

Example 32, step 1

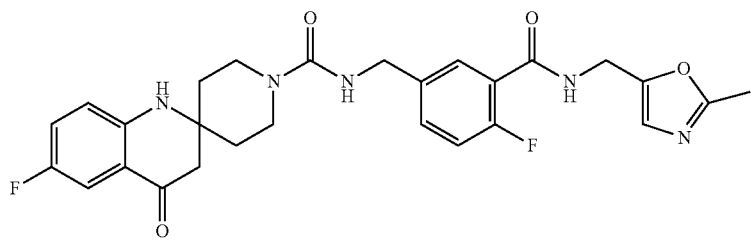

The title compound was prepared in a method similar to Example 32, step 2. The product was purified by reverse phase HPLC (Basic, Method 10) to give the title compound (7.5 mg, 28% yield) as a solid after lyophilization. LCMS: m/z 524.2 (M+H).

Example 122: (E)-6'-fluoro-N-(4-fluoro-3-((4-hydroxybut-2-en-1-yl)carbamoyl)benzyl)-4'-oxo-3',4'-dihydro-1'H-spiro[piperidine-4,2'-quinoline]-1-carboxamide

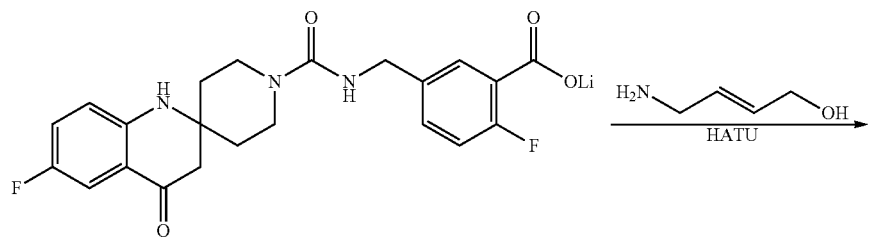

Example 32, step 1

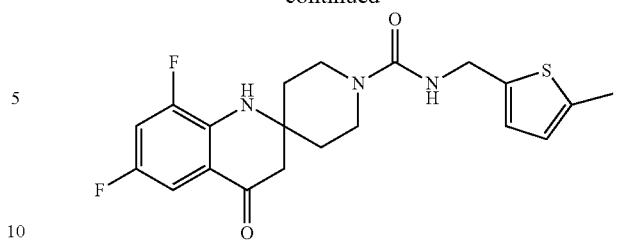

-continued

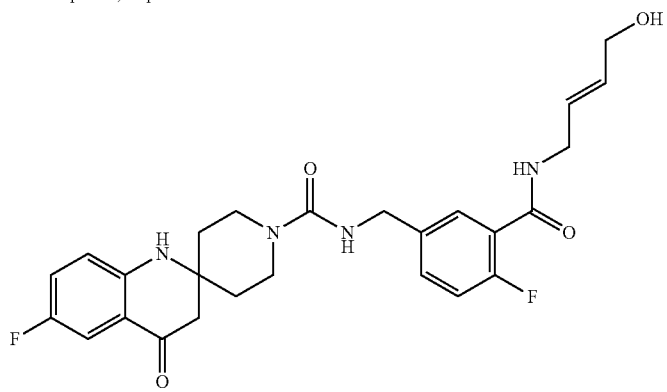

The title compound was prepared in a method similar to Example 32, step 2. The product was purified by reverse phase HPLC (Basic, Method 10) to give the title compound (12.1 mg, 48% yield) as a solid after lyophilization. LCMS: m/z 499.2 (M+H).

Example 123: 6',8'-difluoro-N-((5-methylthiophen-2-yl)methyl)-4'-oxo-3',4'-dihydro-1'H-spiro[piperidine-4,2'-quinoline]-1-carboxamide

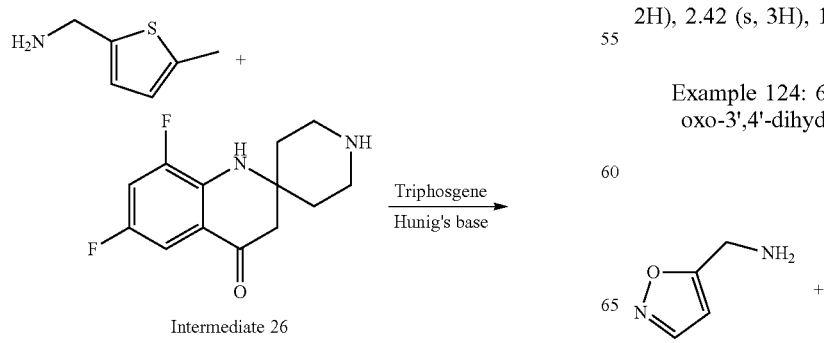

Intermediate 26

The title compound was prepared using a method similar to Example 2, using (5-methylthiophen-2-yl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 406.1 (M+H); $^1$H NMR (400 MHz, Methanol-$d_4$) δ 7.24-7.15 (m, 2H), 7.15 (dd, J=4 Hz, 1H), 6.57 (dd, J=4 Hz, 1.2 Hz, 1H), 4.41 (s, 2H), 3.70-3.64 (m, 2H), 3.37-3.33 (m, 2H), 2.80 (s, 2H), 2.42 (s, 3H), 1.84-1.74 (m, 4H).

Example 124: 6'-fluoro-N-(isoxazol-5-ylmethyl)-4'-oxo-3',4'-dihydro-1'H-spiro[piperidine-4,2'-quinoline]-1-carboxamide

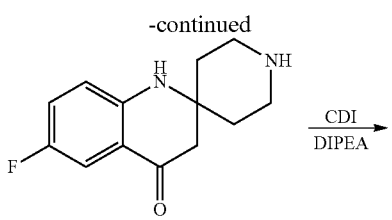

Intermediate 2

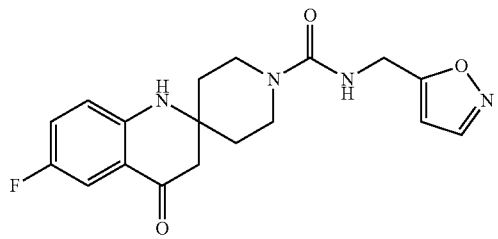

The title compound was prepared by a method similar to Example 1, using isoxazol-5-ylmethanamine instead of Intermediate 1. Intermediate 2 was HCl salt. The product was purified by HPLC (Formic acid, Method 3) to give the title compound as a yellow solid (65 mg, 66% yield). LCMS: m/z 359.5 (M+H); $^1$H NMR (400 MHz, Methanol-$d_4$) δ 8.28 (br s, 1H), 7.29 (dd, J=8, 4 Hz, 1H), 7.19-7.06 (m, 1H), 6.85 (dd, J=8, 4 Hz, 1H), 6.24 (br s, 1H), 4.47 (s, 2H), 3.60-3.40 (m, 4H), 2.66 (s, 2H), 1.84-1.63 (m, 4H).

Example 125: 6',8'-difluoro-N-((6-fluoropyridin-3-yl)methyl)-4'-oxo-3',4'-dihydro-1'H-spiro[piperidine-4,2'-quinoline]-1-carboxamide

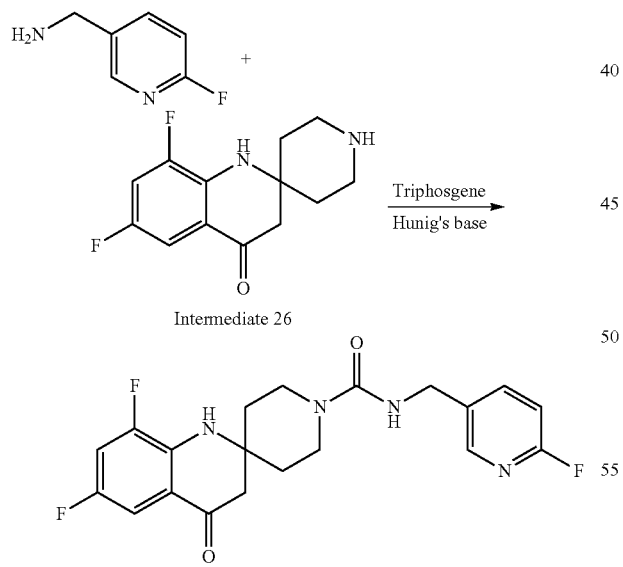

The title compound was prepared using a method similar to Example 2, using (6-fluoropyridin-3-yl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 405.2 (M+H).

Example 126: N-(5-amino-2,4-difluorobenzyl)-6'-fluoro-4'-oxo-3',4'-dihydro-1'H-spiro[piperidine-4,2'-quinoline]-1-carboxamide

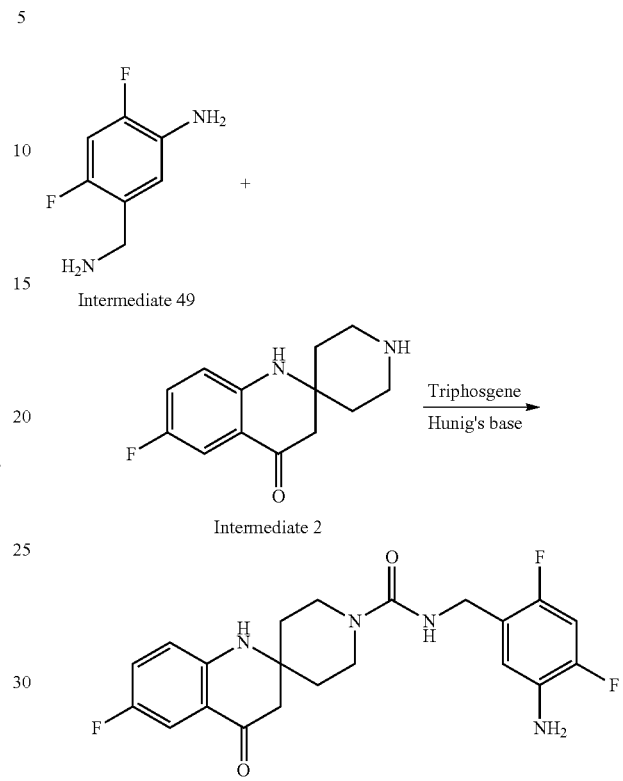

The title compound was prepared by a method similar to Example 2, using Intermediates 49 and 2 (free base) instead of (5-(aminomethyl)-2,4-difluoroaniline and Intermediate 3, respectively. The crude residue was purified by a preparative HPLC (Formic acid, Method 4) followed by a SFC (column: Princeton DEAP 20×150 mm 5 μm; mobile phase: MeOH) to give the title compound (33 mg, 1% yield) as a yellow solid after lyophilization. HRMS: m/z 419.1689 (M+H); $^1$H NMR (400 MHz, Methanol-$d_4$) δ 7.31 (dd, J=9.0, 3.1 Hz, 1H), 7.19-7.08 (m, 1H), 6.91-6.77 (m, 3H), 4.30 (s, 2H), 3.60-3.42 (m, 4H), 2.67 (s, 2H), 1.73 (tdt, J=13.2, 7.6, 4.4 Hz, 4H).

Example 127: 6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide

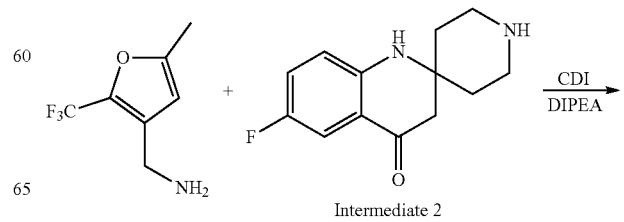

-continued

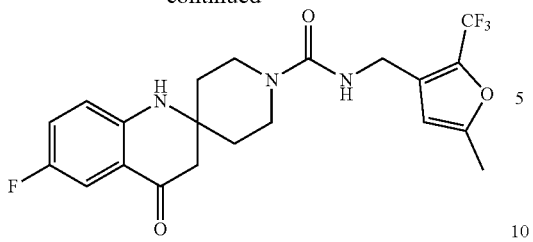

The title compound was prepared by a method similar to Example 1, using (5-methyl-2-(trifluoromethyl)furan-3-yl)methanamine instead of Intermediate 1. The product was purified by HPLC (Basic, Method 5) to give the title compound as a yellow solid (48 mg, 39% yield). LCMS: m/z 440.2 (M+H); $^1$H NMR (400 MHz, Methanol-$d_4$) δ 7.29 (dd, J=9.0, 3.1 Hz, 1H), 7.11 (ddd, J=9.2, 8.1, 3.1 Hz, 1H), 6.85 (dd, J=9.1, 4.3 Hz, 1H), 6.15 (d, J=1.4 Hz, 1H), 4.27 (q, J=1.6 Hz, 2H), 3.54-3.43 (m, 4H), 2.65 (s, 2H), 2.29 (t, J=1.1 Hz, 3H), 1.80-1.64 (m, 4H).

Example 128: 6'-fluoro-N-(4-fluoro-3-(prop-2-yn-1-ylcarbamoyl)benzyl)-4'-oxo-3',4'-dihydro-1'H-spiro[piperidine-4,2'-quinoline]-1-carboxamide

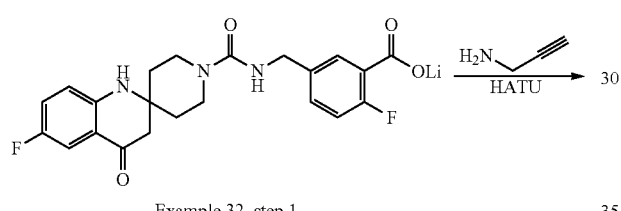

Example 32, step 1

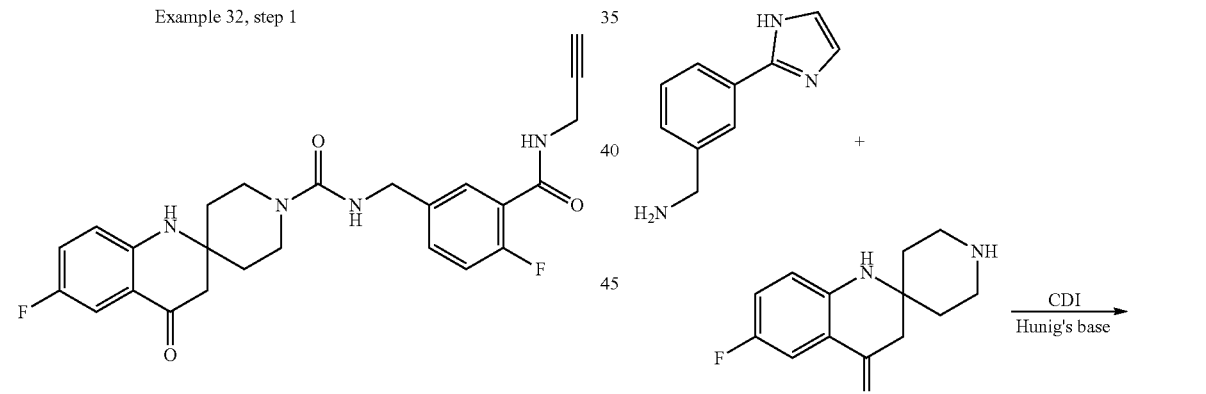

The title compound was prepared in a method similar to Example 32, step 2. The product was purified by reverse phase HPLC (Basic, Method 10) to give the title compound (3.9 mg, 16% yield) as a solid after lyophilization. LCMS: m/z 467.2 (M+H).

Example 129: 6',8'-difluoro-N-(3-(hydroxymethyl)benzyl)-4'-oxo-3',4'-dihydro-1'H-spiro[piperidine-4,2'-quinoline]-1-carboxamide

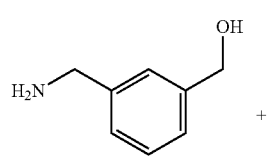

-continued

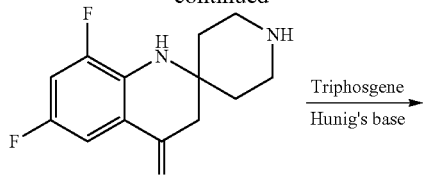

Intermediate 26

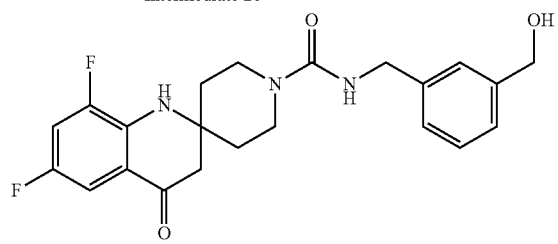

The title compound was prepared using a method similar to Example 2, using (3-(aminomethyl)phenyl)methanol and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 416.0 (M+H).

Example 130: N-(3-(1H-imidazol-2-yl)benzyl)-6'-fluoro-4'-oxo-3',4'-dihydro-1'H-spiro[piperidine-4,2'-quinoline]-1-carboxamide The title compound was prepared by a method similar to Example 1, using (3-(1H-imidazol-2-yl)phenyl)methanamine instead of Intermediate 1. Intermediate 2 was a free base. The crude residue was purified by a preparative reversed-phase HPLC (Basic, Method 3) to give the title compound (44 mg, 3% yield) as a fluffy yellow solid after lyophilization. HRMS: m/z 372.1728 (M+H); $^1$H NMR (400 MHz, Methanol-$d_4$) δ 7.80-7.76 (m, 1H), 7.71 (dt, J=7.7, 1.5 Hz, 1H), 7.40 (t, J=7.7 Hz, 1H), 7.35-7.26 (m, 2H), 7.17-7.07 (m, 3H), 6.85 (dd, J=9.1, 4.2 Hz, 1H), 4.41 (s, 2H), 3.61-3.48 (m, 4H), 2.66 (s, 2H), 1.83-1.66 (m, 4H).

Example 131: 6'-fluoro-N-(4-fluoro-3-(methylsulfonamido)benzyl)-4'-oxo-3',4'-dihydro-1'H-spiro[piperidine-4,2'-quinoline]-1-carboxamide

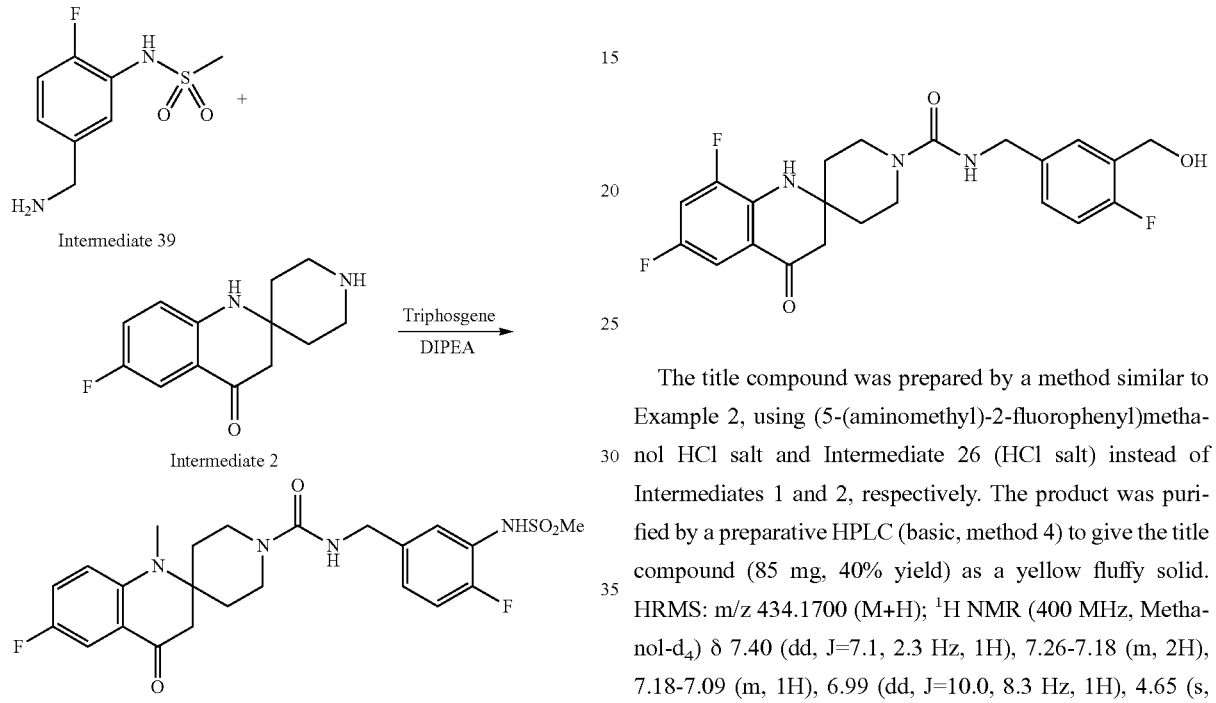

The title compound was prepared by a method similar to Example 2, using Intermediate 39 and Intermediate 2 instead of (4-fluoro-2-methoxyphenyl)methanamine and Intermediate 3, respectively. The product was purified by reversed-phase HPLC (Basic, Method 2) to give the title compound (23.5 mg, 21% yield) as a yellow solid. LCMS: m/z 479.3 (M+H); $^1$H NMR (400 MHz, Methanol-$d_4$) δ 7.44 (d, J=8 Hz, 1H), 7.30 (dd, J=8 Hz, 1H), 7.15-7.09 (m, 3H), 6.85 (dd, J=4 Hz, 1H), 4.32 (s, 2H), 3.51 (t, J=8 Hz, 4H), 2.99 (s, 3H), 2.68 (s, 2H), 1.79-1.70 (m, 4H).

Example 132: 6',8'-difluoro-N-(4-fluoro-3-(hydroxymethyl)benzyl)-4'-oxo-3',4'-dihydro-1'H-spiro[piperidine-4,2'-quinoline]-1-carboxamide

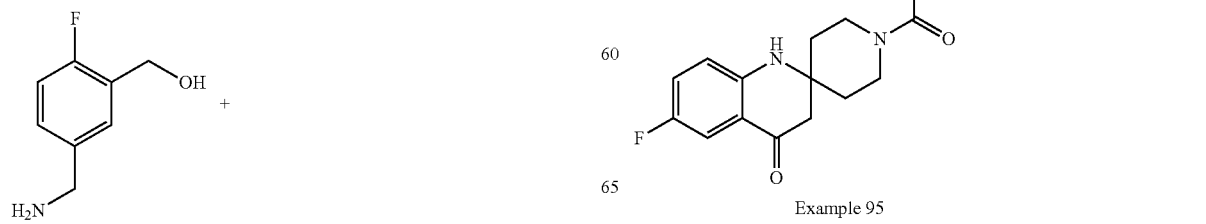

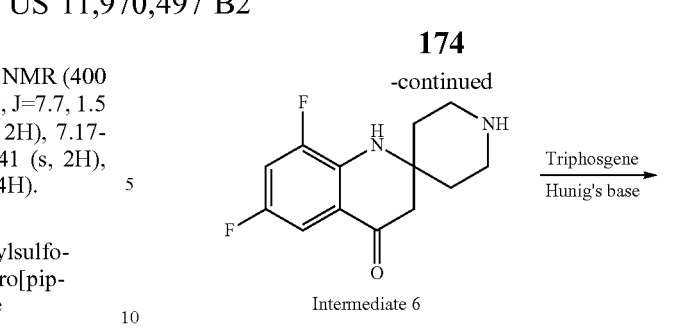

The title compound was prepared by a method similar to Example 2, using (5-(aminomethyl)-2-fluorophenyl)methanol HCl salt and Intermediate 26 (HCl salt) instead of Intermediates 1 and 2, respectively. The product was purified by a preparative HPLC (basic, method 4) to give the title compound (85 mg, 40% yield) as a yellow fluffy solid. HRMS: m/z 434.1700 (M+H); $^1$H NMR (400 MHz, Methanol-$d_4$) δ 7.40 (dd, J=7.1, 2.3 Hz, 1H), 7.26-7.18 (m, 2H), 7.18-7.09 (m, 1H), 6.99 (dd, J=10.0, 8.3 Hz, 1H), 4.65 (s, 2H), 4.33 (s, 2H), 3.73-3.63 (m, 2H), 3.40-3.32 (m, 2H), 2.79 (s, 2H), 1.86-1.72 (m, 4H).

Example 133: N-(3-(cyclopropanesulfonamido)-4-fluorobenzyl)-6'-fluoro-4'-oxo-3',4'-dihydro-1'H-spiro[piperidine-4,2'-quinoline]-1-carboxamide

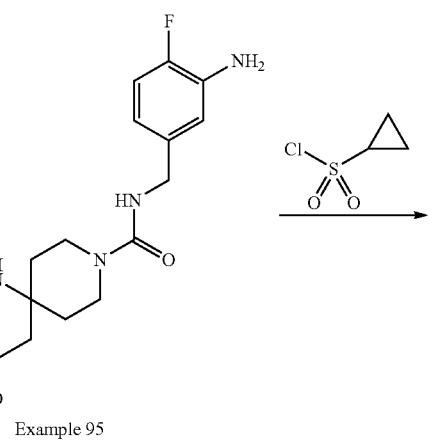

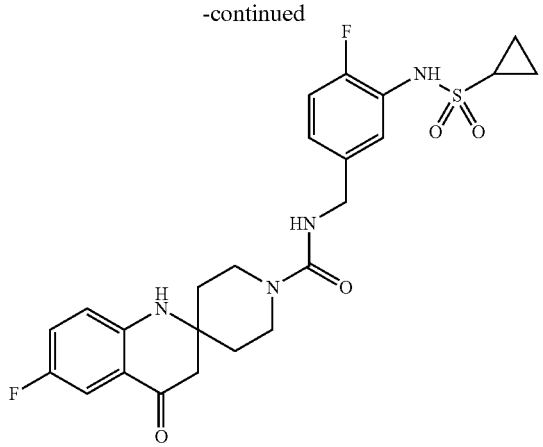

To a stirred solution of Example 95 (35 mg, 0.087 mmol) in THF (874 µL) was added K$_2$CO$_3$ (18.12 mg, 0.131 mmol) followed by cyclopropanesulfonyl chloride (8.9 µL, 0.087 mmol). The reaction mixture was stirred at RT. After 3 h, additional cyclopropanesulfonyl chloride (26.7 µL, 0.261 mmol) and K$_2$CO$_3$ (54.36 mg, 0.393 mmol) were added. Overnight revealed no consumption of SM, so the reaction was then filtered to remove K$_2$CO$_3$, concentrated and reconstituted in DCM:pyridine (900 µL, 1:1 v/v ratio). The reaction was heated to 50° C. and allowed to stir for 5 h. The material was concentrated to a gummy oil, re-suspended in DMSO and purified by HPLC (Basic, Method 2), followed by SFC (column: Phenomenex Kinetex Biphenyl, 21.2×150 mm 5 µm; mobile phase: MeOH) to afford the title compound as a yellow solid. (7.7 mg, 17% yield). LCMS: m/z 503.1 (M−H); $^1$H NMR (400 MHz, Methanol-d$_4$) δ 7.46 (d, J=8.2 Hz, 1H), 7.29 (dd, J=9.0, 3.0 Hz, 1H), 7.15-7.09 (m, 3H), 6.85 (dd, J=9.1, 4.3 Hz, 1H), 4.32 (s, 2H), 3.52 (t, J=5.7 Hz, 5H), 2.68 (s, 2H), 2.57 (ddd, J=12.9, 8.0, 4.8 Hz, 1H), 1.75 (h, J=8.0, 7.5 Hz, 4H), 1.05-0.99 (m, 2H), 0.99-0.89 (m, 2H).

Example 134: 6'-fluoro-N-((3-methyl-1,2,4-oxadiazol-5-yl)methyl)-4'-oxo-3',4'-dihydro-1'H-spiro[piperidine-4,2'-quinoline]-1-carboxamide

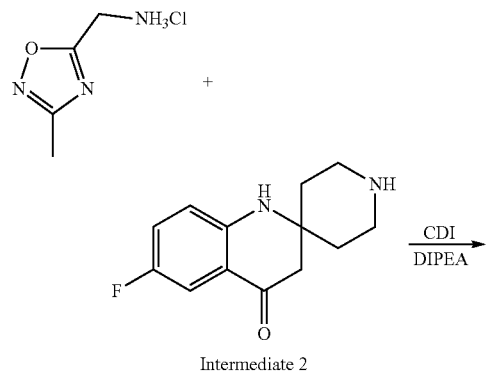

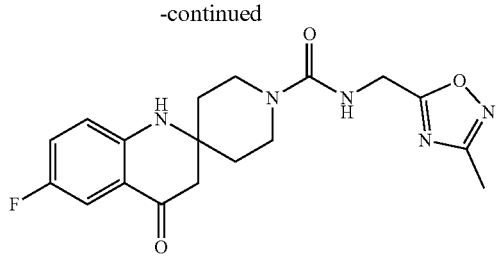

The title compound was prepared by a method similar to Example 1, using (3-methyl-1,2,4-oxadiazol-5-yl)methylamine hydrochloride instead of Intermediate 1. Intermediate 2 was HCl salt. The product was purified by silica gel chromatography (MeOH/DCM) followed by reversed-phase HPLC (Formic acid, Method 3) to give the title compound (32 mg, 36% yield) as a yellow solid after lyophilization. LCMS: m/z 374.4 (M+H); $^1$H NMR (400 MHz, DMSO-d$_6$) δ 7.39 (t, J=5.5 Hz, 1H), 7.27-7.17 (m, 2H), 6.91 (ddd, J=8.4, 4.5, 1.2 Hz, 1H), 6.83 (s, 1H), 4.41 (d, J=5.5 Hz, 2H), 3.53-3.21 (m, 4H), 2.61 (s, 2H), 2.30 (s, 3H), 1.72-1.47 (m, 4H).

Example 135: 6'-fluoro-N-(4-fluoro-3-(1-hydroxyethyl)benzyl)-4'-oxo-3',4'-dihydro-1'H-spiro[piperidine-4,2'-quinoline]-1-carboxamide

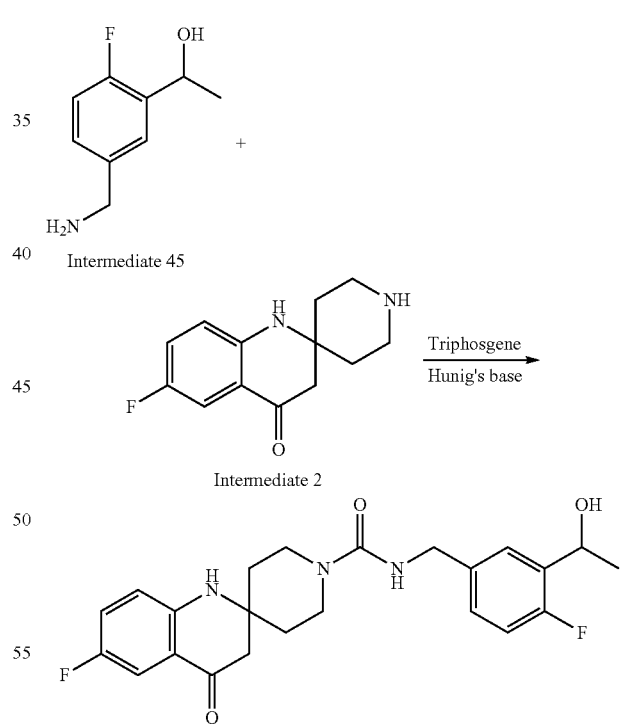

The title compound was prepared by a method similar to Example 2, using Intermediates 45 and 2 (free base) instead of (4-fluoro-2-methoxyphenyl)methanamine and Intermediate 3, respectively. The crude residue was purified by a preparative HPLC (Basic, Method 4) to give the title compound (65 mg, 48% yield) as a fluffy yellow solid after lyophilization. LCMS: m/z 412.3 (M-OH); $^1$H NMR (400 MHz, Methanol-d$_4$) δ 7.46 (d, J=7.2 Hz, 1H), 7.30 (dd, J=9.0, 3.0 Hz, 1H), 7.21-7.08 (m, 2H), 7.02-6.92 (m, 1H), 6.86 (dd, J=9.1, 4.3 Hz, 1H), 5.11 (q, J=6.5 Hz, 1H), 4.34 (s, 2H), 3.59-3.48 (m, 4H), 2.67 (s, 2H), 1.82-1.67 (m, 4H), 1.43 (d, J=6.5 Hz, 3H).

Example 136: N-((6-aminopyridin-3-yl)methyl)-6'-fluoro-4'-oxo-3',4'-dihydro-1'H-spiro[piperidine-4,2'-quinoline]-1-carboxamide

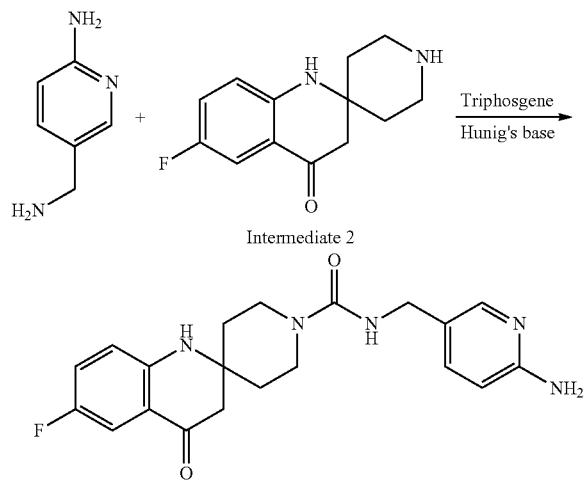

The title compound was prepared by a method similar to Example 1, using 5-(aminomethyl)pyridin-2-amine instead of Intermediate 1. Intermediate 2 was a free base. The crude residue was purified by a preparative reversed-phase HPLC (Basic, Method 2) to give the title compound (75 mg, 62% yield) as a fluffy yellow solid after lyophilization. LCMS: m/z 384.2 (M+H); $^1$H NMR (400 MHz, Methanol-$d_4$) δ 7.81 (d, J=2.3 Hz, 1H), 7.43 (dd, J=8.7, 2.4 Hz, 1H), 7.29 (dd, J=9.0, 3.1 Hz, 1H), 7.16-7.06 (m, 1H), 6.84 (dd, J=9.1, 4.3 Hz, 1H), 6.54 (d, J=8.5 Hz, 1H), 4.17 (s, 2H), 3.56-3.38 (m, 4H), 2.64 (s, 2H), 1.81-1.62 (m, 4H).

Example 137: N-(2-amino-4-fluorobenzyl)-6'-fluoro-4'-oxo-3',4'-dihydro-1'H-spiro[piperidine-4,2'-quinoline]-1-carboxamide

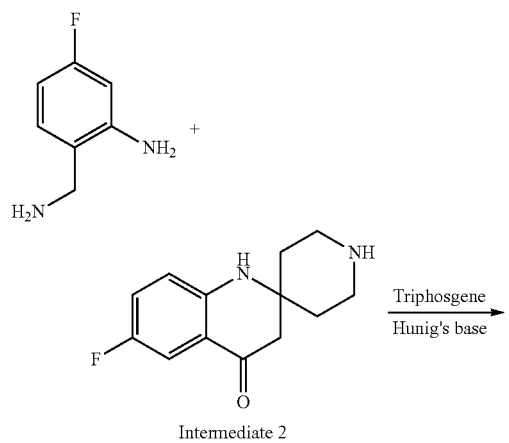

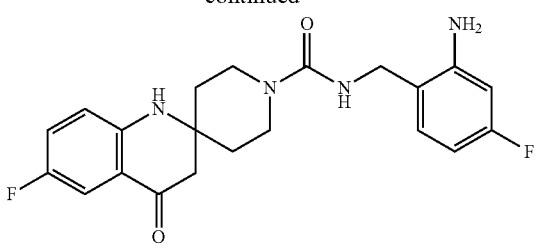

The title compound was prepared by a method similar to Example 2, using 2-(aminomethyl)-5-fluoroaniline and Intermediate 2 (HCl salt) instead of (4-fluoro-2-methoxyphenyl)methanamine, and Intermediate 3, respectively. The crude residue was purified by SFC (column: Princeton DEAP 20×150 mm 5 μm; mobile phase: MeOH) to give the title compound (29 mg, 9% yield) as yellow solid after concentration in vacuo. LCMS: m/z 401.1 (M+H); $^1$H NMR (400 MHz, Methanol-$d_4$) δ 7.46 (d, J=7.2 Hz, 1H), 7.30 (dd, J=9.0, 3.0 Hz, 1H), 7.21-7.08 (m, 2H), 7.02-6.92 (m, 1H), 6.86 (dd, J=9.1, 4.3 Hz, 1H), 5.11 (q, J=6.5 Hz, 1H), 4.34 (s, 2H), 3.59-3.48 (m, 4H), 2.67 (s, 2H), 1.82-1.67 (m, 4H), 1.43 (d, J=6.5 Hz, 3H).

Example 138: 6'-fluoro-N-(oxazol-4-ylmethyl)-4'-oxo-3',4'-dihydro-1'H-spiro[piperidine4,2'-quinoline]-1-carboxamide

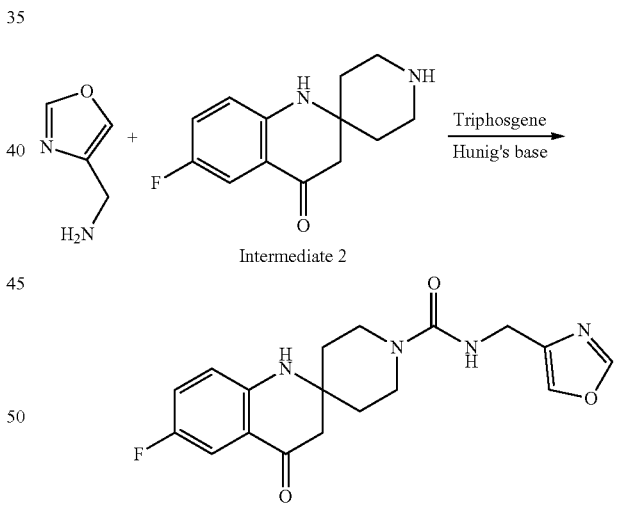

The title compound was prepared by a method similar to Example 2, using oxazol-4-ylmethanamine and Intermediate 2 (HCl salt) instead of (4-fluoro-2-methoxyphenyl)methanamine and Intermediate 3, respectively. The product was purified by preparative TLC (DCM/MeOH=90/10) to give the title compound (85 mg, 48% yield) as a yellow solid. LCMS: m/z 358.95 (M+H); $^1$H NMR (400 MHz, DMSO-$d_6$) δ: 8.24 (1H, s), 7.78 (1H, m), 7.21-7.16 (2H, m), 6.95-6.92 (1H, m), 6.88-6.85 (1H, m), 6.76 (1H, s), 4.08-4.07 (2H, d), 3.39-3.35 (4H, m), 2.57 (2H, s), 1.57-1.50 (4H, m).

Example 139: 6'-fluoro-N-(4-fluoro-3-(2-hydroxy-propan-2-yl)benzyl)-1'-methyl-4'-oxo-3',4'-dihydro-1'H-spiro[piperidine-4,2'-quinoline]-1-carboxamide

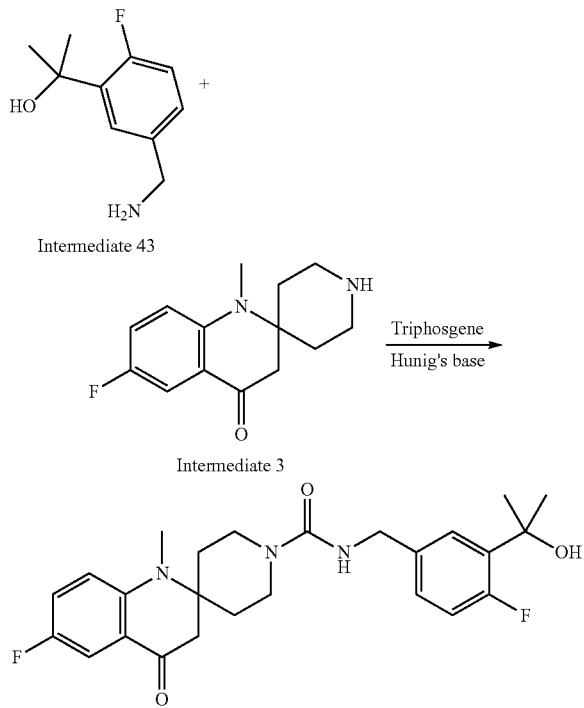

The title compound was prepared by a method similar to Example 2, using Intermediate 43 instead of (4-fluoro-2-methoxyphenyl)methanamine. The product was purified by preparative HPLC (column: Gemini NX 5μ C18 21.2 mm×150 mm; mobile phase: 0.01% ammonium hydroxide in water/ACN) to give the title compound (35 mg, 19% yield) as a yellow solid. LCMS: m/z 458.1 (M+H−18); $^1$H NMR (400 MHz, MeOH-d) δ: 7.54-7.52 (1H, m), 7.42-7.39 (1H, m), 7.23-7.26 (1H, m), 7.14-(1H, m), 6.96-6.91 (2H, m), 4.31-4.30 (2H, m), 3.95-3.92 (2H, m), 3.07-3.01 (2H, t), 3.04-2.91 (5H, m), 1.92-1.97 (2H, m), 1.71-1.53 (2H, d), 1.68-1.53 (6H, s).

Example 140: 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoic acid

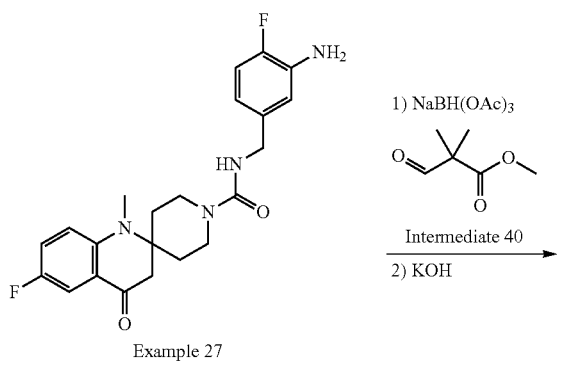

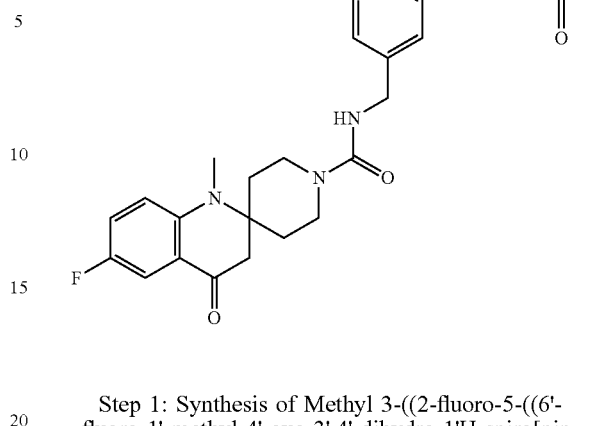

Step 1: Synthesis of Methyl 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoate A mixture of compound Example 27 (153 mg, 0.369 mmol), Intermediate 40 (crude material) and NaBH(OAc)$_3$ (120 mg, 0.566 mmol) in DCM (5 mL) was stirred at RT for 24 h, partitioned between DCM and aqueous NH$_4$Cl solution. The combined organic extract was dried over MgSO$_4$, concentrated and purified by silica gel column chromatography (EtOAc) to give the title compound. LCMS: m/z 529.3 (M+H).

Step 2: Synthesis of 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoic acid Aqueous KOH (KOH 150 mg, 2.67 mmol dissolved in 2 mL of water) was added to a solution of the product in Step 1 in methanol (2 mL). The mixture was heated at 60° C. for 2 h, cooled to RT and partitioned between EtOAc and aqueous 1M HCl. The combined organic extract was dried over MgSO$_4$, concentrated and purified by reverse-phase HPLC (Formic acid, Method 5) to give the title compound as a yellow solid (17 mg, 9% yield over 2 steps). LCMS: m/z 515.4 (M+H); $^1$H NMR (400 MHz, Methanol-d$_4$) δ 7.42 (dd, J=8.6, 3.2 Hz, 1H), 7.27-7.21 (m, 1H), 6.93 (dd, J=9.4, 4.0 Hz, 1H), 6.85 (dd, J=11.7, 8.2 Hz, 1H), 6.78 (dd, J=8.4, 1.6 Hz, 1H), 6.53-6.46 (m, 1H), 4.24 (s, 2H), 4.00-3.90 (m, 2H), 3.28 (s, 2H), 3.11-2.99 (m, 2H), 2.93 (s, 3H), 2.92 (s, 2H), 1.91 (td, J=12.5, 4.2 Hz, 2H), 1.76-1.65 (m, 2H), 1.24 (s, 6H).

Example 141: N-(benzo[c][1,2,5]oxadiazol-4-ylmethyl)-6'-fluoro-4'-oxo-3',4'-dihydro-1'H-spiro[piperidine-4,2'-quinoline]-1-carboxamide

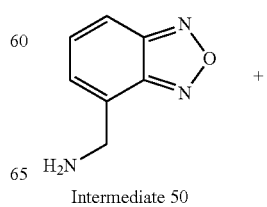

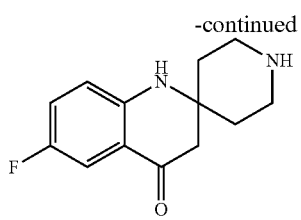

Intermediate 2

→ Triphosgene, Hunig's base

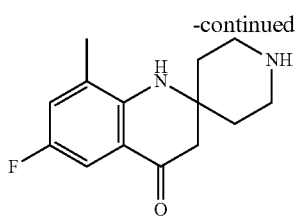

Intermediate 44

→ Triphosgene, Hunig's base

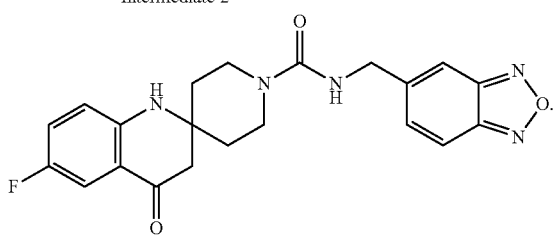

The title compound was prepared by a method similar to Example 2, using Intermediates 50 and 2 (HCl salt) instead of (4-fluoro-2-methoxyphenyl)methanamine and Intermediate 3, respectively. The crude residue was purified by a preparative HPLC to give the title compound (18 mg, 12% yield) as a yellow solid after lyophilization. LCMS: m/z 410.0 (M+H); $^1$H NMR (300 MHz, CDCl$_3$) δ 7.46 7.92-7.89 (1H, d), 7.62-7.51 (1H, m), 7.34-7.20 (4H, m), 6.94-6.90 (1H, m), 6.83 (1H, s), 4.61-4.59 (2H, d), 3.51-3.34 (4H, m), 1.61 (4H, m)

Example 142: N-(3-carbamoyl-4-fluorobenzyl)-6'-fluoro-8'-methyl-4'-oxo-3',4'-dihydro-1'H-spiro[piperidine4,2'-quinoline]-1-carboxamide

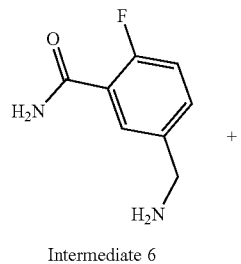

Intermediate 6

The title compound was prepared by a method similar to Example 2, using Intermediates 6 and 44 instead of (4-fluoro-2-methoxyphenyl)methanamine and Intermediate 3, respectively. The product was purified by preparative TLC (DCM/MeOH=90/10) to give the title compound (18 mg, 10% yield) as a yellow solid. LCMS: m/z 442.95 (M+H); $^1$H NMR (400 MHz, DMSO-d$_6$) δ: 7.65 (bs, 1H), 7.56-7.54 (m, 1H), 7.37 (m, 1H), 7.22-7.10 (m, 3H), 5.52 (m, 1H), 4.22-4.21 (d, 2H), 3.65-3.63 (m, 1H), 3.12 (m, 1H), 2.72 (s, 1H), 2.17 (s, 2H), 1.71-1.66 (m, 3H).

Example 143: 6'-fluoro-N-(4-fluoro-3-(propylcarbamoyl)benzyl)-4'-oxo-3',4'-dihydro-1'H-spiro[piperidine-4,2'-quinoline]-1-carboxamide

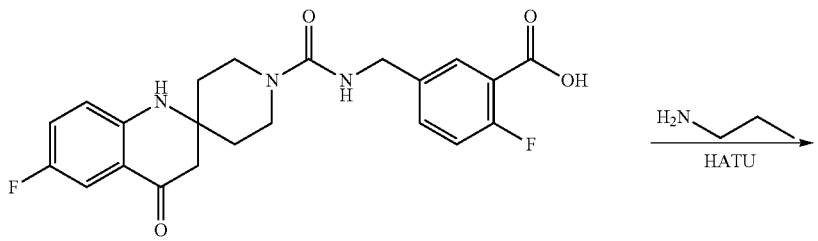

Example 32, Step 1

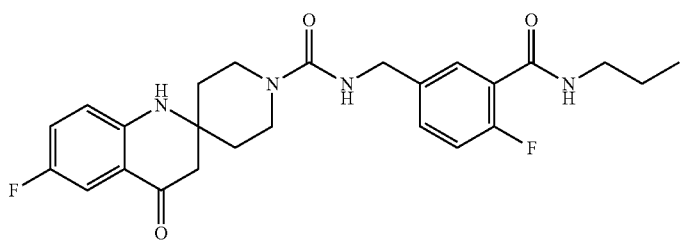

The title compound was prepared by a method similar to Example 32, step 2, using propyl amine instead of (4-(aminomethyl)phenyl)methanol. The product was purified by reverse phase HPLC (Basic, Method 4) to give the title compound (33 mg, 41% yield) as a yellow solid. LCMS: m/z 471.3 (M+H); $^1$H NMR (400 MHz, DMSO-$d_6$) δ 8.25 (q, J=5.2 Hz, 1H), 7.47 (dd, J=6.9, 2.3 Hz, 1H), 7.36 (ddd, J=7.6, 4.9, 2.4 Hz, 1H), 7.31-7.11 (m, 4H), 6.98-6.86 (m, 1H), 6.79 (s, 1H), 4.21 (d, J=5.7 Hz, 2H), 3.49-3.33 (m, 4H), 3.20 (q, J=6.9 Hz, 2H), 2.61 (s, 2H), 1.67-1.42 (m, 6H), 0.89 (t, J=7.4 Hz, 3H).

Example 144: N-(3-(1H-1,2,4-triazol-1-yl)benzyl)-6',8'-difluoro-4'-oxo-3',4'-dihydro-1'H-spiro[piperidine-4,2'-quinoline]-1-carboxamide

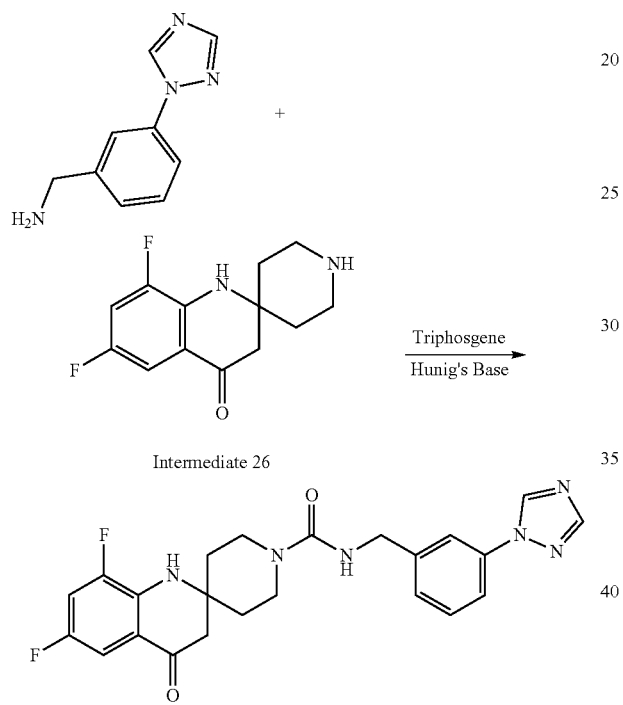

The title compound was prepared using a method similar to Example 2, (3-(1H-1,2,4-triazol-1-yl)phenyl)methanamine and intermediate 26 instead of (4-fluoro-2-methoxyphenyl)methanamine) and intermediate 3, respectively. The crude residue was purified by preparative HPLC (Formic acid, Method 10) to give the title compound. LCMS: m/z 453.2 (M+H).

Example 145: 6'-fluoro-N-((1-methyl-1H-pyrazol-4-yl)methyl)-4'-oxo-3',4'-dihydro-1'H-spiro[piperidine-4,2'-quinoline]-1-carboxamide

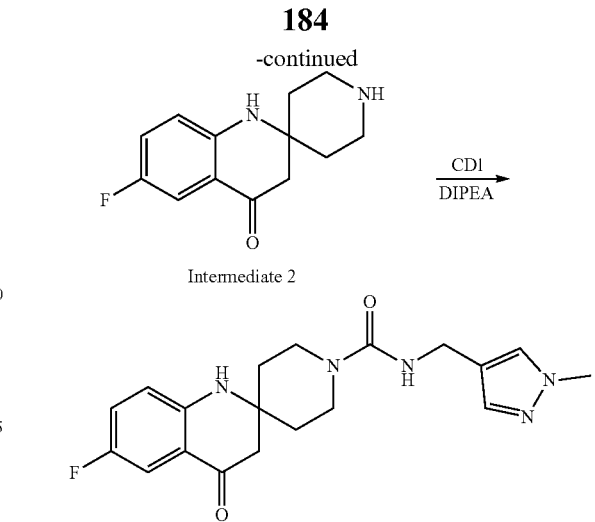

The title compound was prepared by a method similar to Example 1, using (1-methyl-1H-pyrazol-4-yl)methylamine instead of Intermediate 1. Intermediate 2 was HCl salt. The product was purified by silica gel chromatography (MeOH/DCM) followed by reversed-phase HPLC (Basic, Method 3) to give the title compound (26 mg, 39% yield) as a white solid after lyophilization. LCMS: m/z 372.4 (M+H); $^1$H NMR (400 MHz, DMSO-$d_6$) δ 7.49 (s, 1H), 7.26 (s, 1H), 7.25-7.18 (m, 2H), 6.95-6.86 (m, 1H), 6.86-6.75 (m, 2H), 4.02 (d, J=5.4 Hz, 2H), 3.76 (s, 3H), 3.49-3.21 (m, 4H), 2.60 (s, 2H), 1.65-1.42 (m, 4H).

Example 146: 6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide

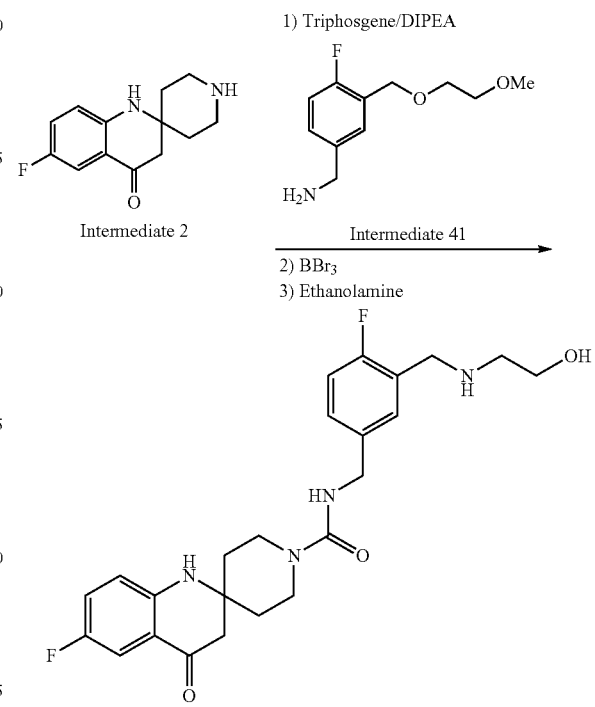

Step 1: Synthesis of 6'-fluoro-N-(4-fluoro-3-((2-methoxyethoxy)methyl)benzyl)-4'-oxo-3',4'-dihydro-1'H-spiro[piperidine-4,2'-quinoline]-1-carboxamide The title compound was prepared by a method similar to Example 2, using Intermediate 41 and Intermediate 2 instead of (4-fluoro-2-methoxyphenyl)methanamine and Intermediate 3, respectively. The product was purified by reversed-phase HPLC (Basic, Method 4) to give the title compound (38 mg, 18% yield) as a yellow solid. LCMS: m/z 474.2 (M+H).

Step 2: Synthesis of N-(3-(bromomethyl)-4-fluorobenzyl)-6'-fluoro-4'-oxo-3',4'-dihydro-1'H-spiro[piperidine-4,2'-quinoline]-1-carboxamide The title compound was prepared by a method similar to Example 70, Step 2. The product was purified by reversed-phase HPLC (Basic, Method 5) to give the title compound (38 mg, 99% yield) as a yellow solid. LCMS: m/z 479.2 (M+H).

Step 3: Synthesis of 6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide To a solution of the product in Step 2 (38 mg, 0.079 mmol) in acetonitrile (397 μL) was added ethanolamine (14 μL, 0.24 mmol). The reaction mixture was stirred at RT for 3 h. The reaction was quenched with brine and extracted with DCM (2×5 mL). The organic layers were dried over sodium sulfate and concentrated under reduced pressure. The residue was then purified by HPLC (Basic, Method 5) to afford the title compound as a white solid (15 mg, 40.8% yield). LCMS: m/z 459.1 (M+H); $^1$H NMR (400 MHz, Methanol-$d_4$) δ 7.28-7.21 (m, 2H), 7.16 (ddd, J=7.5, 5.0, 2.3 Hz, 1H), 7.05 (ddd, J=9.0, 8.2, 3.1 Hz, 1H), 6.96 (dd, J=9.9, 8.5 Hz, 1H), 6.78 (dd, J=9.1, 4.3 Hz, 1H), 4.25 (s, 2H), 3.77 (s, 2H), 3.64-3.58 (m, 2H), 3.49-3.38 (m, 4H), 2.67 (t, J=5.5 Hz, 2H), 2.59 (s, 2H), 1.75-1.58 (m, 4H).

Example 147: 6'-fluoro-N-(4-fluoro-3-(sulfamoylmethyl)benzyl)-4'-oxo-3',4'-dihydro-1'H-spiro[piperidine-4,2'-quinoline]-1-carboxamide

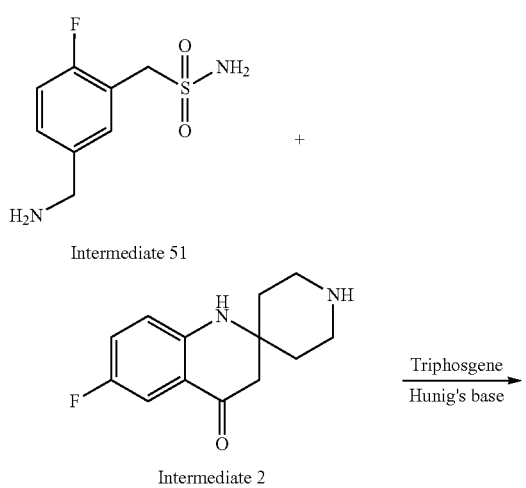

Intermediate 51

+

Intermediate 2

Triphosgene, Hunig's base

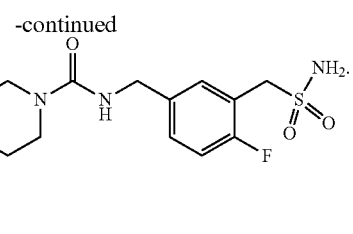

The title compound was prepared by a method similar to Example 2, using Intermediate 51 and Intermediate 2 (free base) instead of (4-fluoro-2-methoxyphenyl)methanamine and Intermediate 3, respectively. The crude residue was purified by a preparative HPLC (Basic, Method 4) to give the title compound (85 mg, 34% yield) as yellow solid after concentration in vacuo. LCMS: m/z 479.1 (M+H); $^1$H NMR (400 MHz, Methanol-$d_4$) δ 7.51-7.38 (m, 1H), 7.34-7.26 (m, 2H), 7.18-7.05 (m, 2H), 6.94-6.79 (m, 1H), 4.40 (s, 2H), 4.33 (s, 2H), 3.56-3.46 (m, 4H), 2.69 (s, 2H), 1.79-1.70 (m, 4H).

Example 148: 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)propanoic acid

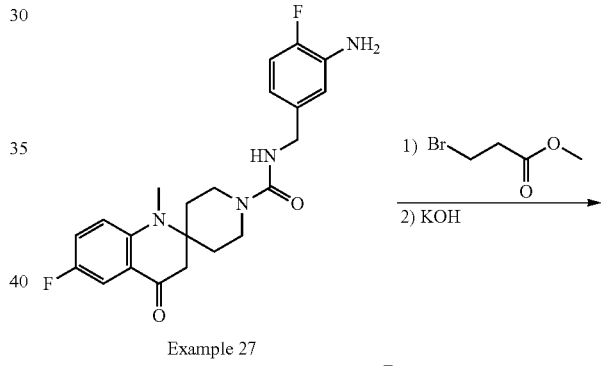

Example 27

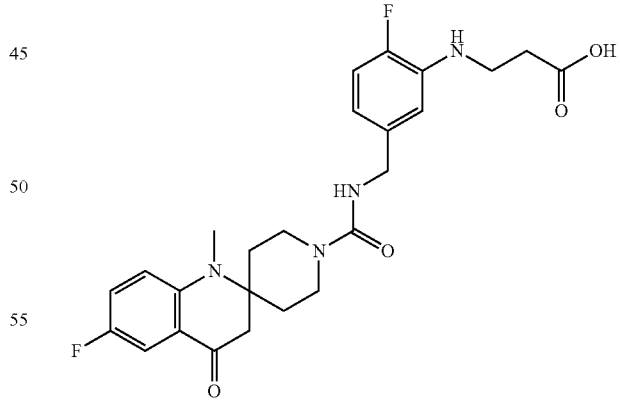

Step 1: Synthesis of Ethyl 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)propanoate A mixture of Example 27 (110 mg, 0.265 mmol), ethyl 3-bromopropionate (250 mg, 1.381 mmol) and potassium carbonate (120 mg, 0.868 mmol) in DMF (3 mL) was heated at 90° C. for 16 h, cooled to RT and partitioned between EtOAc and brine. The combined organic extract was dried over MgSO$_4$ and concentrated. The residual crude product was used directly in the next step. LCMS: m/z 515.4 (M+H).

Step 2: Synthesis of 3-((2-fluoro-5-(((6'-fluoro-1'-methyl-4'-oxo-3',4'-dihydro-1'H-spiro[piperidine-4,2'-quinoline]-1-carboxamido)methyl)phenyl)amino)propanoic acid A solution of potassium hydroxide (520 mg, 9.27 mmol) in water (2 mL) was added to a solution of the product in Step 1 in MeOH (2 mL). The mixture was stirred at RT for 30 min, and most of MeOH was removed in vacuo. The crude reaction mixture was partitioned between EtOAc and aqueous 0.5M HCl. The combined organic extract was dried over MgSO$_4$, concentrated, and purified by reverse-phase HPLC (Formic acid, Method 4) to give the title compound as a yellow solid (8 mg, 6% yield over 2 steps). LCMS: m/z 487.3 (M+H); $^1$H NMR (400 MHz, Methanol-d$_4$) δ 7.45 (dd, J=8.7, 3.2 Hz, 1H), 7.27-7.25 (m, 1H), 6.96 (dd, J=9.4, 4.1 Hz, 1H), 6.88 (dd, J=11.7, 8.2 Hz, 1H), 6.75 (dd, J=8.4, 2.0 Hz, 1H), 6.59-6.50 (m, 1H), 4.28 (s, 2H), 4.04-3.91 (m, 2H), 3.46 (t, J=6.8 Hz, 2H), 3.13-3.04 (m, 2H), 2.96 (s, 3H), 2.95 (s, 2H), 2.62 (t, J=6.8 Hz, 2H), 1.95 (td, J=13.1, 4.6 Hz, 2H), 1.79-1.68 (m, 2H).

Example 149: (R)—N-(3-(1-amino-2,2,2-trifluoroethyl)-4-fluorobenzyl)-6'-fluoro-1'-methyl-4'-oxo-3',4'-dihydro-1'H-spiro[piperidine-4,2'-quinoline]-1-carboxamide

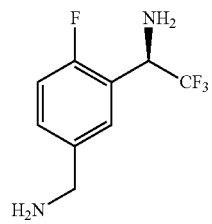

Intermediate 46

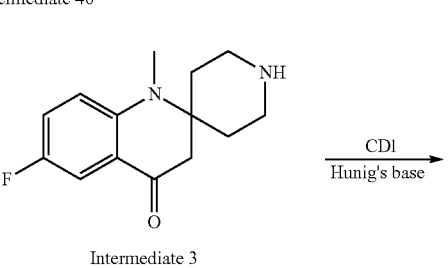

Intermediate 3

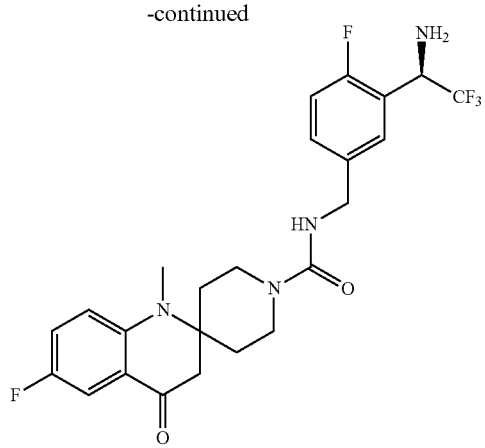

The title compound was prepared by a method similar to Example 1, using Intermediate 46 and Intermediate 3 instead of Intermediates 1 and 2, respectively. The crude residue was purified by a preparative reversed-phase HPLC (Basic, Method 4) to give the title compound (94 mg, 58% yield) as a fluffy yellow solid after lyophilization. LCMS: m/z 497.3 (M+H); $^1$H NMR (400 MHz, Methanol-d$_4$) δ 7.56-7.50 (m, 1H), 7.44 (dd, J=8.7, 3.2 Hz, 1H), 7.39-7.30 (m, 1H), 7.30-7.20 (m, 1H), 7.14-7.05 (m, 1H), 6.95 (dd, J=9.3, 4.0 Hz, 1H), 4.77 (q, J=7.6 Hz, 1H), 4.35 (s, 2H), 4.01-3.91 (m, 2H), 3.13-3.01 (m, 2H), 2.95 (s, 3H), 2.94 (s, 2H), 2.00-1.88 (m, 2H), 1.77-1.68 (m, 2H).

Example 150: N-(4-(difluoromethoxy)benzyl)-6',8'-difluoro-4'-oxo-3',4'-dihydro-1'H-spiro[piperidine-4,2'-quinoline]-1-carboxamide

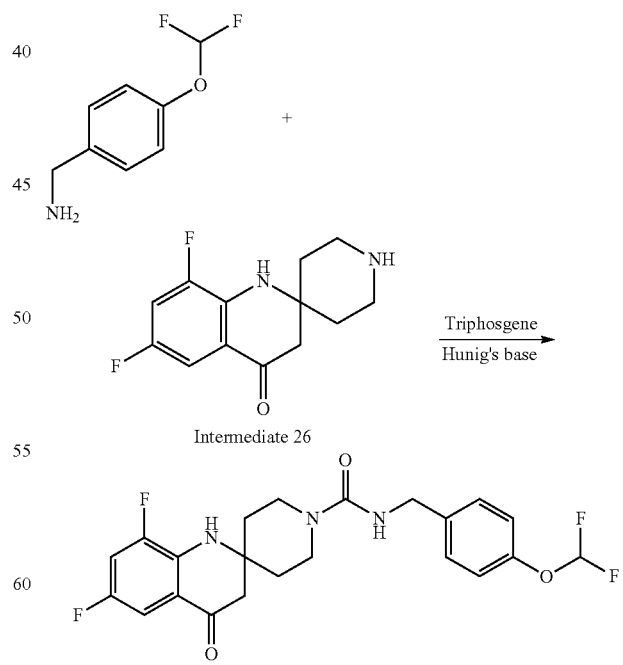

The title compound was prepared using a method similar to Example 2, ((4-(difluoromethoxy)phenyl)methanamine and intermediate 26 instead of (4-fluoro-2-methoxyphenyl)

methanamine) and intermediate 3, respectively. The crude residue was purified by preparative HPLC (Formic acid, Method 10) to give the title compound. LCMS: m/z 452.2 (M+H); $^1$H NMR (400 MHz, Methanol-d$_4$) δ 7.34-7.32 (d, J=8 Hz, 2H), 7.23-7.21 (d, J=8 Hz, 1H), 7.15-7.08 (m, 3H), 6.97 (s, 1H), 4.37-4.34 (s, 2H), 3.73-3.67 (m, 2H), 3.39-3.30 (m, 2H), 2.81 (s, 2H), 1.84-1.77 (m, 4H).

Example 151a: (R)-6'-fluoro-N-(4-fluorobenzyl)-4'-hydroxy-1'-methyl-3',4'-dihydro-1'H-spiro[piperidine-4,2'-quinoline]-1-carboxamide Example 151b: (S)-6'-fluoro-N-(4-fluorobenzyl)-4'-hydroxy-1'-methyl-3',4'-dihydro-1'H-spiro[piperidine-4,2'-quinoline]-1-carboxamide

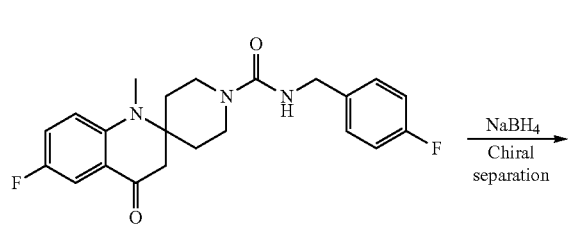

Example 9

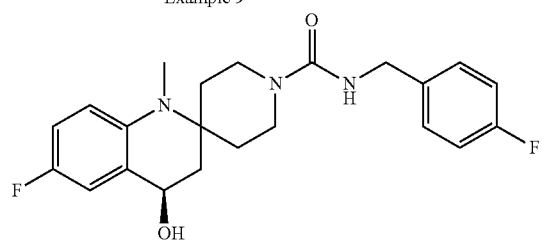

Exemple 151a

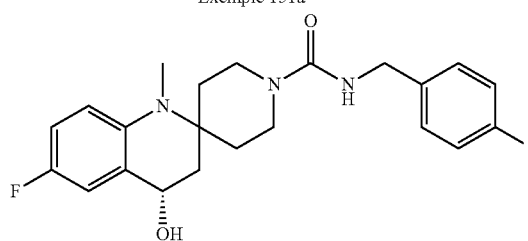

Exemple 151b

The title compounds were prepared by a method similar to Example 152 and Example 153, using Example 9 instead of Example 40. The product was purified by preparative chiral SFC to afford example 151a (49 mg, 21% yield, peak 2 in chiral SFC separation R.t.=4.8 min) and example 151b (52 mg, 22% yield, peak 1 in chiral SFC separation R.t.=3.1 min) as white solids.

Example 151a: LCMS: m/z 402.3 (M+H); $^1$H NMR (400 MHz, MeOH-d$_4$) δ 7.39-7.23 (m, 2H), 7.13-6.96 (m, 3H), 6.84 (td, J=8.6, 3.1 Hz, 1H), 6.64 (dd, J=9.0, 4.5 Hz, 1H), 4.63 (dd, J=10.0, 5.0 Hz, 1H), 4.33 (s, 2H), 4.02-3.84 (m, 2H), 3.24-3.01 (m, 2H), 2.76 (s, 3H), 2.48 (dd, J=13.1, 5.1 Hz, 1H), 2.09-1.85 (m, 2H), 1.72-1.37 (m, 3H).

Example 151b: LCMS: m/z 384.3 (M+H-H$_2$O); 1H NMR (400 MHz, DMSO-d$_6$) δ 7.33-7.25 (m, 2H), 7.18-7.09 (m, 3H), 7.04 (dd, J=9.4, 2.5 Hz, 1H), 6.87 (td, J=8.7, 3.2 Hz, 1H), 6.54 (dd, J=9.0, 4.6 Hz, 1H), 5.39 (d, J=5.9 Hz, 1H), 4.48 (dt, J=10.4, 5.2 Hz, 1H), 4.21 (d, J=5.7 Hz, 2H), 3.91 (d, J=13.7 Hz, 2H), 2.91 (dt, J=39.7, 11.9 Hz, 2H), 2.67 (s, 3H), 2.48-2.43 (m, 1H), 1.81 (dtd, J=57.6, 12.7, 4.5 Hz, 2H), 1.38 (dd, J=64.9, 12.8 Hz, 3H).

Chirality of example 151a was determined by co-crystal structure with KARS.

Example 152: (R)-6'-fluoro-N-(4-fluorobenzyl)-4'-hydroxy-3',4'-dihydro-1'H-spiro[piperidine-4,2'-quinoline]-1-carboxamide and Example 153: (S)-6'-fluoro-N-(4-fluorobenzyl)-4'-hydroxy-3',4'-dihydro-1'H-spiro[piperidine-4,2'-quinoline]-1-carboxamide To a stirred solution of Example 40 (80 mg, 0.208 mmol) in ethanol (5 mL) was added sodium borohydride (20 mg, 0.519 mmol) portion-wise at room temperature. The reaction mixture was stirred at RT overnight then diluted with water (30 mL) and extracted with EtOAc (2×20 mL). The solvent was evaporated and the residue obtained was purified by preparative HPLC (Basic, Method 4). The desired fractions were combined and lyophilized to give the racemic mixture of (R) and (S) alcohols as a white solid. The racemic mixture was then separated by chiral SFC to afford example 152 (17.5 mg, 21% yield, peak 2 in chiral SFC separation R.t.=3.62 min) and example 153 (8.5 mg, 10% yield, peak 1 in chiral SFC separation R.t.=2.40 min) as white solids.

Example 152: LCMS: m/z 370.2 (M+H−18); $^1$H NMR (400 MHz, DMSO-d$_6$) δ 7.27 (ddd, J=8.5, 5.4, 2.4 Hz, 2H), 7.16-7.08 (m, 3H), 6.98 (dd, J=9.9, 3.0 Hz, 1H), 6.76 (td, J=8.7, 3.1 Hz, 1H), 6.56 (dd, J=8.8, 5.0 Hz, 1H), 5.74 (s, 1H), 5.22 (d, J=6.2 Hz, 1H), 4.62-4.54 (m, 1H), 4.20 (d, J=5.7 Hz, 2H), 3.49-3.35 (m, 3H), 3.33-3.28 (m, 1H), 1.97

(dd, J=12.8, 5.7 Hz, 1H), 1.61-1.39 (m, 5H). Example 153: LCMS: m/z 370.2 (M+H−18); $^1$H NMR (400 MHz, DMSO-d$_6$) δ 7.31-7.25 (m, 2H), 7.15-7.09 (m, 3H), 6.98 (dd, J=10.0, 3.0 Hz, 1H), 6.75 (td, J=8.7, 3.1 Hz, 1H), 6.56 (dd, J=8.8, 4.9 Hz, 1H), 5.75 (s, 1H), 5.24 (d, J=6.2 Hz, 1H), 4.59 (dd, J=8.8, 4.5 Hz, 1H), 4.20 (d, J=5.6 Hz, 2H), 3.42 (q, J=6.4, 5.8 Hz, 3H), 3.33 (s, 1H), 1.96 (dd, J=12.7, 5.9 Hz, 1H), 1.63-1.36 (m, 5H).

Chirality of example 152 was determined by co-crystal structure with KARS.

Example 154a: (R)-6'-fluoro-N-(4-fluoro-2-hydroxybenzyl)-4'-hydroxy-3',4'-dihydro-1'H-spiro[piperidine-4,2'-quinoline]-1-carboxamide Example 154b: (S)-6'-fluoro-N-(4-fluoro-2-hydroxybenzyl)-4'-hydroxy-3',4'-dihydro-1'H-spiro[piperidine-4,2'-quinoline]-1-carboxamide

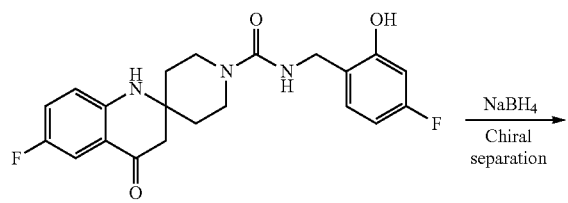

Example 43

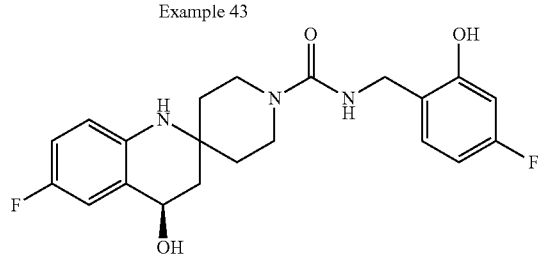

Example 154a

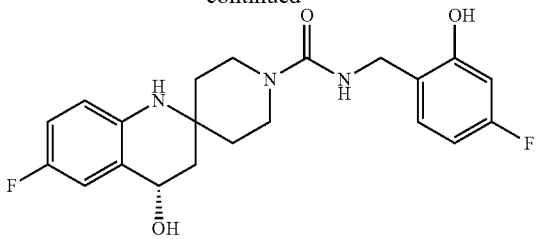

Example 154b

The title compounds were prepared by a method similar to Example 152 and Example 153, using Example 43 instead of Example 40. The product was purified by silica gel chromatography (DCM/MeOH=97/3). The racemic mixture was then separated by chiral SFC to afford example 154a (69 mg, 19% yield, peak 2 in chiral SFC separation) and example 154b (70 mg, 19% yield, peak 1 in chiral SFC separation) as white solids.

Example 154a: LCMS: m/z 404.1 (M+H); $^1$H NMR (400 MHz, Chloroform-d) δ 10.66 (1H, s), 7.25-7.22 (1H, m), 7.11-7.07 (1H, t), 6.99-6.96 (1H, dd), 6.78-6.73 (1H, t), 6.60-6.53 (3H, m), 5.73 (1H, s), 5.22-5.20 (1H, m), 4.61-4.52 (1H, m), 4.12-4.11 (2H, m), 3.45-3.35 (4H, m), 1.99-1.94 (1H, m), 1.60-1.44 (5H, m).

Example 154b: LCMS: m/z 404.4 (M+H); 1H NMR (400 MHz, Chloroform-d) δ 10.66 (1H, s), 7.25-7.22 (1H, m), 7.10-7.07 (1H, t), 6.99-6.96 (1H, dd), 6.78-6.73 (1H, t), 6.60-6.53 (3H, m), 5.73 (1H, s), 5.22-5.20 (1H, m), 4.59-4.57 (1H, m), 4.12-4.11 (2H, m), 3.47-3.34 (4H, m), 1.99-1.94 (1H, m), 1.58-1.44 (5H, m).

Example 155: (R)-6'-fluoro-N-(4-fluorobenzyl)-4'-hydroxy-1'-methyl-3',4'-dihydro-1'H-spiro[piperidine-4,2'-quinoline]-1-carboxamide

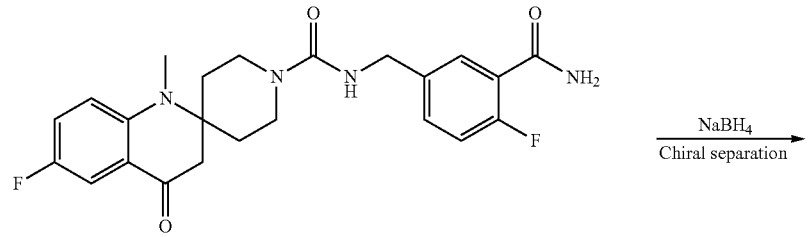

Example 41

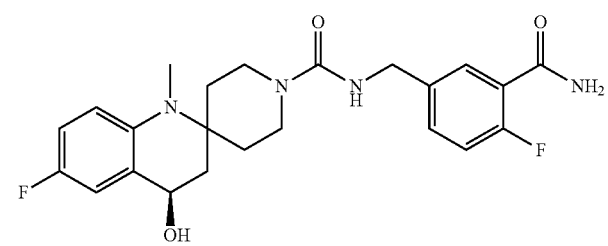

The title compound was prepared by a method similar to Example 152, using Example 41 instead of Example 40. The product was purified by preparative chiral SFC to give the title compound (15 mg, 98% yield, peak 2 in chiral SFC purification) as a white solid. LCMS: m/z 443.4 (M+H); $^1$H NMR (400 MHz, MeOH-d$_4$) δ 7.66 (dd, J=7.3, 2.4 Hz, 1H), 7.38 (ddd, J=7.3, 4.9, 2.4 Hz, 1H), 7.06 (dd, J=10.9, 8.4 Hz, 1H), 6.97 (dd, J=9.3, 3.1 Hz, 1H), 6.74 (td, J=8.7, 3.2 Hz, 1H), 6.54 (dd, J=8.9, 4.5 Hz, 1H), 4.54 (dd, J=10.0, 5.1 Hz, 1H), 4.27 (s, 2H), 3.83 (dq, J=12.0, 3.4 Hz, 2H), 3.13-2.94 (m, 2H), 2.67 (s, 3H), 2.38 (dd, J=13.1, 5.2 Hz, 1H), 1.99-1.90 (m, 1H), 1.87-1.76 (m, 1H), 1.57 (dd, J=13.1, 10.0 Hz, 1H), 1.52-1.32 (m, 2H).

Example 156: N-(2,4-difluoro-5-((2-hydroxyethyl)amino)benzyl)-6'-fluoro-4'-hydroxy-1'-methyl-3',4'-dihydro-1'H-spiro[piperidine-4,2'-quinoline]-1-carboxamide

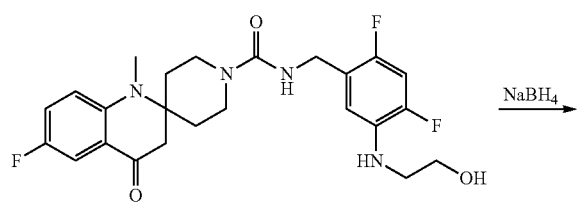

Example 17

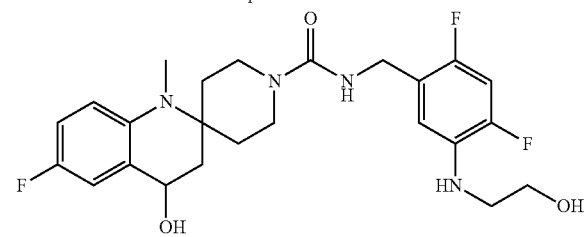

The title compound was prepared by a method similar to Example 165, using Example 17 instead of Example 36. The product was purified by preparative HPLC (basic, method 4) to give the racemic title compound (5 mg, 79% yield) as a white solid. HRMS: m/z 461.2162 (M+H-O); $^1$H NMR (400 MHz, MeOH-d$_4$) δ 7.10-7.02 (m, 1H), 6.88-6.71 (m, 3H), 6.64 (dd, J=9.0, 4.5 Hz, 1H), 4.63 (dd, J=10.0, 5.1 Hz, 1H), 4.33 (s, 2H), 3.97-3.88 (m, 2H), 3.73 (t, J=5.7 Hz, 2H), 3.24 (t, J=5.7 Hz, 2H), 3.21-3.04 (m, 2H), 2.76 (s, 3H), 2.47 (dd, J=13.1, 5.1 Hz, 1H), 2.02 (td, J=12.5, 4.5 Hz, 1H), 1.90 (td, J=12.7, 4.5 Hz, 1H), 1.65 (dd, J=12.9, 10.2 Hz, 1H), 1.60-1.51 (m, 1H), 1.45 (d, J=13.3 Hz, 1H).

Example 157: N-(3-carbamoyl-4-fluorobenzyl)-6',8'-difluoro-4'-hydroxy-3',4'-dihydro-1'H-spiro[piperidine-4,2'-quinoline]-1-carboxamide

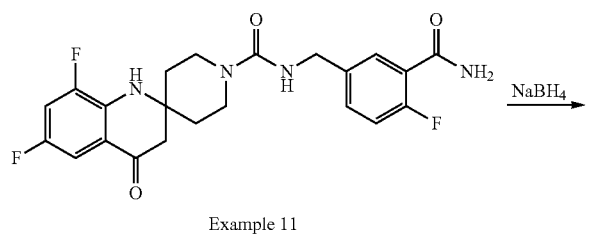

Example 11

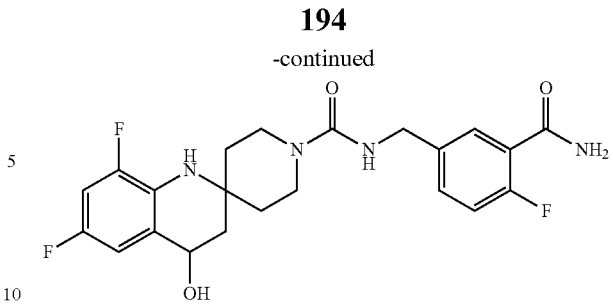

The title compound was prepared by a method similar to Example 165 using Example 11, instead of Example 36. The product was purified by preparative HPLC (Basic, Method 4) to give the racemic title compound (12 mg, 90% yield) as a white solid. HRMS: m/z 431.2525 (M+H-O); $^1$H NMR (400 MHz, MeOH-d$_4$) δ 7.75 (d, J=6.9 Hz, 1H), 7.57-7.41 (m, 1H), 7.24-7.09 (m, 1H), 7.00-6.85 (m, 1H), 6.73 (t, J=10.0 Hz, 1H), 4.81-4.73 (m, 1H), 4.35 (s, 2H), 3.69-3.38 (m, 4H), 2.31-2.10 (m, 1H), 1.92-1.51 (m, 5H).

Example 158: N-(3-amino-4-fluorobenzyl)-6'-fluoro-4'-hydroxy-3',4'-dihydro-1'H-spiro[piperidine-4,2'-quinoline]-1-carboxamide

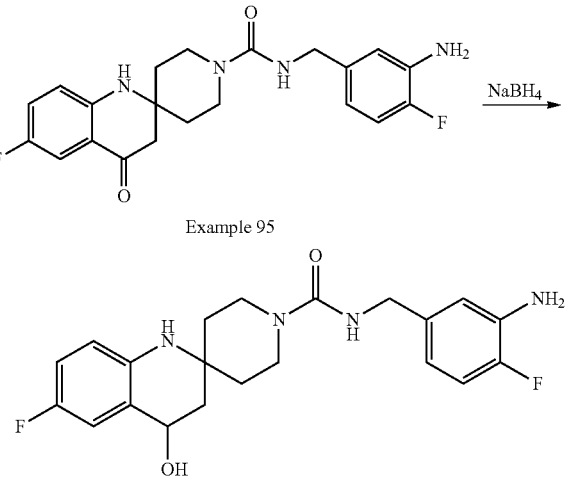

Example 95

The title compound was prepared by a method similar to Example 165, using Example 95 instead of Example 36. The product was purified by preparative HPLC (basic, method 5) to give the racemic title compound (6 mg, 57% yield) as a white solid. LCMS: m/z 385.2 (M+H−18); $^1$H NMR (400 MHz, DMSO-d$_6$) δ 7.02-6.93 (m, 2H), 6.87 (dd, J=11.5, 8.2 Hz, 1H), 6.76 (td, J=8.7, 3.0 Hz, 1H), 6.65 (dd, J=8.9, 2.0 Hz, 1H), 6.55 (dd, J=8.8, 5.0 Hz, 1H), 6.38 (ddd, J=8.1, 4.4, 2.1 Hz, 1H), 5.72 (s, 1H), 5.21 (d, J=5.3 Hz, 1H), 5.07 (s, 2H), 4.65-4.51 (m, 1H), 4.07 (d, J=5.6 Hz, 2H), 3.41 (dt, J=10.0, 4.4 Hz, 3H), 3.32 (d, J=4.8 Hz, 1H), 1.97 (dd, J=12.7, 5.7 Hz, 1H), 1.50 (ddt, J=35.0, 16.2, 5.8 Hz, 5H).

Example 159: 6'-fluoro-N-(4-fluoro-3-(hydroxymethyl)benzyl)-4'-hydroxy-3',4'-dihydro-1'H-spiro[piperidine-4,2'-quinoline]-1-carboxamide

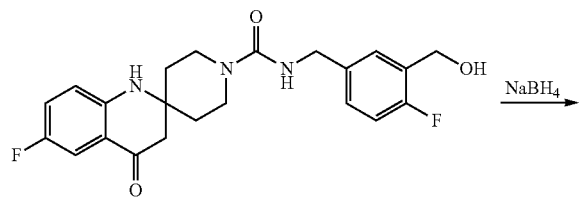

Example 83

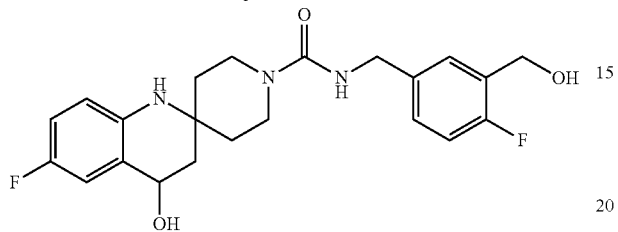

The title compound was prepared by a method similar to Example 165, using Example 83 instead of Example 36. The product was purified by preparative HPLC (Basic, Method 5) to give the racemic title compound (6.2 mg, 76% yield) as a white solid. LCMS: m/z 400.4 (M+H-O); 1 NMR (400 MHz, Methanol-d4) δ 7.40 (dd, J=7.1, 2.1 Hz, 1H), 7.26-7.17 (m, 1H), 7.06-6.95 (m, 2H), 6.74 (td, J=8.6, 2.9 Hz, 1H), 6.60 (dd, J=8.8, 4.8 Hz, 1H), 4.76 (dd, J=8.8, 5.9 Hz, 1H), 4.65 (s, 2H), 4.33 (s, 2H), 3.62-3.43 (m, 4H), 2.09 (dd, J=13.0, 5.9 Hz, 1H), 1.81-1.70 (m, 2H), 1.70-1.52 (m, 3H).

Example 160: N-(3-carbamoyl-4-fluorobenzyl)-6'-fluoro-4'-hydroxy-3',4'-dihydro-1'H-spiro[piperidine-4,2'-quinoline]-1-carboxamide

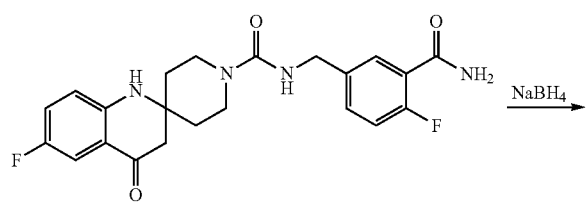

Example 24

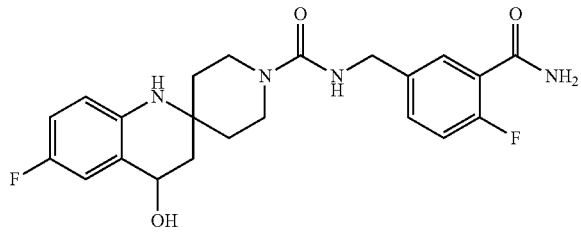

The title compound was prepared by a method similar to Example 165, using Example 24 instead of Example 36. The product was purified by preparative HPLC (Basic, Method 4) to give the racemic title compound (19.1 mg, 93% yield) as a white solid. HRMS: m/z 431.2525 (M+H-O); ¹H NMR (400 MHz, MeOH-d₄) δ 7.71 (dd, J=7.1, 2.2 Hz, 1H), 7.43 (td, J=5.2, 2.5 Hz, 1H), 7.12 (dd, J=10.9, 8.6 Hz, 1H), 6.98 (dd, J=9.6, 2.8 Hz, 1H), 6.70 (td, J=8.6, 2.9 Hz, 1H), 6.57 (dd, J=8.8, 4.8 Hz, 1H), 4.72 (dd, J=8.7, 6.0 Hz, 1H), 4.32 (s, 2H), 3.53-3.39 (m, 4H), 2.12-1.97 (m, 1H), 1.78-1.67 (m, 2H), 1.59 (ddt, J=18.3, 13.6, 6.9 Hz, 3H).

Example 161: N-(3-(2-amino-2-oxoethyl)-4-fluorobenzyl)-6'-fluoro-4'-hydroxy-1'-methyl-3',4'-dihydro-1'H-spiro[piperidine-4,2'-quinoline]-1-carboxamide

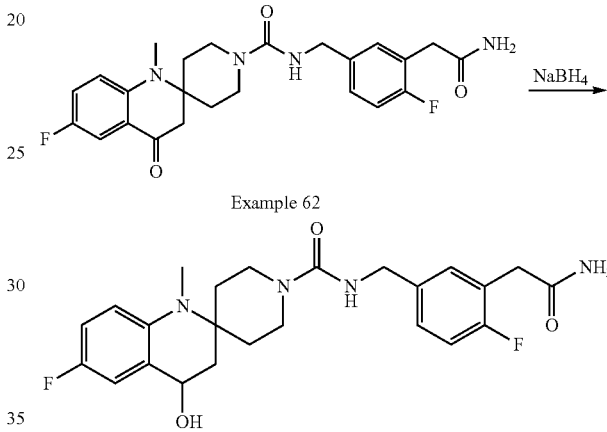

Example 62

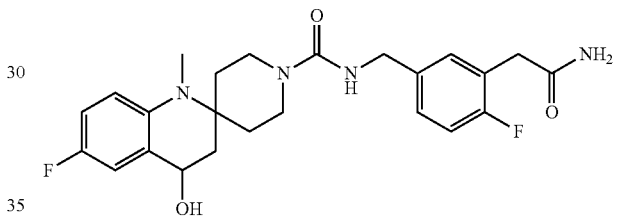

The title compound was prepared by a method similar to Example 165, using Example 62 instead of Example 36. The product was purified by preparative HPLC (basic, method 4) to give the racemic title compound (30.5 mg, 0.066 mmol, 38% yield) as a white solid. LCMS: m/z 459.1 (M+H); ¹H NMR (300 MHz, CD₃OD) δ 7.25-7.19 (2H, m), 7.07-7.69 (3H, m), 6.86-6.79 (1H, m), 6.65-6.60 (1H, m), 4.65-4.32 (1H, m), 4.30-3.93 (2H, d), 3.89-3.67 (2H, m), 3.30 (2H, s), 3.19-2.76 (2H, m), 2.53 (3H, s), 2.50-2.14 (1H, m), 2.07-1.85 (2H, m), 1.68-1.42 (3H, m).

Example 162: 6'-fluoro-N-(4-fluoro-3-((3-hydroxycyclobutyl)carbamoyl)benzyl)-4'-hydroxy-3',4'-dihydro-1'H-spiro[piperidine-4,2'-quinoline]-1-carboxamide

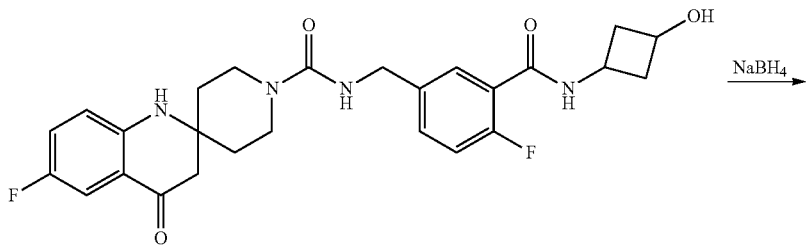

Example 60

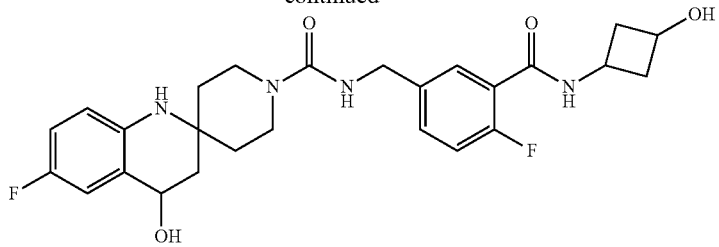

The title compound was prepared by a method similar to Example 165, using Example 60 instead of Example 36. The product was purified by preparative HPLC (basic, method 4) to give the racemic title compound (2 mg, 3.96 μmol, 25% yield) as a white solid. HRMS: m/z 483.2224 (M+H-O); $^1$H NMR (400 MHz, MeOH-$d_4$) δ 7.50-7.44 (m, 1H), 7.37-7.29 (m, 1H), 7.05 (dd, J=9.7 Hz, 1H), 6.96-6.87 (m, 1H), 6.71-6.60 (m, 1H), 6.54-6.45 (m, 1H), 4.69-4.64 (m, 1H), 4.25 (s, 2H), 3.98-3.86 (m, 2H), 3.41 (d, J=18.8 Hz, 4H), 2.71-2.61 (m, 2H), 2.09-1.82 (m, 3H), 1.73-1.46 (m, 5H).

Example 163: 6'-fluoro-N-(4-fluoro-3-(2-hydroxy-ethoxy(benzyl)-4'-hydroxy-1'-methyl-3',4'-dihydro-1'J-spiro[piperidine-4,2'-quinoline]-1-carboxamide

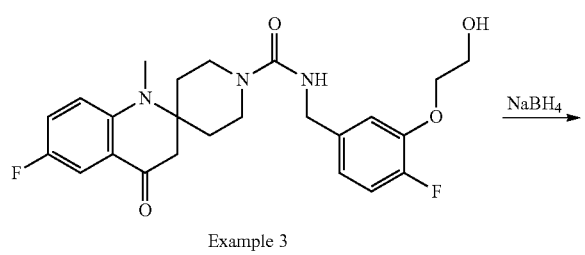

Example 3

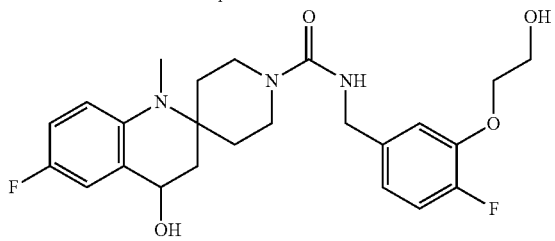

The title compound was prepared by a method similar to Example 165, using Example 3 instead of Example 36. The product was purified by preparative HPLC (Basic, Method 4) to give the racemic title compound (3.8 mg, 54% yield) as a white solid. LCMS: m/z 460.3 (M−H); $^1$H NMR (400 MHz, MeOH-$d_4$) δ 7.09-6.99 (m, 3H), 6.88-6.80 (m, 2H), 6.64 (dd, J=9.0, 4.5 Hz, 1H), 4.63 (dd, J=10.0, 5.1 Hz, 1H), 4.30 (s, 2H), 4.11 (dd, J=5.3, 4.3 Hz, 2H), 3.96-3.86 (m, 4H), 3.23-3.05 (m, 2H), 2.76 (s, 3H), 2.47 (dd, J=13.1, 5.2 Hz, 1H), 1.97 (dtd, J=46.6, 12.4, 4.5 Hz, 2H), 1.70-1.41 (m, 3H).

Example 164: 6'-fluoro-N-(4-fluoro-3-(methylsulfonamido)benzyl)-4'-hydroxy-3',4'-dihydro-1'H-spiro[piperidine-4,2'-quinoline]-1-carboxamide

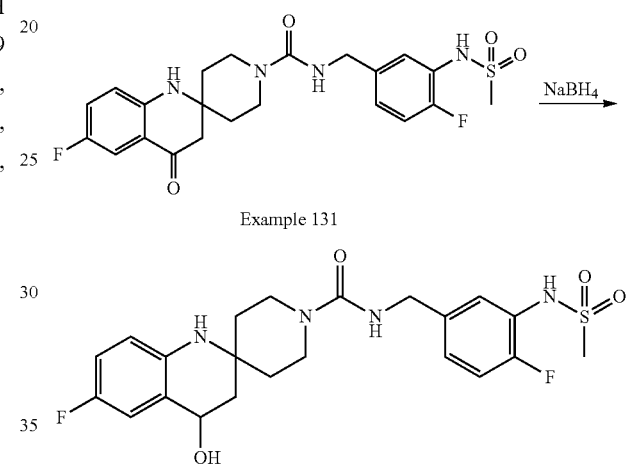

The title compound was prepared by a method similar to Example 165, using Example 131 instead of Example 36. The product was purified by preparative HPLC (Basic, Method 2) to give the racemic title compound (3.3 mg, 33% yield) as a white solid. LCMS: m/z 481.1 (M+H); $^1$H NMR (400 MHz, MeOH-$d_4$) δ 7.43 (d, J=8 Hz, 1H), 7.10-7.07 (m, 1H), 7.01 (dd, J=8 Hz, 3H), 6.76-6.71 (m, 1H), 6.60 (q, J=8 Hz, 1H) 4.32 (s, 2H), 3.55-3.48 (m, J=8 Hz, 4H), 2.97 (s, 3H), 2.15-2.10 (m, 1H), 1.78-1.73 (m, 2H), 1.67-1.59 (m, 4H).

Example 165: 6'-fluoro-N-(4-fluoro-3-((2-hydroxyethyl)amino)benzyl)-4'-hydroxy-1'-methyl-3',4'-dihydro-1'H-spiro[piperidine-4,2'-quinoline]-1-carboxamide

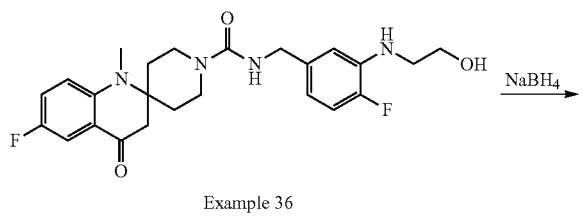

Example 36

-continued

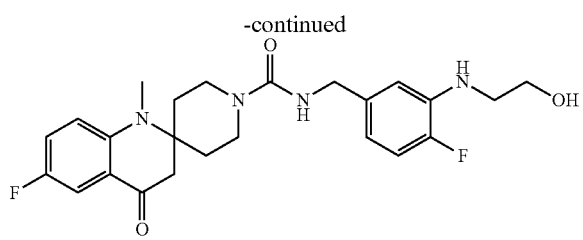

To a stirred solution of Example 36 (14 mg, 0.031 mmol) in EtOH (5 mL) was added sodium borohydride (3.5 mg, 0.092 mmol) portion-wise at RT. The reaction mixture was stirred at RT overnight, concentrated under reduce pressure, then diluted with water (10 mL) and extracted with EtOAc (2×10 mL). The solvent was evaporated and the residue purified by preparative HPLC (Basic, Method 4) to give the title compound (9 mg, 63% yield) as a white solid. LCMS: m/z 443.3 (M+H−18); ¹H NMR (400 MHz, DMSO-d₆) δ 7.04 (dd, J=9.2, 3.3 Hz, 2H), 6.98-6.81 (m, 2H), 6.64 (dd, J=8.7, 1.8 Hz, 1H), 6.54 (dd, J=9.0, 4.6 Hz, 1H), 6.43 (ddd, J=7.9, 4.5, 1.9 Hz, 1H), 5.39 (s, 1H), 5.16 (q, J=3.6 Hz, 1H), 4.77 (s, 1H), 4.48 (d, J=6.0 Hz, 1H), 4.14 (d, J=5.7 Hz, 2H), 3.92 (d, J=13.6 Hz, 2H), 3.57 (t, J=5.8 Hz, 2H), 3.12 (q, J=5.9 Hz, 2H), 2.90 (dt, J=39.8, 11.8 Hz, 2H), 2.67 (s, 3H), 2.48-2.43 (m, 1H), 1.81 (dtd, J=58.4, 12.6, 4.4 Hz, 2H), 1.49-1.41 (m, 2H), 1.29 (d, J=11.6 Hz, 1H).

Example 166: 6'-fluoro-N-(4-fluoro-2-((2-methoxyethyl)amino)benzyl)-4'-hydroxy-1'-methyl-3',4'-dihydro-1'H-spiro[piperidine-4,2'-quinoline]-1-carboxamide

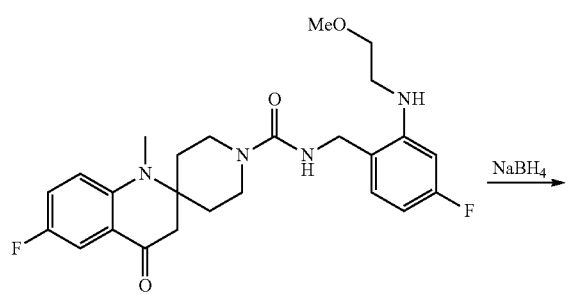

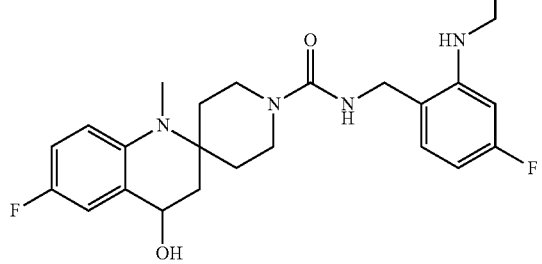

The title compound was prepared by a method similar to Example 165, using Example 20 instead of Example 36. The product was purified by preparative HPLC (Basic, Method 5) to give the racemic title compound (10 mg, 0.020 mmol, 63% yield) as a white solid. LCMS: m/z 475.3 (M+H); ¹H NMR (400 MHz, MeOH-d₄) δ 7.13-6.96 (m, 2H), 6.83 (td, J=8.6, 3.0 Hz, 1H), 6.63 (dd, J=9.0, 4.5 Hz, 1H), 6.38-6.20 (m, 2H), 4.62 (dd, J=10.0, 5.0 Hz, 1H), 4.25 (s, 2H), 3.98-3.80 (m, 2H), 3.61 (t, J=5.5 Hz, 2H), 3.39 (s, 3H), 3.27 (t, J=5.5 Hz, 2H), 3.19-3.01 (m, 2H), 2.75 (s, 3H), 2.46 (dd, J=13.1, 5.1 Hz, 1H), 2.12-1.78 (m, 2H), 1.72-1.34 (m, 3H).

Example 167: N-(3-((R)-1-amino-2,2,2-trifluoroethyl)-4-fluorobenzyl)-6'-fluoro-4'-hydroxy-1'-methyl-3',4'-dihydro-1'H-spiro[piperidine-4,2'-quinoline]-1-carboxamide

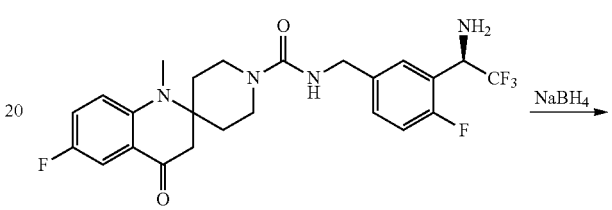

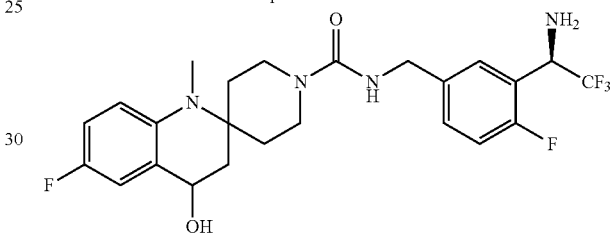

The title compound was prepared by a method similar to Example 165, using Example 149 instead of Example 36. The product was purified by preparative HPLC (Basic, Method 4) to give the racemic title compound (9 mg, 85% yield) as a white solid. HRMS: m/z 481.1548 (M+H-O); ¹H NMR (400 MHz, Methanol-d4) δ 7.47-7.40 (m, 1H), 7.29-7.20 (m, 1H), 7.05-6.93 (m, 2H), 6.74 (td, J=8.7, 3.2 Hz, 1H), 6.54 (dd, J=9.0, 4.5 Hz, 1H), 4.66 (q, J=7.6 Hz, 1H), 4.54 (dd, J=9.9, 5.3 Hz, 1H), 4.26 (s, 2H), 3.89-3.76 (m, 2H), 3.14-2.94 (m, 2H), 2.67 (s, 3H), 2.37 (dd, J=13.1, 5.3 Hz, 1H), 1.99-1.87 (m, 1H), 1.87-1.75 (m, 1H), 1.57 (dd, J=13.0, 10.0 Hz, 1H), 1.51-1.42 (m, 1H), 1.42-1.31 (m, 1H).

Example 168: 6'-fluoro-N-(4-fluoro-2-methoxybenzyl)-4'-hydroxy-3',4'-dihydro-1'H-spiro[piperidine-4,2'-quinoline]-1-carboxamide

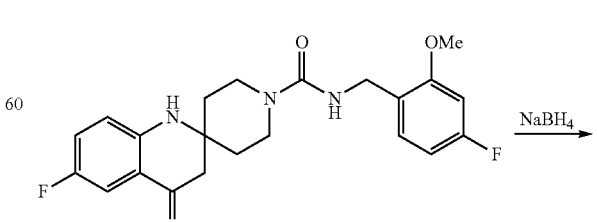

-continued

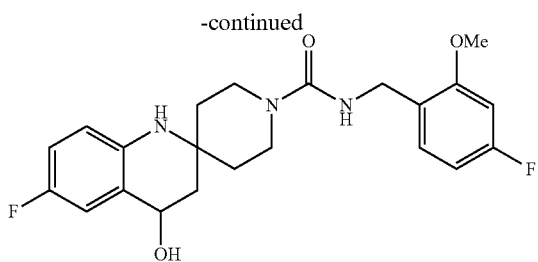

The title compound was prepared by a method similar to Example 165, using Example 114 instead of Example 36. The product was purified by preparative HPLC (basic, method 4) to give the racemic title compound (5 mg, 47% yield) as a white solid. LCMS: m/z 418.3 (M+H); $^1$H NMR (400 MHz, MeOH-$d_4$) δ 7.18 (dd, J=8.3, 6.8 Hz, 1H), 7.02 (dd, J=9.7, 2.5 Hz, 1H), 6.77-6.70 (m, 2H), 6.65-6.57 (m, 2H), 4.76 (dd, J=8.9, 5.9 Hz, 1H), 4.31 (s, 2H), 3.84 (s, 3H), 3.62-3.41 (m, 4H), 2.09 (dd, J=13.0, 5.9 Hz, 1H), 1.75 (ddd, J=13.4, 8.6, 4.7 Hz, 2H), 1.69-1.54 (m, 3H).

Example 169: (R)-6'-fluoro-4'-hydroxy-N-((2-methylfuran-3-yl)methyl)-3',4'-dihydro-1'H-spiro[piperidine-4,2'-quinoline]-1-carboxamide

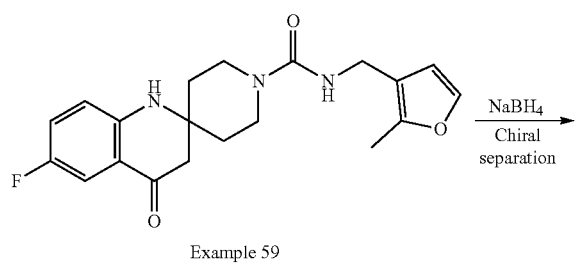

The title compound was prepared by a method similar to Example 152, using Example 59 instead of Example 40. The product was purified by preparative chiral SFC to afford the title compound (57.8 mg, 24.5% yield, peak 2 in chiral SFC separation R.t.=3.83 min) as a white solid. LCMS: m/z 372.5 (M−H); $^1$H NMR (400 MHz, MeOH-$d_4$) δ 7.26 (d, J=1.9 Hz, 1H), 7.03 (dd, J=9.5, 2.9 Hz, 1H), 6.75 (td, J=8.6, 3.0 Hz, 1H), 6.61 (dd, J=8.8, 4.8 Hz, 1H), 6.32 (d, J=1.9 Hz, 1H), 4.77 (dd, J=9.0, 5.9 Hz, 1H), 4.12 (s, 2H), 3.58-3.45 (m, 4H), 2.27 (s, 3H), 2.09 (dd, J=13.0, 5.9 Hz, 1H), 1.80-1.70 (m, 2H), 1.63 (ddt, J=16.4, 12.5, 5.7 Hz, 3H).

Example 170a: (R)—N-(4-amino-3-fluorobenzyl)-6'-fluoro-4'-hydroxy-3',4'-dihydro-1'H-spiro[piperidine-4,2'-quinoline]-1-carboxamide Example 170b: (S)—N-(4-amino-3-fluorobenzyl)-6'-fluoro-4'-hydroxy-3',4'-dihydro-1'H-spiro[piperidine-4,2'-quinoline]-1-carboxamide

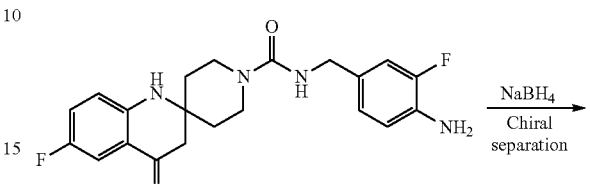

Example 56

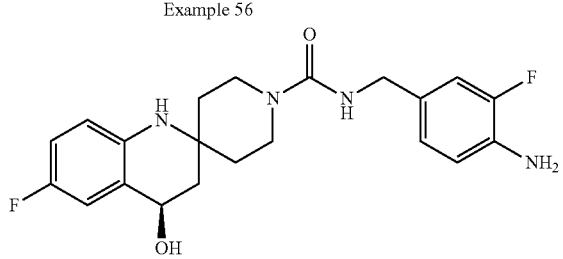

Example 170a

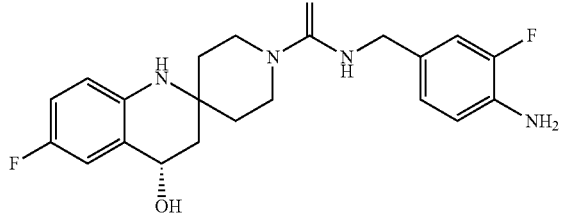

Example 170b

The title compounds were prepared by a method similar to Example 152 and 153, using Example 56 instead of Example 40. The product was purified by chiral SFC to afford example 170a (5 mg, 20% yield, peak 2 in chiral SFC separation) and example 170b (5 mg, 20% yield, peak 1 in chiral SFC separation) as white solids.

Example 170a: LCMS: m/z 425.1 (M+H+Na); $^1$H NMR (400 MHz, DMSO-$d_6$) δ 7.02-6.90 (m, 2H), 6.86 (dd, J=12.5, 1.8 Hz, 1H), 6.80-6.71 (m, 2H), 6.67 (dd, J=9.3, 8.0 Hz, 1H), 6.60-6.50 (m, 1H), 5.73 (s, 1H), 5.22 (d, J=6.2 Hz, 1H), 4.97 (s, 2H), 4.64-4.52 (m, 1H), 4.06 (d, J=5.6 Hz, 2H), 3.48-3.24 (m, 4H), 1.96 (dd, J=12.8, 5.7 Hz, 1H), 1.64-1.31 (m, 5H).

Example 170b: LCMS: m/z 425.1 (M+H+Na); 1H NMR (400 MHz, DMSO-$d_6$) δ 7.02-6.90 (m, 2H), 6.86 (dd, J=12.5, 1.8 Hz, 1H), 6.81-6.71 (m, 2H), 6.67 (dd, J=9.3, 8.0 Hz, 1H), 6.60-6.51 (m, 1H), 5.73 (s, 1H), 5.22 (d, J=6.1 Hz, 1H), 4.97 (s, 2H), 4.65-4.51 (m, 1H), 4.06 (d, J=5.6 Hz, 2H), 3.49-3.25 (m, 4H), 1.96 (dd, J=12.7, 5.7 Hz, 1H), 1.63-1.31 (m, 5H).

Biological Assays and Data

The activity of a compound according to the present invention can be assessed by the following in vitro methods. A compound of formula (I), or a pharmaceutically acceptable salt thereof, exhibits valuable pharmacological properties, e.g. as indicated in tests as provided in the next sections, and are therefore indicated for therapy related to AKR1C3 dependent KARS inhibitors.

Cellular Proliferation Assay to Assess Compounds Activity in H460 (NRF2 Pathway Mutant Cell Line with High AKR1C3 Expression) and Hara (NRF2 Pathway Wild Type Cell Line with Low AKR1C3 Expression).

The cell lines A549 and H460 are NRF2 pathway mutant and specifically contain genetic alterations in KEAP1 (A549: G333C, H460: D236H) (Singh A. et al., 2006 PLoS Medicine 3(10) e420). In these cell lines the NRF2 pathway is constitutively active and these cells express high levels of NRF2 protein and NRF2 pathway target gene AKR1C3. Hara cells do not have any known genetic alterations in the NRF2 pathway, and are classified as wild-type. They have low AKR1C3 expression. In vitro proliferation of H460 and Hara cell lines was monitored following compound treatment to identify compounds that specifically inhibit proliferation of H460 line.

In Vitro Cell Proliferation Assay

Day 1, for H460 800 cells/well or 40 μL of 2×10$^4$ cells/mL and for Hara 2000 cells/well or 40 μL of 5×10$^4$ cells/mL medium (RPMI-1640 supplemented with 10% fetal bovine serum and 1% penicillin/streptomycin) were seeded into 384-well tissue culture plates. Day 2, compounds were serially diluted 1:5 to generate 8 point dose response curves and added to cells for a final top concentration of 10 μM. DMSO (1%) control and MG132 (30 μM) controls are added in columns 23 and 24 respectively on each plate for positive and negative control. After incubation for 3 days at 37° C./5% $CO_2$, 30 μl of CellTiter-Glo reagent (Promega) was added and the plates were incubated for 10 min on plate shaker. The amount of luminescence was determined using a Perkin Elmer Envision plate reader. CellTiter-Glo luminescence values of cells treated with DMSO and MG132 controls were used to normalize the data and calculate percentage activity and AC50s of compounds using the Helios Software suite.

| Ex. # | Structure | Structure name | H460 Qualified absolute $AC_{50}$ (μM) | HARA Qualified absolute $AC_{50}$ (μM) |
|---|---|---|---|---|
| 1 | 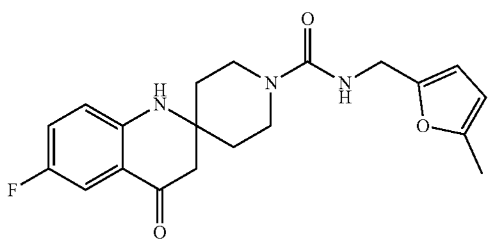 [SMILES: Cc1ccc(CNC(=O)N2CCC3(CC2)CC(=O)c2cc(F)ccc2N3)o1] | 6'-fluoro-N-((5-methylfuran-2-yl)methyl)-4'-oxo-3',4'-dihydro-1'H-spiro[piperidine-4,2'-quinoline]-1-carboxamide | 0.143 | |
| 2 | 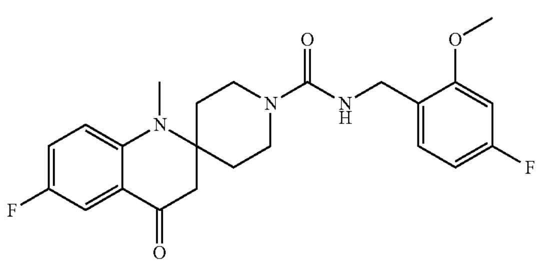 [SMILES: COc1cc(F)ccc1CNC(=O)N1CCC2(CC1)CC(=O)c1cc(F)ccc1N2C] | 6'-fluoro-N-(4-fluoro-2-methoxybenzyl)-1'-methyl-4'-oxo-3',4'-dihydro-1'H-spiro[piperidine-4,2'-quinoline]-1-carboxamide | 0.005 | >10 |
| 3 | 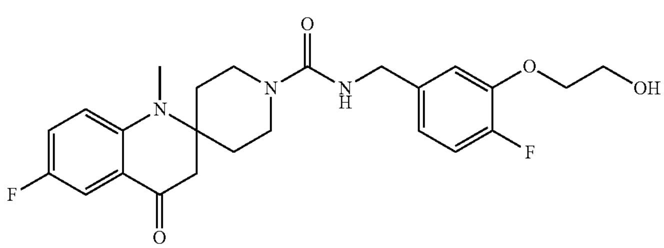 [SMILES: CN1c2ccc(F)cc2C(=O)CC12CCN(C(=O)NCc1ccc(F)c(OCCO)c1)CC2] | 6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide | 0.005 | 1.759 |
| 4 | 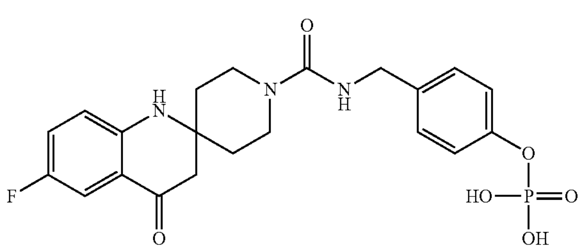 [SMILES: O=C1CC2(CCN(C(=O)NCc3ccc(OP(=O)(O)O)cc3)CC2)Nc2ccc(F)cc21] | 4-((6'-fluoro-4'-oxo-3',4'-dihydro-1'H-spiro[piperidine-4,2'-quinoline]-1-carboxamido)methyl)phenyl dihydrogen phosphate | 0.006 | |

-continued

| Ex. # | Structure | Structure name | H460 Qualified absolute AC$_{50}$ (μM) | HARA Qualified absolute AC$_{50}$ (μM) |
|---|---|---|---|---|
| 5 | 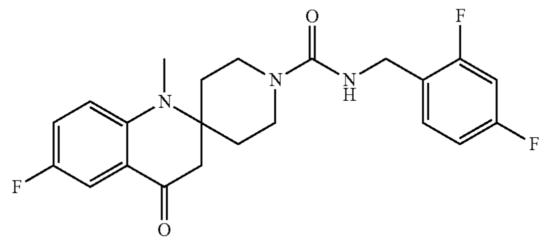 [SMILES: CN1c2ccc(F)cc2C(=O)CC12CCN(C(=O)NCc1ccc(F)cc1F)CC2] | N-(2,4-difluorobenzyl)-6'-fluoro-1'-methyl-4'-oxo-3',4'-dihydro-1'H-spiro[piperidine-4,2'-quinoline]-1-carboxamide | 0.008 | >10 |
| 6 | 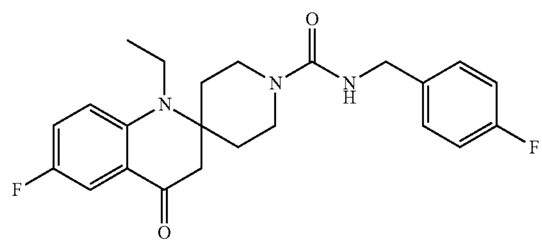 [SMILES: CCN1c2ccc(F)cc2C(=O)CC12CCN(C(=O)NCc1ccc(F)cc1)CC2] | 1'-ethyl-6'-fluoro-N-(4-fluorobenzyl)-4'-oxo-3',4'-dihydro-1'H-spiro[piperidine-4,2'-quinoline]-1-carboxamide | 0.009 | >10 |
| 7 | 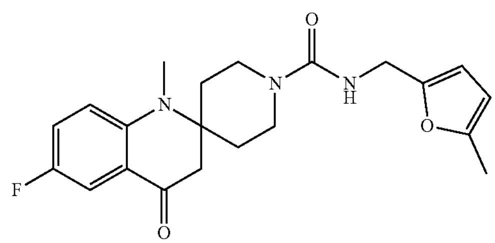 [SMILES: Cc1ccc(CNC(=O)N2CCC3(CC2)CC(=O)c2cc(F)ccc2N3C)o1] | 6'-fluoro-1'-methyl-N-((5-methylfuran-2-yl)methyl)-4'-oxo-3',4'-dihydro-1'H-spiro[piperidine-4,2'-quinoline]-1-carboxamide | 0.010 | |
| 8 | 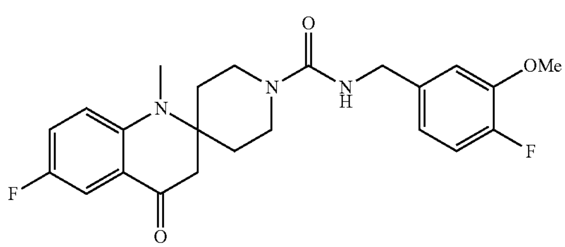 [SMILES: COc1cc(CNC(=O)N2CCC3(CC2)CC(=O)c2cc(F)ccc2N3C)ccc1F] | 6'-fluoro-N-(4-fluoro-3-methoxybenzyl)-1'-methyl-4'-oxo-3',4'-dihydro-1'H-spiro[piperidine-4,2'-quinoline]-1-carboxamide | 0.015 | >10 |
| 9 | 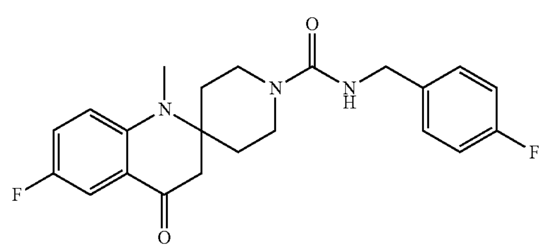 [SMILES: CN1c2ccc(F)cc2C(=O)CC12CCN(C(=O)NCc1ccc(F)cc1)CC2] | 6'-fluoro-N-(4-fluorobenzyl)-1'-methyl-4'-oxo-3',4'-dihydro-1'H-spiro[piperidine-4,2'-quinoline]-1-carboxamide | 0.017 | >10 |
| 10 | 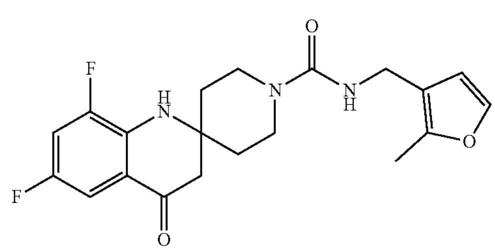 [SMILES: Cc1occc1CNC(=O)N1CCC2(CC1)CC(=O)c1cc(F)cc(F)c1N2] | 6',8'-difluoro-N-((2-methylfuran-3-yl)methyl)-4'-oxo-3',4'-dihydro-1'H-spiro[piperidine-4,2'-quinoline]-1-carboxamide | 0.021 | 5.412 |

| Ex. # | Structure | Structure name | H460 Qualified absolute AC$_{50}$ (μM) | HARA Qualified absolute AC$_{50}$ (μM) |
|---|---|---|---|---|
| 11 | 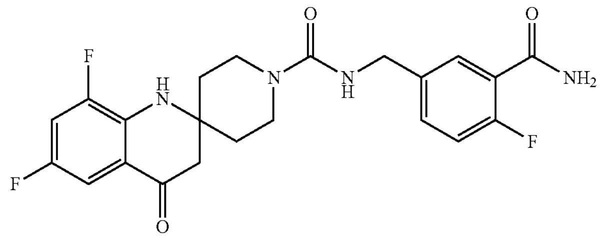 [SMILES: NC(=O)c1cc(CNC(=O)N2CCC3(CC2)CC(=O)c2cc(F)cc(F)c2N3)ccc1F] | N-(3-carbamoyl-4-fluorobenzyl)-6',8'-difluoro-4'-oxo-3',4'-dihydro-1'H-spiro[piperidine-4,2'-quinoline]-1-carboxamide | 0.023 | >10 |
| 12 | 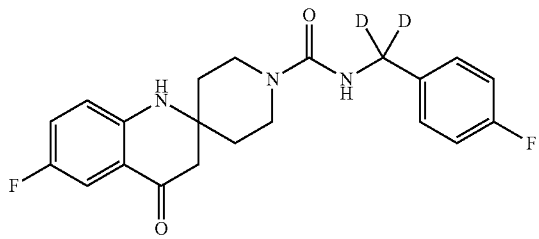 [SMILES: [2H]C([2H])(NC(=O)N1CCC2(CC1)CC(=O)c1cc(F)ccc1N2)c1ccc(F)cc1] | 6'-fluoro-N-((4-fluorophenyl)methyl-d2)-4'-oxo-3',4'-dihydro-1'H-spiro[piperidine-4,2'-quinoline]-1-carboxamide | 0.024 | >10 |
| 13 | 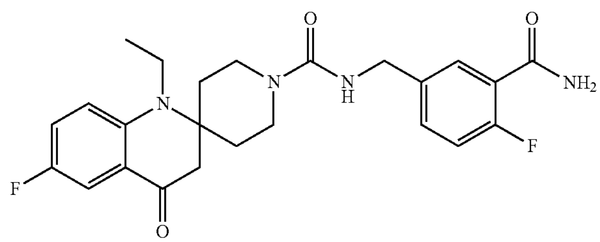 [SMILES: CCN1c2ccc(F)cc2C(=O)CC12CCN(C(=O)NCc1ccc(F)c(C(N)=O)c1)CC2] | N-(3-carbamoyl-4-fluorobenzyl)-1'-ethyl-6'-fluoro-4'-oxo-3',4'-dihydro-1'H-spiro[piperidine-4,2'-quinoline]-1-carboxamide | 0.025 | 7.947 |
| 14 | 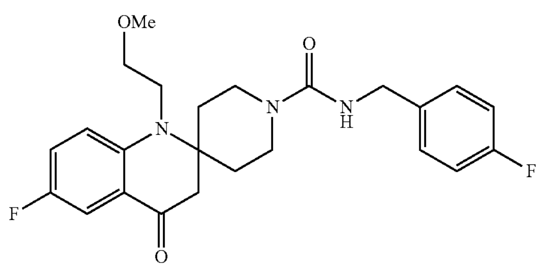 [SMILES: COCCN1c2ccc(F)cc2C(=O)CC12CCN(C(=O)NCc1ccc(F)cc1)CC2] | 6'-fluoro-N-(4-fluorobenzyl)-1'-(2-methoxyethyl)-4'-oxo-3',4'-dihydro-1'H-spiro[piperidine-4,2'-quinoline]-1-carboxamide | 0.029 | 0.795 |
| 15 | 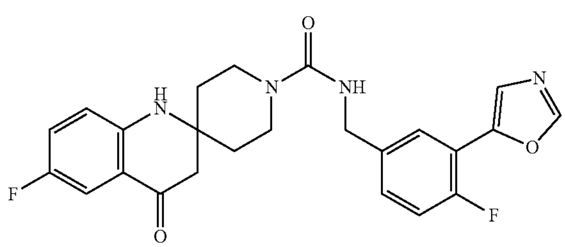 [SMILES: O=C1CC2(CCN(C(=O)NCc3ccc(F)c(-c4cnco4)c3)CC2)Nc2ccc(F)cc21] | 6'-fluoro-N-(4-fluoro-3-(oxazol-5-yl)benzyl)-4'-oxo-3',4'-dihydro-1'H-spiro[piperidine-4,2'-quinoline]-1-carboxamide | 0.029 | 9.44 |
| 16 | 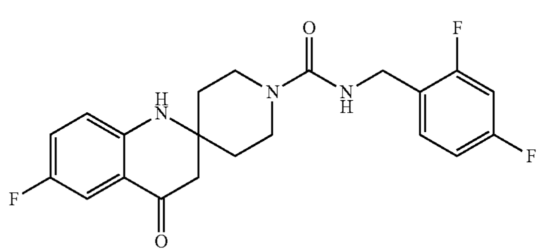 | N-(2,4-difluorobenzyl)-6'-fluoro-4'-oxo-3',4'-dihydro-1'H-spiro[piperidine-4,2'-quinoline]-1-carboxamide | 0.029 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 17 | 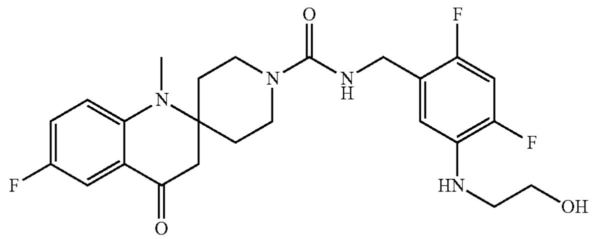 [SMILES: CN1c2ccc(F)cc2C(=O)CC12CCN(C(=O)NCc1cc(NCCO)c(F)cc1F)CC2] | N-(2,4-difluoro-5-((2-hydroxyethyl)amino)benzyl)-6'-fluoro-1'-methyl-4'-oxo-3',4'-dihydro-1'H-spiro[piperidine-4,2'-quinoline]-1-carboxamide | 0.030 | >10 |
| 18 | 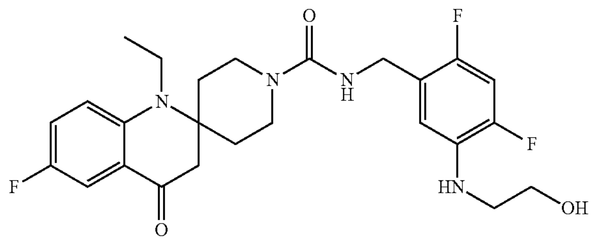 [SMILES: CCN1c2ccc(F)cc2C(=O)CC12CCN(C(=O)NCc1cc(NCCO)c(F)cc1F)CC2] | N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide | 0.030 | 4.192 |
| 19 | 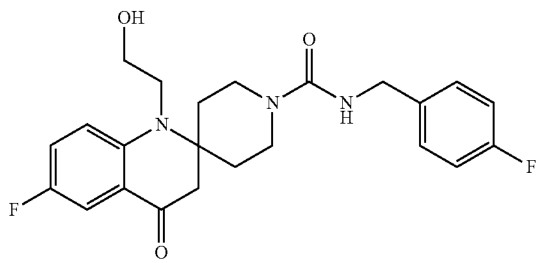 [SMILES: O=C1CC2(CCN(C(=O)NCc3ccc(F)cc3)CC2)N(CCO)c2ccc(F)cc21] | 6'-fluoro-N-(4-fluorobenzyl)-1'-(2-hydroxyethyl)-4'-oxo-3',4'-dihydro-1'H-spiro[piperidine-4,2'-quinoline]-1-carboxamide | 0.031 | 0.694 |
| 20 | 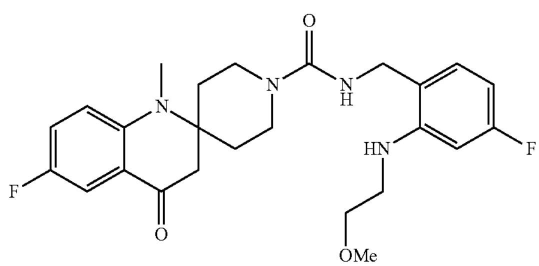 [SMILES: COCCNc1cc(F)ccc1CNC(=O)N1CCC2(CC1)CC(=O)c1cc(F)ccc1N2C] | 6'-fluoro-N-(4-fluoro-2-((2-methoxyethyl)amino)benzyl)-1'-methyl-4'-oxo-3',4'-dihydro-1'H-spiro[pipendine-4,2'-quinoline]-1-carboxamide | 0.033 | >10 |
| 21 | 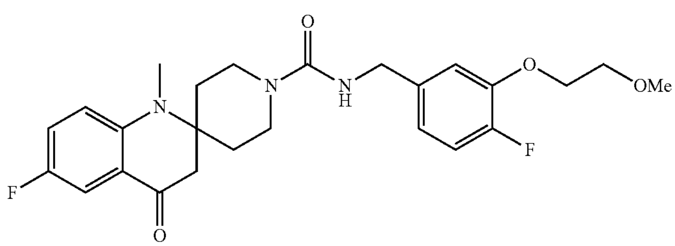 [SMILES: COCCOc1cc(CNC(=O)N2CCC3(CC2)CC(=O)c2cc(F)ccc2N3C)ccc1F] | 6'-fluoro-N-(4-fluoro-3-((2-methoxyethyl)amino)benzyl)-1'-methyl-4'-oxo-3',4'-dihydro-1'H-spiro[piperidine-4,2'-quinoline]-1-carboxamide | 0.034 | >10 |
| 22 | 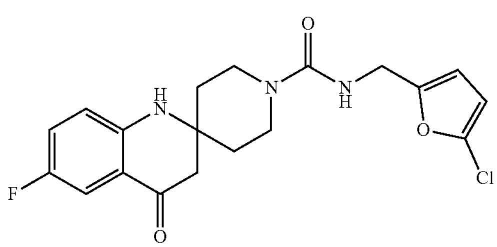 [SMILES: O=C1CC2(CCN(C(=O)NCc3ccc(Cl)o3)CC2)Nc2ccc(F)cc21] | N-((5-chlorofuran-2-yl)methyl)-6'-fluoro-4'-oxo-3',4'-dihydro-1'H-spiro[piperidine-4,2'-quinoline]-1-carboxamide | 0.037 | |

| Ex. # | Structure | Structure name | H460 Qualified absolute AC$_{50}$ (μM) | HARA Qualified absolute AC$_{50}$ (μM) |
|---|---|---|---|---|
| 23 | 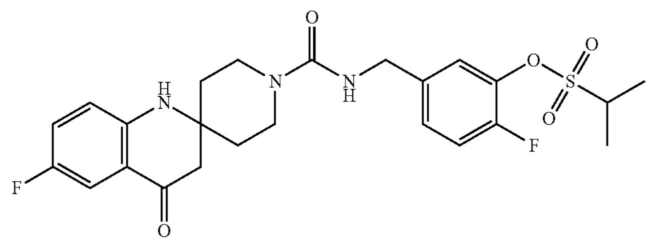 [SMILES: CC(C)S(=O)(=O)Oc1cc(CNC(=O)N2CCC3(CC2)CC(=O)c2cc(F)ccc2N3)ccc1F] | 6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide | 6.903 | >10 |
| 24 | 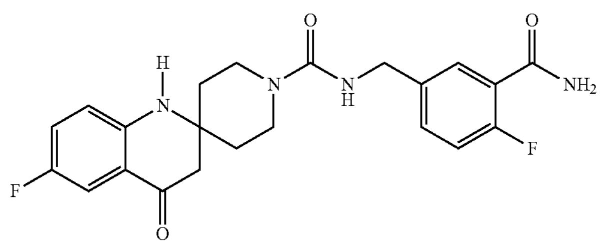 [SMILES: NC(=O)c1cc(CNC(=O)N2CCC3(CC2)CC(=O)c2cc(F)ccc2N3)ccc1F] | N-(3-carbamoyl-4-fluorobenzyl)-6'-fluoro-4'-oxo-3',4'-dihydro-1'H-spiro[piperidine-4,2'-quinoline]-1-carboxamide | 0.046 | 5.935 |
| 25 | 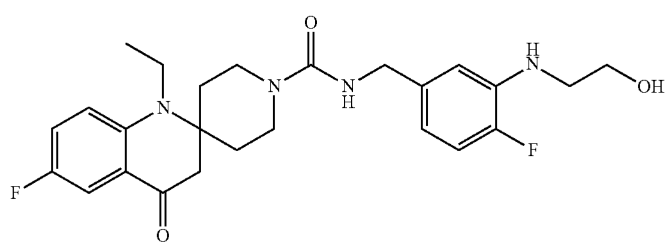 [SMILES: CCN1c2ccc(F)cc2C(=O)CC12CCN(C(=O)NCc1ccc(F)c(NCCO)c1)CC2] | 1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide | 0.047 | 1.660 |
| 26 | 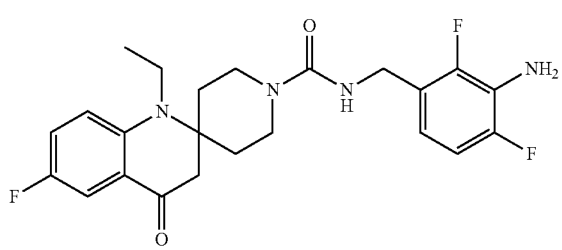 [SMILES: CCN1c2ccc(F)cc2C(=O)CC12CCN(C(=O)NCc1ccc(F)c(N)c1F)CC2] | N-(3-amino-2,4-difluorobenzyl)-1'-ethyl-6'-fluoro-4'-oxo-3',4'-dihydro-1'H-spiro[piperidine-4,2'-quinoline]-1-carboxamide | 0.047 | >10 |
| 27 | 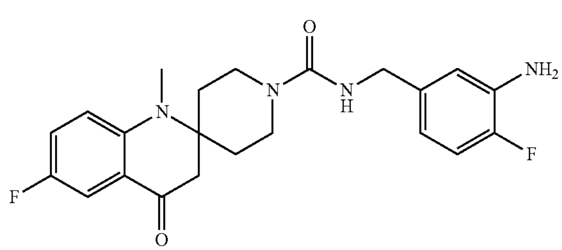 [SMILES: CN1c2ccc(F)cc2C(=O)CC12CCN(C(=O)NCc1ccc(F)c(N)c1)CC2] | N-(3-amino-4-fluorobenzyl)-6'-fluoro-1'-methyl-4'-oxo-3',4'-dihydro-1'H-spiro[piperidine-4,2'-quinoline]-1-carboxamide | 0.048 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 28 | 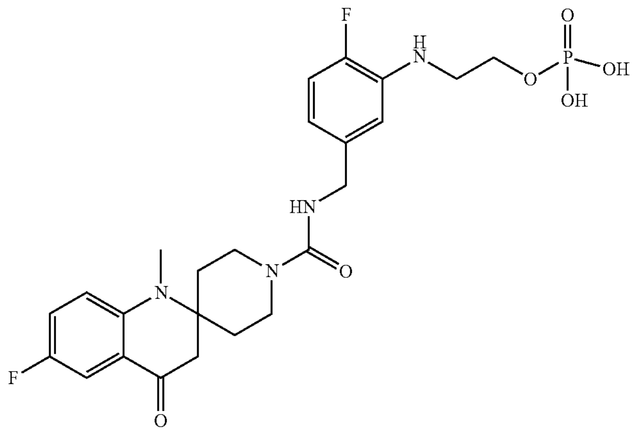 [SMILES: CN1c2ccc(F)cc2C(=O)CC12CCN(C(=O)NCc1ccc(F)c(NCCOP(=O)(O)O)c1)CC2] | 2-((2-fluoro-5-((6'-fluoro-1'-methyl-4'-oxo-3',4'-dihydro-1'H-spiro[piperidine-4,2'-quinoline]-1-carboxamido)methyl)phenyl)amino)ethyl dihydrogen phosphate | 0.052 | >10 |
| 29 | 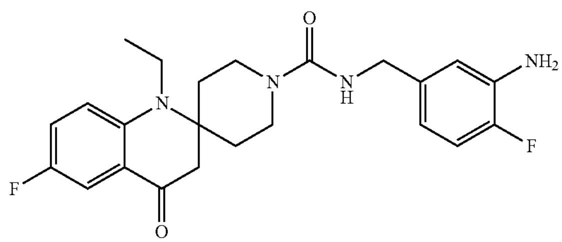 [SMILES: CCN1c2ccc(F)cc2C(=O)CC12CCN(C(=O)NCc1ccc(F)c(N)c1)CC2] | N-(3-amino-4-fluorobenzyl)-1'-ethyl-6'-fluoro-4'-oxo-3',4'-dihydro-1'H-spiro[piperidine-4,2'-quinoline]-1-carboxamide | 0.054 | >10 |
| 30 | 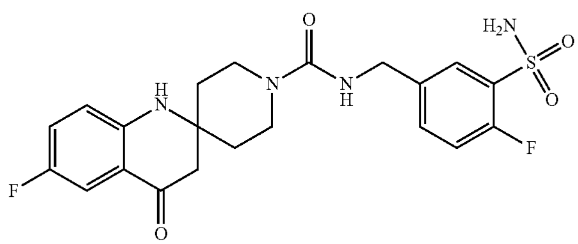 [SMILES: NS(=O)(=O)c1cc(CNC(=O)N2CCC3(CC2)CC(=O)c2cc(F)ccc2N3)ccc1F] | 6'-fluoro-N-(4-fluoro-3-sulfamoylbenzyl)-4'-oxo-3',4'-dihydro-1'H-spiro[piperidine-4,2'-quinoline]-1-carboxamide | 0.061 | >10 |
| 31 | 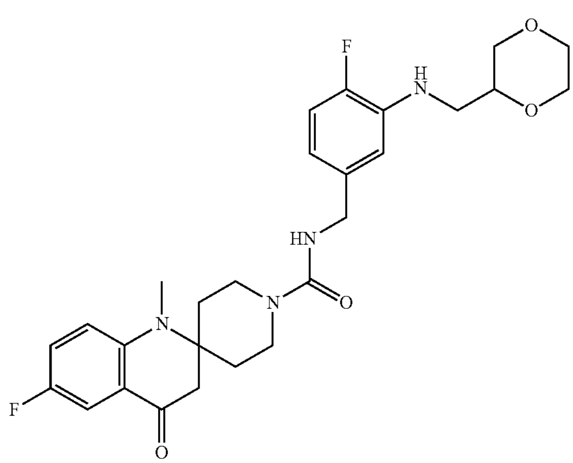 [SMILES: CN1c2ccc(F)cc2C(=O)CC12CCN(C(=O)NCc1ccc(F)c(NCC3COCCO3)c1)CC2] | N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide | 0.064 | |

-continued

| Ex. # | Structure | Structure name | H460 Qualified absolute AC$_{50}$ (μM) | HARA Qualified absolute AC$_{50}$ (μM) |
|---|---|---|---|---|
| 32 | 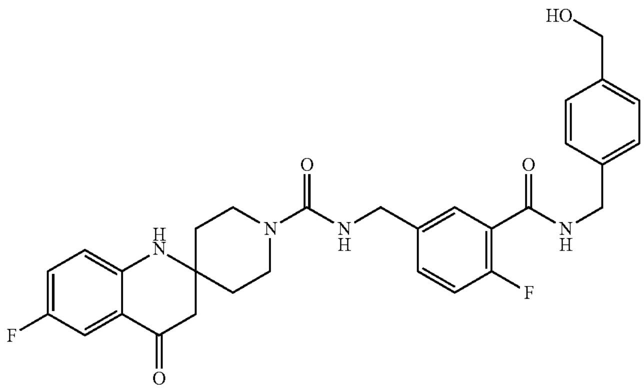 [SMILES: O=C(NCc1ccc(CO)cc1)c1cc(CNC(=O)N2CCC3(CC2)CC(=O)c2cc(F)ccc2N3)ccc1F] | 6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide | 0.064 | |
| 33 | 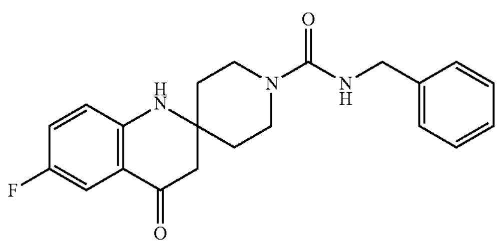 [SMILES: O=C1CC2(CCN(C(=O)NCc3ccccc3)CC2)Nc2ccc(F)cc21] | N-benzyl-6'-fluoro-4'-oxo-3',4'-dihydro-1'H-spiro[piperidine-4,2'-quinoline]-1-carboxamide | 0.075 | 1.189 |
| 34 | 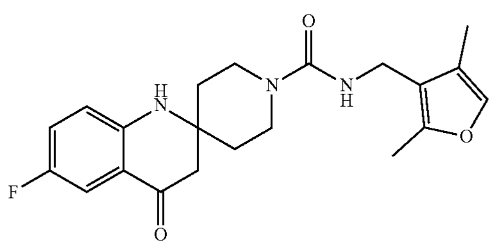 [SMILES: Cc1coc(C)c1CNC(=O)N1CCC2(CC1)CC(=O)c1cc(F)ccc1N2] | N-((2,4-dimethylfuran-3-yl)methyl)-6'-fluoro-4'-oxo-3',4'-dihydro-1'H-spiro[piperidine-4,2'-quinoline]-1-carboxamide | 0.075 | |
| 35 | 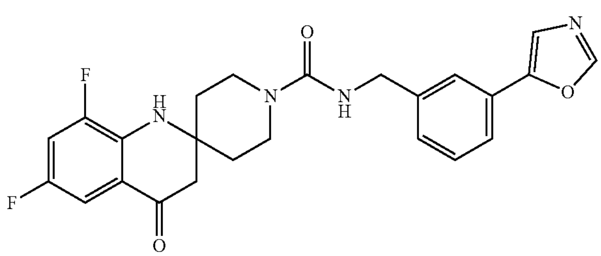 [SMILES: O=C1CC2(CCN(C(=O)NCc3cccc(-c4cnco4)c3)CC2)Nc2c(F)cc(F)cc21] | 6',8'-difluoro-N-(3-(oxazol-5-yl)benzyl)-4'-oxo-3',4'-dihydro-1'H-spiro[piperidine-4,2'-quinoline]-1-carboxamide | 0.077 | 2.721 |
| 36 | 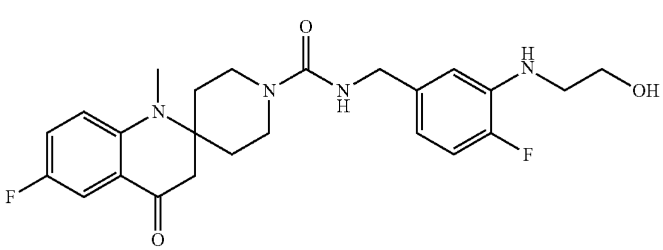 [SMILES: CN1c2ccc(F)cc2C(=O)CC12CCN(C(=O)NCc1ccc(F)c(NCCO)c1)CC2] | 6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide | 0.078 | 1.559 |

-continued

| Ex. # | Structure | Structure name | H460 Qualified absolute AC$_{50}$ (μM) | HARA Qualified absolute AC$_{50}$ (μM) |
|---|---|---|---|---|
| 37 | 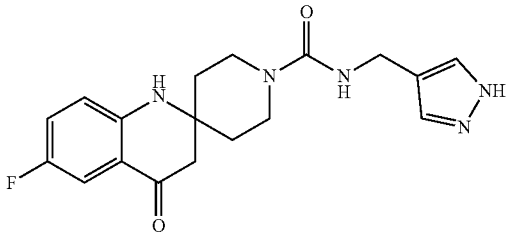 [SMILES: O=C1CC2(CCN(C(=O)NCc3cn[nH]c3)CC2)Nc2ccc(F)cc21] | N-((1H-pyrazol-4-yl)methyl)-6'-fluoro-4'-oxo-3',4'-dihydro-1'H-spiro[piperidine-4,2'-quinoline]-1-carboxamide | 0.081 | |
| 38 | 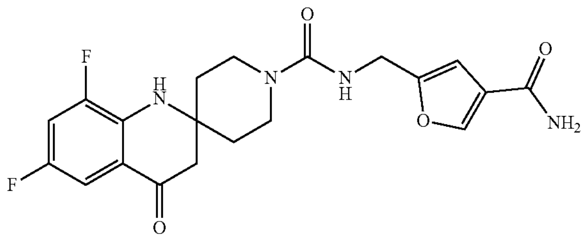 [SMILES: NC(=O)c1coc(CNC(=O)N2CCC3(CC2)CC(=O)c2cc(F)cc(F)c2N3)c1] | N-((4-carbamoylfuran-2-yl)methyl)-6',8'-difluoro-4'-oxo-3',4'-dihydro-1'H-spiro[piperidine-4,2'-quinoline]-1-carboxamide | 0.082 | >10 |
| 39 | 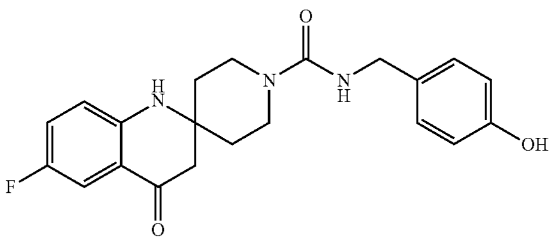 [SMILES: O=C1CC2(CCN(C(=O)NCc3ccc(O)cc3)CC2)Nc2ccc(F)cc21] | 6'-fluoro-N-(4-hydroxybenzyl)-4'-oxo-3',4'-dihydro-1'H-spiro[piperidine-4,2'-quinoline]-1-carboxamide | 0.082 | >10 |
| 40 | 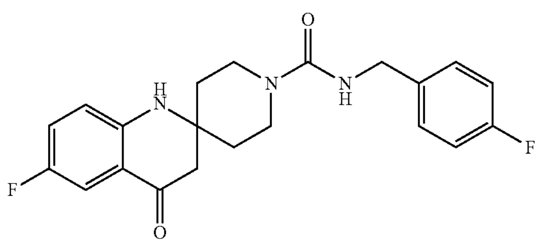 [SMILES: O=C1CC2(CCN(C(=O)NCc3ccc(F)cc3)CC2)Nc2ccc(F)cc21] | 6'-fluoro-N-(4-fluorobenzyl)-4'-oxo-3',4'-dihydro-1'H-spiro[piperidine-4,2'-quinoline]-1-carboxamide | 0.083 | 1.793 |
| 41 | 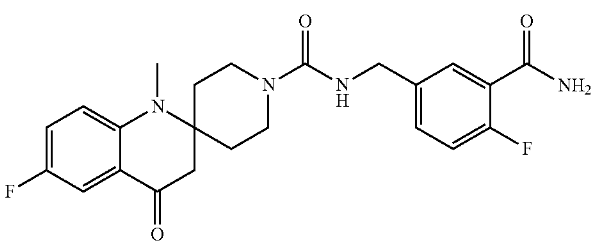 [SMILES: CN1c2ccc(F)cc2C(=O)CC12CCN(C(=O)NCc1ccc(F)c(C(N)=O)c1)CC2] | N-(3-carbamoyl-4-fluorobenzyl)-6'-fluoro-1'-methyl-4'-oxo-3',4'-dihydro-1'H-spiro[piperidine-4,2'-quinoline]-1-carboxamide | 0.093 | >10 |
| 42 | 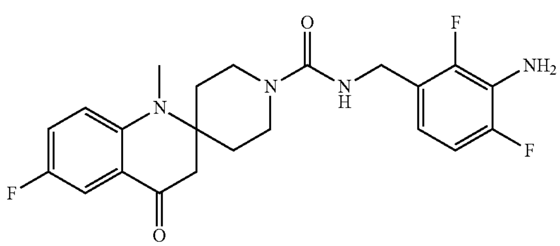 [SMILES: CN1c2ccc(F)cc2C(=O)CC12CCN(C(=O)NCc1ccc(F)c(N)c1F)CC2] | N-(3-amino-2,4-difluorobenzyl)-6'-fluoro-1'-methyl-4'-oxo-3',4'-dihydro-1'H-spiro[piperidine-4,2'-quinoline]-1-carboxamide | 0.094 | >10 |

| Ex. # | Structure name | H460 Qualified absolute $AC_{50}$ (μM) | HARA Qualified absolute $AC_{50}$ (μM) |
|---|---|---|---|
| 43 | 6'-fluoro-N-(4-fluoro-2-hydroxybenzyl)-4'-oxo-3',4'-dihydro-1'H-spiro[piperidine-4,2'-quinoline]-1-carboxamide | 0.099 | >10 |
| 44 | N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide | 0.099 | |
| 45 | (S)-N-(3-((2,3-dihydroxypropyl)amino)-4-fluorobenzyl)-6'-fluoro-1'-methyl-4'-oxo-3',4'-dihydro-1'H-spiro[piperidine-4,2'-quinoline]-1-carboxamide | 0.100 | >10 |
| 46 | 6',8'-difluoro-N-(furan-3-ylmethyl)-4'-oxo-3',4'-dihydro-1'H-spiro[piperidine-4,2'-quinoline]-1-carboxamide | 0.105 | 2.942 |
| 47 | N-((1H-pyrazol-3-yl)methyl)-6'-fluoro-4'-oxo-3',4'-dihydro-1'H-spiro[piperidine-4,2'-quinoline]-1-carboxamide | 0.106 | >10 |

-continued

| Ex. # | Structure | Structure name | H460 Qualified absolute $AC_{50}$ (μM) | HARA Qualified absolute $AC_{50}$ (μM) |
|---|---|---|---|---|
| 48 | 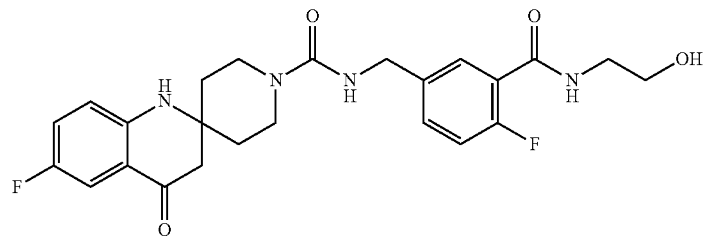 [SMILES: O=C(NCCO)c1cc(CNC(=O)N2CCC3(CC2)CC(=O)c2cc(F)ccc2N3)ccc1F] | 6'-fluoro-N-(4-fluoro-3-((2-hydroxyethyl)carbamoyl)benzyl)-4'-oxo-3',4'-dihydro-1'H-spiro[piperidine-4,2'-quinoline]-1-carboxamide | 0.108 | 7.965 |
| 49 | 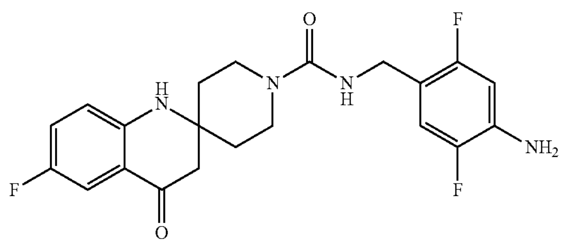 [SMILES: Nc1cc(F)c(CNC(=O)N2CCC3(CC2)CC(=O)c2cc(F)ccc2N3)cc1F] | N-(4-amino-2,5-difluorobenzyl)-6'-fluoro-4'-oxo-3',4'-dihydro-1'H-spiro[piperidine-4,2'-quinoline]-1-carboxamide | 0.113 | >10 |
| 50 | 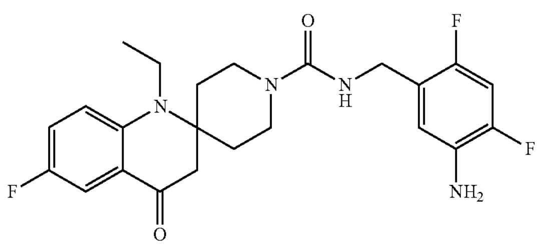 [SMILES: CCN1c2ccc(F)cc2C(=O)CC12CCN(C(=O)NCc1cc(N)c(F)cc1F)CC2] | N-(5-amino-2,4-difluorobenzyl)-1'-ethyl-6'-fluoro-4'-oxo-3',4'-dihydro-1'H-spiro[piperidine-4,2'-quinoline]-1-carboxamide | 0.122 | >10 |
| 51 | 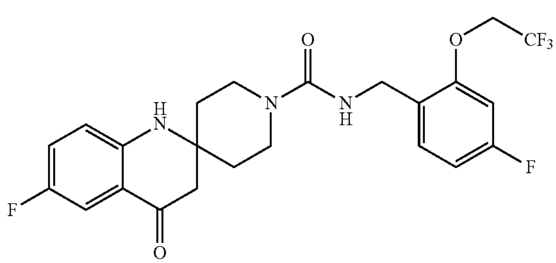 [SMILES: O=C1CC2(CCN(C(=O)NCc3ccc(F)cc3OCC(F)(F)F)CC2)Nc2ccc(F)cc21] | 6'-fluoro-N-(4-fluoro-2-(2,2,2-trifluoroethoxy)benzyl)-4'-oxo-3',4'-dihydro-1'H-spiro[piperidine-4,2'-quinoline]-1-carboxamide | 0.128 | 4.754 |
| 52 | 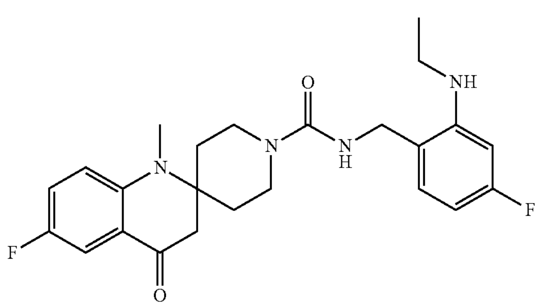 [SMILES: CCNc1cc(F)ccc1CNC(=O)N1CCC2(CC1)CC(=O)c1cc(F)ccc1N2C] | N-(2-(ethylamino)-4-fluorobenzyl)-6'-fluoro-1'-methyl-4'-oxo-3',4'-dihydro-1'H-spiro[piperidine-4,2'-quinoline]-1-carboxamide | 0.139 | >10 |

-continued

| Ex. # | Structure | Structure name | H460 Qualified absolute AC$_{50}$ (μM) | HARA Qualified absolute AC$_{50}$ (μM) |
| --- | --- | --- | --- | --- |
| 53 | 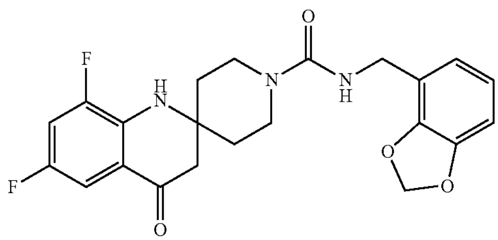 [SMILES: O=C1CC2(CCN(C(=O)NCc3cccc4c3OCO4)CC2)Nc2c(F)cc(F)cc21] | N-(benzo[d][1,3]dioxol-4-ylmethyl)-6',8'-difluoro-4'-oxo-3',4'-dihydro-1'H-spiro[piperidine-4,2'-quinoline]-1-carboxamide | 0.141 | 2.024 |
| 54 | 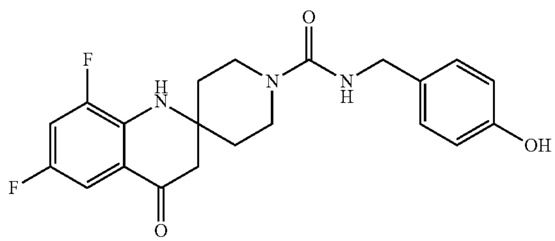 [SMILES: O=C1CC2(CCN(C(=O)NCc3ccc(O)cc3)CC2)Nc2c(F)cc(F)cc21] | 6',8'-difluoro-N-(4-hydroxybenzyl)-4'-oxo-3',4'-dihydro-1'H-spiro[piperidine-4,2'-quinoline]-1-carboxamide | 0.003 | 9.852 |
| 55 | 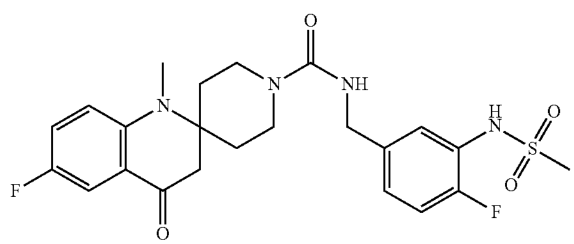 [SMILES: CN1c2ccc(F)cc2C(=O)CC12CCN(C(=O)NCc1ccc(F)c(NS(C)(=O)=O)c1)CC2] | 6'-fluoro-N-(4-fluoro-3-(methylsulfonamido)benzyl)-1'-methyl-4'-oxo-3',4'-dihydro-1'H-spiro[piperidine-4,2'-quinoline]-1-carboxamide | 0.150 | 5.168 |
| 56 | 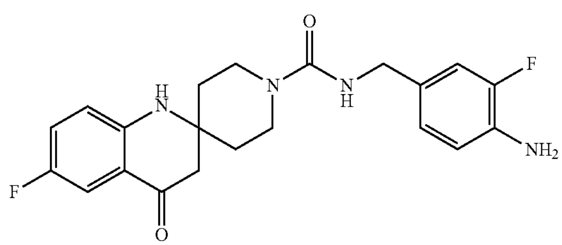 [SMILES: Nc1ccc(CNC(=O)N2CCC3(CC2)CC(=O)c2cc(F)ccc2N3)cc1F] | N-(4-amino-3-fluorobenzyl)-6'-fluoro-4'-oxo-3',4'-dihydro-1'H-spiro[piperidine-4,2'-quinoline]-1-carboxamide | 0.166 | >10 |
| 57 | 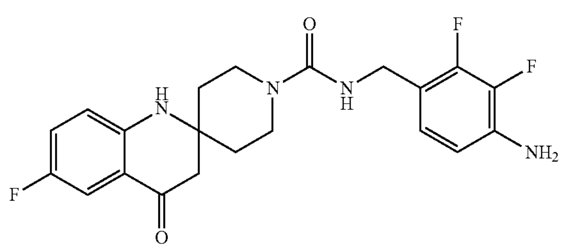 [SMILES: Nc1ccc(CNC(=O)N2CCC3(CC2)CC(=O)c2cc(F)ccc2N3)c(F)c1F] | N-(4-amino-2,3-difluorobenzyl)-6'-fluoro-4'-oxo-3',4'-dihydro-1'H-spiro[piperidine-4,2'-quinoline]-1-carboxamide | 0.170 | >10 |
| 58 | 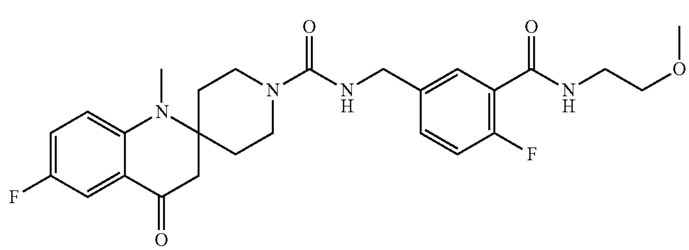 [SMILES: COCCNC(=O)c1cc(CNC(=O)N2CCC3(CC2)CC(=O)c2cc(F)ccc2N3C)ccc1F] | 6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide | 0.181 | |

| Ex. # | Structure | Structure name | H460 Qualified absolute AC$_{50}$ (μM) | HARA Qualified absolute AC$_{50}$ (μM) |
|---|---|---|---|---|
| 59 | 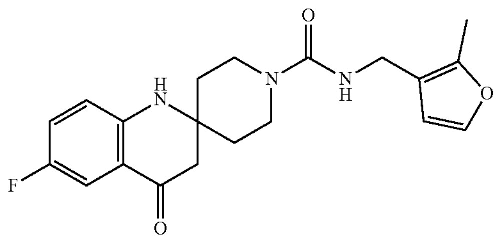 [SMILES: Cc1occc1CNC(=O)N1CCC2(CC1)CC(=O)c1cc(F)ccc1N2] | 6'-fluoro-N-((2-methylfuran-3-yl)methyl)-4'-oxo-3',4'-dihydro-1'H-spiro[piperidine-4,2'-quinoline]-1-carboxamide | 0.185 | |
| 60 | 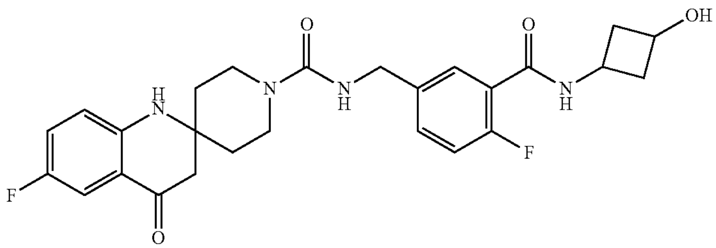 [SMILES: O=C(NC1CC(O)C1)c1cc(CNC(=O)N2CCC3(CC2)CC(=O)c2cc(F)ccc2N3)ccc1F] | 6'-fluoro-N-(4-fluoro-3-((3-hydroxycyclobutyl)carbamoyl)benzyl)-4'-oxo-3',4'-dihydro-1'H-spiro[piperidine-4,2'-quinoline]-1-carboxamide | 0.198 | |
| 61 | 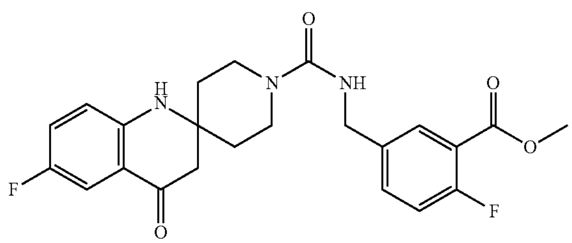 [SMILES: COC(=O)c1cc(CNC(=O)N2CCC3(CC2)CC(=O)c2cc(F)ccc2N3)ccc1F] | methyl 2-fluoro-5-((6'-fluoro-4'-oxo-3',4'-dihydro-1'H-spiro[piperidine-4,2'-quinoline]-1-carboxamido)methyl)benzoate | 0.205 | 3.042 |
| 62 | 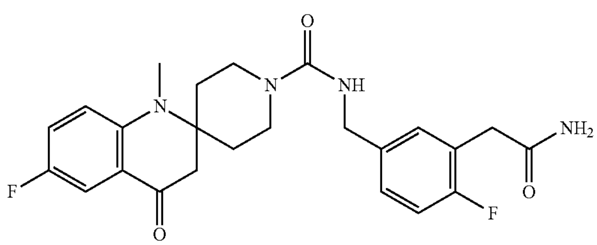 [SMILES: CN1c2ccc(F)cc2C(=O)CC12CCN(C(=O)NCc1ccc(F)c(CC(N)=O)c1)CC2] | N-(3-(2-amino-2-oxoethyl)-4-fluorobenzyl)-6'-fluoro-1'-methyl-4'-oxo-3',4'-dihydro-1'H-spiro[piperidine-4,2'-quinoline]-1-carboxamide | 0.212 | >10 |
| 63 | 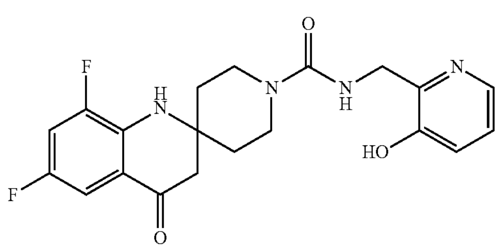 [SMILES: O=C1CC2(CCN(C(=O)NCc3ncccc3O)CC2)Nc2c(F)cc(F)cc21] | 6',8'-difluoro-N-((3-hydroxypyridin-2-yl)methyl)-4'-oxo-3',4'-dihydro-1'H-spiro[piperidine-4,2'-quinoline]-1-carboxamide | 0.222 | >10 |
| 64 | 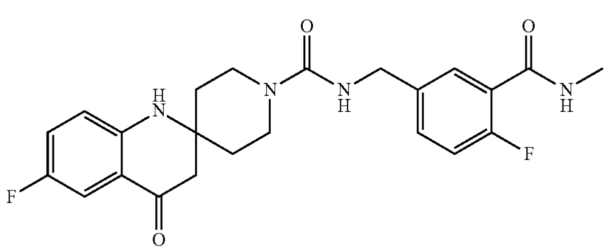 [SMILES: CNC(=O)c1cc(CNC(=O)N2CCC3(CC2)CC(=O)c2cc(F)ccc2N3)ccc1F] | 6'-fluoro-N-(4-fluoro-3-(methylcarbamoyl)benzyl)-4'-oxo-3',4'-dihydro-1'H-spiro[piperidine-4,2'-quinoline]-1-carboxamide | 0.222 | >10 |

| Ex. # | Structure | Structure name | H460 Qualified absolute $AC_{50}$ (μM) | HARA Qualified absolute $AC_{50}$ (μM) |
|---|---|---|---|---|
| 65 | 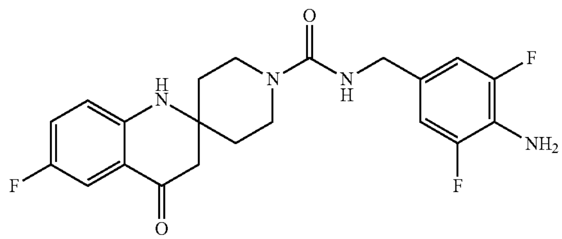 [SMILES: Nc1c(F)cc(CNC(=O)N2CCC3(CC2)CC(=O)c2cc(F)ccc2N3)cc1F] | N-(4-amino-3,5-difluorobenzyl)-6'-fluoro-4'-oxo-3',4'-dihydro-1'H-spiro[piperidine-4,2'-quinoline]-1-carboxamide | 0.222 | >10 |
| 66 | 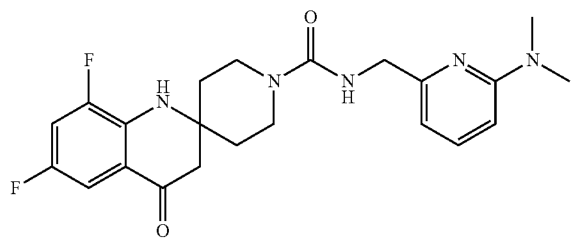 [SMILES: CN(C)c1cccc(CNC(=O)N2CCC3(CC2)CC(=O)c2cc(F)cc(F)c2N3)n1] | N-((6-(dimethylamino)pyridin-2-yl)methyl)-6',8'-difluoro-4'-oxo-3',4'-dihydro-1'H-spiro[piperidine-4,2'-quinoline]-1-carboxamide | 0.223 | >10 |
| 67 | 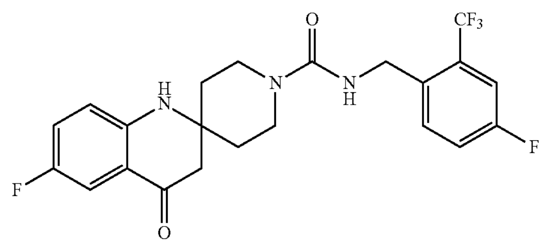 [SMILES: O=C1CC2(CCN(C(=O)NCc3ccc(F)cc3C(F)(F)F)CC2)Nc2ccc(F)cc21] | 6'-fluoro-N-(4-fluoro-2-(trifluoromethyl)benzyl)-4'-oxo-3',4'-dihydro-1'H-spiro[piperidine-4,2'-quinoline]-1-carboxamide | 0.225 | 2.300 |
| 68 | 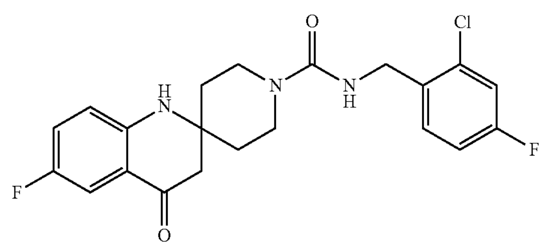 [SMILES: O=C1CC2(CCN(C(=O)NCc3ccc(F)cc3Cl)CC2)Nc2ccc(F)cc21] | N-(2-chloro-4-fluorobenzyl)-6'-fluoro-4'-oxo-3',4'-dihydro-1'H-spiro[piperidine-4,2'-quinoline]-1-carboxamide | 0.226 | 9.143 |
| 69 | 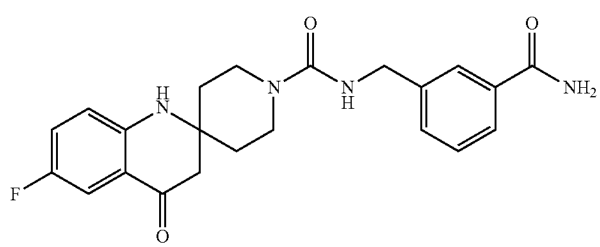 [SMILES: NC(=O)c1cccc(CNC(=O)N2CCC3(CC2)CC(=O)c2cc(F)ccc2N3)c1] | N-(3-carbamoylbenzyl)-6'-fluoro-4'-oxo-3',4'-dihydro-1'H-spiro[piperidine-4,2'-quinoline]-1-carboxamide | 0.233 | >10 |
| 70 | 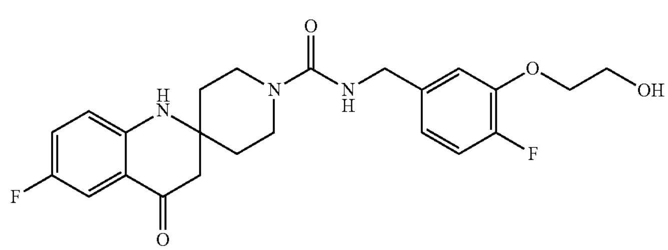 [SMILES: O=C1CC2(CCN(C(=O)NCc3ccc(F)c(OCCO)c3)CC2)Nc2ccc(F)cc21] | 6'-fluoro-N-(4-fluoro-3-(2-hydroxyethoxy)benzyl)-4'-oxo-3',4'-dihydro-1'H-spiro[piperidine-4,2'-quinoline]-1-carboxamide | 0.238 | 3.546 |

-continued

| Ex. # | Structure | Structure name | H460 Qualified absolute AC$_{50}$ (μM) | HARA Qualified absolute AC$_{50}$ (μM) |
|---|---|---|---|---|
| 71 | 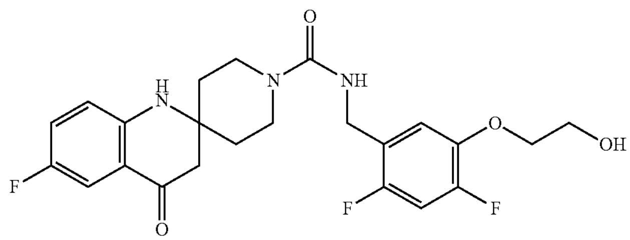 [SMILES: O=C1CC2(CCN(C(=O)NCc3cc(OCCO)c(F)cc3F)CC2)Nc2ccc(F)cc21] | N-(2,4-difluoro-5-(2-hydroxyethoxy)benzyl)-6'-fluoro-4'-oxo-3',4'-dihydro-1'H-spiro[piperidine-4,2'-quinoline]-1-carboxamide | 0.265 | >10 |
| 72 | 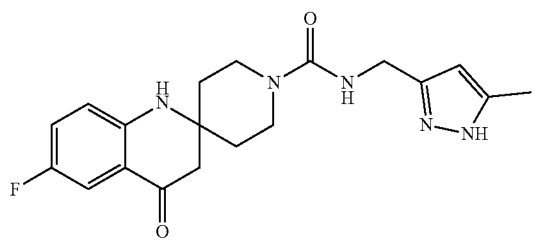 [SMILES: Cc1cc(CNC(=O)N2CCC3(CC2)CC(=O)c2cc(F)ccc2N3)n[nH]1] | 6'-fluoro-N-((5-methyl-1H-pyrazol-3-yl)methyl)-4'-oxo-3',4'-dihydro-1'H-spiro[piperidine-4,2'-quinoline]-1-carboxamide | 0.282 | |
| 73 | 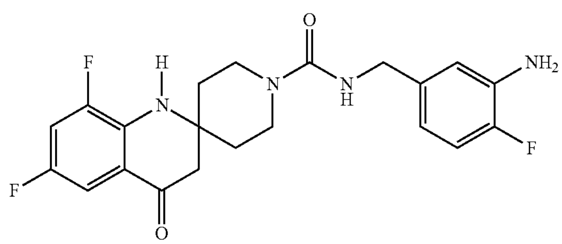 [SMILES: Nc1cc(CNC(=O)N2CCC3(CC2)CC(=O)c2cc(F)cc(F)c2N3)ccc1F] | N-(3-amino-4-fluorobenzyl)-6',8'-difluoro-4'-oxo-3',4'-dihydro-1'H-spiro[piperidine-4,2'-quinoline]-1-carboxamide | 0.295 | 3.483 |
| 74 | 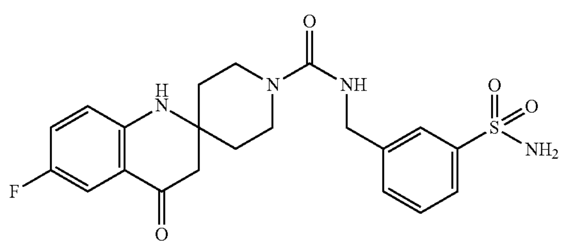 [SMILES: NS(=O)(=O)c1cccc(CNC(=O)N2CCC3(CC2)CC(=O)c2cc(F)ccc2N3)c1] | 6'-fluoro-4'-oxo-N-(3-sulfamoylbenzyl)-3',4'-dihydro-1'H-spiro[piperidine-4,2'-quinoline]-1-carboxamide | 0.305 | >10 |
| 75 | 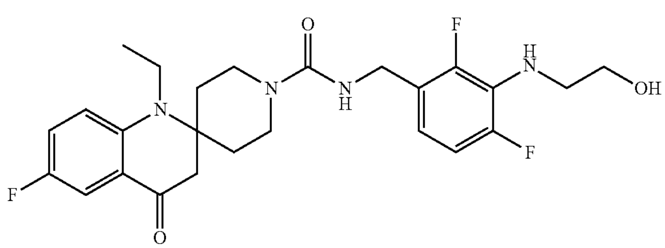 [SMILES: CCN1c2ccc(F)cc2C(=O)CC12CCN(C(=O)NCc1ccc(F)c(NCCO)c1F)CC2] | N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide | 0.306 | >10 |
| 76 | 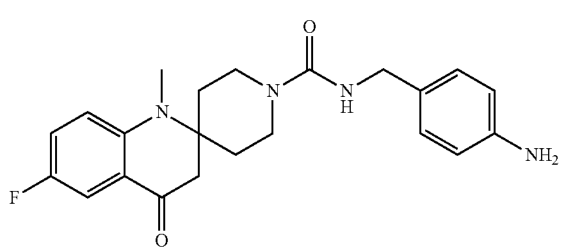 [SMILES: CN1c2ccc(F)cc2C(=O)CC12CCN(C(=O)NCc1ccc(N)cc1)CC2] | N-(4-aminobenzyl)-6'-fluoro-1'-methyl-4'-oxo-3',4'-dihydro-1'H-spiro[piperidine-4,2'-quinoline]-1-carboxamide | 0.309 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 77 | 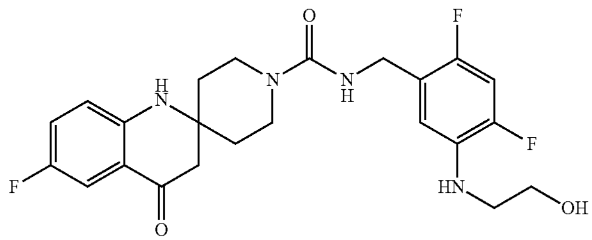 [SMILES: O=C1CC2(CCN(C(=O)NCc3cc(NCCO)c(F)cc3F)CC2)Nc2ccc(F)cc21] | N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide | 0.311 | >10 |
| 78 | 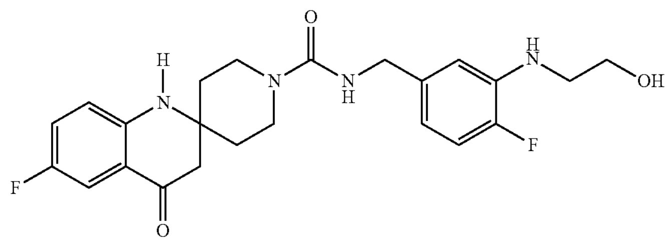 [SMILES: O=C1CC2(CCN(C(=O)NCc3ccc(F)c(NCCO)c3)CC2)Nc2ccc(F)cc21] | 6'-fluoro-N-(4-fluoro-3-((2-hydroxyethyl)amino)benzyl)-4'-oxo-3',4'-dihydro-1'H-spiro[piperidine-4,2'-quinoline]-1-carboxamide | 0.321 | >10 |
| 79 | 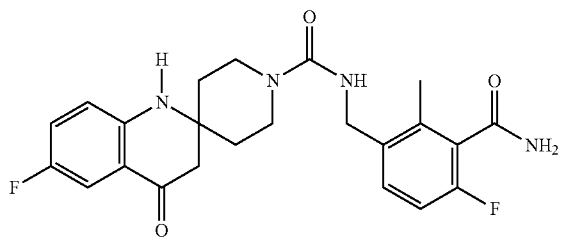 [SMILES: Cc1c(CNC(=O)N2CCC3(CC2)CC(=O)c2cc(F)ccc2N3)ccc(F)c1C(N)=O] | N-(3-carbamoyl-4-fluoro-2-methylbenzyl)-6'-fluoro-4'-oxo-3',4'-dihydro-1'H-spiro[piperidine-4,2'-quinoline]-1-carboxamide | 0.345 | |
| 80 | 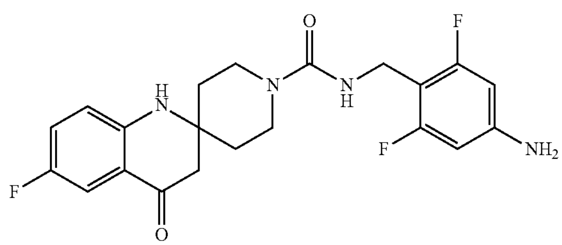 [SMILES: Nc1cc(F)c(CNC(=O)N2CCC3(CC2)CC(=O)c2cc(F)ccc2N3)c(F)c1] | N-(4-amino-2,6-difluorobenzyl)-6'-fluoro-4'-oxo-3',4'-dihydro-1'H-spiro[piperidine-4,2'-quinoline]-1-carboxamide | 0.347 | >10 |
| 81 | 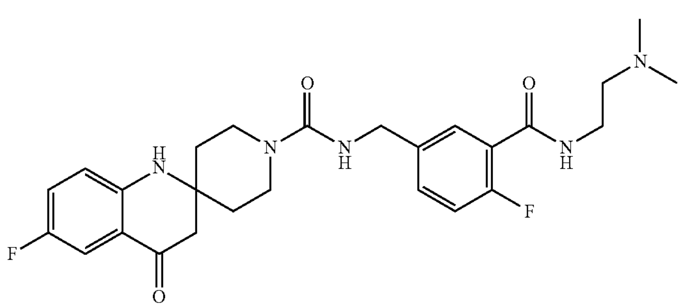 [SMILES: CN(C)CCNC(=O)c1cc(CNC(=O)N2CCC3(CC2)CC(=O)c2cc(F)ccc2N3)ccc1F] | N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide | 0.352 | |
| 82 | 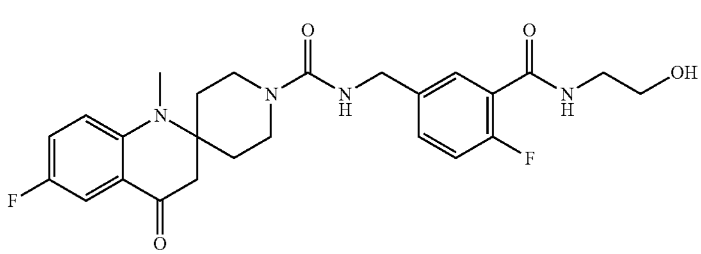 [SMILES: CN1c2ccc(F)cc2C(=O)CC12CCN(C(=O)NCc1ccc(F)c(C(=O)NCCO)c1)CC2] | 6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide | 0.356 | >10 |

-continued

| Ex. # | Structure | Structure name | H460 Qualified absolute $AC_{50}$ (μM) | HARA Qualified absolute $AC_{50}$ (μM) |
|---|---|---|---|---|
| 83 | 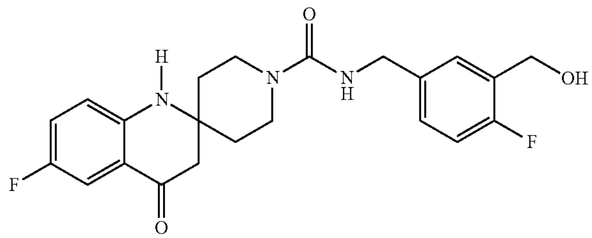 [SMILES: O=C1CC2(CCN(C(=O)NCc3ccc(F)c(CO)c3)CC2)Nc2ccc(F)cc21] | 6'-fluoro-N-(4-fluoro-3-(hydroxymethyl)benzyl)-4'-oxo-3',4'-dihydro-1'H-spiro[piperidine-4,2'-quinoline]-1-carboxamide | 0.361 | >10 |
| 84 | 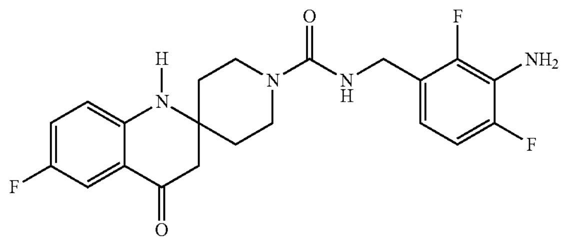 [SMILES: Nc1c(F)ccc(CNC(=O)N2CCC3(CC2)CC(=O)c2cc(F)ccc2N3)c1F] | N-(3-amino-2,4-difluorobenzyl)-6'-fluoro-4'-oxo-3',4'-dihydro-1'H-spiro[piperidine-4,2'-quinoline]-1-carboxamide | 0.367 | >10 |
| 85 | 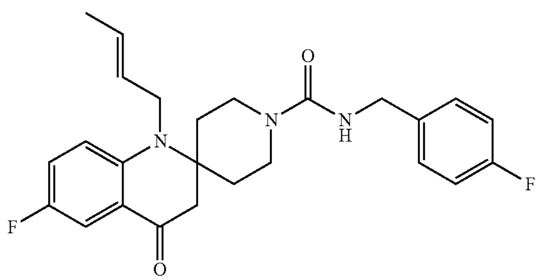 [SMILES: C/C=C/CN1c2ccc(F)cc2C(=O)CC12CCN(C(=O)NCc1ccc(F)cc1)CC2] | (E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide | 0.371 | 9.487 |
| 86 | 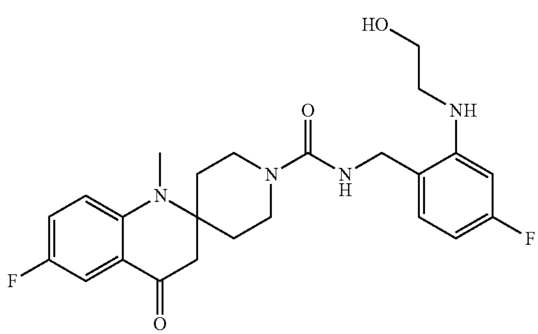 [SMILES: CN1c2ccc(F)cc2C(=O)CC12CCN(C(=O)NCc1ccc(F)cc1NCCO)CC2] | 6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide | 0.379 | >10 |
| 87 | 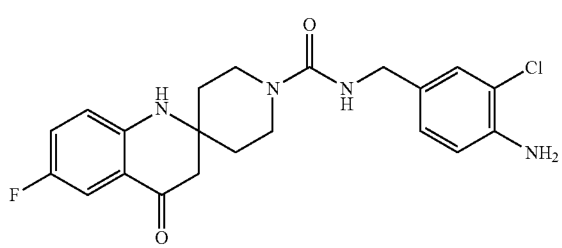 [SMILES: Nc1ccc(CNC(=O)N2CCC3(CC2)CC(=O)c2cc(F)ccc2N3)cc1Cl] | N-(4-amino-3-chlorobenzyl)-6'-fluoro-4'-oxo-3',4'-dihydro-1'H-spiro[piperidine-4,2'-quinoline]-1-carboxamide | 0.388 | >10 |

| Ex. # | Structure | Structure name | H460 Qualified absolute AC$_{50}$ (μM) | HARA Qualified absolute AC$_{50}$ (μM) |
|---|---|---|---|---|
| 88 | 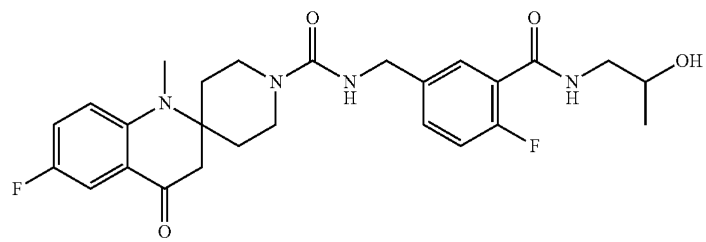 [SMILES: CC(O)CNC(=O)c1cc(CNC(=O)N2CCC3(CC2)CC(=O)c2cc(F)ccc2N3C)ccc1F] | 6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide | 0.421 | |
| 89 | 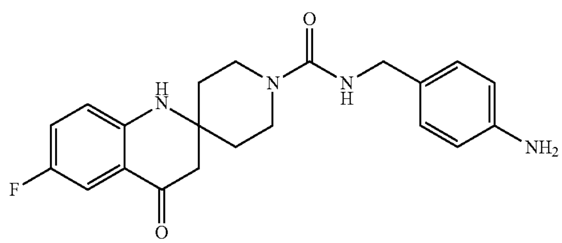 [SMILES: Nc1ccc(CNC(=O)N2CCC3(CC2)CC(=O)c2cc(F)ccc2N3)cc1] | N-(4-aminobenzyl)-6'-fluoro-4'-oxo-3',4'-dihydro-1'H-spiro[piperidine-4,2'-quinoline]-1-carboxamide | 0.436 | >10 |
| 90 | 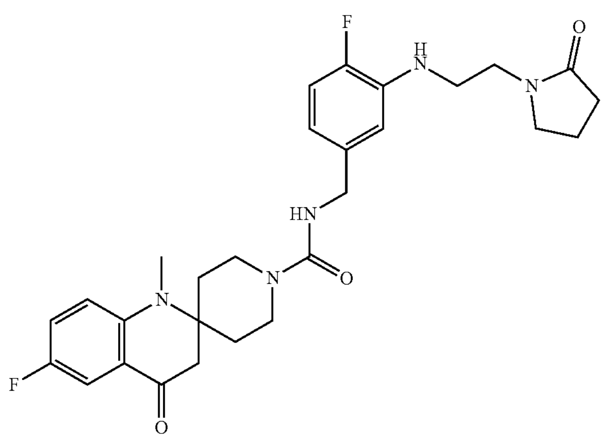 [SMILES: CN1c2ccc(F)cc2C(=O)CC12CCN(C(=O)NCc1ccc(F)c(NCCN3CCCC3=O)c1)CC2] | 6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide | 0.443 | |
| 91 | 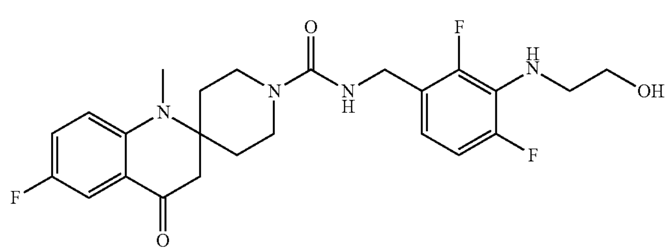 [SMILES: CN1c2ccc(F)cc2C(=O)CC12CCN(C(=O)NCc1ccc(F)c(NCCO)c1F)CC2] | N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide | 0.451 | >10 |
| 92 | 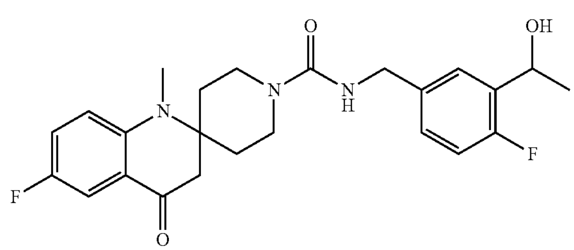 [SMILES: CC(O)c1cc(CNC(=O)N2CCC3(CC2)CC(=O)c2cc(F)ccc2N3C)ccc1F] | 6'-fluoro-N-(4-fluoro-3-(1-hydroxyethyl)benzyl)-1'-methyl-4'-oxo-3',4'-dihydro-1'H-spiro[piperidine-4,2'-quinoline]-1-carboxamide | 0.467 | >10 |

-continued

| Ex. # | Structure | Structure name | H460 Qualified absolute $AC_{50}$ (μM) | HARA Qualified absolute $AC_{50}$ (μM) |
|---|---|---|---|---|
| 93 | 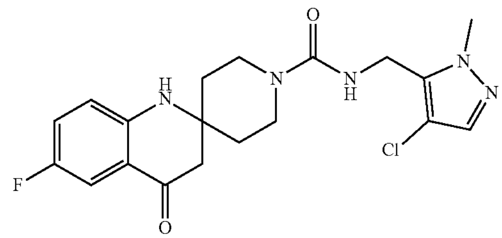 [SMILES: Cn1ncc(Cl)c1CNC(=O)N1CCC2(CC1)CC(=O)c1cc(F)ccc1N2] | N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide | 5.733 | >10 |
| 94 | 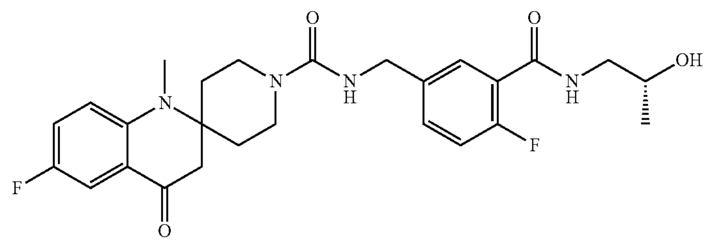 [SMILES: C[C@@H](O)CNC(=O)c1cc(CNC(=O)N2CCC3(CC2)CC(=O)c2cc(F)ccc2N3C)ccc1F] | (R)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide | 0.471 | 9.490 |
| 95 | 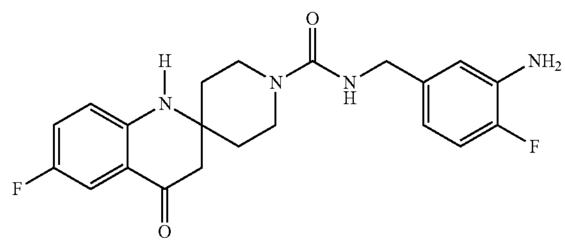 [SMILES: Nc1cc(CNC(=O)N2CCC3(CC2)CC(=O)c2cc(F)ccc2N3)ccc1F] | N-(3-amino-4-fluorobenzyl)-6'-fluoro-4'-oxo-3',4'-dihydro-1'H-spiro[piperidine-4,2'-quinoline]-1-carboxamide | 0.485 | >10 |
| 96 | 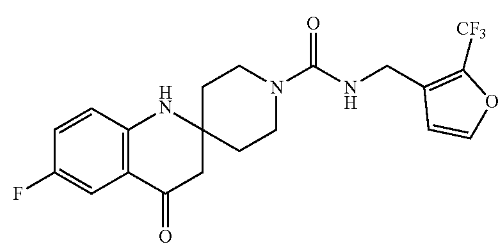 [SMILES: O=C1CC2(CCN(C(=O)NCc3ccoc3C(F)(F)F)CC2)Nc2ccc(F)cc21] | 6'-fluoro-4'-oxo-N-((2-(trifluoromethyl)furan-3-yl)methyl)-3',4'-dihydro-1'H-spiro[piperidine-4,2'-quinoline]-1-carboxamide | 0.489 | |
| 97 | 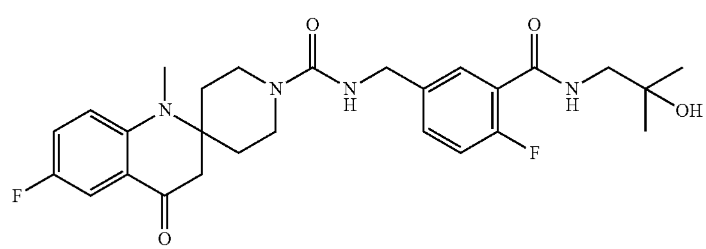 [SMILES: CN1c2ccc(F)cc2C(=O)CC12CCN(C(=O)NCc1ccc(F)c(C(=O)NCC(C)(C)O)c1)CC2] | 6'-fluoro-N-(4-fluoro-3-((2-hydroxy-2-methylpropyl)carbamoyl)benzyl)-1'-methyl-4'-oxo-3',4'-dihydro-1'H-spiro[piperidine-4,2'-quinoline]-1-carboxamide | 0.491 | |
| 98 | 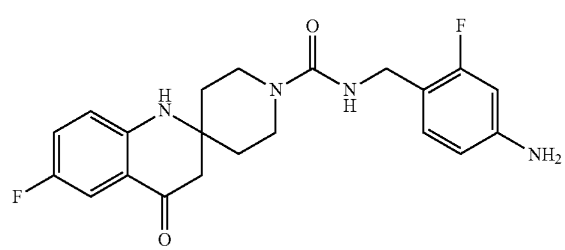 [SMILES: Nc1ccc(CNC(=O)N2CCC3(CC2)CC(=O)c2cc(F)ccc2N3)c(F)c1] | N-(4-amino-2-fluorobenzyl)-6'-fluoro-4'-oxo-3',4'-dihydro-1'H-spiro[piperidine-4,2'-quinoline]-1-carboxamide | 0.498 | >10 |

| Ex. # | Structure | Structure name | H460 Qualified absolute AC$_{50}$ (μM) | HARA Qualified absolute AC$_{50}$ (μM) |
|---|---|---|---|---|
| 99 | 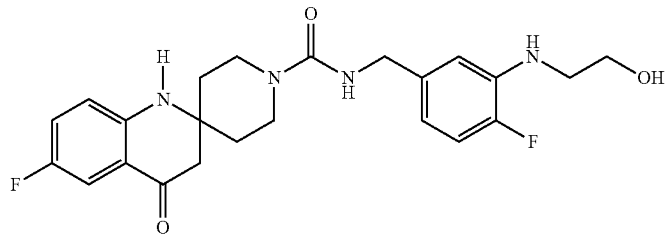 [SMILES: O=C1CC2(CCN(C(=O)NCc3ccc(F)c(NCCO)c3)CC2)Nc2ccc(F)cc21] | 6'-fluoro-N-(4-fluoro-3-((2-methoxyethyl)amino)benzyl)-4'-oxo-3',4'-dihydro-1'H-spiro[piperidine-4,2'-quinoline]-1-carboxamide | 0.507 | >10 |
| 100 | 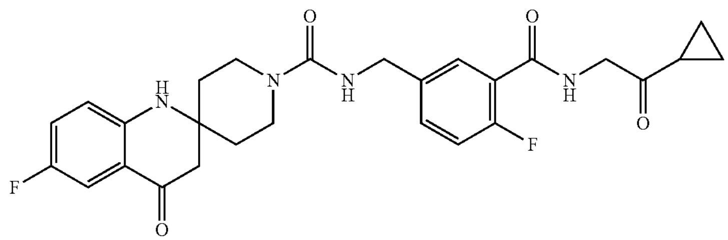 [SMILES: O=C(NCC(=O)C1CC1)c1cc(CNC(=O)N2CCC3(CC2)CC(=O)c2cc(F)ccc2N3)ccc1F] | N-(3-((2-cyclopropyl-2-oxoethyl)carbamoyl)-4-fluorobenzyl)-6'-fluoro-4'-oxo-3',4'-dihydro-1'H-spiro[piperidine-4,2'-quinoline]-1-carboxamide | 0.518 | |
| 101 | 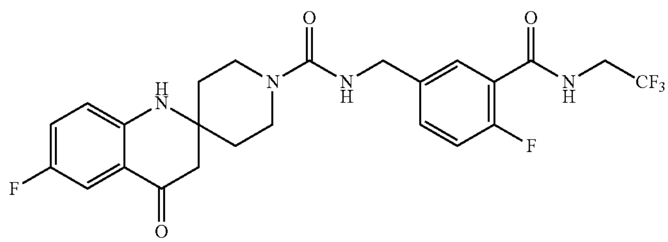 [SMILES: O=C(NCC(F)(F)F)c1cc(CNC(=O)N2CCC3(CC2)CC(=O)c2cc(F)ccc2N3)ccc1F] | 6'-fluoro-N-(4-fluoro-3-((2,2,2-trifluoroethyl)carbamoyl)benzyl)-4'-oxo-3',4'-dihydro-1'H-spiro[piperidine-4,2'-quinoline]-1-carboxamide | 0.528 | >10 |
| 102 | 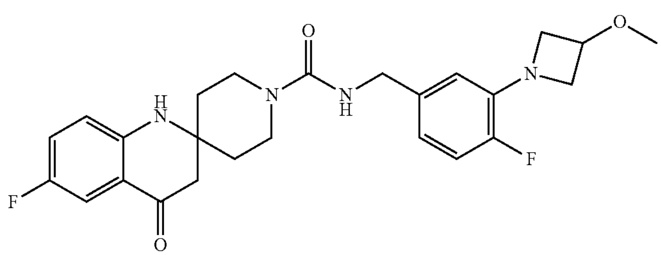 [SMILES: COC1CN(c2cc(CNC(=O)N3CCC4(CC3)CC(=O)c3cc(F)ccc3N4)ccc2F)C1] | 6'-fluoro-N-(4-fluoro-3-(3-methoxyazetidin-1-yl)benzyl)-4'-oxo-3',4'-dihydro-1'H-spiro[piperidine-4,2'-quinoline]-1-carboxamide | 0.555 | 3.716 |
| 103 | 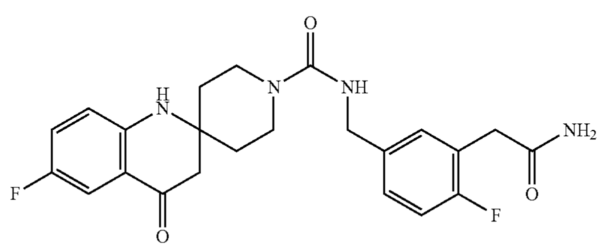 [SMILES: NC(=O)Cc1cc(CNC(=O)N2CCC3(CC2)CC(=O)c2cc(F)ccc2N3)ccc1F] | N-(3-(2-amino-2-oxoethyl)-4-fluorobenzyl)-6'-fluoro-4'-oxo-3',4'-dihydro-1'H-spiro[piperidine-4,2'-quinoline]-1-carboxamide | 0.558 | >10 |
| 104 | 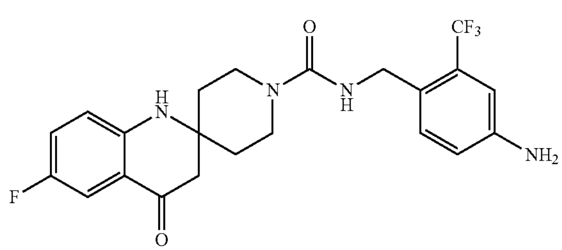 [SMILES: Nc1ccc(CNC(=O)N2CCC3(CC2)CC(=O)c2cc(F)ccc2N3)c(C(F)(F)F)c1] | N-(4-amino-2-(trifluoromethyl)benzyl)-6'-fluoro-4'-oxo-3',4'-dihydro-1'H-spiro[piperidine-4,2'-quinoline]-1-carboxamide | 0.573 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 105 | 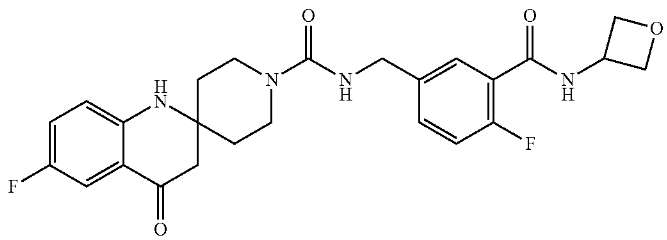 [SMILES: O=C(NC1COC1)c1cc(CNC(=O)N2CCC3(CC2)CC(=O)c2cc(F)ccc2N3)ccc1F] | 6'-fluoro-N-(4-fluoro-3-(oxetan-3-ylcarbamoyl)benzyl)-4'-oxo-3',4'-dihydro-1'H-spiro[piperidine-4,2'-quinoline]-1-carboxamide | 0.580 | >10 |
| 106 | 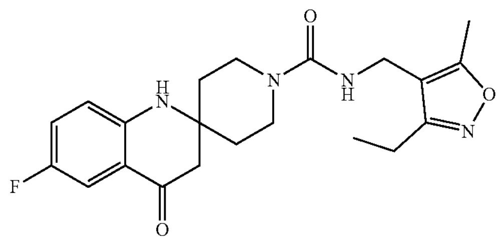 [SMILES: CCc1noc(C)c1CNC(=O)N1CCC2(CC1)CC(=O)c1cc(F)ccc1N2] | N-((3-ethyl-5-methylisoxazol-4-yl)methyl)-6'-fluoro-4'-oxo-3',4'-dihydro-1'H-spiro[piperidine-4,2'-quinoline]-1-carboxamide | 0.598 | |
| 107 | 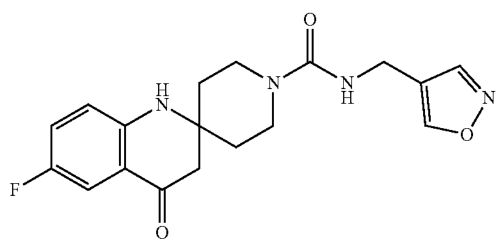 [SMILES: O=C1CC2(CCN(C(=O)NCc3cnoc3)CC2)Nc2ccc(F)cc21] | 6'-fluoro-N-(isoxazol-4-ylmethyl)-4'-oxo-3',4'-dihydro-1'H-spiro[piperidine-4,2'-quinoline]-1-carboxamide | 0.612 | >10 |
| 108 | 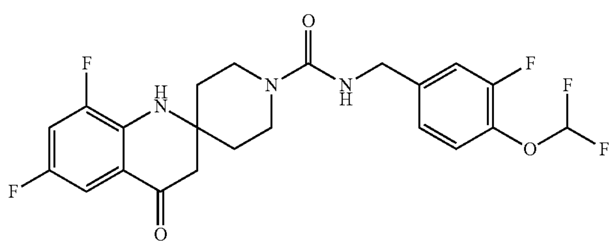 [SMILES: O=C1CC2(CCN(C(=O)NCc3ccc(OC(F)F)c(F)c3)CC2)Nc2c(F)cc(F)cc21] | N-(4-(difluoromethoxy)-3-fluorobenzyl)-6',8'-difluoro-4'-oxo-3',4'-dihydro-1'H-spiro[piperidine-4,2'-quinoline]-1-carboxamide | 0.646 | 3.181 |
| 109 | 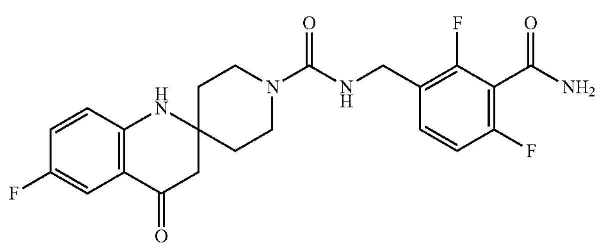 [SMILES: NC(=O)c1c(F)ccc(CNC(=O)N2CCC3(CC2)CC(=O)c2cc(F)ccc2N3)c1F] | N-(3-carbamoyl-2,4-difluorobenzyl)-6'-fluoro-4'-oxo-3',4'-dihydro-1'H-spiro[piperidine-4,2'-quinoline]-1-carboxamide | 0.690 | >10 |
| 110 | 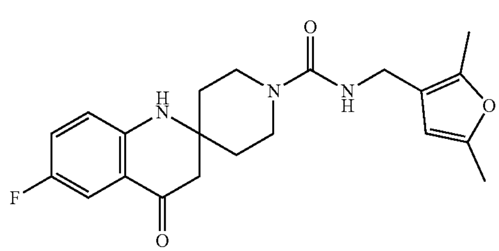 [SMILES: Cc1cc(CNC(=O)N2CCC3(CC2)CC(=O)c2cc(F)ccc2N3)c(C)o1] | N-((2,5-dimethylfuran-3-yl)methyl)-6'-fluoro-4'-oxo-3',4'-dihydro-1'H-spiro[piperidine-4,2'-quinoline]-1-carboxamide | 0.700 | |

-continued

| Ex. # | Structure | Structure name | H460 Qualified absolute AC$_{50}$ (μM) | HARA Qualified absolute AC$_{50}$ (μM) |
|---|---|---|---|---|
| 111 | 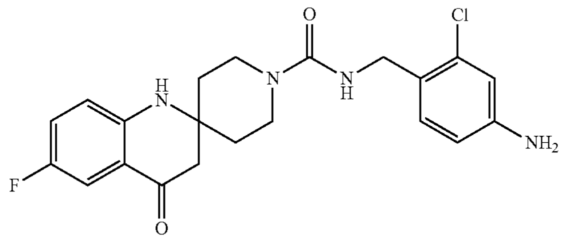 [SMILES: Nc1ccc(CNC(=O)N2CCC3(CC2)CC(=O)c2cc(F)ccc2N3)c(Cl)c1] | N-(4-amino-2-chlorobenzyl)-6'-fluoro-4'-oxo-3',4'-dihydro-1'H-spiro[piperidine-4,2'-quinoline]-1-carboxamide | 0.733 | >10 |
| 112 | 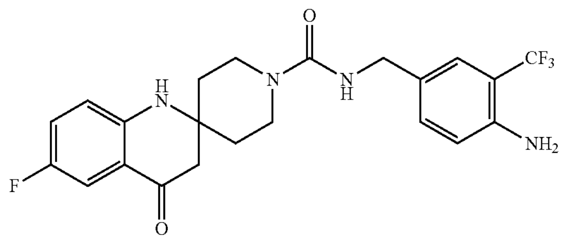 | N-(4-amino-3-(trifluoromethyl)benzyl)-6'-fluoro-4'-oxo-3',4'-dihydro-1'H-spiro[piperidine-4,2'-quinoline]-1-carboxamide | 0.783 | >10 |
| 113 | 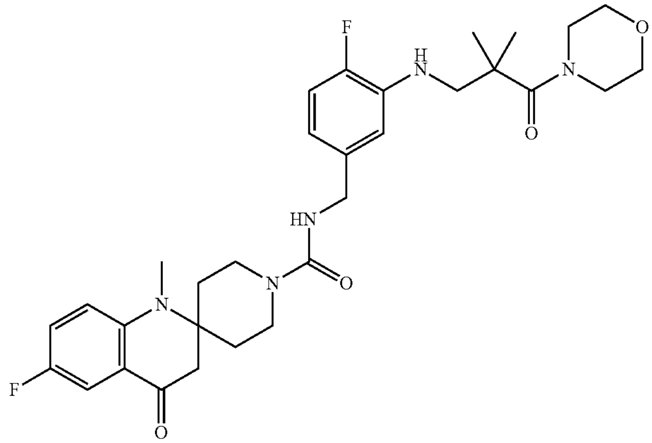 [SMILES: CN1c2ccc(F)cc2C(=O)CC12CCN(C(=O)NCc1ccc(F)c(NCC(C)(C)C(=O)N3CCOCC3)c1)CC2] | N-(3-((2,2-dimethyl-3-morpholino-3-oxopropyl)amino)-4-fluorobenzyl)-6'-fluoro-1'-methyl-4'-oxo-3',4'-dihydro-1'H-spiro[piperidine-4,2'-quinoline]-1-carboxamide | 0.846 | |
| 114 | 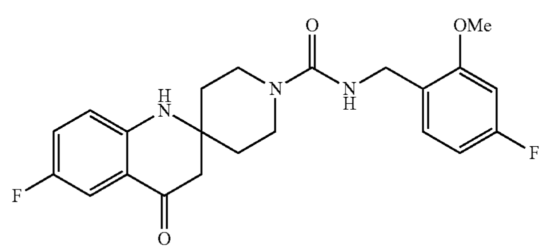 | 6'-fluoro-N-(4-fluoro-2-methoxybenzyl)-4'-oxo-3',4'-dihydro-1'H-spiro[piperidine-4,2'-quinoline]-1-carboxamide | 0.913 | 4.432 |
| 115 | 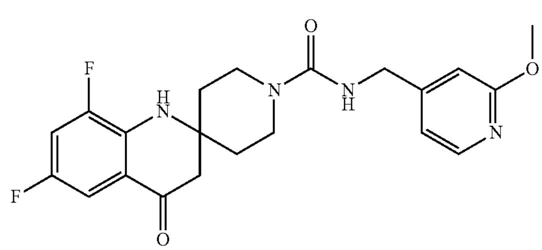 [SMILES: COc1cc(CNC(=O)N2CCC3(CC2)CC(=O)c2cc(F)cc(F)c2N3)ccn1] | 6',8'-difluoro-N-((2-methoxypyridin-4-yl)methyl)-4'-oxo-3',4'-dihydro-1'H-spiro[piperidine-4,2'-quinoline]-1-carboxamide | 0.930 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 116 | 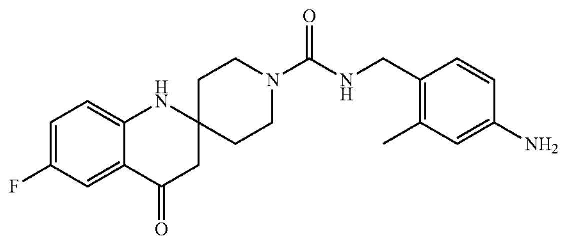 [SMILES: Cc1cc(N)ccc1CNC(=O)N1CCC2(CC1)CC(=O)c1cc(F)ccc1N2] | N-(4-amino-2-methylbenzyl)-6'-fluoro-4'-oxo-3',4'-dihydro-1'H-spiro[piperidine-4,2'-quinoline]-1-carboxamide | 0.935 | >10 |
| 117 | 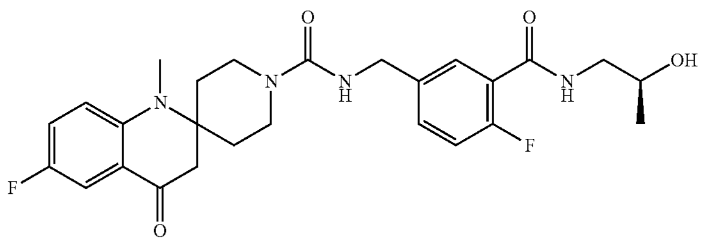 [SMILES: C[C@H](O)CNC(=O)c1cc(CNC(=O)N2CCC3(CC2)CC(=O)c2cc(F)ccc2N3C)ccc1F] | (S)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide | 0.956 | >10 |
| 118 | 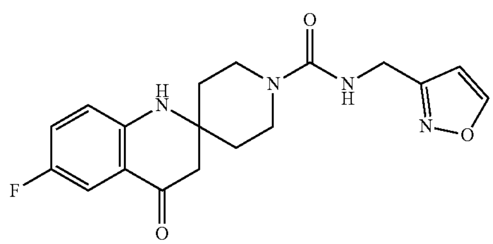 [SMILES: O=C1CC2(CCN(C(=O)NCc3ccon3)CC2)Nc2ccc(F)cc21] | 6'-fluoro-N-(isoxazol-3-ylmethyl)-4'-oxo-3',4'-dihydro-1'H-spiro[piperidine-4,2'-quinoline]-1-carboxamide | 1.014 | >10 |
| 119 | 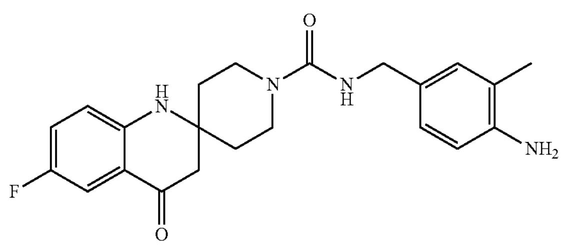 [SMILES: Cc1cc(CNC(=O)N2CCC3(CC2)CC(=O)c2cc(F)ccc2N3)ccc1N] | N-(4-amino-3-methylbenzyl)-6'-fluoro-4'-oxo-3',4'-dihydro-1'H-spiro[piperidine-4,2'-quinoline]-1-carboxamide | 1.023 | >10 |
| 120 | 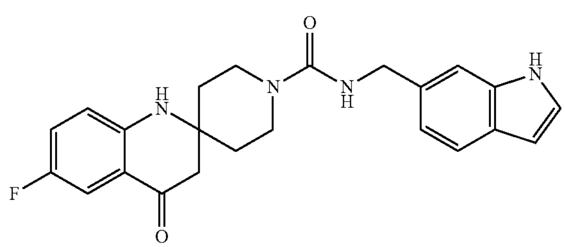 [SMILES: O=C1CC2(CCN(C(=O)NCc3ccc4cc[nH]c4c3)CC2)Nc2ccc(F)cc21] | N-((1H-indol-6-yl)methyl)-6'-fluoro-4'-oxo-3',4'-dihydro-1'H-spiro[piperidine-4,2'-quinoline]-1-carboxamide | 1.050 | >10 |
| 121 | 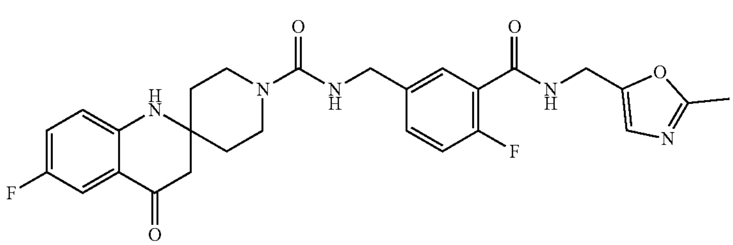 [SMILES: Cc1ncc(CNC(=O)c2cc(CNC(=O)N3CCC4(CC3)CC(=O)c3cc(F)ccc3N4)ccc2F)o1] | 6'-fluoro-N-(4-fluoro-3-(((2-methyloxazol-5-yl)methyl)carbamoyl)benzyl)-4'-oxo-3',4'-dihydro-1'H-spiro[piperidine-4,2'-quinoline]-1-carboxamide | 1.082 | |

-continued

| Ex. # | Structure | Structure name | H460 Qualified absolute AC$_{50}$ (μM) | HARA Qualified absolute AC$_{50}$ (μM) |
|---|---|---|---|---|
| 122 | 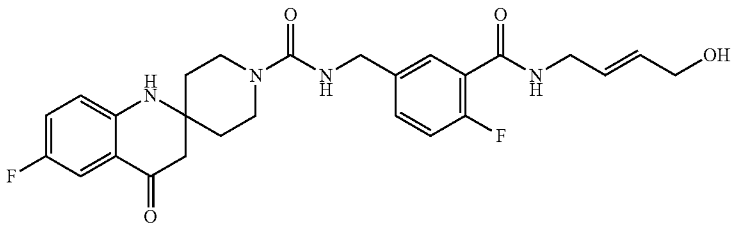 [SMILES: O=C(NC/C=C/CO)c1cc(CNC(=O)N2CCC3(CC2)CC(=O)c2cc(F)ccc2N3)ccc1F] | (E)-6'-fluoro-N-(4-fluoro-3-((4-hydroxybut-2-en-1-yl)carbamoyl)benzyl)-4'-oxo-3',4'-dihydro-1'H-spiro[piperidine-4,2'-quinoline]-1-carboxamide | 1.110 | |
| 123 | 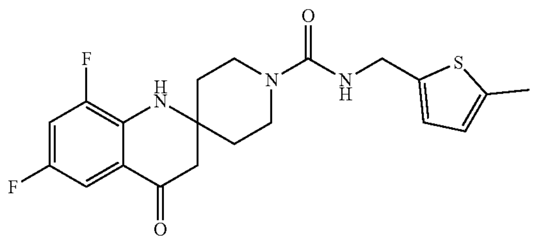 [SMILES: Cc1ccc(CNC(=O)N2CCC3(CC2)CC(=O)c2cc(F)cc(F)c2N3)s1] | 6',8'-difluoro-N-((5-methylthiophen-2-yl)methyl)-4'-oxo-3',4'-dihydro-1'H-spiro[piperidine-4,2'-quinoline]-1-carboxamide | 1.135 | 5.387 |
| 124 | 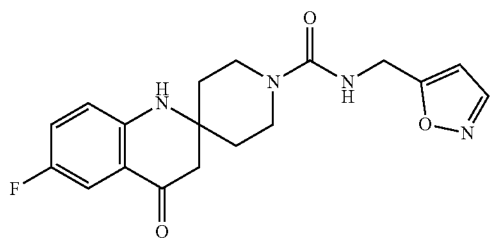 [SMILES: O=C1CC2(CCN(C(=O)NCc3ccno3)CC2)Nc2ccc(F)cc21] | 6'-fluoro-N-(isoxazol-5-ylmethyl)-4'-oxo-3',4'-dihydro-1'H-spiro[piperidine-4,2'-quinoline]-1-carboxamide | 1.157 | >10 |
| 125 | 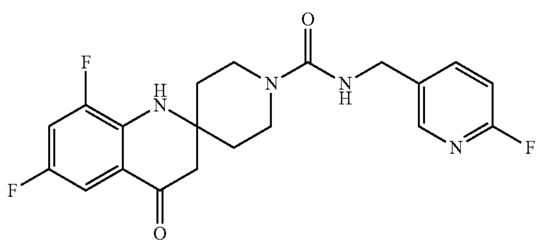 [SMILES: O=C1CC2(CCN(C(=O)NCc3ccc(F)nc3)CC2)Nc2c(F)cc(F)cc21] | 6',8'-difluoro-N-((6-fluoropyridin-3-yl)methyl)-4'-oxo-3',4'-dihydro-1'H-spiro[piperidine-4,2'-quinoline]-1-carboxamide | 1.170 | >10 |
| 126 | 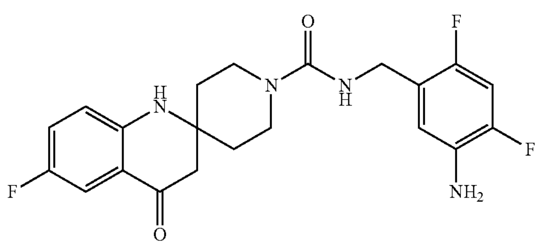 [SMILES: Nc1cc(CNC(=O)N2CCC3(CC2)CC(=O)c2cc(F)ccc2N3)c(F)cc1F] | N-(5-amino-2,4-difluorobenzyl)-6'-fluoro-4'-oxo-3',4'-dihydro-1'H-spiro[piperidine-4,2'-quinoline]-1-carboxamide | 1.293 | >10 |
| 127 | 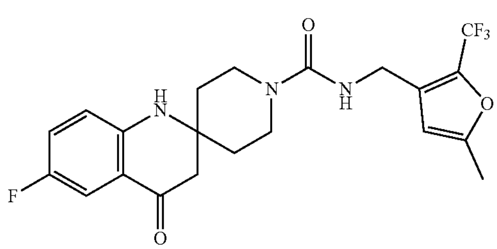 [SMILES: Cc1cc(CNC(=O)N2CCC3(CC2)CC(=O)c2cc(F)ccc2N3)c(C(F)(F)F)o1] | 6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide | 1.430 | |

| Ex. # | Structure | Structure name | H460 Qualified absolute AC$_{50}$ (μM) | HARA Qualified absolute AC$_{50}$ (μM) |
|---|---|---|---|---|
| 128 | 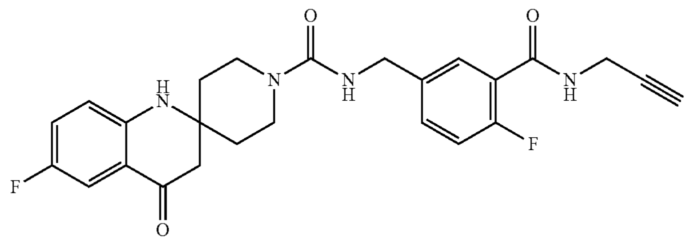 [SMILES: C#CCNC(=O)c1cc(CNC(=O)N2CCC3(CC2)CC(=O)c2cc(F)ccc2N3)ccc1F] | 6'-fluoro-N-(4-fluoro-3-(prop-2-yn-1-ylcarbamoyl)benzyl)-4'-oxo-3',4'-dihydro-1'H-spiro[piperidine-4,2'-quinoline]-1-carboxamide | 1.483 | |
| 129 | 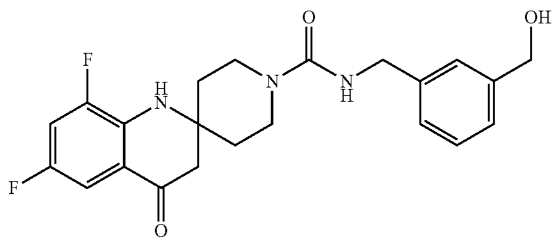 [SMILES: O=C1CC2(CCN(C(=O)NCc3cccc(CO)c3)CC2)Nc2c(F)cc(F)cc21] | 6',8'-difluoro-N-(3-(hydroxymethyl)benzyl)-4'-oxo-3',4'-dihydro-1'H-spiro[piperidine-4,2'-quinoline]-1-carboxamide | 1.519 | >10 |
| 130 | 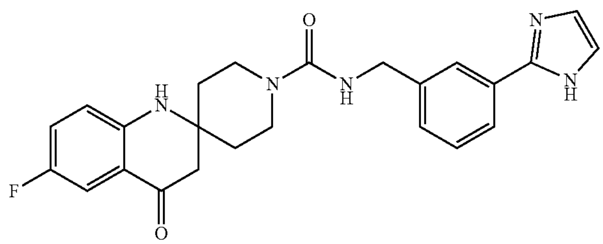 [SMILES: O=C1CC2(CCN(C(=O)NCc3cccc(-c4ncc[nH]4)c3)CC2)Nc2ccc(F)cc21] | N-(3-(1H-imidazol-2-yl)benzyl)-6'-fluoro-4'-oxo-3',4'-dihydro-1'H-spiro[piperidine-4,2'-quinoline]-1-carboxamide | 1.534 | >10 |
| 131 | 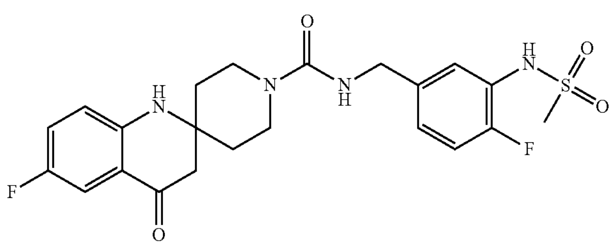 [SMILES: CS(=O)(=O)Nc1cc(CNC(=O)N2CCC3(CC2)CC(=O)c2cc(F)ccc2N3)ccc1F] | 6'-fluoro-N-(4-fluoro-3-(methylsulfonamido)benzyl)-4'-oxo-3',4'-dihydro-1'H-spiro[piperidine-4,2'-quinoline]-1-carboxamide | 1.619 | >10 |
| 132 | 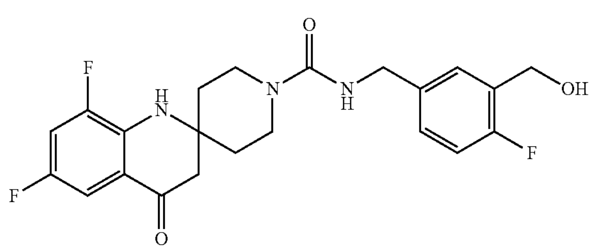 [SMILES: O=C1CC2(CCN(C(=O)NCc3ccc(F)c(CO)c3)CC2)Nc2c(F)cc(F)cc21] | 6',8'-difluoro-N-(4-fluoro-3-(hydroxymethyl)benzyl)-4'-oxo-3',4'-dihydro-1'H-spiro[piperidine-4,2'-quinoline]-1-carboxamide | 1.718 | >10 |
| 133 | 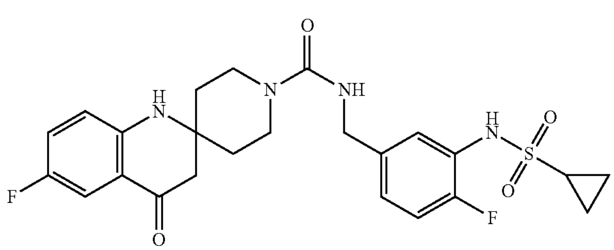 [SMILES: O=C1CC2(CCN(C(=O)NCc3ccc(F)c(NS(=O)(=O)C4CC4)c3)CC2)Nc2ccc(F)cc21] | N-(3-(cyclopropanesulfonamido)-4-fluorobenzyl)-6'-fluoro-4'-oxo-3',4'-dihydro-1'H-spiro[piperidine-4,2'-quinoline]-1-carboxamide | 1.771 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 134 | 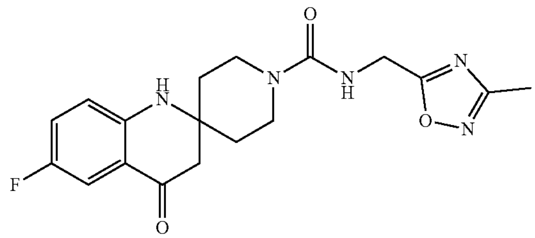 [SMILES: Cc1noc(CNC(=O)N2CCC3(CC2)CC(=O)c2cc(F)ccc2N3)n1] | 6'-fluoro-N-((3-methyl-1,2,4-oxadiazol-5-yl)methyl)-4'-oxo-3',4'-dihydro-1'H-spiro[piperidine-4,2'-quinoline]-1-carboxamide | 1.783 | 0.094 |
| 135 | 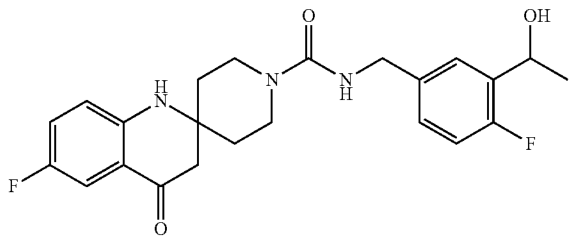 [SMILES: CC(O)c1cc(CNC(=O)N2CCC3(CC2)CC(=O)c2cc(F)ccc2N3)ccc1F] | 6'-fluoro-N-(4-fluoro-3-(1-hydroxyethyl)benzyl)-4'-oxo-3',4'-dihydro-1'H-spiro[piperidine-4,2'-quinoline]-1-carboxamide | 1.862 | >10 |
| 136 | 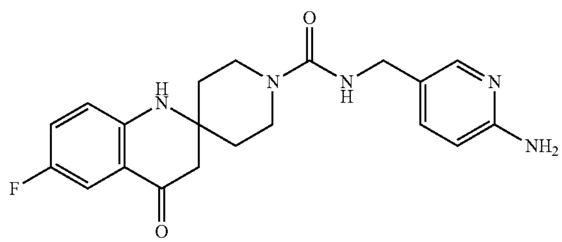 [SMILES: Nc1ccc(CNC(=O)N2CCC3(CC2)CC(=O)c2cc(F)ccc2N3)cn1] | N-((6-aminopyridin-3-yl)methyl)-6'-fluoro-4'-oxo-3',4'-dihydro-1'H-spiro[piperidine-4,2'-quinoline]-1-carboxamide | 1.991 | >10 |
| 137 | 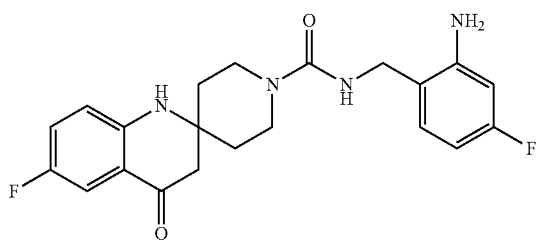 [SMILES: Nc1cc(F)ccc1CNC(=O)N1CCC2(CC1)CC(=O)c1cc(F)ccc1N2] | N-(2-amino-4-fluorobenzyl)-6'-fluoro-4'-oxo-3',4'-dihydro-1'H-spiro[piperidine-4,2'-quinoline]-1-carboxamide | 2.026 | >10 |
| 138 | 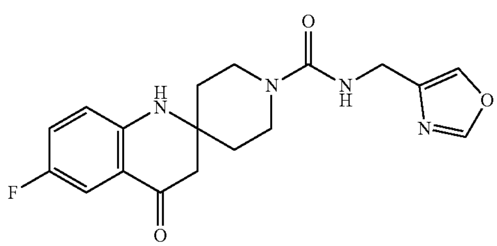 [SMILES: O=C1CC2(CCN(C(=O)NCc3cocn3)CC2)Nc2ccc(F)cc21] | 6'-fluoro-N-(oxazol-4-ylmethyl)-4'-oxo-3',4'-dihydro-1'H-spiro[piperidine-4,2'-quinoline]-1-carboxamide | 2.107 | >10 |
| 139 | 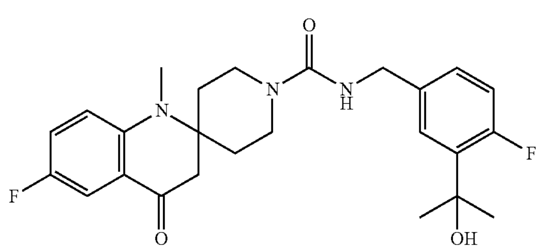 [SMILES: CN1c2ccc(F)cc2C(=O)CC12CCN(C(=O)NCc1ccc(F)c(C(C)(C)O)c1)CC2] | 6'-fluoro-N-(4-fluoro-3-(2-hydroxypropan-2-yl)benzyl)-1'-methyl-4'-oxo-3',4'-dihydro-1'H-spiro[piperidine-4,2'-quinoline]-1-carboxamide | 2.302 | 8.828 |

-continued

| Ex. # | Structure | Structure name | H460 Qualified absolute $AC_{50}$ (μM) | HARA Qualified absolute $AC_{50}$ (μM) |
|---|---|---|---|---|
| 140 | 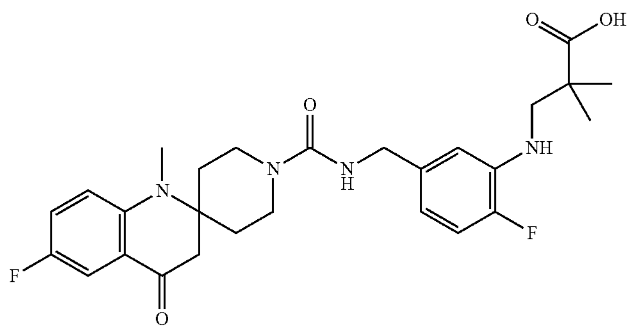 [SMILES: CN1c2ccc(F)cc2C(=O)CC12CCN(C(=O)NCc1ccc(F)c(NCC(C)(C)C(=O)O)c1)CC2] | 3-((2-fluoro-5-((6'-fluoro-i'-methyl-4'-oxo-3',4'-dihydro-1'H-spiro[piperidine-4,2'-quinoline]-1-carboxamido)methyl)phenyl)amino)-2,2-dimethylpropanoic acid | 2.337 | >10 |
| 141 | 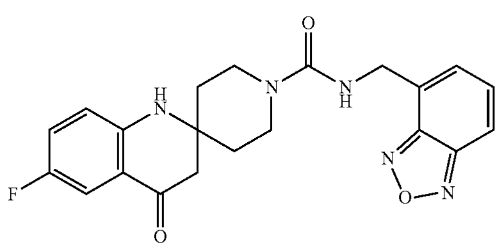 [SMILES: O=C1CC2(CCN(C(=O)NCc3cccc4nonc34)CC2)Nc2ccc(F)cc21] | N-(benzo[c][1,2,5]oxadiazol-4-ylmethyl)-6'-fluoro-4'-oxo-3',4'-dihydro-1'H-spiro[piperidine-4,2'-quinoline]-1-carboxamide | 2.449 | >10 |
| 142 | 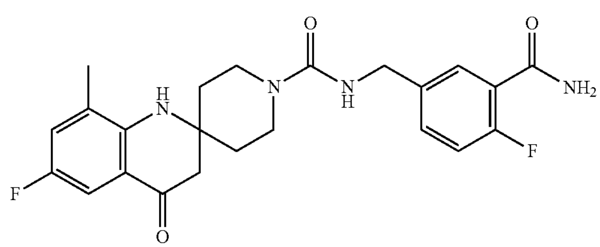 [SMILES: Cc1cc(F)cc2c1NC1(CCN(C(=O)NCc3ccc(F)c(C(N)=O)c3)CC1)CC2=O] | N-(3-carbamoyl-4-fluorobenzyl)-6'-fluoro-8'-methyl-4'-oxo-3',4'-dihydro-1'H-spiro[piperidine-4,2'-quinoline]-1-carboxamide | 2.449 | >10 |
| 143 | 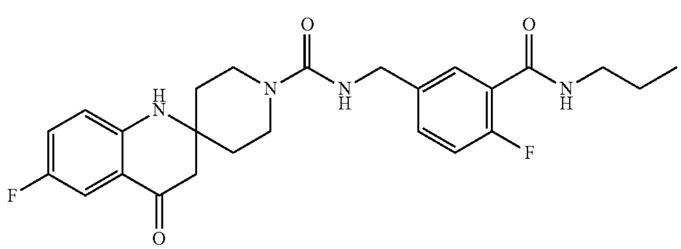 [SMILES: CCCNC(=O)c1cc(CNC(=O)N2CCC3(CC2)CC(=O)c2cc(F)ccc2N3)ccc1F] | 6'-fluoro-N-(4-fluoro-3-(propylcarbamoyl)benzyl)-4'-oxo-3',4'-dihydro-1'H-spiro[piperidine-4,2'-quinoline]-1-carboxamide | 2.625 | >10 |
| 144 | 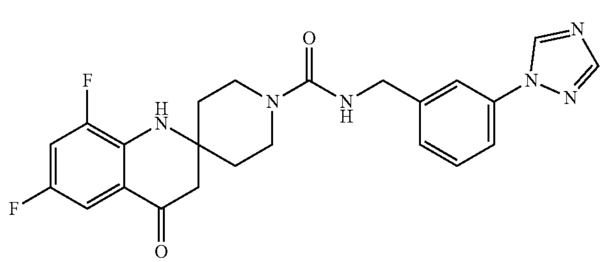 [SMILES: O=C1CC2(CCN(C(=O)NCc3cccc(-n4cncn4)c3)CC2)Nc2c(F)cc(F)cc21] | N-(3-(1H-1,2,4-triazol-1-yl)benzyl)-6',8'-difluoro-4'-oxo-3',4'-dihydro-1'H-spiro[piperidine-4,2'-quinoline]-1-carboxamide | 3.051 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 145 | 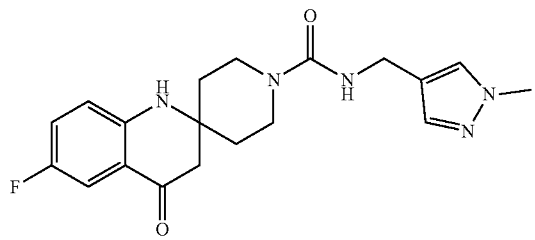 [SMILES: Cn1cc(CNC(=O)N2CCC3(CC2)CC(=O)c2cc(F)ccc2N3)cn1] | 6'-fluoro-N-((1-methyl-1H-pyrazol-4-yl)methyl)-4'-oxo-3',4'-dihydro-1'H-spiro[piperidine-4,2'-quinoline]-1-carboxamide | 3.498 | 6.055 |
| 146 | 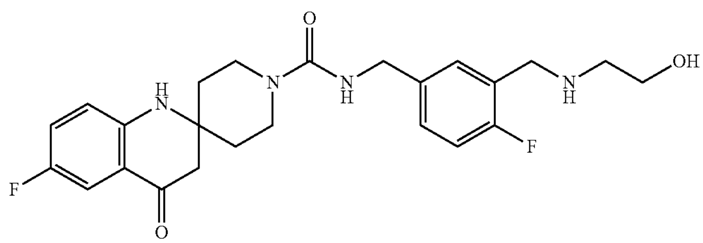 [SMILES: O=C1CC2(CCN(C(=O)NCc3ccc(F)c(CNCCO)c3)CC2)Nc2ccc(F)cc21] | 6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide | 3.653 | 2.794 |
| 147 | 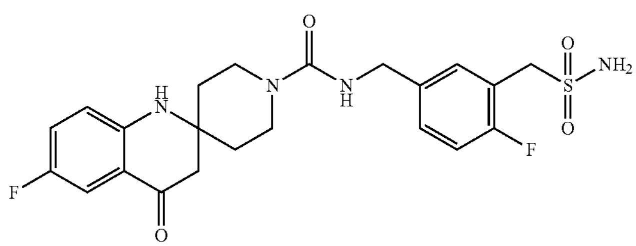 [SMILES: NS(=O)(=O)Cc1cc(CNC(=O)N2CCC3(CC2)CC(=O)c2cc(F)ccc2N3)ccc1F] | 6'-fluoro-N-(4-fluoro-3-(sulfamoylmethyl)benzyl)-4'-oxo-3',4'-dihydro-1'H-spiro[piperidine-4,2'-quinoline]-1-carboxamide | 3.965 | >10 |
| 148 | 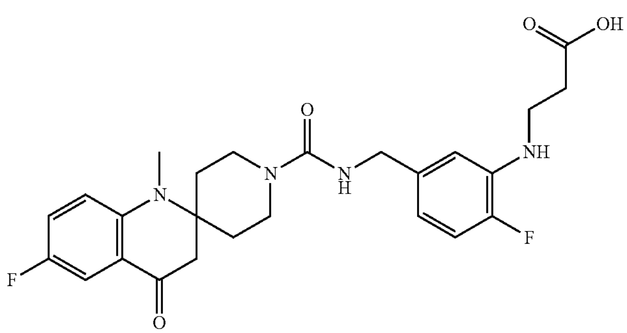 [SMILES: CN1c2ccc(F)cc2C(=O)CC12CCN(C(=O)NCc1ccc(F)c(NCCC(=O)O)c1)CC2] | 3-((2-fluoro-5-((6'-fluoro-1'-methyl-4'-oxo-3',4'-dihydro-1'H-spiro[piperidine-4,2'-quinoline]-1-carboxamido)methyl)phenyl)amino)propanoic acid | 4.933 | |
| 149 | 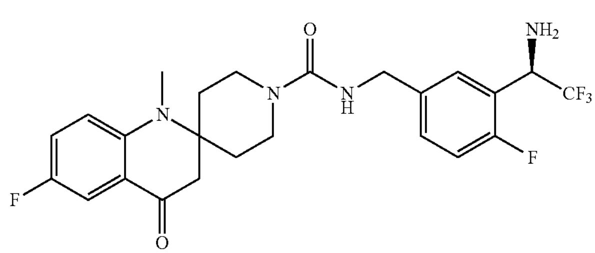 [SMILES: CN1c2ccc(F)cc2C(=O)CC12CCN(C(=O)NCc1ccc(F)c([C@@H](N)C(F)(F)F)c1)CC2] | (R)-N-(3-(1-amino-2,2,2-trifluoroethyl)-4-fluorobenzyl)-6'-fluoro-1'-methyl-4'-oxo-3',4'-dihydro-1'H-spiro[piperidine-4,2'-quinoline]-1-carboxamide | 5.431 | >10 |

-continued

| Ex. # | Structure | Structure name | H460 Qualified absolute AC$_{50}$ (μM) | HARA Qualified absolute AC$_{50}$ (μM) |
|---|---|---|---|---|
| 150 | 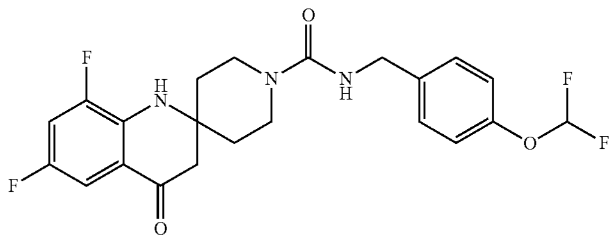 [SMILES: O=C1CC2(CCN(C(=O)NCc3ccc(OC(F)F)cc3)CC2)Nc2c(F)cc(F)cc21] | N-(4-(difluoromethoxy)benzyl)-6',8'-difluoro-4'-oxo-3',4'-dihydro-1'H-spiro[piperidine-4,2'-quinoline]-1-carboxamide | 6.274 | 2.622 |
| 151a | 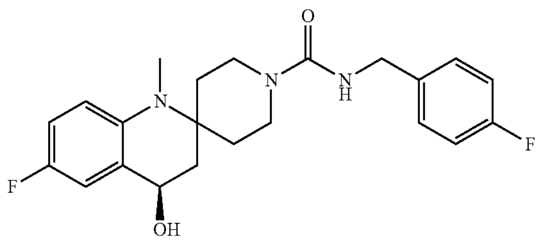 [SMILES: CN1c2ccc(F)cc2[C@H](O)CC12CCN(C(=O)NCc1ccc(F)cc1)CC2] | (R)-6'-fluoro-N-(4-fluorobenzyl)-4'-hydroxy-1'-methyl-3',4'-dihydro-1'H-spiro[piperidine-4,2'-quinoline]-1-carboxamide | 0.024 | 0.020 |
| 151b | 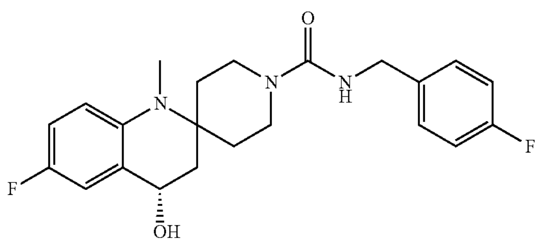 [SMILES: CN1c2ccc(F)cc2[C@@H](O)CC12CCN(C(=O)NCc1ccc(F)cc1)CC2] | (S)-6'-fluoro-N-(4-fluorobenzyl)-4'-hydroxy-1'-methyl-3',4'-dihydro-1'H-spiro[piperidine-4,2'-quinoline]-1-carboxamide | 3.40 | 6.07 |
| 152 | 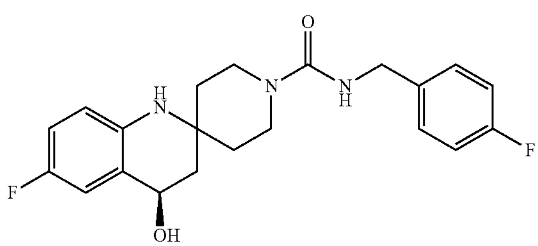 [SMILES: O=C(NCc1ccc(F)cc1)N1CCC2(CC1)C[C@@H](O)c1cc(F)ccc1N2] | (R)-6'-fluoro-N-(4-fluorobenzyl)-4'-hydroxy-3',4'-dihydro-1'H-spiro[piperidine-4,2'-quinoline]-1-carboxamide | 0.021 | 0.016 |
| 153 | 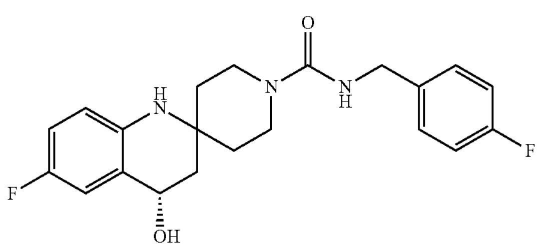 [SMILES: O=C(NCc1ccc(F)cc1)N1CCC2(CC1)C[C@H](O)c1cc(F)ccc1N2] | (S)-6'-fluoro-N-(4-fluorobenzyl)-4'-hydroxy-3',4'-dihydro-1'H-spiro[piperidine-4,2'-quinoline]-1-carboxamide | 2.260 | 2.500 |
| 154a | 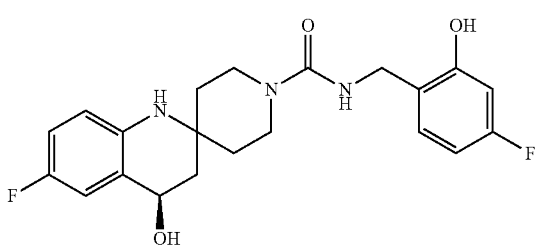 [SMILES: O=C(NCc1ccc(F)cc1O)N1CCC2(CC1)C[C@@H](O)c1cc(F)ccc1N2] | (R)-6'-fluoro-N-(4-fluoro-2-hydroxybenzyl)-4'-hydroxy-3',4'-dihydro-1'H-spiro[piperidine-4,2'-quinoline]-1-carboxamide | 0.005 | 0.005 |

-continued

| Ex. # | Structure name | H460 Qualified absolute AC$_{50}$ (μM) | HARA Qualified absolute AC$_{50}$ (μM) |
|---|---|---|---|
| 154b | (S)-6'-fluoro-N-(4-fluoro-2-hydroxybenzyl)-4'-hydroxy-3',4'-dihydro-1'H-spiro[piperidine-4,2'-quinoline]-1-carboxamide | 0.464 | 0.749 |
| 155 | N-(3-carbamoyl-4-fluorobenzyl)-6'-fluoro-4'-hydroxy-1'-methyl-3',4'-dihydro-1'H-spiro[piperidine-4,2'-quinoline]-1-carboxamide | 0.005 | 0.001 |
| 156 | N-(2,4-difluoro-5-((2-hydroxyethyl)amino)benzyl)-6'-fluoro-4'-hydroxy-1'-methyl-3',4'-dihydro-1'H-spiro[piperidine-4,2'-quinoline]-1-carboxamide | 0.049 | 0.080 |
| 157 | N-(3-carbamoyl-4-fluorobenzyl)-6',8'-difluoro-4'-hydroxy-3',4'-dihydro-1'H-spiro[piperidine-4,2'-quinoline]-1-carboxamide | 0.0001 | 0.002 |
| 158 | N-(3-amino-4-fluorobenzyl)-6'-fluoro-4'-hydroxy-3',4'-dihydro-1'H-spiro[piperidine-4,2'-quinoline]-1-carboxamide | 0.033 | 0.006 |
| 159 | 6'-fluoro-N-(4-fluoro-3-(hydroxymethyl)benzyl)-4'-hydroxy-3',4'-dihydro-1'H-spiro[piperidine-4,2'-quinoline]-1-carboxamide | 0.053 | 0.067 |

-continued

| Ex. # | Structure | Structure name | H460 Qualified absolute $AC_{50}$ (μM) | HARA Qualified absolute $AC_{50}$ (μM) |
|---|---|---|---|---|
| 160 | 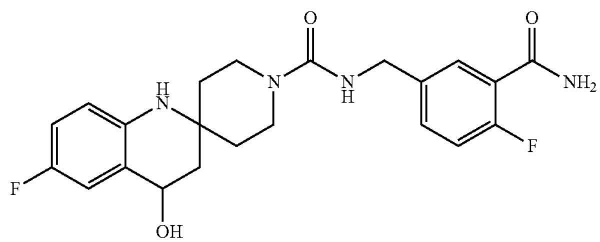 [SMILES: NC(=O)c1cc(CNC(=O)N2CCC3(CC2)CC(O)c2cc(F)ccc2N3)ccc1F] | N-(3-carbamoyl-4-fluorobenzyl)-6'-fluoro-4'-hydroxy-3',4'-dihydro-1'H-spiro[piperidine-4,2'-quinoline]-1-carboxamide | 0.0004 | 0.001 |
| 161 | 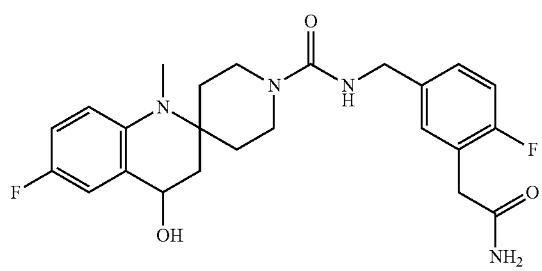 [SMILES: CN1c2ccc(F)cc2C(O)CC12CCN(C(=O)NCc1ccc(F)c(CC(N)=O)c1)CC2] | N-(3-(2-amino-2-oxoethyl)-4-fluorobenzyl)-6'-fluoro-4'-hydroxy-1'-methyl-3',4'-dihydro-1'H-spiro[piperidine-4,2'-quinoline]-1-carboxamide | 0.278 | 0.091 |
| 162 | 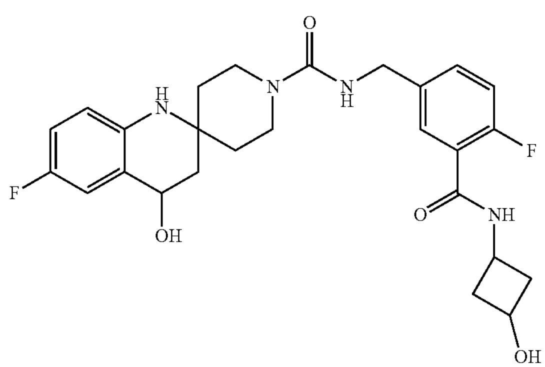 [SMILES: O=C(NC1CC(O)C1)c1cc(CNC(=O)N2CCC3(CC2)CC(O)c2cc(F)ccc2N3)ccc1F] | 6'-fluoro-N-(4-fluoro-3-((3-hydroxycyclobutyl)carbamoyl)benzyl)-4'-hydroxy-3',4'-dihydro-1'H-spiro[piperidine-4,2'-quinoline]-1-carboxamide | 0.047 | ND |
| 163 | 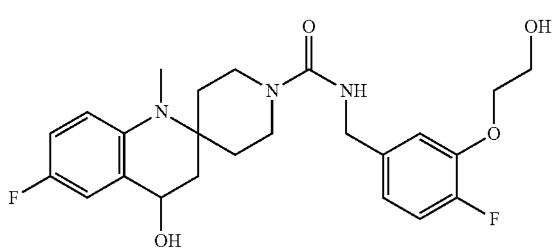 [SMILES: CN1c2ccc(F)cc2C(O)CC12CCN(C(=O)NCc1ccc(F)c(OCCO)c1)CC2] | 6'-fluoro-N-(4-fluoro-3-(2-hydroxyethoxy)benzyl)-4'-hydroxy-1'-methyl-3',4'-dihydro-1'H-spiro[piperidine-4,2'-quinoline]-1-carboxamide | 0.076 | 0.011 |
| 164 | 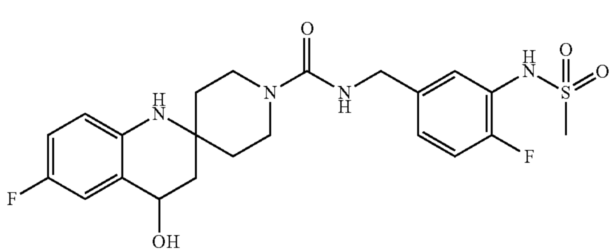 [SMILES: CS(=O)(=O)Nc1cc(CNC(=O)N2CCC3(CC2)CC(O)c2cc(F)ccc2N3)ccc1F] | 6'-fluoro-N-(4-fluoro-3-(methylsulfonamido)benzyl)-4'-hydroxy-3',4'-dihydro-1'H-spiro[piperidine-4,2'-quinoline]-1-carboxamide | 0.253 | 0.234 |

-continued

| Ex. # | Structure | Structure name | H460 Qualified absolute $AC_{50}$ (μM) | HARA Qualified absolute $AC_{50}$ (μM) |
|---|---|---|---|---|
| 165 | 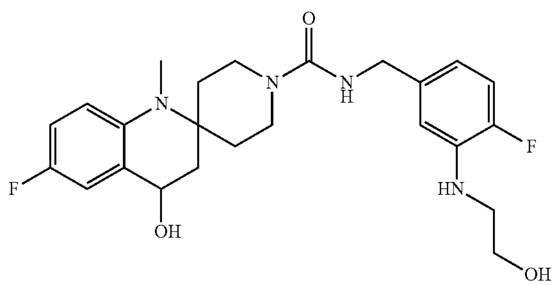 [SMILES: CN1c2ccc(F)cc2C(O)CC12CCN(C(=O)NCc1ccc(F)c(NCCO)c1)CC2] | 6'-fluoro-N-(4-fluoro-3-((2-hydroxyethyl)amino)benzyl)-4'-hydroxy-1'-methyl-3',4'-dihydro-1'H-spiro[piperidine-4,2'-quinoline]-1-carboxamide | 0.049 | 0.023 |
| 166 | 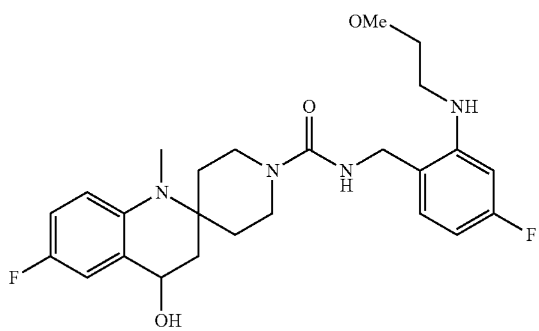 [SMILES: COCCNc1cc(F)ccc1CNC(=O)N1CCC2(CC1)CC(O)c1cc(F)ccc1N2C] | 6'-fluoro-N-(4-fluoro-2-((2-methoxyethyl)amino)benzyl)-4'-hydroxy-1'-methyl-3',4'-dihydro-1'H-spiro[piperidine-4,2'-quinoline]-1-carboxamide | 0.003 | 0.022 |
| 167 | 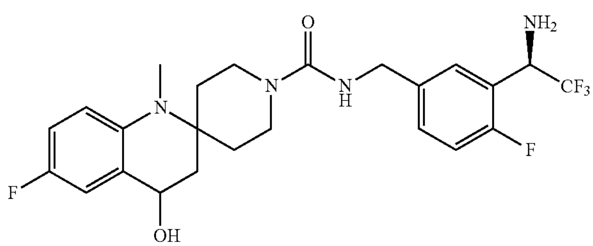 [SMILES: CN1c2ccc(F)cc2C(O)CC12CCN(C(=O)NCc1ccc(F)c([C@@H](N)C(F)(F)F)c1)CC2] | N-(3-((R)-1-amino-2,2,2-trifluoroethyl)-4-fluorobenzyl)-6'-fluoro-4'-hydroxy-1'-methyl-3',4'-dihydro-1'H-spiro[piperidine-4,2'-quinoline]-1-carboxamide | 0.345 | 0.100 |
| 168 | 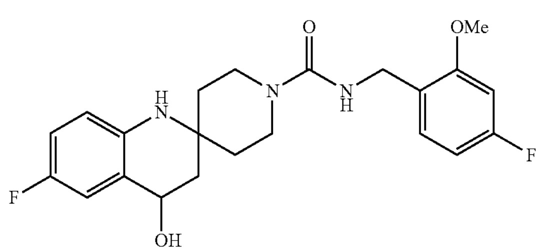 [SMILES: COc1cc(F)ccc1CNC(=O)N1CCC2(CC1)CC(O)c1cc(F)ccc1N2] | 6'-fluoro-N-(4-fluoro-2-methoxybenzyl)-4'-hydroxy-3',4'-dihydro-1'H-spiro[piperidine-4,2'-quinoline]-1-carboxamide | 0.041 | 0.049 |
| 169 | 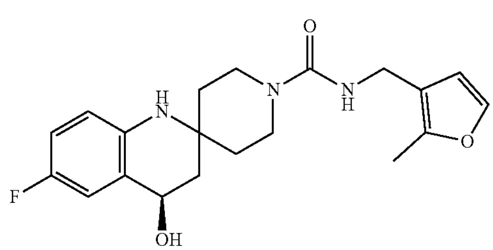 [SMILES: Cc1occc1CNC(=O)N1CCC2(CC1)C[C@@H](O)c1cc(F)ccc1N2] | (R)-6'-fluoro-4'-hydroxy-N-((2-methylfuran-3-yl)methyl)-3',4'-dihydro-1'H-spiro[piperidine-4,2'-quinoline]-1-carboxamide | 0.008 | ND |

-continued

| Ex. # | Structure | Structure name | H460 Qualified absolute $AC_{50}$ (μM) | HARA Qualified absolute $AC_{50}$ (μM) |
|---|---|---|---|---|
| 170a | 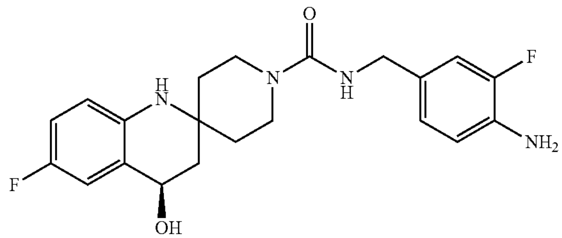 [SMILES: Nc1ccc(CNC(=O)N2CCC3(CC2)C[C@@H](O)c2cc(F)ccc2N3)cc1F] | (R)-N-(4-amino-3-fluorobenzyl)-6'-fluoro-4'-hydroxy-3',4'-dihydro-1'H-spiro[piperidine-4,2'-quinoline]-1-carboxamide | 0.011 | ND |
| 170b | 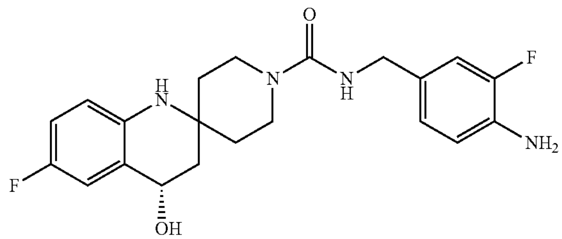 [SMILES: Nc1ccc(CNC(=O)N2CCC3(CC2)C[C@H](O)c2cc(F)ccc2N3)cc1F] | (S)-N-(4-amino-3-fluorobenzyl)-6'-fluoro-4'-hydroxy-3',4'-dihydro-1'H-spiro[piperidine-4,2'-quinoline]-1-carboxamide | 17.30 | ND |

Cellular Proliferation Assay to Assess Compound Activity in an Expanded Panel of 57 NRF2 Pathway Mutant and Wild Type Lung Cancer Cell Lines.

An expanded panel of NRF2 pathway mutant and wild type lung cancer cell lines was run to further demonstrate the selectivity profile of compounds across cell lines with varying levels of AKR1C3 mRNA expression. Both the PrestoBlue Cell Viability Reagent and Cell Titer Glo were multiplexed together as the final assay readout. PrestoBlue is a cell permeable resazurin-based solution that utilizes the reducing power of living cells to quantitatively measure their proliferation. Cell Titer Glo measures the amount of ATP present, an indicator of metabolically active cells.

Expanded Lung Cancer Cell Line Proliferation Assay Outline, Analysis and Profiling Results Cells were seeded into 384 well assay plates (Greiner Bio-One, Catalog #781080) using the Thermo Scientific Matrix WellMate microplate dispenser and Thermo Scientific Matrix WellMate small bore disposable tubing cartridges (Catalog #201-30002) in 30 μl of growth media (RPMI-1640 supplemented with 10% fetal bovine serum and 1% penicillin/streptomycin) per well (1000 to 2000 cells/well depending on doubling time). Following cell plating, assay plates were placed into tissue culture incubator at 37° C./5% $CO_2$ overnight. The next day one assay plate for each cell line was used for a Day 0 Cell Titer Glo and PrestoBlue readout. 3 μl of PrestoBlue Cell Viability Reagent (Thermo Scientific, Catalog #A13262) was added to each well and then assay plates were incubated at 37° C./5% CO2 for 30 minutes prior to fluorescence readout on the EnVision 2105 multimode plate reader (Perkin Elmer). Following the PrestoBlue readout 18 μl of Cell Titer Glo (Promega, Catalog #G7572) was then added to each well, allowing plates to incubate at room temperature for 10 minutes prior to luminescence readout on the EnVision. Compound was then added to the remaining assay plates (each cell line run in triplicates) using the Labcyte Inc Echo 555 acoustic liquid handler. Compounds were arrayed into a Labcyte Inc Echo qualified 384 well LDV microplate (Cat #LP-0200-GNF10). Compounds were serially diluted 1:3.16 to generate an 8 point dose response for a final top concentration of 1 μM. DMSO (0.3%) was used as the neutral control (NC) and MG132 (30 μM) was used as the active control (AC). 90 nl of compounds were added to 30 μl of cells using the Labcyte Inc Echo 555 acoustic liquid handler for a final DMSO assay concentration of 0.3%. Following compound addition, assay plates were spun down in a tabletop centrifuge at 500 rpm for 1 minute and then placed into tissue culture incubator at 37° C./5% $CO_2$ for 72 h. Following the 72 h incubation, all assay plates were readout using PrestoBlue and Cell Titer Glo using the same conditions previously described for the Day 0 readout. The Day 0 readout (untreated cells) was used to compare to the 72 h DMSO treated samples on each assay plate as a way of tracking each cell line's fold growth. NC1 control based normalization was used for data analysis in Helios, which incorporates the DMSO neutral control (NC) and MG132 active control (AC) for generating dose response curves that are then used to calculate the Absolute Qualified AC50 calls for each compound and cell line.

NC1 normalization calculation model: NC1: $x_n = \pm(x-NC)/(AC-NC)$

+/− is set by the inhibition type parameter setting where NC and AC are averages (mean or median) over the corresponding NC and AC well values. The Qualified Absolute AC50 values for Compound 36 and Compound 40 are listed in the table below and are represented as the average activity in both the PrestoBlue and Cell Titer Glo assay readouts.

Absolute Qualified AC50 Values Listed Below are a Representation of Each Compounds' Average Activity in Both the PrestoBlue and Cell Titer Glo Assay Readouts.

| Cell Line | Compound 40 Absolute Qualified AC50 (nM) | Compound 36 Absolute Qualified AC50 (nM) | AKR1C3 RNAseq expression (*TPM) |
|---|---|---|---|
| A427 | >1000 | >1000 | 0.2 |
| HCC2108 | >1000 | >1000 | 0.5 |
| NCI-H524 | >1000 | >1000 | 0.8 |
| NCI-H2286 | >1000 | >1000 | 0.9 |

| Cell Line | Compound 40 Absolute Qualified AC50 (nM) | Compound 36 Absolute Qualified AC50 (nM) | AKR1C3 RNAseq expression (*TPM) |
|---|---|---|---|
| NCI-H23 | >1000 | >1000 | 1 |
| NCI-H1299 | >1000 | >1000 | 1.3 |
| NCI-H1650 | >1000 | >1000 | 1.3 |
| ChaGo-K-1 | >1000 | >1000 | 1.5 |
| NCI-H1838 | >1000 | >1000 | 1.8 |
| LCLC-97TM1 | >1000 | >1000 | 1.9 |
| NCI-H1581 | >1000 | >1000 | 1.9 |
| SW1271 | >1000 | >1000 | 2.4 |
| LCLC-103H | >1000 | >1000 | 2.6 |
| NCI-H1568 | >1000 | >1000 | 2.8 |
| NCI-H226 | >1000 | >1000 | 2.9 |
| HCC78 | >1000 | >1000 | 3 |
| NCI-H661 | >1000 | >1000 | 3 |
| NCI-H1703 | >1000 | >1000 | 3.2 |
| CORL-279 | >1000 | >1000 | 3.6 |
| NCI-H1339 | >1000 | >1000 | 5.2 |
| SBC5 | >1000 | >1000 | 5.5 |
| NCI-H358 | >1000 | >1000 | 5.6 |
| RERF-LC-AI | >1000 | >1000 | 7.6 |
| NCI-H1373 | >1000 | >1000 | 8 |
| NCI-H2347 | >1000 | >1000 | 8.9 |
| NCI-H322 | >1000 | >1000 | 21 |
| CAL-12T | >1000 | >1000 | 23.6 |
| Calu-6 | >1000 | >1000 | 32.5 |
| DV-90 | 159 | 347 | 48.9 |
| NCI-H810 | 983 | >1000 | 52.5 |
| DMS-53 | >1000 | >1000 | 59.7 |
| EBC-1 | >1000 | >1000 | 92.4 |
| HCC-44 | 440 | 705 | 134.3 |
| NCI-H1435 | 273 | 478 | 171.1 |
| NCI-H2405 | 474 | 994 | 189.1 |
| RERF-LC-MS | >1000 | >1000 | 221.6 |
| NCI-H2030 | 364 | 648 | 232.7 |
| NCI-H838 | 641 | >1000 | 233 |
| NCI-H596 | 334 | 754 | 265.6 |
| NCI-H1573 | 293 | 946 | 306.2 |
| LXF-289 | 835 | 781 | 358.4 |
| NCI-H1792 | 196 | 553 | 418.6 |
| NCI-H520 | >1000 | >1000 | 608.9 |
| NCI-H460 | 50 | 268 | 865.3 |
| HCC95 | 69 | 287 | 939.1 |
| LK2 | >1000 | >1000 | 1107 |
| NCI-H2023 | 63 | 347 | 1424.8 |
| PC-14 | 92 | 308 | 1466.3 |
| NCI-H2122 | 56 | 258 | 1507.5 |
| NCI-H2172 | 149 | >1000 | 1522.4 |
| BEN | 57 | 399 | 2573.5 |
| NCI-H1437 | 68 | 257 | 2720.8 |
| A549 | 56 | 301 | 3017.9 |
| NCI-H1944 | 52 | 275 | 3164.3 |
| COLO-699 | >1000 | >1000 | No data available |
| HLC-1 | >1000 | >1000 | No data available |
| VMRC-LCD | 330 | 474 | No data available |

*Transcripts Per Kilobase Million

KARS AMP Transcreener FP Assay to Measure Inhibition of KARS Enzymatic Activity

Lysine-tRNA synthetase (KARS) is an enzyme that catalyzes the reaction of ATP, L-lysine, and tRNA(Lys) to form AMP, diphosphate, and L-lysyl-tRNA(Lys).

The Transceener® AMP/GMP (BellBrook Labs, Madison, WI, USA) is a far red, competitive fluorescence polarization (FP) immunoassay based on the detection of AMP, which is one of the products of aminoacylation of tRNA. In this assay, a fluorescently labeled AMP (AMP Alexa Fluor 633) is used as the tracer that can be recognized by a specific antibody. In the absence of AMP, all the tracer molecules are bound to the antibodies leading to large polarization. The AMP product generated by the enzyme reaction will compete with the tracer for binding to the antibody which leads to a decrease in the polarization. As such, the enzyme activity is inversely proportional to FP values.

Assay Protocol

Human KARS protein (residues 70-584) was expressed and purified using a similar protocol to what is described in literature (Crystal structure of tetrameric form of human lysyl-tRNA synthetase: Implications for multisynthetase complex formation Guo, M., Ignatov, M., Musier-Forsyth, K., Schimmel, P., Yang, X. L. (2008) Proc. Natl. Acad. Sci. Usa 105: 2331-2336).

The KARS enzyme assay was performed in a final volume of 10 µL per well of Corning Costar 384 well plate, flat bottom, black non-treated plate. The final assay concentration was 20 mM HEPES pH 7.5, 1 mM DTT, 50 nM human KARS, 20 µM ATP, 50 µM L-Lysine, 1 µM tRNA and 8 mM MgCl₂. Compounds were serial diluted 1:3 in DMSO in a master plate to generate a 10 concentration points dose response with maximum concentration of 10 mM. 50 nL from compound master plate were spotted in each well of a 384 black plate (Corning 3573), and 5 µL of enzyme mixture containing 100 nM KARS diluted in assay buffer (20 mM HEPES pH 7.5 and 1 mM OTT) were added. The reaction was started by adding 5 µL of the substrate mixture containing 40 µM ATP (final 20 µM ATP), 100 µM L-Lysine (final 50 µM), 2 µM tRNA (final 1 µM), 16 mM MgCl₂ (final 8 mM MgCl₂) diluted in assay buffer (20 mM HEPES pH 7.5 and 1 mM OTT). The mixtures were mixed and incubated for 2 h at RT before the termination of the reaction.

Transcreener® stop and detection buffers were prepared (1× stop buffer [final: 0.5×], 2 nM Tracer [final: 1 nM] and 5 µg/ml anti-AMP antibody [final: 2.5 µg/ml] in deionized water) and 10 µL of the stop and detection mix were added to the reaction wells, mixed for a minute and centrifuged at 1000 rpm for 10 seconds. The plates were read after incubating at RT for 30-60 min using Infinite® M1000 with the following settings: Excitation wavelength: 635 nm; Emission wavelength: 680 nm. FP values of DMSO controls were used to normalize the data and calculate IC50s of compounds using the Helios Software suite.

| Compound | Human KARS Transcreener AMP assay Qualified absolute AC50 (nM) |
|---|---|
| 9 | >10,000 |
| 40 | >10,000 |
| 151a | 9.1 |
| 152 | 9.1 |
| 153 | >10,000 |
| 154a | 11.7 |
| 155 | 19.0 |
| 156 | 23.5 |
| 157 | 34.1 |
| 158 | 42.1 |
| 159 | 45.9 |
| 160 | 47.2 |
| 161 | 71.8 |
| 162 | 73.7 |
| 163 | 98.4 |
| 164 | 105.6 |
| 165 | 199.2 |
| 166 | 242.5 |
| 167 | 917.7 |

Conversion of AKR1C3 Dependent KARS Inhibitor by Purified Human AKR1C3 Enzyme

Aldo-keto Reductase 1C3 (AKR1C3), also called 17β-hydroxysteroid dehydrogenase type 5 (17β-HSD5) or prostaglandin F synthase (PGFS) is a member of the aldo-keto reductase (AKR) superfamily. This enzyme acts as NADP (H)-dependent 3-, 17- and 20-ketosteroid reductase and play central roles in steroid hormone metabolism, as well as metabolism of xenobiotic including polycyclic aromatic hydrocarbons. The kinetic of conversion of compound 40 to compound 152 was measured using purified human AKR1C3 enzyme and LC-MS as readout. FIG. 1 illustrates the kinetic conversion.

Human AKR1C3 Protein Purification

The full-length human AKR1C3 DNA sequence was synthesized by GeneArt (Thermo Fisher scientific) and cloned into the pSpeed-ET vector using Polymerase Incomplete Primer Extension (PIPE) cloning (Methods Mol Biol. 2009; 498:91-103). N-terminal His-tagged protein was obtained by expression of the plasmid in E. Coli strain BL21-CODONPLUS(DE3)-RIL (Agilent 230245). A single colony was grown overnight in a 25 ml culture of Lysogeny Broth containing 50 μg/ml Kanamycin at 30° C. with shaking. This culture was transferred into Terrific Broth containing 50 μg/ml Kanamycin and grown at 37° C. with shaking until an OD of 0.6-1. The cultures were then placed in an 18° C. incubator for 45 min, induced with 1 mM IPTG (for Cyno) or 0.2% arabinose (for Human) and grown overnight at 18° C.

Bacterial cultures were pelleted by centrifugation (7000 rpm for 10 minutes). Pellets were crushed with a hammer, and resuspended in 40 ml of Q-proteome buffer prepared according to Qiagen protocol (Qiagen 37900) with 20 mM imidazole and a protease-inhibitor tablet (Roche05056489001). The lysate was incubated at 4° C. with rotation for 30 min, and then spun down at 24,000 g for 30 min. The supernatant was filtered on a 0.45 μm filter and loaded onto 1 ml HisTrap column (GE Healthcare 17-5319-01) using the AktaXpress chromatography system and eluted with the following buffers:

Wash I (50 mM Tris, 500 mM NaCl, 20 mM Imidazole, 10% Glycerol)

Wash II (50 mM Tris, 500 mM NaCl, 30 mM Imidazole, 10% glycerol)

Elution buffer (50 mM Tris, 150 mM NaCl, 300 mM Imidazole, 10% glycerol)

The peak fractions were pooled and loaded on a 16/60 Superdex 200 gel filtration column (GE Healthcare 28989335) pre-equilibrated with elution buffer (50 mM Tris, 200 mM NaCl, 5% Glycerol). The elution fractions were collected and peak fractions containing correct size protein were pooled and concentrated to >1 mg/ml final concentration using an Amicon 10 k cutoff concentration device (Millipore UFC901024)

Enzyme Kinetic Assay Protocol

Human AKR1C3 protein was expressed and purified using a similar protocol to what is described in literature (Crystal structures of three classes of non-steroidal anti-inflammatory drugs in complex with aldo-keto reductase 1C3. Flanagan, J. U., Yosaatmadja, Y., Teague, R. M., Chai, M. Z., Turnbull, A. P., Squire, C. J. (2012) Plos One 7: e43965-e43965).

The reactions were conducted at 37° C. in pH 7.4 buffer (10 mM Phosphate, 130 mM NaCl, 1 mM DTT, 0.01% Triton) containing NADPH (50 μM). The substrate Compound 40 was made to the desired concentrations with 1% final DMSO concentration. The AKR1C3 concentrations were either 0.25 μM (for reactions containing 100, 50 and 25 μM substrate), or 0.5 μM (for reactions containing 12.5, 6.25 and 3.12 μM substrate). At desired time points, the reactions were quenched with ACN:MeOH (3:1), and both product and substrate concentrations were determined by LC-MS/MS. The reaction rates were analyzed and fitted to Michaelis-Menten equation using GraphPad Prism, and the kinetic constants were calculated.

LC-MS/MS Protocol

Samples were analyzed by mass spectrometry on an AB Sciex 6500 Q-Trap instrument. Achiral chromatographic separation was achieved by gradient HPLC (CTC PAL/Agilent 1260) over 2.5 minutes on an ACE C18-AR column (30×2.1 mm, 3 μm) using mobile phases A and B of water and acetonitrile, respectively, both containing 0.1% formic acid, at a flow rate of 0.7 mL/min. Glyburide was used as the internal standard.

Chiral chromatographic separation was achieved by isocratic HPLC (Shimadzu) over 7 minutes on a Daicel Chiralpak AGP column (150×4 mm, 5 μm) using mobile phase containing 90% of 90:10 10 mM ammonium acetate containing 0.1% formic acid, adjusted to pH 7 with ammonium hydroxide:acetonitrile and 10% methanol, at a flow rate of 0.6 mL/min. Carbamazepine was used as the internal standard.

Example 1

Compound 40 Dose Dependent Pharmacokinetics and Pharmacodynamic (PK/PD) Changes in the KEAP1 Mutant AKR1C3 Expressing Human Lung Cancer Xenograft NCI-H1944

The PK/PD relationship of Compound 40 was assessed in nude mice with established subcutaneous NCI-H1944 (KEAP1 mutant, AKR1C3 expressing) cell line derived lung cancer xenografts (FIG. 2). After a single oral administration of Compound 40, blood and tumor were collected to explore the PK profile of Compound 40 levels in blood and tumor. Compound 152, the active metabolite of the prodrug Compound 40 that inhibits KARS was also measured in tumor and blood. The PK data were compared to the tumor PD marker readouts of DDIT3 and EGR1 mRNA induction, downstream transcriptional readouts of KARS inhibition. The duration of the induction of DDIT3 and especially EGR1 mRNA levels increased with dose escalation, which related to the duration of the PK of the prodrug Compound 40 and the tumor levels of the active inhibitor Compound 152. PD markers remained elevated for 24 hours post-dose, albeit in a dose dependent manner, so once daily dosing was assessed for anti-tumor efficacy in this model.

Example 2

Compound 40 Dose Dependent In Vivo Efficacy in High AKR1C3 Expressing Human Lung Cancer Xenograft NCI-H1944

Anti-cancer efficacy of Compound 40 was assessed in the NCI-H1944 human lung cancer xenograft model in mice that expresses high levels of AKR1C3. NCI-H1944 tumors were established in nude female mice by injection of a tumor cells subcutaneously. When tumors reached approximately 200 mm$^3$, mice were randomized according to tumor volume into treatment groups (n=8 per group) on Day 16. Test agents were administered at the dose levels, route and schedules indicated in the Table 1 and FIG. 3.

There was an efficacy benefit at all dose levels, with deep tumor regression at dose levels above 75 mg/kg of once daily oral (qd, po) dosing of Compound 40. Tumor stasis was observed at the 75 mg/kg qd dose level with a % ΔT/ΔC of 4.9% (ΔT/ΔC=Change in treated tumor volume/change in control tumor volume).

TABLE 1

Compound 40 dose response efficacy in NCI-H1944 lung cancer xenograft model on Day 44. The effect of the treatment on tumor volumes are presented.

| Test agent | Dose, Schedule | Tumor response | |
|---|---|---|---|
| | | ΔT/ΔC (%) | Regression (%) |
| Vehicle | None po, qd | 100 | — |
| Compound 40 | 75 mg/kg po, qd | 4.9 | — |
| Compound 40 | 150 mg/kg po, qd | — | 98.5 |
| Compound 40 | 300 mg/kg po, qd | — | 100 |

Example 3

Compound 40 Dose Dependent In Vivo Efficacy in the KEAP1 Mutant and Moderately AKR1C3 Expressing Human Lung Cancer Xenograft NCI-H460

Anti-cancer efficacy of Compound 40 was assessed in the NCI-H460 human lung cancer xenograft model in mice that expresses moderate levels of AKR1C3. NCI-H460 tumors were established in nude female mice by injection of a tumor cells subcutaneously. When tumors reached approximately 200 mm³, mice were randomized according to tumor volume into treatment groups (n=7 per group) on Day 8. Test agents were administered at the dose levels, route and schedules indicated in the Table 2 and FIG. 3.

Dose dependent efficacy was observed. Tumor stasis was seen at 300 mg/kg qd, with some reduction in efficacy at 150 mg/kg qd. There was a clear reduction in efficacy with the 75 mg/kg qd treatment.

TABLE 2

Compound 40 dose response efficacy in NCI-H460 lung cancer xenograft model on Day 18. The effect of the treatment on tumor volumes are presented.

| Test agent | Dose, Schedule | Tumor response | |
|---|---|---|---|
| | | ΔT/ΔC (%) | Regression (%) |
| Vehicle | None po, qd | 100 | — |
| Compound 40 | 75 mg/kg, po, qd | 25.9 | — |
| Compound 40 | 150 mg/kg, po, qd | 5.6 | — |
| Compound 40 | 300 mg/kg, po, qd | 1.8 | — |

The invention claimed is:
1. A compound of formula (I):

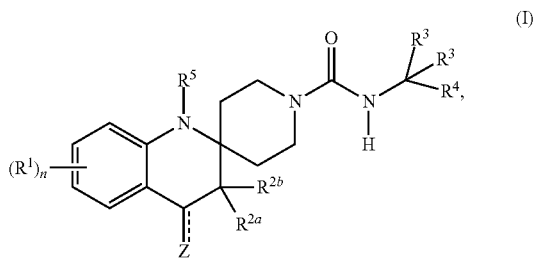

or a pharmaceutically acceptable salt thereof, wherein:
═ is a single bond or a double bond;
Z is either OH, when ═ is a single bond; or O, ═ when is a double bond;

each $R^1$ is fluoro;
$R^{2a}$ and $R^{2b}$ are each independently;
each $R^3$ is independently selected from the group consisting of H and D;
$R^4$ is selected from the group consisting of aryl, a 5 to 6-membered heteroaryl comprising 1, 2, or 3, heteroatoms independently selected from N, O, and S; and a 9 to 10-membered fused bicyclic heteroaryl comprising 1, 2, or 3, heteroatoms independently selected from N and O; wherein any of the foregoing is optionally substituted with one or more $R^6$;
$R^5$ is selected from the group consisting of H; $(C_1-C_6)$alkyl; $(C_2-C_6)$alkenyl; $(C_0-C_4)$alkylOR$^8$;
each $R^6$ is independently selected from the group consisting of halo; $(C_1-C_6)$alkyl; $(C_1-C_6)$alkoxy; halo$(C_1-C_6)$alkyl; OH; aryl; 3 to 6-membered heterocycle; 5- to 6-membered heteroaryl; $(C_0-C_4)$alkylS(O)$_m$$(C_1-C_6)$alkyl; halo$(C_1-C_6)$alkoxy; $(C_0-C_4)$alkylS(O)$_m$N(R$^8$)$_2$; $(C_0-C_4)$alkyl N(R$^8$)$_2$; $(C_0-C_4)$alkyl(CO)OR$^7$; N(R$^8$)S(O)$_m$$(C_1-C_6)$alkyl; N(R$^8$)S(O)$_m$$(C_3-C_6)$cycloalkyl; OP(O)(OH)$_2$; $(C_0-C_3)$alkyl(CO)NHR$^{11}$; $(C_0-C_3)$alkylOR$^7$, and $(C_3-C_{10})$cycloalkyl; wherein each $R^6$, when not being halo, OH, or OP(O)(OH)$_2$, is optionally substituted with one to three $R^9$; or two neighboring $R^6$, together with the atoms to which they attach form a 5 to 7-membered heterocycle or $(C_5-C_8)$cycloalkyl;
each $R^7$ and $R^8$ is independently selected from the group consisting of H or $(C_1-C_6)$alkyl, that is optionally substituted with one to three $R^9$;
each $R^9$ is independently selected from the group consisting of halo; —OH; amino, $(C_1-C_4)$alkylamino, di$(C_1-C_4)$alkylamino, OP(O)(OH)$_2$;$(C_1-C_6)$alkyl; $(C_1-C_3)$alkynyl; $(C_1-C_6)$alkoxy; halo$(C_1-C_6)$alkyl; $(C_0-C_4)$alkylS(O)$_m$$(C_1-C_6)$alkyl; halo$(C_1-C_6)$alkoxy; 3 to 6-membered heterocycle which is optionally substituted with oxo (═O); $(C_0-C_4)$alkylS(O)$_m$N(R$^{10}$)$_2$; $(C_0-C_4)$alkyl(CO)R$^{10}$; $(C_0-C_4)$alkyl(CO)OR$^{10}$; $(C_0-C_4)$alkylNR$^{10}$S(O)$_m$$(C_1-C_6)$alkyl; $(C_0-C_4)$alkylOR$^{10}$; $(C_0-C_4)$alkylN(R$^{10}$)$_2$; $(C_0-C_4)$alkylCN; $(C_0-C_4)$alkylN(R$^{10}$)$_2$; and $(C_0-C_4)$alkyl(CO)N(R$^{10}$)$_2$;
each $R^{10}$ is independently selected from the group consisting of H, $(C_1-C_6)$alkyl; or 3 to 6-membered heterocycle, wherein the 3 to 6-membered heterocycle is optionally substituted with one or more of $(C_1-C_6)$alkyl; and oxo (═O);
each $R^{11}$ is selected from the group consisting of H; 4 to 6-membered heterocycle which is optionally substituted with one to four $R^{12}$; $(C_3-C_6)$cycloalkyl which is optionally substituted with one to four $R^{12}$; $(C_0-C_3)$alkyl$(C_3-C_6)$cycloalkyl $(C_1-C_3)$alkyl which is optionally substituted with halo; CH$_2$-aryl which is optionally substituted with one to three $R^{12}$; $(C_1-C_6)$alkyl; $(C_2-C_6)$alkenyl; or $(C_2-C_6)$alkynyl, wherein each of the $(C_1-C_6)$alkyl; $(C_2-C_6)$alkenyl; and $(C_2-C_6)$alkynyl is optionally substituted with one or more $R^{13}$;
each $R^{12}$ is independently selected from the group consisting of OH, $(C_1-C_3)$alkoxy, NH$_2$; or $(C_1-C_3)$alkyl optionally substituted with one or more OH;
each $R^{13}$ is independently selected from the group consisting of halo, OH, amino, $(C_1-C_4)$alkylamino, di$(C_1-C_4)$alkylamino, $(C_1-C_3)$alkoxy; and C(O)—$(C_3-C_8)$cycloalkyl;
m is 0, 1, or 2; and
n is 1.

2. The compound of claim 1, wherein $R^4$ is phenyl optionally substituted with one or more $R^6$.

3. The compound of claim 1, wherein $R^4$ is 5 to 6-membered heteroaryl optionally substituted with one or more $R^6$.

4. The compound of claim 3, wherein $R^4$ is pyridyl.

5. The compound of claim 3, wherein $R^4$ is selected from the group consisting of furyl, oxazolyl, pyrazolyl, isoxazolyl, thiophenyl, imidazolyl, and oxadiazolyl.

6. The compound of claim 2, being of formula (II),

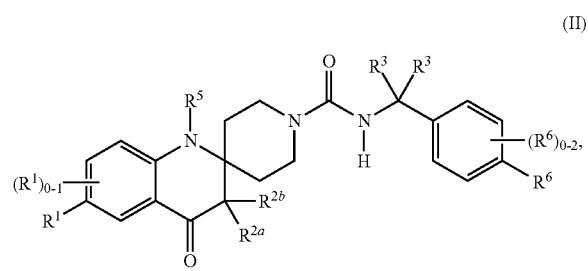

or a pharmaceutically acceptable salt thereof.

7. The compound of claim 1, being of formula (III),

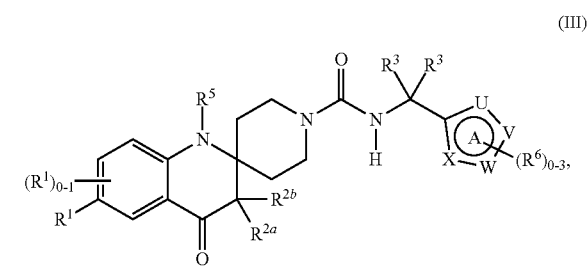

or a pharmaceutically acceptable salt thereof,
wherein ring A is a 5-membered heteroaryl and
u, v, w, and x are each independently selected from the group CH, O, S, N, and NH, provided that at least one of u, v, w, and x is O, S, N or NH.

8. The compound of claim 1,
wherein n is 1; and
$R^4$ is

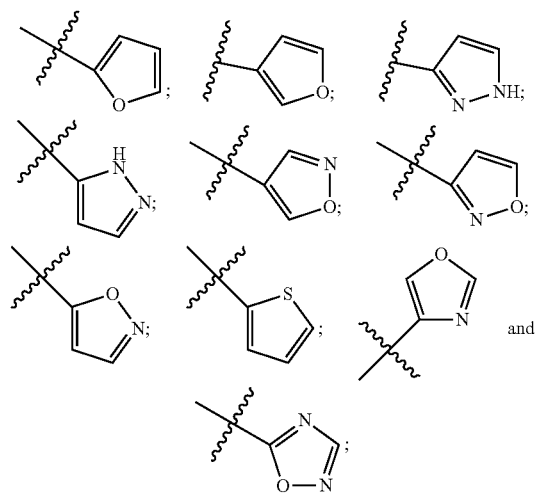

wherein $R^4$ is optionally substituted with one to three $R^6$.

9. The compound of claim 1, wherein Z is O.

10. The compound of claim 1, wherein $R^5$ is H or $(C_1-C_2)$alkyl.

11. The compound of claim 1, wherein $R^5$ is H.

12. The compound of claim 1, wherein each $R^3$ is H.

13. The compound of claim 1, wherein each $R^3$ is deuterium.

14. The compound of claim 1, wherein each $R^6$ is independently selected from halo and $(C_0-C_4)$alkylN$(R^8)_2$.

15. The compound of claim 1, wherein $R^6$ is halo.

16. A compound selected from:
- 6'-fluoro-N-((5-methylfuran-2-yl)methyl)-4'-oxo-3',4'-dihydro-1'H-spiro[piperidine-4,2'-quinoline]-1-carboxamide;
- 6'-fluoro-N-(4-fluoro-2-methoxybenzyl)-1'-methyl-4'-oxo-3',4'-dihydro-1'H-spiro[piperidine-4,2'-quinoline]-1-carboxamide;
- 6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide;
- 4-((6'-fluoro-4'-oxo-3',4'-dihydro-1'H-spiro[piperidine-4,2'-quinoline]-1-carboxamido)methyl)phenyl dihydrogen phosphate;
- N-(2,4-difluorobenzyl)-6'-fluoro-1'-methyl-4'-oxo-3',4'-dihydro-1'H-spiro[piperidine-4,2'-quinoline]-1-carboxamide;
- 1'-ethyl-6'-fluoro-N-(4-fluorobenzyl)-4'-oxo-3',4'-dihydro-1'H-spiro[piperidine-4,2'-quinoline]-1-carboxamide;
- 6'-fluoro-1'-methyl-N-((5-methylfuran-2-yl)methyl)-4'-oxo-3',4'-dihydro-1'H-spiro[piperidine-4,2'-quinoline]-1-carboxamide;
- 6'-fluoro-N-(4-fluoro-3-methoxybenzyl)-1'-methyl-4'-oxo-3',4'-dihydro-1'H-spiro[piperidine-4,2'-quinoline]-1-carboxamide;
- 6'-fluoro-N-(4-fluorobenzyl)-1'-methyl-4'-oxo-3',4'-dihydro-1'H-spiro[piperidine-4,2'-quinoline]-1-carboxamide;
- 6',8'-difluoro-N-((2-methylfuran-3-yl)methyl)-4'-oxo-3',4'-dihydro-1'H-spiro[piperidine-4,2'-quinoline]-1-carboxamide;
- N-(3-carbamoyl-4-fluorobenzyl)-6',8'-difluoro-4'-oxo-3',4'-dihydro-1'H-spiro[piperidine-4,2'-quinoline]-1-carboxamide
- 6'-fluoro-N-((4-fluorophenyl)methyl-d2)-4'-oxo-3',4'-dihydro-1'H-spiro[piperidine-4,2'-quinoline]-1-carboxamide;
- N-(3-carbamoyl-4-fluorobenzyl)-1'-ethyl-6'-fluoro-4'-oxo-3',4'-dihydro-1'H-spiro[piperidine-4,2'-quinoline]-1-carboxamide;
- 6'-fluoro-N-(4-fluorobenzyl)-1'-(2-methoxyethyl)-4'-oxo-3',4'-dihydro-1'H-spiro[piperidine-4,2'-quinoline]-1-carboxamide;
- 6'-fluoro-N-(4-fluoro-3-(oxazol-5-yl)benzyl)-4'-oxo-3',4'-dihydro-1'H-spiro[piperidine-4,2'-quinoline]-1-carboxamide;
- N-(2,4-difluorobenzyl)-6'-fluoro-4'-oxo-3',4'-dihydro-1'H-spiro[piperidine-4,2'-quinoline]-1-carboxamide
- N-(2,4-difluoro-5-((2-hydroxyethyl)amino)benzyl)-6'-fluoro-1'-methyl-4'-oxo-3',4'-dihydro-1'H-spiro[piperidine-4,2'-quinoline]-1-carboxamide;
- N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide;

6'-fluoro-N-(4-fluorobenzyl)-1'-(2-hydroxyethyl)-4'-oxo-3',4'-dihydro-1'H-spiro[piperidine-4,2'-quinoline]-1-carboxamide;
6'-fluoro-N-(4-fluoro-2-((2-methoxyethyl)amino)benzyl)-1'-methyl-4'-oxo-3',4'-dihydro-1'H-spiro[piperidine-4,2'-quinoline]-1-carboxamide;
6'-fluoro-N-(4-fluoro-3-((2-methoxyethyl)amino)benzyl)-1'-methyl-4'-oxo-3',4'-dihydro-1'H-spiro[piperidine-4,2'-quinoline]-1-carboxamide;
N-((5-chlorofuran-2-yl)methyl)-6'-fluoro-4'-oxo-3',4'-dihydro-1'H-spiro[piperidine-4,2'-quinoline]-1-carboxamide;
6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide;
N-(3-carbamoyl-4-fluorobenzyl)-6'-fluoro-4'-oxo-3',4'-dihydro-1'H-spiro[piperidine-4,2'-quinoline]-1-carboxamide;
1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;
N-(3-amino-2,4-difluorobenzyl)-1'-ethyl-6'-fluoro-4'-oxo-3',4'-dihydro-1'H-spiro[piperidine-4,2'-quinoline]-1-carboxamide;
N-(3-amino-4-fluorobenzyl)-6'-fluoro-1'-methyl-4'-oxo-3',4'-dihydro-1'H-spiro[piperidine-4,2'-quinoline]-1-carboxamide;
2-((2-fluoro-5-((6'-fluoro-1'-methyl-4'-oxo-3',4'-dihydro-1'H-spiro[piperidine-4,2'-quinoline]-1-carboxamido)methyl)phenyl)amino)ethyl dihydrogen phosphate;
N-(3-amino-4-fluorobenzyl)-1'-ethyl-6'-fluoro-4'-oxo-3',4'-dihydro-1'H-spiro[piperidine-4,2'-quinoline]-1-carboxamide;
6'-fluoro-N-(4-fluoro-3-sulfamoylbenzyl)-4'-oxo-3',4'-dihydro-1'H-spiro[piperidine-4,2'-quinoline]-1-carboxamide;
N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide;
6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide;
N-benzyl-6'-fluoro-4'-oxo-3',4'-dihydro-1'H-spiro[piperidine-4,2'-quinoline]-1-carboxamide
N-((2,4-dimethylfuran-3-yl)methyl)-6'-fluoro-4'-oxo-3',4'-dihydro-1'H-spiro[piperidine-4,2'-quinoline]-1-carboxamide;
6',8'-difluoro-N-(3-(oxazol-5-yl)benzyl)-4'-oxo-3',4'-dihydro-1'H-spiro[piperidine-4,2'-quinoline]-1-carboxamide;
6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide;
N-((1H-pyrazol-4-yl)methyl)-6'-fluoro-4'-oxo-3',4'-dihydro-1'H-spiro[piperidine-4,2'-quinoline]-1-carboxamide;
N-((4-carbamoylfuran-2-yl)methyl)-6',8'-difluoro-4'-oxo-3',4'-dihydro-1'H-spiro[piperidine-4,2'-quinoline]-1-carboxamide;
6'-fluoro-N-(4-hydroxybenzyl)-4'-oxo-3',4'-dihydro-1'H-spiro[piperidine-4,2'-quinoline]-1-carboxamide;
6'-fluoro-N-(4-fluorobenzyl)-4'-oxo-3',4'-dihydro-1'H-spiro[piperidine-4,2'-quinoline]-1-carboxamide;
N-(3-carbamoyl-4-fluorobenzyl)-6'-fluoro-1'-methyl-4'-oxo-3',4'-dihydro-1'H-spiro[piperidine-4,2'-quinoline]-1-carboxamide;
N-(3-amino-2,4-difluorobenzyl)-6'-fluoro-1'-methyl-4'-oxo-3',4'-dihydro-1'H-spiro[piperidine-4,2'-quinoline]-1-carboxamide;
6'-fluoro-N-(4-fluoro-2-hydroxybenzyl)-4'-oxo-3',4'-dihydro-1'H-spiro[piperidine-4,2'-quinoline]-1-carboxamide;
N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;
(S)-N-(3-((2,3-dihydroxypropyl)amino)-4-fluorobenzyl)-6'-fluoro-1'-methyl-4'-oxo-3',4'-dihydro-1'H-spiro[piperidine-4,2'-quinoline]-1-carboxamide;
6',8'-difluoro-N-(furan-3-ylmethyl)-4'-oxo-3',4'-dihydro-1'H-spiro[piperidine-4,2'-quinoline]-1-carboxamide;
N-((1H-pyrazol-3-yl)methyl)-6'-fluoro-4'-oxo-3',4'-dihydro-1'H-spiro[piperidine-4,2'-quinoline]-1-carboxamide;
6'-fluoro-N-(4-fluoro-3-((2-hydroxyethyl)carbamoyl)benzyl)-4'-oxo-3',4'-dihydro-1'H-spiro[piperidine-4,2'-quinoline]-1-carboxamide;
N-(4-amino-2,5-difluorobenzyl)-6'-fluoro-4'-oxo-3',4'-dihydro-1'H-spiro[piperidine-4,2'-quinoline]-1-carboxamide;
N-(5-amino-2,4-difluorobenzyl)-1'-ethyl-6'-fluoro-4'-oxo-3',4'-dihydro-1'H-spiro[piperidine-4,2'-quinoline]-1-carboxamide;
6'-fluoro-N-(4-fluoro-2-(2,2,2-trifluoroethoxy)benzyl)-4'-oxo-3',4'-dihydro-1'H-spiro[piperidine-4,2'-quinoline]-1-carboxamide;
N-(2-(ethylamino)-4-fluorobenzyl)-6'-fluoro-1'-methyl-4'-oxo-3',4'-dihydro-1'H-spiro[piperidine-4,2'-quinoline]-1-carboxamide;
N-(benzo[d][1,3]dioxol-4-ylmethyl)-6',8'-difluoro-4'-oxo-3',4'-dihydro-1'H-spiro[piperidine-4,2'-quinoline]-1-carboxamide;
6',8'-difluoro-N-(4-hydroxybenzyl)-4'-oxo-3',4'-dihydro-1'H-spiro[piperidine-4,2'-quinoline]-1-carboxamide;
6'-fluoro-N-(4-fluoro-3-(methylsulfonamido)benzyl)-1'-methyl-4'-oxo-3',4'-dihydro-1'H-spiro[piperidine-4,2'-quinoline]-1-carboxamide;
N-(4-amino-3-fluorobenzyl)-6'-fluoro-4'-oxo-3',4'-dihydro-1'H-spiro[piperidine-4,2'-quinoline]-1-carboxamide;
N-(4-amino-2,3-difluorobenzyl)-6'-fluoro-4'-oxo-3',4'-dihydro-1'H-spiro[piperidine-4,2'-quinoline]-1-carboxamide;
6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide;
6'-fluoro-N-((2-methylfuran-3-yl)methyl)-4'-oxo-3',4'-dihydro-1'H-spiro[piperidine-4,2'-quinoline]-1-carboxamide;
6'-fluoro-N-(4-fluoro-3-((3-hydroxycyclobutyl)carbamoyl)benzyl)-4'-oxo-3',4'-dihydro-1'H-spiro[piperidine-4,2'-quinoline]-1-carboxamide;
Methyl 2-fluoro-5-((6'-fluoro-4'-oxo-3',4'-dihydro-1'H-spiro[piperidine-4,2'-quinoline]-1-carboxamido)methyl)benzoate;
N-(3-(2-amino-2-oxoethyl)-4-fluorobenzyl)-6'-fluoro-1'-methyl-4'-oxo-3',4'-dihydro-1'H-spiro[piperidine-4,2'-quinoline]-1-carboxamide;
6',8'-difluoro-N-((3-hydroxypyridin-2-yl)methyl)-4'-oxo-3',4'-dihydro-1'H-spiro[piperidine-4,2'-quinoline]-1-carboxamide;

6'-fluoro-N-(4-fluoro-3-(methylcarbamoyl)benzyl)-4'-oxo-3',4'-dihydro-1'H-spiro[piperidine-4,2'-quinoline]-1-carboxamide;

N-(4-amino-3,5-difluorobenzyl)-6'-fluoro-4'-oxo-3',4'-dihydro-1'H-spiro[piperidine-4,2'-quinoline]-1-carboxamide;

N-((6-(dimethylamino)pyridin-2-yl)methyl)-6',8'-difluoro-4'-oxo-3',4'-dihydro-1'H-spiro[piperidine-4,2'-quinoline]-1-carboxamide;

6'-fluoro-N-(4-fluoro-2-(trifluoromethyl)benzyl)-4'-oxo-3',4'-dihydro-1'H-spiro[piperidine-4,2'-quinoline]-1-carboxamide;

N-(2-chloro-4-fluorobenzyl)-6'-fluoro-4'-oxo-3',4'-dihydro-1'H-spiro[piperidine-4,2'-quinoline]-1-carboxamide;

N-(3-carbamoylbenzyl)-6'-fluoro-4'-oxo-3',4'-dihydro-1'H-spiro[piperidine-4,2'-quinoline]-1-carboxamide;

6'-fluoro-N-(4-fluoro-3-(2-hydroxyethoxy)benzyl)-4'-oxo-3',4'-dihydro-1'H-spiro[piperidine-4,2'-quinoline]-1-carboxamide;

N-(2,4-difluoro-5-(2-hydroxyethoxy)benzyl)-6'-fluoro-4'-oxo-3',4'-dihydro-1'H-spiro[piperidine-4,2'-quinoline]-1-carboxamide;

6'-fluoro-N-((5-methyl-1H-pyrazol-3-yl)methyl)-4'-oxo-3',4'-dihydro-1'H-spiro[piperidine-4,2'-quinoline]-1-carboxamide;

N-(3-amino-4-fluorobenzyl)-6',8'-difluoro-4'-oxo-3',4'-dihydro-1'H-spiro[piperidine-4,2'-quinoline]-1-carboxamide;

6'-fluoro-4'-oxo-N-(3-sulfamoylbenzyl)-3',4'-dihydro-1'H-spiro[piperidine-4,2'-quinoline]-1-carboxamide;

N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide;

N-(4-aminobenzyl)-6'-fluoro-1'-methyl-4'-oxo-3',4'-dihydro-1'H-spiro[piperidine-4,2'-quinoline]-1-carboxamide;

N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;

N-(3-carbamoyl-4-fluoro-2-methylbenzyl)-6'-fluoro-4'-oxo-3',4'-dihydro-1'H-spiro[piperidine-4,2'-quinoline]-1-carboxamide;

N-(4-amino-2,6-difluorobenzyl)-6'-fluoro-4'-oxo-3',4'-dihydro-1'H-spiro[piperidine-4,2'-quinoline]-1-carboxamide;

N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide;

6'-fluoro-N-(4-fluoro-3-(hydroxymethyl)benzyl)-4'-oxo-3',4'-dihydro-1'H-spiro[piperidine-4,2'-quinoline]-1-carboxamide;

N-(3-amino-2,4-difluorobenzyl)-6'-fluoro-4'-oxo-3',4'-dihydro-1'H-spiro[piperidine-4,2'-quinoline]-1-carboxamide;

(E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide;

6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide;

N-(4-amino-3-chlorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(4-aminobenzyl)-6'-fluoro-4'-oxo-3',4'-dihydro-1'H-spiro[piperidine-4,2'-quinoline]-1-carboxamide;

6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide;

N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-(1-hydroxyethyl)benzyl)-1'-methyl-4'-oxo-3',4'-dihydro-1'H-spiro[piperidine-4,2'-quinoline]-1-carboxamide;

N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide;

(R)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(3-amino-4-fluorobenzyl)-6'-fluoro-4'-oxo-3',4'-dihydro-1'H-spiro[piperidine-4,2'-quinoline]-1-carboxamide;

6'-fluoro-4'-oxo-N-((2-(trifluoromethyl)furan-3-yl)methyl)-3',4'-dihydro-1'H-spiro[piperidine-4,2'-quinoline]-1-carboxamide;

6'-fluoro-N-(4-fluoro-3-((2-hydroxy-2-methylpropyl)carbamoyl)benzyl)-1'-methyl-4'-oxo-3',4'-dihydro-1'H-spiro[piperidine-4,2'-quinoline]-1-carboxamide;

N-(4-amino-2-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)amino)benzyl)-4'-oxo-3',4'-dihydro-1'H-spiro[piperidine-4,2'-quinoline]-1-carboxamide;

N-(3-((2-cyclopropyl-2-oxoethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2,2,2-trifluoroethyl)carbamoyl)benzyl)-4'-oxo-3',4'-dihydro-1'H-spiro[piperidine-4,2'-quinoline]-1-carboxamide;

6'-fluoro-N-(4-fluoro-3-(3-methoxyazetidin-1-yl)benzyl)-4'-oxo-3',4'-dihydro-1'H-spiro[piperidine-4,2'-quinoline]-1-carboxamide;

N-(3-(2-amino-2-oxoethyl)-4-fluorobenzyl)-6'-fluoro-4'-oxo-3',4'-dihydro-1'H-spiro[piperidine-4,2'-quinoline]-1-carboxamide;

N-(4-amino-2-(trifluoromethyl)benzyl)-6'-fluoro-4'-oxo-3',4'-dihydro-1'H-spiro[piperidine-4,2'-quinoline]-1-carboxamide;

6'-fluoro-N-(4-fluoro-3-(oxetan-3-ylcarbamoyl)benzyl)-4'-oxo-3',4'-dihydro-1'H-spiro[piperidine-4,2'-quinoline]-1-carboxamide;

N-((3-ethyl-5-methylisoxazol-4-yl)methyl)-6'-fluoro-4'-oxo-3',4'-dihydro-1'H-spiro[piperidine-4,2'-quinoline]-1-carboxamide;

6'-fluoro-N-(isoxazol-4-ylmethyl)-4'-oxo-3',4'-dihydro-1'H-spiro[piperidine-4,2'-quinoline]-1-carboxamide;

N-(4-(difluoromethoxy)-3-fluorobenzyl)-6',8'-difluoro-4'-oxo-3',4'-dihydro-1'H-spiro[piperidine-4,2'-quinoline]-1-carboxamide;

N-(3-carbamoyl-2,4-difluorobenzyl)-6'-fluoro-4'-oxo-3',4'-dihydro-1'H-spiro[piperidine-4,2'-quinoline]-1-carboxamide;

N-((2,5-dimethylfuran-3-yl)methyl)-6'-fluoro-4'-oxo-3',4'-dihydro-1'H-spiro[piperidine-4,2'-quinoline]-1-carboxamide;

N-(4-amino-2-chlorobenzyl)-6'-fluoro-4'-oxo-3',4'-dihydro-1'H-spiro[piperidine-4,2'-quinoline]-1-carboxamide;

N-(4-amino-3-(trifluoromethyl)benzyl)-6'-fluoro-4'-oxo-3',4'-dihydro-1'H-spiro[piperidine-4,2'-quinoline]-1-carboxamide;

N-(3-((2,2-dimethyl-3-morpholino-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-2-methoxybenzyl)-4'-oxo-3',4'-dihydro-1'H-spiro[piperidine-4,2'-quinoline]-1-carboxamide;

6',8'-difluoro-N-((2-methoxypyridin-4-yl)methyl)-4'-oxo-3',4'-dihydro-1'H-spiro[piperidine-4,2'-quinoline]-1-carboxamide;

N-(4-amino-2-methylbenzyl)-6'-fluoro-4'-oxo-3',4'-dihydro-1'H-spiro[piperidine-4,2'-quinoline]-1-carboxamide;

(S)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

6'-fluoro-N-(isoxazol-3-ylmethyl)-4'-oxo-3',4'-dihydro-1'H-spiro[piperidine-4,2'-quinoline]-1-carboxamide;

N-(4-amino-3-methylbenzyl)-6'-fluoro-4'-oxo-3',4'-dihydro-1'H-spiro[piperidine-4,2'-quinoline]-1-carboxamide;

N-((1H-indol-6-yl)methyl)-6'-fluoro-4'-oxo-3',4'-dihydro-1'H-spiro[piperidine-4,2'-quinoline]-1-carboxamide;

6'-fluoro-N-(4-fluoro-3-(((2-methyloxazol-5-yl)methyl)carbamoyl)benzyl)-4'-oxo-3',4'-dihydro-1'H-spiro[piperidine-4,2'-quinoline]-1-carboxamide;

(E)-6'-fluoro-N-(4-fluoro-3-((4-hydroxybut-2-en-1-yl)carbamoyl)benzyl)-4'-oxo-3',4'-dihydro-1'H-spiro[piperidine-4,2'-quinoline]-1-carboxamide;

6',8'-difluoro-N-((5-methylthiophen-2-yl)methyl)-4'-oxo-3',4'-dihydro-1'H-spiro[piperidine-4,2'-quinoline]-1-carboxamide;

6'-fluoro-N-(isoxazol-5-ylmethyl)-4'-oxo-3',4'-dihydro-1'H-spiro[piperidine-4,2'-quinoline]-1-carboxamide;

6',8'-difluoro-N-((6-fluoropyridin-3-yl)methyl)-4'-oxo-3',4'-dihydro-1'H-spiro[piperidine-4,2'-quinoline]-1-carboxamide;

N-(5-amino-2,4-difluorobenzyl)-6'-fluoro-4'-oxo-3',4'-dihydro-1'H-spiro[piperidine-4,2'-quinoline]-1-carboxamide;

6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide;

6'-fluoro-N-(4-fluoro-3-(prop-2-yn-1-ylcarbamoyl)benzyl)-4'-oxo-3',4'-dihydro-1'H-spiro[piperidine-4,2'-quinoline]-1-carboxamide;

6',8'-difluoro-N-(3-(hydroxymethyl)benzyl)-4'-oxo-3',4'-dihydro-1'H-spiro[piperidine-4,2'-quinoline]-1-carboxamide;

N-(3-(1H-imidazol-2-yl)benzyl)-6'-fluoro-4'-oxo-3',4'-dihydro-1'H-spiro[piperidine-4,2'-quinoline]-1-carboxamide;

6'-fluoro-N-(4-fluoro-3-(methylsulfonamido)benzyl)-4'-oxo-3',4'-dihydro-1'H-spiro[piperidine-4,2'-quinoline]-1-carboxamide;

6',8'-difluoro-N-(4-fluoro-3-(hydroxymethyl)benzyl)-4'-oxo-3',4'-dihydro-1'H-spiro[piperidine-4,2'-quinoline]-1-carboxamide;

N-(3-(cyclopropanesulfonamido)-4-fluorobenzyl)-6'-fluoro-4'-oxo-3',4'-dihydro-1'H-spiro[piperidine-4,2'-quinoline]-1-carboxamide;

6'-fluoro-N-((3-methyl-1,2,4-oxadiazol-5-yl)methyl)-4'-oxo-3',4'-dihydro-1'H-spiro[piperidine-4,2'-quinoline]-1-carboxamide;

6'-fluoro-N-(4-fluoro-3-(1-hydroxyethyl)benzyl)-4'-oxo-3',4'-dihydro-1'H-spiro[piperidine-4,2'-quinoline]-1-carboxamide;

N-((6-aminopyridin-3-yl)methyl)-6'-fluoro-4'-oxo-3',4'-dihydro-1'H-spiro[piperidine-4,2'-quinoline]-1-carboxamide;

N-(2-amino-4-fluorobenzyl)-6'-fluoro-4'-oxo-3',4'-dihydro-1'H-spiro[piperidine-4,2'-quinoline]-1-carboxamide;

6'-fluoro-N-(oxazol-4-ylmethyl)-4'-oxo-3',4'-dihydro-1'H-spiro[piperidine-4,2'-quinoline]-1-carboxamide;

6'-fluoro-N-(4-fluoro-3-(2-hydroxypropan-2-yl)benzyl)-1'-methyl-4'-oxo-3',4'-dihydro-1'H-spiro[piperidine-4,2'-quinoline]-1-carboxamide;

3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoic acid;

N-(benzo[c][1,2,5]oxadiazol-4-ylmethyl)-6'-fluoro-4'-oxo-3',4'-dihydro-1'H-spiro[piperidine-4,2'-quinoline]-1-carboxamide;

N-(3-carbamoyl-4-fluorobenzyl)-6'-fluoro-8'-methyl-4'-oxo-3',4'-dihydro-1'H-spiro[piperidine-4,2'-quinoline]-1-carboxamide;

6'-fluoro-N-(4-fluoro-3-(propylcarbamoyl)benzyl)-4'-oxo-3',4'-dihydro-1'H-spiro[piperidine-4,2'-quinoline]-1-carboxamide;

N-(3-(1H-1,2,4-triazol-1-yl)benzyl)-6',8'-difluoro-4'-oxo-3',4'-dihydro-1'H-spiro[piperidine-4,2'-quinoline]-1-carboxamide;

6'-fluoro-N-((1-methyl-1H-pyrazol-4-yl)methyl)-4'-oxo-3',4'-dihydro-1'H-spiro[piperidine-4,2'-quinoline]-1-carboxamide;

6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide;

6'-fluoro-N-(4-fluoro-3-(sulfamoylmethyl)benzyl)-4'-oxo-3',4'-dihydro-1'H-spiro[piperidine-4,2'-quinoline]-1-carboxamide;

3-((2-fluoro-5-((6'-fluoro-1'-methyl-4'-oxo-3',4'-dihydro-1'H-spiro[piperidine-4,2'-quinoline]-1-carboxamido)methyl)phenyl)amino)propanoic acid;

(R)-N-(3-(1-amino-2,2,2-trifluoroethyl)-4-fluorobenzyl)-6'-fluoro-1'-methyl-4'-oxo-3',4'-dihydro-1'H-spiro[piperidine-4,2'-quinoline]-1-carboxamide;

N-(4-(difluoromethoxy)benzyl)-6',8'-difluoro-4'-oxo-3',4'-dihydro-1'H-spiro[piperidine-4,2'-quinoline]-1-carboxamide;

(R)-6'-fluoro-N-(4-fluorobenzyl)-4'-hydroxy-1'-methyl-3',4'-dihydro-1'H-spiro[piperidine-4,2'-quinoline]-1-carboxamide;

(S)-6'-fluoro-N-(4-fluorobenzyl)-4'-hydroxy-1'-methyl-3',4'-dihydro-1'H-spiro[piperidine-4,2'-quinoline]-1-carboxamide;

(R)-6'-fluoro-N-(4-fluorobenzyl)-4'-hydroxy-3',4'-dihydro-1'H-spiro[piperidine-4,2'-quinoline]-1-carboxamide;

(S)-6'-fluoro-N-(4-fluorobenzyl)-4'-hydroxy-3',4'-dihydro-1'H-spiro[piperidine-4,2'-quinoline]-1-carboxamide;
(R)-6'-fluoro-N-(4-fluoro-2-hydroxybenzyl)-4'-hydroxy-3',4'-dihydro-1'H-spiro[piperidine-4,2'-quinoline]-1-carboxamide;
(S)-6'-fluoro-N-(4-fluoro-2-hydroxybenzyl)-4'-hydroxy-3',4'-dihydro-1'H-spiro[piperidine-4,2'-quinoline]-1-carboxamide:
N-(3-carbamoyl-4-fluorobenzyl)-6'-fluoro-4'-hydroxy-1'-methyl-3',4'-dihydro-1'H-spiro[piperidine-4,2'-quinoline]-1-carboxamide;
N-(2,4-difluoro-5-((2-hydroxyethyl)amino)benzyl)-6'-fluoro-4'-hydroxy-1'-methyl-3',4'-dihydro-1'H-spiro[piperidine-4,2'-quinoline]-1-carboxamide;
N-(3-carbamoyl-4-fluorobenzyl)-6',8'-difluoro-4'-hydroxy-3',4'-dihydro-1'H-spiro[piperidine-4,2'-quinoline]-1-carboxamide;
N-(3-amino-4-fluorobenzyl)-6'-fluoro-4'-hydroxy-3',4'-dihydro-1'H-spiro[piperidine-4,2'-quinoline]-1-carboxamide;
6'-fluoro-N-(4-fluoro-3-(hydroxymethyl)benzyl)-4'-hydroxy-3',4'-dihydro-1'H-spiro[piperidine-4,2'-quinoline]-1-carboxamide;
N-(3-carbamoyl-4-fluorobenzyl)-6'-fluoro-4'-hydroxy-3',4'-dihydro-1'H-spiro[piperidine-4,2'-quinoline]-1-carboxamide;
N-(3-(2-amino-2-oxoethyl)-4-fluorobenzyl)-6'-fluoro-4'-hydroxy-1'-methyl-3',4'-dihydro-1'H-spiro[piperidine-4,2'-quinoline]-1-carboxamide;
6'-fluoro-N-(4-fluoro-3-((3-hydroxycyclobutyl)carbamoyl)benzyl)-4'-hydroxy-3',4'-dihydro-1'H-spiro[piperidine-4,2'-quinoline]-1-carboxamide;
6'-fluoro-N-(4-fluoro-3-(2-hydroxyethoxy)benzyl)-4'-hydroxy-1'-methyl-3',4'-dihydro-1'H-spiro[piperidine-4,2'-quinoline]-1-carboxamide;
6'-fluoro-N-(4-fluoro-3-(methylsulfonamido)benzyl)-4'-hydroxy-3',4'-dihydro-1'H-spiro[piperidine-4,2'-quinoline]-1-carboxamide;
6'-fluoro-N-(4-fluoro-3-((2-hydroxyethyl)amino)benzyl)-4'-hydroxy-1'-methyl-3',4'-dihydro-1'H-spiro[piperidine-4,2'-quinoline]-1-carboxamide;
6'-fluoro-N-(4-fluoro-2-((2-methoxyethyl)amino)benzyl)-4'-hydroxy-1'-methyl-3',4'-dihydro-1'H-spiro[piperidine-4,2'-quinoline]-1-carboxamide;
N-(3-((R)-1-amino-2,2,2-trifluoroethyl)-4-fluorobenzyl)-6'-fluoro-4'-hydroxy-1'-methyl-3',4'-dihydro-1'H-spiro[piperidine-4,2'-quinoline]-1-carboxamide;
6'-fluoro-N-(4-fluoro-2-methoxybenzyl)-4'-hydroxy-3',4'-dihydro-1'H-spiro[piperidine-4,2'-quinoline]-1-carboxamide;
(R)-6'-fluoro-4'-hydroxy-N-((2-methylfuran-3-yl)methyl)-3',4'-dihydro-1'H-spiro[piperidine-4,2'-quinoline]-1-carboxamide;
(R)-N-(4-amino-3-fluorobenzyl)-6'-fluoro-4'-hydroxy-3',4'-dihydro-1'H-spiro[piperidine-4,2'-quinoline]-1-carboxamide; and
(S)—N-(4-amino-3-fluorobenzyl)-6'-fluoro-4'-hydroxy-3',4'-dihydro-1'H-spiro[piperidine-4,2'-quinoline]-1-carboxamide;
or a pharmaceutically acceptable salt thereof.

17. A compound selected from:
6'-fluoro-N-(4-fluoro-2-methoxybenzyl)-1'-methyl-4'-oxo-3',4'-dihydro-1'H-spiro[piperidine-4,2'-quinoline]-1-carboxamide;
6'-fluoro-N-(4-fluoro-3-(2-hydroxyethoxy)benzyl)-1'-methyl-4'-oxo-3',4'-dihydro-1'H-spiro[piperidine-4,2'-quinoline]-1-carboxamide;
4-((6'-fluoro-4'-oxo-3',4'-dihydro-1'H-spiro[piperidine-4,2'-quinoline]-1-carboxamido)methyl)phenyl dihydrogen phosphate;
N-(2,4-difluorobenzyl)-6'-fluoro-1'-methyl-4'-oxo-3',4'-dihydro-1'H-spiro[piperidine-4,2'-quinoline]-1-carboxamide;
1'-ethyl-6'-fluoro-N-(4-fluorobenzyl)-4'-oxo-3',4'-dihydro-1'H-spiro[piperidine-4,2'-quinoline]-1-carboxamide;
6'-fluoro-N-(4-fluoro-3-methoxybenzyl)-1'-methyl-4'-oxo-3',4'-dihydro-1'H-spiro[piperidine-4,2'-quinoline]-1-carboxamide;
6'-fluoro-N-(4-fluorobenzyl)-1'-methyl-4'-oxo-3',4'-dihydro-1'H-spiro[piperidine-4,2'-quinoline]-1-carboxamide;
N-(3-carbamoyl-4-fluorobenzyl)-6',8'-difluoro-4'-oxo-3',4'-dihydro-1'H-spiro[piperidine-4,2'-quinoline]-1-carboxamide;
6'-fluoro-N-((4-fluorophenyl)methyl-d2)-4'-oxo-3',4'-dihydro-1'H-spiro[piperidine-4,2'-quinoline]-1-carboxamide;
N-(3-carbamoyl-4-fluorobenzyl)-1'-ethyl-6'-fluoro-4'-oxo-3',4'-dihydro-1'H-spiro[piperidine-4,2'-quinoline]-1-carboxamide;
6'-fluoro-N-(4-fluorobenzyl)-1'-(2-methoxyethyl)-4'-oxo-3',4'-dihydro-1'H-spiro[piperidine-4,2'-quinoline]-1-carboxamide;
6'-fluoro-N-(4-fluoro-3-(oxazol-5-yl)benzyl)-4'-oxo-3',4'-dihydro-1'H-spiro[piperidine-4,2'-quinoline]-1-carboxamide;
N-(2,4-difluorobenzyl)-6'-fluoro-4'-oxo-3',4'-dihydro-1'H-spiro[piperidine-4,2'-quinoline]-1-carboxamide;
N-(2,4-difluoro-5-((2-hydroxyethyl)amino)benzyl)-6'-fluoro-1'-methyl-4'-oxo-3',4'-dihydro-1'H-spiro[piperidine-4,2'-quinoline]-1-carboxamide;
N-(2,4-difluoro-5-((2-hydroxyethyl)amino)benzyl)-1'-ethyl-6'-fluoro-4'-oxo-3',4'-dihydro-1'H-spiro[piperidine-4,2'-quinoline]-1-carboxamide;
6'-fluoro-N-(4-fluorobenzyl)-1'-(2-hydroxyethyl)-4'-oxo-3',4'-dihydro-1'H-spiro[piperidine-4,2'-quinoline]-1-carboxamide;
6'-fluoro-N-(4-fluoro-2-((2-methoxyethyl)amino)benzyl)-1'-methyl-4'-oxo-3',4'-dihydro-1'H-spiro[piperidine-4,2'-quinoline]-1-carboxamide;
6'-fluoro-N-(4-fluoro-3-((2-methoxyethyl)amino)benzyl)-1'-methyl-4'-oxo-3',4'-dihydro-1'H-spiro[piperidine-4,2'-quinoline]-1-carboxamide;
6'-fluoro-N-(4-fluoro-3-((1-methylethyl)sulfonamido)benzyl)-4'-oxo-3',4'-dihydro-1'H-spiro[piperidine-4,2'-quinoline]-1-carboxamide;
N-(3-carbamoyl-4-fluorobenzyl)-6'-fluoro-4'-oxo-3',4'-dihydro-1'H-spiro[piperidine-4,2'-quinoline]-1-carboxamide;
1'-ethyl-6'-fluoro-N-(4-fluoro-3-((2-hydroxyethyl)amino)benzyl)-4'-oxo-3',4'-dihydro-1'H-spiro[piperidine-4,2'-quinoline]-1-carboxamide;
N-(3-amino-2,4-difluorobenzyl)-1'-ethyl-6'-fluoro-4'-oxo-3',4'-dihydro-1'H-spiro[piperidine-4,2'-quinoline]-1-carboxamide;
N-(3-amino-4-fluorobenzyl)-6'-fluoro-1'-methyl-4'-oxo-3',4'-dihydro-1'H-spiro[piperidine-4,2'-quinoline]-1-carboxamide;

2-((2-fluoro-5-((6'-fluoro-1'-methyl-4'-oxo-3',4'-dihydro-1'H-spiro[piperidine-4,2'-quinoline]-1-carboxamido)methyl)phenyl)amino)ethyl dihydrogen phosphate;

N-(3-amino-4-fluorobenzyl)-1'-ethyl-6'-fluoro-4'-oxo-3',4'-dihydro-1'H-spiro[piperidine-4,2'-quinoline]-1-carboxamide;

6'-fluoro-N-(4-fluoro-3-sulfamoylbenzyl)-4'-oxo-3',4'-dihydro-1'H-spiro[piperidine-4,2'-quinoline]-1-carboxamide;

N-(3-(((1,4-dioxan-2-yl)methyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-((4-(hydroxymethyl)benzyl)carbamoyl)benzyl)-4'-oxo-3',4'-dihydro-1'H-spiro[piperidine-4,2'-quinoline]-1-carboxamide;

N-benzyl-6'-fluoro-4'-oxo-3',4'-dihydro-1'H-spiro[piperidine-4,2'-quinoline]-1-carboxamide;

6',8'-difluoro-N-(3-(oxazol-5-yl)benzyl)-4'-oxo-3',4'-dihydro-1'H-spiro[piperidine-4,2'-quinoline]-1-carboxamide;

6'-fluoro-N-(4-fluoro-3-((2-hydroxyethyl)amino)benzyl)-1'-methyl-4'-oxo-3',4'-dihydro-1'H-spiro[piperidine-4,2'-quinoline]-1-carboxamide;

6'-fluoro-N-(4-hydroxybenzyl)-4'-oxo-3',4'-dihydro-1'H-spiro[piperidine-4,2'-quinoline]-1-carboxamide;

6'-fluoro-N-(4-fluorobenzyl)-4'-oxo-3',4'-dihydro-1'H-spiro[piperidine-4,2'-quinoline]-1-carboxamide;

N-(3-carbamoyl-4-fluorobenzyl)-6'-fluoro-1'-methyl-4'-oxo-3',4'-dihydro-1'H-spiro[piperidine-4,2'-quinoline]-1-carboxamide;

N-(3-amino-2,4-difluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-2-hydroxybenzyl)-4'-oxo-3',4'-dihydro-1'H-spiro[piperidine-4,2'-quinoline]-1-carboxamide;

N-(3-((2,2-dimethyl-3-(4-methylpiperazin-1-yl)-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

(S)—N-(3-((2,3-dihydroxypropyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-4'-oxo-3',4'-dihydro-1'H-spiro[piperidine-4,2'-quinoline]-1-carboxamide;

N-(4-amino-2,5-difluorobenzyl)-6'-fluoro-4'-oxo-3',4'-dihydro-1'H-spiro[piperidine-4,2'-quinoline]-1-carboxamide;

N-(5-amino-2,4-difluorobenzyl)-1'-ethyl-6'-fluoro-4'-oxo-3',4'-dihydro-1'H-spiro[piperidine-4,2'-quinoline]-1-carboxamide;

6'-fluoro-N-(4-fluoro-2-(2,2,2-trifluoroethoxy)benzyl)-4'-oxo-3',4'-dihydro-1'H-spiro[piperidine-4,2'-quinoline]-1-carboxamide;

N-(2-(ethylamino)-4-fluorobenzyl)-6'-fluoro-1'-methyl-4'-oxo-3',4'-dihydro-1'H-spiro[piperidine-4,2'-quinoline]-1-carboxamide;

N-(benzo[d][1,3]dioxol-4-ylmethyl)-6',8'-difluoro-4'-oxo-3',4'-dihydro-1'H-spiro[piperidine-4,2'-quinoline]-1-carboxamide;

6',8'-difluoro-N-(4-hydroxybenzyl)-4'-oxo-3',4'-dihydro-1'H-spiro[piperidine-4,2'-quinoline]-1-carboxamide;

6'-fluoro-N-(4-fluoro-3-(methylsulfonamido)benzyl)-1'-methyl-4'-oxo-3',4'-dihydro-1'H-spiro[piperidine-4,2'-quinoline]-1-carboxamide;

N-(4-amino-3-fluorobenzyl)-6'-fluoro-4'-oxo-3',4'-dihydro-1'H-spiro[piperidine-4,2'-quinoline]-1-carboxamide;

N-(4-amino-2,3-difluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)carbamoyl)benzyl)-1'-methyl-4'-oxo-3',4'-dihydro-1'H-spiro[piperidine-4,2'-quinoline]-1-carboxamide;

6'-fluoro-N-(4-fluoro-3-((3-hydroxycyclobutyl)carbamoyl)benzyl)-4'-oxo-3',4'-dihydro-1'H-spiro[piperidine-4,2'-quinoline]-1-carboxamide;

methyl 2-fluoro-5-((6'-fluoro-4'-oxo-3',4'-dihydro-1'H-spiro[piperidine-4,2'-quinoline]-1-carboxamido)methyl)benzoate;

N-(3-(2-amino-2-oxoethyl)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-(methylcarbamoyl)benzyl)-4'-oxo-3',4'-dihydro-1'H-spiro[piperidine-4,2'-quinoline]-1-carboxamide;

N-(4-amino-3,5-difluorobenzyl)-6'-fluoro-4'-oxo-3',4'-dihydro-1'H-spiro[piperidine-4,2'-quinoline]-1-carboxamide;

6'-fluoro-N-(4-fluoro-2-(trifluoromethyl)benzyl)-4'-oxo-3',4'-dihydro-1'H-spiro[piperidine-4,2'-quinoline]-1-carboxamide;

N-(2-chloro-4-fluorobenzyl)-6'-fluoro-4'-oxo-3',4'-dihydro-1'H-spiro[piperidine-4,2'-quinoline]-1-carboxamide;

N-(3-carbamoylbenzyl)-6'-fluoro-4'-oxo-3',4'-dihydro-1'H-spiro[piperidine-4,2'-quinoline]-1-carboxamide;

6'-fluoro-N-(4-fluoro-3-(2-hydroxyethoxy)benzyl)-4'-oxo-3',4'-dihydro-1'H-spiro[piperidine-4,2'-quinoline]-1-carboxamide;

N-(2,4-difluoro-5-(2-hydroxyethoxy)benzyl)-6'-fluoro-4'-oxo-3',4'-dihydro-1'H-spiro[piperidine-4,2'-quinoline]-1-carboxamide;

N-(3-amino-4-fluorobenzyl)-6',8'-difluoro-4'-oxo-3',4'-dihydro-1'H-spiro[piperidine-4,2'-quinoline]-1-carboxamide;

6'-fluoro-4'-oxo-N-(3-sulfamoylbenzyl)-3',4'-dihydro-1'H-spiro[piperidine-4,2'-quinoline]-1-carboxamide;

N-(2,4-difluoro-3-((2-hydroxyethyl)amino)benzyl)-1'-ethyl-6'-fluoro-4'-oxo-3',4'-dihydro-1'H-spiro[piperidine-4,2'-quinoline]-1-carboxamide;

N-(4-aminobenzyl)-6'-fluoro-1'-methyl-4'-oxo-3',4'-dihydro-1'H-spiro[piperidine-4,2'-quinoline]-1-carboxamide;

N-(2,4-difluoro-5-((2-hydroxyethyl)amino)benzyl)-6'-fluoro-4'-oxo-3',4'-dihydro-1'H-spiro[piperidine-4,2'-quinoline]-1-carboxamide;

6-fluoro-N-(4-fluoro-3-((2-hydroxyethyl)amino)benzyl)-4'-oxo-3',4'-dihydro-1'H-spiro[piperidine-4,2'-quinoline]-1-carboxamide;

N-(3-carbamoyl-4-fluoro-2-methylbenzyl)-6'-fluoro-4'-oxo-3',4'-dihydro-1'H-spiro[piperidine-4,2'-quinoline]-1-carboxamide;

N-(4-amino-2,6-difluorobenzyl)-6'-fluoro-4'-oxo-3',4'-dihydro-1'H-spiro[piperidine-4,2'-quinoline]-1-carboxamide;

N-(3-((2-(dimethylamino)ethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxyethyl)carbamoyl)benzyl)-1'-methyl-4'-oxo-3',4'-dihydro-1'H-spiro[piperidine-4,2'-quinoline]-1-carboxamide;

6'-fluoro-N-(4-fluoro-3-(hydroxymethyl)benzyl)-4'-oxo-3',4'-dihydro-1'H-spiro[piperidine-4,2'-quinoline]-1-carboxamide;

N-(3-amino-2,4-difluorobenzyl)-6'-fluoro-4'-oxo-3',4'-dihydro-1'H-spiro[piperidine-4,2'-quinoline]-1-carboxamide:

(E)-1'-(but-2-en-1-yl)-6'-fluoro-N-(4-fluorobenzyl)-4'-oxo-3',4'-dihydro-1'H-spiro[piperidine-4,2'-quinoline]-1-carboxamide;

6'-fluoro-N-(4-fluoro-2-((2-hydroxyethyl)amino)benzyl)-1'-methyl-4'-oxo-3',4'-dihydro-1'H-spiro[piperidine-4,2'-quinoline]-1-carboxamide;

N-(4-amino-3-chlorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(4-aminobenzyl)-6'-fluoro-4'-oxo-3',4'-dihydro-1'H-spiro[piperidine-4,2'-quinoline]-1-carboxamide;

6'-fluoro-N-(4-fluoro-3-((2-(2-oxopyrrolidin-1-yl)ethyl)amino)benzyl)-1'-methyl-4'-oxo-3',4'-dihydro-1'H-spiro[piperidine-4,2'-quinoline]-1-carboxamide;

N-(2,4-difluoro-3-((2-hydroxyethyl)amino)benzyl)-6'-fluoro-1'-methyl-4'-oxo-3',4'-dihydro-1'H-spiro[piperidine-4,2'-quinoline]-1-carboxamide;

6'-fluoro-N-(4-fluoro-3-(1-hydroxyethyl)benzyl)-1'-methyl-4'-oxo-3',4'-dihydro-1'H-spiro[piperidine-4,2'-quinoline]-1-carboxamide;

(R)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(3-amino-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-hydroxy-2-methylpropyl)carbamoyl)benzyl)-1'-methyl-4'-oxo-3',4'-dihydro-1'H-spiro[piperidine-4,2'-quinoline]-1-carboxamide;

N-(4-amino-2-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2-methoxyethyl)amino)benzyl)-4'-oxo-3',4'-dihydro-1'H-spiro[piperidine-4,2'-quinoline]-1-carboxamide;

N-(3-((2-cyclopropyl-2-oxoethyl)carbamoyl)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-((2,2,2-trifluoroethyl)carbamoyl)benzyl)-4'-oxo-3',4'-dihydro-1'H-spiro[piperidine-4,2'-quinoline]-1-carboxamide;

6'-fluoro-N-(4-fluoro-3-(3-methoxyazetidin-1-yl)benzyl)-4'-oxo-3',4'-dihydro-1'H-spiro[piperidine-4,2'-quinoline]-1-carboxamide;

N-(3-(2-amino-2-oxoethyl)-4-fluorobenzyl)-6'-fluoro-4'-oxo-3',4'-dihydro-1'H-spiro[piperidine-4,2'-quinoline]-1-carboxamide;

N-(4-amino-2-(trifluoromethyl)benzyl)-6'-fluoro-4'-oxo-3',4'-dihydro-1'H-spiro[piperidine-4,2'-quinoline]-1-carboxamide;

6'-fluoro-N-(4-fluoro-3-(oxetan-3-ylcarbamoyl)benzyl)-4'-oxo-3',4'-dihydro-1'H-spiro[piperidine-4,2'-quinoline]-1-carboxamide;

N-(4-(difluoromethoxy)-3-fluorobenzyl)-6',8'-difluoro-4'-oxo-3',4'-dihydro-1'H-spiro[piperidine-4,2'-quinoline]-1-carboxamide;

N-(3-carbamoyl-2,4-difluorobenzyl)-6'-fluoro-4'-oxo-3',4'-dihydro-1'H-spiro[piperidine-4,2'-quinoline]-1-carboxamide;

N-(4-amino-2-chlorobenzyl)-6'-fluoro-4'-oxo-3',4'-dihydro-1'H-spiro[piperidine-4,2'-quinoline]-1-carboxamide;

N-(4-amino-3-(trifluoromethyl)benzyl)-6'-fluoro-4'-oxo-3',4'-dihydro-1'H-spiro[piperidine-4,2'-quinoline]-1-carboxamide;

N-(3-((2,2-dimethyl-3-morpholino-3-oxopropyl)amino)-4-fluorobenzyl)-6'-fluoro-1'-methyl-4'-oxo-3',4'-dihydro-1'H-spiro[piperidine-4,2'-quinoline]-1-carboxamide;

6'-fluoro-N-(4-fluoro-2-methoxybenzyl)-4'-oxo-3',4'-dihydro-1'H-spiro[piperidine-4,2'-quinoline]-1-carboxamide;

N-(4-amino-2-methylbenzyl)-6'-fluoro-4'-oxo-3',4'-dihydro-1'H-spiro[piperidine-4,2'-quinoline]-1-carboxamide;

(S)-6'-fluoro-N-(4-fluoro-3-((2-hydroxypropyl)carbamoyl)benzyl)-1'-methyl-4'-oxo-3',4'-dihydro-1'H-spiro[piperidine-4,2'-quinoline]-1-carboxamide;

N-(4-amino-3-methylbenzyl)-6'-fluoro-4'-oxo-3',4'-dihydro-1'H-spiro[piperidine-4,2'-quinoline]-1-carboxamide;

6'-fluoro-N-(4-fluoro-3-(((2-methyloxazol-5-yl)methyl)carbamoyl)benzyl)-4'-oxo-3',4'-dihydro-1'H-spiro[piperidine-4,2'-quinoline]-1-carboxamide;

(E)-6'-fluoro-N-(4-fluoro-3-((4-hydroxybut-2-en-1-yl)carbamoyl)benzyl)-4'-oxo-3',4'-dihydro-1'H-spiro[piperidine-4,2'-quinoline]-1-carboxamide;

N-(5-amino-2,4-difluorobenzyl)-6'-fluoro-4'-oxo-3',4'-dihydro-1'H-spiro[piperidine-4,2'-quinoline]-1-carboxamide;

6'-fluoro-N-(4-fluoro-3-(prop-2-yn-1-ylcarbamoyl)benzyl)-4'-oxo-3',4'-dihydro-1'H-spiro[piperidine-4,2'-quinoline]-1-carboxamide;

6',8'-difluoro-N-(3-(hydroxymethyl)benzyl)-4'-oxo-3',4'-dihydro-1'H-spiro[piperidine-4,2'-quinoline]-1-carboxamide;

N-(3-(1H-imidazol-2-yl)benzyl)-6'-fluoro-4'-oxo-3',4'-dihydro-1'H-spiro[piperidine-4,2'-quinoline]-1-carboxamide;

6'-fluoro-N-(4-fluoro-3-(methylsulfonamido)benzyl)-4'-oxo-3',4'-dihydro-1'H-spiro[piperidine-4,2'-quinoline]-1-carboxamide;

6',8'-difluoro-N-(4-fluoro-3-(hydroxymethyl)benzyl)-4'-oxo-3',4'-dihydro-1'H-spiro[piperidine-4,2'-quinoline]-1-carboxamide;

N-(3-(cyclopropanesulfonamido)-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-(1-hydroxyethyl)benzyl)-4'-oxo-3',4'-dihydro-1'H-spiro[piperidine-4,2'-quinoline]-1-carboxamide;

N-(2-amino-4-fluorobenzyl)-6'-fluoro-4'-oxo-3',4'-dihydro-1'H-spiro[piperidine-4,2'-quinoline]-1-carboxamide;

6'-fluoro-N-(4-fluoro-3-(2-hydroxypropan-2-yl)benzyl)-1'-methyl-4'-oxo-3',4'-dihydro-1'H-spiro[piperidine-4,2'-quinoline]-1-carboxamide;

3-((2-fluoro-5-((6'-fluoro-1'-methyl-4'-oxo-3',4'-dihydro-1'H-spiro[piperidine-4,2'-quinoline]-1-carboxamido)methyl)phenyl)amino)-2,2-dimethylpropanoic acid;

N-(3-carbamoyl-4-fluorobenzyl)-6'-fluoro-8'-methyl-4'-oxo-3',4'-dihydro-1'H-spiro[piperidine-4,2'-quinoline]-1-carboxamide;

6'-fluoro-N-(4-fluoro-3-(propylcarbamoyl)benzyl)-4'-oxo-3',4'-dihydro-1'H-spiro[piperidine-4,2'-quinoline]-1-carboxamide;

N-(3-(1H-1,2,4-triazol-1-yl)benzyl)-6',8'-difluoro-4'-oxo-3',4'-dihydro-1'H-spiro[piperidine-4,2'-quinoline]-1-carboxamide;

6'-fluoro-N-(4-fluoro-3-(((2-hydroxyethyl)amino)methyl)benzyl)-4'-oxo-3',4'-dihydro-1'H-spiro[piperidine-4,2'-quinoline]-1-carboxamide;

6'-fluoro-N-(4-fluoro-3-(sulfamoylmethyl)benzyl)-4'-oxo-3',4'-dihydro-1'H-spiro[piperidine-4,2'-quinoline]-1-carboxamide;

R)-N-(3-(1-amino-2,2,2-trifluoroethyl)-4-fluorobenzyl)-6'-fluoro-1'-methyl-4'-oxo-3',4'-dihydro-1'H-spiro[piperidine-4,2'-quinoline]-1-carboxamide; and N-(4-(difluoromethoxy)benzyl)-6',8'-difluoro-4'-oxo-3',4'-dihydro-1'H-spiro[piperidine-4,2'-quinoline]-1-carboxamide;

or a pharmaceutically acceptable salt thereof.

18. A compound selected from:

6'-fluoro-N-((5-methylfuran-2-yl)methyl)-4'-oxo-3',4'-dihydro-1'H-spiro[piperidine-4,2'-quinoline]-1-carboxamide;

6'-fluoro-1'-methyl-N-((5-methylfuran-2-yl)methyl)-4'-oxo-3',4'-dihydro-1'H-spiro[piperidine-4,2'-quinoline]-1-carboxamide;

6',8'-difluoro-N-((2-methylfuran-3-yl)methyl)-4'-oxo-3',4'-dihydro-1'H-spiro[piperidine-4,2'-quinoline]-1-carboxamide;

N-((5-chlorofuran-2-yl)methyl)-6'-fluoro-4'-oxo-3',4'-dihydro-1'H-spiro[piperidine-4,2'-quinoline]-1-carboxamide;

N-((2,4-dimethylfuran-3-yl)methyl)-6'-fluoro-4'-oxo-3',4'-dihydro-1'H-spiro[piperidine-4,2'-quinoline]-1-carboxamide;

N-((1H-pyrazol-4-yl)methyl)-6'-fluoro-4'-oxo-3',4'-dihydro-1'H-spiro[piperidine-4,2'-quinoline]-1-carboxamide;

N-((4-carbamoylfuran-2-yl)methyl)-6',8'-difluoro-4'-oxo-3',4'-dihydro-1'H-spiro[piperidine-4,2'-quinoline]-1-carboxamide;

6',8'-difluoro-N-(furan-3-ylmethyl)-4'-oxo-3',4'-dihydro-1'H-spiro[piperidine-4,2'-quinoline]-1-carboxamide;

N-((1H-pyrazol-3-yl)methyl)-6'-fluoro-4'-oxo-3',4'-dihydro-1'H-spiro[piperidine-4,2'-quinoline]-1-carboxamide;

6'-fluoro-N-((2-methylfuran-3-yl)methyl)-4'-oxo-3',4'-dihydro-1'H-spiro[piperidine-4,2'-quinoline]-1-carboxamide;

6',8'-difluoro-N-((3-hydroxypyridin-2-yl)methyl)-4'-oxo-3',4'-dihydro-1'H-spiro[piperidine-4,2'-quinoline]-1-carboxamide;

N-((6-(dimethylamino)pyridin-2-yl)methyl)-6',8'-difluoro-4'-oxo-3',4'-dihydro-1'H-spiro[piperidine-4,2'-quinoline]-1-carboxamide;

6'-fluoro-N-((5-methyl-1H-pyrazol-3-yl)methyl)-4'-oxo-3',4'-dihydro-1'H-spiro[piperidine-4,2'-quinoline]-1-carboxamide;

N-((4-chloro-1-methyl-1H-pyrazol-5-yl)methyl)-6'-fluoro-4'-oxo-3',4'-dihydro-1'H-spiro[piperidine-4,2'-quinoline]-1-carboxamide;

6'-fluoro-4'-oxo-N-((2-(trifluoromethyl)furan-3-yl)methyl)-3',4'-dihydro-1'H-spiro[piperidine-4,2'-quinoline]-1-carboxamide;

N-((3-ethyl-5-methylisoxazol-4-yl)methyl)-6'-fluoro-4'-oxo-3',4'-dihydro-1'H-spiro[piperidine-4,2'-quinoline]-1-carboxamide;

6'-fluoro-N-(isoxazol-4-ylmethyl)-4'-oxo-3',4'-dihydro-1'H-spiro[piperidine-4,2'-quinoline]-1-carboxamide;

N-((2,5-dimethylfuran-3-yl)methyl)-6'-fluoro-4'-oxo-3',4'-dihydro-1'H-spiro[piperidine-4,2'-quinoline]-1-carboxamide;

6',8'-difluoro-N-((2-methoxypyridin-4-yl)methyl)-4'-oxo-3',4'-dihydro-1'H-spiro[piperidine-4,2'-quinoline]-1-carboxamide;

6'-fluoro-N-(isoxazol-3-ylmethyl)-4'-oxo-3',4'-dihydro-1'H-spiro[piperidine-4,2'-quinoline]-1-carboxamide;

N-((1H-indol-6-yl)methyl)-6'-fluoro-4'-oxo-3',4'-dihydro-1'H-spiro[piperidine-4,2'-quinoline]-1-carboxamide;

6',8'-difluoro-N-((5-methylthiophen-2-yl)methyl)-4'-oxo-3',4'-dihydro-1'H-spiro[piperidine-4,2'-quinoline]-1-carboxamide;

6'-fluoro-N-(isoxazol-5-ylmethyl)-4'-oxo-3',4'-dihydro-1'H-spiro[piperidine-4,2'-quinoline]-1-carboxamide;

6',8'-difluoro-N-((6-fluoropyridin-3-yl)methyl)-4'-oxo-3',4'-dihydro-1'H-spiro[piperidine-4,2'-quinoline]-1-carboxamide;

6'-fluoro-N-((5-methyl-2-(trifluoromethyl)furan-3-yl)methyl)-4'-oxo-3',4'-dihydro-1'H-spiro[piperidine-4,2'-quinoline]-1-carboxamide;

6'-fluoro-N-((3-methyl-1,2,4-oxadiazol-5-yl)methyl)-4'-oxo-3',4'-dihydro-1'H-spiro[piperidine-4,2'-quinoline]-1-carboxamide;

N-((6-aminopyridin-3-yl)methyl)-6'-fluoro-4'-oxo-3',4'-dihydro-1'H-spiro[piperidine-4,2'-quinoline]-1-carboxamide;

6'-fluoro-N-(oxazol-4-ylmethyl)-4'-oxo-3',4'-dihydro-1'H-spiro[piperidine-4,2'-quinoline]-1-carboxamide;

N-(benzo[c][1,2,5]oxadiazol-4-ylmethyl)-6'-fluoro-4'-oxo-3',4'-dihydro-1'H-spiro[piperidine-4,2'-quinoline]-1-carboxamide; and 6'-fluoro-N-((1-methyl-1H-pyrazol-4-yl)methyl)-4'-oxo-3',4'-dihydro-1'H-spiro[piperidine-4,2'-quinoline]-1-carboxamide;

or a pharmaceutically acceptable salt thereof.

19. A method of treating cancer, wherein the method comprises administering to the subject the compound of formula (I) according to claim 1, or a pharmaceutically acceptable salt thereof.

20. The method according to claim 19, wherein the cancer is selected from non-small cell lung cancer (NSCLC), liver cancer, head and neck cancer, esophageal cancer, uterine cancer, breast cancer, bladder cancer, cervical cancer, colorectal cancer, kidney cancer, melanoma, stomach cancer, castration-resistant prostate cancer (CRPC), T-cell acute lymphoblastic leukemia (T-ALL), acute myeloid leukemia (AML), and myelodysplastic syndrome (MDS), wherein the method comprises administering to the subject the compound of formulae (I) to (III), or a pharmaceutically acceptable salt thereof.

21. The method according to claim 20, wherein the non-small cell lung cancer (NSCLC) is selected from adenocarcinoma, squamous cell carcinoma, large cell carcinoma, large cell neuroendocrine carcinoma, adenosquamous carcinoma, and sarcomatoid carcinoma.

22. A method of treating cancer with a genetic or epigenetic alteration in the genes NFE2L2, KEAP1, CUL3, AKR1C$_3$, or any other condition resulting in the activation of NRF2 transcriptional activity or AKR1C3 gene expression comprising administering to a subject in need thereof, a therapeutically effective amount of a compound of formula (I), or a pharmaceutically acceptable salt thereof.

* * * * *